US012303567B2

(12) United States Patent
Mulligan et al.

(10) Patent No.: US 12,303,567 B2
(45) Date of Patent: *May 20, 2025

(54) COMPOSITIONS OF PROTEIN COMPLEXES AND METHODS OF USE THEREOF

(71) Applicant: Bonum Therapeutics, Inc., Seattle, WA (US)

(72) Inventors: John Thomas Mulligan, Seattle, WA (US); Shannon Lee Okada, Seattle, WA (US); Justin Richard Killebrew, Seattle, WA (US); Diane Louise Hollenbaugh, Seattle, WA (US)

(73) Assignee: BONUM THERAPEUTICS, INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/108,514

(22) Filed: Feb. 10, 2023

(65) Prior Publication Data

US 2024/0024501 A1 Jan. 25, 2024

Related U.S. Application Data

(63) Continuation of application No. 17/504,385, filed on Oct. 18, 2021, now Pat. No. 11,642,417, which is a continuation of application No. PCT/US2021/032313, filed on May 13, 2021.

(60) Provisional application No. 63/024,422, filed on May 13, 2020.

(51) Int. Cl.
*A61K 47/68* (2017.01)
*C07K 16/24* (2006.01)
*C07K 16/28* (2006.01)

(52) U.S. Cl.
CPC ...... *A61K 47/6813* (2017.08); *A61K 47/6845* (2017.08); *A61K 47/6849* (2017.08); *C07K 16/246* (2013.01); *C07K 16/249* (2013.01); *C07K 16/2818* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 3,959,008 A | 5/1976 | Warner et al. |
| 7,186,804 B2 | 3/2007 | Gillies et al. |
| 8,728,474 B2 | 5/2014 | Honjo et al. |
| 8,945,571 B2 | 2/2015 | Mössner et al. |
| 9,102,725 B2 | 8/2015 | Korman et al. |
| 9,266,938 B2 | 2/2016 | Ast et al. |
| 9,447,159 B2 | 9/2016 | Ast et al. |
| 9,526,797 B2 | 12/2016 | Gerdes et al. |
| 9,546,203 B2 | 1/2017 | Kannan |
| 9,580,486 B2 | 2/2017 | Gavin et al. |
| 9,844,582 B2 | 12/2017 | Wittrup et al. |
| 9,932,380 B2 | 4/2018 | Gavin et al. |
| 10,093,711 B2 | 10/2018 | Kannan |
| 10,118,970 B2 | 11/2018 | Fuh et al. |
| 10,184,009 B2 | 1/2019 | Ast et al. |
| 10,202,464 B2 | 2/2019 | Ast et al. |
| 10,294,287 B2 | 5/2019 | Greve |
| 10,316,104 B2 | 6/2019 | Ast et al. |
| 10,323,098 B2 | 6/2019 | Ast et al. |
| 10,561,739 B2 | 2/2020 | Howard et al. |
| 10,562,949 B2 | 2/2020 | Hosse et al. |
| 10,562,950 B2 | 2/2020 | Kannan |
| 10,570,204 B2 | 2/2020 | Johnson et al. |
| 10,603,360 B2 | 3/2020 | Gerdes et al. |
| 10,669,338 B2 | 6/2020 | Chang et al. |
| 10,766,938 B2 | 9/2020 | Greve |
| 10,774,126 B2 | 9/2020 | Greve |
| 10,815,303 B2 | 10/2020 | Yue et al. |
| 10,829,535 B2 | 11/2020 | Gavin et al. |
| 10,858,412 B2 | 12/2020 | Mumm |
| 10,875,901 B2 | 12/2020 | Greve |
| 10,898,576 B2 | 1/2021 | Xie et al. |
| 11,008,401 B2 | 5/2021 | Fuh et al. |
| 11,028,174 B1 | 6/2021 | Gong et al. |
| 11,053,294 B2 | 7/2021 | Karow et al. |
| 11,098,099 B2 | 8/2021 | Klein et al. |
| 11,130,822 B2 | 9/2021 | Ast et al. |
| 11,352,403 B2 | 6/2022 | Winston et al. |
| 11,359,000 B2 | 6/2022 | Struthers et al. |
| 11,365,232 B2 | 6/2022 | Hosse et al. |
| 11,413,331 B2 | 8/2022 | Codarri Deak et al. |

(Continued)

FOREIGN PATENT DOCUMENTS

| | | |
|---|---|---|
| CN | 107915777 A | 4/2018 |
| EP | 4149554 A1 | 3/2023 |

(Continued)

OTHER PUBLICATIONS

ABC Review: What are Stable Linkers? https://www.adcreview.com/the-review/linkers/what-are-stable-linkers/. 4 pages (Accessed on Jul. 22, 2020).
Alberstein, et al., Design principles of protein switches. Curr Opin Struct Biol, vol. 72; Feb. 2022: 71-78.
Borcherds et al., Optimal Affinity Enhancement by a Conserved Flexible Linker Controls p53 Mimicry in Mdmx. Biophysical Journal 112: 2038-2042 (2017).
Chen, et al., Autoinhibition of MDMX by intramolecular p53 mimicry. PNAS, vol. 112, No. 15; Apr. 2015: 4624-4629.
Creative Biolabs: Non-cleavable Linker. https://www.creative-biolabs.com/adc/non-cleavable-linker.htm. 4 pages (Accessed on Jul. 22, 2020).

(Continued)

*Primary Examiner* — Phuong Huynh
(74) *Attorney, Agent, or Firm* — WILSON SONSINI GOODRICH & ROSATI

(57) ABSTRACT

Provided herein are protein complexes comprising a sensor domain and a therapeutic domain linked by a linker, and methods of use thereof. In aspects of the present disclosure, activity of the therapeutic domain comprises a dependence on sensor domain binding to target markers.

19 Claims, 40 Drawing Sheets

Specification includes a Sequence Listing.

(56) References Cited

U.S. PATENT DOCUMENTS

| | | |
|---|---|---|
| 11,471,490 B2 | 10/2022 | Andresen et al. |
| 11,535,669 B2 | 12/2022 | Sabzevari et al. |
| 11,542,312 B2 | 1/2023 | Merchant et al. |
| 11,642,417 B2 * | 5/2023 | Mulligan ........... A61K 47/6879 424/85.2 |
| 2003/0143559 A1 | 7/2003 | Bracken et al. |
| 2014/0294759 A1 | 10/2014 | Chu et al. |
| 2016/0034043 A1 | 2/2016 | Le Grand et al. |
| 2016/0175397 A1 | 6/2016 | Umana et al. |
| 2017/0198308 A1 | 7/2017 | Qi et al. |
| 2018/0326010 A1 | 11/2018 | Codarri Deak et al. |
| 2018/0326011 A1 | 11/2018 | Codarri et al. |
| 2019/0177439 A1 | 6/2019 | Wu |
| 2019/0300592 A1 | 10/2019 | Struthers et al. |
| 2019/0314455 A1 | 10/2019 | Ptacin et al. |
| 2019/0338032 A1 | 11/2019 | Campbell et al. |
| 2020/0026890 A1 | 1/2020 | Iglesias et al. |
| 2020/0115429 A1 | 4/2020 | Greve |
| 2020/0140547 A1 | 5/2020 | Bedi et al. |
| 2020/0172591 A1 | 6/2020 | Hosse et al. |
| 2020/0188526 A1 | 6/2020 | Klein et al. |
| 2020/0268902 A1 | 8/2020 | Xu et al. |
| 2020/0270334 A1 | 8/2020 | Deane et al. |
| 2020/0308285 A1 | 10/2020 | Wang et al. |
| 2020/0317787 A1 | 10/2020 | Li et al. |
| 2020/0331966 A1 | 10/2020 | Stover et al. |
| 2020/0339624 A1 | 10/2020 | Chu et al. |
| 2021/0017247 A1 | 1/2021 | Jones et al. |
| 2021/0024601 A1 | 1/2021 | Carlson et al. |
| 2021/0047382 A1 | 2/2021 | Greve |
| 2021/0094997 A1 | 4/2021 | Gavin et al. |
| 2021/0130430 A1 | 5/2021 | Winston et al. |
| 2021/0139560 A1 | 5/2021 | Larson et al. |
| 2021/0171596 A1 | 6/2021 | Moore et al. |
| 2021/0196796 A1 | 7/2021 | Penaflor-Aspuria et al. |
| 2021/0206806 A1 | 7/2021 | Larraillet et al. |
| 2021/0221864 A1 | 7/2021 | Williams et al. |
| 2021/0260163 A1 | 8/2021 | Yu et al. |
| 2021/0292415 A1 | 9/2021 | Clemens et al. |
| 2021/0388049 A1 | 12/2021 | Li et al. |
| 2022/0072103 A1 | 3/2022 | Codarri Deak et al. |
| 2022/0112260 A1 | 4/2022 | Greve |
| 2022/0162314 A1 | 5/2022 | Yeung et al. |
| 2022/0227837 A1 | 7/2022 | Li |
| 2022/0235133 A1 | 7/2022 | Li et al. |
| 2022/0251202 A1 | 8/2022 | Djuretic et al. |
| 2022/0289822 A1 | 9/2022 | Lu et al. |
| 2022/0306714 A1 | 9/2022 | Yao et al. |
| 2022/0324930 A1 | 10/2022 | Winston et al. |
| 2022/0324933 A1 | 10/2022 | Li |
| 2022/0356221 A1 | 11/2022 | Lu et al. |
| 2023/0028476 A1 | 1/2023 | Alam |
| 2023/0051423 A1 | 2/2023 | Winston et al. |
| 2023/0071733 A1 | 3/2023 | Codarri Deak et al. |
| 2023/0087600 A1 | 3/2023 | Coker et al. |
| 2023/0108562 A1 | 4/2023 | Lu et al. |
| 2023/0111786 A1 | 4/2023 | Korman et al. |
| 2023/0134725 A1 | 5/2023 | Rabizadeh et al. |
| 2023/0181471 A1 | 6/2023 | Dahmana et al. |
| 2023/0181712 A1 | 6/2023 | Umaña et al. |
| 2023/0181754 A1 | 6/2023 | Pattabiraman et al. |
| 2023/0183331 A1 | 6/2023 | Kreft et al. |
| 2023/0201364 A1 | 6/2023 | Pattabiraman et al. |
| 2023/0201365 A1 | 6/2023 | Kreft et al. |
| 2023/0210947 A1 | 7/2023 | Perez et al. |
| 2024/0024501 A1 | 1/2024 | Mulligan et al. |

FOREIGN PATENT DOCUMENTS

| | | |
|---|---|---|
| WO | WO-0051630 A2 | 9/2000 |
| WO | WO-2005082023 A2 | 9/2005 |
| WO | WO-2012107416 A2 | 8/2012 |
| WO | WO-2012107417 A1 | 8/2012 |
| WO | WO-2013026831 A1 | 2/2013 |
| WO | WO-2015118016 A1 | 8/2015 |
| WO | WO-2015123527 A1 | 8/2015 |
| WO | WO-2016200645 A1 | 12/2016 |
| WO | WO-2017220989 A1 | 12/2017 |
| WO | WO-2018184964 A1 | 10/2018 |
| WO | WO-2018218215 A1 | 11/2018 |
| WO | WO-2019010224 A1 | 1/2019 |
| WO | WO-2019143669 A1 | 7/2019 |
| WO | WO-2019147837 A2 | 8/2019 |
| WO | WO-2019173832 A2 | 9/2019 |
| WO | WO-2019222295 A1 | 11/2019 |
| WO | WO-2019222296 A1 | 11/2019 |
| WO | WO-2019246392 A1 | 12/2019 |
| WO | WO-2020014285 A2 | 1/2020 |
| WO | WO-2020069398 A1 | 4/2020 |
| WO | WO-2020088459 A1 | 5/2020 |
| WO | WO-2020242884 A1 | 12/2020 |
| WO | WO-2020247843 A2 | 12/2020 |
| WO | WO-2020259536 A1 | 12/2020 |
| WO | WO-2021011353 A1 | 1/2021 |
| WO | WO-2021016640 A1 | 1/2021 |
| WO | WO-2021030483 A1 | 2/2021 |
| WO | WO-2021030688 A1 | 2/2021 |
| WO | WO-2021035188 A1 | 2/2021 |
| WO | WO-2021142471 A1 | 7/2021 |
| WO | WO-2021178804 A1 | 9/2021 |
| WO | WO-2021231773 A1 | 11/2021 |
| WO | WO-2021236676 A1 | 11/2021 |
| WO | WO-2022036079 A1 | 2/2022 |
| WO | WO-2022117692 A2 | 6/2022 |
| WO | WO-2022125694 A1 | 6/2022 |
| WO | WO-2022125711 A1 | 6/2022 |
| WO | WO-2022148853 A1 | 7/2022 |
| WO | WO-2022150791 A2 | 7/2022 |
| WO | WO-2022155263 A2 | 7/2022 |
| WO | WO-2022155541 A1 | 7/2022 |
| WO | WO-2022165443 A1 | 8/2022 |
| WO | WO-2022174102 A1 | 8/2022 |
| WO | WO-2022189377 A1 | 9/2022 |
| WO | WO-2022189380 A1 | 9/2022 |
| WO | WO-2022262496 A1 | 12/2022 |
| WO | WO-2023281479 A1 | 1/2023 |
| WO | WO-2023281480 A1 | 1/2023 |
| WO | WO-2023281485 A1 | 1/2023 |
| WO | WO-2023023065 A1 | 2/2023 |
| WO | WO-2023023131 A2 | 2/2023 |
| WO | WO-2023050826 A1 | 4/2023 |
| WO | WO-2023062048 A1 | 4/2023 |
| WO | WO-2023070056 A2 | 4/2023 |
| WO | WO-2023102493 A2 | 6/2023 |
| WO | WO-2023122573 A1 | 6/2023 |

OTHER PUBLICATIONS

Dueber, et al., Reprogramming control of an allosteric signaling switch through modular recombination, Science, vol. 301; Sep. 2003: 1904-1908.

Edwards et al. The remarkable flexibility of the human antibody repertoire; isolation of over one thousand different antibodies to a single protein. BLyS.J Mol Biol. 334(1):103-18 (2003).

Hsu, E. J., et al. A cytokine receptor-masked IL2 prodrug selectively activates tumor-infiltrating lymphocytes for potent antitumor therapy. Nature communications, 12 (2021): Article: 2768.

Khowsathit, J. et al., Computational design of an allosteric antibody switch by deletionand rescue of a complex structural constellation. ACS Cent. Sci. 2020, 6.3, 390-403.

Liang et al., Targeting IFNa to tumor by anti-PD-L1 creates feedforward antitumor responses to overcome checkpoint blockade resistance. Nature Communications 2018; 9: 4586. 11 Pages.

Lloyd et al. Modelling the human immune response: performance of a 1011 human antibody repertoire against a broad panel of therapeutically relevant antigens. Protein Eng Des Sel 22(3):159-168 (2009).

Ortiz-Sanchez et al.: Antibody-cytokine fusion proteins: applications in cancer therapy. Expert Opin Biol Ther. 8(5):609-632 (2008).

PCT/US2021/032313 International Search Report and Written Opinion dated Sep. 22, 2021.

(56) References Cited

OTHER PUBLICATIONS

Piche-Nicholas NM, et al., Changes in complementarity-determining regions significantly alter IgG binding to the neonatal Fc receptor (FcRn) and pharmacokinetics. MAbs. Jan. 2018;10(1):81-94.
U.S. Appl. No. 17/504,385 Notice of Allowance dated Jan. 30, 2023.
U.S. Appl. No. 17/504,385 Office Action dated Feb. 22, 2022.
U.S. Appl. No. 17/504,385 Office Action dated May 3, 2022.
U.S. Appl. No. 17/504,385 Office Action dated Sep. 1, 2022.
Adkins, Irena. et al. Abstract 3510: SOT201 is a novel targeted IL-15Rbg agonist to alleviate PD-1-mediated immune cell suppression and potentiate anti-tumor efficacy. Cancer Res. 82(Suppl 2):3510 (2022).
Boyman, Onur. et al. Selective Stimulation of T Cell Subsets with Antibody-cytokine Immune Complexes. Science 311(5769):1924-1927 (2006).
Carralot, Jean. et al. 1195 Generation of a highly potent, cis-signaling PD1-IL2 immunocytokine using a novel chemical synthesis and conjugation platform. J. Immunother. Cancer 10(Suppl 2):A1237, 1-1 (2022).
Chen, Jihong. et al. Preclinical evaluation of IAP0971, a novel immunocytokine that binds specifically to PD1 and fuses IL15/IL15R α complex. Antibody therapeutics 6(1):38-48 (2023).
Datar, Ila. et al. Expression Analysis and Significance of PD-1, LAG-3, and TIM-3 in Human Non-Small Cell Lung Cancer Using Spatially Resolved and Multiparametric Single-Cell Analysis. Clinical Cancer Research 25(15):4663-4673 (2019).
Deak, Laura Codarri. et al. Beyond checkpoint inhibition: PD-1 cis-targeting of an IL-2Rβγ-biased interleukin-2 variant as a novel approach to build on checkpoint inhibition. Oncoimmunology 12(1):2197360, 1-3 (2023).
EP20210803280.3 Extended European Search Report dated Apr. 30, 2024.
Eryilmaz, Ertan. et al. Abstract 572: Tumor-activated PD1-directed IL-2 increased antigen specific T cells in tumors and demonstrated anti-tumor activity in mice. Cancer Research 83(Suppl 7):572 (2023).
Gutierrez, Martin. et al. 779 A phase 1/2, open label, first-in-human, dose escalation and expansion study of SAR445877 administered as monotherapy in adults with advanced solid tumors. Journal for Immuno Therapy of Cancer 11(Suppl 1):A876, 1-1 (2023).
Herzog, Thomas J. et al. ARTISTRY-7: phase III trial of nemvaleukin alfa plus pembrolizumab vs chemotherapy for platinum-resistant ovarian cancer. Future Oncol 19(23):1577-1591 (2023).
Ji, Changhua. et al. Pharmacokinetics, pharmacodynamics, and toxicity of a PD-1-targeted IL-15 in cynomolgus monkeys. PLoS One 19(2):e0298240, 1-21 (2022).
Krieg, Carsten. et al. Improved IL-2 Immunotherapy by Selective Stimulation of IL-2 Receptors on Lymphocytes and Endothelial Cells. Proceedings of the National Academy of Sciences of the United States of America 107(26):11906-11911 (2010).
Long, Georgina V. et al. Overall Survival and Response with Nivolumab and Relatlimab in Advanced Melanoma. NEJM Evid 2(4):Evidoa2200239, 1-10 (2022).
McKean, Meredith. et al. A first-in-human, multicenter, phase 1/2, open-label study of XTX202, a masked and tumor-selective recombinant human interleukin-2 (IL-2) protein, in patients with advanced solid tumors. Journal of Clinical Oncology 40(Suppl 16):TPS2697, 1-1 (2022).
Moynihan, Kelly D. et al. Abstract 3518: AB248 is a CD8+ T cell selective IL-2 designed for superior safety and anti-tumor efficacy. Cancer Res 82:3518, 1-1 (2022).
Nicolini, Valeria. et al. Combination with the novel tumor-targeted CEA-IL2v immunocytokine enhances the activity of ADCC-competent and glycoengineered antibodies in vitro and in vivo. Cancer Res 74(19 Suppl):2579 (2014).
Nirschl, Christopher J. et al. Discovery of a Conditionally Activated IL-2 that Promotes Antitumor Immunity and Induces Tumor Regression. Cancer Immunol Res 10(5):581-596 (2022).
Perdyan, Adrian. et al. The Effectiveness of Cancer Immune Checkpoint Inhibitor Retreatment and Rechallenge—A Systematic Review. Cancers (Basel) 15(13):3490, 1-20 (2023).
Raeber, Miro E. et al. A systematic review of interleukin-2-based immunotherapies in clinical trials for cancer and autoimmune diseases. EBioMedicine 90:104539, 1-25 (2023).
Rosenberg, Steven A. IL-2: the first effective immunotherapy for human cancer. J Immunol. 192(12):5451-5458 (2014).
Shanebeck, Kurt. et al. 1183 ASKG915—an anti-PD-1 antibody-IL-15 prodrug fusion molecule with enhanced therapeutic potentials. J. Immunother. Cancer 10(Suppl 2):A1227, 1-1 (2022).
Study of JK08 in Patients With Unresectable Locally Advanced or Metastatic Cancer, National Library of Medicine, First posted: Nov. 17, 2022 and last updated Apr. 17, 2024 https://clinicaltrials.gov/study/NCT05620134, Clinical Trials Identifier NCT05620134.
Sznol, Mario and Naiyer Rizvi. Teaching an old dog new tricks: re-engineering IL-2 for immuno-oncology applications. J Immunother Cancer 11(1):e006346, 1-3 (2023).
Tomala, Jakub. et al. Chimera of IL-2 Linked to Light Chain of Anti-IL-2 mAb Mimics IL-2/anti-IL-2 mAb Complexes Both Structurally and Functionally. ACS chemical biology 8(5): 871-876 (2013).
Tomasovic, Luke M. et al. Molecular Engineering of Interleukin-2 for Enhanced Therapeutic Activity in Autoimmune Diseases. BioDrugs 38(2):227-248 (2024).
Ye, Fan. et al. 1104 A safe and highly potent PD-1-IL-2 fusion (AWT020) that decouples the efficacy and toxicity of IL-2 therapy. Cancer 10(Suppl 2):A1147, 1-1 (2022).
Research, C. for D. E. and FDA approves Opdualag for unresectable or metastatic melanoma. FDA (2022).

* cited by examiner

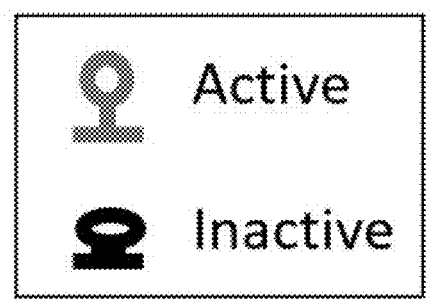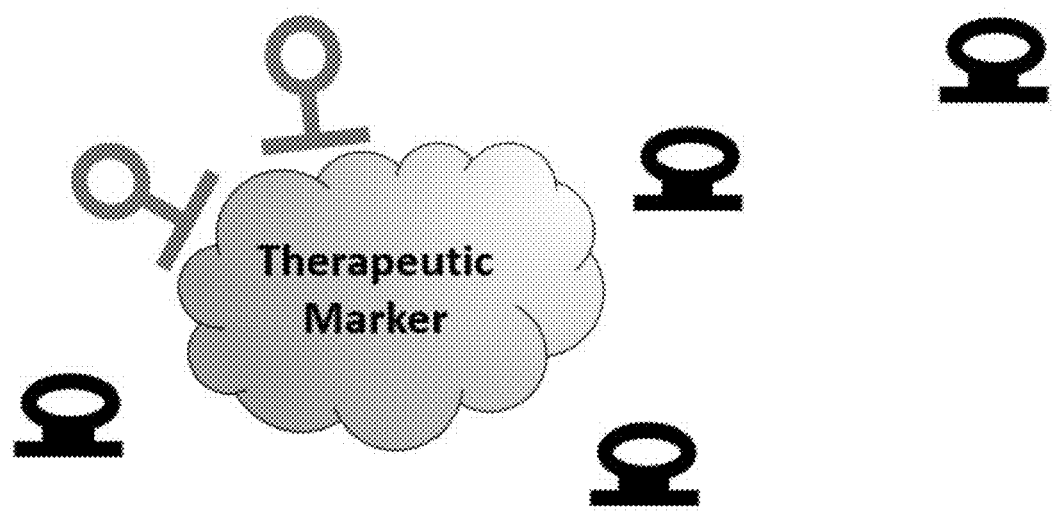
FIG. 2

(SEQ ID NO: 40)

FIG. 3

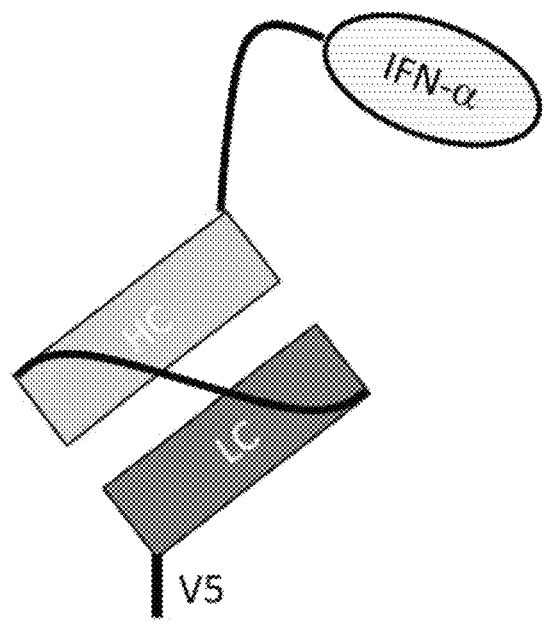

MSTSTCDLPQTHSLGSRRTLML
LAQMRRISLFSCLKDRHDFGFP
QEEFGNQFQKAETIPVLHEMIQ
QIFNLFSTKDSSAAWDETLLDK
FYTELYQQLNDLEACVIQGVGV
TETPLMKEDSILAVRKYFQRIT
LYLKEKKYSPCAWEVVRAEIMR
SFSLSTNLQESLRSKE
<u>GGGGSGGGGSGGGGSGGGGS</u>
QVQLVQSGAEVKKPGASVKVSC
KASGYTFSNYYVHWVRQAPGQG
LEWMGWMDPNSGGTGYAHQFQG
RVTMTRDTSTSTVYMELSSLRS
EDTAVYYCAKEVFSGWYDYWGQ
GTLVTVSS
<u>ASGGGGSGGGGSGGGGSHAS</u>
DIQMTQSPSSLSASVGDRVTIT
CRASQSISSYLNWYQQKPGKAP
KLLIYAASSLQSGVPSRFSGSG
SGTDFTLTISSLQPEDFATYYC
QQSYSTPYTFGQGTKVEIK
GKPIPNPLLGLDST

(SEQ ID NO: 41)

FIG. 8

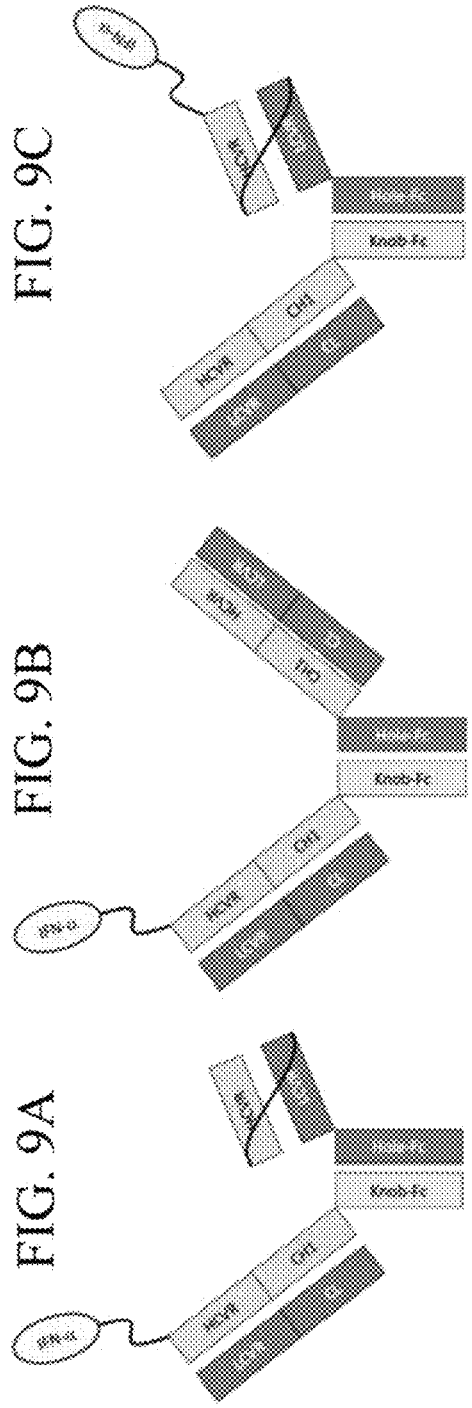
FIG. 9A
SEQ ID NO: 42-44
FIG. 9B
SEQ ID NO: 45-47
SEQ ID NO: 181-182 & 212
SEQ ID NO: 183-185
SEQ ID NO: 186-188
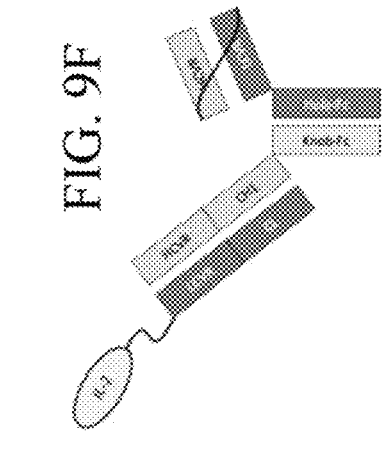
FIG. 9C
SEQ ID NO: 48, 49, 44
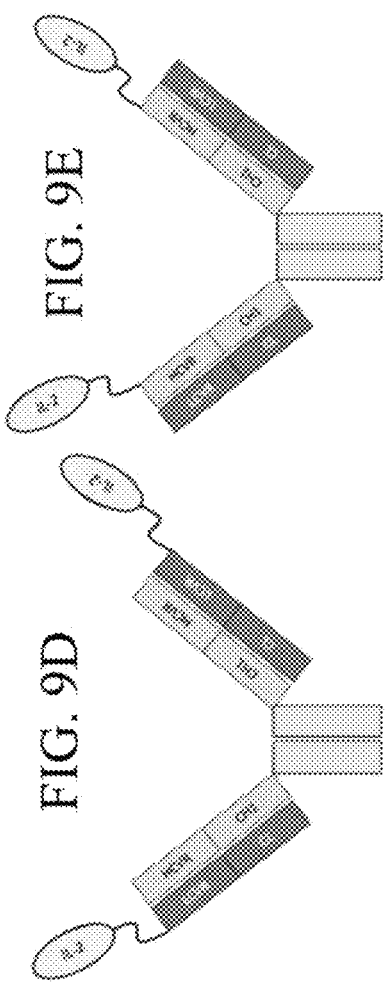
FIG. 9D
SEQ ID NO: 51-52
FIG. 9E
SEQ ID NO: 53-54
SEQ ID NO: 174-175
FIG. 9F
SEQ ID NO: 77-79

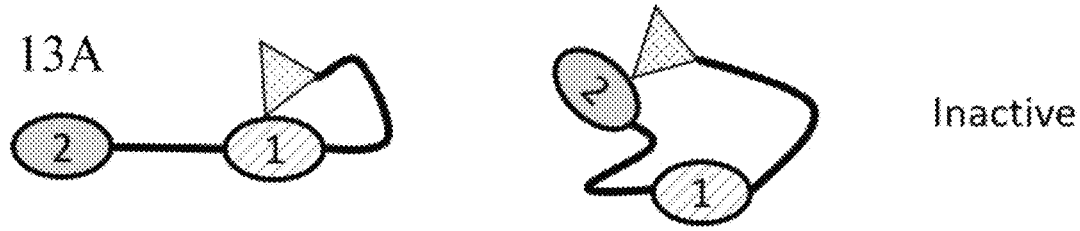
FIG. 13A      Inactive
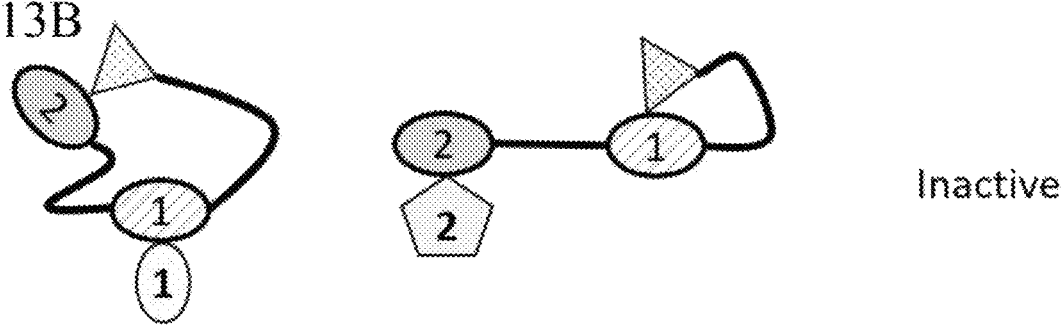
FIG. 13B      Inactive
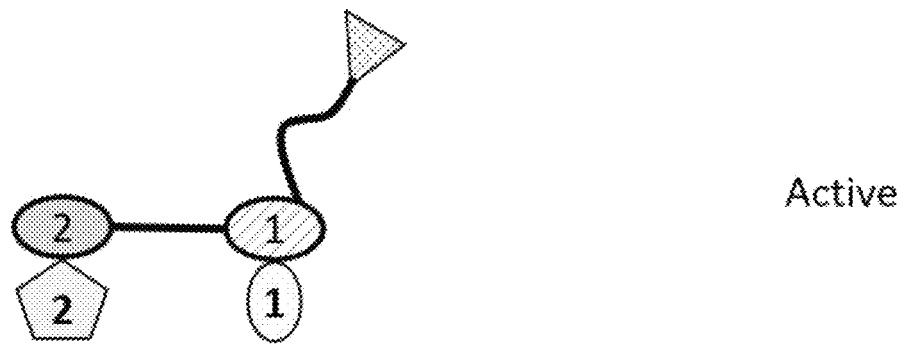
FIG. 13C      Active
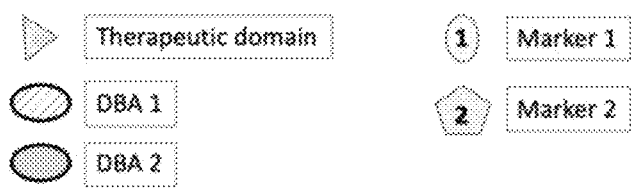

| | Fab: Her2 | PD1 |
|---|---|---|
| scFv | | |
| PD1/IL2 DBA 2B07 variant | 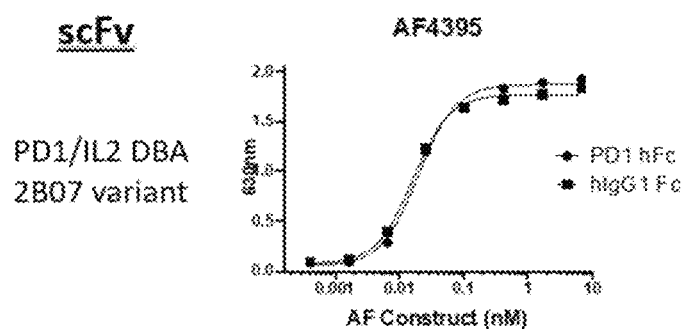<br>FIG. 17A | 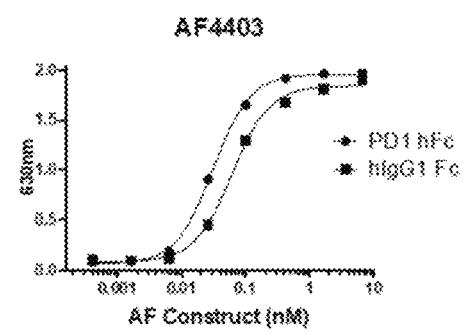<br>FIG. 17B |
| PD1/IL2 DBA 7A04 variant | 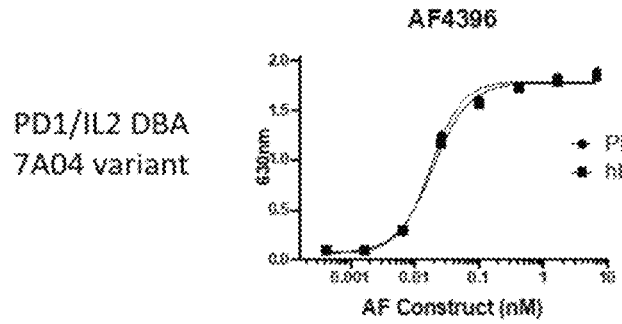<br>FIG. 17C | 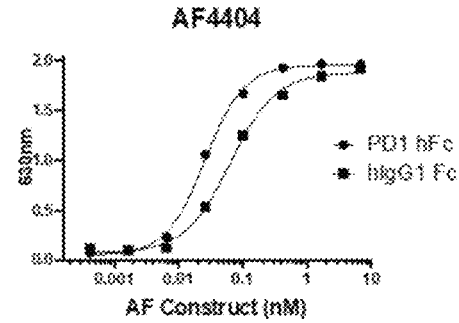<br>FIG. 17D |

| CloneID | IFNα binding (@5uM) | ELISA | SEQUENCES |
|---|---|---|---|
| i47_A03 | + | - | SEQ ID NO: 262 |
| I47_A11 | + | - | N/A |
| I47_A12 | + | - | N/A |
| I47_B03 | + | - | SEQ ID NO: 263 |
| I47_B07 | + | - | SEQ ID NO: 264 |
| I47_B11 | + | - | SEQ ID NO: 264 |
| AF317 | (KD < 10nM) | +++ | SEQ ID NO: 257 |
| AF372 | - | - | SEQ ID NO: 258 |

COMPOSITIONS OF PROTEIN COMPLEXES AND METHODS OF USE THEREOF

CROSS-REFERENCE

This application is a continuation of U.S. patent application Ser. No. 17/504,385, filed Oct. 18, 2021, now issued as U.S. Pat. No. 11,642,417, which is a continuation of International Application Serial No. PCT/US2021/32313, filed May 13, 2021, which claims the benefit of U.S. Provisional Patent Application No. 63/024,422, filed May 13, 2020, each of which is entirely incorporated herein by reference in its entirety.

SEQUENCE LISTING

The instant application contains a Sequence Listing which has been submitted electronically in XML format and is hereby incorporated by reference in its entirety. Said XML copy, created on Feb. 10, 2023, is named 64504_701_302_SL.xml and is 615,078 bytes in size.

BACKGROUND

Many promising therapeutics that are needed locally exhibit toxicity upon systemic administration. There is a need for drugs that can be delivered systemically but can be regulated to exhibit therapeutic activity locally or in the presence of markers for disease.

SUMMARY

In various aspects, the present disclosure provides a complex comprising: a) a therapeutic domain; b) a linker; and c) a sensor domain, wherein the therapeutic domain is linked to the sensor domain by the linker, and wherein the sensor domain is capable of binding the therapeutic domain and a marker.

In some aspects, the sensor domain is bound to the therapeutic domain in an absence of the marker. In some aspects, the therapeutic domain is blocked from binding the sensor domain upon binding of the sensor domain to the marker. In some aspects, the activity of the therapeutic domain is reduced upon binding of the therapeutic domain to the sensor domain. In some aspects, the therapeutic domain is capable of exhibiting therapeutic activity upon binding of the sensor domain to the marker. In some aspects, the therapeutic domain is therapeutically active upon binding of the sensor domain to the marker.

In some aspects, the sensor domain comprises an antibody. In some aspects, the antibody is an antibody fragment or antibody derivative. In some aspects, the complex comprises an Fc domain. In some aspects, the complex comprises a domain that improves kinetic properties. In some aspects, the complex includes two heavy chains and two light chains.

In some aspects, the complex comprises two therapeutic domains. In some aspects, the complex comprises two sensor domains. In some aspects, the complex is a regulated therapeutic protein. In some aspects, the therapeutic domain is a cytokine, a chemokine, an antibody, an antibody fragment, a peptide agonist, a peptide antagonist, an enzyme, a soluble receptor, a growth factor, a protein toxin, a soluble ligand, a small molecule, or any combination thereof. In some aspects, the antibody or the antibody fragment comprises an IgG, a single domain antibody fragment, a nanobody, or a single chain variable fragment (scFv).

In some aspects, the therapeutic domain is an IL-2 receptor agonist. In some aspects, the IL-2 receptor agonist is IL-2, IL-15, or variants or fusions thereof. In some aspects, the therapeutic domain is IFNα, IFNγ IL-12, IL-4, IL-8, IL-10, IL-15, IL-18, IL-21, TGF beta, an anti-CD3 antibody, an anti-CD28 antibody or ligand, an antibody to or ligand of CD40, GITR, OX40, CD137, CD27, or Death Receptors, the extracellular domain of TGFBR2, VEGF-C, kynureninase, IL-7, TNF, MICA, MICB, CD47, an anti-CTLA4 antibody, an anti-PD-L1 antibody, or an anti-PD-1 antibody. In some aspects, the therapeutic domain binds to the sensor domain.

In some aspects, the linker is a polypeptide linker. In some aspects, the linker comprises from 2 to 200 amino acids in length. In some aspects, the linker is: attached to a heavy chain of the sensor domain, attached to a light chain of the sensor domain, is a fusion with an N-terminus of the sensor domain, or is a fusion with a C-terminus of the sensor domain. In some aspects, the linker is: attached to a heavy chain of the therapeutic domain, attached to a light chain of the therapeutic domain, is a fusion with an N-terminus of the therapeutic domain, or is a fusion with a C-terminus of the therapeutic domain.

In some aspects, the activity of the therapeutic domain is reduced when bound to the sensor domain. In some aspects, the therapeutic domain is inactive when bound to the sensor domain. In some aspects, the sensor domain blocks the activity of the therapeutic domain when bound to the therapeutic domain. In some aspects, the therapeutic domain is active when the sensor domain is bound to the marker. In some aspects, an affinity of the sensor domain for the marker is equal to or greater than an affinity of the sensor domain for the therapeutic domain.

In some aspects, an affinity of the sensor domain for the marker is at least 2 times, 5 times, 10 times, 100 times, 1000 times, 10000, or 100000 times greater than an affinity of the sensor domain for the therapeutic domain.

In some aspects, the sensor domain is an antibody or a fragment thereof. In some aspects, the sensor domain comprises one or both antigen binding domains of a bispecific antibody. In some aspects, the bispecific antibody comprises a first antigen binding domain that is capable of binding to the therapeutic domain and is capable of binding to the marker, and a second antigen binding domain that is capable of binding to the marker. In some aspects, the bispecific antibody comprises a first antigen binding domain that is capable of binding to the therapeutic domain and the marker and a second antigen binding domain that is capable of binding to a second marker. In some aspects, the bispecific antibody comprises a first antigen binding domain that is capable of binding to the therapeutic domain and the marker and a second antigen binding domain that is capable of binding to the therapeutic domain and a second marker. In some aspects, the bispecific antibody comprises a single therapeutic domain.

In some aspects, the therapeutic domain is IFNα, the first marker is ATP, and the second marker is CEA. In some aspects, the sensor domain binds to an IL-2 receptor agonist and to PD-1. In some aspects, the IL-2 receptor agonist is IL-2, IL-15, or variants or fusions thereof. In some aspects, the sensor domain binds to IFNα and PD-L1.

In some aspects, the marker is a surface protein, a cell surface marker, or soluble ATP. In some aspects, the marker is a secreted protein. In some aspects, the marker is expressed by a cancer cell. In some aspects, the marker is expressed by an immune cell. In some aspects, the marker is PD-1. In some aspects, the marker is PD-L1. In some aspects, the marker is CEACAM5. In some aspects, the marker is FAP. In some aspects, the marker is LRRC15. In some aspects, the marker is expressed by a stromal cell. In some aspects, the marker is expressed by an endothelial cell. In some aspects, the marker is a metabolite. In some aspects, the marker is adenosine, AMP, ADP, or ATP. In some aspects, the marker is kynurenine.

In some aspects, the sensor domain comprises a complementarity determining region selected from TABLE 13 or TABLE 18. In some aspects, the sensor domain is selected from TABLE 13. In some aspects, the complex is selected from TABLE 15.

In some aspects, the sensor domain comprises a complementarity determining region having at least 80%, at least 85%, at least 90%, at least 95%, at least 97%, at least 99%, or 100% sequence identity to any one of SEQ ID NO: 1-SEQ ID NO: 20 or SEQ ID NO: 142-SEQ ID NO: 173, or SEQ ID NO: 238-252. In some aspects, the sensor domain has at least 80%, at least 85%, at least 90%, at least 95%, at least 97%, at least 99%, or 100% sequence identity to any one of SEQ ID NO: 21-SEQ ID NO: 27, SEQ ID NO: 31-SEQ ID NO: 39, or SEQ ID NO: 127-SEQ ID NO: 141. In some aspects, the protein complex has at least 80%, at least 85%, at least 90%, at least 95%, at least 97%, at least 99%, or 100% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, SEQ ID NO: 289-293, or a fragment thereof.

In various aspects, the present disclosure provides a method comprising administering any of the above complexes to a subject in need thereof. In various aspects, the present disclosure provides a method of treating a subject in need thereof comprising administering any of the above complexes to the subject in need thereof. In some aspects, the administering comprises intravenous, intramuscular, or subcutaneous administration. In some aspects, the subject in need thereof has cancer. In some aspects, the subject in need thereof has an autoimmune disease. In some aspects, the subject in need thereof has a viral disease. In some aspects, the therapeutic domain treats the subject in need thereof. In some aspects, the subject in need thereof is a mammal. In some aspects, the subject in need thereof is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 1A shows an exemplary dual binding protein complex in an inactive state. The protein complex has a sensor domain and a therapeutic domain. The sensor domain and therapeutic domain are linked by a linker. The sensor domain is shown bound to the therapeutic domain, rendering the therapeutic domain inactive. FIG. 1B shows an exemplary dual binding protein complex in an active state. The protein complex has a sensor domain and a therapeutic domain. The sensor domain and therapeutic domain are linked by a linker. The sensor domain is shown bound to a marker (e.g., a tumor marker or other disease marker), rendering the therapeutic domain active.

FIG. 2 shows an example of a protein complex in an active state when bound to a tumor and examples of protein complex in an inactive state when not bound to a tumor.

FIG. 3 shows an exemplary gBlock sequence used for cell-free expression of scFv antibodies. FIG. 3 discloses SEQ ID NO: 40.

FIG. 8 shows a schematic of a protein complex comprising a cytokine therapeutic domain and a DBA (at left) and said protein complex's sequence (at right). FIG. 8 discloses SEQ ID NO: 41.

FIGS. 9A-F show schematics of other protein complexes of the present disclosure comprising one or more sensor domains and one or more therapeutic domain. FIG. 9A shows a first embodiment of the protein complex disclosed herein; FIG. 9B shows a second embodiment of the protein complex disclosed herein; FIG. 9C shows a third embodiment of the protein complex disclosed herein; FIG. 9D shows a fourth embodiment of the protein complex disclosed herein; FIG. 9E shows a fifth embodiment of the protein complex disclosed herein; and FIG. 9F shows a sixth embodiment of the protein complex disclosed herein.

FIGS. 13A-C show a schematic of a bispecific antibody comprising a therapeutic domain and two sensor domains such that both sensor domains must bind their target marker to allow activity of the therapeutic domain. FIG. 13A shows that when neither target is present, the therapeutic domain is inactive; FIG. 13B shows that when only one target is present, the therapeutic domain is inactive; and FIG. 13C shows that when both targets are present, the therapeutic domain is active.

FIG. 15A provides the IL-2 activity of an PD-1/IL-2 DBA-IL-2 complex.

FIG. 15B provides the IL-2 activity of an anti-Her2 antibody-IL-2 complex. FIG. 15C provides the activity of an anti-IL-2 antibody-IL-2 complex. FIG. 15D provides the activity of an anti-PD-1 antibody-IL-2 complex.

FIG. 16A, FIG. 16B, and FIG. 16C provide the IL-2 activities of three different PD-1/IL-2 DBA-IL-2 complexes. FIG. 16D provides the activity of an anti-PD-1 antibody-IL-2 complex. FIG. 16E provides the activity of an anti-Her-2 antibody-IL-2 complex. FIG. 16F provides the activity of an anti-IL-2 antibody-IL-2 complex.

FIGS. 17A-H provide IL-2 activity of protein complexes comprising the structure depicted in FIG. 14C in wells coated with PD-1-Fc or an IgG1 control protein. Activity was measured as growth of a 630 nm signal from HEK-Blue™ IL-2 reporter cells. FIGS. 17B and 17D provide results for two PD-1/IL-2 DBA complexes comprising anti-PD-1 domains in the Fab arms and a PD-1/IL-2 DBA scFv on the Fc arm. FIGS. 17A, 17C, and 17E-H provide results for control protein complexes.

DETAILED DESCRIPTION

Figure 1A:
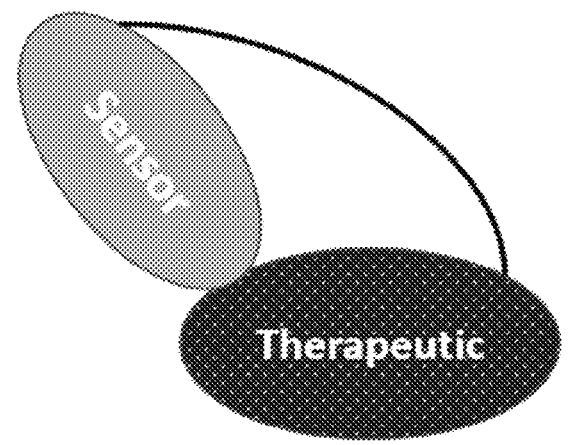
FIGS. 1A and 1B shows a schematic of the protein complexes of the present disclosure.
Figure 1B:
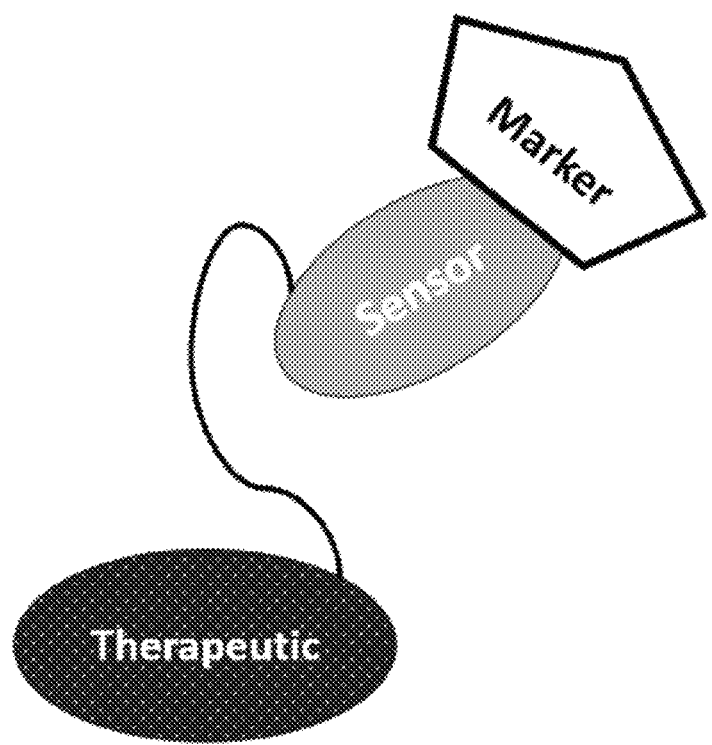
Figure 4:
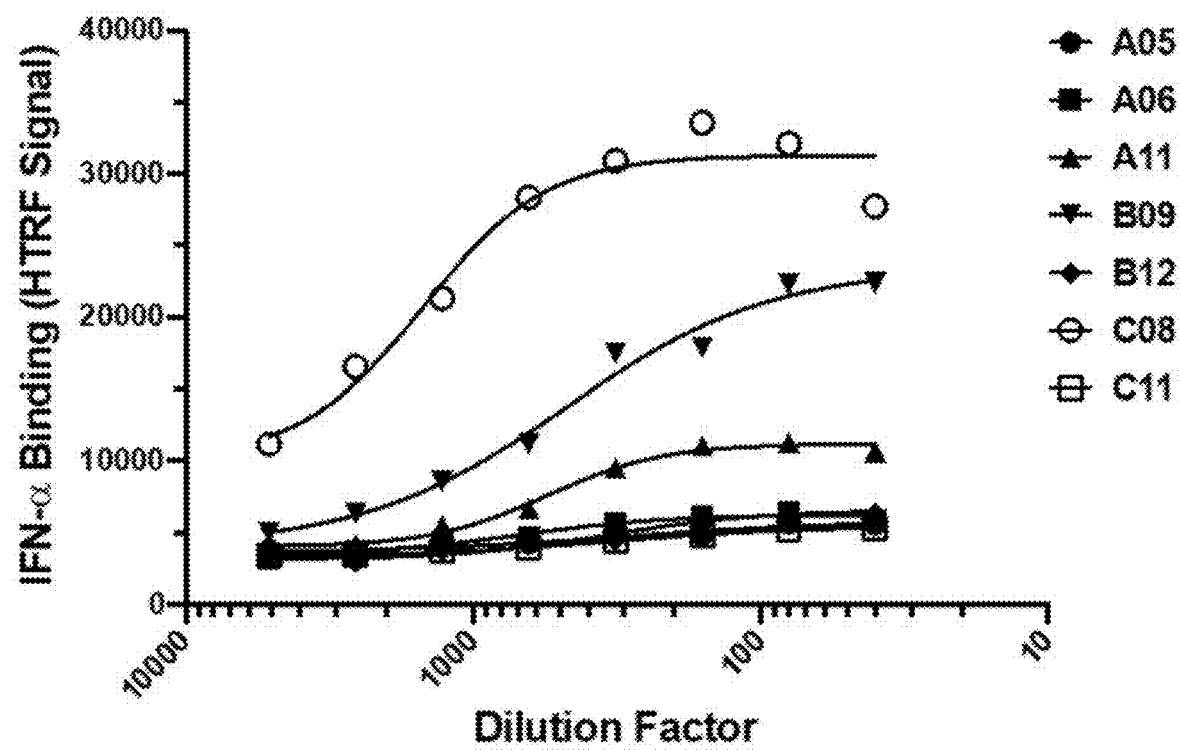
FIG. 4 shows candidate PD-L1/IFNα DBAs bind IFNα.
Figure 5:
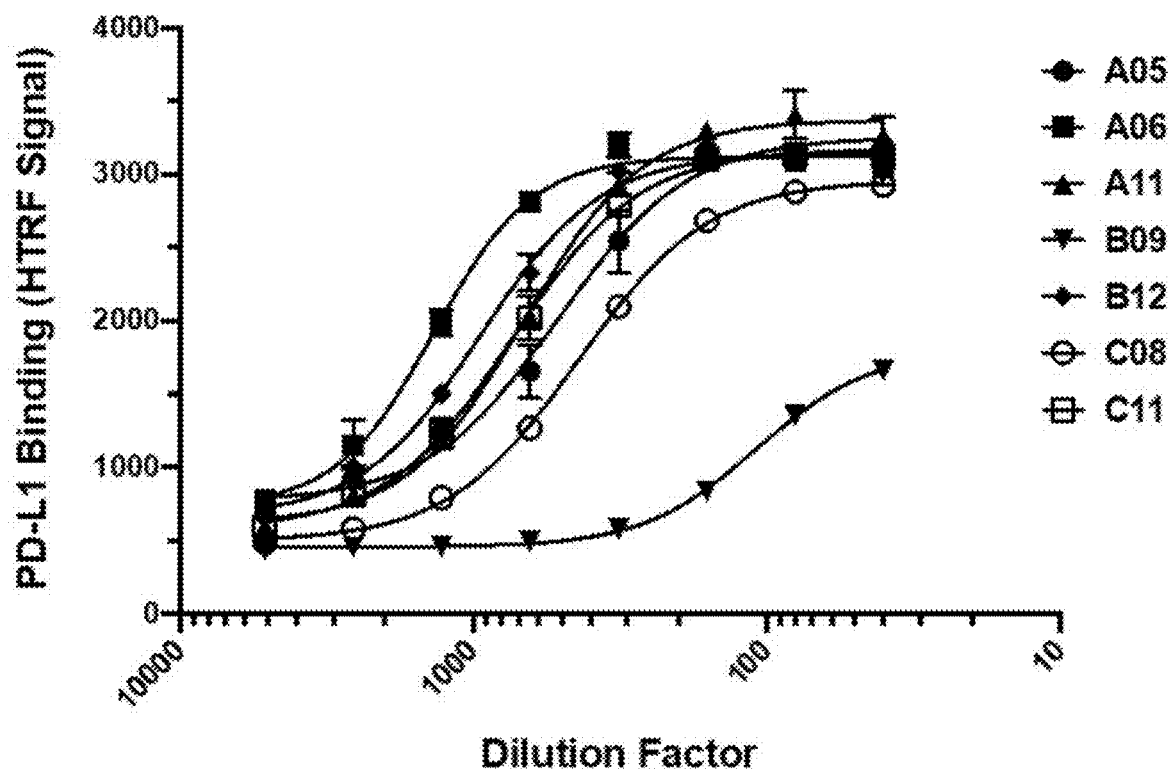
FIG. 5 shows candidate PD-L1/IFNα DBAs bind PD-L1.
Figure 6:
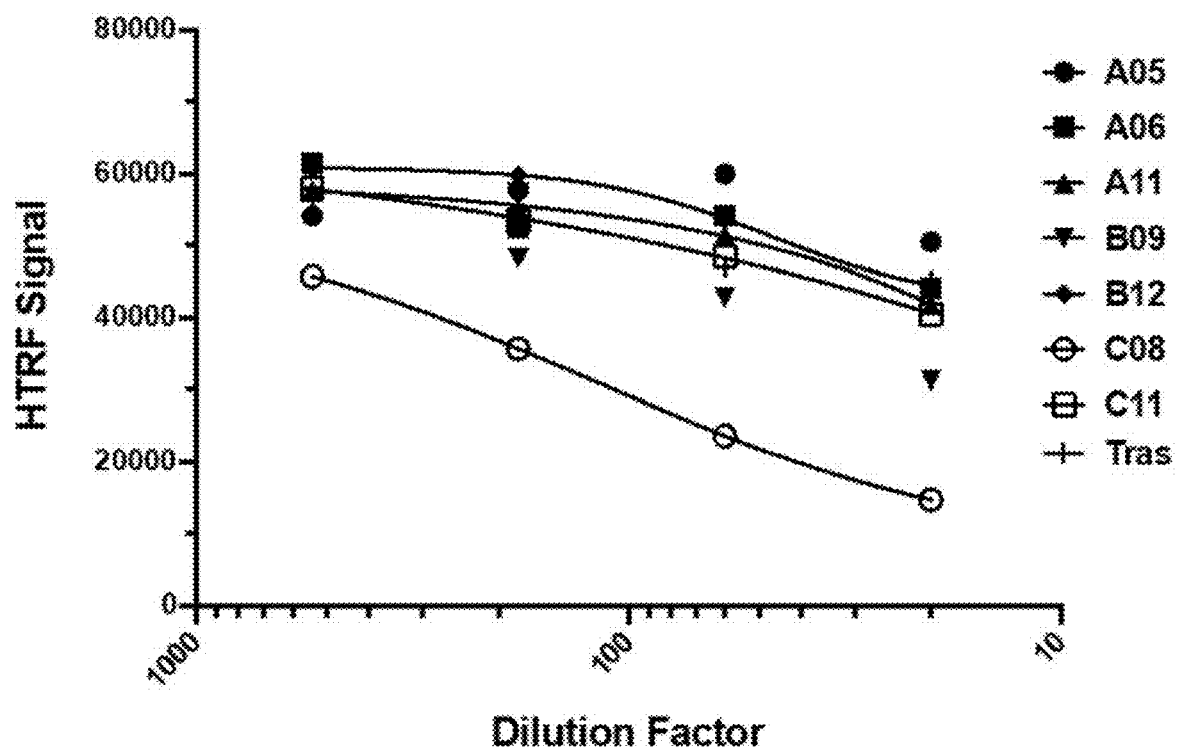
FIG. 6 shows inhibition of IFNα binding to IFNAR by candidate PD-L1/IFNα DBAs.

The present disclosure provides compositions of protein complexes and methods of use thereof. Promising therapeutics are often unable to be realized due to harmful side effects, or systemic on-target toxicity. Provided herein are protein complexes, which specifically exhibit therapeutic efficacy locally, where the relevant cells and targets are present. Moreover, protein complexes of the present disclosure are self-regulated, remaining inactive in the absence of a specific marker and activating in the presence of the specific marker. The protein complexes disclosed herein may include a sensor domain (e.g., an antibody or scFv) that is linked to a therapeutic domain (e.g., a cytokine, a therapeutic antibody domain, a receptor, a ligand) via a linker. The sensor domain may be a dual binding protein that has affinity for the therapeutic domain and a specific marker, such that the marker and the therapeutic domain compete for binding to the sensor domain. In some embodiments, the dual binding protein is a dual binding antibody. In the absence of the marker, the sensor domain binds the therapeutic domain, rendering the therapeutic domain unable to exert activity. When the sensor domain is bound to the marker, the therapeutic domain is unbound and may exert activity. In some embodiments, regulation of therapeutic activity by the complex may be reversible, that is, when the sensor domain disassociates from the marker, the sensor domain may bind the therapeutic domain, rendering the therapeutic domain once again unable to exert activity. Thus, the protein complexes of the present disclosure comprise sensor domains that regulate therapeutic domains in the presence of the marker, bind the marker, and render the therapeutic domain active. Various structures and compositions of protein complexes are disclosed herein, including pharmaceutical formulations. Also provided herein are methods for treating a subject in need thereof by administering the protein complex to the subject.

As used herein, a "marker" may refer to the moiety that is bound by the sensor domain of the protein complexes disclosed herein. Non-limiting examples of a "marker" include a protein, a protein modification, a carbohydrate, a metabolite, or any other molecule that can be bound by an antibody. A marker may also refer to a disease-specific marker, such as a molecular marker of a disease state (e.g., cancer).

As used herein, a "target" may refer to a molecule through which the therapeutic domain of the protein complexes disclosed herein may act. Non-limiting examples of a "target" include cytokine receptor, a cytokine, a ligand, an enzyme substrate, or any other molecule that, when contacted by the therapeutic domain, has a therapeutic impact on a subject (e.g., human or non-human animal) administered the protein complex.

As used herein, an "antibody" may refer to an antibody, an antibody derivative, or fragment(s) thereof that contains part or all of an antibody variable domain.

The term "recombinant nucleic acid" refers to synthetic nucleic acid having a nucleotide sequence that is not naturally occurring. A recombinant nucleic acid may be synthesized in the laboratory. A recombinant nucleic acid is prepared by using recombinant DNA technology by using enzymatic modification of DNA, such as enzymatic restriction digestion, ligation, and DNA cloning. A recombinant nucleic acid as used herein can be DNA, or RNA. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell.

The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

Protein Complexes

The present disclosure provides complexes that may self-regulate therapeutic activity. Protein complexes of the present disclosure may include a sensor domain and a therapeutic domain. The sensor domain and therapeutic domain may be linked by a linker. The sensor domain may regulate the activity of the therapeutic domain. Regulation of the activity of the therapeutic domain may include binding of the sensor domain to the therapeutic domain, rendering the therapeutic domain unable to exert therapeutic activity. Regulation of the activity of the therapeutic domain may further include unbinding, or release, of the therapeutic domain by the sensor domain upon binding of the sensor domain to a marker. The marker may be expressed by a cell associated with a disease. For example, the disease may be cancer, the cell may be a tumor cell, and the marker may be a tumor-specific marker that is expressed on tumor cells. Thus, the protein complexes of the present disclosure are superior drug candidates as the sensor domain-dependent activity of the therapeutic domain allows for localized activity, even upon systemic administration of the protein complex. Compared to therapeutic domains administered on their own, the protein complexes of the present disclosure exhibit regulated therapeutic activity of the therapeutic domain. As a result, compared to free therapeutic domains administered on their own, the protein complexes of the present disclosure exhibit reduced systemic on-target toxicity.

The protein complexes of the present disclosure can have an Fc region. The protein complexes of the present disclosure can have a domain that improves kinetic properties. For example, the protein complexes of the present disclosure may be further coupled to a half-life extender, such as an Fc region, albumin, PEG, or another zwitterionic polymer. The protein complexes of the present disclosure may have two heavy chains and two light chains. The protein complexes of the present disclosure may have two heavy chains and one light chain. The protein complexes of the present disclosure may include multiple sensor domains and multiple therapeutic domains. For example, a protein complex of the present disclosure may include two sensor domains and two therapeutic domains, all of which are linked and in which the two therapeutic domains are bound to the two sensor domains. In some embodiments, a protein complex of the present disclosure may include two sensor domains and one therapeutic domain, all of which are linked and in which the therapeutic domain may bind to both sensor domains or only one of the two sensor domains.

In some embodiments, the marker may be a surface protein, such as a cell surface protein. The marker may also be soluble ATP. In some embodiments, the marker may be a secreted protein. For example, the secreted protein may be a protein that is released by proliferating tumor cells. In some embodiments, the marker may be expressed by a cancer cell. The marker may be expressed by an immune cell. The marker may be expressed by a stromal cell. The marker may be expressed by an endothelial cell. Exemplary markers include PD1, PD-L1, CEACAM5, FAP, LRRC15, a metabolite, adenosine, AMP, ADP, ATP, or kynurenine. Other markers may include CRIPTO, CD19, CD20, CD22, CD30, CD33, Glycoprotein NMB, CanAg, HER2 (ErbB2/Neu), CD56 (NCAM), CD70, CD79, CD138, PSCA, PSMA (prostate specific membrane antigen), BCMA, E-selectin, EphB2, Melanotransferin, Mucl6 and TMEFF2, or any other marker described in U.S. Pat. No. 10,561,739, incorporated herein by reference in its entirety. Other markers may also include BMPR1B, E16, STEAP1, 0772P, MPF, Napi3b, Sema 5b, PSCA hlg, ETBR, MSG783, STEAP2, TrpM4, CD21, CD79b, FcRH2, NCA, MDP, IL20Rα, Brevican, EphB2R, ASLG659, PSCA, GEDA, BAFF-R, CD79a, CXCR5, HLA-DOB, P2X5, CD72, FCRHI, IRTA2, or any other marker described in WO 2005/082023, incorporated herein by reference in its entirety.

In some embodiments, binding of the sensor domain to the therapeutic domain versus binding of the sensor domain to a marker is regulated by the relative affinity of the sensor domain for the therapeutic domain. In some embodiments, the sensor domain may have a dissociation constant (Kd) for the marker that is lower than the dissociation constant of the sensor domain for the therapeutic domain. Thus, the sensor may have a higher affinity (lower Kd) for the marker than for the therapeutic domain. The sensor domains of the present disclosure may be engineered, for example by affinity maturation, to have a higher affinity (lower dissociation constant) for the marker than the therapeutic domain. In the absence of the marker, the sensor domain of the present disclosure may have a sufficiently high affinity for the therapeutic domain such that the therapeutic domain is bound by the sensor domain. In the presence of the marker, the affinity of the sensor domain for the marker is sufficiently high (low dissociation constant), such that the marker outcompetes the therapeutic domain for binding to the sensor domain. As a result, the equilibrium binding shifts from a state in which the sensor domain is bound to the therapeutic domain to a state in which the therapeutic domain is unbound and the sensor domain binds to the marker.

The sensor domain may have an affinity for the marker that is at least 2-fold higher than an affinity for the therapeutic domain. The sensor domain may have an affinity for the marker that is at least 5-fold higher than an affinity for the therapeutic domain. The sensor domain may have an affinity for the marker that is at least 10-fold higher than an affinity for the therapeutic domain. The sensor domain may have an affinity for the marker that is at least 15-fold higher than an affinity for the therapeutic domain. The sensor domain may have an affinity for the marker that is at least 20-fold higher than an affinity for the therapeutic domain. The sensor domain may have an affinity for the marker that is at least 25-fold higher than an affinity for the therapeutic domain. The sensor domain may have an affinity for the marker that is at least 30-fold higher than an affinity for the therapeutic domain. The sensor domain may have an affinity for the marker that is at least 35-fold higher than an affinity for the therapeutic domain. The sensor domain may have an affinity for the marker that is at least 40-fold higher than an affinity for the therapeutic domain. The sensor domain may have an affinity for the marker that is at least 45-fold higher than an affinity for the therapeutic domain. The sensor domain may have an affinity for the marker that is at least 50-fold higher than an affinity for the therapeutic domain. The sensor domain may have an affinity for the marker that is at least 60-fold higher than an affinity for the therapeutic domain. The sensor domain may have an affinity for the marker that is at least 70-fold higher than an affinity for the therapeutic domain. The sensor domain may have an affinity for the marker that is at least 80-fold higher than an affinity for the therapeutic domain. The sensor domain may have an affinity for the marker that is at least 90-fold higher than an affinity for the therapeutic domain. The sensor domain may have an affinity for the marker that is at least 100-fold higher than an affinity for the therapeutic domain. The sensor domain may have an affinity for the marker that is at least 150-fold higher than an affinity for the therapeutic domain. The sensor domain may have an affinity for the marker that is at least 200-fold higher than an affinity for the therapeutic domain. The sensor domain may have an affinity for the marker that is at least 250-fold higher than an affinity for the therapeutic domain. The sensor domain may have an affinity for the marker that is at least 300-fold higher than an affinity for the therapeutic domain. The sensor domain may have an affinity for the marker that is at least 350-fold higher than an affinity for the therapeutic domain. The sensor domain may have an affinity for the marker that is at least 400-fold higher than an affinity for the therapeutic domain. The sensor domain may have an affinity for the marker that is at least 450-fold higher than an affinity for the therapeutic domain. The sensor domain may have an affinity for the marker that is at least 500-fold higher than an affinity for the therapeutic domain. The sensor domain may have an affinity for the marker that is at least 1000-fold higher than an affinity for the therapeutic domain. The sensor domain may have an affinity for the marker that is at least 10000-fold higher than an affinity for the therapeutic domain. The sensor domain may have an affinity for the marker that is at least 100000-fold higher than an affinity for the therapeutic domain. The sensor domain may have an affinity for the marker that is from 2 to 10-fold higher than an affinity for the therapeutic domain. The sensor domain may have an affinity for the marker that is from 10 to 20-fold higher than an affinity for the therapeutic domain. The sensor domain may have an affinity for the marker that is from 20 to 30-fold higher than an affinity for the therapeutic domain. The sensor domain may have an affinity for the marker that is from 30 to 40-fold higher than an affinity for the therapeutic domain. The sensor domain may have an affinity for the marker that is from 40 to 50-fold higher than an affinity for the therapeutic domain. The sensor domain may have an affinity for the marker that is from 50 to 100-fold higher than an affinity for the therapeutic domain. The sensor domain may have an affinity for the marker that is from 100 to 150-fold higher than an affinity for the therapeutic domain. The sensor domain may have an affinity for the marker that is from 150 to 200-fold higher than an affinity for the therapeutic domain. The sensor domain may have an affinity for the marker that is from 200 to 250-fold higher than an affinity for the therapeutic domain. The sensor domain may have an affinity for the marker that is from 250 to 300-fold higher than an affinity for the therapeutic domain. The sensor domain may have an affinity for the marker that is from 300 to 350-fold higher than an affinity for the therapeutic domain. The sensor domain may have an affinity for the marker that is from 350 to 400-fold higher than an affinity for the therapeutic domain. The sensor domain may have an affinity for the marker that is from 400 to 450-fold higher than an affinity for the therapeutic domain. The sensor domain may have an affinity for the marker that is from 450 to 500-fold higher than an affinity for the therapeutic domain. The sensor domain may have an affinity for the marker that is from 500 to 1000-fold higher than an affinity for the therapeutic domain. The sensor domain may have an affinity for the marker that is from 10 to 80-fold higher than an affinity for the therapeutic domain. The sensor domain may have an affinity for the marker that is from 30 to 70-fold higher than an affinity for the therapeutic domain. The sensor domain may have an affinity for the marker that is from 40 to higher than an affinity for the therapeutic domain. The sensor domain may have an affinity for the marker that is from 20 to 50-fold higher than an affinity for the therapeutic domain. The sensor domain may have an affinity for the marker that is from 10 to 1000-fold higher than an affinity for the therapeutic domain. The sensor domain may have an affinity for the marker that is from 70 to 500-fold higher than an affinity for the therapeutic domain. The sensor domain may have an affinity for the marker that is from 100 to 500-fold higher than an affinity for the therapeutic domain. The sensor domain may have an affinity for the marker that is from 500 to 750-fold higher than an affinity for the therapeutic domain. The sensor domain may have an affinity for the marker that is from 250 to 750-fold higher than an affinity for the therapeutic domain. The sensor domain may have an affinity for the marker that is from 1000 to 100000-fold higher than an affinity for the therapeutic domain. The sensor domain may have an affinity for the marker that is from 2 to 100000-fold higher than an affinity for the therapeutic domain.

A protein complex of the present disclosure, or a fragment thereof, may comprise one or more complementary determining regions (CDRs) having have at least 80% sequence identity to any one of the CDRs disclosed herein. For example, a protein complex of the present disclosure, or a fragment thereof, may comprise one or more CDRs having at least 80% sequence identity to any one of SEQ ID NO: 1-SEQ ID NO: 20, SEQ ID NO: 142-173, or SEQ ID NO:

238-252. A protein complex of the present disclosure, or a fragment thereof, may comprise one or more CDRs having at least 85% sequence identity to any one of SEQ ID NO: 1-SEQ ID NO: 20, SEQ ID NO: 142-173, or SEQ ID NO: 238-252. A protein complex of the present disclosure, or a fragment thereof, may comprise one or more CDRs having at least 90% sequence identity to any one of SEQ ID NO: 1-SEQ ID NO: 20, SEQ ID NO: 142-173, or SEQ ID NO: 238-252. A protein complex of the present disclosure, or a fragment thereof, may comprise one or more CDRs having at least 92% sequence identity to any one of SEQ ID NO: 1-SEQ ID NO: 20, SEQ ID NO: 142-173, or SEQ ID NO: 238-252. A protein complex of the present disclosure, or a fragment thereof, may comprise one or more CDRs having at least 95% sequence identity to any one of SEQ ID NO: 1-SEQ ID NO: 20, SEQ ID NO: 142-173, or SEQ ID NO: 238-252. A protein complex of the present disclosure, or a fragment thereof, may comprise one or more CDRs having at least 97% sequence identity to any one of SEQ ID NO: 1-SEQ ID NO: 20, SEQ ID NO: 142-173, or SEQ ID NO: 238-252. A protein complex of the present disclosure, or a fragment thereof, may comprise one or more CDRs having at least 99% sequence identity to any one of SEQ ID NO: 1-SEQ ID NO: 20, SEQ ID NO: 142-173, or SEQ ID NO: 238-252. A protein complex of the present disclosure, or a fragment thereof, may comprise one or more CDRs having any one of SEQ ID NO: 1-SEQ ID NO: 20, SEQ ID NO: 142-173, or SEQ ID NO: 238-252.

A protein complex, or a fragment thereof, can have at least 80% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex can have at least 85% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex can have at least 90% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex can have at least 92% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex can have at least 95% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex can have at least 97% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex can have at least 99% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof. A protein complex is any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof.

A protein complex of the present disclosure may have at least 95% sequence identity to any one of SEQ ID NO: 41, SEQ ID NO: 44, SEQ ID NO: 80-SEQ ID NO: 112, SEQ ID NO: 174-175, SEQ ID NO: 181-182, SEQ ID NO: 195-196, SEQ ID NO: 205-206, SEQ ID NO: 210-212, SEQ ID NO: 220-223, SEQ ID NO: 226-231, SEQ ID NO: 259-261, SEQ ID NO: 266-282, or SEQ ID NO: 289-293, or a fragment thereof and have one or more CDRs with at least 80% sequence identity to any one SEQ ID NO: 1-SEQ ID NO: 20, SEQ ID NO: 142-173, or SEQ ID NO: 238-252. The protein complexes of the present disclosure can have CDRs selected from SEQ ID NO: 1-SEQ ID NO: 20, SEQ ID NO: 142-173, or SEQ ID NO: 238-252 arranged in any combination or order.

A fragment of any of the above may retain the functional binding domains of the sensor or any functional therapeutic domains of the therapeutic. For example, a dual binding antibody protein complex can include the entire antibody or a fragment having regions of the antibody that are capable of binding to a marker and the therapeutic domain. In the latter case, the fragment may be an scFv that can bind to a marker and the therapeutic domain. Exemplary sequence of protein complexes of the present disclosure is shown below in TABLE 1.

TABLE 1

Exemplary Protein Complexes

| SEQ ID NO | Sequence | Description |
|---|---|---|
| SEQ ID NO: 41 | MSTSTCDLPQTHSLGSRRTLMLLAQMRRISL FSCLKDRHDFGFPQEEFGNQFQKAETIPVLH EMIQQIFNLFSTKDSSAAWDETLLDKFYTEL YQQLNDLEACVIQGVGVTETPLMKEDSILAV RKYFQRITLYLKEKKYSPCAWEVVRAEIMRS FSLSTNLQESLRSKEGGGGSGGGGSGGGGSG GGGSQVQLVQSGAEVKKPGASVKVSCKASGY TFSNYYVHWVRQAPGQGLEWMGWMDPNSGGT GYAHQFQGRVTMTRDTSTSTVYMELSSLRSE | Protein complex comprising a DBA/cytokine complex having a PD-L1/IFNα scFv sensor domain and an IFNα therapeut TABLE 1-continued Exemplary Protein Complexes

| SEQ ID NO | Sequence | Description |
|---|---|---|
| | DTAVYYCAKEVFSGWYDYWGQGTLVTVSSAS GGGGSGGGGSGGGGSHASDIQMTQSPSSLSA SVGDRVTITCRASQSISSYLNWYQQKPGKAP KLLIYAASSLQSGVPSRFSGSGSGTDFTLTI SSLQPEDFATYYCQQSYSTPYTFGQGTKVEI KGKPIPNPLLGLDST | Heavy_GS20_PDL1-IFN_1A05_H_139V S58P_Q69H_K70Q |
| SEQ ID NO: 42 | QVQLVQSGAEVKKPGASVKVSCKASGYTFTK NYMHWVRQAPGQGLEWLGWVSPDSGYTGYAQ KFQGRVTMTRDTSTSTVYMELSSLRSEDTAV YYCTTDLLSLELDDAFDIWGQGTMVTVSSAS GGGGSGGGGSGGGGSHASDIQMTQSPSSLSA SVGDRVTITCRASQSISSWLAWYQQKPGKAP KLLIYAASTLQSGVPSRFSGSGSGTDFTLTI SSLQPEDFATYYCQQSYSTPLTFGGGTKLEI KPRGPTIKPCPPCKCPAPNAAGGPSVFIFPP KIKDVLMISLSPIVTCVVVDVSEDDPDVQIS WFVNNVEVHTAQTQTHREDYNSTLRVVSALP IQHQDWMSGKEFKCKVNNKDLGAPIERTISK PKGSVRAPQVYVLPPCEEEMTKKQVTLSCAV TDFMPEDIYVEWTNNGKTELNYKNTEPVLDS DGSYFMVSKLRVEKKNWVERNSYSCSVVHEG LHNHHTTKSFSRTPGK | Protein complex comprising a DBA/cytokine complex having a PD-L1 antibody sensor domain and an IFNα therapeutic domain, where the DBA is an scFv PDL1-IFN_uIFN_2D10sc Fv_KiH_PDL1-IFN_1A05_H_N36G_Pep1 |
| SEQ ID NO: 43 | CDLPQTHSLGSRRTLMLLAQMRRISLFSCLK DRHDFGFPQEEFGNQFQKAETIPVLHEMIQQ IFNLFSTKDSSAAWDETLLDKFCTELYQQLN DLEACVMQEERVGETPLMNADSILAVKKYFR RITLYLTEKKYSPCAWEVVRAEIVRSLSLST NLQERLRRKEGGGGSGGGGSGGGGSGGGGSQ VQLVQSGAEVKKPGASVKVSCKASGYTFSGY YIHWVRQAPGQGLEWMGWMDSNSGGTGYAQK FQGRVTMTRDTSTSTVYMELSSLRSEDTAVY YCAKEVFSGWYDYWGQGTLVTVSSAKTTAPS VYPLAPVCGDTTGSSVTLGCLVKGYFPEPVT LTWNSGSLSSGVHTFPAVLQSDLYTLSSSVT VTSSTWPSQSITCNVAHPASSTKVDKKIEPR GPTIKPCPPCKCPAPNAAGGPSVFIFPPKIK DVLMISLSPIVTCVVVDVSEDDPDVQISWFV NNVEVHTAQTQTHREDYNSTLRVVSALPIQH QDWMSGKEFKCKVNNKDLGAPIERTISKPKG SVRAPQVCVLPPPEEEMTKKQVTLWCMVTDF MPEDIYVEWTNNGKTELNYKNTEPVLDSDGS YFMYSKLRVEKKNWVERNSYSCSVVHEGLHN HHTTKSFSRTPGK | First heavy chain of a protein complex comprising a DBA/cytokine complex having a PD-L1 binding domain and an IFNα therapeutic domain PDL1-IFN_uIFN_2D10sc Fv_KiH_PDL1-IFN_1A05_H_N36G_Pep2 |
| SEQ ID NO: 44 | DIQMTQSPSSLSASVGDRVTITCRASQSISS YLNWYQQKPGKAPKLLIYAASSLQSGVPSRF SGSGSGTDFTLTISSLQPEDFATYYCQQSYS TPYTFGQGTKVEIKRADAAPTVSIFPPSSEQ LTSGGASVVCFLNNFYPKDINVKWKIDGSER QNGVLNSWTDQDSKDSTYSMSSTLTLTKDEY ERHNSYTCEATHKTSTSPIVKSFNRNEC | Light chain of a protein complex comprising a DBA/cytokine complex having a PD-L1 scFv sensor domain and an IFNα therapeutic domain PDL1-IFN_uIFN_2D10sc Fv_KiH_PDL1-IFN_1A05_H_N36G_Pep3 |
| SEQ ID NO: 303 | QVQLVESGGGVVQPGRSLRLDCKASGITFSN SGMHWVRQAPGKGLEWVAVIWYDGSKRYYAD SVKGRFTISRDNSKNTLFLQMNSLRAEDTAV YYCATNDDYWGQGTLVTVSSAKTTAPSVYPL APVCGDTTGSSVTLGCLVKGYFPEPVTLTWN SGSLSSGVHTFPAVLQSDLYTLSSSVTVTSS TWPSQSITCNVAHPASSTKVDKKIEPRGPTI KPCPPCKCPAPNAAGGPSVFIFPPKIKDVLM ISLSPIVTCVVVDVSEDDPDVQISWFVNNVE VHTAQTQTHREDYNSTLRVVSALPIQHQDWM SGKEFKCKVNNKDLGAPIERTISKPKGSVRA PQVYVLPPPEKEMTKKQVSLTCLVKDFMPED IYVEWTNNGKTELNYKNTEPVLKSDGSYFMY SKLTVEKKNWVERNSYSCSVVHEGLHNHHTT KSFSRTPGGGGSGGGGSGGGGSGGGGSQVQ LVQSGAEVKKPGASVKVSCKASGDTFTRYYV HWVRQAPGQGLEWMGIINPSGGYASYAQKFQ GRVTMTRDTSTSTVYMELSSLRSEDTAVYYC | PD1-IL2_3x_Cterm_Nivo_2B07_H_H37Y_L_A107Y_S109R; AF4505_pep2 |

TABLE 1-continued

Exemplary Protein Complexes

| SEQ ID NO | Sequence | Description |
|---|---|---|
| | AAGLFIWGQGTLVTVSSASGGGGSGGGGSGG<br>GGSHASDIQMTQSPSSLSASVGDRVTITCRA<br>SQSIGRWLAWYQQKPGKAPKLLIYSASNLET<br>GVPSRFSGSGSGTDFTLTISSLQPEDFATYY<br>CQQYNRFPVTFGPGTKVDIK | |
| SEQ ID NO: 304 | QVQLVESGGGVVQPGRSLRLDCKASGITFSN<br>SGMHWVRQAPGKGLEWVAVIWYDGSKRYYAD<br>SVKGRFTISRDNSKNTLFLQMNSLRAEDTAV<br>YYCATNDDYWGQGTLVTVSSAKTTAPSVYPL<br>APVCGDTTGSSVTLGCLVKGYFPEPVTLTWN<br>SGSLSSGVHTFPAVLQSDLYTLSSSVTVTSS<br>TWPSQSITCNVAHPASSTKVDKKIEPRGPTI<br>KPCPPCKCPAPNAAGGPSVFIFPPKIKDVLM<br>ISLSPIVTCVVVDVSEDDPDVQISWFVNNVE<br>VHTAQTQTHREDYNSTLRVVSALPIQHQDWM<br>SGKEFKCKVNNKDLGAPIERTISKPKGSVRA<br>PQVYVLPPPEKEMTKKQVSLTCLVKDFMPED<br>IYVEWTNNGKTELNYKNTEPVLKSDGSYFMY<br>SKLTVEKKNWVERNSYSCSVVHEGLHNHHTT<br>KSFSRTPGGGGSGGGGSGGGGSGGGGSQVQ<br>LVQSGAEVKKPGASVKVSCKASGYTFTRYYM<br>HWVRQAPGQGLEWMGIINPRAGYTSYALKFQ<br>GRVTMTRDTSTSTVYMELSSLRSEDTAVYYC<br>TSGWDVWGQGTLVTVSSASGGGGSGGGGSGG<br>GGSHASDIQMTQSPSSLSASVGDRVTITCRA<br>SQSISTWLAWYQQKPGKAPKLLIYAASSLDS<br>GVPSRFSGSGSGTDFTLTISSLQPEDFATYY<br>CQQSYSFPVTFGQGTKVEIK | PD1-IL2_3x_Cterm_Nivo_704var_AF4504_pep2 |
| SEQ ID NO: 181 | APTSSSTKKTQLQLEHLLLDLQMILNGINNY<br>KNPKLTDMLTFEFYMPKKATELKHLQCLERE<br>LKPLEEVLNLAQSKNFHLRPRDLISNINVIV<br>LELKGSETTFMCEYADETATIVEFLNRWITF<br>CQSIISTLTGGGGSGGGGSGGGGSGGGGSQV<br>QLVQSGAEVKKPGASVKVSCKASGDTFTRYY<br>VHWVRQAPGQGLEWMGIINPSGGYASYAQKF<br>QGRVTMTRDTSTSTVYMELSSLRSEDTAVYY<br>CAAGLFIWGQGTLVTVSSAKTTAPSVYPLAP<br>VCGDTTGSSVTLGCLVKGYFPEPVTLTWNSG<br>SLSSGVHTFPAVLQSDLYTLSSSVTVTSSTW<br>PSQSITCNVAHPASSTKVDKKIEPRGPTIKP<br>CPPCKCPAPNAAGGPSVFIFPPKIKDVLMIS<br>LSPIVTCVVVDVSEDDPDVQISWFVNNVEVH<br>TAQTQTHREDYNSTLRVVSALPIQHQDWMSG<br>KEFKCKVNNKDLGAPIERTISKPKGSVRAPQ<br>VYVLPPPEEEMTKKQVTLTCMVTDFMPEDIY<br>VEWTNNGKTELNYKNTEPVLDSDGSYFMYSD<br>LRVEKKNWVERNSYSCSVVHEGLHNHHTTES<br>FSRTPGK | PD1-IL2_3x_Asym_PD1-IL2_2B07_H_H37Y_L_W38Y_A107Y |
| SEQ ID NO: 182 | QVQLVQSGAEVKKPGASVKVSCKASGDTFTR<br>YYVHWVRQAPGQGLEWMGIINPSGGYASYAQ<br>KFQGRVTMTRDTSTSTVYMELSSLRSEDTAV<br>YYCAAGLFIWGQGTLVTVSSAKTTAPSVYPL<br>APVCGDTTGSSVTLGCLVKGYFPEPVTLTWN<br>SGSLSSGVHTFPAVLQSDLYTLSSSVTVTSS<br>TWPSQSITCNVAHPASSTKVDKKIEPRGPTI<br>KPCPPCKCPAPNAAGGPSVFIFPPKIKDVLM<br>ISLSPIVTCVVVDVSEDDPDVQISWFVNNVE<br>VHTAQTQTHREDYNSTLRVVSALPIQHQDWM<br>SGKEFKCKVNNKDLGAPIERTISKPKGSVRA<br>PQVYVLPPPEKEMTKKQVSLTCLVKDFMPED<br>IYVEWTNNGKTELNYKNTEPVLKSDGSYFMY<br>SKLTVEKKNWVERNSYSCSVVHEGLHNHHTT<br>KSFSRTPGGGGSGGGSHHHHHH | PD1-IL2_3x_Asym_PD1-IL2_2B07_H_H37Y_L_W38Y_A107Y |
| SEQ ID NO: 183 | APTSSSTKKTQLQLEHLLLDLQMILNGINNY<br>KNPKLTDMLTFEFYMPKKATELKHLQCLERE<br>LKPLEEVLNLAQSKNFHLRPRDLISNINVIV<br>LELKGSETTFMCEYADETATIVEFLNRWITF<br>CQSIISTLTGGGGSGGGGSGGGGSGGGGSQV<br>QLVQSGAEVKKPGASVKVSCKASGYTFTDYY<br>MHWVRQAPGQGLEWMGIINPRAGYTSYALKF<br>QGRVTMTRDTSTSTVYMELSSLRSEDTAVYY<br>CTSGWDVWGQGTLVTVSSAKTTAPSVYPLAP | PD1-IL2_3x_Asym_PD1-IL2_7A04_H_M115W_L_Q68D |

TABLE 1-continued

Exemplary Protein Complexes

| SEQ ID NO | Sequence | Description |
|---|---|---|
| | VCGDTTGSSVTLGCLVKGYFPEPVTLTWNSG SLSSGVHTFPAVLQSDLYTLSSSVTVTSSTW PSQSITCNVAHPASSTKVDKKIEPRGPTIKP CPPCKCPAPNAAGGPSVFIFPPKIKDVLMIS LSPIVTCVVVDVSEDDPDVQISWFVNNVEVH TAQTQTHREDYNSTLRVVSALPIQHQDWMSG KEFKCKVNNKDLGAPIERTISKPKGSVRAPQ VYVLPPPEEEMTKKQVTLTCMVTDFMPEDIY VEWTNNGKTELNYKNTEPVLDSDGSYFMYSD LRVEKKNWVERNSYSCSVVHEGLHNHHTTES FSRTPGK | |
| SEQ ID NO: 184 | QVQLVQSGAEVKKPGASVKVSCKASGYTFTD YYMHWVRQAPGQGLEWMGIINPRAGYTSYAL KFQGRVTMTRDTSTSTVYMELSSLRSEDTAV YYCTSGWDVWGQGTLVTVSSAKTTAPSVYPL APVCGDTTGSSVTLGCLVKGYFPEPVTLTWN SGSLSSGVHTFPAVLQSDLYTLSSSVTVTSS TWPSQSITCNVAHPASSTKVDKKIEPRGPTI KPCPPCKCPAPNAAGGPSVFIFPPKIKDVLM ISLSPIVTCVVVDVSEDDPDVQISWFVNNVE VHTAQTQTHREDYNSTLRVVSALPIQHQDWM SGKEFKCKVNNKDLGAPIERTISKPKGSVRA PQVYVLPPPEKEMTKKQVSLTCLVKDFMPED IYVEWTNNGKTELNYKNTEPVLKSDGSYFMY SKLTVEKKNWVERNSYSCSVVHEGLHNHHTT KSFSRTPGGGGSGGGSHHHHHH | PD1- IL2_3x_Asym_PD1- IL2_7A04_H_M115W_ L_Q68D |

A. Sensor Domains

Protein complexes of the present disclosure include sensor domains. A sensor domain may be any protein that is capable of sensing the presence of a first moiety and regulating a second moiety, where the first moiety is a marker (e.g., a tumor cell marker) and the second moiety is a therapeutic domain (e.g., a cytokine therapeutic domain). For example, the present disclosure provides a sensor domain that may be an antibody or antibody fragment capable of binding a first moiety and binding and blocking the activity of a second moiety, wherein the first moiety is a marker (e.g., a tumor marker) and the second moiety is a therapeutic domain (e.g., a cytokine therapeutic domain). In the absence of the first moiety, the sensor domain binds the second moiety. If the first moiety is introduced into the system, the sensor domain binds the first moiety and unbinds the second moiety. Thus, the binding and unbinding of the second moiety is reversible. The sensor domain inactivates or blocks the activity of the therapeutic domain by binding the therapeutic domain and preventing it from binding to its target (e.g., a receptor, a ligand, or a substrate). The sensor domain regulates the therapeutic domain by releasing it to act on its target upon binding of a marker.

In some embodiments, the sensor domain is a dual binding protein such as a dual binding antibody. A dual binding protein may be capable of binding the marker and the therapeutic domain. A dual binding protein of the present disclosure may be selected or engineered to bind the marker and the therapeutic domain. The dual binding protein may have a higher affinity for the marker as compared to the therapeutic domain. The dual binding protein may be affinity matured to have a higher affinity for the marker as compared to the therapeutic domain.

In some embodiments, the sensor domain is an antibody. The sensor domain may also be a fragment of an antibody. A fragment of an antibody consistent with the sensor domains disclosed herein retains its ability to exhibit dual binding to both a marker and a therapeutic domain. One or both domains of a bispecific antibody may be sensor domains of the protein complexes of the present disclosure. In the instance that bispecific antibodies are used, the bispecific antibody may include a first antigen binding domain that may bind a therapeutic domain and a marker and may also include a second antigen binding domain capable of binding the marker. In some embodiments, the bispecific antibody may have a first antigen binding domain that binds a therapeutic domain and a first marker, and a second antigen binding domain that binds a second marker. In some embodiments, the bispecific antibody may have a first antigen binding domain that binds a therapeutic domain and a first marker, and a second antigen binding domain that binds a therapeutic domain and a second marker. In some embodiments the first and second antigen binding domains may bind to the same therapeutic domain (FIG. 13).

In some embodiments the two sensor domains may bind to a single IFNα domain attached by a linker to two antibody domains; a first antibody domain that may bind to CEA (a first marker) and to the IFNα domain, and a second antibody domain that may bind to ATP (a second marker), and to the IFNα domain such that the IFNα is able to bind its receptor only in the presence of CEA and ATP (FIG. 13).

In some embodiments, the sensor domain is an anti-PD1 or anti-PDL1 antibody or fragment thereof (e.g., an scFv that binds PD1 or PD-L1). In some embodiments, the sensor domain binds to a marker comprising a surface protein, such as a cell surface protein, soluble ATP, a secreted protein, PD1, PD-L1, CEACAM5, FAP, LRRC15, a metabolite, adenosine, AMP, ADP, ATP, or kynurenine, or CRIPTO, CD19, CD20, CD22, CD30, CD33, Glycoprotein NMB, CanAg, HER2 (ErbB2/Neu), CD56 (NCAM), CD70, CD79, CD138, PSCA, PSMA (prostate specific membrane antigen), BCMA, E-selectin, EphB2, Melanotransferin, Muc16 and TMEFF2, BMPR1B, E16, STEAP1, 0772P, MPF, Napi3b, Sema 5b, PSCA hlg, ETBR, MSG783, STEAP2, TrpM4, CD21, CD79b, FcRH2, NCA, MDP, IL20Rα, Brevican, EphB2R, ASLG659, PSCA, GEDA, BAFF-R, CD79a, CXCR5, HLA-DOB, P2X5, CD72, FCRHI, IRTA2, a sialic acid, or any other marker described in U.S. Pat. No. 10,561,739, incorporated herein by reference in its entirety or WO 2005/082023, incorporated herein by reference in its entirety.

In some embodiments, the sensor domain comprises a condition-dependent target affinity. Many cell types, including a range of cancer cell types, generate specific extracellular and tissue-specific microenvironments distinct from those of healthy cells. Recently, significant attention has been placed on the link between extracellular sodium depletion and certain brain cancers. As a further example, some cancers generate low pH microenvironments which can affect changes in the membranome protonation and conformational patterns. Accordingly, a sensor domain may comprise enhanced affinity for a target marker in the presence of a particular condition. A sensor domain may be responsive to pH, temperature, salinity, osmotic pressure, or any combination thereof. For example, a sensor domain may comprise an order of magnitude greater affinity for a target molecule or an order of magnitude lower affinity for a therapeutic domain in the presence of a particular condition. The particular condition may affect the sensor (e.g., a charge or conformation of the sensor), the target (e.g., a charge or solubility of the target), or both.

B. Therapeutic Domains

Protein complexes of the present disclosure include therapeutic domains. A therapeutic domain of the present disclosure is linked to a sensor domain via a linker to form a protein complex. The therapeutic domain may exert therapeutic activity by binding to a target. For example, the therapeutic domain may be a cytokine and its target may be a receptor target. Upon binding of the cytokine to its receptor target, the cytokine may modulate cellular proliferation, activation, differentiation, and/or may exert anti-tumor or anti-viral activity. Therapeutic domains consistent with the protein complexes of the present disclosure include a cytokine, a chemokine, an antibody, an antibody fragment, a peptide agonist, a peptide antagonist, an enzyme, a soluble receptor, a growth factor, a protein toxin, a soluble ligand, a small molecule, or combinations thereof. In some embodiments, an antibody or antibody fragment comprises an IgG, an IgA, an IgD, an IgE, an IgM, an Fab, an F(ab)'2, a single domain antibody fragment (e.g., a nanobody), a diabody, an scFab, an scFv, an (scFv)$_2$, or any fragment (e.g., an Fc domain or CH domain) or combination thereof.

In some embodiments, the protein complexes of the present disclosure comprise a therapeutic domain comprising an IL-2 receptor agonist, IL-12 receptor agonist, or IFNα, or variants or fusions of these cytokines. In some embodiments, the therapeutic domain may be IFNα, IFNγ IL-12 IL-4, IL-8, IL-10, IL-15, IL-18, IL-21, TGF beta, an anti-CD3 antibody, an anti-CD28 antibody or ligand, an antibody to or ligand of CD40, GITR, OX40, CD137, CD27, or Death Receptors, the extracellular domain of TGFBR2, VEGF-C, kynureninase, IL-7, TNF, MICA, MICB, CD47, an anti-CTLA4 antibody, an anti-PD-L1 antibody, or an anti-PD-1 antibody. The therapeutic domain may also be a fragment of any of the above mentioned moieties. A fragment retains functional regions of the moiety needed for binding to its target (e.g., IL-2 receptor) and any functional regions needed for activity.

C. Linkers

A protein complex disclosed herein may comprise a linker. The linker may connect two domains, such as a sensor domain and a therapeutic domain. The linker may connect two portions of a sensor domain, for example a light chain variable domain and a heavy chain variable domain. Various linkers are consistent with the protein complexes of the present disclosure. In some embodiments, the linker may be an amino acid linker or a chemical linker.

The linker may be a stable linker. For example, a linker may maintain a connection between a therapeutic domain and a sensor domain even upon binding of the sensor domain to a marker and, thereby, unbinding of the therapeutic domain from the sensor domain. For example, although the sensor domain may unbind the therapeutic domain, the therapeutic domain may remain linked to the sensor domain via the linker. Examples of linkers that are consistent with this activity may include non-cleavable linkers.

The linker may also be a flexible linker. A flexible linker is a linker that is long enough to allow for the therapeutic domain to bind to its target, once it is unbound from the sensor domain. Flexibility of the linker may affect therapeutic efficacy. For example, upon binding of the sensor domain to a marker and unbinding of the therapeutic domain, the therapeutic domain needs to be able to encounter and bind its therapeutic target (e.g., a receptor on the same cell surface as the marker or a receptor on an adjacent cell surface to the marker). If the linker is not flexible enough to allow for the therapeutic domain to binds its therapeutic target, therapeutic efficacy may be reduced or not exerted. When the linker is flexible, therapeutic domains may be able to bind their therapeutic target and exert high therapeutic efficacy. Flexibility of a linker may arise from the length of the linker. For example, short linkers may sterically hinder the therapeutic domain from binding its target. Longer linkers may allow for the protein complex to be more flexible and allow for therapeutic domains to bind their target. In some embodiments, a linker that is too long may impact the ability of the sensor domain to bind the therapeutic domain and inhibit activity in the absence of the marker. In some embodiments, a linker that is too long may impact the stability of a protein therapeutic domain or the half-life of the protein therapeutic domain in vivo.

In some embodiments, the linker may be attached to a heavy chain of the sensor domain or a light chain of the sensor domain. A linker may be fused to the N-terminus or C-terminus of the sensor domain. In some embodiments, the linker may be attached to a heavy chain or light chain of the therapeutic domain or is fused with the N-terminus or C-terminus of the therapeutic domain. For example, a linker may be attached to an N-terminus or C-terminus of an scFV or an ScFab.

Amino Acid Linkers. An amino acid linker may comprise any amino acid residues. In some embodiments, favored amino acid residues are amino acid residues that are entropically flexible. Favored amino acid residues in an amino acid linker of the present disclosure may include glycine and serine. Other preferred amino acid residues may include alanine, proline, threonine, and glutamic acid. In preferred embodiments, the amino acid linker may comprise from 3 to 60 amino acid residues in length. In some embodiments, the amino acid linker may comprise 20 amino acid residues. In some embodiments, the amino acid linker may comprise 40 amino acid residues. In some embodiments, the amino acid linker may comprise 60 amino acid residues. In some embodiments, the amino acid linker may comprise 80 amino acid residues. An amino acid linker may comprise at least 5 amino acid residues. An amino acid linker may comprise at least 10 amino acid residues. An amino acid linker may comprise at least 15 amino acid residues. An amino acid linker may comprise at least 20 amino acid residues. An amino acid linker may comprise at least 25 amino acid residues. An amino acid linker may comprise at least 30 amino acid residues. An amino acid linker may comprise at least 35 amino acid residues. An amino acid linker may comprise at least 40 amino acid residues. An amino acid linker may comprise at least 45 amino acid residues. An amino acid linker may comprise at least 50 amino acid residues. An amino acid linker may comprise at least 55 amino acid residues. An amino acid linker may comprise at least 60 amino acid residues. An amino acid linker may comprise at least 65 amino acid residues. An amino acid linker may comprise at least 70 amino acid residues. An amino acid linker may comprise at least 75 amino acid residues. An amino acid linker may comprise at least 80 amino acid residues. An amino acid linker may comprise at least 85 amino acid residues. An amino acid linker may comprise at least 90 amino acid residues. An amino acid linker may comprise at least 95 amino acid residues. An amino acid linker may comprise at least 100 amino acid residues. An amino acid linker may comprise at least 110 amino acid residues. An amino acid linker may comprise at least 120 amino acid residues. An amino acid linker may comprise at least 130 amino acid residues. An amino acid linker may comprise at least 140 amino acid residues. An amino acid linker may comprise at least 150 amino acid residues. An amino acid linker may comprise at least 160 amino acid residues. An amino acid linker may comprise at least 170 amino acid residues. An amino acid linker may comprise at least 180 amino acid residues. An amino acid linker may comprise at least 190 amino acid residues. An amino acid linker may comprise at least 200 amino acid residues. An amino acid linker may comprise at least 300 amino acid residues. An amino acid linker may comprise at least 400 amino acid residues. An amino acid linker may comprise at least 500 amino acid residues. An amino acid linker may comprise from 5 to 10 amino acid residues. An amino acid linker may comprise from 10 to 15 amino acid residues. An amino acid linker may comprise from 15 to 20 amino acid residues. An amino acid linker may comprise from 20 to 25 amino acid residues. An amino acid linker may comprise from 25 to 30 amino acid residues. An amino acid linker may comprise from 30 to 35 amino acid residues. An amino acid linker may comprise from 35 to 40 amino acid residues. An amino acid linker may comprise from 40 to 45 amino acid residues. An amino acid linker may comprise from 45 to 50 amino acid residues. An amino acid linker may comprise from 50 to 55 amino acid residues. An amino acid linker may comprise from 55 to 60 amino acid residues. An amino acid linker may comprise from 60 to 65 amino acid residues. An amino acid linker may comprise from 65 to 70 amino acid residues. An amino acid linker may comprise from 70 to 75 amino acid residues. An amino acid linker may comprise from 75 to 80 amino acid residues. An amino acid linker may comprise from 80 to 85 amino acid residues. An amino acid linker may comprise from 85 to 90 amino acid residues. An amino acid linker may comprise from 90 to 95 amino acid residues. An amino acid linker may comprise from 95 to 100 amino acid residues. An amino acid linker may comprise from 5 to 80 amino acid residues. An amino acid linker may comprise from 20 to 40 amino acid residues. An amino acid linker may comprise from 20 to 80 amino acid residues. An amino acid linker may comprise from 30 to 60 amino acid residues. An amino acid linker may comprise from 40 to 50 amino acid residues. An amino acid linker may comprise from 10 to 30 amino acid residues. An amino acid linker may comprise from 10 to 20 amino acid residues. An amino acid linker may comprise from 5 to 25 amino acid residues. An amino acid linker may comprise from 25 to 75 amino acid residues. An amino acid linker may comprise from 100 to 500 amino acid residues. An amino acid linker may comprise from 100 to 300 amino acid residues. An amino acid linker may comprise from 5 to 500 amino acid residues. An amino acid linker may comprise no more than 100 amino acid residues. An amino acid linker may comprise no more than 90 amino acid residues. An amino acid linker may comprise no more than 80 amino acid residues. An amino acid linker may comprise no more than 70 amino acid residues. An amino acid linker may comprise no more than 60 amino acid residues. An amino acid linker may comprise no more than 50 amino acid residues. An amino acid linker may comprise no more than 40 amino acid residues. An amino acid linker may comprise no more than 30 amino acid residues. An amino acid linker may comprise no more than 20 amino acid residues. An amino acid linker may comprise no more than 10 amino acid residues. An amino acid linker may comprise no more than 95 amino acid residues. An amino acid linker may comprise no more than 90 amino acid residues. An amino acid linker may comprise no more than 85 amino acid residues. An amino acid linker may comprise no more than 80 amino acid residues. An amino acid linker may comprise no more than 75 amino acid residues. An amino acid linker may comprise no more than 70 amino acid residues. An amino acid linker may comprise no more than 65 amino acid residues. An amino acid linker may comprise no more than 60 amino acid residues. An amino acid linker may comprise no more than 55 amino acid residues. An amino acid linker may comprise no more than 50 amino acid residues. An amino acid linker may comprise no more than 45 amino acid residues. An amino acid linker may comprise no more than 40 amino acid residues. An amino acid linker may comprise no more than 35 amino acid residues. An amino acid linker may comprise no more than 30 amino acid residues. An amino acid linker may comprise no more than 25 amino acid residues. An amino acid linker may comprise no more than 20 amino acid residues. An amino acid linker may comprise no more than 15 amino acid residues. An amino acid linker may comprise no more than 10 amino acid residues. An amino acid linker may comprise no more than 200 amino acid residues. An amino acid linker may comprise no more than 300 amino acid residues. An amino acid linker may comprise no more than 400 amino acid residues. An amino acid linker may comprise no more than 500 amino acid residues.

Non-Cleavable Linkers.

A non-cleavable linker of the present disclosure may include a chemical linker that is stable. Examples of non-cleavable linkers consistent for use in protein complexes of the present disclosure to link the sensor domain and the therapeutic domain may include a thioether linker, an alkyl linker, a polymeric linker. A linker may be an SMCC linker or a PEG linker. In preferred embodiments, the linker may be a PEG linker.

A non-cleavable linker may also include a non-proteolytically cleavable peptide. A non-proteolytically cleavable peptide may be inert to proteases present in a given sample or organism. For example, a peptide may be inert to all human protease cleavage sequences, and thereby may comprise a high degree of stability within humans and human samples. Such a peptide may also comprise a secondary structure which renders a protease cleavage site inert or inaccessible to a protease. A non-cleavable linker of the present disclosure may comprise a half-life for cleavage of at least 1 hour, at least 2 hours, at least 4 hours, at least 8 hours, at least 12 hours, at least 16 hours, at least 1 day, at least 2 days, at least 3 days, at least 1 week, at least 2 weeks, or at least 1 month in the presence of human proteases at 25° C. in pH 7 buffer.

D. Protein Complex Structures

The present disclosure provides a wide variety of protein complexes spanning a range of structures. A protein complex of the present disclosure may comprise a therapeutic domain and a sensor domain expressed as a single unit. A therapeutic domain may be expressed as an N-terminal extension of a sensor domain, as a C-terminal extension of a sensor domain, or disposed within a sensor domain. For example, a protein complex may comprise a peptide which comprises, from N-terminus to C-terminus, a therapeutic domain, a peptide linker, an scFv domain, and optionally a tag, such as a purification tag (e.g., a V5 or myc tag) or a localization signal. Alternatively, a therapeutic domain and a sensor domain may be coupled (e.g., chemically coupled) subsequent to expression.

A protein complex may comprise a plurality of protein subunits. The plurality of protein subunits (e.g., a therapeutic domain and a sensor domain, two sensor domains, or two subunits of a sensor domain) may be chemically or physically coupled following expression. The plurality of protein subunits may comprise a plurality of sensor and/or therapeutic domains. A sensor and/or a therapeutic domain may be comprised of a single protein subunit, of multiple protein subunits, or by portions thereof. For example, a sensor domain may comprise an antibody Fab region comprising portions of an immunoglobulin light chain and an immunoglobulin heavy chain.

A plurality of protein subunits may comprise physical handles which facilitate their selective coupling. The physical handles may enable spontaneous, irreversible, and/or non-mediated (e.g., not requiring a chaperone protein or a catalytic complex) coupling between the protein subunits, thereby enabling complex and asymmetric protein complexes. For example, two distinct protein complex subunits expressed in a single Chinese hamster ovary (CHO) cell, may comprise physical handles which spontaneously and irreversibly couple prior to cellular export. Such physical handles may comprise a 'knob-into-hole' (KIH) construct or a charge-swap construct, in which two protein subunits comprise physical structures with mutual binding affinities and specificities. Such physical handles may comprise a covalently binding pair, such as a plurality of thiols configured to form disulfide bonds. Physical handles may enable facile production of protein complexes comprising identical or distinct domains.

A protein complex may comprise two or more identical domains. An example of such a protein complex is provided in FIG. 14A, which illustrates an antibody (multi-sensor domain) coupled to two IL-2 therapeutic domains. In this example, the protein complex comprises two protein immunoglobulin light chain subunits and two immunoglobulin heavy chain subunits complexed to form a competent antibody. The two immunoglobulin heavy chain subunits comprise N-terminal linkers coupled to IL-2 therapeutic domains. Each immunoglobulin heavy chain is coupled to an immunoglobulin light chain, such that the protein complex comprises two Fab regions, each separately coupled to a therapeutic domain by a linker.

While the above example provides a symmetric protein complex with two identical sensor domains and two identical therapeutic domains, a protein complex may also comprise a plurality of distinct sensor and/or therapeutic domains. Such a protein complex may comprise an immunoglobulin unit with a first arm comprised of a heavy chain-light chain pair, and a second arm comprised of an antibody fragment such as an scFv, an scFab, a VH, or a fragment thereof. In such cases, the heavy chain, the antibody fragment, or the light chain may comprise an N-terminal extension with a linker and a therapeutic domain, as illustrated in FIGS. 9A, C, and F, respectively. Alternatively, the heavy chain, the antibody fragment, or the light chain may comprise a C-terminal extension with a linker and a therapeutic domain. A protein complex may also comprise a symmetric immunoglobulin unit with a single therapeutic domain. For example, as shown in FIG. 9B, an immunoglobulin unit may comprise an N-terminal linker and therapeutic unit on a single heavy chain. Alternatively, an immunoglobulin unit may comprise an N-terminal linker and therapeutic unit on a single light chain. An immunoglobulin unit may also comprise a pair of antibody fragments coupled to a single Fc region. An immunoglobulin unit may comprise a nanobody. An immunoglobulin unit may comprise a diabody.

In some cases, a plurality of distinct sensor domains are associated with a plurality of distinct therapeutic domains. Such a plurality of sensor domains may comprise common targets. For example, a protein complex may comprise a first sensor domain associated with an IL-2 therapeutic domain and comprising affinities for IL-2 and PD-1, and a second sensor domain associated with an IFNα therapeutic domain and comprising an affinity for IFNα and PD-1. Alternatively, a plurality of sensor domains may comprise separate targets. For example, a protein complex may comprise a first sensor domain associated with an IL-2 therapeutic domain and comprising affinities for IL-2 and PD-1, and a second sensor domain associated with an IFNα therapeutic domain and comprising an affinity for IFNα and CEACAM5.

A protein complex may comprise a therapeutic domain targeted by one or more than one sensor domain. A protein complex comprising such a plurality of sensor domains may comprise a multi-target dependence for activity. This concept is illustrated in FIGS. 13A-13C, which provides a protein complex comprising a therapeutic domain, a first sensor domain targeting the therapeutic domain and a first target (Marker 1'), and a second sensor domain targeting the therapeutic domain and a second target (Marker 2'). In this example, the presence of Marker 1 leads to therapeutic domain binding to DBA 2, while the presence of Marker 2 leads to therapeutic domain binding to DBA 1. However, the presence of Marker 1 and Marker 2 liberates the therapeutic domain, enhancing its activity. Accordingly, the activity of the protein complex is requisite upon the presence of both of its markers. An example of such a system may be a protein complex comprising a first sensor domain which targets IL-2 and PD-1, and a second sensor domain which targets IL-2 and CEACAM5, such that CEACAM5 and PD-1 are requisite for IL-2 activity by the protein complex. A protein complex may comprise a dependence for at least 2, at least 3, at least 4, or at least 5 target markers. A protein complex may comprise a dependence for at most 5, at most 4, at most 3, at most 2, or for a single target marker.

Multi-marker activity dependence may enhance the selectivity of a protein complex. Some cells, including many forms of cancerous cells, comprise minor variations in their surfaceomes relative to healthy cells, rendering monospecific targeting unfeasible for distinguishing diseased cells. Accordingly, selectively targeting a particular diseased cell or tissue may require targeting a plurality of markers. A protein complex of the present disclosure may target at least 2, at least 3, at least 4, or at least 5 markers. A protein complex of the present disclosure may target at most 5, at most 4, at most 3, or at most 2 markers. In some cases, at least one of the markers targeted by a protein complex is commonly shared between a target cell or tissue and a healthy cell or tissue. In some cases, all of the markers targeted by a protein complex are commonly shared between a target cell or tissue and a healthy cell or tissue.

A sensor domain of the present disclosure may target at least 2, at least 3, at least 4, at least 5, at least 6, at least 7, at least 8, at least 9, or at least 10 markers and no therapeutic domain. A sensor domain of the present disclosure may target at most 2, at most 3, at most 4, at most 5, at most 6, at most 7, at most 8, at most 9, or at most 10 markers and no therapeutic domain. A sensor domain of the present disclosure may target a single therapeutic domain and at least 1, at least 2, at least 3, at least 4, at least 5, at least 6, at least 7, at least 8, at least 9, or at least 10 markers. A sensor domain of the present disclosure may target a single therapeutic domain and at most 1, at most 2, at most 3, at most 4, at most 5, at most 6, at most 7, at most 8, at most 9, or at most 10 markers. A sensor domain of the present disclosure may target at least two therapeutic domains and at least 1, at least 2, at least 3, at least 4, at least 5, at least 6, at least 7, at least 8, at least 9, or at least 10 markers. A sensor domain of the present disclosure may target at least two therapeutic domains and at most 1, at most 2, at most 3, at most 4, at most 5, at most 6, at most 7, at most 8, at most 9, or at most 10 markers.

Two sensor domains may comprise identical affinities for a therapeutic domain, or may comprise different affinities for the therapeutic domain. Two sensor domains may comprise affinities for a therapeutic domain differing by at least 1 order of magnitude, at least 2 orders of magnitude, at least 3 orders of magnitude, or at least 4 orders of magnitude for a therapeutic domain. Two sensor domains may comprise affinities for a therapeutic domain which differ by at most 4 orders of magnitude, at most 3 orders of magnitude, at most 2 orders of magnitude, or at most 1 order of magnitude. A combination of different therapeutic domain affinities by a plurality of sensor domains may enhance the affinity of a protein complex for a target marker. For example, a protein complex may comprise a first sensor domain which weakly targets a first cell surface marker and weakly targets a therapeutic domain, and a second sensor domain which strongly targets a second cell surface marker and strongly targets the therapeutic domain, such that the protein complex exhibits weak activity in the presence of the cell surface second marker and strong activity in the presence of the first and the second cell surface markers.

Two sensor domains of a protein complex may also target separate therapeutic domains. For example, a protein complex may comprise a first sensor domain which targets IL-2 and PD-1, and a second sensor domain which targets IFNα and CEACAM5. A protein complex may comprise a sensor domain which does not target a therapeutic domain. Such a sensor domain may aid in target localization, or may enhance the activity of a separate sensor domain for a therapeutic domain. An example of a protein complex comprising a sensor domain which does not target a therapeutic domain is provided in FIG. 14C. This system comprises a monospecific anti-PD-1 antibody, wherein a first heavy chain comprises a C-terminal linker coupled to a therapeutic domain, and a second heavy chain comprises a C-terminal linker coupled to a sensor domain with dual specificity for the therapeutic domain and for a target marker.

A protein complex may comprise a single target, 2 targets, 3 targets, 4 targets, or more than 4 targets. A protein complex may comprise at least 2 targets, at least 3 targets, or at least 4 targets. A protein complex may comprise at most 4 targets, at most 3 targets, or at most 2 targets. A protein complex may comprise a single sensor domain, 2 sensor domains, 3 sensor domains, 4 sensor domains, or more than 4 sensor domains. A protein complex may comprise at least 2 sensor domains, at least 3 sensor domains, or at least 4 sensor domains. For example, a protein complex may comprise an IgM antibody comprising Fab region sensor domains, or an IgA antibody comprising 4 Fab region sensor domains.

A protein complex may comprise a range of sensor-to-therapeutic domain ratios. A protein complex may comprise equal numbers of sensor domains and therapeutic domains, examples of which are provided by FIG. 14A, which illustrates a protein complex with 2 sensor domains and 2 therapeutic domains, and FIG. 8, which illustrates a protein complex with a single sensor domain and a single therapeutic domain. A protein complex may comprise a greater number of sensor domains than therapeutic domains, such as the protein complexes of FIGS. 9A, 9B, 9C, 9F, and 14B, which each comprise two sensor domains and one therapeutic domain. In such cases, a therapeutic domain may be capable of interacting with multiple sensor domains, or may be constrained from interacting with more than one sensor domain. The number of therapeutic domains with which a sensor domain may interact may depend on its linker. A linker may be sufficiently short so as to prevent a therapeutic domain from interacting with a sensor domain, or may be sufficiently long so as to allow a therapeutic domain to interact with multiple sensor domains.

In specific cases, a protein complex may comprise an antibody with Fc-coupled therapeutic and sensor domains. As illustrated in FIG. 14C, a protein complex may comprise an antibody with a first heavy chain C-terminal extension comprising a linker and a therapeutic domain, and a second heavy chain C-terminal extension comprising a linker and a sensor domain. An antibody of this design may comprise common targets across its Fab and C-terminal extension sensor domain. For example, the antibody Fab regions and C-terminal extension sensor domain may each target PD-1. Conversely, an antibody of this design may comprise separate targets across its Fab regions and C-terminal extension sensor domain.

In some embodiments, an amino acid in the protein complex described herein may comprise a conservative substitution. A conservative substitution may comprise a substitution of one amino acid with a different amino acid with similar biochemical properties (e.g. charge, hydrophobicity, and size). Examples of conservative substitutions, as well as substitutions that may be, but are not necessarily, preferred, are provided in TABLE 33.

TABLE 33

Exemplary Conservative Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE 33-continued

Exemplary Conservative Substitutions

| Original Residue | Exemplary Substitutions | Preferred Substitutions |
|---|---|---|
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

In some embodiments, the present disclosure describes a recombinant nucleic acid that encodes the protein complex disclosed herein. In some embodiments, the recombinant nucleic acid comprises a plasmid or a vector that encodes the entire protein complex. In some embodiments, the recombinant nucleic acid comprises plasmids or vectors that encode the therapeutic domain, the sensor domain, and the linker respectively. In some embodiments, the recombinant nucleic acid comprises plasmids or vectors that encode any two of the therapeutic domain, the sensor domain, and the linker together.

Pharmaceutical Formulations

A protein complex or a recombinant nucleic acid encoding the protein complex of the present disclosure may be formulated as a pharmaceutical composition. A pharmaceutical composition may comprise a pharmaceutically acceptable carrier or excipient. As used herein "pharmaceutically acceptable" or "pharmacologically acceptable" includes molecular entities and compositions that do not produce an adverse, allergic or other untoward reaction when administered to a subject, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients are often also incorporated into the compositions.

Applications

A protein complex of the present disclosure may be used for various therapeutic applications. A protein complex of the present disclosure may be used as a therapeutic to administer to a subject in need thereof. The subject may be a human or non-human mammal. The subject may have a disease. The disease may be cancer. The cancer may be acute lymphoblastic leukemia (ALL); acute myeloid leukemia (AML); cancer in adolescents; adrenocortical carcinoma; aids-related cancers; kaposi sarcoma (soft tissue sarcoma); aids-related lymphoma (lymphoma); primary cns lymphoma (lymphoma); anal cancer; appendix cancer—see gastrointestinal carcinoid tumors; astrocytomas, childhood (brain cancer); atypical teratoid/rhabdoid tumor, childhood, central nervous system (brain cancer); basal cell carcinoma of the skin—see skin cancer; bile duct cancer; bladder cancer; bone cancer (includes ewing sarcoma and osteosarcoma and malignant fibrous histiocytoma); brain tumors; breast cancer; bronchial tumors (lung cancer); burkitt lymphoma—see non-hodgkin lymphoma; carcinoid tumor (gastrointestinal); carcinoma of unknown primary; cardiac (heart) tumors, childhood; central nervous system; atypical teratoid/rhabdoid tumor, childhood (brain cancer); medulloblastoma and other cns embryonal tumors, childhood (brain cancer); germ cell tumor, childhood (brain cancer); primary cns lymphoma; cervical cancer; childhood cancers; cancers of childhood, unusual; cholangiocarcinoma—see bile duct cancer; chordoma, childhood (bone cancer); chronic lymphocytic leukemia (CLL); chronic myelogenous leukemia (CIVIL); chronic myeloproliferative neoplasms; colorectal cancer; craniopharyngioma, childhood (brain cancer); cutaneous t-cell lymphoma—see lymphoma (mycosis fungoides and sézary syndrome); ductal carcinoma in situ (DCIS)—see breast cancer; embryonal tumors, medulloblastoma and other central nervous system, childhood (brain cancer); endometrial cancer (uterine cancer); ependymoma, childhood (brain cancer); esophageal cancer; esthesioneuroblastoma (head and neck cancer); ewing sarcoma (bone cancer); extracranial germ cell tumor, childhood; extragonadal germ cell tumor; eye cancer; intraocular melanoma; retinoblastoma; fallopian tube cancer; fibrous histiocytoma of bone, malignant, and osteosarcoma; gallbladder cancer; gastric (stomach) cancer; gastrointestinal carcinoid tumor; gastrointestinal stromal tumors (GIST) (soft tissue sarcoma); germ cell tumors; childhood central nervous system germ cell tumors (brain cancer); childhood extracranial germ cell tumors; extragonadal germ cell tumors; ovarian germ cell tumors; testicular cancer; gestational trophoblastic disease; hairy cell leukemia; head and neck cancer; heart tumors, childhood; hepatocellular (liver) cancer; histiocytosis, langerhans cell; hodgkin lymphoma; hypopharyngeal cancer (head and neck cancer); intraocular melanoma; islet cell tumors, pancreatic neuroendocrine tumors; kaposi sarcoma (soft tissue sarcoma); kidney (renal cell) cancer; langerhans cell histiocytosis; laryngeal cancer (head and neck cancer); leukemia; lip and oral cavity cancer (head and neck cancer); liver cancer; lung cancer (non-small cell, small cell, pleuropulmonary blastoma, and tracheobronchial tumor); lymphoma; male breast cancer; malignant fibrous histiocytoma of bone and osteosarcoma; melanoma; melanoma, intraocular (eye); merkel cell carcinoma (skin cancer); mesothelioma, malignant; metastatic cancer; metastatic squamous neck cancer with occult primary (head and neck cancer); midline tract carcinoma with nut gene changes; mouth cancer (head and neck cancer); multiple endocrine neoplasia syndromes; multiple myeloma/plasma cell neoplasms; mycosis fungoides (lymphoma); myelodysplastic syndromes, myelodysplastic/myeloproliferative neoplasms; myelogenous leukemia, chronic (CIVIL); myeloid leukemia, acute (AML); myeloproliferative neoplasms, chronic; nasal cavity and paranasal sinus cancer (head and neck cancer); nasopharyngeal cancer (head and neck cancer); neuroblastoma; non-hodgkin lymphoma; non-small cell lung cancer; oral cancer, lip and oral cavity cancer and oropharyngeal cancer (head and neck cancer); osteosarcoma and malignant fibrous histiocytoma of bone; ovarian cancer; pancreatic cancer; pancreatic neuroendocrine tumors (islet cell tumors); papillomatosis (childhood laryngeal); paraganglioma; paranasal sinus and nasal cavity cancer (head and neck cancer); parathyroid cancer; penile cancer; pharyngeal cancer (head and neck cancer); pheochromocytoma; pituitary tumor; plasma cell neoplasm/multiple myeloma; pleuropulmonary blastoma (lung cancer); pregnancy and breast cancer; primary central nervous system (CNS) lymphoma; primary peritoneal cancer; prostate cancer; rectal cancer; recurrent cancer; renal cell (kidney) cancer; retinoblastoma; rhabdomyosarcoma, childhood (soft tissue sarcoma); salivary gland cancer (head and neck cancer); sarcoma; childhood rhabdomyosarcoma (soft tissue sarcoma); childhood vascular tumors (soft tissue sarcoma); ewing sarcoma (bone cancer); kaposi sarcoma (soft tissue sarcoma); osteosarcoma (bone cancer); soft tissue sarcoma; uterine sarcoma; Sezary syndrome (lymphoma); skin cancer; small cell lung cancer; small intestine cancer; soft tissue sarcoma; squamous cell carcinoma of the skin—see skin cancer; squamous neck cancer with occult primary, metastatic (head and neck cancer); stomach (gastric) cancer; t-cell lymphoma, cutaneous—see lymphoma (mycosis fungoides and Sezary syndrome); testicular cancer; throat cancer (head and neck cancer); nasopharyngeal cancer; oropharyngeal cancer; hypopharyngeal cancer; thymoma and thymic carcinoma; thyroid cancer; tracheobronchial tumors (lung cancer); transitional cell cancer of the renal pelvis and ureter (kidney (renal cell) cancer); unknown primary carcinoma; unusual cancers of childhood; ureter and renal pelvis, transitional cell cancer (kidney (renal cell) cancer; urethral cancer; uterine cancer, endometrial; uterine sarcoma; vaginal cancer; vascular tumors (soft tissue sarcoma); vulvar cancer; Wilms tumor and other childhood kidney tumors; or cancer in young adults or any cancer mentioned at https://www.cancer.gov/types.

In addition to the treatment of cancer, the protein complexes of the present disclosure have potential applications in a variety of other settings where targeted, conditional activity may be advantageous. In autoimmune and inflammatory disease, therapeutics that act through global immune suppression have the disadvantage of leaving patients more susceptible to a variety of opportunistic infections. Additionally, the short half-life and lack of accumulation in disease tissues may limit the efficacy of immune-dampening recombinant cytokines. The protein complexes of the present disclosure may address these shortcomings by allowing targeted delivery of immune modulators including IL-4, IL-10, TGF-β, and TNFR2 selectively to affected anatomical locations while remaining silent in the periphery. Additional applications may include cell type-specific therapeutic targeting, such Treg cell-directed IL-2. Targeted, conditional activation of opioid agonists in specific organs or in the presence of markers of inflammation may reduce the addictive risk of pain control.

A protein complex may be administered as a pharmaceutical composition. A pharmaceutical composition of the disclosure can be a combination of any protein complex described herein with other chemical components, such as carriers, stabilizers, diluents, dispersing agents, suspending agents, thickening agents, and/or excipients. The pharmaceutical composition facilitates administration of a protein complex described herein to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, inhalation, dermal, intra-articular, intrathecal, intranasal, and topical administration. A pharmaceutical composition can be administered in a local or systemic manner, for example, via injection of the protein complex described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a protein complex described herein in water-soluble form. Suspensions of protein complexes described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduces the aggregation of such protein complexes described herein to allow for the preparation of highly concentrated solutions. Alternatively, the protein complexes described herein can be lyophilized or in powder form for re-constitution with a suitable vehicle, e.g., sterile pyrogen-free water, before use. In some embodiments, a purified protein complex is administered intravenously. A protein complex of the present disclosure may comprise a sufficiently long serum half life (e.g., as demonstrated in EXAMPLE 17) to enable dosing regimens comprising daily, alternating day, twice weekly, weekly, biweekly, or monthly dosing frequencies. A protein complex of the present disclosure may comprise a serum half-life of at least 12 hours, at least 24 hours, at least 36 hours, at least 48 hours, at least 72 hours, at least 96 hours, at least 120 hours, at least 168 hours, at least 250 hours, at least 320 hours, or at least 400 hours. The serum half-life may be a human serum half-life, a murine serum half-life, a porcine serum-half life, a bovine serum half-life, a canine serum half-life, a feline serum half-life, or a leporine serum half-life.

A protein complex of the disclosure can be applied directly to an organ, or an organ tissue or cells, during a surgical procedure, or via transdermal, subcutaneous, intramuscular, intratumoral, intrathecal, topical, or local delivery. In some embodiments, a protein complex of the present disclosure may be injected directly into the synovium (e.g., for administration of a protein complex comprising IL-10 for rheumatoid arthritis). In some embodiments, a protein complex may be applied directly to a cancerous tissue (e.g., a tumor). The protein complexes described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the protein complex described herein are administered in pharmaceutical compositions to a subject suffering from a condition. In some instances the pharmaceutical composition will affect the physiology of the animal, such as the immune system, inflammatory response, or other physiologic affect. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a protein complex described herein can be manufactured, for example, by expressing the protein complex in a recombinant system, purifying the protein complex, lyophilizing the protein complex, mixing, or dissolving. The pharmaceutical compositions can include at least one pharmaceutically acceptable carrier, diluent, or excipient and compounds described herein as free-base or pharmaceutically-acceptable salt form.

Methods for the preparation of protein complexes described herein include formulating the protein complex described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

Certain methods described herein comprise administering to the subject an intravenous pharmaceutical composition comprising a protein complex of the present disclosure, for example, as described herein. Intravenous pharmaceutical compositions of protein complexes include any formulation suitable for administration to a subject via any intravenous method, including a bolus, an infusion which occurs over time or any other intravenous method known in the art. In some aspects, the rate of infusion is such that the dose is administered over a period of less than five minutes, more than five minutes but less than 15 minutes or greater than 15 minutes. In other aspects, the rate of infusion is such that the dose is administered over a period of less than 5 minutes. In other aspects, the rate of infusion is such that the dose is administered over a period of greater than 5 minutes and less than 15 minutes. In some other aspects, the rate of infusion is such that the dose is administered over a period of greater than 15 minutes.

"Product" or "dosage form" as used herein refers to any solid, semi-solid, lyophilized, aqueous, liquid or frozen formulation or preparation used for administration. Upon administration, the rate of release of an active moiety from a product is often greatly influenced by the excipients and/or product characteristics which make up the product itself. For example, an enteric coat on a tablet is designed to separate that tablet's contents from the stomach contents to prevent, for example, degradation of the stomach which often induces gastrointestinal discomfort or injury. According to the currently accepted conventional understanding, systemic exposure of the active moiety will be relatively insensitive to the small formulation changes.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

A protein complex of the present disclosure may be administered to a patient in an effective amount. The term "effective amount," as used herein, can refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. Compositions containing such agents or compounds can be administered for prophylactic, enhancing, and/or therapeutic treatments. An appropriate "effective" amount in any individual case can be determined using techniques, such as a dose escalation study.

The methods, compositions, and kits of this disclosure can comprise a method to prevent, treat, arrest, reverse, or ameliorate the symptoms of a condition. The treatment can comprise treating a subject (e.g., an individual, a domestic animal, a wild animal or a lab animal afflicted with a disease or condition) with a protein complex of the disclosure. Protein complexes of the present disclosure may be administered to treat a disease in a subject. The subject can be a human. A subject can be a human; a non-human primate such as a chimpanzee, or other ape or monkey species; a farm animal such as a cattle, horse, sheep, goat, swine; a domestic animal such as a rabbit, dog, and cat; a laboratory animal including a rodent, such as a rat, mouse and guinea pig, or the like. A subject can be of any age. A subject can be, for example, an elderly adult, adult, adolescent, pre-adolescent, child, toddler, infant, or fetus in utero.

Treatment can be provided to the subject before clinical onset of disease. Treatment can be provided to the subject after clinical onset of disease. Treatment can be provided to the subject after 1 day, 1 week, 6 months, 12 months, or 2 years or more after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment can also include treating a human in a clinical trial. A treatment can comprise administering to a subject a pharmaceutical composition, such as one or more of the pharmaceutical compositions described throughout the disclosure. A treatment can comprise a once daily dosing. A treatment can comprise delivering a protein complex of the disclosure to a subject, either intravenously, subcutaneously, intramuscularly, by inhalation, dermally, intra-articular injection, orally, intrathecally, transdermally, intranasally, via a peritoneal route, or directly onto or into a diseased tissue, e.g., via topical, intra-articular injection route or injection route of application.

In some embodiments, the present disclosure provides a method for treating a cancer, the method comprising administering to a subject in need thereof an effective amount of a protein complex of the present disclosure.

In some embodiments, the present disclosure provides a method for treating a cancer, the method comprising administering to a patient in need thereof an effective amount of a pharmaceutical composition comprising a protein complex of the present disclosure and a pharmaceutically acceptable carrier.

Kits

A protein complex of the present disclosure may be provided in various kits. In some embodiments, pharmaceutical compositions comprising a protein complex of the present disclosure may be supplied as a kit. A kit may comprise a container that comprises a protein complex. Therapeutic protein complexes can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic protein complexes. Such a kit may further comprise written information on indications and usage of the pharmaceutical composition.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

EXAMPLES

The following examples are illustrative and non-limiting to the scope of the devices, methods, systems, and kits described herein.

Example 1

Selection of IFNα and PD-L1 Specific Dual Binding Antibodies (DBAs)

This example describes isolation of sensor domains of the present disclosure, specifically, selection of IFNα and PD-L1 specific dual binding antibodies (DBAs). Anti-PD-L1 and anti-IFNα DBAs were isolated from a Tumbler antibody phage display library (Distributed Bio, Inc.). The antibody phage display library was constructed to incorporate the heavy chain CDR1, heavy chain CDR2, and light chain diversity of the Superhuman 2.0 antibody library combined with 10 heavy chain ("HC") CDR3 sequences (SEQ ID NO: 1-SEQ ID NO: 10) from the PD-L1 binding antibodies described, as shown below in TABLE 2.

TABLE 2

| HC-CDR3 of PD-L1 binders | | |
|---|---|---|
| SEQ ID NO | Sequence | Description |
| SEQ ID NO: 1 | CARDRIAVAGFDYW | HC-CDR3 of PD-L1 binder |
| SEQ ID NO: 2 | CAKEVFSGWYDYW | HC-CDR3 of PD-L1 binder |
| SEQ ID NO: 3 | CTTDLLSLELDDAFDIW | HC-CDR3 of PD-L1 binder |
| SEQ ID NO: 4 | CARSLFPTIFGVEVAFDIW | HC-CDR3 of PD-L1 binder |

TABLE 2-continued

| HC-CDR3 of PD-L1 binders | | |
|---|---|---|
| SEQ ID NO | Sequence | Description |
| SEQ ID NO: 5 | CARDSYYYDSFDYW | HC-CDR3 of PD-L1 binder |
| SEQ ID NO: 6 | CARHGEWGSGWPFDYW | HC-CDR3 of PD-L1 binder |
| SEQ ID NO: 7 | CARDLLPAIFSGEVNDAFDIW | HC-CDR3 of PD-L1 binder |
| SEQ ID NO: 8 | CARETIAVAGFDPW | HC-CDR3 of PD-L1 binder |
| SEQ ID NO: 9 | CARDVLPTIFGVVSDAFDIW | HC-CDR3 of PD-L1 binder |
| SEQ ID NO: 10 | CARGDYGDYFDYW | HC-CDR3 of PD-L1 binder |

Figure 3:
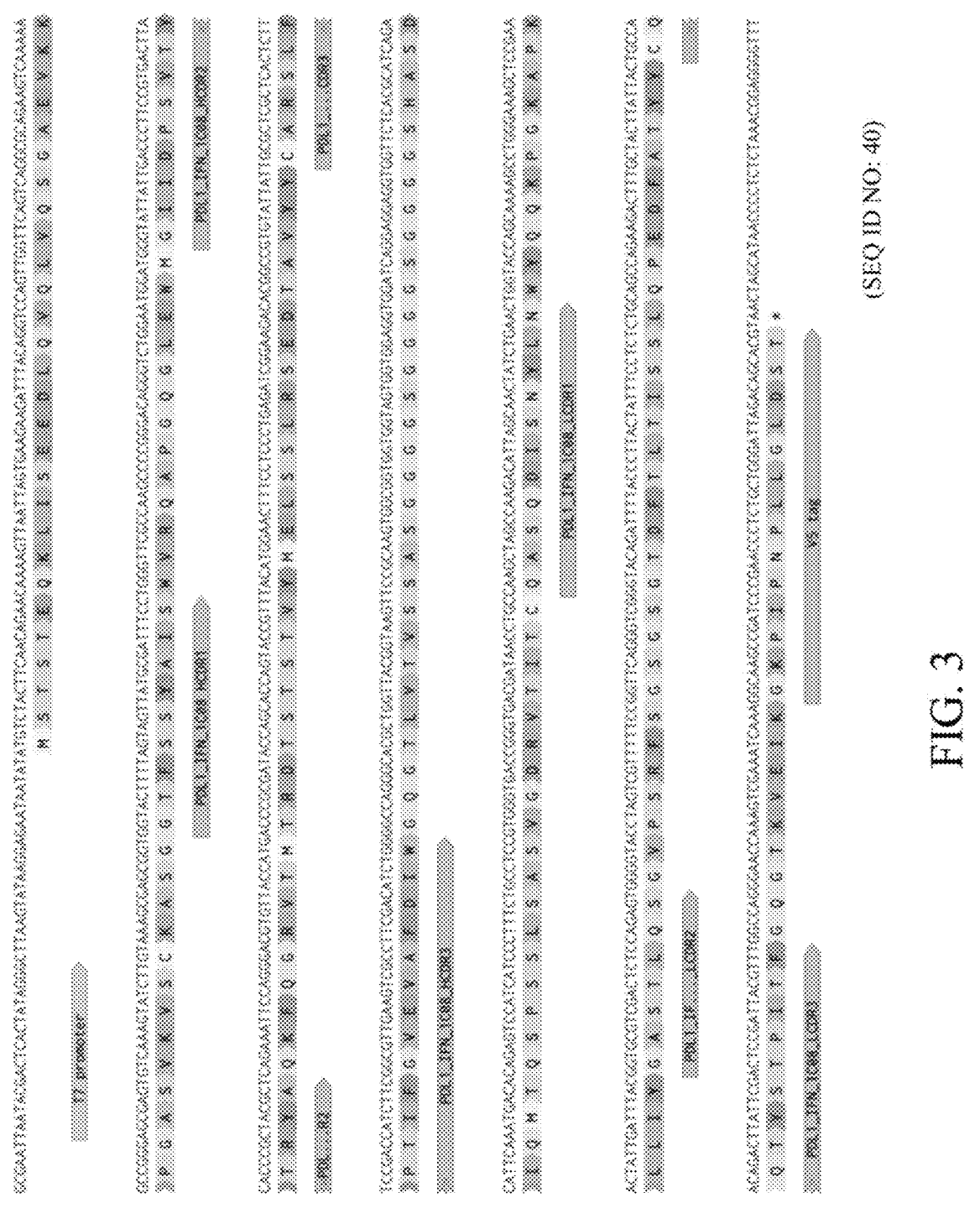

The library was subjected to four rounds of selection alternating between PD-L1 (to develop the PD-L1 binding, where PD-L1 serves as a marker) and IFNα (to develop IFNα binding, where IFNα is the therapeutic domain regulated by the sensor domain). Each round the phage library was incubated with the antigen (PD-L1 or IFNα), captured on magnetic beads, washed on a Kingfisher magnetic particle processor, eluted from the magnetic beads, and amplified by passaging in *E. coli*. In Round 1, the phage library was incubated with 50 nM of a human PD-L1-Fc fusion (R&D Systems, Prod. Num. 156-B7) and captured on protein G magnetic beads. In Round 2, the phage library was incubated with 100 nM of biotinylated human IFNα (Genscript, Prod. Num. Z03003, biotinylated using standard protocols) and captured on streptavidin magnetic beads. In Round 3, the phage library was incubated with 50 nM of a cynomolgus PD-L1-Fc fusion and captured on protein G magnetic beads. In Round 4, the phage library was incubated with 50 nM of biotinylated human IFNα and captured on streptavidin magnetic beads. The final selection was plated as single colonies and 380 colonies were picked for Sanger sequencing. Forty-one unique clones were chosen for expression. The scFv sequence for each clone was codon-optimized for *E. coli* expression and the corresponding DNA sequences synthesized as gBlocks (Integrated DNA Technologies, Inc.) with a T7 promoter, a translation initiation site, a Myc tag, the scFv sequence, a V5 tag sequence, and a T7 terminator. If the framework sequence of the antibody variable regions differed from the germline sequence, a second version of the clone was synthesized with the germline sequence. An exemplary sequence of a gBlock expression fragment is shown in FIG. 3 (SEQ ID NO: 40, GCGAATTAATACGACTCACTATAGGGCT-TAAGTATAAGGAGAATAATATATGTCTA CTT-CAACAGAACAAAAGTTAATTAGTGAAGAAGATT-TACAGGTCCAGTTGGTTCAG
TCAGGCGCAGAAGTCAAAAAGCCGG-GAGCGAGTGTCAAAGTATCTTGTAAAGCGA
GCGGTGGTACTTTTAGTAGTTATGCGAT-TTCCTGGGTTCGCCAAGCCCCGGGACAGG GTCTG-GAATGGATGGGTATTATTGACCCTTCCGTGACTTA-CACCCGCTACGCTCAGA
AATTCCAGGGACGTGTTACCATGACCCGCGA-TACCAGCACCAGTACCGTTTACATG
GAACTTTCCTCCCTGAGATCGGAA-GACACGGCCGTGTATTATTGCGCTCGCTCACTC TTTCCGACCATCTTCGGCGTTGAAGTCGCCTTCGACATCTGGGGCCAGGGCACGCTGGTTACGGTAAGTTCCGCAAGTGGCGGTGGTGGTAGTGGTGGAGGTGGATCAGGAGG AGGTGGTTCTCACGCATCAGACATTCAAATGACACAGAGTCCATCATCCCTTTCTGC CTCCGTGGGTGACCGGGTGACGATAACCTGCCAAGCTAGCCAAGACATTAGCAACTATCTGAACTGGTACCAGCAAAAGCCTGGGAAAGCTCCGAAACTATTGATTTACGGTGCGTCGACTCTCCAGAGTGGGGTACCTAGTCGTTTTTCCGGTTCAGGGTCGGGTACA GATTTTACCCTTACTATTTCCTCTCTGCAGCCAGAAGACTTTGCTACTTATTACTGCC AACAGACTTATTCGACTCCGATTACGTTTGGCCAGGGAACCAAAGTCGAAATCAAAGGCAAGCCGATCCCGAACCCTCTGCTGGGATTAGACAGCACGTAACTAGCATAACCCCTCTCTAAACGGAGGGGTTT). Proteins from each of the gBlock fragments were expressed using a cell-free transcription/translation system (Cosmo Bio USA, Inc., PUREfrex2.1, Product #GFK-PF213 with DS Supplement, Prod. #GFK-PF005).

The cell-free expression samples containing V5-tagged scFvs were serially diluted in a 384-well plate. Alexa Fluor 647-labeled anti-V5 antibody was added to each well along with Eu-labeled IFNα 2a or PD-L1. Plates were incubated at room temperature for 2 hours and the HTRF signal was read on an Envision (Perkin Elmer) equipped with an HTRF laser module. To examine the ability of DBA binding domains to block Interferon alpha Receptor 2 (IFNAR2) binding to IFNα, V5-tagged DBA scFvs were synthesized using the TABLE 3-continued DBAs and Controls

| SEQ ID NO | Sequence | Description |
|---|---|---|
| | NYLNWYQQKPGKAPKLLIYAASSLQSGVP<br>SRFSGSGSGTDFTLTISSLQPEDFATYYC<br>QQSYSTPPTFGQGTRLEIK | |
| SEQ ID NO: 26 | QVQLVQSGAEVKKPGASVKVSCKASGGTF<br>SSYAISWVRQAPGQGLEWMGIIDPSVTYT<br>RYAQKFQGRVTMTRDTSTSTVYMELSSLR<br>SEDTAVYYCARSLFPTIFGVEVAFDIWGQ<br>GTLVTVSSASGGGGSGGGGSGGGGSHASD<br>IQMTQSPSSLSASVGDRVTITCQASQDIS<br>NYLNWYQQKPGKAPKLLIYGASTLQSGVP<br>SRFSGSGSGTDFTLTISSLQPEDFATYYC<br>QQTYSTPITFGQGTKVEIK | DBA capable of binding a PD-L1 marker and IFNα therapeutic domain |
| SEQ ID NO: 27 | QVQLVQSGAEVKKPGASVKVSCKASGGTF<br>SSYAISWVRQAPGQGLEWMGWMDANNGNT<br>GYAQKFQGRVTMTRDTSTSTVYMELSSLR<br>SEDTAVYYCARSLFPTIFGVEVAFDIWGQ<br>GTLVTVSSASGGGGSGGGGSGGGGSHASD<br>IQMTQSPSSLSASVGDRVTITCRASQSVS<br>SYLNWYQQKPGKAPKLLIYKASSLESGVP<br>SRFSGSGSGTDFTLTISSLQPEDFATYYC<br>QQSSSTPLSFGGGTKVEIK | DBA capable of binding a PD-L1 marker and IFNα therapeutic domain |
| SEQ ID NO: 28 | EVQLVESGGGLVQPGGSLRLSCAASGFNI<br>KDTYIHWVRQAPGKGLEWVARIYPTNGYT<br>RYADSVKGRFTISADTSKNTAYLQMNSLR<br>AEDTAVYYCSRWGGDGFYAMDYWGQGTLV<br>TVSSASGGGGSGGGGSGGGGSHASDIQMT<br>QSPSSLSASVGDRVTITCRASQDVNTAVA<br>WYQQKPGKAPKLLIYSASFLYSGVPSRFS<br>GSRSGTDFTLTISSLQPEDFATYYCQQHY<br>TTPPTFGQGTKVEIK | Anti-HER2 control |
| SEQ ID NO: 29 | EVQLVESGGGLVQPGGSLRLSCAASGFTF<br>SDSWIHWVRQAPGKGLEWVAWISPYGGST<br>YYADSVKGRFTISADTSKNTAYLQMNSLR<br>AEDTAVYYCARRHWPGGFDYWGQGTLVTV<br>SSAASGGGGSGGGGSGGGGSHASDIQMTQ<br>SPSSLSASVGDRVTITCRASQDVSTAVAW<br>YQQKPGKAPKLLIYSASFLYSGVPSRFSG<br>SGSGTDFTLTISSLQPEDFATYYCQQYLY<br>HPATFGQGTKVEIK | Anti-PD-L1 control |
| SEQ ID NO: 30 | EVQLVESGGGLVQPGGSLRLSCATSGYTF<br>TEYIIHWVRQAPGKGLEWVASINPDYDIT<br>NYNQRFKGRFTISLDKSKRTAYLQMNSLR<br>AEDTAVYYCASWISDFFDYWGQGTLVTVS<br>SASGGGGSGGGGSGGGGSHASDIQMTQSP<br>SSLSASVGDRVTITCRASQSVSTSSYSYM<br>HWYQQKPGKAPKVLISYASNLESGVPSRF<br>SGSGSGTDFTLTISSLQPEDFATYYCQHS<br>WGIPRTFGQGTKVEIK | Anti-IFNα control |

TABLE 4

Fluorescence Signal Values from Binding and Inhibition Curves

| Name | PDL1 Binding | IFNα Binding | IFNAR2-IFN binding |
|---|---|---|---|
| PDL1-IFN-R01-A03 | 2,715 | 20,447 | 42,528 |
| PDL1-IFN-R01-A04 | 2,377 | 10,890 | 45,590 |
| PDL1-IFN-R01-A05 (SEQ ID NO: 21) | 3,113 | 7,115 | 50,505 |
| PDL1-IFN-R01-A06 (SEQ ID NO: 22) | 2,781 | 8,563 | 44,019 |
| PDL1-IFN-R01-A07 | 3,010 | 4,496 | 52,343 |
| PDL1-IFN-R01-A08 | 2,274 | 19,905 | 40,314 |
| PDL1-IFN-R01-A09 | 1,628 | 6,585 | 50,070 |
| PDL1-IFN-R01-A09V2 | 1,894 | 5,264 | 49,709 |
| PDL1-IFN-R01-A10 | 1,969 | 6,105 | 48,781 |
| PDL1-IFN-R01-A11 (SEQ ID NO: 23) | 2,965 | 14,613 | 41,796 |
| PDL1-IFN-R01-A12 | 2,133 | 9,478 | 53,273 |
| PDL1-IFN-R01-B01 | 3,172 | 7,460 | 44,230 |
| PDL1-IFN-R01-B02 | 2,695 | 7,190 | 42,135 |
| PDL1-IFN-R01-B03 | 2,383 | 4,072 | 44,076 |
| PDL1-IFN-R01-B04 | 2,518 | 12,736 | 42,948 |
| PDL1-IFN-R01-B04V2 | 2,703 | 12,952 | 43,748 |
| PDL1-IFN-R01-B05 | 2,074 | 3,480 | 50,563 |
| PDL1-IFN-R01-B06 | 3,084 | 17,212 | 43,958 |
| PDL1-IFN-R01-B07 | 2,897 | 6,271 | 40,647 |
| PDL1-IFN-R01-B07V2 | 2,907 | 6,111 | 42,880 |
| PDL1-IFN-R01-B08 | 2,924 | 4,042 | 46,089 |
| PDL1-IFN-R01-B09 (SEQ ID NO: 24) | 1,378 | 35,717 | 31,232 |
| PDL1-IFN-R01-B10 | 899 | 4,118 | 46,508 |
| PDL1-IFN-R01-B11 | 2,525 | 14,580 | 43,204 |

TABLE 4-continued

Fluorescence Signal Values from Binding and Inhibition Curves

| Name | PDL1 Binding | IFNα Binding | IFNAR2-IFN binding |
|---|---|---|---|
| PDL1-IFN-R01-B12 (SEQ ID NO: 25) | 2,977 | 9,230 | 44,505 |
| PDL1-IFN-R01-C01 | 2,780 | 6,975 | 47,032 |
| PDL1-IFN-R01-C02 | 2,923 | 4,123 | 49,398 |
| PDL1-IFN-R01-C03 | 2,671 | 6,522 | 46,323 |
| PDL1-IFN-R01-C04 | 2,917 | 7,761 | 48,699 |
| PDL1-IFN-R01-C05 | 2,802 | 3,427 | 47,470 |
| PDL1-IFN-R01-C06 | 399 | 4,380 | 49,878 |
| PDL1-IFN-R01-C06V2 | 391 | 4,130 | 47,685 |
| PDL1-IFN-R01-C07 | 2,139 | 24,494 | 43,262 |
| PDL1-IFN-R01-C08 (SEQ ID NO: 26) | 2,746 | 45,175 | 14,739 |
| PDL1-IFN-R01-C08V2 | 2,812 | 55,319 | 16,753 |
| PDL1-IFN-R01-C09 | 2,388 | 4,346 | 48,696 |
| PDL1-IFN-R01-C10 | 2,489 | 12,727 | 43,275 |
| PDL1-IFN-R01-C10V2 | 2,665 | 11,972 | 43,576 |
| PDL1-IFN-R01-C11 (SEQ ID NO: 27) | 3,043 | 7,730 | 40,503 |
| PDL1-IFN-R01-C12 | 1,006 | 13,135 | 44,871 |
| PDL1-IFN-R01-D01 | 582 | 7,018 | 39,109 |
| PDL1-IFN-R01-D03 | 2,904 | 6,084 | 42,638 |
| PDL1-IFN-R01-D05 | 2,325 | 6,402 | 49,246 |
| PDL1-IFN-R01-D06 | 2,907 | 8,326 | 45,581 |
| PDL1-IFN-R01-D07 | 414 | 4,974 | 38,164 |
| anti-Her2 control (SEQ ID NO: 28) | 425 | 4,275 | 52,922 |
| Anti-PD-L1 control (SEQ ID NO: 29) | 2,445 | 1,803 | 39,121 |
| Anti-IFN control (SEQ ID NO: 30) | 416 | 19,098 | 51,190 |
| No DNA control | 422 | 4,135 | 45,042 |

Example 2

Isolation of a Set of Dual-Binding Antibodies (DBAs) that Bind Human PD-1 and Human IL-2

This example describes the isolation of sensor domains of the present disclosure, specifically, a set of DBAs that bind human PD-1 and human IL-2. Anti-PD-1 and anti-IL-2 DBAs were isolated from a Tumbler antibody phage display library (Distributed Bio, Inc.). The antibody phage display library was constructed to incorporate the heavy chain CDR1, heavy chain CDR2, and light chain diversity of the Superhuman 2.0 antibody library combined with 10 heavy chain CDR3 sequences from PD-1 binding antibodies (SEQ ID NO: 11-SEQ ID NO: 20).

TABLE 5

HC-CDR3 of PD-1 binders

| SEQ ID NO | Sequence | Description |
|---|---|---|
| SEQ ID NO: 11 | CAAGLFIW | HC-CDR3 of PD-1 binder |
| SEQ ID NO: 12 | CAGGWLDW | HC-CDR3 of PD-1 binder |
| SEQ ID NO: 13 | CARDHLGGSYQPW | HC-CDR3 of PD-1 binder |
| SEQ ID NO: 14 | CARDLVGVSPGINYVPRYYYYYGMDVW | HC-CDR3 of PD-1 binder |
| SEQ ID NO: 15 | CARDTGLGYYYGSGDFDYW | HC-CDR3 of PD-1 binder |
| SEQ ID NO: 16 | CARSGYSYGYYFDYW | HC-CDR3 of PD-1 binder |
| SEQ ID NO: 17 | CARTGGYPAIDSW | HC-CDR3 of PD-1 binder |
| SEQ ID NO: 18 | CASGWDVW | HC-CDR3 of PD-1 binder |
| SEQ ID NO: 19 | CASSPLQWVDVW | HC-CDR3 of PD-1 binder |
| SEQ ID NO: 20 | CTSGMDVW | HC-CDR3 of PD-1 binder |

This library was subjected to four rounds of selection with standard protocols. In brief, the phage library was incubated with the antigen, then captured on magnetic beads and washed on a Kingfisher magnetic particle processor, eluted form the magnetic beads and amplified by passaging in *E. coli*. Round 1 was incubated with 50 nM human PD-1-His fusion (R&D Systems, Prod. Num. 8986-PD) and captured with TRIS NTA Biotin (Sigma-Aldrich Prod. Num. 75543) and streptavidin magnetic beads. Round 2 was incubated with 100 nM biotinylated IL-2 (Creative Biomart, Prod. Num. IL2-501H, biotinylated using standard protocols) and captured on streptavidin magnetic beads. Round 3 was incubated with 50 nM cynomolgus PD-1-Fc fusion (R&D Systems, Prod. Num. 8578-PD) and captured on protein G magnetic beads. Round 4 was incubated with 50 nM biotinylated human IL-2 and captured on streptavidin magnetic beads. The final selection was plated as single colonies and 380 colonies picked for Sanger sequencing. One hundred and fifty-one unique clones were chosen for expression. The scFv sequence for each clone was codon-optimized for *E. coli* expression and the corresponding DNA sequences sent to Integrated DNA Technologies, Inc. (IDT) for synthesis as gBlocks with a T7 promoter, a translation initiation site and a T7 terminator (see an exemplary gBlock sequence in FIG. 3). Protein from each gBlock encoding an scFv was expressed using the PURExpress In vitro Protein Synthesis Kit (New England Biolabs, Inc., Prod. Num. E6800). The PURExpress scFv proteins were used directly in HTRF binding assays and cell-based functional assays. Each scFv was tested for binding to PD-1 and to human IL-2. Eighty-one of the antibodies showed dual-binding activity for both PD-1 and IL-2 and a summary of fluorescence signal values of binding curves is shown in TABLE 7. To examine the ability of DBA binding domains to block IL-2 receptor binding, V5-tagged DBA scFvs were serially diluted in a 384 well plate. Europium-labeled Streptavidin, biotin-labeled IL-2 (Acro Biosystems, Prod. Num. IL2-H82E4), IL-2 Receptor beta (Fc-IL2RB) (Acro Biosystems, Prod. Num. ILB-H5253), and APC-labeled anti-Fc antibody. Plates were incubated at room temperature for 2 hours, and the HTRF signal was read on an Envision (Perkin Elmer) as a measure of IL-2:IL2RB binding. Four scFvs (SEQ ID NO: 31-SEQ ID NO: 34) bound PD-1, bound IL-2 and blocked binding of IL-2 to IL-2RB (TABLE 7).

TABLE 6

DBAs and Controls

| SEQ ID NO | Sequence | Description |
|---|---|---|
| SEQ ID NO: 31 | QVQLVQSGAEVKKPGVSVKVSCKASGYTFPRSYIHWVRQAPGQGLEWMGWINPHSGDTYYAQNFQGRVTMTRDTSTSTVYMELSSLRSEDTAVYYCARDTGLGYYYGSGDFDYWGQGTLVTVSSASGGGGSGGGGSGGGGSHASDIQMTQSPSSLSASVGDRVTITCRASQSISRYLNWYQQKPGKAPKLLIYTASSLQSGVPSRFSGSGSGTDFTLTISSLQPEDFATYYCQQANRFPLTFGPGTKVDIK | DBA capable of binding a PD-1 marker and IL-2 therapeutic |
| SEQ ID NO: 32 | QVQLVQSGAEVKKPGASVKVSCKASGYTFPRYHIHWVRQAPGQGLEWMGMINPSGGTTTYAQKFQGRVTMTRDTSTSTVYMELSSLRSEDTAVYYCARDTGLGYYYGSGDFDYWGQGTLVTVSSASGGGGSGGGGSGGGGSHASDIQMTQSPSSLSASVGDRVTITCRASQSISSWLAWYQQKPGKAPKLLIYAASSLQSGVPSRFSGSGSGTDFTLTISSLQPEDFATYYCQQSHSFPLTFGGGTKVEIK | DBA capable of binding a PD-1 marker and IL-2 therapeutic |
| SEQ ID NO: 33 | QVQLVQSGAEVKKPGASVKVSCKASGYTFTRYYIHWVRQAPGQGLEWMGWINAYNGDTNYAQKLQGRVTMTRDTSTSTVYMELSSLRSEDTAVYYCARDSYYYDSFDYWGQGTLVTVSSASGGGGGGGGSGGGGSHASDIQMTQSPSSLSASVGDRVTITCRASQTITDWLAWYQQKPGKAPKLLIYGASNLQGGVPSRFSGSGSGTDFTLTISSLQPEDFATYYCQQYYSSWTFGQGTKVEIK | DBA capable of binding a PD-1 marker and IL-2 therapeutic |
| SEQ ID NO: 34 | QVQLVQSGAEVKKPGASVKVSCKASGYTFTSYYMHWVRQAPGQGLEWMGIINPSDGSTTYAQSFQGRVTMTRDTSTSTVYMELSSLRSEDTAVYYCASGWDVWGQGTLVTVSSASGGGGSGGGGSGGGGSHASDIVMTQSPDSLAVSLGERATINCKSSQSVFSSANNKNYLAWYQQKPGQPPKLLIYWASTRESGVPDRFSGSGSGTDFTLTISSLQAEDVAVYYCQQYFGTPVTFGGGTKVEIK | DBA capable of binding a PD-1 marker and IL-2 therapeutic |

TABLE 7

| Name | PD1 Binding | IL2 Binding | IL2RB Blocking |
|---|---|---|---|
| No DNA | 5 | 6 | 1,490 |
| PD1-IL2-R01-H08 | 576 | −9 | 1,829 |
| PD1-IL2-R01-H09 | 1,015 | 131 | 1,772 |
| PD1-IL2-R02-A03 | 1,508 | 635 | 1,714 |
| PD1-IL2-R02-A04 | 909 | 978 | 1,618 |
| PD1-IL2-R02-A05 | 1,557 | 23 | 1,735 |
| PD1-IL2-R02-A06 | 357 | 515 | 1,772 |
| PD1-IL2-R02-A08 | 995 | 520 | 1,612 |
| PD1-IL2-R02-A09 | 1,421 | 1,470 | 1,495 |
| PD1-IL2-R02-A10 | 500 | 838 | 1,847 |
| PD1-IL2-R02-A11 | 1,625 | 1,559 | 1,783 |
| PD1-IL2-R02-A12 | 1,725 | 130 | 1,586 |
| PD1-IL2-R02-B01 | 746 | 1,077 | 1,516 |
| PD1-IL2-R02-B02 | 1,740 | 1,107 | 1,849 |
| PD1-IL2-R02-B04 | 11 | 2,346 | 1,536 |
| PD1-IL2-R02-B05 | 1,665 | 2,489 | 1,613 |
| PD1-IL2-R02-B06 | 1,527 | 32 | 1,605 |
| PD1-IL2-R02-B07 | 1,685 | 628 | 1,814 |
| PD1-IL2-R02-B08 | 1,446 | 92 | 1,680 |
| PD1-IL2-R02-B10 | 211 | 343 | 1,607 |
| PD1-IL2-R02-B11 | 1,426 | 915 | 1,509 |
| PD1-IL2-R02-B12 | 1,264 | 316 | 1,762 |
| PD1-IL2-R02-C01 | 1,463 | 296 | 1,743 |
| PD1-IL2-R02-C02 (SEQ ID NO: 31) | 1,299 | 298 | 1,069 |
| PD1-IL2-R02-C03 (SEQ ID NO: 32) | 1,383 | 293 | 1,211 |
| PD1-IL2-R02-C04 | 1,622 | 575 | 1,857 |
| PD1-IL2-R02-C06 | 1,376 | 34 | 1,684 |
| PD1-IL2-R02-C07 | 34 | 87 | 1,607 |
| PD1-IL2-R02-C08 | 1,468 | 619 | 1,671 |
| PD1-IL2-R02-C10 | 174 | 256 | 1,757 |
| PD1-IL2-R02-C12 | 1,367 | 340 | 1,723 |
| PD1-IL2-R02-D01 | 1,421 | 68 | 1,614 |
| PD1-IL2-R02-D02 | 1,473 | 539 | 1,726 |
| PD1-IL2-R06-A10 | 1,269 | 9 | 1,796 |
| PD1-IL2-R06-A11 | 1,376 | 34 | 1,762 |
| PD1-IL2-R06-A12 | 1,305 | 7 | 1,681 |
| PD1-IL2-R06-B01 | 10 | 2,109 | 1,307 |
| PD1-IL2-R06-B02 | 1,666 | 15 | 1,799 |
| PD1-IL2-R06-B03 | 923 | 4 | 1,661 |
| PD1-IL2-R06-B04 | 1,782 | 28 | 1,666 |
| PD1-IL2-R06-B06 | 1,223 | 17 | 1,648 |
| PD1-IL2-R06-B08 | 1,777 | 1,160 | 1,738 |
| PD1-IL2-R06-B10 | 13 | 31 | 1,847 |
| PD1-IL2-R06-B11 | 1,534 | 24 | 1,699 |
| PD1-IL2-R06-B12 | 822 | 1,125 | 1,604 |
| PD1-IL2-R06-C02 | 1,667 | 26 | 1,671 |
| PD1-IL2-R06-C04 | 1,491 | 7 | 1,759 |
| PD1-IL2-R06-C08 | 1,448 | 8 | 1,693 |
| PD1-IL2-R06-C09 | 1,158 | 1,525 | 1,602 |
| PD1-IL2-R06-C11 | 1,879 | −2 | 1,785 |
| PD1-IL2-R06-C12 | 1,669 | 1,998 | 1,033 |
| PD1-IL2-R06-D02 | 280 | 432 | 1,677 |
| PD1-IL2-R06-D03 | 9 | 93 | 1,606 |
| PD1-IL2-R06-D05 | 505 | −3 | 1,786 |
| PD1-IL2-R06-D07 | 1,577 | 24 | 1,820 |
| PD1-IL2-R06-D10 | 1,751 | 49 | 1,719 |

TABLE 7-continued

| Name | PD1 Binding | IL2 Binding | IL2RB Blocking |
|---|---|---|---|
| PD1-IL2-R06-D11 | 405 | 593 | 1,576 |
| PD1-IL2-R06-D12 | 1,024 | 1,423 | 1,649 |
| PD1-IL2-R06-E01 | 1,628 | 3 | 1,724 |
| PD1-IL2-R06-E02 | 1,554 | 16 | 1,598 |
| PD1-IL2-R06-E04 (SEQ ID NO: 33) | 50 | 247 | 1,108 |
| PD1-IL2-R06-E05 | 1,364 | 14 | 1,734 |
| PD1-IL2-R06-E06 | 1,627 | 15 | 1,735 |
| PD1-IL2-R06-E07 | 1,801 | 12 | 1,698 |
| PD1-IL2-R06-E09 | 1,467 | 11 | 1,511 |
| PD1-IL2-R06-E11 | 1,805 | 294 | 1,767 |
| PD1-IL2-R06-E12 | 4 | −7 | 1,735 |
| PD1-IL2-R06-F01 | 196 | 280 | 1,629 |
| PD1-IL2-R06-F03 | 1,377 | 28 | 1,642 |
| PD1-IL2-R06-F04 | 26 | 779 | 1,726 |
| PD1-IL2-R06-F05 | 1,493 | 18 | 1,625 |
| PD1-IL2-R06-F06 | 1,577 | 46 | 1,595 |
| PD1-IL2-R06-F07 | 1,544 | 335 | 1,682 |
| PD1-IL2-R06-F08 | 1,570 | 9 | 1,780 |
| PD1-IL2-R06-F09 | 30 | 41 | 1,776 |
| PD1-IL2-R06-F10 | 1,745 | 24 | 1,607 |
| PD1-IL2-R06-F11 | 1,586 | 12 | 1,574 |
| PD1-IL2-R06-F12 | 623 | 8 | 1,645 |
| PD1-IL2-R06-G01 | 130 | 184 | 1,640 |
| PD1-IL2-R06-G02 | 1,754 | 20 | 1,623 |
| PD1-IL2-R06-G04 | 1,348 | 13 | 1,596 |
| PD1-IL2-R06-G05 | 1,382 | 10 | 1,846 |
| PD1-IL2-R06-G06 | 1,383 | 4 | 1,744 |
| PD1-IL2-R06-G08 | 1,708 | 124 | 1,533 |
| PD1-IL2-R06-G09 | 557 | 756 | 1,527 |
| PD1-IL2-R06-G10 | 1,595 | 35 | 1,703 |
| PD1-IL2-R06-G11 | 1,469 | 17 | 1,709 |
| PD1-IL2-R06-G12 | 1,281 | 1,479 | 1,713 |
| PD1-IL2-R06-H01 | 381 | 4 | 1,647 |
| PD1-IL2-R06-H02 | 1,501 | 20 | 1,748 |
| PD1-IL2-R06-H03 | 1,132 | 1,449 | 1,617 |
| PD1-IL2-R06-H04 | 355 | 1 | 1,677 |
| PD1-IL2-R06-H05 | 1,409 | 21 | 1,561 |
| PD1-IL2-R06-H06 | 1,491 | 23 | 1,650 |
| PD1-IL2-R06-H07 | 12 | 13 | 1,701 |
| PD1-IL2-R06-H08 | 847 | 1,118 | 1,746 |
| PD1-IL2-R06-H09 | 1,732 | 22 | 1,662 |
| PD1-IL2-R06-H10 | 830 | 1,151 | 1,569 |
| PD1-IL2-R07-A03 | 1,786 | 28 | 1,511 |
| PD1-IL2-R07-A04 | 730 | 973 | 1,613 |
| PD1-IL2-R07-A05 | 477 | 663 | 1,327 |
| PD1-IL2-R07-A08 | 1,628 | 841 | 1,618 |
| PD1-IL2-R07-A09 (SEQ ID NO: 34) | 1,235 | 2,040 | 910 |
| PD1-IL2-R07-A10 | 1,716 | 63 | 1,518 |
| PD1-IL2-R07-B01 | 1,397 | 32 | 1,565 |
| PD1-IL2-R07-B02 | 192 | 321 | 1,634 |
| PD1-IL2-R07-B03 | 65 | 202 | 1,604 |
| PD1-IL2-R07-B04 | 1,862 | 410 | 1,527 |
| PD1-IL2-R07-B05 | 965 | 351 | 1,389 |
| PD1-IL2-R07-B06 | 1,882 | 44 | 1,497 |
| PD1-IL2-R07-B07 | 6 | 2,549 | 1,517 |
| PD1-IL2-R07-B08 | 906 | 1,047 | 1,475 |
| PD1-IL2-R07-B09 | 1,788 | 27 | 1,384 |
| PD1-IL2-R07-B10 | 18 | 19 | 1,635 |
| PD1-IL2-R07-B11 | 1,765 | 9 | 1,641 |
| PD1-IL2-R07-C01 | 230 | 367 | 1,536 |
| PD1-IL2-R07-C02 | 236 | 304 | 1,500 |
| PD1-IL2-R07-C03 | 20 | 1,347 | 1,536 |
| PD1-IL2-R07-C07 | 15 | 275 | 1,665 |
| PD1-IL2-R07-C10 | 1,064 | 317 | 1,550 |
| PD1-IL2-R07-C11 | 1,523 | 642 | 1,460 |
| PD1-IL2-R07-C12 | 1,377 | 49 | 1,707 |
| PD1-IL2-R07-D01 | 1,541 | 79 | 1,657 |
| PD1-IL2-R07-D03 | 1,483 | 33 | 1,481 |
| PD1-IL2-R07-D04 | 923 | 1,104 | 1,517 |
| PD1-IL2-R07-D06 | 1,664 | 416 | 1,734 |
| PD1-IL2-R07-D07 | 6 | 835 | 1,512 |
| PD1-IL2-R07-D10 | 1,580 | 193 | 1,572 |
| PD1-IL2-R07-D11 | 1,401 | 798 | 1,614 |
| PD1-IL2-R07-E02 | 1,473 | 992 | 1,830 |
| PD1-IL2-R07-E03 | 1,459 | 422 | 1,683 |
| PD1-IL2-R07-E05 | 512 | 913 | 1,513 |
| PD1-IL2-R07-E06 | 1,483 | 1,178 | 1,526 |
| PD1-IL2-R07-E07 | 1,181 | 1,060 | 1,524 |
| PD1-IL2-R07-E08 | 1,604 | 472 | 1,717 |
| PD1-IL2-R07-E09 | 1,733 | 23 | 1,569 |
| PD1-IL2-R07-E10 | 1,472 | 251 | 1,545 |
| PD1-IL2-R07-E11 | 1,146 | 56 | 1,777 |
| PD1-IL2-R07-E12 | 1,698 | 106 | 1,764 |
| PD1-IL2-R07-F01 | 3 | 17 | 1,529 |
| PD1-IL2-R07-F02 | 348 | 752 | 1,537 |
| PD1-IL2-R07-F03 | 1,788 | 520 | 1,750 |
| PD1-IL2-R07-F04 | 1,416 | 145 | 1,767 |
| PD1-IL2-R07-F06 | 1,422 | 438 | 1,579 |
| PD1-IL2-R07-F09 | 1,589 | 17 | 1,456 |
| PD1-IL2-R07-F10 | 24 | 19 | 1,778 |
| PD1-IL2-R07-F12 | 505 | 196 | 1,553 |
| PD1-IL2-R07-G01 | 4 | 214 | 1,560 |
| PD1-IL2-R07-G02 | 1,610 | 61 | 1,735 |
| PD1-IL2-R07-G04 | 82 | 147 | 1,600 |
| PD1-IL2-R07-G05 | 981 | 216 | 1,475 |
| PD1-IL2-R07-G06 | 860 | 512 | 1,655 |
| PD1-R04-C10 | 1,552 | 4 | 1,550 |
| PD1-R07-A05 | 653 | 19 | 1,730 |
| PD1-R07-A10 | 484 | 25 | 2,290 |
| PD1-R07-C09 | 1,911 | 20 | 2,080 |
| PD1-R07-D03 | 1,733 | 22 | 2,208 |
| PD1-R07-D05 | 1,760 | 16 | 1,578 |
| PD1-R07-D06 | 1,997 | 22 | 1,749 |
| PD1-R07-E05 | 633 | 24 | 2,246 |
| PD1-R07-G12 | 907 | 11 | 1,577 |
| PD1-R15-B02 | 1,671 | 28 | 1,797 |
| PDL1-DB03-H02 | 18 | 11 | 1,725 |
| Anti-Her2 (SEQ ID NO: 28) | 4 | 20 | 1,636 |

Example 3

Competitive Binding for Targets of Dual Binding Antibodies (DBAs)

Figure 7:
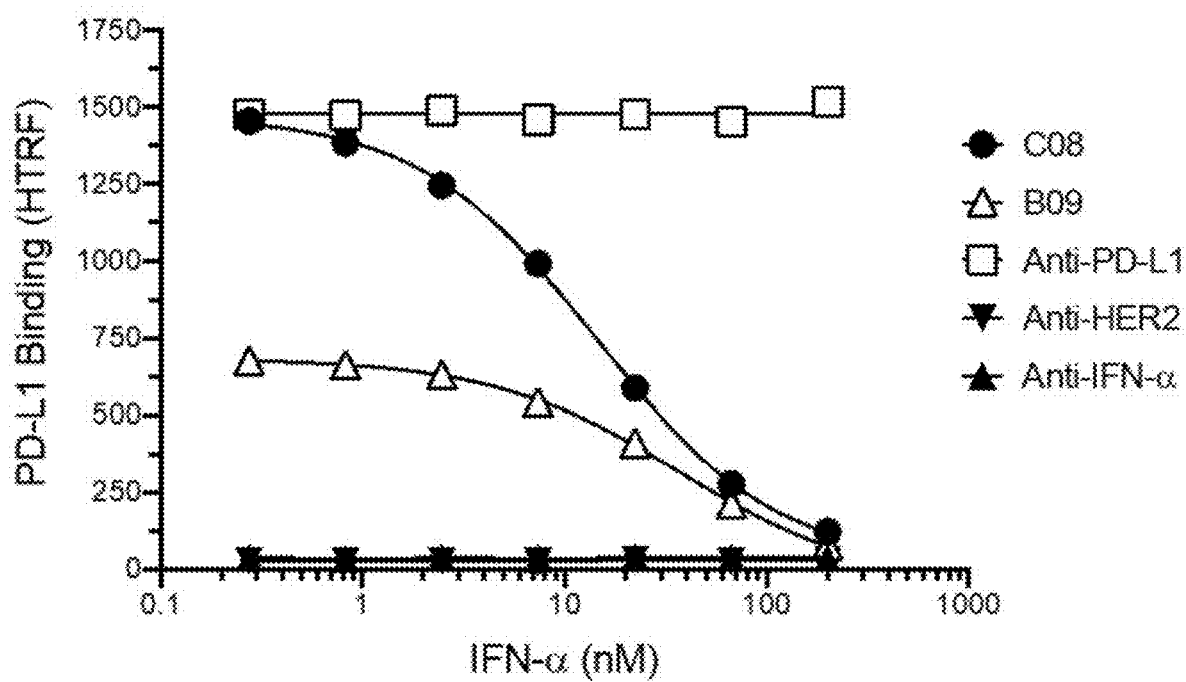
FIG. 7 shows IFNα can compete with PD-L1 for binding to candidate PD-L1/IFNα DBAs of SEQ ID NO: 24 and SEQ ID NO: 26.

This example describes competitive binding between the marker and the therapeutic domain of dual binding antibodies (DBAs). To test the ability of PD-L1 (marker) to compete with IFNα (therapeutic) for binding to the DBA binding domains, V5-tagged DBA or control scFvs were synthesized using the PUREfrex 2.1 in vitro translation system and added to a 384 well plate at a single dilution. Eu-labeled PD-L1 and Alexa Fluor 647-labeled anti-V5 antibody were added to all wells and incubated for 30 minutes at room temperature. Titrated concentrations of IFNα were added to all wells and the plate was incubated for 1 hour at room temperature. The HTRF signal was read on Envision (Perkin Elmer). As shown in FIG. 7, IFNα competed with PD-L1 for binding to DBA clones B09 (SEQ ID NO: 24) and C08 (SEQ ID NO: 26), whereas the binding of an anti-PD-L1 monospecific antibody was unaffected by the concentration of IFNα.

Example 4

Screening Dual Binding Antibodies (DBAs) for Improved Binding Affinity

This example illustrates screening dual binding antibodies (DBAs) for improved binding affinity. The sequences for each DBA were aligned with the parental, single specificity antibody from which it was derived and with other DBAs derived from the same parental, single specificity antibody. Using this sequence information, variants with amino acid substitutions in and adjacent to the CDR regions were designed to test for altered binding to either antigen. Additionally, consideration was given to sequence variants that may improve stability. Representative variants are shown in TABLE 8 and TABLE 9. CDR sequences provided in TABLE 8 and TABLE 9 correspond to HCDR1-HCDR2-HCDR3, with substitutions underlined and in bold. Sequences of dual binding PD-L1 and IFNα variants are provided in TABLE 10.

TABLE 8

Heavy chain CDR regions of anti-PDL1 02_A08, DBA PDL1-IFN_1A05, and variants

| SEQ ID NO | Description | CDR Sequence |
|---|---|---|
| SEQ ID NO: 305 | Parental monospecific antibody PDL1_02_A08 | CKASGYTFSGYYMHW - WMGWMDPNSGYTGYAHQFQGRV - CAKEVFSGWYDYWGQ |
| SEQ ID NO: 306 | Dual-binding antibody (DBA) PDL1-IFN_R01_A05 | CKASGYTFSNYYIHW - WMGWMDSNSGGTGYAQKFQGRV - CAKEVFSGWYDYWGQ |
| SEQ ID NO: 307 | DBA variant H_N36G | CKASGYTFSGYYIHW - WMGWMDSNSGGTGYAQKFQGRV - CAKEVFSGWYDYWGQ |
| SEQ ID NO: 308 | DBA variant H_I39V_S58P_Q69H_K70Q | CKASGYTFSNYYVHW - WMGWMDPNSGGTGYAHQFQGRV - CAKEVFSGWYDYWGQ |
| SEQ ID NO: 309 | DBA variant H_G64Y_Q69H | CKASGYTFSNYYIHW - WMGWMDSNSGYTGYAHKFQGRV - CAKEVFSGWYDYWGQ |

TABLE 9

Light chain CDR regions of anti-PDL1 02_A08, DBA PDL1-IFN_1A05, and variants

| SEQ ID NO | Construct | CDR Sequence |
|---|---|---|
| SEQ ID NO: 310 | Parental monospecific antibody PDL1_02_A08 | CRASQTISSYLNWY - IYAASTLESGVPSR - YYCQQGYSTPITFG PGTKVDIK |
| SEQ ID NO: 311 | Dual-binding antibody (DBA) PDL1-IFN_R01_A05 | CRASQSISSYLNWY - IYAASSLQSGVPSR - YYCQQSYSTPYTFG QGTKVEIK |
| SEQ ID NO: 312 | L_Q68E | CRASQSISSYLNWY - IYAASSLESGVPSR - YYCQQSYSTPYTFG QGTKVEIK |
| SEQ ID NO: 313 | L_Q68E_E125D | CRASQSISSYLNWY - IYAASSLESGVPSR - YYCQQSYSTPYTFG QGTKVDIK |

TABLE 10

Sequences of dual binding PD-L1 and IFNα variants

| SEQ ID NO | Variant | Sequence |
|---|---|---|
| SEQ ID NO: 35 | H_N36G | QVQLVQSGAEVKKPGASVKVSCKASGYTFSGYYIHW VRQAPGQGLEWMGWMDSNSGGTGYAQKFQGRVTMTR DTSTSTVYMELSSLRSEDTAVYYCAKEVFSGWYDYW GQGTLVTVSSASGGGGSGGGGSGGGGSHASDIQMTQ SPSSLSASVGDRVTITCRASQSISSYLNWYQQKPGK APKLLIYAASSLQSGVPSRFSGSGSGTDFTLTISSL QPEDFATYYCQQSYSTPYTFGQGTKVEIK |
| SEQ ID NO: 36 | H_I39V_S58P_Q69H_K70Q | QVQLVQSGAEVKKPGASVKVSCKASGYTFSNYYVHW VRQAPGQGLEWMGWMDPNSGGTGYAHQFQGRVTMTR DTSTSTVYMELSSLRSEDTAVYYCAKEVFSGWYDYW GQGTLVTVSSASGGGGSGGGGSGGGGSHASDIQMTQ SPSSLSASVGDRVTITCRASQSISSYLNWYQQKPGK APKLLIYAASSLQSGVPSRFSGSGSGTDFTLTISSL QPEDFATYYCQQSYSTPYTFGQGTKVEIK |
| SEQ ID NO: 37 | H_G64Y_Q69H | QVQLVQSGAEVKKPGASVKVSCKASGYTFSNYYIHW VRQAPGQGLEWMGWMDSNSGYTGYAHKFQGRVTMTR DTSTSTVYMELSSLRSEDTAVYYCAKEVFSGWYDYW |

TABLE 10-continued

Sequences of dual binding PD-L1 and IFNα variants

| SEQ ID NO | Variant | Sequence |
|---|---|---|
| | | GQGTLVTVSSASGGGGSGGGGSGGGGSHASDIQMTQ<br>SPSSLSASVGDRVTITCRASQSISSYLNWYQQKPGK<br>APKLLIYAASSLQSGVPSRFSGSGSGTDFTLTISSL<br>QPEDFATYYCQQSYSTPYTFGQGTKVEIK |
| SEQ ID NO: 38 | L_Q68E | QVQLVQSGAEVKKPGASVKVSCKASGYTFSNYYIHW<br>VRQAPGQGLEWMGWMDSNSGGTGYAQKFQGRVTMTR<br>DTSTSTVYMELSSLRSEDTAVYYCAKEVFSGWYDYW<br>GQGTLVTVSSASGGGGSGGGGSGGGGSHASDIQMTQ<br>SPSSLSASVGDRVTITCRASQSISSYLNWYQQKPGK<br>APKLLIYAASSLESGVPSRFSGSGSGTDFTLTISSL<br>QPEDFATYYCQQSYSTPYTFGQGTKVEIK |
| SEQ ID NO: 39 | L_Q68E_E125D | QVQLVQSGAEVKKPGASVKVSCKASGYTFSNYYIHW<br>VRQAPGQGLEWMGWMDSNSGGTGYAQKFQGRVTMTR<br>DTSTSTVYMELSSLRSEDTAVYYCAKEVFSGWYDYW<br>GQGTLVTVSSASGGGGSGGGGSGGGGSHASDIQMTQ<br>SPSSLSASVGDRVTITCRASQSISSYLNWYQQKPGK<br>APKLLIYAASSLESGVPSRFSGSGSGTDFTLTISSL<br>QPEDFATYYCQQSYSTPYTFGQGTKVDIK |

The scFv sequence for each variant was codon-optimized for *E. coli* expression and the corresponding DNA sequences synthesized as gBlocks (Integrated DNA Technologies, Inc.) with a T7 promoter, a translation initiation site, a Myc tag, the scFv sequence, a V5 tag sequence and a T7 terminator. Proteins encoded by the gBlock fragments were expressed using a cell-free transcription/translation system (Cosmo Bio USA, Inc., PUREfrex2.1, Product #GFK-PF213 with DS Supplement, Prod. #GFK-PF005). The cell-free expression samples were assayed for PD-L1 and IFNα binding as described in EXAMPLE 1.

Variants with different binding affinities may also be generated by display methods, such as phage display and mRNA display. Libraries for use in these methods may be created from the parental antibody by varying CDRs with random amino acid changes or by varying positions in the CDRs identified as suitable for change.

Example 5

Binding Affinity of Dual Binding Antibodies (DBAs)

This example describes binding affinity of protein complexes, specifically, dual binding antibodies (DBAs). Variants were synthesized as V5-tagged scFvs using the PUREfrex 2.1 in vitro translation system and diluted 1:30 in 1× kinetics buffer (KB, forteBIO) for testing. Biotinylated anti-V5 antibody (clone SV5-Pk1 BioRad, biotinylated using EZ-Link® Sulfo-NHS-LC-Biotin, THERMO) was diluted to 80 nM in 1×KB, then loaded onto streptavidin biosensor tips (SA, forteBIO) on an OctetRED96e instrument. These tips were then loaded with scFv for 240 seconds. The loaded tips were transferred to 1×KB for 60 seconds to establish baseline, then dipped into 160 nM ACRO human PDL1-his for 150 seconds to measure association, then into 1×KB for 180 seconds to measure dissociation. Immediately following this dissociation, baseline signal in 1×KB was measured, the tips were dipped into 5,000 nM IFNα2b (GenScript) for 150 seconds to measure association, then into 1×KB for 240 seconds to measure dissociation. Data were fit to a 1:1 kinetics model. Response for binding of IFNα2b was qualitative negative or positive. Sequences of the DBA variants used in TABLE 11 are provided in TABLE 8 and TABLE 9.

TABLE 11

Kinetics of binding of DBA variants

| | KD (PD-L1, nM) | IFNα binding (@5 uM) |
|---|---|---|
| H_G64Y_Q69H | 13 | +/− |
| H_I39V_S58P_Q69H_K70Q | 8 | − |
| H_N36G | 37 | + |
| L_Q68E | 21 | + |
| L_Q68E_E125D | 21 | + |
| PDL1-IFN_R01_A05 | 120 | Not tested |

The affinity of the DBA in this or other antibody formats may be measured in a similar manner to generate quantitative or semi-quantitative measurements using standard methods of measurement of protein interaction, including biolayer interferometry (e.g., Octet, Molecular Devices LLC) surface plasmon resonance (e.g., BiaCore, GE Healthcare Life Sciences), kinetic exclusion (KinExA, Sapidyne Instruments, Inc.), or other biophysical methods. In addition, apparent affinity of a target for the DBA in the covalently linked construct may be measured with these methods by competition for a nonlinked binding agent.

Example 6

Dual Binding Antibody (DBA)-Cytokine Protein Complexes

This example describes dual binding antibody (DBA)-cytokine protein complexes of the present disclosure. Various DBA-cytokine protein complexes of the present disclosure were designed to include a cytokine, a linker, and one or more dual binding antibody domains. An exemplary protein complex is shown in FIG. 8 (at left) and its amino acid sequence is shown in FIG. 8 (at right). Pictorial representations of other exemplary constructs are shown in FIG. 9 (SEQ ID NO: 42-SEQ ID NO: 54 and SEQ ID NO: 77-SEQ ID NO: 79).

A series of DBA-cytokine protein complexes may be designed with two marker binding domains and one therapeutic domain. The DBAs used in this series, provided in TABLE 13 with sequences provided in TABLE 14, exhibit a range of affinities for the marker and the therapeutic domain. Exemplary DBA complexes are provided in TABLE 12, TABLE 15, and TABLE 16.

TABLE 12

Exemplary DBA Cytokine Protein Complexes

| SEQ ID NO | Sequences | Description |
|---|---|---|
| SEQ ID NO: 42 | QVQLVQSGAEVKKPGASVKVSCKASGYTFTK NYMHWVRQAPGQGLEWLGWVSPDSGYTGYAQ KFQGRVTMTRDTSTSTVYMELSSLRSEDTAV YYCTTDLLSLELDDAFDIWGQGTMVTVSSAS GGGGSGGGGSGGGGSHASDIQMTQSPSSLSA SVGDRVTITCRASQSISSWLAWYQQKPGKAP KLLIYAASTLQSGVPSRFSGSGSGTDFTLTI SSLQPEDFATYYCQQSYSTPLTFGGGTKLEI KPRGPTIKPCPPCKCPAPNAAGGPSVFIFPP KIKDVLMISLSPIVTCVVVDVSEDDPDVQIS WFVNNVEVHTAQTQTHREDYNSTLRVVSALP IQHQDWMSGKEFKCKVNNKDLGAPIERTISK PKGSVRAPQVYVLPPCEEEMTKKQVTLSCAV TDFMPEDIYVEWTNNGKTELNYKN TABLE 12-continued

| Exemplary DBA Cytokine Protein Complexes | | |
|---|---|---|
| SEQ ID NO | Sequences | Description |
| | AISWVRQAPGQGLEWMGIIDPSVTYTRYAQK FQGRVTMTRDTSTSTVYMELSSLRSEDTAVY YCARSLFPTIFGVEVAFDIWGQGTLVTVSSA KTTAPSVYPLAPVCGDTTGSSVTLGCLVKGY FPEPVTLTWNSGSLSSGVHTFPAVLQSDLYT LSSSVTVTSSTWPSQSITCNVAHPASSTKVD KKIEPRGPTIKPCPPCKCPAPNAAGGPSVFI FPPKIKDVLMISLSPIVTCVVVDVSEDDPDV QISWFVNNVEVHTAQTQTHREDYNSTLRVVS ALPIQHQDWMSGKEFKCKVNNKDLGAPIERT ISKPKGSVRAPQVCVLPPPEEEMTKKQVTLW CMVTDFMPEDIYVEWTNNGKTELNYKNTEPV LDSDGSYFMYSKLRVEKKNWVERNSYSCSVV HEGLHNHHTTKSFSRTPGK | therapeutic domain and having an IFNα therapeutic activity |
| SEQ ID NO: 47 | DIQMTQSPSSLSASVGDRVTITCQASQSISN YLAWYQQKPGKAPKLLIYKASSLESGVPSRF SGSGSGTDFTLTISSLQPEDFATYYCQQTYS TPITFGQGTKVEIKRADAAPTVSIFPPSSEQ LTSGGASVVCFLNNFYPKDINVKWKIDGSER QNGVLNSWTDQDSKDSTYSMSSTLTLTKDEY ERHNSYTCEATHKTSTSPIVKSFNRNEC | PD-L1/IFNα protein complexes having a DBA sensor domain capable of binding a PD-L1 marker and IFNα therapeutic domain and having an IFNα therapeutic activity |
| SEQ ID NO: 48 | CDLPQTHSLGSRRTLMLLAQMRRISLFSCLK DRHDFGFPQEEFGNQFQKAETIPVLHEMIQQ IFNLFSTKDSSAAWDETLLDKFCTELYQQLN DLEACVMQEERVGETPLMNADSILAVKKYFR RITLYLTEKKYSPCAWEVVRAEIVRSLSLST NLQERLRRKEGGGGSGGGGSGGGGSGGGGSQ VQLVQSGAEVKKPGASVKVSCKASGGTFSSY AISWVRQAPGQGLEWMGIIDPSVTYTRYAQK FQGRVTMTRDTSTSTVYMELSSLRSEDTAVY YCARSLFPTIFGVEVAFDIWGQGTLVTVSSA SGGGGSGGGGSGGGGSHASDIQMTQSPSSLS ASVGDRVTITCQASQDISNYLNWYQQKPGKA PKLLIYGASTLQSGVPSRFSGSGSGTDFTLT ISSLQPEDFATYYCQQTYSTPITFGQGTKVE IKAKTTAPSVYPLAPVCGDTTGSSVTLGCLV KGYFPEPVTLTWNSGSLSSGVHTFPAVLQSD LYTLSSSVTVTSSTWPSQSITCNVAHPASST KVDKKIEPRGPTIKPCPPCKCPAPNAAGGPS VFIFPPKIKDVLMISLSPIVTCVVVDVSEDD PDVQISWFVNNVEVHTAQTQTHREDYNSTLR VVSALPIQHQDWMSGKEFKCKVNNKDLGAPI ERTISKPKGSVRAPQVYVLPPCEEEMTKKQV TLSCAVTDFMPEDIYVEWTNNGKTELNYKNT EPVLDSDGSYFMVSKLRVEKKNWVERNSYSC SVVHEGLHNHHTTKSFSRTPGK | Exemplary Seq_C_Pep1 Asymmetric DBA-Cytokine Complex scFv-IgG format |
| SEQ ID NO: 49 | QVQLVQSGAEVKKPGASVKVSCKASGYTFSG YYIHWVRQAPGQGLEWMGWMDSNSGGTGYAQ KFQGRVTMTRDTSTSTVYMELSSLRSEDTAV YYCAKEVFSGWYDYWGQGTLVTVSSAKTTAP SVYPLAPVCGDTTGSSVTLGCLVKGYFPEPV TLTWNSGSLSSGVHTFPAVLQSDLYTLSSSV TVTSSTWPSQSITCNVAHPASSTKVDKKIEP RGPTIKPCPPCKCPAPNAAGGPSVFIFPPKI KDVLMISLSPIVTCVVVDVSEDDPDVQISWF VNNVEVHTAQTQTHREDYNSTLRVVSALPIQ HQDWMSGKEFKCKVNNKDLGAPIERTISKPK GSVRAPQVCVLPPPEEEMTKKQVTLWCMVTD FMPEDIYVEWTNNGKTELNYKNTEPVLDSDG SYFMYSKLRVEKKNWVERNSYSCSVVHEGLH NHHTTKSFSRTPGK | Exemplary Seq_C_Pep2 Asymmetric DBA-Cytokine Complex scFv-IgG format |
| SEQ ID NO: 50 | DIQMTQSPSSLSASVGDRVTITCRASQSISS YLNWYQQKPGKAPKLLIYAASSLQSGVPSRF SGSGSGTDFTLTISSLQPEDFATYYCQQSYS TPYTFGQGTKVEIKRADAAPTVSIFPPSSEQ LTSGGASVVCFLNNFYPKDINVKWKIDGSER QNGVLNSWTDQDSKDSTYSMSSTLTLTKDEY ERHNSYTCEATHKTSTSPIVKSFNRNEC | ExemplarySeq_C_Pep3 Asymmetric DBA-Cytokine Complex scFv-IgG format |

TABLE 12-continued

Exemplary DBA Cytokine Protein Complexes

| SEQ ID NO | Sequences | Description |
| --- | --- | --- |
| SEQ ID NO: 51 | QVQLVQSGAEVKKPGASVKVSCKASGYTFST YYIHWVRQAPGQGLEWMGIINPSGGGTVYAQ KFQGRVTMTRDTSTSTVYMELSSLRSEDTAV YYCAAGLFIWGQGTLVTVSSAKTTAPSVYPL APVCGDTTGSSVTLGCLVKGYFPEPVTLTWN SGSLSSGVHTFPAVLQSDLYTLSSSVTVTSS TWPSQSITCNVAHPASSTKVDKKIEPRGPTI KPCPPCKCPAPNAAGGPSVFIFPPKIKDVLM ISLSPIVTCVVVDVSEDDPDVQISWFVNNVE VHTAQTQTHREDYNSTLRVVSALPIQHQDWM SGKEFKCKVNNKDLGAPIERTISKPKGSVRA PQVYVLPPPEEEMTKKQVTLTCMVTDFMPED IYVEWTNNGKTELNYKNTEPVLDSDGSYFMY SKLRVEKKNWVERNSYSCSVVHEGLHNHHTT KSFSRTPGK | PD1-IL2_6C12_N36T_Sym_L_Long_Pep1 Symmetric DBA-Cytokine Complex IgG format |
| SEQ ID NO: 52 | APTSSSTKKTQLQLEHLLLDLQMILNGINNY KNPKLTRMLTFKFYMPKKATELKHLQCLEEE LKPLEEVLNLAQSKNFHLRPRDLISNINVIV LELKGSETTFMCEYADETATIVEFLNRWITF CQSIISTLTVPGVGVPGAGVPGVGVPGGGVP GVGVPGGGVPGAGVPGGGVPGVGVPGAGVPG VGVPGGGDIQMTQSPSSLSASVGDRVTITCR ASQYISSGLAWYQQKPGKAPKLLIYKASSLD NGVPSRFSGSGSGTDFTLTISSLQPEDFATY YCQQYERLPLTFGGGTKVEIKRADAAPTVSI FPPSSEQLTSGGASVVCFLNNFYPKDINVKW KIDGSERQNGVLNSWTDQDSKDSTYSMSSTL TLTKDEYERHNSYTCEATHKTSTSPIVKSFN RNEC | PD1-IL2_6C12_N36T_Sym_L_Long_Pep2 Symmetric DBA-Cytokine Complex IgG format |
| SEQ ID NO: 53 | APTSSSTKKTQLQLEHLLLDLQMILNGINNY KNPKLTRMLTFKFYMPKKATELKHLQCLEEE LKPLEEVLNLAQSKNFHLRPRDLISNINVIV LELKGSETTFMCEYADETATIVEFLNRWITF CQSIISTLTGGGGSGGGGSGGGGSGGGGSQV QLVQSGAEVKKPGASVKVSCKASGYTFSTYY IHWVRQAPGQGLEWMGIINPSGGGTVYAQKF QGRVTMTRDTSTSTVYMELSSLRSEDTAVYY CAAGLFIWGQGTLVTVSSAKTTAPSVYPLAP VCGDTTGSSVTLGCLVKGYFPEPVTLTWNSG SLSSGVHTFPAVLQSDLYTLSSSVTVTSSTW PSQSITCNVAHPASSTKVDKKIEPRGPTIKP CPPCKCPAPNAAGGPSVFIFPPKIKDVLMIS LSPIVTCVVVDVSEDDPDVQISWFVNNVEVH TAQTQTHREDYNSTLRVVSALPIQHQDWMSG KEFKCKVNNKDLGAPIERTISKPKGSVRAPQ VYVLPPPEEEMTKKQVTLTCMVTDFMPEDIY VEWTNNGKTELNYKNTEPVLDSDGSYFMYSK LRVEKKNWVERNSYSCSVVHEGLHNHHTTKS FSRTPGK | PD1-IL2_6C12_N36T_D68E_Sym_H_Short_Pep1 Symmetric DBA-Cytokine Complex IgG format |
| SEQ ID NO: 54 | DIQMTQSPSSLSASVGDRVTITCRASQYISS GLAWYQQKPGKAPKLLIYKASSLENGVPSRF SGSGSGTDFTLTISSLQPEDFATYYCQQYER LPLTFGGGTKVEIKRADAAPTVSIFPPSSEQ LTSGGASVVCFLNNFYPKDINVKWKIDGSER QNGVLNSWTDQDSKDSTYSMSSTLTLTKDEY ERHNSYTCEATHKTSTSPIVKSFNRNEC | PD1-IL2_6C12_N36T_D68E_Sym_H_Short_Pep2 Symmetric DBA-Cytokine Complex IgG format |
| SEQ ID NO: 77 | QVQLVQSGAEVKKPGASVKVSCKASGYTFTT YYVHWVRQAPGQGLEWMGIINPSGGSTSYAQ NFQGRVTMTRDTSTSTVYMELSSLRSEDTAV YYCASGWDVWGQGTTVTVSSAKTTAPSVYPL APVCGDTTGSSVTLGCLVKGYFPEPVTLTWN SGSLSSGVHTFPAVLQSDLYTLSSSVTVTSS TWPSQSITCNVAHPASSTKVDKKIEPRGPTI KPCPPCKCPAPNAAGGPSVFIFPPKIKDVLM ISLSPIVTCVVVDVSEDDPDVQISWFVNNVE VHTAQTQTHREDYNSTLRVVSALPIQHQDWM SGKEFKCKVNNKDLGAPIERTISKPKGSVRA PQVYVLPPPEEEMTKKQVTLTCMVTDFMPED IYVEWTNNGKTELNYKNTEPVLDSDGSYFMY SDLRVEKKNWVERNSYSCSVVHEGLHNHHTT ESFSRTPGK | PD1-IL2_L_7A05scFv_PD1-R07-A05_Pep1 Asymmetric DBA-Cytokine Complex IgG-scFv format |

TABLE 12-continued

Exemplary DBA Cytokine Protein Complexes

| SEQ ID NO | Sequences | Description |
|---|---|---|
| SEQ ID NO: 78 | QVQLVQSGAEVKKPGASVKVSCKASGYTFTTYYVHWVRQAPGQGLEWMGIINPSGGSTSYAQNFQGRVTMTRDTSTSTVYMELSSLRSEDTAVYYCASGWDVWGQGTTVTVSSASGGGGSGGGGSGGGGSHASEIVMTQSPATLSVSPGERATLSCRASQSVNTYLAWYQQKPGQAPRLLIYGASTRATGIPARFSGSGSGTEFTLTISSLQSEDFAVYYCQQYGSSPVTFGQGTRLEIKPRGPTIKPCPPCKCPAPNAAGGPSVFIFPPKIKDVLMISLSPIVTCVVVDVSEDDPDVQISWFVNNVEVHTAQTQTHREDYNSTLRVVSALPIQHQDWMSGKEFKCKVNNKDLGAPIERTISKPKGSVRAPQVYVLPPPEKEMTKKQVSLTCLVKDFMPEDIYVEWTNNGKTELNYKNTEPVLKSDGSYFMYSKLTVEKKNWVERNSYSCSVVHEGLHNHHTTKSFSRTPGGGGSGGGSHHHHHH | PD1-IL2_L_7A05scFv_PD1-R07-A05_Pep2 Asymmetric DBA-Cytokine Complex IgG-scFv format |
| SEQ ID NO: 79 | APTSSSTKKTQLQLEHLLLDLQMILNGINNYKNPKLTDMLTFKFYMPKKATELKHLQCLEEELKPLEEVLNLAQSKNFHLRPRDLISNINVIVLELKGSETTFMCEYADETATIVEFLNRWITFCQSIISTLTGGGGSGGGGSGGGGSGGGGSEIVMTQSPATLSVSPGERATLSCRASQSVNTYLAWYQQKPGQAPRLLIYGASTRATGIPARFSGSGSGTEFTLTISSLQSEDFAVYYCQQYGSSPVTFGQGTRLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC | PD1-IL2_L_7A05scFv_PD1-R07-A05_Pep3 Asymmetric DBA-Cytokine Complex IgG-scFv format |

TABLE 13

Dual-Binding Antibodies (DBAs)

| Dual-Binding Antibody | Marker | Therapeutic | HV* SEQ ID NO: | LV** SEQ ID NO: | HV_cdr1 SEQ ID NO: | HV_cdr2 SEQ ID NO: | HV_cdr3 SEQ ID NO: | LV_cdr1 SEQ ID NO: | LV_cdr2 SEQ ID NO: | LV_cdr3 SEQ ID NO: |
|---|---|---|---|---|---|---|---|---|---|---|
| AB001718 | PD-1 | IL-2 | 127 | 135 | 142 | 148 | 154 | 157 | 163 | 168 |
| AB001744 | PD-1 | IL-2 | 128 | 136 | 143 | 148 | 154 | 158 | 163 | 169 |
| AB002022 | PD-1 | IL-2 | 129 | 137 | 144 | 149 | 154 | 159 | 164 | 170 |
| AB001609 | PD-L1 | IFNα | 130 | 138 | 145 | 150 | 155 | 160 | 165 | 171 |
| AB001638 | PD-L1 | IFNα | 130 | 139 | 145 | 150 | 155 | 161 | 165 | 172 |
| AB001843 | PD-L1 | IFNα | 131 | 140 | 146 | 151 | 156 | 162 | 166 | 173 |
| AB001866 | PD-L1 | IFNα | 132 | 140 | 147 | 152 | 156 | 162 | 166 | 173 |
| AB001875 | PD-L1 | IFNα | 133 | 140 | 143 | 153 | 156 | 162 | 166 | 173 |
| AB001909 | PD-L1 | IFNα | 134 | 141 | 143 | 151 | 156 | 162 | 167 | 173 |

*HV refers to the heavy chain variable region of the respective antibodies
**LV refers to the light chain variable region of the respective antibodies

TABLE 14

Sequences of DBA Protein Components

| SEQ ID NO: | DBA Protein Component | Sequence |
|---|---|---|
| SEQ ID NO: 127 | AB001718_HV | QVQLVQSGAEVKKPGASVKVSCKASGDTFSTYYVHWVRQAPGQGLEWMGIINPSGGGTVYAQKFQGRVTMTRDTSTSTVYMELSSLRSEDTAVYYCAAGLFIWGQGTLVTVSS |
| SEQ ID NO: 128 | AB001744_HV | QVQLVQSGAEVKKPGASVKVSCKASGYTFSNYYIHWVRQAPGQGLEWMGIINPSGGGTVYAQKFQGRVTMTRDTSTSTVYMELSSLRSEDTAVYYCAAGLFIWGQGTLVTVSS |

TABLE 14-continued

Sequences of DBA Protein Components

| SEQ ID NO: | DBA Protein Component | Sequence |
| --- | --- | --- |
| SEQ ID NO: 129 | AB002022_HV | QVQLVQSGAEVKKPGASVKVSCKASG DTFTRHYVHWVRQAPGQGLEWMGIIN PSGGYASYAQKFQGRVTMTRDTSTST VYMELSSLRSEDTAVYYCAAGLFIWG QGTLVTVSS |
| SEQ ID NO: 130 | AB001609_HV | QVQLVQSGAEVKKPGASVKVSCKASG GTFSSYAISWVRQAPGQGLEWMGIID PSVTYTRYAQKFQGRVTMTRDTSTST VYMELSSLRSEDTAVYYCARSLFPTI FGVEVAFDIWGQGTLVTVSS |
| SEQ ID NO: 131 | AB001843_HV | QVQLVQSGAEVKKPGASVKVSCKASG YTFSGYYIHWVRQAPGQGLEWMGWMD SNSGGTGYAQKFQGRVTMTRDTSTST VYMELSSLRSEDTAVYYCAKEVFSGW YDYWGQGTLVTVSS |
| SEQ ID NO: 132 | AB001866_HV | QVQLVQSGAEVKKPGASVKVSCKASG YTFSNYYVHWVRQAPGQGLEWMGWMD PNSGGTGYAHQFQGRVTMTRDTSTST VYMELSSLRSEDTAVYYCAKEVFSGW YDYWGQGTLVTVSS |
| SEQ ID NO: 133 | AB001875_HV | QVQLVQSGAEVKKPGASVKVSCKASG YTFSNYYIHWVRQAPGQGLEWMGWMD SNSGYTGYAQQFQGRVTMTRDTSTST VYMELSSLRSEDTAVYYCAKEVFSGW YDYWGQGTLVTVSS |
| SEQ ID NO: 134 | AB001909_HV | QVQLVQSGAEVKKPGASVKVSCKASG YTFSNYYIHWVRQAPGQGLEWMGWMD SNSGGTGYAQKFQGRVTMTRDTSTST VYMELSSLRSEDTAVYYCAKEVFSGW YDYWGQGTLVTVSS |
| SEQ ID NO: 135 | AB001718_LV | DIQMTQSPSSLSASVGDRVTITCRAS QYISSGLAWYQQKPGKAPKLLIYKAS SLDNGVPSRFSGSGSGTDFTLTISSL QPEDFATYYCQQYERLPLTFGGGTKV EIK |
| SEQ ID NO: 136 | AB001744_LV | DIQMTQSPSSLSASVGDRVTITCRAS QSIGTGLAWYQQKPGKAPKLLIYKAS SLDNGVPSRFSGSGSGTDFTLTISSL QPEDFATYYCQQYNRAPLTFGGGTKV EIK |
| SEQ ID NO: 137 | AB002022_LV | DIQMTQSPSSLSASVGDRVTITCRAS QSIGRWLAWYQQKPGKAPKLLIYSAS NLETGVPSRFSGSGSGTDFTLTISSL QPEDFATYYCQQYESFPVTFGPGTKV DIK |
| SEQ ID NO: 138 | AB001609_LV | DIQMTQSPSSLSASVGDRVTITCRAS QSISNRLAWYQQKPGKAPKLLIYKAS SLESGVPSRFSGSGSGTDFTLTISSL QPEDFATYYCQQSNSTPFTFGQGTKV EIK |
| SEQ ID NO: 139 | AB001638_LV | DIQMTQSPSSLSASVGDRVTITCQAS QSISNYLAWYQQKPGKAPKLLIYKAS SLESGVPSRFSGSGSGTDFTLTISSL QPEDFATYYCQQTYSTPITFGQGTKV EIK |
| SEQ ID NO: 140 | AB001843_LV | DIQMTQSPSSLSASVGDRVTITCRAS QSISSYLNWYQQKPGKAPKLLIYAAS SLQSGVPSRFSGSGSGTDFTLTISSL QPEDFATYYCQQSYSTPYTFGQGTKV EIK |

TABLE 14-continued

Sequences of DBA Protein Components

| SEQ ID NO: | DBA Protein Component | Sequence |
|---|---|---|
| SEQ ID NO: 141 | AB001909_LV | DIQMTQSPSSLSASVGDRVTITCRAS QSISSYLNWYQQKPGKAPKLLIYAAS SLESGVPSRFSGSGSGTDFTLTISSL QPEDFATYYCQQSYSTPYTFGQGTKV DIK |
| SEQ ID NO: 142 | AB001718_HV_cdr1 | GDTFSTYYVH |
| SEQ ID NO: 143 | AB001744_HV_cdr1 | GYTFSNYYIH |
| SEQ ID NO: 144 | AB002022_HV_cdr1 | GDTFTRHYVH |
| SEQ ID NO: 145 | AB001609_HV_cdr1 | GGTFSSYAIS |
| SEQ ID NO: 146 | AB001843_HV_cdr1 | GYTFSGYYIH |
| SEQ ID NO: 147 | AB001866_HV_cdr1 | GYTFSNYYVH |
| SEQ ID NO: 148 | AB001718_HV_cdr2 | IINPSGGGTVYAQKFQG |
| SEQ ID NO: 149 | AB002022_HV_cdr2 | IINPSGGYASYAQKFQG |
| SEQ ID NO: 150 | AB001609_HV_cdr2 | IIDPSVTYTRYAQKFQG |
| SEQ ID NO: 151 | AB001843_HV_cdr2 | WMDSNSGGTGYAQKFQG |
| SEQ ID NO: 152 | AB001866_HV_cdr2 | WMDPNSGGTGYAHQFQG |
| SEQ ID NO: 153 | AB001875_HV_cdr2 | WMDSNSGYTGYAQQFQG |
| SEQ ID NO: 154 | AB001718_HV_cdr3 | AAGLFI |
| SEQ ID NO: 155 | AB001609_HV_cdr3 | ARSLFPTIFGVEVAFDI |
| SEQ ID NO: 156 | AB001843_HV_cdr3 | AKEVFSGWYDY |
| SEQ ID NO: 157 | AB001718_LV_cdr1 | RASQYISSGLA |
| SEQ ID NO: 158 | AB001744_LV_cdr1 | RASQSIGTGLA |
| SEQ ID NO: 159 | AB002022_LV_cdr1 | RASQSIGRWLA |
| SEQ ID NO: 160 | AB001609_LV_cdr1 | RASQSISNRLA |
| SEQ ID NO: 161 | AB001638_LV_cdr1 | QASQSISNYLA |
| SEQ ID NO: 162 | AB001843_LV_cdr1 | RASQSISSYLN |
| SEQ ID NO: 163 | AB001718_LV_cdr2 | KASSLDN |
| SEQ ID NO: 164 | AB002022_LV_cdr2 | SASNLET |
| SEQ ID NO: 165 | AB001609_LV_cdr2 | KASSLES |
| SEQ ID NO: 166 | AB001843_LV_cdr2 | AASSLQS |
| SEQ ID NO: 167 | AB001909_LV_cdr2 | AASSLES |
| SEQ ID NO: 168 | AB001718_LV_cdr3 | QQYERLPL |
| SEQ ID NO: 169 | AB001744_LV_cdr3 | QQYNRAPL |
| SEQ ID NO: 170 | AB002022_LV_cdr3 | QQYESFPV |
| SEQ ID NO: 171 | AB001609_LV_cdr3 | QQSNSTPF |
| SEQ ID NO: 172 | AB001638_LV_cdr3 | QQTYSTPI |
| SEQ ID NO: 173 | AB001843_LV_cdr3 | QQSYSTPY |

TABLE 15

Exemplary DBA-Cytokine Protein Complexes

| Name | DBA/ Therapeutic | DBA | Type | DBA domains | Therapeutic domains | 2nd Ab domain | Heavy Chain 1 SEQ ID NO: | Heavy Chain 2 SEQ ID NO: | Heavy Chain 3 SEQ ID NO: |
|---|---|---|---|---|---|---|---|---|---|
| AF003229 | PD-1/IL-2 | AB001718 | FIG. 9b | 2 | 1 | N/A | 80 | 97 | 114 |
| AF003230 | PD-1/IL-2 | AB001744 | FIG. 9b | 2 | 1 | N/A | 81 | 98 | 115 |
| AF003232 | PD-1/IL-2 | AB002022 | FIG. 9b | 2 | 1 | N/A | 82 | 99 | 116 |
| AF003250 | PD-1/IL-2 | AB001718 | FIG. 9a | 1 | 1 | anti-PD-1 | 83 | 100 | 117 |
| AF003251 | PD-1/IL-2 | AB001744 | FIG. 9a | 1 | 1 | anti-PD-1 | 84 | 101 | 118 |
| AF003253 | PD-1/IL-2 | AB002022 | FIG. 9a | 1 | 1 | anti-PD-1 | 85 | 102 | 119 |
| AF003103 | PD-L1/IFNα | AB001609 | FIG. 9b | 2 | 1 | N/A | 86 | 103 | 120 |
| AF003104 | PD-L1/IFNα | AB001909 | FIG. 9b | 2 | 1 | N/A | 87 | 104 | 126 |
| AF003105 | PD-L1/IFNα | AB001843 | FIG. 9b | 2 | 1 | N/A | 88 | 105 | 122 |
| AF003106 | PD-L1/IFNα | AB001875 | FIG. 9b | 2 | 1 | N/A | 89 | 106 | 123 |
| AF003217 | PD-L1/IFNα | AB001609 | FIG. 9a | 1 | 1 | anti-PD-L1 | 90 | 107 | 124 |
| AF003218 | PD-L1/IFNα | AB001843 | FIG. 9a | 1 | 1 | anti-PD-L1 | 91 | 108 | 125 |
| AF003219 | PD-L1/IFNα | AB001909 | FIG. 9a | 1 | 1 | anti-PD-L1 | 92 | 109 | 126 |
| AF002618 | PD-L1/IFNα | AB001609 | FIG. 9d | 2 | 2 | N/A | 93 | | 110 |
| AF002639 | PD-L1/IFNα | AB001875 | FIG. 9d | 2 | 2 | N/A | 94 | | 111 |
| AF002645 | PD-L1/IFNα | AB001609 | FIG. 9e | 2 | 2 | N/A | 95 | | 112 |
| AF002666 | PD-L1/IFNα | AB001875 | FIG. 9e | 2 | 2 | N/A | 96 | | 277 |

TABLE 16

Sequences of Peptides in TABLE 15

| SEQ ID NO: | DBA | Sequence |
|---|---|---|
| SEQ ID NO: 80 | AF003229_Pep1 | APTSSSTKKTQLQLEHLLLDLQMILNGINNYKNPKLTDMLTF KFYMPKKATELKHLQCLEEELKPLEEVLNLAQSKNFHLRPRD LISNINVIVLELKGSETTFMCEYADETATIVEFLNRWITFCQ SIISTLTGGGGSGGGGSGGGGSGGGGSQVQLVQSGAEVKKPG ASVKVSCKASGDTFSTYYVHWVRQAPGQGLEWMGIINPSGGG TVYAQKFQGRVTMTRDTSTSTVYMELSSLRSEDTAVYYCAAG LFIWGQGTLVTVSSAKTTAPSVYPLAPVCGDTTGSSVTLGCL VKGYFPEPVTLTWNSGSLSSGVHTFPAVLQSDLYTLSSSVTV TSSTWPSQSITCNVAHPASSTKVDKKIEPRGPTIKPCPPCKC PAPNAAGGPSVFIFPPKIKDVLMISLSPIVTCVVVDVSEDDP DVQISWFVNNVEVHTAQTQTHREDYNSTLRVVSALPIQHQDW MSGKEFKCKVNNKDLGAPIERTISKPKGSVRAPQVYVLPPPE EEMTKKQVTLTCMVTDFMPEDIYVEWTNNGKTELNYKNTEPV LDSDGSYFMYSDLRVEKKNWVERNSYSCSVVHEGLHNHHTTE SFSRTPGK |
| SEQ ID NO: 81 | AF003230_Pep1 | APTSSSTKKTQLQLEHLLLDLQMILNGINNYKNPKLTDMLTF KFYMPKKATELKHLQCLEEELKPLEEVLNLAQSKNFHLRPRD LISNINVIVLELKGSETTFMCEYADETATIVEFLNRWITFCQ SIISTLTGGGGSGGGGSGGGGSGGGGSQVQLVQSGAEVKKPG ASVKVSCKASGYTFSNYYIHWVRQAPGQGLEWMGIINPSGGG TVYAQKFQGRVTMTRDTSTSTVYMELSSLRSEDTAVYYCAAG LFIWGQGTLVTVSSAKTTAPSVYPLAPVCGDTTGSSVTLGCL VKGYFPEPVTLTWNSGSLSSGVHTFPAVLQSDLYTLSSSVTV TSSTWPSQSITCNVAHPASSTKVDKKIEPRGPTIKPCPPCKC PAPNAAGGPSVFIFPPKIKDVLMISLSPIVTCVVVDVSEDDP DVQISWFVNNVEVHTAQTQTHREDYNSTLRVVSALPIQHQDW MSGKEFKCKVNNKDLGAPIERTISKPKGSVRAPQVYVLPPPE EEMTKKQVTLTCMVTDFMPEDIYVEWTNNGKTELNYKNTEPV LDSDGSYFMYSDLRVEKKNWVERNSYSCSVVHEGLHNHHTTE SFSRTPGK |
| SEQ ID NO: 82 | AF003232_Pep1 | APTSSSTKKTQLQLEHLLLDLQMILNGINNYKNPKLTDMLTF KFYMPKKATELKHLQCLEEELKPLEEVLNLAQSKNFHLRPRD LISNINVIVLELKGSETTFMCEYADETATIVEFLNRWITFCQ SIISTLTGGGGSGGGGSGGGGSGGGGSQVQLVQSGAEVKKPG ASVKVSCKASGDTFTRHYVHWVRQAPGQGLEWMGIINPSGGY ASYAQKFQGRVTMTRDTSTSTVYMELSSLRSEDTAVYYCAAG LFIWGQGTLVTVSSAKTTAPSVYPLAPVCGDTTGSSVTLGCL VKGYFPEPVTLTWNSGSLSSGVHTFPAVLQSDLYTLSSSVTV TSSTWPSQSITCNVAHPASSTKVDKKIEPRGPTIKPCPPCKC PAPNAAGGPSVFIFPPKIKDVLMISLSPIVTCVVVDVSEDDP DVQISWFVNNVEVHTAQTQTHREDYNSTLRVVSALPIQHQDW MSGKEFKCKVNNKDLGAPIERTISKPKGSVRAPQVYVLPPPE EEMTKKQVTLTCMVTDFMPEDIYVEWTNNGKTELNYKNTEPV |

TABLE 16-continued

Sequences of Peptides in TABLE 15

| SEQ ID NO: | DBA | Sequence |
|---|---|---|
| | | LDSDGSYFMYSDLRVEKKNWVERNSYSCSVVHEGLHNHHTTE SFSRTPGK |
| SEQ ID NO: 83 | AF003250_ Pep1 | APTSSSTKKTQLQLEHLLLDLQMILNGINNYKNPKLTDMLTF KFYMPKKATELKHLQCLEEELKPLEEVLNLAQSKNFHLRPRD LISNINVIVLELKGSETTFMCEYADETATIVEFLNRWITFCQ SIISTLTGGGGSGGGGSGGGGSGGGGSQVQLVQSGAEVKKPG ASVKVSCKASGDTFSTYYVHWVRQAPGQGLEWMGIINPSGGG TVYAQKFQGRVTMTRDTSTSTVYMELSSLRSEDTAVYYCAAG LFIWGQGTLVTVSSAKTTAPSVYPLAPVCGDTTGSSVTLGCL VKGYFPEPVTLTWNSGSLSSGVHTFPAVLQSDLYTLSSSVTV TSSTWPSQSITCNVAHPASSTKVDKKIEPRGPTIKPCPPCKC PAPNAAGGPSVFIFPPKIKDVLMISLSPIVTCVVVDVSEDDP DVQISWFVNNVEVHTAQTQTHREDYNSTLRVVSALPIQHQDW MSGKEFKCKVNNKDLGAPIERTISKPKGSVRAPQVYVLPPPE EEMTKKQVTLTCMVTDFMPEDIYVEWTNNGKTELNYKNTEPV LDSDGSYFMYSDLRVEKKNWVERNSYSCSVVHEGLHNHHTTE SFSRTPGK |
| SEQ ID NO: 84 | AF003251_ Pep1 | APTSSSTKKTQLQLEHLLLDLQMILNGINNYKNPKLTDMLTF KFYMPKKATELKHLQCLEEELKPLEEVLNLAQSKNFHLRPRD LISNINVIVLELKGSETTFMCEYADETATIVEFLNRWITFCQ SIISTLTGGGGSGGGGSGGGGSGGGGSQVQLVQSGAEVKKPG ASVKVSCKASGYTFSNYYIHWVRQAPGQGLEWMGIINPSGGG TVYAQKFQGRVTMTRDTSTSTVYMELSSLRSEDTAVYYCAAG LFIWGQGTLVTVSSAKTTAPSVYPLAPVCGDTTGSSVTLGCL VKGYFPEPVTLTWNSGSLSSGVHTFPAVLQSDLYTLSSSVTV TSSTWPSQSITCNVAHPASSTKVDKKIEPRGPTIKPCPPCKC PAPNAAGGPSVFIFPPKIKDVLMISLSPIVTCVVVDVSEDDP DVQISWFVNNVEVHTAQTQTHREDYNSTLRVVSALPIQHQDW MSGKEFKCKVNNKDLGAPIERTISKPKGSVRAPQVYVLPPPE EEMTKKQVTLTCMVTDFMPEDIYVEWTNNGKTELNYKNTEPV LDSDGSYFMYSDLRVEKKNWVERNSYSCSVVHEGLHNHHTTE SFSRTPGK |
| SEQ ID NO: 85 | AF003253_ Pep1 | APTSSSTKKTQLQLEHLLLDLQMILNGINNYKNPKLTDMLTF KFYMPKKATELKHLQCLEEELKPLEEVLNLAQSKNFHLRPRD LISNINVIVLELKGSETTFMCEYADETATIVEFLNRWITFCQ SIISTLTGGGGSGGGGSGGGGSGGGGSQVQLVQSGAEVKKPG ASVKVSCKASGDTFTRHYVHWVRQAPGQGLEWMGIINPSGGY ASYAQKFQGRVTMTRDTSTSTVYMELSSLRSEDTAVYYCAAG LFIWGQGTLVTVSSAKTTAPSVYPLAPVCGDTTGSSVTLGCL VKGYFPEPVTLTWNSGSLSSGVHTFPAVLQSDLYTLSSSVTV TSSTWPSQSITCNVAHPASSTKVDKKIEPRGPTIKPCPPCKC PAPNAAGGPSVFIFPPKIKDVLMISLSPIVTCVVVDVSEDDP DVQISWFVNNVEVHTAQTQTHREDYNSTLRVVSALPIQHQDW MSGKEFKCKVNNKDLGAPIERTISKPKGSVRAPQVYVLPPPE EEMTKKQVTLTCMVTDFMPEDIYVEWTNNGKTELNYKNTEPV LDSDGSYFMYSDLRVEKKNWVERNSYSCSVVHEGLHNHHTTE SFSRTPGK |
| SEQ ID NO: 86 | AF003103_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GGTFSSYAISWVRQAPGQGLEWMGIIDPSVTYTRYAQKFQGR VTMTRDTSTSTVYMELSSLRSEDTAVYYCARSLFPTIFGVEV AFDIWGQGTLVTVSSAKTTAPSVYPLAPVCGDTTGSSVTLGC LVKGYFPEPVTLTWNSGSLSSGVHTFPAVLQSDLYTLSSSVT VTSSTWPSQSITCNVAHPASSTKVDKKIEPRGPTIKPCPPCK CPAPNAAGGPSVFIFPPKIKDVLMISLSPIVTCVVVDVSEDD PDVQISWFVNNVEVHTAQTQTHREDYNSTLRVVSALPIQHQD WMSGKEFKCKVNNKDLGAPIERTISKPKGSVRAPQVCVLPPP EEEMTKKQVTLWCMVTDFMPEDIYVEWTNNGKTELNYKNTEP VLDSDGSYFMYSKLRVEKKNWVERNSYSCSVVHEGLHNHHTT KSFSRTPGK |
| SEQ ID NO: 87 | AF003104_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GYTFSNYYIHWVRQAPGQGLEWMGWMDSNSGGTGYAQKFQGR VTMTRDTSTSTVYMELSSLRSEDTAVYYCAKEVFSGWYDYWG |

TABLE 16-continued

Sequences of Peptides in TABLE 15

| SEQ ID NO: | DBA | Sequence |
|---|---|---|
| | | QGTLVTVSSAKTTAPSVYPLAPVCGDTTGSSVTLGCLVKGYF PEPVTLTWNSGSLSSGVHTFPAVLQSDLYTLSSSVTVTSSTW PSQSITCNVAHPASSTKVDKKIEPRGPTIKPCPPCKCPAPNA AGGPSVFIFPPKIKDVLMISLSPIVTCVVVDVSEDDPDVQIS WFVNNVEVHTAQTQTHREDYNSTLRVVSALPIQHQDWMSGKE FKCKVNNKDLGAPIERTISKPKGSVRAPQVCVLPPPEEEMTK KQVTLWCMVTDFMPEDIYVEWTNNGKTELNYKNTEPVLDSDG SYFMYSKLRVEKKNWVERNSYSCSVVHEGLHNHHTTKSFSRT PGK |
| SEQ ID NO: 88 | AF003105_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GYTFSGYYIHWVRQAPGQGLEWMGWMDSNSGGTGYAQKFQGR VTMTRDTSTSTVYMELSSLRSEDTAVYYCAKEVFSGWYDYWG QGTLVTVSSAKTTAPSVYPLAPVCGDTTGSSVTLGCLVKGYF PEPVTLTWNSGSLSSGVHTFPAVLQSDLYTLSSSVTVTSSTW PSQSITCNVAHPASSTKVDKKIEPRGPTIKPCPPCKCPAPNA AGGPSVFIFPPKIKDVLMISLSPIVTCVVVDVSEDDPDVQIS WFVNNVEVHTAQTQTHREDYNSTLRVVSALPIQHQDWMSGKE FKCKVNNKDLGAPIERTISKPKGSVRAPQVCVLPPPEEEMTK KQVTLWCMVTDFMPEDIYVEWTNNGKTELNYKNTEPVLDSDG SYFMYSKLRVEKKNWVERNSYSCSVVHEGLHNHHTTKSFSRT PGK |
| SEQ ID NO: 89 | AF003106_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GYTFSNYYIHWVRQAPGQGLEWMGWMDSNSGYTGYAQQFQGR VTMTRDTSTSTVYMELSSLRSEDTAVYYCAKEVFSGWYDYWG QGTLVTVSSAKTTAPSVYPLAPVCGDTTGSSVTLGCLVKGYF PEPVTLTWNSGSLSSGVHTFPAVLQSDLYTLSSSVTVTSSTW PSQSITCNVAHPASSTKVDKKIEPRGPTIKPCPPCKCPAPNA AGGPSVFIFPPKIKDVLMISLSPIVTCVVVDVSEDDPDVQIS WFVNNVEVHTAQTQTHREDYNSTLRVVSALPIQHQDWMSGKE FKCKVNNKDLGAPIERTISKPKGSVRAPQVCVLPPPEEEMTK KQVTLWCMVTDFMPEDIYVEWTNNGKTELNYKNTEPVLDSDG SYFMYSKLRVEKKNWVERNSYSCSVVHEGLHNHHTTKSFSRT PGK |
| SEQ ID NO: 90 | AF003217_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GGTFSSYAISWVRQAPGQGLEWMGIIDPSVTYTRYAQKFQGR VTMTRDTSTSTVYMELSSLRSEDTAVYYCARSLFPTIFGVEV AFDIWGQGTLVTVSSAKTTAPSVYPLAPVCGDTTGSSVTLGC LVKGYFPEPVTLTWNSGSLSSGVHTFPAVLQSDLYTLSSSVT VTSSTWPSQSITCNVAHPASSTKVDKKIEPRGPTIKPCPPCK CPAPNAAGGPSVFIFPPKIKDVLMISLSPIVTCVVVDVSEDD PDVQISWFVNNVEVHTAQTQTHREDYNSTLRVVSALPIQHQD WMSGKEFKCKVNNKDLGAPIERTISKPKGSVRAPQVCVLPPP EEEMTKKQVTLWCMVTDFMPEDIYVEWTNNGKTELNYKNTEP VLDSDGSYFMYSKLRVEKKNWVERNSYSCSVVHEGLHNHHTT KSFSRTPGK |
| SEQ ID NO: 91 | AF003218_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GYTFSGYYIHWVRQAPGQGLEWMGWMDSNSGGTGYAQKFQGR VTMTRDTSTSTVYMELSSLRSEDTAVYYCAKEVFSGWYDYWG QGTLVTVSSAKTTAPSVYPLAPVCGDTTGSSVTLGCLVKGYF PEPVTLTWNSGSLSSGVHTFPAVLQSDLYTLSSSVTVTSSTW PSQSITCNVAHPASSTKVDKKIEPRGPTIKPCPPCKCPAPNA AGGPSVFIFPPKIKDVLMISLSPIVTCVVVDVSEDDPDVQIS WFVNNVEVHTAQTQTHREDYNSTLRVVSALPIQHQDWMSGKE FKCKVNNKDLGAPIERTISKPKGSVRAPQVCVLPPPEEEMTK KQVTLWCMVTDFMPEDIYVEWTNNGKTELNYKNTEPVLDSDG |

TABLE 16-continued

Sequences of Peptides in TABLE 15

| SEQ ID NO: | DBA | Sequence |
|---|---|---|
| | | SYFMYSKLRVEKKNWVERNSYSCSVVHEGLHNHHTTKSFSRT PGK |
| SEQ ID NO: 92 | AF003219_ Pep1 | CDLPQTHSLGSRRTLMLLAQMRRISLFSCLKDRHDFGFPQEE FGNQFQKAETIPVLHEMIQQIFNLFSTKDSSAAWDETLLDKF CTELYQQLNDLEACVMQEERVGETPLMNADSILAVKKYFRRI TLYLTEKKYSPCAWEVVRAEIVRSLSLSTNLQERLRRKEGGG GSGGGGSGGGGSGGGGSQVQLVQSGAEVKKPGASVKVSCKAS GYTFSNYYIHWVRQAPGQGLEWMGWMDSNSGGTGYAQKFQGR VTMTRDTSTSTVYMELSSLRSEDTAVYYCAKEVFSGWYDYWG QGTLVTVSSAKTTAPSVYPLAPVCGDTTGSSVTLGCLVKGYF PEPVTLTWNSGSLSSGVHTFPAVLQSDLYTLSSSVTVTSSTW PSQSITCNVAHPASSTKVDKKIEPRGPTIKPCPPCKCPAPNA AGGPSVFIFPPKIKDVLMISLSPIVTCVVVDVSEDDPDVQIS WFVNNVEVHTAQTQTHREDYNSTLRVVSALPIQHQDWMSGKE FKCKVNNKDLGAPIERTISKPKGSVRAPQVCVLPPPEEEMTK KQVTLWCMVTDFMPEDIYVEWTNNGKTELNYKNTEPVLDSDG SYFMYSKLRVEKKNWVERNSYSCSVVHEGLHNHHTTKSFSRT PGK |
| SEQ ID NO: 93 | AF002618_ Pep1 | QVQLVQSGAEVKKPGASVKVSCKASGGTFSSYAISWVRQAPG QGLEWMGIIDPSVTYTRYAQKFQGRVTMTRDTSTSTVYMELS SLRSEDTAVYYCARSLFPTIFGVEVAFDIWGQGTLVTVSSAK TTAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNAAGGPSVFIFPP KIKDVLMISLSPIVTCVVVDVSEDDPDVQISWFVNNVEVHTA QTQTHREDYNSTLRVVSALPIQHQDWMSGKEFKCKVNNKDLG APIERTISKPKGSVRAPQVYVLPPPEEEMTKKQVTLTCMVTD FMPEDIYVEWTNNGKTELNYKNTEPVLDSDGSYFMYSKLRVE KKNWVERNSYSCSVVHEGLHNHHTTKSFSRTPGK |
| SEQ ID NO: 94 | AF002639_ Pep1 | QVQLVQSGAEVKKPGASVKVSCKASGYTFSNYYIHWVRQAPG QGLEWMGWMDSNSGYTGYAQQFQGRVTMTRDTSTSTVYMELS SLRSEDTAVYYCAKEVFSGWYDYWGQGTLVTVSSAKTTAPSV YPLAPVCGDTTGSSVTLGCLVKGYFPEPVTLTWNSGSLSSGV HTFPAVLQSDLYTLSSSVTVTSSTWPSQSITCNVAHPASSTK VDKKIEPRGPTIKPCPPCKCPAPNAAGGPSVFIFPPKIKDVL MISLSPIVTCVVVDVSEDDPDVQISWFVNNVEVHTAQTQTHR EDYNSTLRVVSALPIQHQDWMSGKEFKCKVNNKDLGAPIERT ISKPKGSVRAPQVYVLPPPEEEMTKKQVTLTCMVTDFMPEDI YVEWTNNGKTELNYKNTEPVLDSDGSYFMYSKLRVEKKNWVE RNSYSCSVVHEGLHNHHTTKSFSRTPGK |
| SEQ ID NO: 95 | AF002645_ Pep1 | CDLPQTHSLGSRRTLMLLAQMRRISLFSCLKDRHDFGFPQEE FGNQFQKAETIPVLHEMIQQIFNLFSTKDSSAAWDETLLDKF YTELYQQLNDLEACVIQGVGVTETPLMKEDSILAVRKYFQRI TLYLKEKKYSPCAWEVVRAEIMRSFSLSTNLQESLRSKEVPG VGVPGAGVPGVGVPGGGVPGVGVPGGGVPGAGVPGGGVPGVG VPGAGVPGVGVPGGGQVQLVQSGAEVKKPGASVKVSCKASGG TFSSYAISWVRQAPGQGLEWMGIIDPSVTYTRYAQKFQGRVT MTRDTSTSTVYMELSSLRSEDTAVYYCARSLFPTIFGVEVAF DIWGQGTLVTVSSAKTTAPSVYPLAPVCGDTTGSSVTLGCLV KGYFPEPVTLTWNSGSLSSGVHTFPAVLQSDLYTLSSSVTVT SSTWPSQSITCNVAHPASSTKVDKKIEPRGPTIKPCPPCKCP APNAAGGPSVFIFPPKIKDVLMISLSPIVTCVVVDVSEDDPD VQISWFVNNVEVHTAQTQTHREDYNSTLRVVSALPIQHQDWM SGKEFKCKVNNKDLGAPIERTISKPKGSVRAPQVYVLPPPEE EMTKKQVTLTCMVTDFMPEDIYVEWTNNGKTELNYKNTEPVL DSDGSYFMYSKLRVEKKNWVERNSYSCSVVHEGLHNHHTTKS FSRTPGK |
| SEQ ID NO: 96 | AF002666_ Pep1 | CDLPQTHSLGSRRTLMLLAQMRRISLFSCLKDRHDFGFPQEE FGNQFQKAETIPVLHEMIQQIFNLFSTKDSSAAWDETLLDKF YTELYQQLNDLEACVIQGVGVTETPLMKEDSILAVRKYFQRI TLYLKEKKYSPCAWEVVRAEIMRSFSLSTNLQESLRSKEVPG VGVPGAGVPGVGVPGGGVPGVGVPGGGVPGAGVPGGGVPGVG VPGAGVPGVGVPGGGQVQLVQSGAEVKKPGASVKVSCKASGY TFSNYYIHWVRQAPGQGLEWMGWMDSNSGYTGYAQQFQGRVT MTRDTSTSTVYMELSSLRSEDTAVYYCAKEVFSGWYDYWGQG TLVTVSSAKTTAPSVYPLAPVCGDTTGSSVTLGCLVKGYFPE PVTLTWNSGSLSSGVHTFPAVLQSDLYTLSSSVTVTSSTWPS QSITCNVAHPASSTKVDKKIEPRGPTIKPCPPCKCPAPNAAG GPSVFIFPPKIKDVLMISLSPIVTCVVVDVSEDDPDVQISWF VNNVEVHTAQTQTHREDYNSTLRVVSALPIQHQDWMSGKEFK |

TABLE 16-continued

Sequences of Peptides in TABLE 15

| SEQ ID NO: | DBA | Sequence |
|---|---|---|
| | | CKVNNKDLGAPIERTISKPKGSVRAPQVYVLPPPEEEMTKKQ VTLTCMVTDFMPEDIYVEWTNNGKTELNYKNTEPVLDSDGSY FMYSKLRVEKKNWVERNSYSCSVVHEGLHNHHTTKSFSRTPG K |
| SEQ ID NO: 97 | AF003229_ Pep2 | QVQLVQSGAEVKKPGASVKVSCKASGDTFSTYYVHWVRQAPG QGLEWMGIINPSGGGTVYAQKFQGRVTMTRDTSTSTVYMELS SLRSEDTAVYYCAAGLFIWGQGTLVTVSSAKTTAPSVYPLAP VCGDTTGSSVTLGCLVKGYFPEPVTLTWNSGSLSSGVHTFPA VLQSDLYTLSSSVTVTSSTWPSQSITCNVAHPASSTKVDKKI EPRGPTIKPCPPCKCPAPNAAGGPSVFIFPPKIKDVLMISLS PIVTCVVVDVSEDDPDVQISWFVNNVEVHTAQTQTHREDYNS TLRVVSALPIQHQDWMSGKEFKCKVNNKDLGAPIERTISKPK GSVRAPQVYVLPPPEKEMTKKQVSLTCLVKDFMPEDIYVEWT NNGKTELNYKNTEPVLKSDGSYFMYSKLTVEKKNWVERNSYS CSVVHEGLHNHHTTKSFSRTPGGGSGGGSHHHHHH |
| SEQ ID NO: 98 | AF003230_ Pep2 | QVQLVQSGAEVKKPGASVKVSCKASGYTFSNYYIHWVRQAPG QGLEWMGIINPSGGGTVYAQKFQGRVTMTRDTSTSTVYMELS SLRSEDTAVYYCAAGLFIWGQGTLVTVSSAKTTAPSVYPLAP VCGDTTGSSVTLGCLVKGYFPEPVTLTWNSGSLSSGVHTFPA VLQSDLYTLSSSVTVTSSTWPSQSITCNVAHPASSTKVDKKI EPRGPTIKPCPPCKCPAPNAAGGPSVFIFPPKIKDVLMISLS PIVTCVVVDVSEDDPDVQISWFVNNVEVHTAQTQTHREDYNS TLRVVSALPIQHQDWMSGKEFKCKVNNKDLGAPIERTISKPK GSVRAPQVYVLPPPEKEMTKKQVSLTCLVKDFMPEDIYVEWT NNGKTELNYKNTEPVLKSDGSYFMYSKLTVEKKNWVERNSYS CSVVHEGLHNHHTTKSFSRTPGGGSGGGSHHHHHH |
| SEQ ID NO: 99 | AF003232_ Pep2 | QVQLVQSGAEVKKPGASVKVSCKASGDTFTRHYVHWVRQAPG QGLEWMGIINPSGGYASYAQKFQGRVTMTRDTSTSTVYMELS SLRSEDTAVYYCAAGLFIWGQGTLVTVSSAKTTAPSVYPLAP VCGDTTGSSVTLGCLVKGYFPEPVTLTWNSGSLSSGVHTFPA VLQSDLYTLSSSVTVTSSTWPSQSITCNVAHPASSTKVDKKI EPRGPTIKPCPPCKCPAPNAAGGPSVFIFPPKIKDVLMISLS PIVTCVVVDVSEDDPDVQISWFVNNVEVHTAQTQTHREDYNS TLRVVSALPIQHQDWMSGKEFKCKVNNKDLGAPIERTISKPK GSVRAPQVYVLPPPEKEMTKKQVSLTCLVKDFMPEDIYVEWT NNGKTELNYKNTEPVLKSDGSYFMYSKLTVEKKNWVERNSYS CSVVHEGLHNHHTTKSFSRTPGGGSGGGSHHHHHH |
| SEQ ID NO: 100 | AF003250_ Pep2 | QVQLVQSGAEVKKPGASVKVSCKASGYTFTTYYVHWVRQAPG QGLEWMGIINPSGGSTSYAQNFQGRVTMTRDTSTSTVYMELS SLRSEDTAVYYCASGWDVWGQGTTVTVSSASGGGGSGGGGSG GGGSHASEIVMTQSPATLSVSPGERATLSCRASQSVNTYLAW YQQKPGQAPRLLIYGASTRATGIPARFSGSGSGTEFTLTISS LQSEDFAVYYCQQYGSSPVTFGQGTRLEIKPRGPTIKPCPPC KCPAPNAAGGPSVFIFPPKIKDVLMISLSPIVTCVVVDVSED DPDVQISWFVNNVEVHTAQTQTHREDYNSTLRVVSALPIQHQ DWMSGKEFKCKVNNKDLGAPIERTISKPKGSVRAPQVYVLPP PEKEMTKKQVSLTCLVKDFMPEDIYVEWTNNGKTELNYKNTE PVLKSDGSYFMYSKLTVEKKNWVERNSYSCSVVHEGLHNHHT TKSFSRTPGGGSGGGSHHHHHH |
| SEQ ID NO: 101 | AF003251_ Pep2 | QVQLVQSGAEVKKPGASVKVSCKASGYTFTTYYVHWVRQAPG QGLEWMGIINPSGGSTSYAQNFQGRVTMTRDTSTSTVYMELS SLRSEDTAVYYCASGWDVWGQGTTVTVSSASGGGGSGGGGSG GGGSHASEIVMTQSPATLSVSPGERATLSCRASQSVNTYLAW YQQKPGQAPRLLIYGASTRATGIPARFSGSGSGTEFTLTISS LQSEDFAVYYCQQYGSSPVTFGQGTRLEIKPRGPTIKPCPPC KCPAPNAAGGPSVFIFPPKIKDVLMISLSPIVTCVVVDVSED DPDVQISWFVNNVEVHTAQTQTHREDYNSTLRVVSALPIQHQ DWMSGKEFKCKVNNKDLGAPIERTISKPKGSVRAPQVYVLPP PEKEMTKKQVSLTCLVKDFMPEDIYVEWTNNGKTELNYKNTE PVLKSDGSYFMYSKLTVEKKNWVERNSYSCSVVHEGLHNHHT TKSFSRTPGGGSGGGSHHHHHH |
| SEQ ID NO: 102 | AF003253_ Pep2 | QVQLVQSGAEVKKPGASVKVSCKASGYTFTTYYVHWVRQAPG QGLEWMGIINPSGGSTSYAQNFQGRVTMTRDTSTSTVYMELS SLRSEDTAVYYCASGWDVWGQGTTVTVSSASGGGGSGGGGSG GGGSHASEIVMTQSPATLSVSPGERATLSCRASQSVNTYLAW YQQKPGQAPRLLIYGASTRATGIPARFSGSGSGTEFTLTISS LQSEDFAVYYCQQYGSSPVTFGQGTRLEIKPRGPTIKPCPPC KCPAPNAAGGPSVFIFPPKIKDVLMISLSPIVTCVVVDVSED DPDVQISWFVNNVEVHTAQTQTHREDYNSTLRVVSALPIQHQ |

TABLE 16-continued

Sequences of Peptides in TABLE 15

| SEQ ID NO: | DBA | Sequence |
|---|---|---|
| | | DWMSGKEFKCKVNNKDLGAPIERTISKPKGSVRAPQVYVLPP PEKEMTKKQVSLTCLVKDFMPEDIYVEWTNNGKTELNYKNTE PVLKSDGSYFMYSKLTVEKKNWVERNSYSCSVVHEGLHNHHT TKSFSRTPGGGSGGGSHHHHHH |
| SEQ ID NO: 103 | AF003103_Pep2 | QVQLVQSGAEVKKPGASVKVSCKASGGTFSSYAISWVRQAPG QGLEWMGIIDPSVTYTRYAQKFQGRVTMTRDTSTSTVYMELS SLRSEDTAVYYCARSLFPTIFGVEVAFDIWGQGTLVTVSSAK TTAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNAAGGPSVFIFPP KIKDVLMISLSPIVTCVVVDVSEDDPDVQISWFVNNVEVHTA QTQTHREDYNSTLRVVSALPIQHQDWMSGKEFKCKVNNKDLG APIERTISKPKGSVRAPQVYVLPPCEEEMTKKQVTLSCAVTD FMPEDIYVEWTNNGKTELNYKNTEPVLDSDGSYFMVSKLRVE KKNWVERNSYSCSVVHEGLHNHHTTKSFSRTPGKHHHHHH |
| SEQ ID NO: 104 | AF003104_Pep2 | QVQLVQSGAEVKKPGASVKVSCKASGYTFSNYYIHWVRQAPG QGLEWMGWMDSNGGTGYAQKFQGRVTMTRDTSTSTVYMELS SLRSEDTAVYYCAKEVFSGWYDYWGQGTLVTVSSAKTTAPSV YPLAPVCGDTTGSSVTLGCLVKGYFPEPVTLTWNSGSLSSGV HTFPAVLQSDLYTLSSSVTVTSSTWPSQSITCNVAHPASSTK VDKKIEPRGPTIKPCPPCKCPAPNAAGGPSVFIFPPKIKDVL MISLSPIVTCVVVDVSEDDPDVQISWFVNNVEVHTAQTQTHR EDYNSTLRVVSALPIQHQDWMSGKEFKCKVNNKDLGAPIERT ISKPKGSVRAPQVYVLPPCEEEMTKKQVTLSCAVTDFMPEDI YVEWTNNGKTELNYKNTEPVLDSDGSYFMVSKLRVEKKNWVE RNSYSCSVVHEGLHNHHTTKSFSRTPGKHHHHHH |
| SEQ ID NO: 105 | AF003105_Pep2 | QVQLVQSGAEVKKPGASVKVSCKASGYTFSGYYIHWVRQAPG QGLEWMGWMDSNSGGTGYAQKFQGRVTMTRDTSTSTVYMELS SLRSEDTAVYYCAKEVFSGWYDYWGQGTLVTVSSAKTTAPSV YPLAPVCGDTTGSSVTLGCLVKGYFPEPVTLTWNSGSLSSGV HTFPAVLQSDLYTLSSSVTVTSSTWPSQSITCNVAHPASSTK VDKKIEPRGPTIKPCPPCKCPAPNAAGGPSVFIFPPKIKDVL MISLSPIVTCVVVDVSEDDPDVQISWFVNNVEVHTAQTQTHR EDYNSTLRVVSALPIQHQDWMSGKEFKCKVNNKDLGAPIERT ISKPKGSVRAPQVYVLPPCEEEMTKKQVTLSCAVTDFMPEDI YVEWTNNGKTELNYKNTEPVLDSDGSYFMVSKLRVEKKNWVE RNSYSCSVVHEGLHNHHTTKSFSRTPGKHHHHHH |
| SEQ ID NO: 106 | AF003106_Pep2 | QVQLVQSGAEVKKPGASVKVSCKASGYTFSNYYIHWVRQAPG QGLEWMGWMDSNSGYTGYAQQFQGRVTMTRDTSTSTVYMELS SLRSEDTAVYYCAKEVFSGWYDYWGQGTLVTVSSAKTTAPSV YPLAPVCGDTTGSSVTLGCLVKGYFPEPVTLTWNSGSLSSGV HTFPAVLQSDLYTLSSSVTVTSSTWPSQSITCNVAHPASSTK VDKKIEPRGPTIKPCPPCKCPAPNAAGGPSVFIFPPKIKDVL MISLSPIVTCVVVDVSEDDPDVQISWFVNNVEVHTAQTQTHR EDYNSTLRVVSALPIQHQDWMSGKEFKCKVNNKDLGAPIERT ISKPKGSVRAPQVYVLPPCEEEMTKKQVTLSCAVTDFMPEDI YVEWTNNGKTELNYKNTEPVLDSDGSYFMVSKLRVEKKNWVE RNSYSCSVVHEGLHNHHTTKSFSRTPGKHHHHHH |
| SEQ ID NO: 107 | AF003217_Pep2 | QVQLVQSGAEVKKPGASVKVSCKASGYTFTKNYMHWVRQAPG QGLEWLGWVSPDSGYTGYAQKFQGRVTMTRDTSTSTVYMELS SLRSEDTAVYYCTTDLLSLELDDAFDIWGQGTMVTVSSASGG GGSGGGGSGGGGSHASDIQMTQSPSSLSASVGDRVTITCRAS QSISSWLAWYQQKPGKAPKLLIYAASTLQSGVPSRFSGSGSG TDFTLTISSLQPEDFATYYCQQSYSTPLTFGGGTKLEIKPRG PTIKPCPPCKCPAPNAAGGPSVFIFPPKIKDVLMISLSPIVT CVVVDVSEDDPDVQISWFVNNVEVHTAQTQTHREDYNSTLRV VSALPIQHQDWMSGKEFKCKVNNKDLGAPIERTISKPKGSVR APQVYVLPPCEEEMTKKQVTLSCAVTDFMPEDIYVEWTNNGK TELNYKNTEPVLDSDGSYFMVSKLRVEKKNWVERNSYSCSVV HEGLHNHHTTKSFSRTPGK |
| SEQ ID NO: 108 | AF003218_Pep2 | QVQLVQSGAEVKKPGASVKVSCKASGYTFTKNYMHWVRQAPG QGLEWLGWVSPDSGYTGYAQKFQGRVTMTRDTSTSTVYMELS SLRSEDTAVYYCTTDLLSLELDDAFDIWGQGTMVTVSSASGG GGSGGGGSGGGGSHASDIQMTQSPSSLSASVGDRVTITCRAS QSISSWLAWYQQKPGKAPKLLIYAASTLQSGVPSRFSGSGSG TDFTLTISSLQPEDFATYYCQQSYSTPLTFGGGTKLEIKPRG PTIKPCPPCKCPAPNAAGGPSVFIFPPKIKDVLMISLSPIVT CVVVDVSEDDPDVQISWFVNNVEVHTAQTQTHREDYNSTLRV VSALPIQHQDWMSGKEFKCKVNNKDLGAPIERTISKPKGSVR |

TABLE 16-continued

Sequences of Peptides in TABLE 15

| SEQ ID NO: | DBA | Sequence |
|---|---|---|
| | | APQVYVLPPCEEEMTKKQVTLSCAVTDFMPEDIYVEWTNNGK TELNYKNTEPVLDSDGSYFMVSKLRVEKKNWVERNSYSCSVV HEGLHNHHTTKSFSRTPGK |
| SEQ ID NO: 109 | AF003219_ Pep2 | QVQLVQSGAEVKKPGASVKVSCKASGYTFTKNYMHWVRQAPG QGLEWLGWVSPDSGYTGYAQKFQGRVTMTRDTSTSTVYMELS SLRSEDTAVYYCTTDLLSLELDDAFDIWGQGTMVTVSSASGG GGSGGGGSGGGGSHASDIQMTQSPSSLSASVGDRVTITCRAS QSISSWLAWYQQKPGKAPKLLIYAASTLQSGVPSRFSGSGSG TDFTLTISSLQPEDFATYYCQQSYSTPLTFGGGTKLEIKPRG PTIKPCPPCKCPAPNAAGGPSVFIFPPKIKDVLMISLSPIVT CVVVDVSEDDPDVQISWFVNNVEVHTAQTQTHREDYNSTLRV VSALPIQHQDWMSGKEFKCKVNNKDLGAPIERTISKPKGSVR APQVYVLPPCEEEMTKKQVTLSCAVTDFMPEDIYVEWTNNGK TELNYKNTEPVLDSDGSYFMVSKLRVEKKNWVERNSYSCSVV HEGLHNHHTTKSFSRTPGK |
| SEQ ID NO: 110 | AF002618_ Pep2 | CDLPQTHSLGSRRTLMLLAQMRRISLFSCLKDRHDFGFPQEE FGNQFQKAETIPVLHEMIQQIFNLFSTKDSSAAWDETLLDKF YTELYQQLNDLEACVIQGVGVTETPLMKEDSILAVRKYFQRI TLYLKEKKYSPCAWEVVRAEIMRSFSLSTNLQESLRSKEGGG GSGGGGSGGGGSGGGGSDIQMTQSPSSLSASVGDRVTITCRA SQSISNRLAWYQQKPGKAPKLLIYKASSLESGVPSRFSGSGS GTDFTLTISSLQPEDFATYYCQQSNSTPFTFGQGTKVEIKRA DAAPTVSIFPPSSEQLTSGGASVVCFLNNFYPKDINVKWKID GSERQNGVLNSWTDQDSKDSTYSMSSTLTLTKDEYERHNSYT CEATHKTSTSPIVKSFNRNEC |
| SEQ ID NO: 111 | AF002639_ Pep2 | CDLPQTHSLGSRRTLMLLAQMRRISLFSCLKDRHDFGFPQEE FGNQFQKAETIPVLHEMIQQIFNLFSTKDSSAAWDETLLDKF YTELYQQLNDLEACVIQGVGVTETPLMKEDSILAVRKYFQRI TLYLKEKKYSPCAWEVVRAEIMRSFSLSTNLQESLRSKEGGG GSGGGGSGGGGSGGGGSDIQMTQSPSSLSASVGDRVTITCRA SQSISSYLNWYQQKPGKAPKLLIYAASSLQSGVPSRFSGSGS GTDFTLTISSLQPEDFATYYCQQSYSTPYTFGQGTKVEIKRA DAAPTVSIFPPSSEQLTSGGASVVCFLNNFYPKDINVKWKID GSERQNGVLNSWTDQDSKDSTYSMSSTLTLTKDEYERHNSYT CEATHKTSTSPIVKSFNRNEC |
| SEQ ID NO: 112 | AF002645_ Pep2 | DIQMTQSPSSLSASVGDRVTITCRASQSISNRLAWYQQKPGK APKLLIYKASSLESGVPSRFSGSGSGTDFTLTISSLQPEDFA TYYCQQSNSTPFTFGQGTKVEIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC |
| SEQ ID NO: 114 | AF003229_ Pep3 | DIQMTQSPSSLSASVGDRVTITCRASQYISSGLAWYQQKPGK APKLLIYKASSLDNGVPSRFSGSGSGTDFTLTISSLQPEDFA TYYCQQYERLPLTFGGGTKVEIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC |
| SEQ ID NO: 115 | AF003230_ Pep3 | DIQMTQSPSSLSASVGDRVTITCRASQSIGTGLAWYQQKPGK APKLLIYKASSLDNGVPSRFSGSGSGTDFTLTISSLQPEDFA TYYCQQYNRAPLTFGGGTKVEIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC |
| SEQ ID NO: 116 | AF003232_ Pep3 | DIQMTQSPSSLSASVGDRVTITCRASQSIGRWLAWYQQKPGK APKLLIYSASNLETGVPSRFSGSGSGTDFTLTISSLQPEDFA TYYCQQYESFPVTFGPGTKVDIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC |
| SEQ ID NO: 126 | AF003219_ Pep3 | DIQMTQSPSSLSASVGDRVTITCRASQSISSYLNWYQQKPGK APKLLIYAASSLESGVPSRFSGSGSGTDFTLTISSLQPEDFA TYYCQQSYSTPYTFGQGTKVDIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC |

Example 7

Reduced Type I IFNα Reporter Activation by a PD-L1/IFNα Protein Complex

Figure 10:
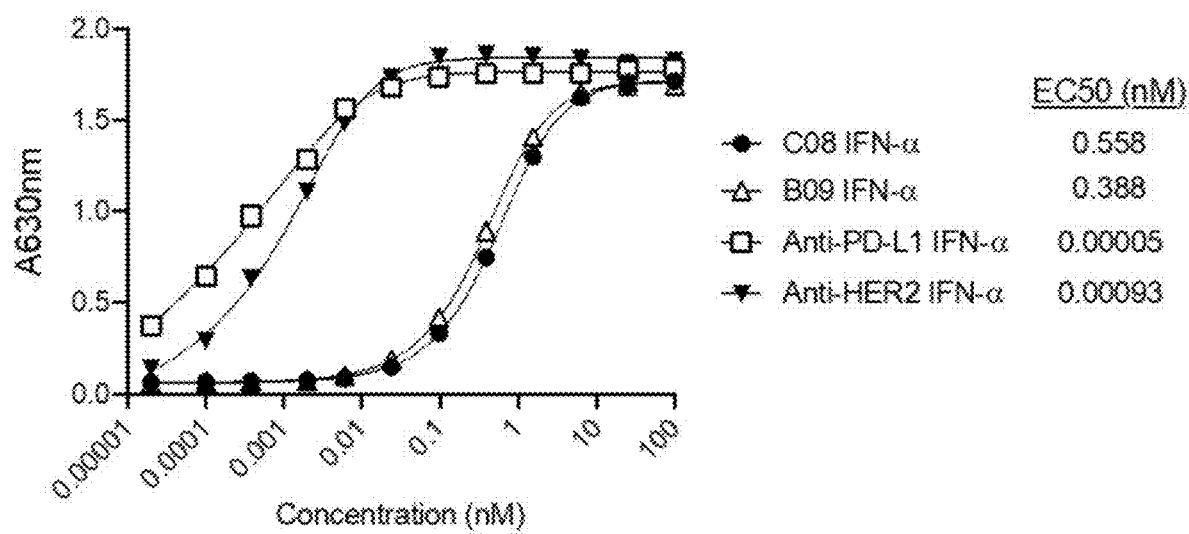
FIG. 10 shows that interferon signaling by two exemplary PD-L1/IFNα DBA cytokine protein complexes (C08 IFNα and B09 IFNα, SEQ ID NO: 57-SEQ ID NO: 58 and SEQ ID NO: 59-SEQ ID NO: 60 respectively) is reduced as compared to two control IFNα-antibody protein complexes (Anti-HER2 IFNα and Anti-PD-L1 IFNα, SEQ ID NO: 63-SEQ ID NO: 64 and SEQ ID NO: 61-SEQ ID NO: 62 respectively).

This example demonstrates reduced Type I IFNα reporter activation by a PD-L1/IFNα protein complex of the present disclosure, specifically a PD-L1/IFNα DBA/cytokine complexes, relative to unregulated antibody-IFNα immune cytokines. The DBA-cytokine protein complexes and control immune cytokines used in this experiment were IgG proteins with IFNα fused to the N-terminus of the heavy chain through a linker composed of 4 repeats of "GGGGS," as exemplified in FIG. 9E. The genes for two DBA-cytokine complexes, C08 IFNα (CDLPQTHSLGSRRTLML-LAQMRRISLFSCLKDRHDFGFPQEEFGNQFQKAE-TIPVLHEM IQQIFNLFSTKDSSAAWDETLLDKFYTE-LYQQLNDLEACVIQGVGVTETPLMKEDSILAV RKYFQRITLYLKEKKYSPCAWEVVRAEIMRSFSL-STNLQESLRSKEGGGGSGGGGSGGG GSGGGGSQVQLVQSGAEVKKPGASVKVSCK-ASGGTFSSYAISWVRQAPGQGLEWMGII DPSVTYTRYAQKFQGRVTMTRDTST-STVYMELSSLRSEDTAVYYCARSLFPTIFGVEVA FDIWGQGTLVTVSSAKTTAPSVY-PLAPVCGDTTGSSVTLGCLVKGYFPEPVTLTWNSGS LSSGVHTFPAVLQSDLYTLSSSVTVTSSTWPSQSITCN-VAHPASSTKVDKKIEPRGPTIKP CPPCKCPAP-NAAGGPSVFIFPPKIKDVLMISLSPIV-TCVVVDVSEDDPDVQISWFVNNVE VHTAQTQTHREDYNSTLRVVSAL-PIQHQDWMSGKEFKCKVNNKDLGAPIERTISKPKG SVRAPQVYVLPPPEEEMTKKQVTLTCMVTDFM-PEDIYVEWTNNGKTELNYKNTEPVLD SDGSYFMYSKLRVEKKNWVERNSYS-CSVVHEGLHNHHTTKSFSRTPGK; SEQ ID NO: 57 and DIQMTQSPSSLSASVGDRVTITCQASQDIS-NYLNWYQQKPGKAPKWYGASTLQSGVPS RFSGSGSGTDFTLTISSLQPEDFATYYCQQTYST-PITFGQGTKVEIKRADAAPTVSIFPPSS EQLTSG-GASVVCFLNNFYPKDINVKWKIDGSERQNGVLN-SWTDQDSKDSTYSMSSTLT LTKDEYERHNSYTCEATHKTSTSPIVKSFNRNEC; SEQ ID NO: 58) and B09 IFNα (CDLPQTHSLGSRRTLML-LAQMIRRISLFSCLKDRHDFGFPQEEFGNQFQKAE-TIPVLHEM IQQIFNLFSTKDSSAAWDETLLDKFYTE-LYQQLNDLEACVIQGVGVTETPLMKEDSILAV RKYFQRITLYLKEKKYSPCAWEVVRAEIMRSFSL-STNLQESLRSKEGGGGSGGGGSGGG GSGGGGSQVQLVQSGAEVKKPGASVKVSCK-ASGGTFTGYYMHWVRQAPGQGLEWM GWVNPNSGNTGYAQKFQGRVTMTRDTST-STVYMELSSLRSEDTAVYYCARSLFPTIFG VEVAFDIWGQGTLVTVSSAKTTAPSVY-PLAPVCGDTTGSSVTLGCLVKGYFPEPVTLTW NSGSLSSGVHTFPAVLQSDLYTLSSSVTVTSSTWP-SQSITCNVAHPASSTKVDKKIEPRGP TIKPCPPCK-CPAPNAAGGPSVFIFPPKIKDVLMISLSPIV-TCVVVDVSEDDPDVQISWFVN NVEVHTAQTQTHREDYNSTLRVVSAL- PIQHQDWMSGKEFKCKVNNKDLGAPIERTISK PKGSVRAPQVYVLPPPEEEMTKKQVTLTCMVTDFM- PEDIYVEWTNNGKTELNYKNTEP VLDSDGSYFMYSKLRVEKKNWVERNSYS- CSVVHEGLHNHEITTKSFSRTPGK; SEQ ID NO: 59 and DIQMTQSPSSLSASVGDRVTITCQASQDIS- NYLNWYQQKPGKAPKLLIYAASSLQSGVPS RFSGSGSGTDFTLTISSLQPEDFATYYCQQSYS- PPPTFGQGTKLEIKRADAAPTVSIFPPSS EQLTSG- GASVVCFLNNFYPKDINVKWKIDGSERQNGVLN- SWTDQDSKDSTYSMSSTLT LTKDEYERHNSYTCEATHKTSTSPIVKSFNRNEC; SEQ ID NO: 60), and two control immune-cytokines, anti-Her2 IFNα (CDLPQTHSLGSRRTLMLLAQMIRRISLF- SCLKDRHDFGFPQEEFGNQFQKAETIPVLHEM IQQIFNLFSTKDSSAAWDETLLDKFYTELYQQLN- DLEACVIQGVGVTETPLMKEDSILAV RKYFQRIT- LYLKEKKYSPCAWEVVRAEIMRSFSLSTNLQESLR- SKEGGGGSGGGGSGGG GSGGGGSQVQLVQSGAEVKKPGASVKVSCK- ASGGTFSSYAISWVRQAPGQGLEWMG WINPNSGGTNYAQKFQGRVTMTRDTST- STVYMELSSLRSEDTAVYYCARSLFPTIFGVE VAFDIWGQGTTVTVSSAKTTAPSVY- PLAPVCGDTTGSSVTLGCLVKGYFPEPVTLTWNS GSLSSGVHTFPAVLQSDLYTLSSSVTVTSSTWP- SQSITCNVAHPASSTKVDKKIEPRGPTI KPCPPCK- CPAPNAAGGPSVFIFPPKIKDVLMISLSPIV- TCVVVDVSEDDPDVQISWFVNN VEVHTAQTQTHREDYNSTLRVVSAL- PIQHQDWMSGKEFKCKVNNKDLGAPIERTISKP KGSVRAPQVYVLPPPEEEMTKKQVTLTCMVTDFM- PEDIYVEWTNNGKTELNYKNTEP VLDSDGSYFMYSKLRVEKKNWVERNSYS- CSVVHEGLHNHEITTKSFSRTPGK; SEQ ID NO: 61 and DIQMTQSPSSLSASVGDRVTITCRASQSBDR- LAWYQQKPGKAPKLLIYKASSLESGVPSR FSGSGSGTDFTLTISSLQPEDFATYYCQQSYS- TPFTFGPGTKVDIKRADAAPTVSIFPPSSE QLTSG- GASVVCFLNNFYPKDINVKWKIDGSERQNGVLN- SWTDQDSKDSTYSMSSTLTL TKDEYERHNSYTCEATHKTSTSPIVKSFNRNEC; SEQ ID NO: 62) and anti-PD-L1 IFNα (CDLPQTHSLGSRRTLMLLAQMRRISLF- SCLKDRHDFGFPQEEFGNQFQKAETIPVLHEM IQQIFNLFSTKDSSAAWDETLLDKFYTELYQQLN- DLEACVIQGVGVTETPLMKEDSILAV RKYFQRIT- LYLKEKKYSPCAWEVVRAEIMRSFSLSTNLQESLR- SKEGGGGSGGGGSGGG GSGGGGSEVQLVESGGGLVQPGGSLRLS- CAASGFNIKDTYIHWVRQAPGKGLEWVARI YPTNGYTRYADSVKGRFTISADTSKNTAYLQMNSL- RAEDTAVYYCSRWGGDGFYAMD YWGQGTLVTVS- SAKTTAPSVYPLAPVCGDTTGSSVTLGCLVKGYF- PEPVTLTWNSGSL SSGVHTFPAVLQSDLYTLSSSVTVTSSTWPSQSITCN- VAHPASSTKVDKKIEPRGPTIKPC PPCKCPAP- NAAGGPSVFIFPPKIKDVLMISLSPIV- TCVVVDVSEDDPDVQISWFVNNVEV HTAQTQTHREDYNSTLRVVSAL- PIQHQDWMSGKEFKCKVNNKDLGAPIERTISKPKGS VRAPQVYVLPPPEEEMTKKQVTLTCMVTDFM- PEDIYVEWTNNGKTELNYKNTEPVLDS DGSYFMYSKLRVEKKNWVERNSYS- CSVVHEGLHNHHTTKSFSRTPGK; SEQ ID NO: 63 and DIQMTQSPSSLSASVGDRVTITCRASQDVNTA- VAWYQQKPGKAPKLLIYSASFLYSGVP SRFSGSRSGTDFTLTISSLQPEDFA- TYYCQQHYTTPPTFGQGTKVEIKRADAAPTVSIFPPS SEQLTSGGASVVCFLNNFYPKDINVKWKIDGSER- QNGVLNSWTDQDSKDSTYSMSSTL TLTKDEYERHN- SYTCEATHKTSTSPIVKSFNRNEC; SEQ ID NO: 64) were synthesized, expressed in HEK293 cells and Protein A purified (GenScript). Titrated concentrations of the DBA-cytokine complexes and antibody-cytokine controls were added to a 96-well plate along with 50,000 type I IFNα reporter cells (InvivoGen) in complete DMEM (+10% FBS, 2 mM L-glutamine, sodium pyruvate). Plates were incubated at 37° C. overnight and developed by adding 20 uL of culture supernatant to 180 uL QUANTI-Blue Solution (InvivoGen). After a 30 minute incubation at room temperature, plates were read on an Envision (Perkin Elmer) at 630 nm. In the absence of PD-L1, the IFNα tethered PD-L1-IFNα DBA complexes C08 and B09 show decreased reporter activation compared to equimolar amounts of the control anti-PD-L1 or anti-HER2 IFNα immunocytokines (FIG. 10).

Example 8

Reduced CD8+ T Cell STAT5 Phosphorylation by a PD-1/IL-2 Dual Binding Antibody (DBA) Cytokine Complexes This example describes CD8+ T-cell STAT5 phosphorylation by PD-1/IL-2 DBA-cytokine complexes of the present disclosure. Genes for the PD-1/IL-2 DBAs shown in TABLE 17 were synthesized and expressed in HEK293 as IgG proteins with IL-2 fused to the N-terminus of the heavy or light chain through a linker (Genscript). Although only two of the antibodies blocked IL-2 binding to IL-2RB as scFvs, over 30 of the antibodies were able to reduce IL-2 signaling by a linked IL-2 domain. An exemplary set of these DBAs were chosen for analysis and compared to a control anti-HER2-IL-2 immunocytokine (TABLE 17).

TABLE 17

IgG PD-1/IL-2 DBA protein complexes

| Name | Heavy Chain Sequence SEQ ID NO | Light Chain Sequence SEQ ID NO |
|---|---|---|
| Anti-HER2 | (SEQ ID NO: 65) EVQLVESGGGLVQPGGSLR LSCAASGFNIKDTYIHWVR QAPGKGLEWVARIYPTNGY TRYADSVKGRFTISADTSK NTAYLQMNSLRAEDTAVYY CSRWGGDGFYAMDYWGQGT LVTVSSAKTTAPSVYPLAP VCGDTTGSSVTLGCLVKGY FPEPVTLTWNSGSLSSGVH TFPAVLQSDLYTLSSSVTV TSSTWPSQSITCNVAHPAS STKVDKKIEPRGPTIKPCP PCKCPAPNAAGGPSVFIFP PKIKDVLMISLSPIVTCVV VDVSEDDPDVQISWFVNNV EVHTAQTQTHREDYNSTLR VVSALPIQHQDWMSGKEFK CKVNNKDLGAPIERTISKP KGSVRAPQVYVLPPPEEEM TKKQVTLTCMVTDFMPEDI YVEWTNNGKTELNYKNTEP VLDSDGSYFMYSKLRVEKK NWVERNSYSCSVVHEGLHN HHTTKSFSRTPGK | (SEQ ID NO: 66) APTSSSTKKTQLQLEHLLL DLQMILNGINNYKNPKLTR MLTFKFYMPKKATELKHLQ CLEEELKPLEEVLNLAQSK NFHLRPRDLISNINVIVLE LKGSETTFMCEYADETATI VEFLNRWITFCQSIISTLT VPGVGVPGAGVPGVGVPGG GVPGVGVPGGGVPGAGVPG GGVPGVGVPGAGVPGVGVP GGGDIQMTQSPSSLSASVG DRVTITCRASQDVNTAVAW YQQKPGKAPKLLIYSASFL YSGVPSRFSGSRSGTDFTL TISSLQPEDFATYYCQQHY TTPPTFGQGTKVEIKRADA APTVSIFPPSSEQLTSGGA SVVCFLNNFYPKDINVKWK IDGSERQNGVLNSWTDQDS KDSTYSMSSTLTLTKDEYE RHNSYTCEATHKTSTSPIV KSFNRNEC |
| 2-A08 | (SEQ ID NO: 67) QVQLVQSGAEVKKPGASVK VSCKVSGYTFTSYDINWVR QAPGQGLEWMGWINPNSGD TGYAQKFQGRVTMTRDTST STVYMELSSLRSEDTAVYY CARDTGLGYYYGSGDFDYW GQGTLVTVSSAKTTAPSVY PLAPVCGDTTGSSVTLGCL VKGYFPEPVTLTWNSGSLS SGVHTFPAVLQSDLYTLSS SVTVTSSTWPSQSITCNVA HPASSTKVDKKIEPRGPTI KPCPPCKCPAPNAAGGPSV FIFPPKIKDVLMISLSPIV TCVVVDVSEDDPDVQISWF VNNVEVHTAQTQTHREDYN STLRVVSALPIQHQDWMSG KEFKCKVNNKDLGAPIERT ISKPKGSVRAPQVYVLPPP EEEMTKKQVTLTCMVTDFM PEDIYVEWTNNGKTELNYK NTEPVLDSDGSYFMYSKLR VEKKNWVERNSYSCSVVHE GLHNHHTTKSFSRTPGK | (SEQ ID NO: 68) APTSSSTKKTQLQLEHLLL DLQMILNGINNYKNPKLTR MLTFKFYMPKKATELKHLQ CLEEELKPLEEVLNLAQSK NFHLRPRDLISNINVIVLE LKGSETTFMCEYADETATI VEFLNRWITFCQSIISTLT VPGVGVPGAGVPGVGVPGG GVPGVGVPGGGVPGAGVPG GGVPGVGVPGAGVPGVGVP GGGDIQMTQSPSSLSASVG DRVTITCQASQDIHNYLNW YQQKPGKAPKLLIYDVSNL ETGVPSRFSGSGSGTDFTL TISSLQPEDFATYYCQQAI SFPLTFGGGTKVEIKRADA APTVSIFPPSSEQLTSGGA SVVCFLNNFYPKDINVKWK IDGSERQNGVLNSWTDQDS KDSTYSMSSTLTLTKDEYE RHNSYTCEATHKTSTSPIV KSFNRNEC |
| 2-A11 | (SEQ ID NO: 69) QVQLVQSGAEVKKPGASVK VSCKASGHTFTRYYMHWVR QAPGQGLEWMGIINPSGGY ATYAQKFQGRVTMTRDTST STVYMELSSLRSEDTAVYY CASGWDVWGQGTLVTVSSA KTTAPSVYPLAPVCGDTTG SSVTLGCLVKGYFPEPVTL TWNSGSLSSGVHTFPAVLQ SDLYTLSSSVTVTSSTWPS QSITCNVAHPASSTKVDKK IEPRGPTIKPCPPCKCPAP NAAGGPSVFIFPPKIKDVL MISLSPIVTCVVVDVSEDD PDVQISWFVNNVEVHTAQT QTHREDYNSTLRVVSALPI QHQDWMSGKEFKCKVNNKD LGAPIERTISKPKGSVRAP QVYVLPPPEEEMTKKQVTL TCMVTDFMPEDIYVEWTNN GKTELNYKNTEPVLDSDGS YFMYSKLRVEKKNWVERNS YSCSVVHEGLHNHHTTKSF SRTPGK | (SEQ ID NO: 70) APTSSSTKKTQLQLEHLLL DLQMILNGINNYKNPKLTR MLTFKFYMPKKATELKHLQ CLEEELKPLEEVLNLAQSK NFHLRPRDLISNINVIVLE LKGSETTFMCEYADETATI VEFLNRWITFCQSIISTLT VPGVGVPGAGVPGVGVPGG GVPGVGVPGGGVPGAGVPG GGVPGVGVPGAGVPGVGVP GGGDIQMTQSPSSLSASVG DRVTITCRASQSINSWLAW YQQKPGKAPKLLIYATSTL ESGVPSRFSGSGSGTDFTL TISSLQPEDFATYYCQQSY SFPPTFGQGTKVEIKRADA APTVSIFPPSSEQLTSGGA SVVCFLNNFYPKDINVKWK IDGSERQNGVLNSWTDQDS KDSTYSMSSTLTLTKDEYE RHNSYTCEATHKTSTSPIV KSFNRNEC |
| 2-B05 | (SEQ ID NO: 71) QVQLVQSGAEVKKPGASVK VSCKASGYTFTNYYIHWVR QAPGQGLEWMGIINPRAGY TSYALKFQGRVTMTRDTST STVYMELSSLRSEDTAVYY CAGGWLDWGQGTLVTVSSA KTTAPSVYPLAPVCGDTTG SSVTLGCLVKGYFPEPVTL TWNSGSLSSGVHTFPAVLQ SDLYTLSSSVTVTSSTWPS QSITCNVAHPASSTKVDKK IEPRGPTIKPCPPCKCPAP NAAGGPSVFIFPPKIKDVL MISLSPIVTCVVVDVSEDD PDVQISWFVNNVEVHTAQT QTHREDYNSTLRVVSALPI QHQDWMSGKEFKCKVNNKD LGAPIERTISKPKGSVRAP QVYVLPPPEEEMTKKQVTL TCMVTDFMPEDIYVEWTNN GKTELNYKNTEPVLDSDGS YFMYSKLRVEKKNWVERNS YSCSVVHEGLHNHHTTKSF SRTPGK | (SEQ ID NO: 72) APTSSSTKKTQLQLEHLLL DLQMILNGINNYKNPKLTR MLTFKFYMPKKATELKHLQ CLEEELKPLEEVLNLAQSK NFHLRPRDLISNINVIVLE LKGSETTFMCEYADETATI VEFLNRWITFCQSIISTLT VPGVGVPGAGVPGVGVPGG GVPGVGVPGGGVPGAGVPG GGVPGVGVPGAGVPGVGVP GGGDIQMTQSPSSLSASVG DRVTITCRASQSISSWLAW YQQKPGKAPKLLIYAASSL QSGVPSRFSGSGSGTDFTL TISSLQPEDFATYYCQQSF TMPITFGQGTRLEIKRADA APTVSIFPPSSEQLTSGGA SVVCFLNNFYPKDINVKWK IDGSERQNGVLNSWTDQDS KDSTYSMSSTLTLTKDEY ERHNSYTCEATHKTSTSP IVKSFNRNEC |
| 2-B07 | (SEQ ID NO: 73) QVQLVQSGAEVKKPGASVK VSCKASGDTFTRYHVHWVR QAPGQGLEWMGIINPSGGY | (SEQ ID NO: 74) APTSSSTKKTQLQLEHLLL DLQMILNGINNYKNPKLTR MLTFKFYMPKKATELKHLQ |

TABLE 17-continued

IgG PD-1/IL-2 DBA protein complexes

| Name | Heavy Chain Sequence SEQ ID NO | Light Chain Sequence SEQ ID NO |
|---|---|---|
| | ASYAQKFQGRVTMTRDTST STVYMELSSLRSEDTAVYY CAAGLFIWGQGTLVTVSSA KTTAPSVYPLAPVCGDTTG SSVTLGCLVKGYFPEPVTL TWNSGSLSSGVHTFPAVLQ SDLYTLSSSVTVTSSTWPS QSITCNVAHPASSTKVDKK IEPRGPTIKPCPPCKCPAP NAAGGPSVFIFPPKIKDVL MISLSPIVTCVVVDVSEDD PDVQISWFVNNVEVHTAQT QTHREDYNSTLRVVSALPI QHQDWMSGKEFKCKVNNKD LGAPIERTISKPKGSVRAP QVYVLPPPEEEMTKKQVTL TCMVTDFMPEDIYVEWTNN GKTELNYKNTEPVLDSDGS YFMYSKLRVEKKNWVERNS YSCSVVHEGLHNHHTTKSF SRTPGK | CLEEELKPLEEVLNLAQSK NFHLRPRDLISNINVIVLE LKGSETTFMCEYADETATI VEFLNRWITFCQSIISTLT VPGVGVPGAGVPGVGVPGG GVPGVGVPGGGVPGAGVPG GGVPGVGVPGAGVPGVGVP GGGDIQMTQSPSSLSASVG DRVTITCRASQSIGRWLAW YQQKPGKAPKLLIYSASNL ETGVPSRFSGSGSGTDFTL TISSLQPEDFATYYCQQAN SFPVTFGPGTKVDIKRADA APTVSIFPPSSEQLTSGGA SVVCFLNNFYPKDINVKWK IDGSERQNGVLNSWTDQDS KDSTYSMSSTLTLTKDEYE RHNSYTCEATHKTSTSPIV KSFNRNEC |
| 7-A04 | (SEQ ID NO: 75) QVQLVQSGAEVKKPGASVK VSCKASGYTFTDYYMHWVR QAPGQGLEWMGIINPRAGY TSYALKFQGRVTMTRDTST STVYMELSSLRSEDTAVYY CTSGMDVWGQGTLVTVSSA KTTAPSVYPLAPVCGDTTG SSVTLGCLVKGYFPEPVTL TWNSGSLSSGVHTFPAVLQ SDLYTLSSSVTVTSSTWPS QSITCNVAHPASSTKVDKK IEPRGPTIKPCPPCKCPAP NAAGGPSVFIFPPKIKDVL MISLSPIVTCVVVDVSEDD PDVQISWFVNNVEVHTAQT QTHREDYNSTLRVVSALPI QHQDWMSGKEFKCKVNNKD LGAPIERTISKPKGSVRAP QVYVLPPPEEEMTKKQVTL TCMVTDFMPEDIYVEWTNN GKTELNYKNTEPVLDSDGS YFMYSKLRVEKKNWVERNS YSCSVVHEGLHNHHTTKSF SRTPGK | (SEQ ID NO: 76) APTSSSTKKTQLQLEHLLL DLQMILNGINNYKNPKLTR MLTFKFYMPKKATELKHLQ CLEEELKPLEEVLNLAQSK NFHLRPRDLISNINVIVLE LKGSETTFMCEYADETATI VEFLNRWITFCQSIISTLT VPGVGVPGAGVPGVGVPGG GVPGVGVPGGGVPGAGVPG GGVPGVGVPGAGVPGVGVP GGGDIQMTQSPSSLSASVG DRVTITCRASQSISTWLAW YQQKPGKAPKLLIYAASSL QSGVPSRFSGSGSGTDFTL TISSLQPEDFATYYCQQSY SFPVTFGQGTKVEIKRADA APTVSIFPPSSEQLTSGGA SVVCFLNNFYPKDINVKWK IDGSERQNGVLNSWTDQDS KDSTYSMSSTLTLTKDEYE RHNSYTCEATHKTSTSPIV KSFNRNEC |

Figure 11:
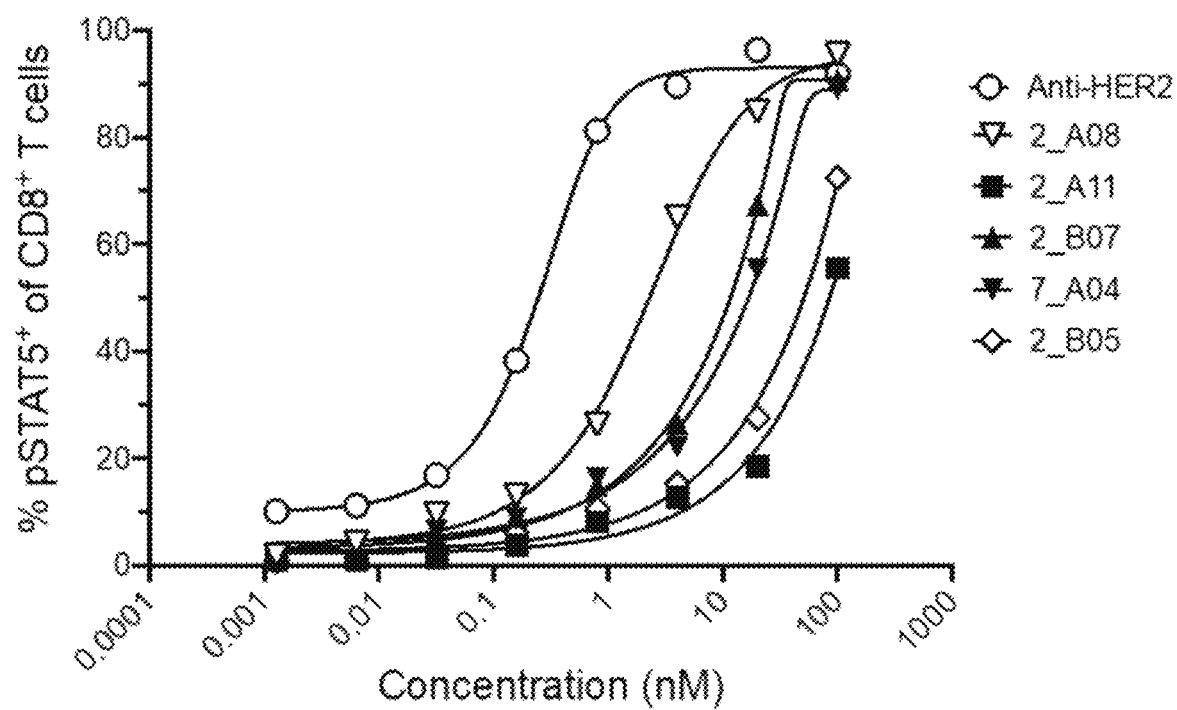
FIG. 11 shows that IL-2 signaling by five exemplary PD-1/IL-2 DBA-cytokine protein complexes (2_A08, 2_A11, 2_B05, 2_B07, and 7_A04, SEQ ID NO: 67-SEQ ID NO: 68, SEQ ID NO: 69-SEQ ID NO: 70, SEQ ID NO: 71-SEQ ID NO: 72, SEQ ID NO: 73-SEQ ID NO: 74 and SEQ ID NO: 75-SEQ ID NO: 76 respectively) is reduced as compared to a control IL-2-Anti-HER2 protein complex (SEQ ID NO: 65-SEQ ID NO: 66).

The PD-1/IL-2 DBA-cytokine complexes were serially diluted in complete RPMI (+10% FBS, 2 mM L-glutamine, sodium pyruvate) and added to a 96-well plate. $2 \times 10^5$ human PBMCs were added to each well and plates were incubated at 37° C. for 20 minutes. An equal volume prewarmed fixation buffer (Biolegend) was then added to each well and plates were incubated at 37° C. for 10 minutes. Cells were then fixed in pre-chilled Perm Buffer III (BD Biosciences) for 30 minutes at 4° C. Cells were washed with FACS wash buffer (PBS+2% FBS, 2 mM EDTA) and stained with fluorophore labeled antibodies directed against CD3, CD4, CD8, (BioLegend) and phospho-STAT5 (BD Biosciences) diluted 1:20 in FACS wash buffer. Cells were incubated 1 hour at 4° C., washed with FACS wash buffer, and analyzed on a SA3800 Spectral Analyzer. In the absence of PD-1, the PD-1/IL-2 DBA/cytokine complexes induced less STAT5 phosphorylation in T cells compared to the monospecific control anti-HER2 IL-2 immunocytokine (FIG. 11).

Example 9

Figure 12:
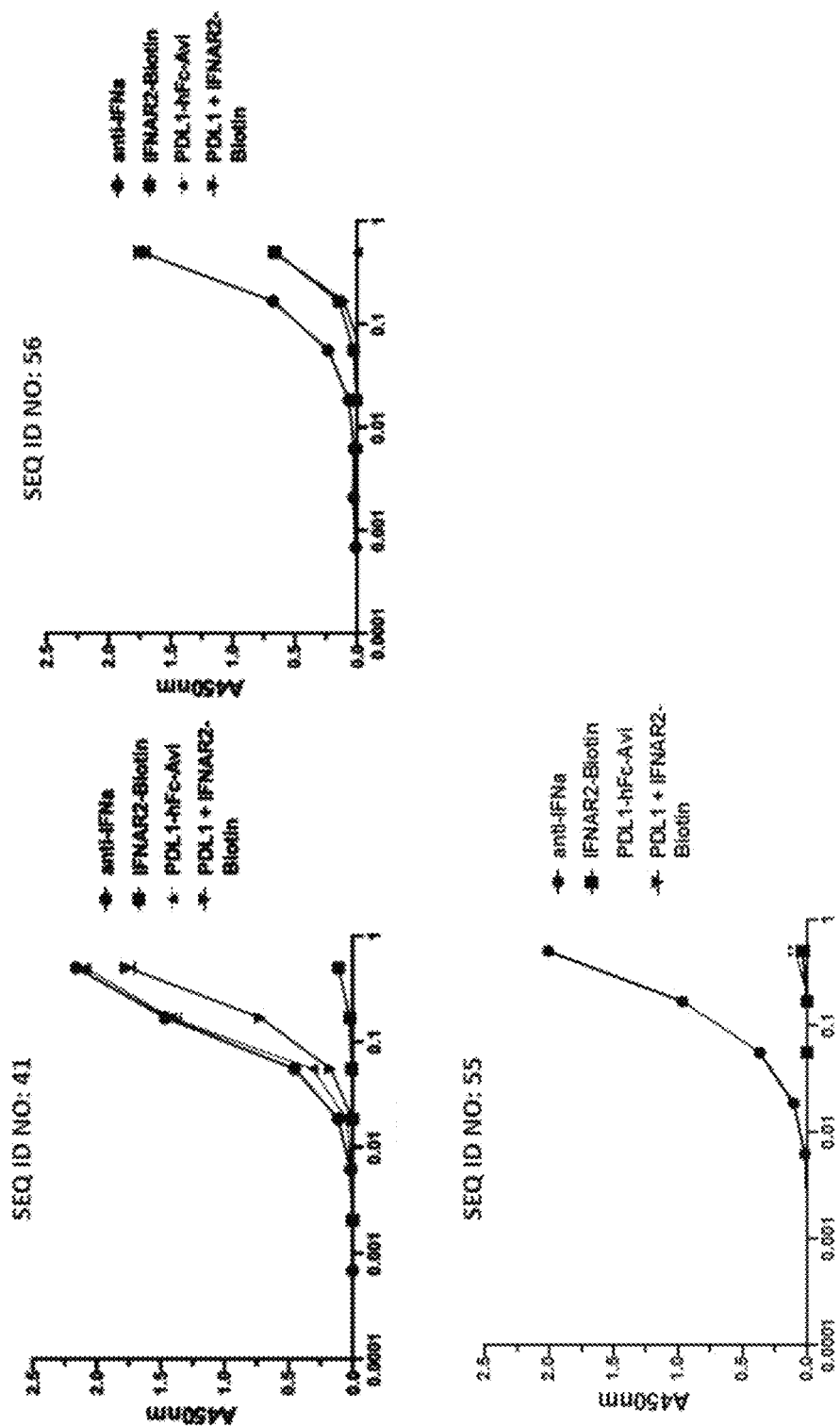
FIG. 12 shows PD-L1 regulated IFNα activity of an exemplary PD-L1/IFNα DBA-cytokine protein complex.

Regulated Interferon Receptor Binding by a PD-L1/IFNα Dual Binding Antibody (DBA) Cytokine Complex This example describes regulated interferon receptor binding by a PD-L1/IFNα DBA-cytokine complex. DBA-cytokine complexes of SEQ ID NO: 41 and SEQ ID NO: 55 (MSTSTCDLPQTHSLGSRRTLMLLAQMRRISLF-SCLKDRHDFGFPQEEFGNQFQKAETIP VLHEMIQQIFNLFSTKDSSAAWDETLLDKFYTE-LYQQLNDLEACVIQGVGVTETPLMKE DSI-LAVRKYFQRITLYLKEKKYSPCAWEVVRAE-IMRSFSLSTNLQESLRSKEGGGGSGG GGSGGGGSGGGGSQVQLVQSGAEVKKP-GASVKVSCKASGNTFTDYYMHWVRQAPGQ GLEWMGWMNPNSGNTGYAQKFQGRVTMTRDTST-STVYMELSSLRSEDTAVYYCARS LFP-TIFGVEVAFDIWGQGTLVTVSSAS-GGGGSGGGGSGGGGSHASDIQMTQSPSSLSAS VGDRVTITCQASQDISNYLNWYQQKPGKAPKLLI-YAASSLESGVPSRFSGSGSGTDFTLT ISSLQPEDFA-TYYCQQSYSTPPTFGQGTRLEIKGKPIPNPLLGLDST) were chosen for analysis with a negative control with a similar structure based on a HER2 binding scFv (SEQ ID NO: 56, MSTSTCDLPQTHSLGSRRTLMLLAQMRRIS-LFSCLKDRHDFGFPQEEFGNQFQKAETIPV LHEMIQQIFNLFSTKDSSAAWDETLLDKFYTE-LYQQLNDLEACVIQGVGVTETPLMKED SILAVRKYFQRITLYLKEKKYSPCAWEVVRAE-IMRSFSLSTNLQESLRSKEGGGGSGGG GSGGGGSGGGGSEVQLVESGGGLVQPGGSLRLS-CAASGFNIKDTYIHWVRQAPGKGLE WVARIYPTNGYTRYADSVKGRFTISADTSKNTAY-LQMNSLRAEDTAVYYCSRWGGDG FYAMDYWGQGTLVTVSSASGGGGSGGGGSGGGG-SHASDIQMTQSPSSLSASVGDRVTI TCRASQDVNTA-VAWYQQKPGKAPKLLIYSASFLY-SGVPSRFSGSRSGTDFTLTISSLQPE DFATYYCQQHYTTPPTFGQGTKVEIKGKPIPN-PLLGLDST). The proteins were expressed using a cell-free transcription/translation system (Cosmo Bio USA, Inc., PUREfrex2.1, Product #GFK-PF213 with DS Supplement, Prod. #GFK-PF005). 96-well ELISA plates were coated with anti-V5 antibody (SV5-pk1) at 50 ng/well overnight at 4° C. The plates were washed twice by adding 200 μl/well of SuperBlock with 0.05% Tween 20 (SBT), and the final SBT wash was incubated for 15 min at room temperature before aspiration. A dilution series of the protein for each construct in SBT was then added to the anti-V5-coated plates at 50 μl/well and incubated for 1 hour at room temperature. Each plate was then washed three times with PBS with 0.05% Tween 20 (PBST). Bound constructs were then probed with either anti-IFNα, IFNAR2-Biotin, PDL1-hFc-Avi or the combination of IFNAR2-Biotin and PDL1-hFc-Avi in SBT at 50 μl/well for 1 hour at room temperature. Plates were washed 3× with PB ST. Goat anti-mIgG-HRP or Streptavidin-HRP was added at 50 μl/well and incubated for 30 min at room temperature followed by 3× wash with PB ST. Plates were developed by adding 50 μl/well of TMB and the reaction was terminated with an equal volume of ELISA stop solution. As shown in FIG. 12 (top left), IFNAR2 binding to the DBA-IFNα complex (SEQ ID NO: 41) increased in a dose dependent manner with the addition of PD-L1. IFNAR2 binding to a control HER2-specific antibody-IFNα complex (SEQ ID NO: 56) was unaffected by the addition of PD-L1 (FIG. 12 top right). IFNAR2 binding to a DBA-IFNα complex containing SEQ ID NO: 55, was not affected by addition of PD-L1 at these concentrations (FIG. 12 bottom). The protein complex of SEQ ID NO: 55 is similar to the protein complex of SEQ ID NO: 41, except that the sensor domain of SEQ ID NO: 55 has a higher affinity for IFNα than the sensor domain of SEQ ID NO: 41. Protein complexes of the present invention may need the correct balance between their affinity for the marker and their affinity for the therapeutic domain.

Example 10

PD-L1/IFNα Protein Complexes for PD-L1 Dependent IFNα Activity In Vitro

This example describes PD-L1/IFNα protein complexes for PD-L1 dependent IFNα activity in vitro. PD-L1/IFNα protein complexes comprise a DBA capable of binding PD-L1 marker and an IFNα therapeutic domain where the protein complex is linked to the IFNα therapeutic cytokine via a linker. In the absence of PD-L1, the PD-L1 sensor domain binds the IFNα therapeutic domain, rendering the IFNα therapeutic inert. In the presence of PD-L1 (e.g., PD-L1 is expressed on a cell, such as a tumor cell or immune cell), the PD-L1 sensor domain binds PD-L1, thereby unbinding the IFNα therapeutic domain and allowing for IFNα to exhibit therapeutic activity.

PD-L1/IFNα protein complexes are designed and recombinantly expressed or chemically synthesized. PD-L1/IFNα protein complexes are administered in vitro to a cell (e.g., in cell culture). In the absence of the PD-L1 marker, the IFNα domain remains bound to the PD-L1 sensor domain and no therapeutic effect is observed. The cell may express PD-L1 endogenously or after activation, or following introduction of a gene encoding PD-L1. If the cell is a tumor cell expressing a PD-L1 marker, the therapeutic effect may be inhibition of cell growth or induction of IFNα-responsive genes. Where the cell is an immune cell, the therapeutic effect may be cell growth, activation or induction of IFN-responsive genes. Where the cell is part of a mixture of cell types, any of these changes may be monitored for a responding cell population in the mixture.

Example 11

PD-L1 Dependent IFNα Activity In Vivo

This example describes PD-L1/IFNα protein complexes for PD-L1 dependent IFNα activity in vivo. PD-L1/IFNα protein complexes comprise a PD-L1 sensor domain (e.g., an anti-PD-L1 antibody or an anti-PD-L1 scFv) linked to an IFNα cytokine via a linker, where the IFNα cytokine is a therapeutic. In the absence of PD-L1, the PD-L1 sensor domain binds the IFNα therapeutic domain, rendering the IFNα therapeutic inert. In the presence of PD-L1 (e.g., PD-L1 is expressed on a cell, such as a tumor cell or immune cell), the PD-L1 sensor domain binds PD-L1, thereby unbinding the IFNα therapeutic domain and allowing for IFNα to exhibit therapeutic activity.

PD-L1/IFNα protein complexes are recombinantly expressed or chemically synthesized. PD-L1/IFNα protein complexes are administered in vivo to a subject in need thereof. Administration is performed intravenously, intramuscularly, subcutaneously, intradermally, intraperitoneally, or mucosally. In the absence of PD-L1, the IFNα therapeutic domain remains bound to the PD-L1 sensor domain and no therapeutic efficacy is observed (e.g., cell proliferation in the subject is uninhibited). In the presence of PD-L1, the PD-L1 sensor domain binds PD-L1 and unbinds the IFNα therapeutic domain. Therapeutic efficacy is observed (e.g., cell proliferation is inhibited or immune cell activation occurs). The cell is a tumor cell expressing PD-L1. The subject is a human or non-human animal in need thereof. The subject has a disease. The disease is cancer.

Example 12

PD-1 Dependent IL-2 Activity In Human Cells

This example describes PD-1/IL-2 protein complexes for PD-1 dependent IL-2 activity in human cells, in vitro and in vivo. PD-1/IL-2 protein complexes comprise a PD-1 sensor domain (e.g., an anti-PD-1 antibody or an anti-PD-1 scFv) linked to an IL-2 cytokine therapeutic domain via a linker, where the IL-2 cytokine is a therapeutic. In the absence of PD-1, the PD-1 sensor domain binds the IL-2 therapeutic domain, rendering the IL-2 therapeutic inert. In the presence of PD-1 (e.g., PD-1 is expressed on a cell, such as an immune cell), the PD-1 sensor domain binds PD-1, thereby unbinding the IL-2 therapeutic domain and allowing for IL-2 to exhibit therapeutic activity.

PD-1/IL-2 protein complexes are recombinantly expressed or chemically synthesized. PD-1/IL-2 protein complexes are administered in vitro to a human cell or in vivo to a mouse or to a human subject in need thereof. The human cell is a cell expressing PD-1. Administration to a mouse or to a human subject is performed intravenously, intramuscularly, subcutaneously, intradermally, intraperitoneally, or mucosally. In the absence of PD-1, the IL-2 therapeutic domain remains bound to the PD-1 sensor domain and no therapeutic efficacy is observed (e.g., cell activation in vitro and in the subject is unaltered). In the presence of PD-1, the PD-1 sensor domain binds PD-1 and unbinds the IL-2 therapeutic domain. Therapeutic efficacy is observed (e.g., cell activation is observed in vitro and, in the subject, in vivo). The subject has a disease. The disease is cancer. The cell may express PD-1 endogenously or after activation, or following introduction of a gene encoding PD-1. The therapeutic effect may be cell growth, differentiation, activation or induction of IL2-responsive genes. In vitro, if the cell is part of a mixture of cell types, any of these changes may be monitored for a responding cell population in the mixture.

Example 13

Bioactivity in Tumor Tissues

This example describes bioactivity in tumor tissues. A protein complex of the present disclosure is recombinantly expressed or chemically synthesized. The protein complex includes a sensor domain linked to a therapeutic domain. The linker is a peptide linker. The sensor domain is capable of binding to the therapeutic and a marker. In the absence if the marker, the sensor domain binds the therapeutic domain, rendering the therapeutic domain unable to bind to its target and unable to exert therapeutic activity. In the presence of the marker, the sensor domain binds the marker rendering the therapeutic domain free to bind to its target and able to exert therapeutic activity. The protein complex is administered in vitro to a cell or in vivo to a subject in need thereof. The cell expresses the marker to which the sensor domain binds. The cell is a tumor cell or immune cell. The subject is a human or non-human animal. The subject has a disease. The disease is cancer. Administration to a subject is performed intravenously, intramuscularly, subcutaneously, intradermally, intraperitoneally, or mucosally.

Upon administration of the protein-complex, the sensor domain binds the marker in vitro or in vivo in the subject and unbinds the therapeutic domain. Therapeutic efficacy is observed in vitro or in vivo in the subject, for example, cell proliferation of tumor cells is slowed down or completely halted and tumor cells are eliminated.

Example 14

Activity in Tumor Models of Protein Complexes

This example describes activity in tumor models. The tumor models assess the efficacy and systemic on-target effects of the protein complexes. The tumor model assesses the ability of a protein complex of the present disclosure to exhibit sensor domain regulated activity of the therapeutic domain.

A protein complex of the present disclosure is recombinantly expressed or chemically synthesized. The protein complex includes a sensor domain linked to a therapeutic domain. The linker is a peptide linker. The sensor domain is capable of binding to the therapeutic domain and a marker. In the absence of the marker, the sensor domain binds the therapeutic domain rendering the therapeutic domain unable to bind to its target and unable to exert therapeutic activity. In the presence of the marker, the sensor domain binds the marker rendering the therapeutic domain free to bind to its target and able to exert therapeutic activity. The protein complex is administered in a tumor model, in vitro or in vivo. The tumor cells or the immune cells in the tumor model express the marker to which the sensor domain binds. Administration in vivo is performed intravenously, intramuscularly, subcutaneously, intradermally, intraperitoneally, or mucosally.

Tumor measurement. Prior to administration of the protein-complex, or in a control sample where the protein-complex is not administered, measurements of the tumor indicate that the tumor is continuing to proliferate. For example, a solid tumor in a tumor model (e.g., a mouse model of a tumor) is measured using calipers. Prior to administration of the protein-complex, or in a control sample where the protein-complex is not administered, the solid tumor continues to grow in size, as indicated by increasing measurements of tumor size with calipers. Upon administration of the protein-complex, over time, the sensor domain binds the marker expressed on the tumor and the therapeutic domain is unbound, thus, resulting in therapeutic efficacy. Therapeutic efficacy is validated by observing decreasing measurements of tumor size with calipers over time.

Immune activation. Prior to administration of the protein-complex, or in a control sample where the protein-complex is not administered, the solid tumor continues to grow in size, as indicated by increasing measurements of tumor size with calipers. Upon administration of the protein-complex, over time, the sensor domain binds the marker and the therapeutic domain is unbound, thus, resulting in therapeutic efficacy. Therapeutic efficacy is validated by observing differences in the immune cells in the tumor, lymph node or systemically, when compared to the control sample. The differences may be immune cell phenotypes, activation state, differentiation state or specificity.

Systemic induction of cytokine markers. No induction of cytokine markers or reduced systemic induction of cytokine markers, when compared to the control, is observed upon administration of the protein complex.

Weight loss. No weight loss or reduced weight loss, when compared to the control, is observed upon administration of the protein complex.

Example 15

PD-1/IL-2 DBA Cytokine Complex Induction of STAT5 Phosphorylation in a Lymphocyte Cell Line This example describes PD-1/IL-2 DBA-cytokine complex induction of STAT5 phosphorylation in a lymphocytic cell line. To assess the dependence of PD-1/IL-2 DBA-cytokine complex activity on binding to PD-1, a PD-1-expressing variant is generated of an IL-2R+ T cell line such as Hut78 or Jurkat E6.1. The PD-1+ and PD-1− variant cell lines are treated with titrating concentrations of a PD-1/IL-2 DBA-cytokine complex of this disclosure, and STAT5 phosphorylation is assessed by phospho-flow, TR-FRET, or other assays for measuring IL-2 signaling.

A HEK 293 IL-2 reporter cell line is engineered to express PD-1. The PD-1+ and PD-1-variant cell lines are treated with titrating concentrations of PD-1/IL-2 DBA-cytokine complexes, and reporter activity is assessed as a measurement of IL-2 signaling. The PD-1/IL-2 DBA-cytokine complex exhibits increased potency on PD-1+ variant cell lines.

Example 16

PD-1/IL-2 DBA Cytokine Complex Induction of STAT5 Phosphorylation and Other Markers of Activation, and Proliferation in Primary Lymphocytes This example describes PD-1/IL-2 DBA-cytokine complex induction of STAT5 phosphorylation and other markers of activation and proliferation in primary lymphocytes. PBMCs are labeled with cell proliferation dye and incubated for 4 days with titrating concentrations of a PD-1/IL-2 DBA-cytokine complex of the present disclosure. PBMCs are stained with antibodies directed against immune cell phenotyping markers to distinguish CD4+ and CD8+ T cells, Treg cells, and natural killer (NK) cells and markers of cell activation, such as CD25. Dye dilution on immune cell subsets is examined by flow cytometry as a measurement of proliferation.

Total T cells are isolated from PBMCs using immunomagnetic negative selection (STEMCELL) and stimulated with plate-bound anti-CD3 and soluble anti-CD28 for 72 hours to induce expression of PD-1. The PD-1+ T cells are incubated for 20 minutes with titrating concentrations of PD-1/IL-2 DBA-cytokine complexes. STAT5 phosphorylation is measured in fixed and permeabilized T cells by flow cytometry. In some experiments, PD-1 may be blocked on T cells with anti-PD-1 prior to treatment with PD-1/IL-2 DBA-cytokine complexes to assess the dependence of PD-1/IL-2 DBA-cytokine complex activity on binding to PD-1. The PD-1/IL-2 DBA-cytokine complex induces minimal STAT5 phosphorylation when PD-1 is blocked, showing activity that is conditional on its ability to bind PD-1.

Example 17

In Vivo PD-1/IL-2 DBA Cytokine Complex Signaling in Non-Tumor Peripheral Tissues This example describes PD-1/IL-2 DBA-cytokine complex pharmacokinetics in the blood of wild-type mice and the signaling of the complex in non-tumor peripheral tissue. The serum half-lives and peripheral tissue activities of PD-1/IL-2 DBA-cytokine complexes and suitable non-regulated controls such as anti-PD-1, anti-HER2-IL-2, or anti-PD-1-IL-2 were measured in mice dosed intravenously (i.v.) with the complexes. Blood, spleens, or both were collected at various timepoints after treatment and stained to identify CD8+ T cells and NK cells.

Figure 18:
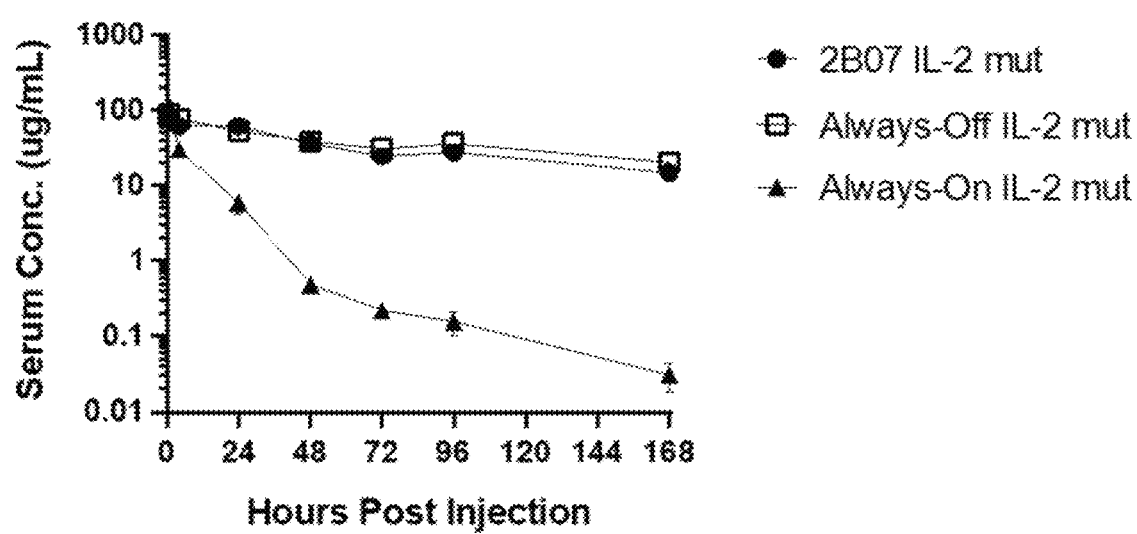
FIG. 18 provides rates of serum concentration decreases in the blood of wild-type mice of a PD-1/IL-2 DBA-cytokine complex ('2B07 IL-2 mut') and two control complexes.
Figure 19A:
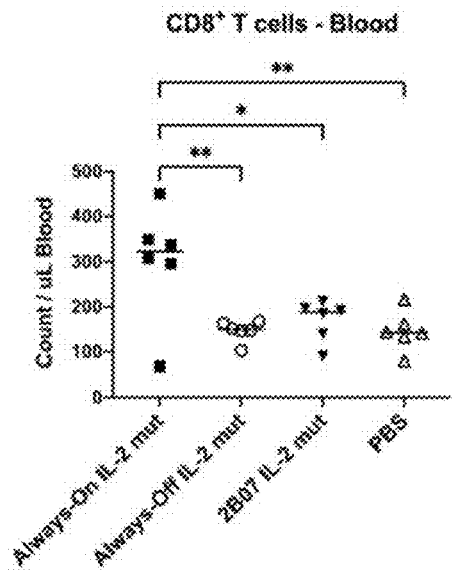
FIG. 19A, FIG. 19B, FIG. 19C, and FIG. 19D provide CD8$^+$ T cell and NK cell counts in blood and spleen tissue collected from wild-type mice 5 days following treatment with a PD-1/IL-2 DBA-cytokine complex ('2B07 IL-2 mut') and two control complexes.
Figure 19B:
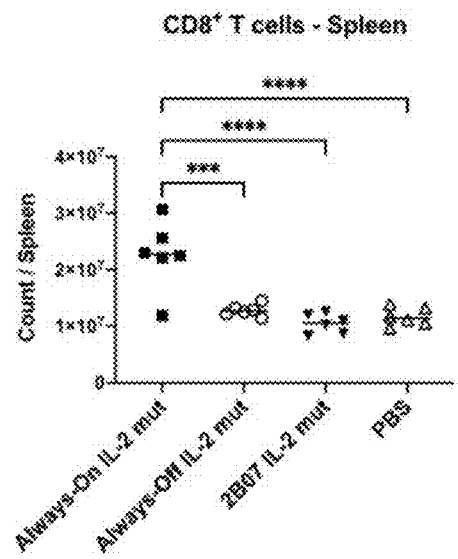
Figure 19C:
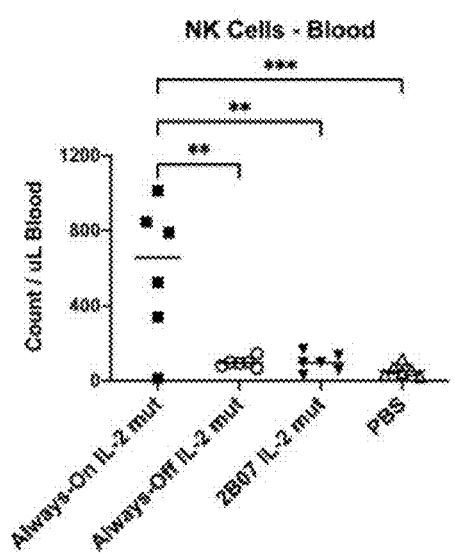
Figure 19D:
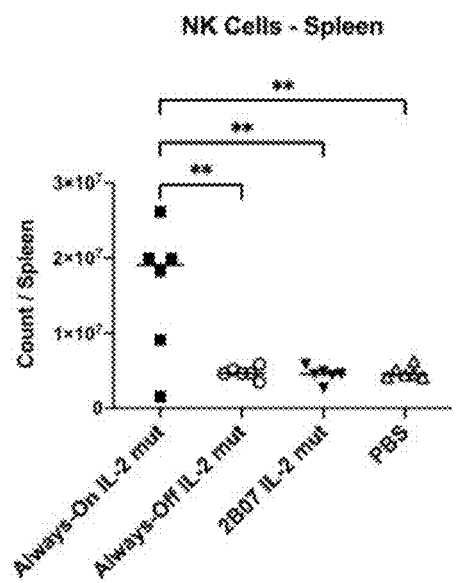

To examine the half-life of PD-1/IL-2 DBA-cytokine complex in circulation, wild-type C57BL/6 mice received a single 2.5 milligrams per kilogram intravenous dose of a PD-1/IL-2 DBA-cytokine complex (2B07 IL-2 mut; SEQ ID NO: 205-206), anti-HER2/IL-2-cytokine complex (Always-on IL-2 mut; SEQ ID NO: 64 and SEQ ID NO: 207), or anti-IL-2/IL-2-cytokine complex (Always-off IL-2 mut; SEQ ID SEQ ID NO: 208-209), as outlined in TABLE 20. Mice were bled via retro-orbital sinus at 30 minutes, 4, 24, 48, 72, 96, and 168 hours post-dosing. The blood was collected into serum separator tubes, and the isolated serum was frozen at −80° C. until analysis. To determine serum levels of the cytokine complexes, 96-well high-binding ELISA plates were coated with 1 ug/mL rabbit anti-hu IL-2 capture antibody (clone ab9618, Abcam) in carbonate-bicarbonate buffer overnight at 4 C. Plates were washed three times and blocked for 1 hour with SuperBlock blocking buffer (Thermo Scientific). Serum samples from the various timepoints and treatment groups were diluted in SuperBlock, added to the plates, and incubated 1 hr. To detect cytokine complexes, plates were incubated with goat anti-mouse Fc-HRP (Jackson ImmunoResearch) at 1:5000 in SuperBlock for 1 hour. The plates were then washed and developed with TMB substrate. Absorbance (OD) was measured using an EnVision 2105 microplate reader (PerkinElmer) at 450 nm. As shown in FIG. 18, at all timepoints examined the PD-1/IL-2 DBA-cytokine complex was detected at similar serum concentrations as the anti-IL-2/IL-2-cytokine complex. In contrast, the serum concentration of the non-regulated anti-HER2/IL-2-cytokine complex showed a greater decrease in serum concentration over time.

TABLE 20

IgG PD-1/IL-2 DBA and control protein complexes

| Protein Complexes | SEQ ID NO: | Sequence |
|---|---|---|
| 2B07 IL-2 mut | SEQ ID NO: 205 | APASSSTKKTQLQLEHLLLDLQMILNGINNYKNPKL TRMLTAKFAMPKKATELKHLQCLEEELKPLEEVLNG AQSKNFHLRPRDLISNINVIVLELKGSETTFMCEYA DETATIVEFLNRWITFAQSIISTLTGGGGSGGGGSG GGGSGGGGSQVQLVQSGAEVKKPGASVKVSCKASGD TFTRHYVHWVRQAPGQGLEWMGIINPSGGYASYAQK FQGRVTMTRDTSTSTVYMELSSLRSEDTAVYYCAAG LFIWGQGTLVTVSSAKTTAPSVYPLAPVCGDTTGSS VTLGCLVKGYFPEPVTLTWNSGSLSSGVHTFPAVLQ SDLYTLSSSVTVTSSTWPSQSITCNVAHPASSTKVD KKIEPRGPTIKPCPPCKCPAPNAAGGPSVFIFPPKI KDVLMISLSPIVTCVVVDVSEDDPDVQISWFVNNVE VHTAQTQTHREDYNSTLRVVSALPIQHQDWMSGKEF KCKVNNKDLGAPIERTISKPKGSVRAPQVYVLPPPE EEMTKKQVTLTCMVTDFMPEDIYVEWTNNGKTELNY KNTEPVLDSDGSYFMYSKLRVEKKNWVERNSYSCSV VHEGLHNHHTTKSFSRTPGK |
| | SEQ ID NO: 206 | DIQMTQSPSSLSASVGDRVTITCRASQSIGRWLAWY QQKPGKAPKLLIYSASNLETGVPSRFSGSGSGTDFT LTISSLQPEDFATYYCQQYESFPVTFGPGTKVDIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| anti-HER2/ IL-2-cytokine complex | SEQ ID NO: 64 | DIQMTQSPSSLSASVGDRVTITCRASQDVNTAVAWY QQKPGKAPKLLIYSASFLYSGVPSRFSGSRSGTDFT LTISSLQPEDFATYYCQQHYTTPPTFGQGTKVEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| | SEQ ID NO: 207 | APASSSTKKTQLQLEHLLLDLQMILNGINNYKNPKL TRMLTAKFAMPKKATELKHLQCLEEELKPLEEVLNG AQSKNFHLRPRDLISNINVIVLELKGSETTFMCEYA DETATIVEFLNRWITFAQSIISTLTGGGGSGGGGSG GGGSGGGGSEVQLVESGGGLVQPGGSLRLSCAASGF NIKDTYIHWVRQAPGKGLEWVARIYPTNGYTRYADS VKGRFTISADTSKNTAYLQMNSLRAEDTAVYYCSRW GGDGFYAMDYWGQGTLVTVSSAKTTAPSVYPLAPVC GDTTGSSVTLGCLVKGYFPEPVTLTWNSGSLSSGVH TFPAVLQSDLYTLSSSVTVTSSTWPSQSITCNVAHP ASSTKVDKKIEPRGPTIKPCPPCKCPAPNAAGGPSV FIFPPKIKDVLMISLSPIVTCVVVDVSEDDPDVQIS WFVNNVEVHTAQTQTHREDYNSTLRVVSALPIQHQD WMSGKEFKCKVNNKDLGAPIERTISKPKGSVRAPQV YVLPPPEEEMTKKQVTLTCMVTDFMPEDIYVEWTNN GKTELNYKNTEPVLDSDGSYFMYSKLRVEKKNWVER NSYSCSVVHEGLHNHHTTKSFSRTPGK |
| Always-off IL-2 mut | SEQ ID NO: 208 | APASSSTKKTQLQLEHLLLDLQMILNGINNYKNPKL TRMLTAKFAMPKKATELKHLQCLEEELKPLEEVLNG AQSKNFHLRPRDLISNINVIVLELKGSETTFMCEYA DETATIVEFLNRWITFAQSIISTLTGGGGSGGGGSG GGGSGGGGSEVQLVESGGGLVKPGGSLRLSCAASGF TFSSYTLAWVRQAPGKGLEWVAAIDSSSYTYSPDTV RGRFTISRDNAKNSLYLQMNSLRAEDTAVYYCARDS NWDALDYWGQGTLVTVSSAKTTAPSVYPLAPVCGDT TGSSVTLGCLVKGYFPEPVTLTWNSGSLSSGVHTFP AVLQSDLYTLSSSVTVTSSTWPSQSITCNVAHPASS TKVDKKIEPRGPTIKPCPPCKCPAPNAAGGPSVFIF PPKIKDVLMISLSPIVTCVVVDVSEDDPDVQISWFV NNVEVHTAQTQTHREDYNSTLRVVSALPIQHQDWMS GKEFKCKVNNKDLGAPIERTISKPKGSVRAPQVYVL PPPEEEMTKKQVTLTCMVTDFMPEDIYVEWTNNGKT ELNYKNTEPVLDSDGSYFMYSKLRVEKKNWVERNSY SCSVVHEGLHNHHTTKSFSRTPGK |
| | SEQ ID NO: 209 | DIQMTQSPSSLSASVGDRVSITCKASQNVGTNVGWY QQKPGKAPKALIYSASFRYSGVPSRFSGSGSGTDFT LTISSLQPEDFATYFCQQYYTYPYTFGGGTKLEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |

To examine the activity of PD-1/IL-2 DBA-cytokine complexes in peripheral tissues, wild-type C57BL/6 mice received a single 2.5 milligrams per kilogram intravenous dose of PD-1/IL-2 DBA-cytokine complex (2B07 IL-2 mut; SEQ ID NO: 205-206), anti-HER2/IL-2-cytokine complex (Always-on IL-2 mut; SEQ ID NO: 64 and SEQ ID NO: 207), anti-IL-2/IL-2-cytokine complex (Always-off IL-2 mut; SEQ ID NO: 208-209), as shown in TABLE 20 or PBS.

Prior to dosing, the presence of intact IL-2 within each IL-2 cytokine complex was confirmed by ELISA as a means of verifying their potential for biological activity. Blood and spleens were collected 5 days following treatment and analyzed by flow cytometry to quantify the number of CD8+ T cells and NK cells per spleen and per microliter of blood. The PD-1/IL-2 DBA-cytokine complex did not induce expansion of CD8 T cells or NK cells, whereas the HER2/IL-2-cytokine complex induced expansion of peripheral CD8+ T cells and NK cells (FIG. 19A-D).

Example 18

Figure 20:
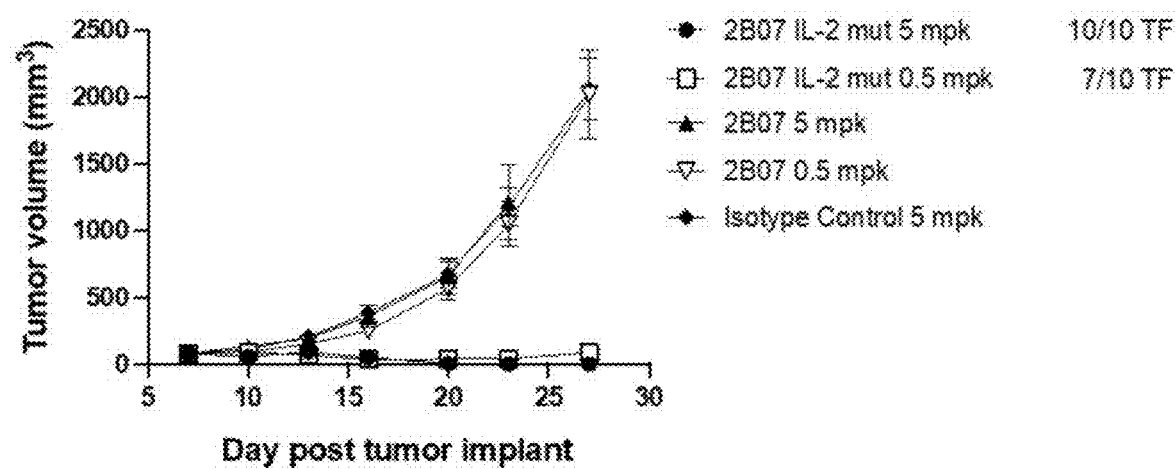
FIG. 20 provides tumor volume measurements as a function of the number of days post tumor cell implant in mice. Mice received various intravenous doses of a PD-1/IL-2 DBA-IL-2 complex, a PD-1/IL-2 DBA complex lacking IL-2, or an isotype control.
Figure 21A:
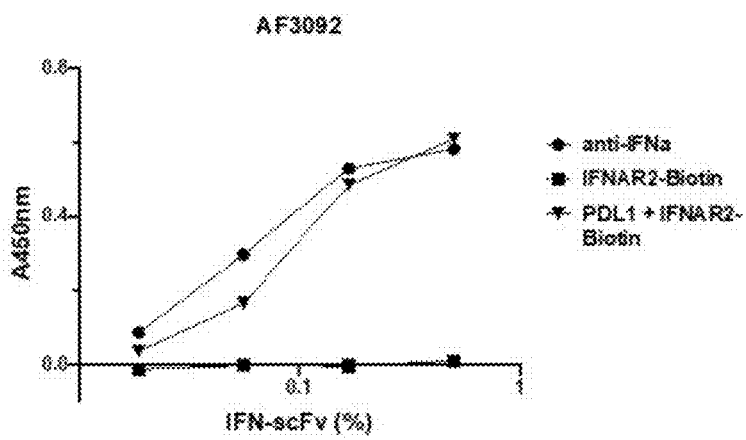
FIG. 21A, FIG. 21B, FIG. 21C, FIG. 21D, FIG. 21E, and FIG. 21F, provide results for IFNAR2 binding in the presence (triangles) and absence (squares) of PD-L1 for six separate DBA PDL1-IFN variants.
Figure 21B:
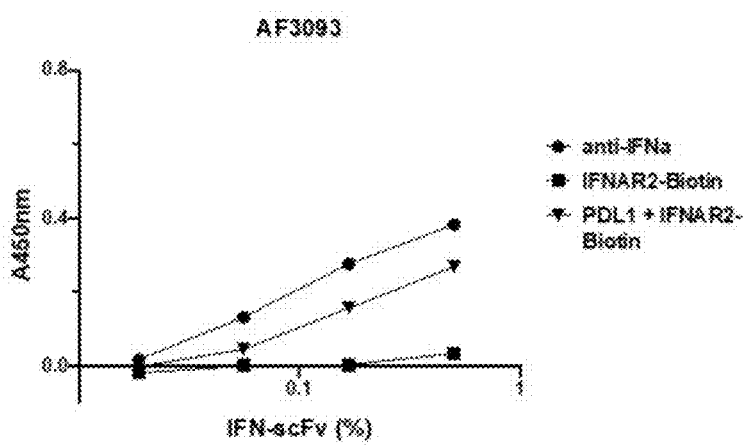
Figure 21C:
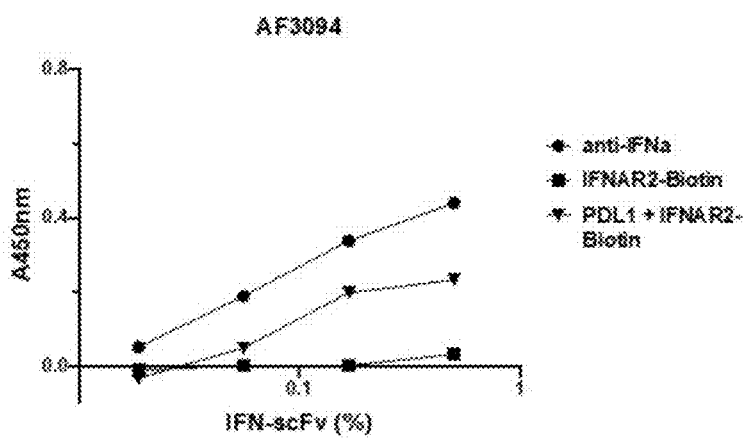
Figure 21D:
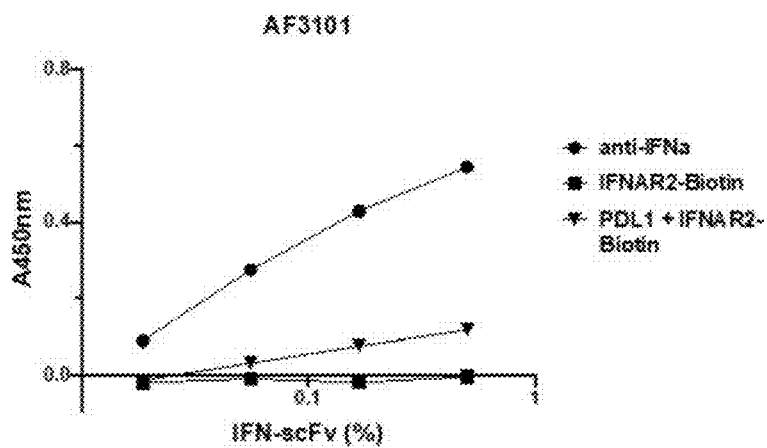
Figure 21E:
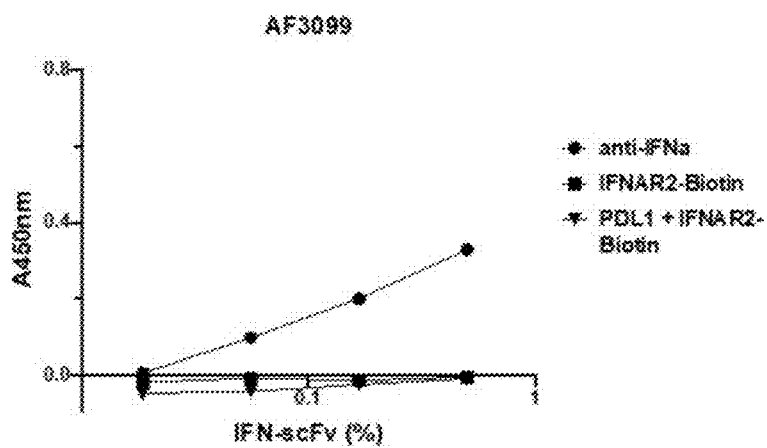
Figure 21F:
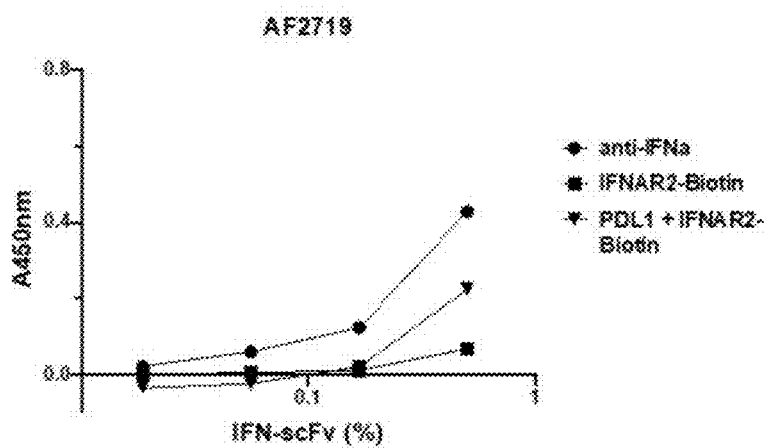
Figure 22A:
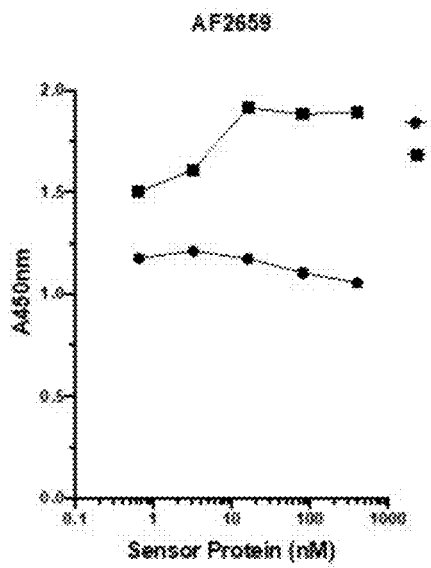
FIG. 22A, FIG. 22B, FIG. 22C, FIG. 22D, FIG. 22E, FIG. 22F, FIG. 22G, and FIG. 22H provide IFNAR2 binding by five PD-L1/IFNα DBA-cytokine complexes and three control complexes.
Figure 22B:
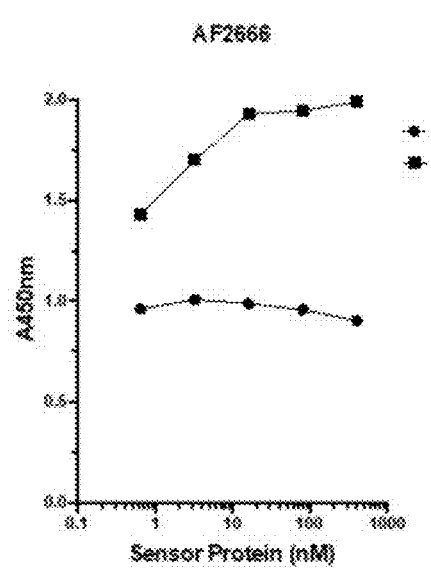
Figure 22C:
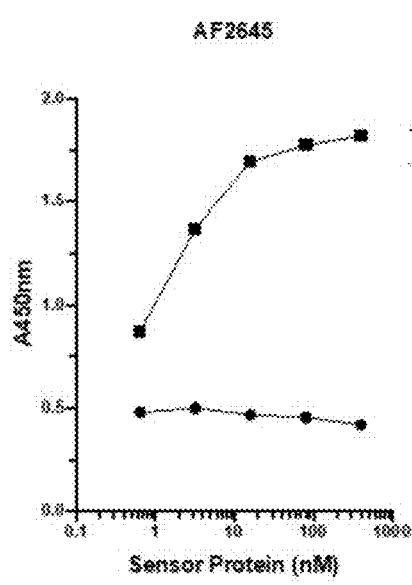
Figure 22D:
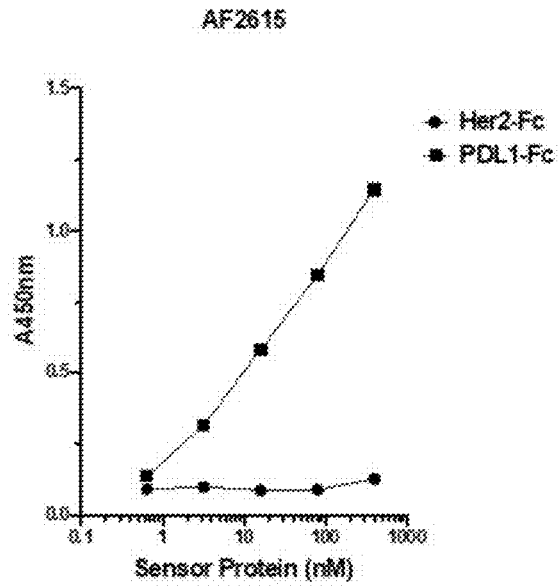
Figure 22E:
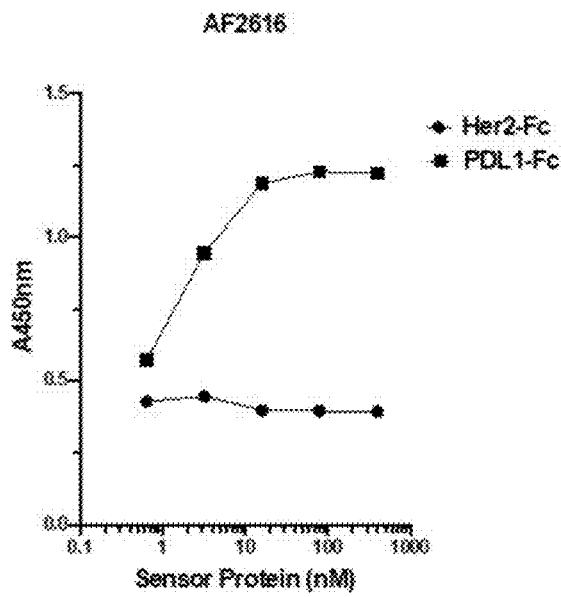
Figure 22F:
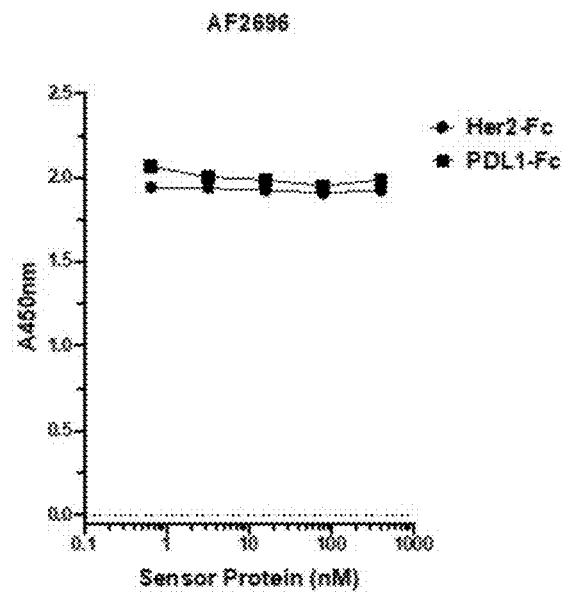
Figure 22G:
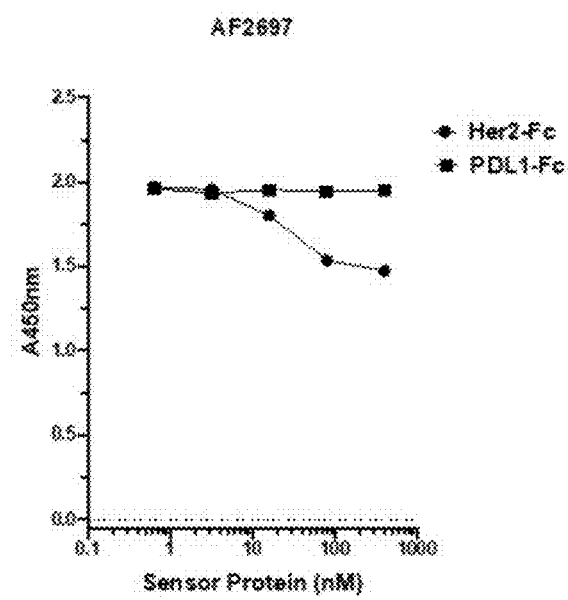
Figure 22H:
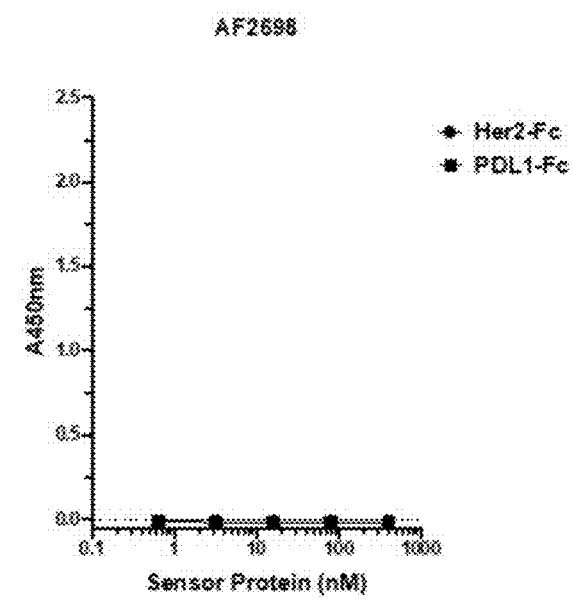
Figure 23A:
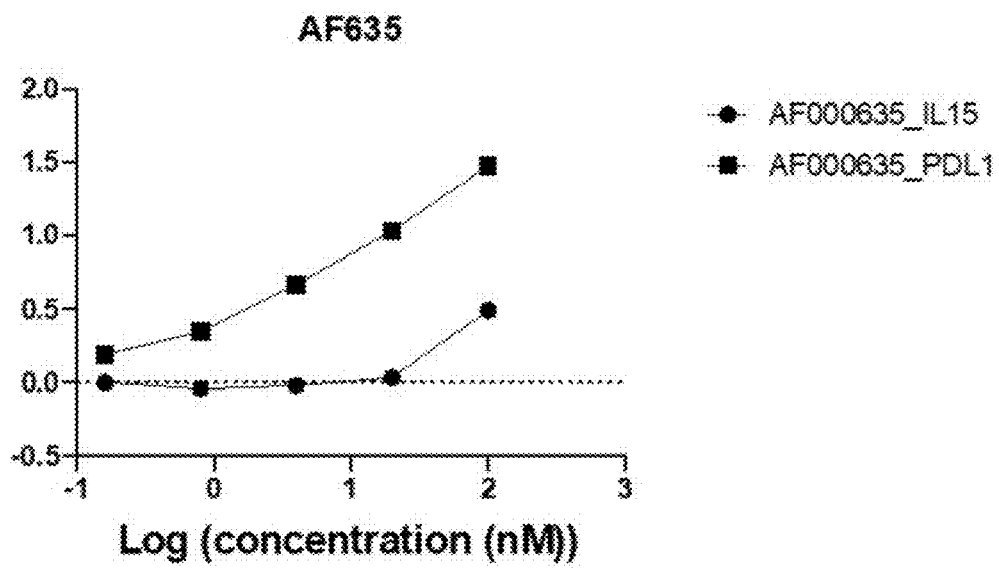
FIG. 23A, FIG. 23B, FIG. 23C, and FIG. 23D provide ELISA measurements for PD-L1 and IL-15 binding by four separate anti-PD-L1 and anti-IL-15 DBAs.
Figure 23B:
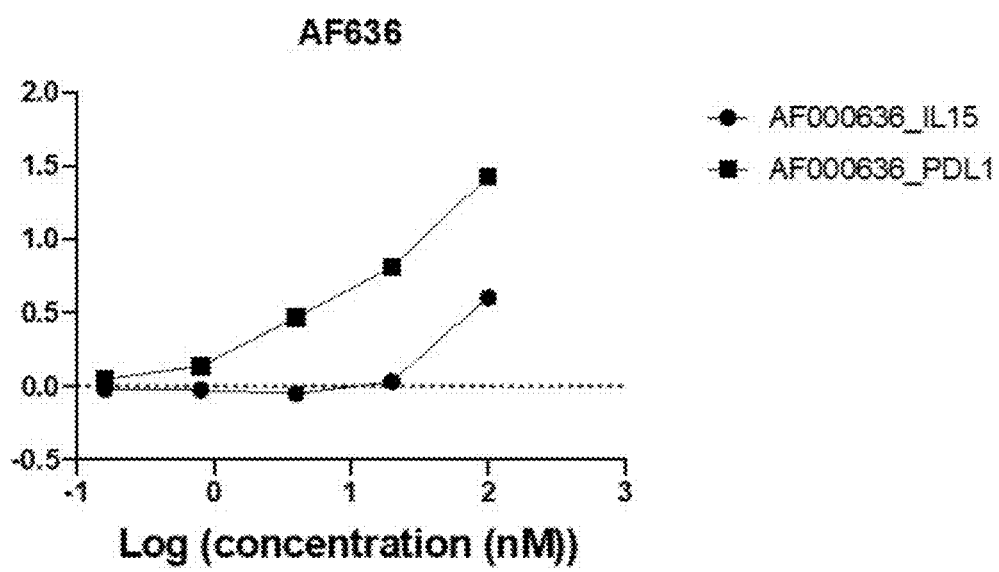
Figure 23C:
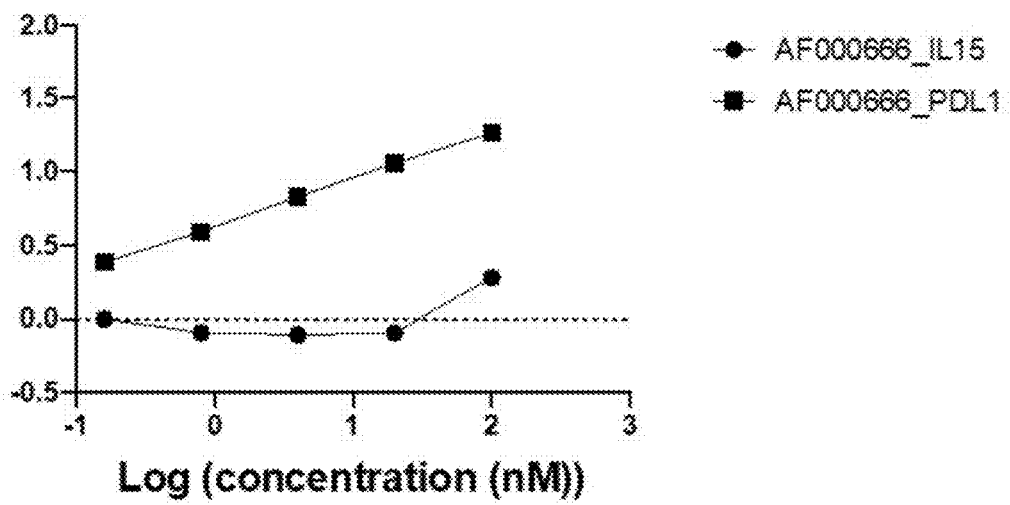
Figure 23D:
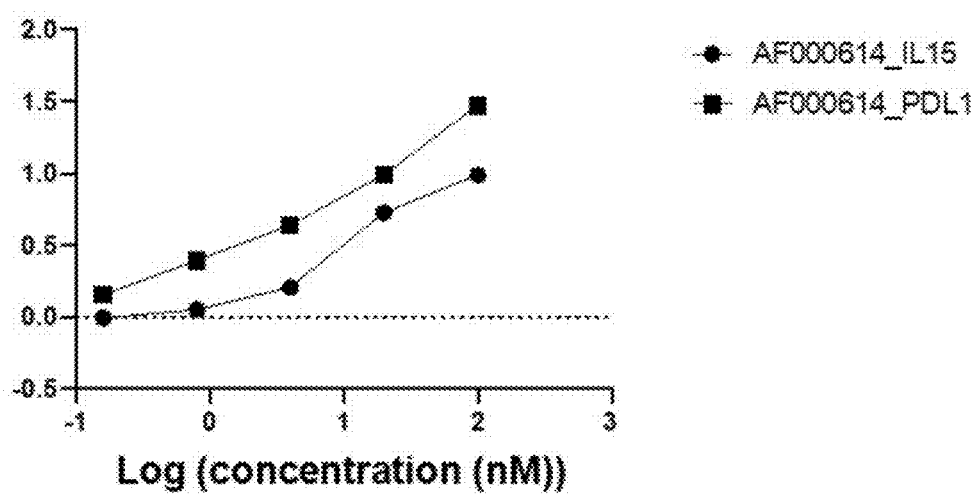
Figure 24A:
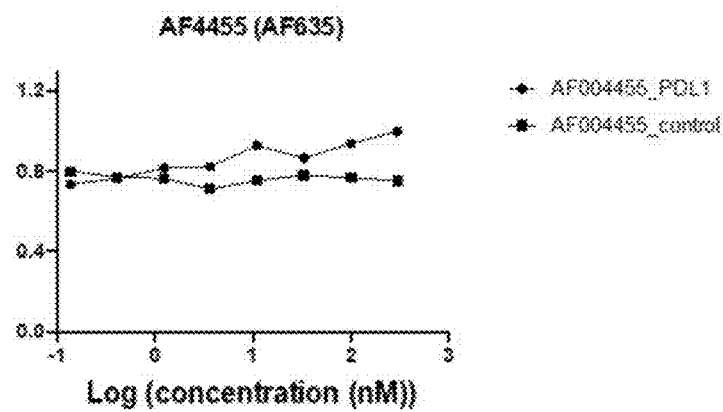
FIG. 24A, FIG. 24B, FIG. 24C, FIG. 24D, FIG. 24E, and FIG. 24F provide IL-15 activity as measured by HEK-Blue™ IL-2 reporter cell colorimetric responses for four scFv DBA-IL-15 complexes and two monospecific anti-IL-15 antibody IL-15 complexes.
Figure 24B:
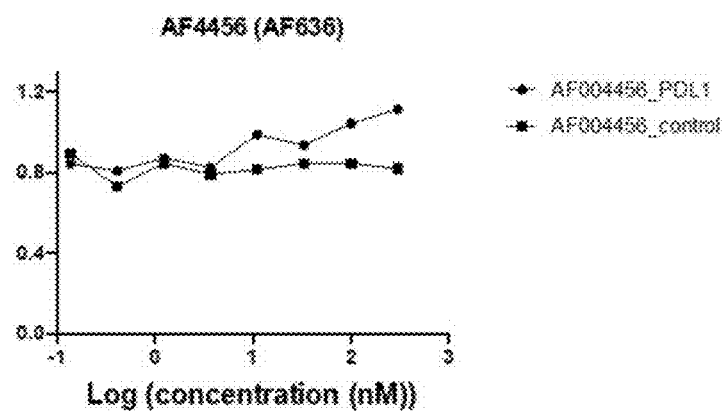
Figure 24C:
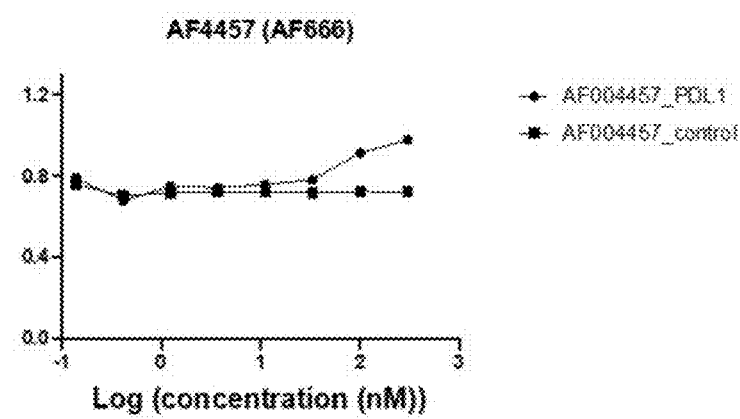
Figure 24D:
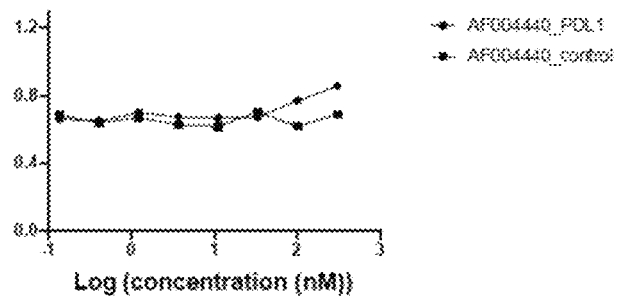
Figure 24E:
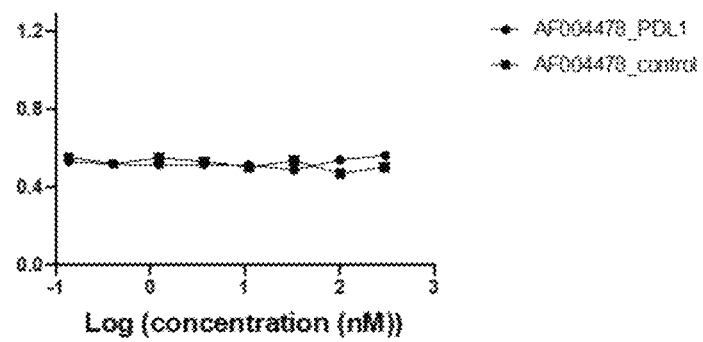
Figure 24F:
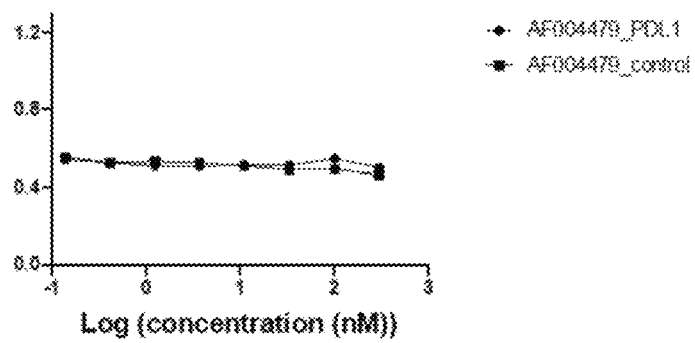
Figure 25A:
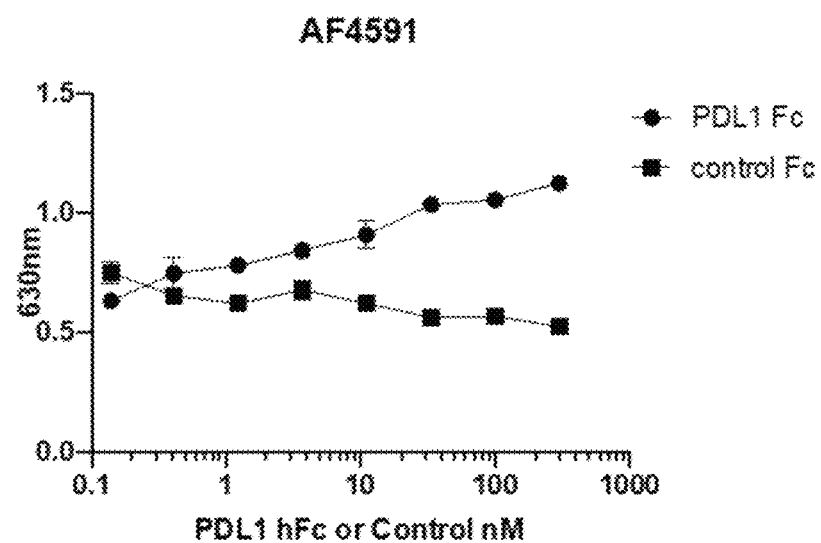
FIG. 25A, FIG. 25B, FIG. 25C, and FIG. 25D provide IL-15 activity as measured by HEK-Blue™ IL-2 reporter cell colorimetric responses for two DBA-IL-15 complexes and PDL1-IFN DBA control protein complexes.
Figure 25B:
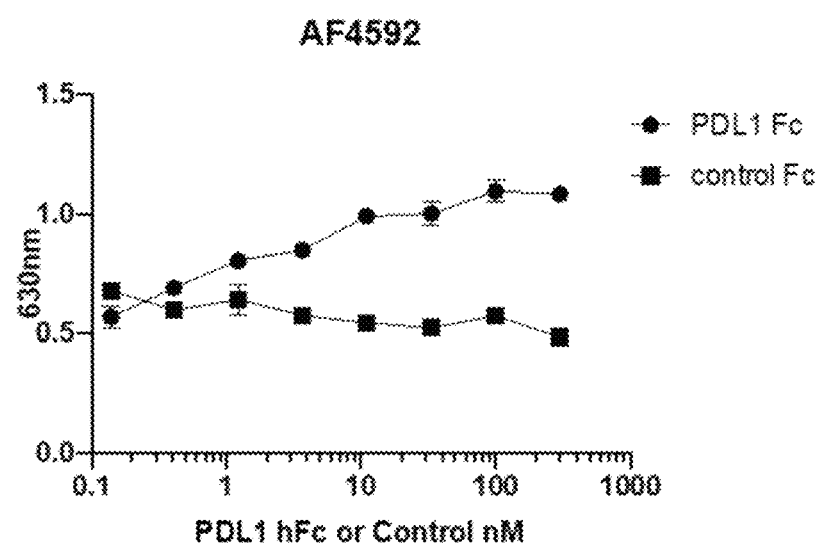
Figure 25C:
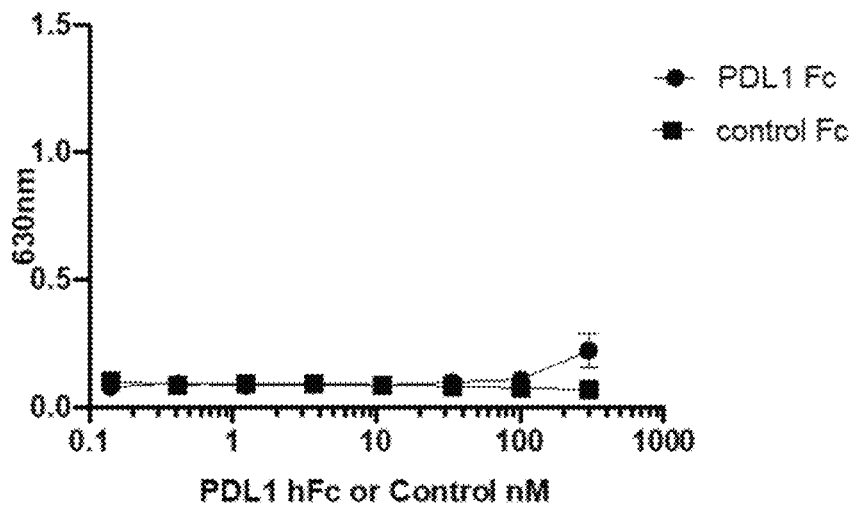
Figure 25D:
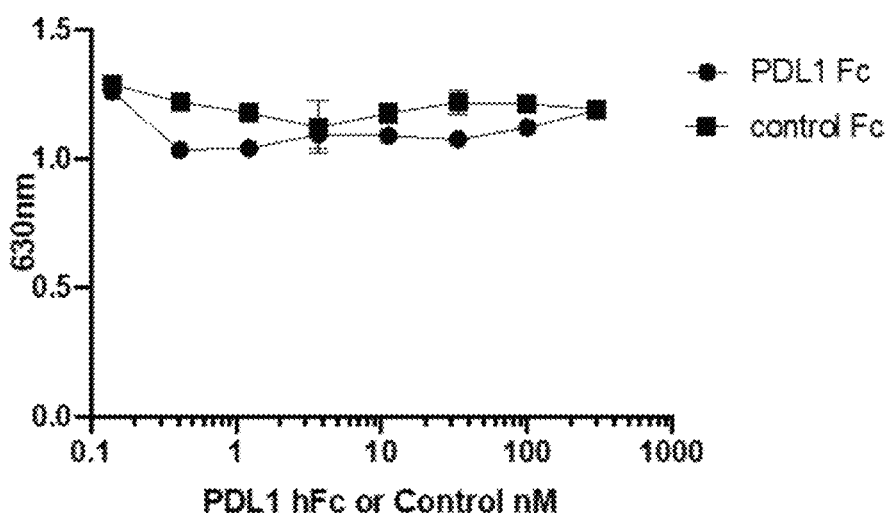

PD-1/IL-2 DBA Cytokine Complex Modulation of Anti-Tumor Immunity in Syngeneic Tumor Models This example describes PD-1/IL-2 DBA-cytokine complex modulation of anti-tumor immunity in a MC38 syngeneic mouse tumor model. A PD-1/IL-2 DBA-cytokine complex was assessed for the ability to drive anti-tumor immunity in vivo. 500,000 MC38 tumor cells were implanted subcutaneously in human PD-1 knock-in mice (GenOway). Tumors were measured twice weekly, and volumes calculated as (Length×Width×Width/2). Mice were randomized into treatment groups, and treatments were initiated when tumors reached a volume of ~100 mm³. Mice were treated intravenously with PD-1/IL-2 DBA-cytokine complex (2B07 IL-2 mut; SEQ ID NO: 210-212), PD-1/IL-2 DBA lacking IL-2 (2B07; SEQ ID NO: 212-213), or an isotype control (SEQ ID NO: 214-215), as shown in TABLE 21 below, at the indicated doses of 5 or 0.5 milligrams per kilogram on days 7, 10, and 13 post tumor implantation. The PD-1/IL-2 DBA-cytokine complex showed increased tumor growth inhibition compared to either the PD-1/IL-2 DBA lacking IL-2 or the isotype control (FIG. 20).

TABLE 21

IgG PD-1/IL-2 DBA and control protein complexes

| Protein Complex | SEQ ID NO: | Sequence |
|---|---|---|
| 2B07 IL-2 mut | SEQ ID NO: 210 | APASSSTKKTQLQLEHLLLDLQMILNGINNYKNPKL TRMLTAKFAMPKKATELKHLQCLEEELKPLEEVLNG AQSKNFHLRPRDLISNINVIVLELKGSETTFMCEYA DETATIVEFLNRWITFAQSIISTLTGGGGSGGGGSG GGGSGGGGSQVQLVQSGAEVKKPGASVKVSCKASGD TFTRYYVHWVRQAPGQGLEWMGIINPSGGYASYAQK FQGRVTMTRDTSTSTVYMELSSLRSEDTAVYYCAAG LFIWGQGTLVTVSSAKTTAPSVYPLAPVCGDTTGSS VTLGCLVKGYFPEPVTLTWNSGSLSSGVHTFPAVLQ SDLYTLSSSVTVTSSTWPSQSITCNVAHPASSTKVD KKIEPRGPTIKPCPPCKCPAPNAAGGPSVFIFPPKI KDVLMISLSPIVTCVVVDVSEDDPDVQISWFVNNVE VHTAQTQTHREDYNSTLRVVSALPIQHQDWMSGKEF KCKVNNKDLGAPIERTISKPGSVRAPQVYVLPPPE EEMTKKQVTLTCMVTDFMPEDIYVEWTNNGKTELNY KNTEPVLDSDGSYFMYSDLRVEKKNWVERNSYSCSV VHEGLHNHHTTESFSRTPGK |
| | SEQ ID NO: 211 | QVQLVQSGAEVKKPGASVKVSCKASGDTFTRYYVHW VRQAPGQGLEWMGIINPSGGYASYAQKFQGRVMTRT DTSTSTVYMELSSLRSEDTAVYYCAAGLFIWGQGTL VTVSSAKTTAPSVYPLAPVCGDTTGSSVTLGCLVKG YFPEPVTLTWNSGSLSSGVHTFPAVLQSDLYTLSSS VTVTSSTWPSQSITCNVAHPASSTKVDKKIEPRGPT IKPCPPCKCPAPNAAGGPSVFIFPPKIKDVLMISLS PIVTCVVVDVSEDDPDVQISWFVNNVEVHTAQTQTH REDYNSTLRVVSALPIQHQDWMSGKEFKCKVNNKDL GAPIERTISKPKGSVRAPQVYVLPPPEKEMTKKQVS LTCLVKDFMPEDIYVEWTNNGKTELNYKNTEPVLKS |

TABLE 21-continued

IgG PD-1/IL-2 DBA and control protein complexes

| Protein Complex | SEQ ID NO: | Sequence |
|---|---|---|
| | | DGSYFMYSKLTVEKKNWVERNSYSCSVVHEGLHNHH TTKSFSRTPGK |
| | SEQ ID NO: 212 | DIQMTQSPSSLSASVGDRVTITCRASQSIGRYLAWY QQKPGKAPKLLIYSASNLETGVPSRFSGSGSGTDFT LTISSLQPEDFATYYCQQYNSFPVTFGPGTKVDIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| PD-1/IL-2 DBA lacking IL-2 | SEQ ID NO: 212 | DIQMTQSPSSLSASVGDRVTITCRASQSIGRYLAWY QQKPGKAPKLLIYSASNLETGVPSRFSGSGSGTDFT LTISSLQPEDFATYYCQQYNSFPVTFGPGTKVDIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| | SEQ ID NO: 213 | QVQLVQSGAEVKKPGASVKVSCKASGDTFTRYYVHW VRQAPGQGLEWMGIINPSGGYASYAQKFQGRVMTRT DTSTSTVYMELSSLRSEDTAVYYCAAGLFIWGQGTL VTVSSAKTTAPSVYPLAPVCGDTTGSSVTLGCLVKG YFPEPVTLTWNSGSLSSGVHTFPAVLQSDLYTLSSS VTVTSSTWPSQSITCNVAHPASSTKVDKKIEPRGPT IKPCPPCKCPAPNAAGGPSVFIFPPKIKDVLMISLS PIVTCVVVDVSEDDPDVQISWFVNNVEVHTAQTQTH REDYNSTLRVVSALPIQHQDWMSGKEFKCKVNNKDL GAPIERTISKPKGSVRAPQVYVLPPPEEEMTKKQVT LTCMVTDFMPEDIYVEWTNNGKTELNYKNTEPVLDS DGSYFMYSKLRVEKKNWVERNSYSCSVVHEGLHNHH TTKSFSRTPGK |
| isotype control | SEQ ID NO: 214 | EVQLVESGGGLVQPGGSLRLSCAASGFNIKDTYIHW VRQAPGKGLEWVARIYPTNGYTRYADSVKGRFTISA DTSKNTAYLQMNSLRAEDTAVYYCSRWGGDGFYAMD YWGQGTLVTVSSAKTTAPSVYPLAPVCGDTTGSSVT LGCLVKGYFPEPVTLTWNSGSLSSGVHTFPAVLQSD LYTLSSSVTVTSSTWPSQSITCNVAHPASSTKVDKK IEPRGPTIKPCPPCKCPAPNAAGGPSVFIFPPKIKD VLMISLSPIVTCVVVDVSEDDPDVQISWFVNNVEVH TAQTQTHREDYNSTLRVVSALPIQHQDWMSGKEFKC KVNNKDLGAPIERTISKPKGSVRAPQVYVLPPPEEE MTKKQVTLTCMVTDFMPEDIYVEWTNNGKTELNYKN TEPVLDSDGSYFMYSKLRVEKKNWVERNSYSCVVH EGLHNHHTTKSFSRTPGK |
| | SEQ ID NO: 215 | DIQMTQSPSSLSASVGDRVTITCRASQDVNTAVAWY QQKPGKAPKLLIYSASFLYSGVPSRFSGSRSGTDFT LTISSLQPEDFATYYCQQHYTTPPTFGQGTKVEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |

Example 19

PD-1/IL-2 DBA Cytokine Complex Modulation of Anti-Tumor Immunity in Xenograft/Human Immune Cell Admixture Models This example describes PD-1/IL-2 DBA-cytokine complex modulation of anti-tumor immunity in xenograft/human immune cell admixture models. To examine the ability of PD-1/IL-2 DBA-cytokine complexes to drive anti-tumor immunity in an in vivo setting, an admixture system is used. Total human PBMCs or a combination of human T cells and monocyte-derived dendritic cells (moDCs) are mixed with human tumor cells (e.g., HPAC, A375, H441) at a 1:4 ratio and co-implanted subcutaneously into the flanks of NSG mice. One day later, treatment with a PD-1/IL-2 DBA-cytokine complex of the present disclosure, or suitable non-regulated controls such as anti-PD-1, anti-HER2-IL-2, or anti-PD-1-IL-2, is initiated. Tumors are measured at least twice weekly and volumes calculated as (Length×Width×Height/2). PD-1/IL-2 DBA-cytokine complexes exhibit increased anti-tumor efficacy compared to anti-PD-1 and anti-HER2-IL-2 and decreased off-tumor activity compared to anti-PD-1-IL-2.

Example 20

PD-L1/IFN-α DBA Cytokine Complex Induction of Myeloid Cell Maturation in the Presence of Plate-Bound PD-L1 or PD-L1-Expressing Tumor Cells This example describes PD-L1/IFN-α DBA-cytokine complex induction of myeloid cell maturation in the presence of plate-bound PD-L1 or PD-L1-expressing tumor cells. $CD14^+$ monocytes are purified from fresh human PBMCs by immunomagnetic negative selection (STEMCELL). Monocyte-derived dendritic cells (moDCs) are generated by culturing purified monocytes with hGM-CSF and hIL-4 in RPMI-1640 medium containing 10% FBS for 5 days. To examine the conditional activity of PD-L1/IFN-α DBA-cytokine complex, monocytes or moDCs are added to plates coated with either PD-L1 or HER-2 along with titrating concentrations of a PD-L1/IFN-α DBA-cytokine complex of the present disclosure. In some experiments, human monocytes or moDCs are co-cultured with tumor cell lines expressing varying levels of PD-L1 and titrating concentrations of PD-L1/IFN-α DBA-cytokine complex. Cultures are incubated overnight at 37° C., and expression of CD80, CD83, CD86, and HLA-DR is assessed by flow cytometry as a measurement of myeloid cell activation. PD-L1/IFN-α DBA-cytokine complex is expected to induce monocyte and moDC activation solely in the presence of PD-L1.

Example 21

PD-L1/IFN-α DBA Cytokine Complex Induction of T Cell Activation in a Mixed Lymphocyte Reaction This example describes PD-L1/IFN-α DBA-cytokine complex induction of T cell activation in a mixed lymphocyte reaction. To assess the direct and indirect effects of PD-L1/IFN-α DBA-cytokine complex on T cell function, CD14+ monocytes are isolated from human PBMCs using immunomagnetic negative selection (STEMCELL) and cultured for 5 days in the presence of hGM-CSF and hIL-4 to induce moDCs. CD8+ T cells are purified from human PBMCs of a different healthy donor and labeled with cell proliferation dye. The two cell types are combined in plates coated with PD-L1 or HER2 along with titrating concentrations of a PD-L1/IFN-α DBA-cytokine complex of the present disclosure. In other experiments, the two cell types are cultured with titrating concentrations of PD-L1/IFN-α DBA-cytokine complex and tumor cell lines expressing varying levels of PD-L1. In other experiments, the cells may be of mouse origin. Cultures are incubated for 5 days, and T cell dye dilution is assessed by flow cytometry as a measurement of proliferation. The concentration of cytokines (e.g., IFN-γ) in culture supernatants is assessed by ELISA. The PD-L1/IFN-α DBA-cytokine complex increases T cell activation and proliferation solely in the presence of PD-L1.

Example 22

In Vivo PD-L1/IFN-α DBA Cytokine Complex Signaling in Peripheral Tissues

This example describes in vivo PD-L1/IFN-α DBA-cytokine complex signaling in peripheral tissues. To examine PD-L1/IFN-α DBA-cytokine complex activity in non-tumor tissue, wild-type C57BL/6 mice are injected intravenously (i.v.) with 100 ug of either a PD-L1/IFN-α DBA-cytokine complex of the present disclosure or a non-regulated immunocytokine of a comparable structure consisting of anti-PD-L1 and IFN-α (PD-L1-IFNα immunocytokine). Animals are weighed daily to monitor IFN-α induced toxicity. Serum is collected at 6 and 24 hours post dosing, and MCP-1, IL-6, IL-10, TNF-α, and IFN-γ levels are quantified by ELISA. In some groups, RNA is isolated from the spleen and liver 6 and 24 hours post dosing. Induction of IFN-stimulated genes including ISG15, IRF7, and MX2 is assessed by qPCR. Mice that received unregulated anti-PD-L1-IFN-α immunocytokine experience weight loss, increased serum cytokine levels, and IFN target gene induction, whereas those dosed with the PD-L1/IFN-α DBA-cytokine complex display minimal evidence of peripheral IFN-α signaling.

Example 23

PD-L1-IFN-α DBA-Cytokine Complex Modulation of Anti-Tumor Immunity in Syngeneic Tumor Models This example describes PD-L1/IFN-α DBA-cytokine complex modulation of anti-tumor immunity in syngeneic tumor models. PD-L1/IFN-α DBA cytokine complex proteins are assessed for their ability to drive anti-tumor immunity in vivo. Wild-type or human PD-L1-expressing syngeneic mouse tumor cells (e.g., MC38, CT26, 4T1, or A20) are implanted subcutaneously into wild-type or human PD-L1 knock-in mice (Genoway). Tumors are measured at least twice weekly and volumes are calculated as (Length×Width×Height/2). Mice are randomized into different groups and therapy is initiated when tumors reached a volume of ~100 mm 3. Mice are treated i.v. or intratumorally with a PD-L1/IFN-α DBA-cytokine complex of the present disclosure or suitable nonregulated controls such as anti-PD-L1, anti-HER2-IFN-α immunocytokine, or anti-PD-L1-IFN-α immunocytokine. In some experiments, mice are sacrificed 5 days post treatment, and tumors are harvested and enzymatically dissociated for immunophenotyping. The frequency and phenotype of tumor-infiltrating immune cell subsets, including CD4+ and CD8+ T cells, Treg cells, NK cells, and DCs, is determined by flow cytometry. The PD-L1/IFN-α DBA-cytokine complex inhibits tumor growth to an equal or greater extent than anti-HER2-IFN-α, but with less off-tumor activity. The PD-L1/IFNα DBA-cytokine complex increases an anti-tumor immune response as indicated by the amount and phenotype of immune infiltrates to an equal or greater extent than anti-HER2-IFNα immunocytokine, but with less off-tumor activity.

Example 24

PD-L1/IFN-α DBA Modulation of Anti-Tumor Immunity in Xenograft/Human Immune Cell Admixture Models This example describes PD-L1/IFN-α DBA-cytokine complex modulation of anti-tumor immunity in xenograft/ human immune cell admixture models. To examine the ability of PD-L1/IFN-α DBA-cytokine complexes to drive anti-tumor immunity in an in vivo setting, an admixture system is used. Total human PBMCs or a combination of human T cells and moDCs are mixed with human tumor cells (e.g., HPAC, A375, H441) at a 1:4 ratio and co-implanted subcutaneously into the flanks of NSG mice. One day later, i.v. treatment with a PD-L1/IFN-α DBA-cytokine complex of the present disclosure or suitable non-regulated controls such as anti-PD-L1, anti-HER2-IFN-α immunocytokine, or anti-PD-L1-IFN-α immunocytokine is initiated. Tumors are measured at least twice weekly and volumes are calculated as (Length×Width×Height/2). The PD-L1/IFN-α DBA-cytokine complex inhibits tumor growth to an equal or greater extent than anti-HER2-IFN-α, but with less off-tumor activity.

Example 25

In Vitro and In Vivo Characterization of Protein Complexes

This example describes the evaluation of DBA-cytokine complexes for in vitro and in vivo stability. A protein complex of the present disclosure is recombinantly expressed or chemically synthesized. The protein complex includes a sensor domain linked to a therapeutic domain. The linker is a peptide linker. The sensor domain is capable of binding to the therapeutic domain and a marker. In the absence if the marker, the sensor domain binds the therapeutic domain rendering the therapeutic domain unable to bind to its target and unable to exert therapeutic activity. In the presence of the marker, the sensor domain binds the marker rendering the therapeutic domain free to bind to its target and able to exert therapeutic activity.

In vitro, the protein complexes are tested for stability and functionality at baseline or after incubation in conditions of stress, such as elevated temperature, pH changes, oxidative buffers, or serum/plasma, using methods of biophysical characterization to measure fragmentation, unfolding, or aggregation, and/or using methods to test for changes in functional activity. In vivo, the pharmacokinetic properties of the proteins are measured following dosing in a mammal, such as a mouse, rat, or non-human primate, and properties of distribution, clearance and degradation are measured. These measurements are used to engineer or select the optimal therapeutic form of the DBA-protein complex.

Example 26

Regulated IL-2 Receptor Signaling by a PD-1/IL-2 Dual Binding Antibody (DBA) Cytokine Complex This example describes PD-1 regulated IL-2 activity in a HEK-Blue™ IL-2 reporter cell by PD-1/IL-2 DBA-cytokine complexes. The DBA-cytokine complexes and control antibody-cytokine complexes were produced in three formats shown in FIGS. 14A-C by expression in mammalian cells using standard protocols. The wells of a 384-well ELISA plate were coated with constant concentration of PD-1-Fc or an IgG1 control protein captured with an anti-Fc antibody (Jackson ImmunoResearch, Prod. #109-005-098). The cytokine complexes were serially diluted 1:4 for 8 points in growth media from a starting concentration of 6 nM and incubated briefly before addition of the HEK-Blue™ IL-2 reporter cells.

Figure 14:
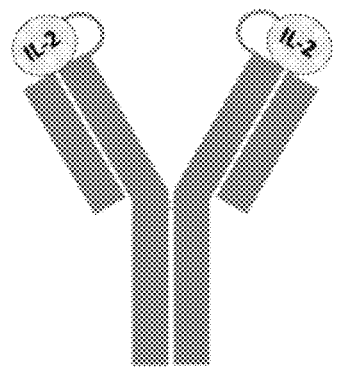
FIG. 14A, FIG. 14B, and FIG. 14C illustrate immunoglobulin-containing protein complexes consistent with the present disclosure.
Figure 15A:
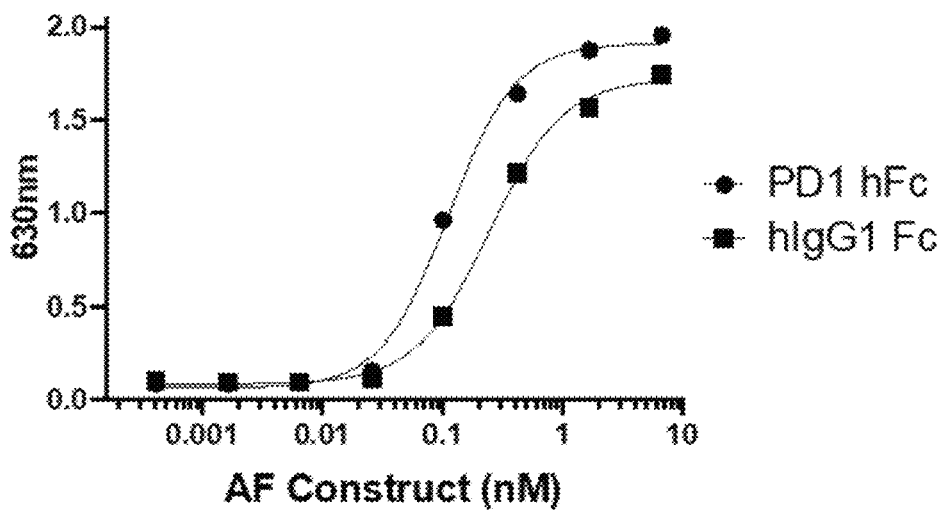
FIGS. 15A-D provide IL-2 activity of IL-2-linked protein complexes comprising the structure depicted in FIG. 14A in wells coated with PD-1-Fc or an IgG1 control protein. Activity was measured as growth of a 630 nm signal from HEK-Blue™ IL-2 reporter cells (an engineered human kidney cell line which generates a detectable color change in upon activation of its IL-2 receptor).
Figure 15B:
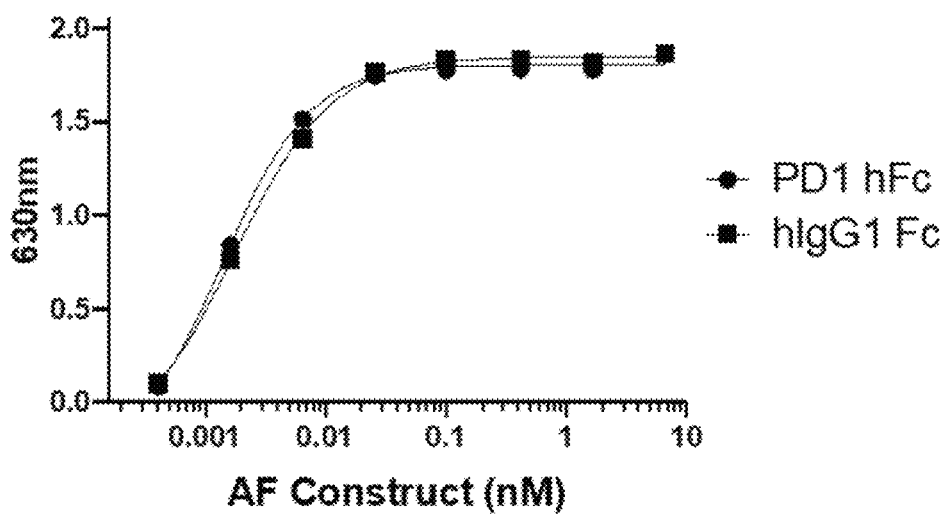
Figure 15C:
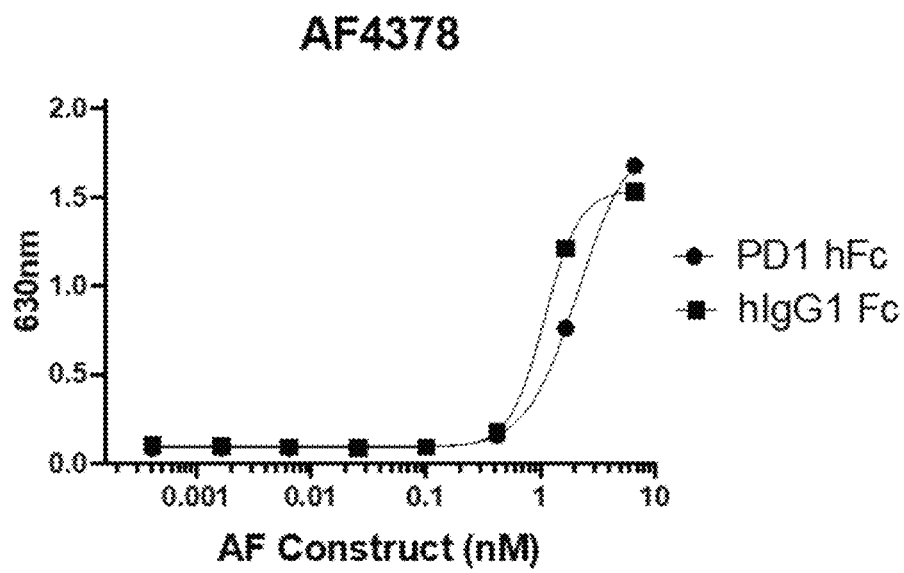
Figure 15D:
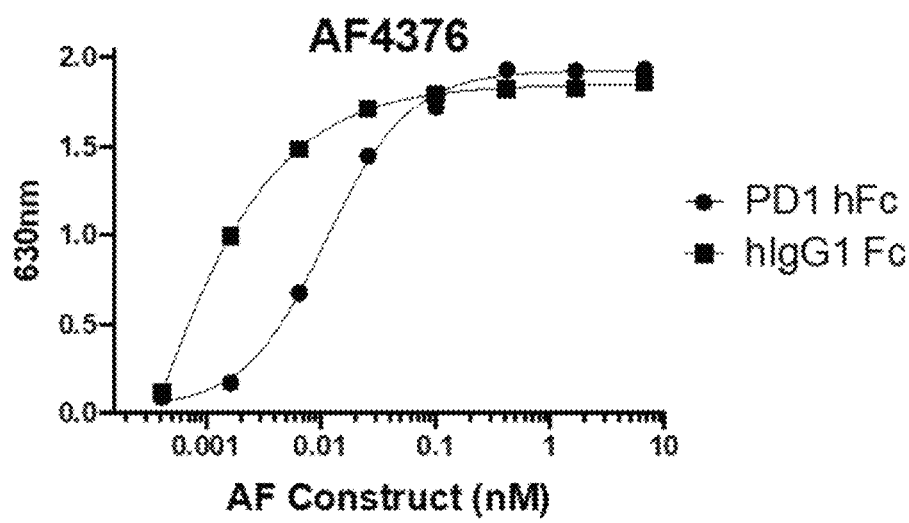
Figure 16A:
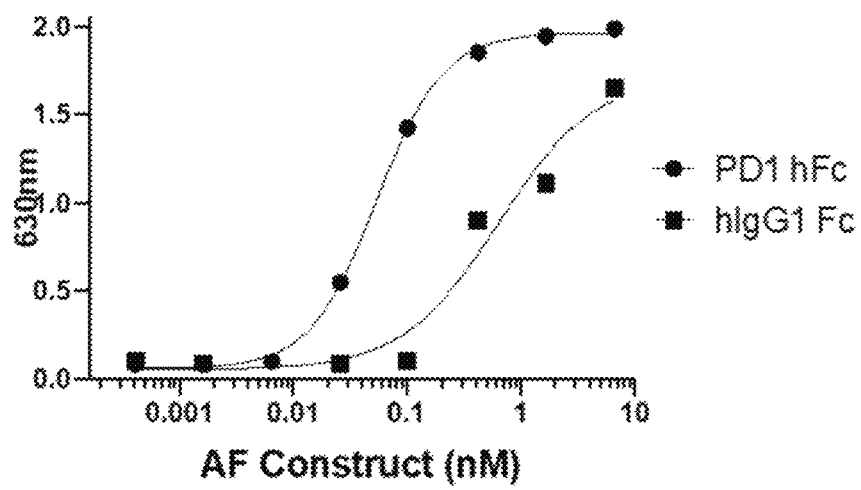
FIGS. 16A-F provide IL-2 activity of protein complexes comprising the structure depicted in FIG. 14B in wells coated with PD-1-Fc or an IgG1 control protein. Activity was measured as growth of a 630 nm signal from HEK-Blue™ IL-2 reporter cells.
Figure 16B:
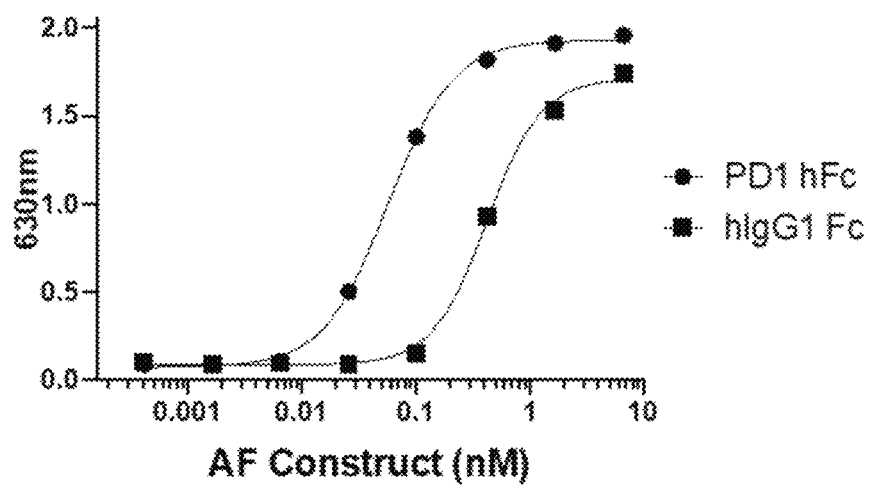
Figure 16C:
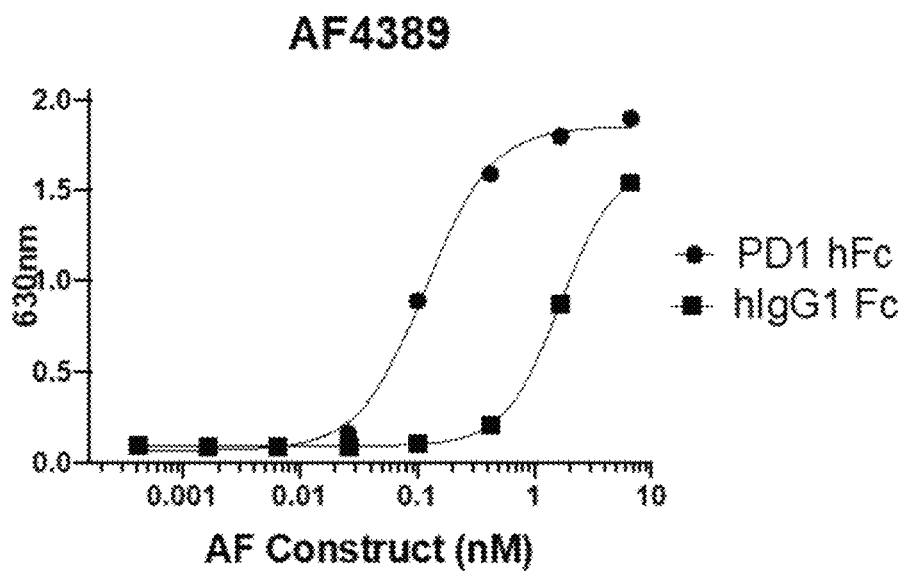
Figure 16D:
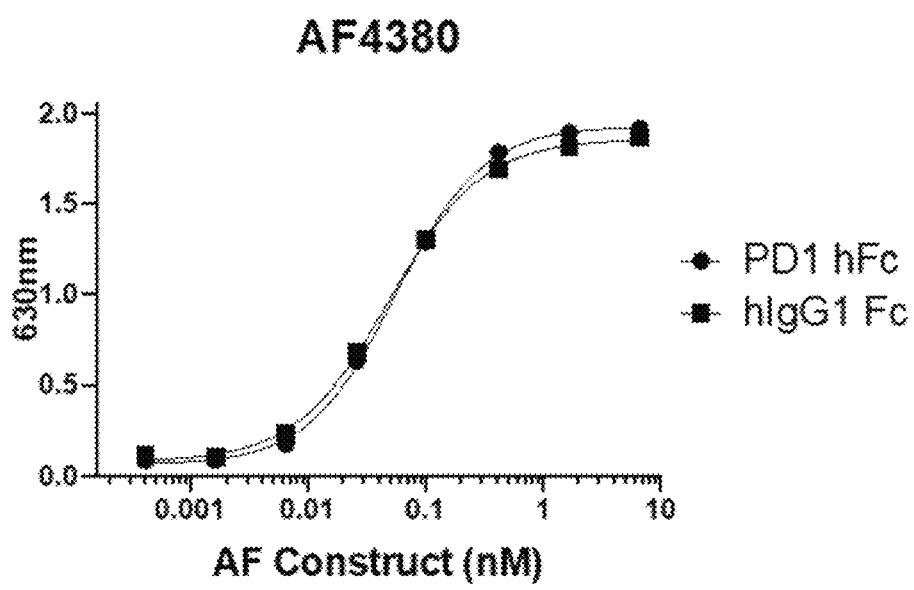
Figure 16E:
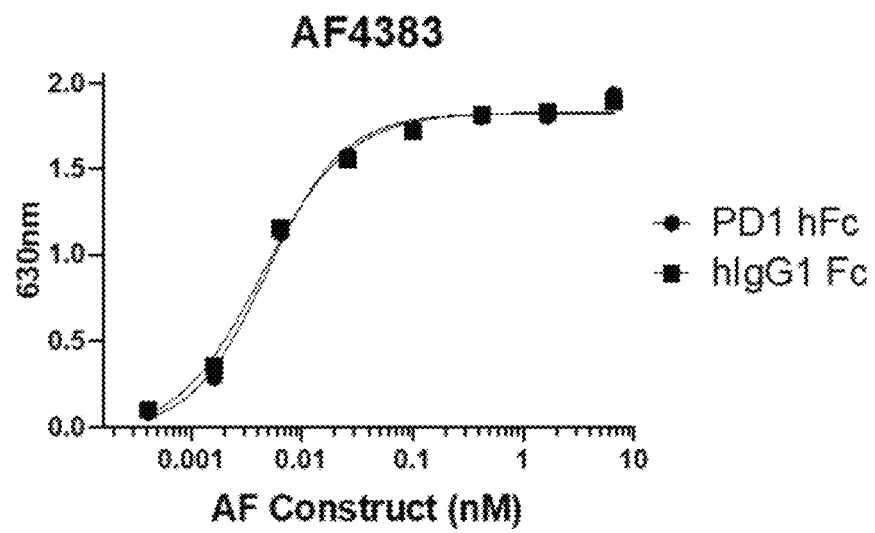
Figure 16F:
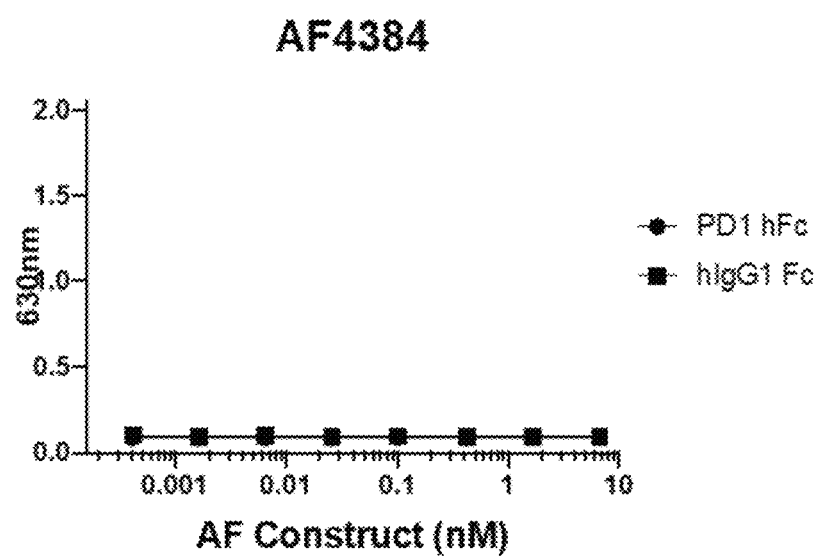

Results with a protein complexes comprising the structure shown in FIG. 14A are shown in FIG. 15A-D. As depicted in FIG. 14A, this symmetric format is comprised of one IL-2 linked to each antibody variable domain. The IL-2 activity of the PD-1/IL-2 DBA-IL-2 complex AF4379 comprising SEQ ID NO: 174-175 had an EC50 of 31 pM in the PD-1 coated wells versus 62 pM in the IgG1 coated wells, as shown in FIG. 15A, demonstrating PD-1 dependence. The IL-2 activity of antibody-cytokine complexes AF4377 comprising SEQ ID NO: 64 and 176 (anti-Her2 antibody) and AF4378 comprising SEQ ID NO: 177-178 (anti-IL-2 antibody) was unchanged in the presence of PD-1 (as shown in FIG. 15B and FIG. 15C, respectively), while the IL-2 activity of the anti-PD-1 antibody AF4376 comprising SEQ ID NO: 179-180 is reduced in the presence of PD-1, as shown in FIG. 15D. Sequences of the protein complexes are summarized in TABLE 22 below.

TABLE 22

IgG PD-1/IL-2 DBA with heavy chain IL-2 therapeutic domains, and control protein complexes

| Protein Complex | SEQ ID NO: | Sequence |
|---|---|---|
| AF4379 | SEQ ID NO: 174 | APTSSSTKKTQLQLEHLLLDLQMILNGINNYKNPKL TDMLTFEFYMPKKATELKHLQCLERELKPLEEVLNL AQSKNFHLRPRDLISNINVIVLELKGSETTFMCEYA DETATIVEFLNRWITFCQSIISTLTGGGGSGGGGSG GGGSGGGGSQVQLVQSGAEVKKPGASVKVSCKASGD TFTRYYVHWVRQAPGQGLEWMGIINPSGGYASYAQK FQGRVTMTRDTSTSTVYMELSSLRSEDTAVYYCAAG LFIWGQGTLVTVSSAKTTAPSVYPLAPVCGDTTGSS VTLGCLVKGYFPEPVTLTWNSGSLSSGVHTFPAVLQ SDLYTLSSSVTVTSSTWPSQSITCNVAHPASSTKVD KKIEPRGPTIKPCPPCKCPAPNAAGGPSVFIFPPKI KDVLMISLSPIVTCVVVDVSEDDPDVQISWFVNNVE VHTAQTQTHREDYNSTLRVVSALPIQHQDWMSGKEF KCKVNNKDLGAPIERTISKPKGSVRAPQVYVLPPPE EEMTKKQVTLTCMVTDFMPEDIYVEWTNNGKTELNY KNTEPVLDSDGSYFMYSKLRVEKKNWVERNSYSCSV VHEGLHNHHTTKSFSRTPGK |
| | SEQ ID NO: 175 | DIQMTQSPSSLSASVGDRVTITCRASQSIGRYLAWY QQKPGKAPKLLIYSASNLETGVPSRFSGSGSGTDFT LTISSLQPEDFATYYCQQYNSFPVTFGPGTKVDIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| AF4377 | SEQ ID NO: 64 | DIQMTQSPSSLSASVGDRVTITCRASQDVNTAVAWY QQKPGKAPKLLIYSASFLYSGVPSRFSGSRSGTDFT LTISSLQPEDFATYYCQQHYTTPPTFGQGTKVEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| | SEQ ID NO: 176 | APTSSSTKKTQLQLEHLLLDLQMILNGINNYKNPKL TDMLTFEFYMPKKATELKHLQCLERELKPLEEVLNL AQSKNFHLRPRDLISNINVIVLELKGSETTFMCEYA DETATIVEFLNRWITFCQSIISTLTGGGGSGGGGSG GGGSGGGGSEVQLVESGGGLVQPGGSLRLSCAASGF NIKDTYIHWVRQAPGKGLEWVARIYPTNGYTRYADS VKGRFTISADTSKNTAYLQMNSLRAEDTAVYYCSRW GGDGFYAMDYWGQGTLVTVSSAKTTAPSVYPLAPVC GDTTGSSVTLGCLVKGYFPEPVTLTWNSGSLSSGVH TFPAVLQSDLYTLSSSVTVTSSTWPSQSITCNVAHP ASSTKVDKKIEPRGPTIKPCPPCKCPAPNAAGGPSV FIFPPKIKDVLMISLSPIVTCVVVDVSEDDPDVQIS WFVNNVEVHTAQTQTHREDYNSTLRVVSALPIQHQD WMSGKEFKCKVNNKDLGAPIERTISKPKGSVRAPQV YVLPPPEEEMTKKQVTLTCMVTDFMPEDIYVEWTNN GKTELNYKNTEPVLDSDGSYFMYSKLRVEKKNWVER NSYSCSVVHEGLHNHHTTKSFSRTPGK |

TABLE 22-continued

IgG PD-1/IL-2 DBA with heavy chain IL-2 therapeutic domains, and control protein complexes

| Protein Complex | SEQ ID NO: | Sequence |
|---|---|---|
| AF4378 | SEQ ID NO: 177 | APTSSSTKKTQLQLEHLLLDLQMILNGINNYKNPKL TDMLTFEFYMPKKATELKHLQCLERELKPLEEVLNL AQSKNFHLRPRDLISNINVIVLELKGSETTFMCEYA DETATIVEFLNRWITFCQSIISTLTGGGGSGGGGSG GGGSGGGGSEVQLVESGGGLVKPGGSLRLSCAASGF TFSSYTLAWVRQAPGKGLEWVAAIDSSSYTYSPDTV RGRFTISRDNAKNSLYLQMNSLRAEDTAVYYCARDS NWDALDYWGQGTLVTVSSAKTTAPSVYPLAPVCGDT TGSSVTLGCLVKGYFPEPVTLTWNSGSLSSGVHTFP AVLQSDLYTLSSSVTVTSSTWPSQSITCNVAHPASS TKVDKKIEPRGPTIKPCPPCKCPAPNAAGGPSVFIF PPKIKDVLMISLSPIVTCVVVDVSEDDPDVQISWFV NNVEVHTAQTQTHREDYNSTLRVVSALPIQHQDWMS GKEFKCKVNNKDLGAPIERTISKPKGSVRAPQVYVL PPPEEEMTKKQVTLTCMVTDFMPEDIYVEWTNNGKT ELNYKNTEPVLDSDGSYFMYSKLRVEKKNWVERNSY SCSVVHEGLHNHHTTKSFSRTPGK |
| | SEQ ID NO: 178 | DIQMTQSPSSLSASVGDRVSITCKASQNVGTNVGWY QQKPGKAPKALIYSASFRYSGVPSRFSGSGSGTDFT LTISSLQPEDFATYFCQQYYTYPYTFGGGTKLEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| AF4376 | SEQ ID NO: 179 | APTSSSTKKTQLQLEHLLLDLQMILNGINNYKNPKL TDMLTFEFYMPKKATELKHLQCLERELKPLEEVLNL AQSKNFHLRPRDLISNINVIVLELKGSETTFMCEYA DETATIVEFLNRWITFCQSIISTLTGGGGSGGGGSG GGGSGGGGSQVQLVESGGGVVQPGRSLRLDCKASGI TFSNSGMHWVRQAPGKGLEWVAVIWYDGSKRYYADS VKGRFTISRDNSKNTLFLQMNSLRAEDTAVYYCATN DDYWGQGTLVTVSSAKTTAPSVYPLAPVCGDTTGSS VTLGCLVKGYFPEPVTLTWNSGSLSSGVHTFPAVLQ SDLYTLSSSVTVTSSTWPSQSITCNVAHPASSTKVD KKIEPRGPTIKPCPPCKCPAPNAAGGPSVFIFPPKI |

TABLE 22-continued

IgG PD-1/IL-2 DBA with heavy chain IL-2 therapeutic domains, and control protein complexes

| Protein Complex | SEQ ID NO: | Sequence |
|---|---|---|
| | | KDVLMISLSPIVTCVVVDVSEDDPDVQISWFVNNVE VHTAQTQTHREDYNSTLRVVSALPIQHQDWMSGKEF KCKVNNKDLGAPIERTISKPKGSVRAPQVYVLPPPE EEMTKKQVTLTCMVTDFMPEDIYVEWTNNGKTELNY KNTEPVLDSDGSYFMYSKLRVEKKNWVERNSYSCSV VHEGLHNHHTTKSFSRTPGK |
| | SEQ ID NO: 180 | EIVLTQSPATLSLSPGERATLSCRASQSVSSYLAWY QQKPGQAPRLLIYDASNRATGIPARFSGSGSGTDFT LTISSLEPEDFAVYYCQQSSNWPRTFGQGTKVEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |

Figure 14B:
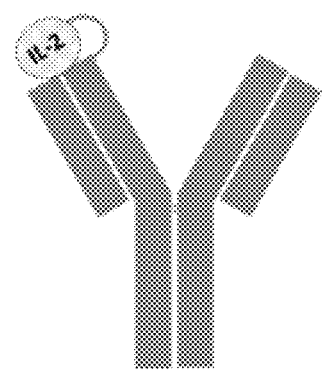
Figure 14C:
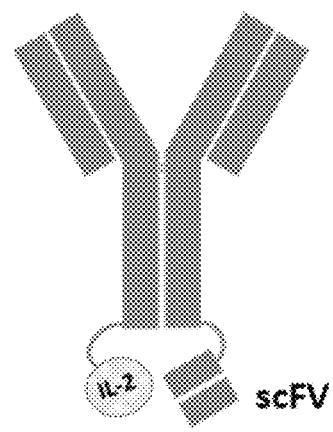

Results with protein complexes comprising the structures depicted in FIG. 14B, are shown in FIGS. 16A-F. This format is composed of an asymmetric complex comprised of two antibody domains with a single IL-2 linked to one of the domains. The IL-2 activity of the PD-1/IL-2 DBA-IL-2 complexes AF4386 (comprising SEQ ID NO: 212 and 181-182, results shown in FIG. 16A), AF4387 (comprising SEQ ID NO: 183-185, results shown in FIG. 16B) and AF4389 (comprising SEQ ID NO: 186-188, results shown in FIG. 16C) had an EC50 of 50 pM, 57 pM and 118 pM respectively in the PD-1 coated wells and 1.79 nM, 419 pM and 1.67 nM respectively in the IgG1 coated wells, demonstrating PD-1 dependence. The IL-2 activity of the anti-PD1 control protein AF4380 (comprising SEQ ID NO: 180, 189-190, results shown in FIG. 16D), the anti-Her2 control protein AF4383 (comprising SEQ ID NO: 64, 191-192, results shown in FIG. 16E), and the anti-IL-2 control protein AF4384 (comprising SEQ ID NO: 178, 193-194, results shown in FIG. 16F) were unchanged. Sequences of the protein complexes are summarized in TABLE 23 below.

TABLE 23

IgG PD-1/IL-2 PDA with single IL-2, and control protein complexes

| Protein Complex | SEQ ID NO: | Sequence |
|---|---|---|
| AF4386 | SEQ ID NO: 181 | APTSSSTKKTQLQLEHLLLDLQMILNGINNYKNPKLTDMLTFEFYMPKKATELKHLQ CLERELKPLEEVLNLAQSKNFHLRPRDLISNINVIVLELKGSETTFMCEYADETATIVE FLNRWITFCQSIISTLTGGGGSGGGGSGGGGSGGGGSQVQLVQSGAEVKKPGASV KVSCKASGDTFTRYYVHWVRQAPGQGLEWMGIINPSGGYASYAQKFQGRVTMT RDTSTSTVYMELSSLRSEDTAVYYCAAGLFIWGQGTLVTVSSAKTTAPSVYPLAPVC GDTTGSSVTLGCLVKGYFPEPVTLTWNSGSLSSGVHTFPAVLQSDLYTLSSSVTVTSS TWPSQSITCNVAHPASSTKVDKKIEPRGPTIKPCPPCKCPAPNAAGGPSVFIFPPKIK DVLMISLSPIVTCVVVDVSEDDPDVQISWFVNNVEVHTAQTQTHREDYNSTLRVV SALPIQHQDWMSGKEFKCKVNNKDLGAPIERTISKPKGSVRAPQVYVLPPPEEEMT KKQVTLTCMVTDFMPEDIYVEWTNNGKTELNYKNTEPVLDSDGSYFMYSDLRVEK KNWVERNSYSCSVVHEGLHNHHTTESFSRTPGK |
| | SEQ ID NO: 182 | QVQLVQSGAEVKKPGASVKVSCKASGDTFTRYYVHWVRQAPGQGLEWMGIINPS GGYASYAQKFQGRVTMTRDTSTSTVYMELSSLRSEDTAVYYCAAGLFIWGQGTLV TVSSAKTTAPSVYPLAPVCGDTTGSSVTLGCLVKGYFPEPVTLTWNSGSLSSGVHTF PAVLQSDLYTLSSSVTVTSSTWPSQSITCNVAHPASSTKVDKKIEPRGPTIKPCPPCK CPAPNAAGGPSVFIFPPKIKDVLMISLSPIVTCVVVDVSEDDPDVQISWFVNNVEV HTAQTQTHREDYNSTLRVVSALPIQHQDWMSGKEFKCKVNNKDLGAPIERTISKP KGSVRAPQVYVLPPPEKEMTKKQVSLTCLVKDFMPEDIYVEWTNNGKTELNYKNT EPVLKSDGSYFMYSKLTVEKKNWVERNSYSCSVVHEGLHNHHTTKSFSRTPGGGG SGGGSHHHHHH |

TABLE 23-continued

IgG PD-1/IL-2 PDA with single IL-2, and control protein complexes

| Protein Complex | SEQ ID NO: | Sequence |
|---|---|---|
| | SEQ ID NO: 212 | DIQMTQSPSSLSASVGDRVTITCRASQSIGRYLAWYQQKPGKAPKLLIYSASNLETG VPSRFSGSGSGTDFTLTISSLQPEDFATYYCQQYNSFPVTFGPGTKVDIKRADAAPT VSIFPPSSEQLTSGGASVVCFLNNFYPKDINVKWKIDGSERQNGVLNSWTDQDSK DSTYSMSSTLTLTKDEYERHNSYTCEATHKTSTSPIVKSFNRNEC |
| AF4387 | SEQ ID NO: 183 | APTSSSTKKTQLQLEHLLLDLQMILNGINNYKNPKLTDMLTFEFYMPKKATELKHLQ CLERELKPLEEVLNLAQSKNFHLRPRDLISNINVIVLELKGSETTFMCEYADETATIVE FLNRWITFCQSIISTLTGGGGSGGGGSGGGGSGGGGSQVQLVQSGAEVKKPGASV KVSCKASGYTFTDYYMHWVRQAPGQGLEWMGIINPRAGYTSYALKFQGRVTMT RDTSTSTVYMELSSLRSEDTAVYYCTSGWDVWGQGTLVTVSSAKTTAPSVYPLAPV CGDTTGSSVTLGCLVKGYFPEPVTLTWNSGSLSSGVHTFPAVLQSDLYTLSSSVTVT SSTWPSQSITCNVAHPASSTKVDKKIEPRGPTIKPCPPCKCPAPNAAGGPSVFIFPPK IKDVLMISLSPIVTCVVVDVSEDDPDVQISWFVNNVEVHTAQTQTHREDYNSTLRV VSALPIQHQDWMSGKEFKCKVNNKDLGAPIERTISKPKGSVRAPQVYVLPPPEEE MTKKQVTLTCMVTDFMPEDIYVEWTNNGKTELNYKNTEPVLDSDGSYFMYSDLR VEKKNWVERNSYSCSVVHEGLHNHHTTESFSRTPGK |
| | SEQ ID NO: 184 | QVQLVQSGAEVKKPGASVKVSCKASGYTFTDYYMHWVRQAPGQGLEWMGIINP RAGYTSYALKFQGRVTMTRDTSTSTVYMELSSLRSEDTAVYYCTSGWDVWGQGTL VTVSSAKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTIKPCPPC KCPAPNAAGGPSVFIFPPKIKDVLMISLSPIVTCVVVDVSEDDPDVQISWFVNNVEV HTAQTQTHREDYNSTLRVVSALPIQHQDWMSGKEFKCKVNNKDLGAPIERTISKP KGSVRAPQVYVLPPPEKEMTKKQVSLTCLVKDFMPEDIYVEWTNNGKTELNYKNT EPVLKSDGSYFMYSKLTVEKKNWVERNSYSCSVVHEGLHNHHTTKSFSRTPGGGG SGGGSHHHHHH |
| | SEQ ID NO: 185 | DIQMTQSPSSLSASVGDRVTITCRASQSISTWLAWYQQKPGKAPKLLIYAASSLDSG VPSRFSGSGSGTDFTLTISSLQPEDFATYYCQQSYSFPVTFGQGTKVEIKRADAAPTV SIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC |
| AF4389 | SEQ ID NO: 186 | APTSSSTKKTQLQLEHLLLDLQMILNGINNYKNPKLTDMLTFEFYMPKKATELKHLQ CLERELKPLEEVLNLAQSKNFHLRPRDLISNINVIVLELKGSETTFMCEYADETATIVE FLNRWITFCQSIISTLTGGGGSGGGGSGGGGGGGSQVQLVQSGAEVKKPGASV KVSCKASGHTFTRYYMHWVRQAPGQGLEWMGIINPSGGYATYAQKFQGRVTMT RDTSTSTVYMELSSLRSEDTAVYYCASGLFIWGQGTLVTVSSAKTTAPSVYPLAPVC GDTTGSSVTLGCLVKGYFPEPVTLTWNSGSLSSGVHTFPAVLQSDLYTLSSSVTVTSS TWPSQSITCNVAHPASSTKVDKKIEPRGPTIKPCPPCKCPAPNAAGGPSVFIFPPKIK DVLMISLSPIVTCVVVDVSEDDPDVQISWFVNNVEVHTAQTQTHREDYNSTLRVV SALPIQHQDWMSGKEFKCKVNNKDLGAPIERTISKPKGSVRAPQVYVLPPPEEEMT KKQVTLTCMVTDFMPEDIYVEWTNNGKTELNYKNTEPVLDSDGSYFMYSDLRVEK KNWVERNSYSCSVVHEGLHNHHTTESFSRTPGK |
| | SEQ ID NO: 187 | QVQLVQSGAEVKKPGASVKVSCKASGHTFTRYYMHWVRQAPGQGLEWMGIINP SGGYATYAQKFQGRVTMTRDTSTSTVYMELSSLRSEDTAVYYCASGLFIWGQGTL VTVSSAKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTIKPCPPC KCPAPNAAGGPSVFIFPPKIKDVLMISLSPIVTCVVVDVSEDDPDVQISWFVNNVEV HTAQTQTHREDYNSTLRVVSALPIQHQDWMSGKEFKCKVNNKDLGAPIERTISKP KGSVRAPQVYVLPPPEKEMTKKQVSLTCLVKDFMPEDIYVEWTNNGKTELNYKNT EPVLKSDGSYFMYSKLTVEKKNWVERNSYSCSVVHEGLHNHHTTKSFSRTPGGGG SGGGSHHHHHH |
| | SEQ ID NO: 188 | DIQMTQSPSSLSASVGDRVTITCRASQSINSWLAWYQQKPGKAPKLLIYATSTLESG VPSRFSGSGSGTDFTLTISSLQPEDFATYYCQQYYRFPVTFGQGTKVEIKRADAAPT VSIFPPSSEQLTSGGASVVCFLNNFYPKDINVKWKIDGSERQNGVLNSWTDQDSK DSTYSMSSTLTLTKDEYERHNSYTCEATHKTSTSPIVKSFNRNEC |
| AF4380 | SEQ ID NO: 180 | EIVLTQSPATLSLSPGERATLSCRASQSVSSYLAWYQQKPGQAPRLL IYDASNRATGIPARFSGSGSGTDFTLTISSLEPEDFAVYYCQQSSNW PRTFGQGTKVEIKRADAAPTVSIFPPSSEQLTSGGASVVCFLNNFYP KDINVKWKIDGSERQNGVLNSWTDQDSKDSTYSMSSTLTLTKDEY ERHNSYTCEATHKTSTSPIVKSFNRNEC |
| | SEQ ID NO: 189 | APTSSSTKKTQLQLEHLLLDLQMILNGINNYKNPKLTDMLTFEFYMPKKATELKHLQ CLERELKPLEEVLNLAQSKNFHLRPRDLISNINVIVLELKGSETTFMCEYADETATIVE FLNRWITFCQSIISTLTGGGGSGGGGSGGGGSGGGGSQVQLVESGGGVVQPGRSL RLDCKASGITFSNSGMHWVRQAPGKGLEWVAVIWYDGSKRYYADSVKGRFTISR DNSKNTLFLQMNSLRAEDTAVYYCATNDDYWGQGTLVTVSSAKTTAPSVYPLAPV CGDTTGSSVTLGCLVKGYFPEPVTLTWNSGSLSSGVHTFPAVLQSDLYTLSSSVTVT SSTWPSQSITCNVAHPASSTKVDKKIEPRGPTIKPCPPCKCPAPNAAGGPSVFIFPPK IKDVLMISLSPIVTCVVVDVSEDDPDVQISWFVNNVEVHTAQTQTHREDYNSTLRV VSALPIQHQDWMSGKEFKCKVNNKDLGAPIERTISKPKGSVRAPQVYVLPPPEEE |

TABLE 23-continued

IgG PD-1/IL-2 PDA with single IL-2, and control protein complexes

| Protein Complex | SEQ ID NO: | Sequence |
|---|---|---|
| | | MTKKQVTLTCMVTDFMPEDIYVEWTNNGKTELNYKNTEPVLDSDGSYFMYSDLR<br>VEKKNWVERNSYSCSVVHEGLHNHHTTESFSRTPGK |
| | SEQ ID NO: 190 | QVQLVESGGGVVQPGRSLRLDCKASGITFSNSGMHWVRQAPGKGLEWVAVIWY<br>DGSKRYYADSVKGRFTISRDNSKNTLFLQMNSLRAEDTAVYYCATNDDYWGQGTL<br>VTVSSAKTTAPSVYPLAPVCGDTTGSSVTLGCLVKGYFPEPVTLTWNSGSLSSGVHT<br>FPAVLQSDLYTLSSSVTVTSSTWPSQSITCNVAHPASSTKVDKKIEPRGPTIKPCPPC<br>KCPAPNAAGGPSVFIFPPKIKDVLMISLSPIVTCVVVDVSEDDPDVQISWFVNNVEV<br>HTAQTQTHREDYNSTLRVVSALPIQHQDWMSGKEFKCKVNNKDLGAPIERTISKP<br>KGSVRAPQVYVLPPPEKEMTKKQVSLTCLVKDFMPEDIYVEWTNNGKTELNYKNT<br>EPVLKSDGSYFMYSKLTVEKKNWVERNSYSCSVVHEGLHNHHTTKSFSRTPGGGG<br>SGGGSHHHHHH |
| AF4383 | SEQ ID NO: 64 | DIQMTQSPSSLSASVGDRVTITCRASQDVNTAVAWYQQKPGKAPK<br>LLIYSASFLYSGVPSRFSGSRSGTDFTLTISSLQPEDFATYYCQQHYT<br>TPPTFGQGTKVEIKRADAAPTVSIFPPSSEQLTSGGASVVCFLNNFY<br>PKDINVKWKIDGSERQNGVLNSWTDQDSKDSTYSMSSTLTLTKDE<br>YERHNSYTCEATHKTSTSPIVKSFNRNEC |
| | SEQ ID NO: 191 | APTSSSTKKTQLQLEHLLLDLQMILNGINNYKNPKLTDMLTFEFYMPKKATELKHLQ<br>CLERELKPLEEVLNLAQSKNFHLRPRDLISNINVIVLELKGSETTFMCEYADETATIVE<br>FLNRWITFCQSIISTLTGGGSGGGGSGGGGSGGGGSEVQLVESGGGLVQPGGSL<br>RLSCAASGFNIKDTYIHWVRQAPGKGLEWVARIYPTNGYTRYADSVKGRFTISADT<br>SKNTAYLQMNSLRAEDTAVYYCSRWGGDGFYAMDYWGQGTLVTVSSAKTTAPS<br>VYPLAPVCGDTTGSSVTLGCLVKGYFPEPVTLTWNSGSLSSGVHTFPAVLQSDLYTL<br>SSSVTVTSSTWPSQSITCNVAHPASSTKVDKKIEPRGPTIKPCPPCKCPAPNAAGGP<br>SVFIFPPKIKDVLMISLSPIVTCVVVDVSEDDPDVQISWFVNNVEVHTAQTQTHRED<br>YNSTLRVVSALPIQHQDWMSGKEFKCKVNNKDLGAPIERTISKPKGSVRAPQVYVL<br>PPPEEEMTKKQVTLTCMVTDFMPEDIYVEWTNNGKTELNYKNTEPVLDSDGSYF<br>MYSDLRVEKKNWVERNSYSCSVVHEGLHNHHTTESFSRTPGK |
| | SEQ ID NO: 192 | EVQLVESGGGLVQPGGSLRLSCAASGFNIKDTYIHWVRQAPGKGLEWVARIYPTNGYTRY<br>ADSVKGRFTISADTSKNTAYLQMNSLRAEDTAVYYCSRWGGDGFYAMDYWGQGTLVTVS<br>SAKTTAPSVYPLAPVCGDTTGSSVTLGCLVKGYFPEPVTLTWNSGSLSSGVHTFPAVLQSDL<br>YTLSSSVTVTSSTWPSQSITCNVAHPASSTKVDKKIEPRGPTIKPCPPCKCPAPNAAGGPSVF<br>IFPPKIKDVLMISLSPIVTCVVVDVSEDDPDVQISWFVNNVEVHTAQTQTHREDYNSTLRVV<br>SALPIQHQDWMSGKEFKCKVNNKDLGAPIERTISKPKGSVRAPQVYVLPPPEKEMTKKQV<br>SLTCLVKDFMPEDIYVEWTNNGKTELNYKNTEPVLKSDGSYFMYSKLTVEKKNWVERNSYS<br>CSVVHEGLHNHHTTKSFSRTPGGGGSGGGSHHHHHH |
| AF4384 | SEQ ID NO: 178 | DIQMTQSPSSLSASVGDRVSITCKASQNVGTNVGWYQQKPGKAPKALIYSASFRYS<br>GVPSRFSGSGSGTDFTLTISSLQPEDFATYFCQQYYTYPYTFGGGTKLEIKRADAAPT<br>VSIFPPSSEQLTSGGASVVCFLNNFYPKDINVKWKIDGSERQNGVLNSWTDQDSK<br>DSTYSMSSTLTLTKDEYERHNSYTCEATHKTSTSPIVKSFNRNEC |
| | SEQ ID NO: 193 | APTSSSTKKTQLQLEHLLLDLQMILNGINNYKNPKLTDMLTFEFYMPKKATELKHLQ<br>CLERELKPLEEVLNLAQSKNFHLRPRDLISNINVIVLELKGSETTFMCEYADETATIVE<br>FLNRWITFCQSIISTLTGGGSGGGGSGGGGSGGGGSEVQLVESGGGLVKPGGSL<br>RLSCAASGFTFSSYTLAWVRQAPGKGLEWVAAIDSSSYTYSPDTVRGRFTISRDNAK<br>NSLYLQMNSLRAEDTAVYYCARDSNWDALDYWGQGTLVTVSSAKTTAPSVYPLA<br>PVCGDTTGSSVTLGCLVKGYFPEPVTLTWNSGSLSSGVHTFPAVLQSDLYTLSSSVT<br>VTSSTWPSQSITCNVAHPASSTKVDKKIEPRGPTIKPCPPCKCPAPNAAGGPSVFIFP<br>PKIKDVLMISLSPIVTCVVVDVSEDDPDVQISWFVNNVEVHTAQTQTHREDYNSTL<br>RVVSALPIQHQDWMSGKEFKCKVNNKDLGAPIERTISKPKGSVRAPQVYVLPPPEE<br>EMTKKQVTLTCMVTDFMPEDIYVEWTNNGKTELNYKNTEPVLDSDGSYFMYSDL<br>RVEKKNWVERNSYSCSVVHEGLHNHHTTESFSRTPGK |
| | SEQ ID NO: 194 | EVQLVESGGGLVKPGGSLRLSCAASGFTFSSYTLAWVRQAPGKGLEWVAAIDSSSY<br>TYSPDTVRGRFTISRDNAKNSLYLQMNSLRAEDTAVYYCARDSNWDALDYWGQG<br>TLVTVSSAKTTAPSVYPLAPVCGDTTGSSVTLGCLVKGYFPEPVTLTWNSGSLSSGV<br>HTFPAVLQSDLYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPDVQISWFVNNV<br>EVHTAQTQTHREDYNSTLRVVSALPIQHQDWMSGKEFKCKVNNKDLGAPIERTIS<br>KPKGSVRAPQVYVLPPPEKEMTKKQVSLTCLVKDFMPEDIYVEWTNNGKTELNYK<br>NTEPVLKSDGSYFMYSKLTVEKKNWVERNSYSCSVVHEGLHNHHTTKSFSRTPGG<br>GGSGGGSHHHHHH |

Figures 17E, 17F:
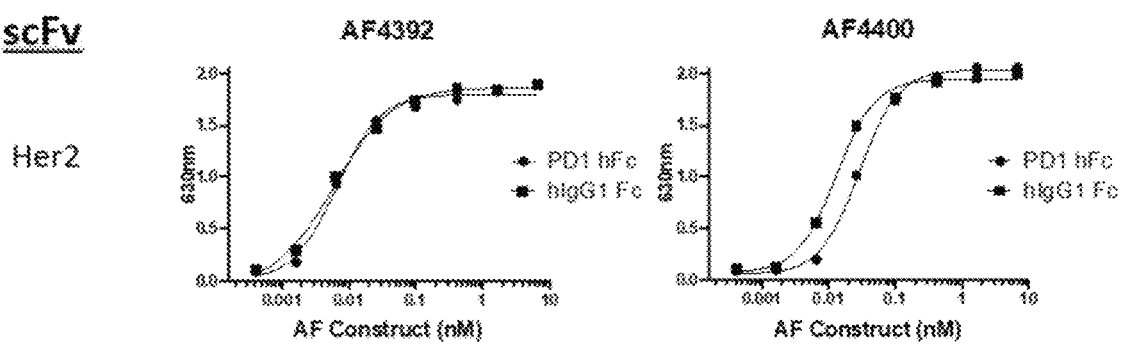
Figures 17G, 17H:
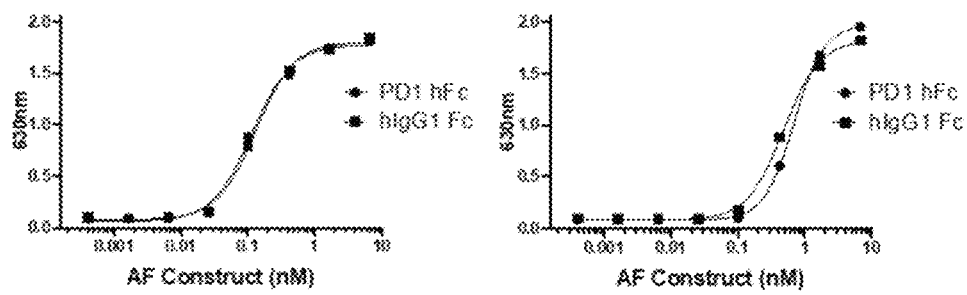

Results with protein complexes comprising the structures depicted in FIG. 14C are shown in FIGS. 17A-H. As depicted in FIG. 14C, these complexes are asymmetric and comprised of two identical monospecific Fab arms with a single IL-2 attached to one Fc domain by flexible linker and a single scFv attached to the other Fc domain by a flexible linker. The active PD-1/IL-2 DBA complexes, AF4403 comprising SEQ ID NO: 180, 195, 199 and AF4404 comprising SEQ ID NO: 180, 196, 199, are composed of anti-PD-1 domains in the Fab arms and a PD-1/IL-2 DBA scFv on the Fc arm. The control antibody-cytokine complexes are composed of a) antibody-cytokine complexes with an irrelevant antibody on the Fab arms with the DBA scFv on the Fc (AF4395 comprising SEQ ID NO: 64, 197, 202 and AF4396 comprising SEQ ID NO: 64, 198, 202), b) antibody-cytokine complexes with a non-DBA scFv on the Fc arm (AF4400 comprising SEQ ID NO: 180, 199-200 and AF4401 comprising SEQ ID NO: 180, 199, 201), and c) antibody-cytokine complexes with non-DBA antibodies in both the Fab and scFv domains (AF4392 comprising SEQ ID NO: 64, 202-203 and AF4393 comprising SEQ ID NO: 64, 202, 204). As shown in FIGS. 17B and 17D, the IL-2 activity of the DBA-cytokine complexes AF4403 and AF4404 had an EC50 of 31 pM and 26 pM respectively in the PD-1 coated wells and 62 pM and 64 pM respectively in the control wells, demonstrating PD-1 dependence of the IL-2 activity. None of the control proteins AF4395, AF4396, AF4400, AF4401, AF4392 and AF4393 described above showed a lower EC50 on PD-1 coated wells than on wells coated with the IgG1 protein, as shown in FIGS. 17A, 17C and 17E-H. Sequences of the protein complexes are summarized in TABLE 24 below.

TABLE 24

IgG PD-1 with C-terminal scFv and IL-2, and control protein complexes

| Protein Complex | SEQ ID NO: | Sequence |
|---|---|---|
| AF4403 | SEQ ID NO: 180 | EIVLTQSPATLSLSPGERATLSCRASQSVSSYLAWYQQKPGQAPRLL IYDASNRATGIPARFSGSGSGTDFTLTISSLEPEDFAVYYCQQSSNW PRTFGQGTKVEIKRADAAPTVSIFPPSSEQLTSGGASVVCFLNNFYP KDINVKWKIDGSERQNGVLNSWTDQDSKDSTYSMSSTLTLTKDEY ERHNSYTCEATHKTSTSPIVKSFNRNEC |
| | SEQ ID NO: 195 | QVQLVESGGGVVQPGRSLRLDCKASGITFSNSGMHWVRQAPGKG LEWVAVIWYDGSKRYYADSVKGRFTISRDNSKNTLFLQMNSLRAE DTAVYYCATNDDYWGQGTLVTVSSAKTTAPSVYPLAPVCGDTTG SSVTLGCLVKGYFPEPVTLTWNSGSLSSGVHTFPAVLQSDLYTLSSS VTVTSSTWPSQSITCNVAHPASSTKVDKKIEPRGPTIKPCPPCKCPAP NAAGGPSVFIFPPKIKDVLMISLSPIVTCVVVDVSEDDPDVQISWFV NNVEVHTAQTQTHREDYNSTLRVVSALPIQHQDWMSGKEFKCKV NNKDLGAPIERTISKPKGSVRAPQVYVLPPPEKEMTKKQVSLTCLV KDFMPEDIYVEWTNNGKTELNYKNTEPVLKSDGSYFMYSKLTVEK KNWVERNSYSCSVVHEGLHNHHTTKSFSRTPGGGGSGGGGSGG GGSGGGGSQVQLVQSGAEVKKPGASVKVSCKASGDTFTRYYVHW VRQAPGQGLEWMGIINPSGGYASYAQKFQGRVTMTRDTSTSTVY MELSSLRSEDTAVYYCAAGLFIWGQGTLVTVSSASGGGGGGGS GGGGSHASDIQMTQSPSSLSASVGDRVTITCRASQSIGRYLAWYQQ KPGKAPKLLIYSASNLETGVPSRFSGSGSGTDFTLTISSLQPEDFATY YCQQYNSFPVTFGPGTKVDIKGGGSGGGSHHHHHH |
| | SEQ ID NO: 199 | QVQLVESGGGVVQPGRSLRLDCKASGITFSNSGMHWVRQAPGKG LEWVAVIWYDGSKRYYADSVKGRFTISRDNSKNTLFLQMNSLRAE DTAVYYCATNDDYWGQGTLVTVSSAKTTAPSVYPLAPVCGDTTG SSVTLGCLVKGYFPEPVTLTWNSGSLSSGVHTFPAVLQSDLYTLSSS VTVTSSTWPSQSITCNVAHPASSTKVDKKIEPRGPTIKPCPPCKCPAP NAAGGPSVFIFPPKIKDVLMISLSPIVTCVVVDVSEDDPDVQISWFV NNVEVHTAQTQTHREDYNSTLRVVSALPIQHQDWMSGKEFKCKV NNKDLGAPIERTISKPKGSVRAPQVYVLPPPEEEMTKKQVTLTCMV TDFMPEDIYVEWTNNGKTELNYKNTEPVLDSDGSYFMYSDLRVEK KNWVERNSYSCSVVHEGLHNHHTTESFSRTPGGGGSGGGGSGG GGSAPTSSSTKKTQLQLEHLLLDLQMILNGINNYKNPKLTDMLTFE FYMPKKATELKHLQCLERELKPLEEVLNLAQSKNFHLRPRDLISNI NVIVLELKGSETTFMCEYADETATIVEFLNRWITFCQSIISTLT |
| AF4404 | SEQ ID NO: 180 | EIVLTQSPATLSLSPGERATLSCRASQSVSSYLAWYQQKPGQAPRLL IYDASNRATGIPARFSGSGSGTDFTLTISSLEPEDFAVYYCQQSSNW PRTFGQGTKVEIKRADAAPTVSIFPPSSEQLTSGGASVVCFLNNFYP KDINVKWKIDGSERQNGVLNSWTDQDSKDSTYSMSSTLTLTKDEY ERHNSYTCEATHKTSTSPIVKSFNRNEC |
| | SEQ ID NO: 196 | QVQLVESGGGVVQPGRSLRLDCKASGITFSNSGMHWVRQAPGKG LEWVAVIWYDGSKRYYADSVKGRFTISRDNSKNTLFLQMNSLRAE DTAVYYCATNDDYWGQGTLVTVSSAKTTAPSVYPLAPVCGDTTG SSVTLGCLVKGYFPEPVTLTWNSGSLSSGVHTFPAVLQSDLYTLSSS VTVTSSTWPSQSITCNVAHPASSTKVDKKIEPRGPTIKPCPPCKCPAP NAAGGPSVFIFPPKIKDVLMISLSPIVTCVVVDVSEDDPDVQISWFV NNVEVHTAQTQTHREDYNSTLRVVSALPIQHQDWMSGKEFKCKV NNKDLGAPIERTISKPKGSVRAPQVYVLPPPEKEMTKKQVSLTCLV KDFMPEDIYVEWTNNGKTELNYKNTEPVLKSDGSYFMYSKLTVEK KNWVERNSYSCSVVHEGLHNHHTTKSFSRTPGGGGSGGGGSGG GGSGGGGSQVQLVQSGAEVKKPGASVKVSCKASGYTFTDYYMH WVRQAPGQGLEWMGIINPRAGYTSYALKFQGRVTMTRDTSTSTV YMELSSLRSEDTAVYYCTSGWDVWGQGTLVTVSSASGGGGSGGG GSGGGGSHASDIQMTQSPSSLSASVGDRVTITCRASQSISTWLAWY QQKPGKAPKLLIYAASSLDSGVPSRFSGSGSGTDFTLTISSLQPEDFA TYYCQQSYSFPVTFGQGTKVEIKGGGSGGGSHHHHHH |

TABLE 24-continued

IgG PD-1 with C-terminal scFv and IL-2, and control protein complexes

| Protein Complex | SEQ ID NO: | Sequence |
|---|---|---|
| | SEQ ID NO: 199 | QVQLVESGGGVVQPGRSLRLDCKASGITFSNSGMHWVRQAPGKG<br>LEWVAVIWYDGSKRYYADSVKGRFTISRDNSKNTLFLQMNSLRAE<br>DTAVYYCATNDDYWGQGTLVTVSSAKTTAPSVYPLAPVCGDTTG<br>SSVTLGCLVKGYFPEPVTLTWNSGSLSSGVHTFPAVLQSDLTLSSS<br>VTVTSSTWPSQSITCNVAHPASSTKVDKKIEPRGPTIKPCPPCKPAP<br>NAAGGPSVFIFPPKIKDVLMISLSPIVTCVVVDVSEDDPDVQISWFV<br>NNVEVHTAQTQTHREDYNSTLRVVSALPIQHQDWMSGKEFKCKV<br>NNKDLGAPIERTISKPKGSVRAPQVYVLPPPEEEMTKKQVTLTCMV<br>TDFMPEDIYVEWTNNGKTELNYKNTEPVLDSDGSYFMYSDLRVEK<br>KNWVERNSYSCSVVHEGLHNHHTTESFSRTPGGGGGSGGGGSGG<br>GGSAPTSSSTKKTQLQLEHLLLDLQMILNGINNYKNPKLTDMLTFE<br>FYMPKKATELKHLQCLERELKPLEEVLNLAQSKNFHLRPRDLISNI<br>NVIVLELKGSETTFMCEYADETATIVEFLNRWITFCQSIISTLT |
| AF4395 | SEQ ID NO: 64 | DIQMTQSPSSLSASVGDRVTITCRASQDVNTAVAWYQQKPGKAPK<br>LLIYSASFLYSGVPSRFSGSRSGTDFTLTISSLQPEDFATYYCQQHYT<br>TPPTFGQGTKVEIKRADAAPTVSIFPPSSEQLTSGGASVVCFLNNFY<br>PKDINVKWKIDGSERQNGVLNSWTDQDSKDSTYSMSSTLTLTKDE<br>YERHNSYTCEATHKTSTSPIVKSFNRNEC |
| | SEQ ID NO: 197 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEKEMTKKQ<br>VSLTCLVKDFMPEDIYVEWTNNGKTELNYKNTEPVLKSDGSYFMY<br>SKLTVEKKNWVERNSYSCSVVHEGLHNHHTTKSFSRTPGGGGGSG<br>GGGSGGGGSGGGGSQVQLVQSGAEVKKPGASVKVSCKASGDTFT<br>RYYVHWVRQAPGQGLEWMGIINPSGGYASYAQKFQGRVTMTRDT<br>STSTVYMELSSLRSEDTAVYYCAAGLFIWGQGTLVTVSSASGGGGS<br>GGGGSGGGGSHASDIQMTQSPSSLSASVGDRVTITCRASQSIGRYL<br>AWYQQKPGKAPKLLIYSASNLETGVPSRFSGSGSGTDFTLTISSLQP<br>EDFATYYCQQYNSFPVTFGPGTKVDIKGGGSGGGSHHHHHH |
| | SEQ ID NO: 202 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEEEMTKKQ<br>VTLTCMVTDFMPEDIYVEWTNNGKTELNYKNTEPVLDSDGSYFM<br>YSDLRVEKKNWVERNSYSCSVVHEGLHNHHTTESFSRTPGGGGGS<br>GGGGSGGGGSAPTSSSTKKTQLQLEHLLLDLQMILNGINNYKNPKL<br>TDMLTFEFYMPKKATELKHLQCLERELKPLEEVLNLAQSKNFHLRP<br>RDLISNINVIVLELKGSETTFMCEYADETATIVEFLNRWITFCQSIIST<br>LT |
| AF4396 | SEQ ID NO: 64 | DIQMTQSPSSLSASVGDRVTITCRASQDVNTAVAWYQQKPGKAPK<br>LLIYSASFLYSGVPSRFSGSRSGTDFTLTISSLQPEDFATYYCQQHYT<br>TPPTFGQGTKVEIKRADAAPTVSIFPPSSEQLTSGGASVVCFLNNFY<br>PKDINVKWKIDGSERQNGVLNSWTDQDSKDSTYSMSSTLTLTKDE<br>YERHNSYTCEATHKTSTSPIVKSFNRNEC |
| | SEQ ID NO: 198 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEKEMTKKQ<br>VSLTCLVKDFMPEDIYVEWTNNGKTELNYKNTEPVLKSDGSYFMY<br>SKLTVEKKNWVERNSYSCSVVHEGLHNHHTTKSFSRTPGGGGGSG<br>GGGSGGGGSGGGGSQVQLVQSGAEVKKPGASVKVSCKASGYTFT<br>DYYMHWVRQAPGQGLEWMGIINPRAGYTSYALKFQGRVTMTRD<br>TSTSTVYMELSSLRSEDTAVYYCTSGWDVWGQGTLVTVSSASGGG |

TABLE 24-continued

IgG PD-1 with C-terminal scFv and IL-2, and control protein complexes

| Protein Complex | SEQ ID NO: | Sequence |
|---|---|---|
| | | GSGGGGSGGGGSHASDIQMTQSPSSLSASVGDRVTITCRASQSIST<br>WLAWYQQKPGKAPKLLIYAASSLDSGVPSRFSGSGSGTDFTLTISSL<br>QPEDFATYYCQQSYSFPVTFGQGTKVEIKGGGSGGGSHHHHHH |
| | SEQ ID NO: 202 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEEEMTKKQ<br>VTLTCMVTDFMPEDIYVEWTNNGKTELNYKNTEPVLDSDGSYFM<br>YSDLRVEKKNWVERNSYSCSVVHEGLHNHHTTESFSRTPGGGGGS<br>GGGGSGGGGSAPTSSSTKKTQLQLEHLLLDLQMILNGINNYKNPKL<br>TDMLTFEFYMPKKATELKHLQCLERELKPLEEVLNLAQSKNFHLRP<br>RDLISNINVIVLELKGSETTFMCEYADETATIVEFLNRWITFCQSIIST<br>LT |
| AF4400 | SEQ ID NO: 180 | EIVLTQSPATLSLSPGERATLSCRASQSVSSYLAWYQQKPGQAPRLL<br>IYDASNRATGIPARFSGSGSGTDFTLTISSLEPEDFAVYYCQQSSNW<br>PRTFGQGTKVEIKRADAAPTVSIFPPSSEQLTSGGASVVCFLNNFYP<br>KDINVKWKIDGSERQNGVLNSWTDQDSKDSTYSMSSTLTLTKDEY<br>ERHNSYTCEATHKTSTSPIVKSFNRNEC |
| | SEQ ID NO: 199 | QVQLVESGGGVVQPGRSLRLDCKASGITFSNSGMHWVRQAPGKG<br>LEWVAVIWYDGSKRYYADSVKGRFTISRDNSKNTLFLQMNSLRAE<br>DTAVYYCATNDDYWGQGTLVTVSSAKTTAPSVYPLAPVCGDTTG<br>SSVTLGCLVKGYFPEPVTLTWNSGSLSSGVHTFPAVLQSDLYTLSSS<br>VTVTSSTWPSQSITCNVAHPASSTKVDKKIEPRGPTIKPCPPCKCPAP<br>NAAGGPSVFIFPPKIKDVLMISLSPIVTCVVVDVSEDDPDVQISWFV<br>NNVEVHTAQTQTHREDYNSTLRVVSALPIQHQDWMSGKEFKCKV<br>NNKDLGAPIERTISKPKGSVRAPQVYVLPPPEEEMTKKQVTLTCMV<br>TDFMPEDIYVEWTNNGKTELNYKNTEPVLDSDGSYFMYSDLRVEK<br>KNWVERNSYSCSVVHEGLHNHHTTESFSRTPGGGGSGGGGSGG<br>GGSAPTSSSTKKTQLQLEHLLLDLQMILNGINNYKNPKLTDMLTFE<br>FYMPKKATELKHLQCLERELKPLEEVLNLAQSKNFHLRPRDLISNI<br>NVIVLELKGSETTFMCEYADETATIVEFLNRWITFCQSIISTLT |
| | SEQ ID NO: 200 | QVQLVESGGGVVQPGRSLRLDCKASGITFSNSGMHWVRQAPGKG<br>LEWVAVIWYDGSKRYYADSVKGRFTISRDNSKNTLFLQMNSLRAE<br>DTAVYYCATNDDYWGQGTLVTVSSAKTTAPSVYPLAPVCGDTTG<br>SSVTLGCLVKGYFPEPVTLTWNSGSLSSGVHTFPAVLQSDLYTLSSS<br>VTVTSSTWPSQSITCNVAHPASSTKVDKKIEPRGPTIKPCPPCKCPAP<br>NAAGGPSVFIFPPKIKDVLMISLSPIVTCVVVDVSEDDPDVQISWFV<br>NNVEVHTAQTQTHREDYNSTLRVVSALPIQHQDWMSGKEFKCKV<br>NNKDLGAPIERTISKPKGSVRAPQVYVLPPPEKEMTKKQVSLTCLV<br>KDFMPEDIYVEWTNNGKTELNYKNTEPVLKSDSGSYFMYSKLTVEK<br>KNWVERNSYSCSVVHEGLHNHHTTKSFSRTPGGGGSGGGGSGG<br>GGSGGGGSEVQLVESGGGLVQPGGSLRLSCAASGFNIKDTYIHWV<br>RQAPGKGLEWVARIYPTNGYTRYADSVKGRFTISADTSKNTAYLQ<br>MNSLRAEDTAVYYCSRWGGDGFYAMDYWGQGTLVTVSSASGGG<br>GSGGGGSGGGGSHASDIQMTQSPSSLSASVGDRVTITCRASQDVNT<br>AVAWYQQKPGKAPKLLIYSASFLYSGVPSRFSGSRSGTDFTLTISSL<br>QPEDFATYYCQQHYTTPPTFGQGTKVEIKGGGSGGGSHHHHHH |
| AF4401 | SEQ ID NO: 180 | EIVLTQSPATLSLSPGERATLSCRASQSVSSYLAWYQQKPGQAPRLL<br>IYDASNRATGIPARFSGSGSGTDFTLTISSLEPEDFAVYYCQQSSNW<br>PRTFGQGTKVEIKRADAAPTVSIFPPSSEQLTSGGASVVCFLNNFYP<br>KDINVKWKIDGSERQNGVLNSWTDQDSKDSTYSMSSTLTLTKDEY<br>ERHNSYTCEATHKTSTSPIVKSFNRNEC |
| | SEQ ID NO: 199 | QVQLVESGGGVVQPGRSLRLDCKASGITFSNSGMHWVRQAPGKG<br>LEWVAVIWYDGSKRYYADSVKGRFTISRDNSKNTLFLQMNSLRAE<br>DTAVYYCATNDDYWGQGTLVTVSSAKTTAPSVYPLAPVCGDTTG<br>SSVTLGCLVKGYFPEPVTLTWNSGSLSSGVHTFPAVLQSDLYTLSSS<br>VTVTSSTWPSQSITCNVAHPASSTKVDKKIEPRGPTIKPCPPCKCPAP<br>NAAGGPSVFIFPPKIKDVLMISLSPIVTCVVVDVSEDDPDVQISWFV<br>NNVEVHTAQTQTHREDYNSTLRVVSALPIQHQDWMSGKEFKCKV<br>NNKDLGAPIERTISKPKGSVRAPQVYVLPPPEEEMTKKQVTLTCMV<br>TDFMPEDIYVEWTNNGKTELNYKNTEPVLDSDGSYFMYSDLRVEK<br>KNWVERNSYSCSVVHEGLHNHHTTESFSRTPGGGGSGGGGSGG |

TABLE 24-continued

IgG PD-1 with C-terminal scFv and IL-2, and control protein complexes

| Protein Complex | SEQ ID NO: | Sequence |
|---|---|---|
| | | GGSAPTSSSTKKTQLQLEHLLLDLQMILNGINNYKNPKLTDMLTFE<br>FYMPKKATELKHLQCLERELKPLEEVLNLAQSKNFHLRPRDLISNI<br>NVIVLELKGSETTFMCEYADETATIVEFLNRWITFCQSIISTLT |
| | SEQ ID NO: 201 | QVQLVESGGGVVQPGRSLRLDCKASGITFSNSGMHWVRQAPGKG<br>LEWVAVIWYDGSKRYYADSVKGRFTISRDNSKNTLFLQMNSLRAE<br>DTAVYYCATNDDYWGQGTLVTVSSAKTTAPSVYPLAPVCGDTTG<br>SSVTLGCLVKGYFPEPVTLTWNSGSLSSGVHTFPAVLQSDLYTLSSS<br>VTVTSSTWPSQSITCNVAHPASSTKVDKKIEPRGPTIKPCPPCKCPAP<br>NAAGGPSVFIFPPKIKDVLMISLSPIVTCVVVDVSEDDPDVQISWFV<br>NNVEVHTAQTQTHREDYNSTLRVVSALPIQHQDWMSGKEFKCKV<br>NNKDLGAPIERTISKPKGSVRAPQVYVLPPPEKEMTKKQVSLTCLV<br>KDFMPEDIYVEWTNNGKTELNYKNTEPVLKSDGSYFMYSKLTVEK<br>KNWVERNSYSCSVVHEGLHNHHTTKSFSRTPGGGGSGGGGSGG<br>GGSGGGGSEVQLVESGGGLVKPGGSLRLSCAASGFTFSSYTLAWV<br>RQAPGKGLEWVAAIDSSSYTYSPDTVRGRFTISRDNAKNSLYLQM<br>NSLRAEDTAVYYCARDSNWDALDYWGQGTLVTVSSASGGGGSG<br>GGGSGGGGSHASDIQMTQSPSSLSASVGDRVSITCKASQNVGTNVG<br>WYQQKPGKAPKALIYSASFRYSGVPSRFSGSGSGTDFTLTISSLQPE<br>DFATYFCQQYTYPYTFGGGTKLEIKGGGSGGGSHHHHHH |
| AF4392 | SEQ ID NO: 64 | DIQMTQSPSSLSASVGDRVTITCRASQDVNTAVAWYQQKPGKAPK<br>LLIYSASFLYSGVPSRFSGSRSGTDFTLTISSLQPEDFATYYCQQHYT<br>TPPTFGQGTKVEIKRADAAPTVSIFPPSSEQLTSGGASVVCFLNNFY<br>PKDINVKWKIDGSERQNGVLNSWTDQDSKDSTYSMSSTLTLTKDE<br>YERHNSYTCEATHKTSTSPIVKSFNRNEC |
| | SEQ ID NO: 202 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEEEMTKKQ<br>VTLTCMVTDFMPEDIYVEWTNNGKTELNYKNTEPVLDSDGSYFM<br>YSDLRVEKKNWVERNSYSCSVVHEGLHNHHTTESFSRTPGGGGGS<br>GGGGSGGGGSAPTSSSTKKTQLQLEHLLLDLQMILNGINNYKNPKL<br>TDMLTFEFYMPKKATELKHLQCLERELKPLEEVLNLAQSKNFHLRP<br>RDLISNINIVLELKGSETTFMCEYADETATIVEFLNRWITFCQSIIST<br>LT |
| | SEQ ID NO: 203 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEKEMTKKQ<br>VSLTCLVKDFMPEDIYVEWTNNGKTELNYKNTEPVLKSDGSYFMY<br>SKLTVEKKNWVERNSYSCSVVHEGLHNHHTTKSFSRTPGGGGSG<br>GGGSGGGGSGGGGSEVQLVESGGGLVQPGGSLRLSCAASGFNIKD<br>TYIHWVRQAPGKGLEWVARIYPTNGYTRYADSVKGRFTISADTSK<br>NTAYLQMNSLRAEDTAVYYCSRWGGDGFYAMDYWGQGTLVTVS<br>SASGGGGSGGGGSGGGGSHASDIQMTQSPSSLSASVGDRVTITCRA<br>SQDVNTAVAWYQQKPGKAPKLLIYSASFLYSGVPSRFSGSRSGTDF<br>TLTISSLQPEDFATYYCQQHYTTPPTFGQGTKVEIKGGGSGGGSHH<br>HHHH |
| AF4393 | SEQ ID NO: 64 | DIQMTQSPSSLSASVGDRVTITCRASQDVNTAVAWYQQKPGKAPK<br>LLIYSASFLYSGVPSRFSGSRSGTDFTLTISSLQPEDFATYYCQQHYT<br>TPPTFGQGTKVEIKRADAAPTVSIFPPSSEQLTSGGASVVCFLNNFY<br>PKDINVKWKIDGSERQNGVLNSWTDQDSKDSTYSMSSTLTLTKDE<br>YERHNSYTCEATHKTSTSPIVKSFNRNEC |
| | SEQ ID NO: 202 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEEEMTKKQ |

TABLE 24-continued

IgG PD-1 with C-terminal scFv and IL-2, and control protein complexes

| Protein Complex | SEQ ID NO: | Sequence |
|---|---|---|
| | | VTLTCMVTDFMPEDIYVEWTNNGKTELNYKNTEPVLDSDGSYFM<br>YSDLRVEKKNWVERNSYSCSVVHEGLHNHHTTESFSRTPGGGGGS<br>GGGGSGGGGSAPTSSSTKKTQLQLEHLLLDLQMILNGINNYKNPKL<br>TDMLTFEFYMPKKATELKHLQCLERELKPLEEVLNLAQSKNFHLRP<br>RDLISNINVIVLELKGSETTFMCEYADETATIVEFLNRWITFCQSIIST<br>LT |
| | SEQ ID NO: 204 | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSAKTTAPSVYPLAPV<br>CGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCP<br>PCKCPAPNAAGGPSVFIFPPKIKDVLMISLSPIVTCVVVDVSEDDPD<br>VQISWFVNNVEVHTAQTQTHREDYNSTLRVVSALPIQHQDWMSG<br>KEFKCKVNNKDLGAPIERTISKPKGSVRAPQVYVLPPPEKEMTKKQ<br>VSLTCLVKDFMPEDIYVEWTNNGKTELNYKNTEPVLKSDGSYFMY<br>SKLTVEKKNWVERNSYSCSVVHEGLHNHHTTKSFSRTPGGGGGSG<br>GGGSGGGGSGGGGSEVQLVESGGGLVKPGGSLRLSCAASGFTFSS<br>YTLAWVRQAPGKGLEWVAAIDSSSYTYSPDTVRGRFTISRDNAKN<br>SLYLQMNSLRAEDTAVYYCARDSNWDALDYWGQGTLVTVSSASG<br>GGGSGGGGSGGGGSHASDIQMTQSPSSLSASVGDRVSITCKASQNV<br>GTNVGWYQQKPGKAPKALIYSASFRYSGVPSRFSGSGSGTDFTLTI<br>SSLQPEDFATYFCQQYYTYPYTFGGGTKLEIKGGGSGGGSHHHHH<br>H |

Example 27

Improved Regulation by Engineering DBA Affinity Using Standard Methods

This example describes the use of standard techniques to modify DBA affinity and improve the range of sensor-dependent activation of a DBA-cytokine construct. A series of variants of the DBA PDL1-IFN R01 A05 (EXAMP TABLE 25-continued DBA-cytokine protein complexes

| Protein Complex | SEQ ID NO: | Sequence |
|---|---|---|
| AF2719 | SEQ ID NO: 41 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGTET PLMKEDSILAVRKYFQRITLYLKEKKYSPCAWEVVRAEIMRSFSLSTNLQESLRSKEG GGGSGGGGSGGGGSGGGGSQVQLVQSGAEVKKPGASVKVSCKASGYTFSNYYV HWVRQAPGQGLEWMGWMDPNSGGTGYAHQFQGRVTMTRDTSTSTVYMELS SLRSEDTAVYYCAKEVFSGWYDYWGQGTLVTVSSASGGGGSGGGGSGGGGSHAS DIQMTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIKGKPIPNPLL GLDST |
| AF3101 | SEQ ID NO: 289 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGVTET PLMKEDSILAVRKYFQRITLYLKEKKYSPCAWEVVRAEIMRSFSLSTNLQESLRSKEG GGGSGGGGSGGGGSGGGGSQVQLVQSGAEVKKPGASVKVSCKASGYTFSNYYIH WVRQAPGQGLEWMGWMDGNSGGTGYAQKFQGRVTMTRDTSTSTVYMELSSL RSEDTAVYYCAKEVFSGWYDYWGQGTLVTVSSASGGGGSGGGGSGGGGSHASDI QMTQSPSSLSASVGDRVTITCRASQSISSYLNWYQQKPGKAPKLLIYAASSLQSGVP SRFSGSGSGTDFTLTISSLQPEDFATYYCQQSYSTPYTFGQGTKVEIKGKPIPNPLLGL DST |
| AF3093 | SEQ ID NO: 290 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGVTET PLMKEDSILAVRKYFQRITLYLKEKKYSPCAWEVVRAEIMRSFSLSTNLQESLRSKEG GGGSGGGGSGGGGSGGGGSQVQLVQSGAEVKKPGASVKVSCKASGYTFSNYYIH WVRQAPGQGLEWMGWMDSNSGYTGYAQKFQGRVTMTRDTSTSTVYMELSSL RSEDTAVYYCAKEVFSGWYDYWGQGTLVTVSSASGGGGSGGGGSGGGGSHASDI QMTQSPSSLSASVGDRVTITCRASQSISSYLNWYQQKPGKAPKLLIYAASSLQSGVP SRFSGSGSGTDFTLTISSLQPEDFATYYCQQSYSTPYTFGQGTKVEIKGKPIPNPLLGL DST |
| AF3094 | SEQ ID NO: 291 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGVTET PLMKEDSILAVRKYFQRITLYLKEKKYSPCAWEVVRAEIMRSFSLSTNLQESLRSKEG GGGSGGGGSGGGGSGGGGSQVQLVQSGAEVKKPGASVKVSCKASGYTFSNYYIH WVRQAPGQGLEWMGWMDPNSGYTGYAHQFQGRVTMTRDTSTSTVYMELSSL RSEDTAVYYCAKEVFSGWYDYWGQGTLVTVSSASGGGGSGGGGSGGGGSHASDI QMTQSPSSLSASVGDRVTITCRASQSISSYLNWYQQKPGKAPKLLIYAASSLQSGVP SRFSGSGSGTDFTLTISSLQPEDFATYYCQQSYSTPYTFGQGTKVEIKGKPIPNPLLGL DST |

Example 28

Regulated Interferon Receptor Binding by PD-L1/IFNα Dual Binding Antibodies

This example describes regulated interferon receptor binding by PD-L1/IFNα DBA-cytokine complexes. DBA-cytokine complexes AF2659 (SEQ ID NO: 276-277), AF2666 (SEQ ID NO: 96 and 277), AF2645 (SEQ ID NO: 95 and 112), AF2615 (SEQ ID NO: 279-280) and AF2616 (SEQ ID NO: 281-282) were chosen for analysis. The DBAs used to assemble these complexes were derived from three parental PD-L1/IFNα DBAs described in EXAMPLE 1: PDL1-IFN-R01-A05 (AF2659 and AF2666), PDL1-IFN-R01-008 (AF2645) and PDL1-IFN-R01-B12 (AF2615 and AF2616) using standard antibody engineering techniques as described in EXAMPLE 4. Three control antibody-cytokine constructs were assembled from monospecific antibodies: AF2696 (anti-PDL1, SEQ ID NO: 283-284), AF2697 (anti-Her2, SEQ ID NO: 214 and 286) and AF2698 (anti-IFNα, SEQ ID NO: 287-288). Protein complex sequences are provided in TABLE 26 below. The eight antibody-cytokine complexes were produced as symmetric IgG molecules with IFNα appended to the N-terminus of the heavy chain through a flexible linker (AF2659, AF2666 and AF2645, shown schematically in FIG. 9*e*) or the N-terminus of the light chain through a flexible linker (AF2615, AF2616, AF2696, AF2697 and AF2698, shown schematically in FIG. 9*d*). The proteins were expressed in mammalian cells and purified using standard protocols. An ELISA assay was performed with a constant amount of the antibody-cytokine construct coated on each well probed with biotinylated interferon receptor (IFNAR2) in the presence of varying amounts of PD-L1-Fc or Her2-Fc. 384-well ELISA plates were coated with anti-Fc antibody at 10 micrograms/ml overnight at 4° C. and washed twice with SuperBlock. Twenty microliters of a 66.7 nM antibody-cytokine complex was added to each well, incubated for one hour and washed three times in PBS. Biotinylated IFNAR2 protein was added to each well at a final concentration of 5 nM with PD-L1-Fc protein or HER2-Fc protein at a final concentration of 0.64 nM, 3.2 nM, 16 nM, 80 nM, or 400 nM. The plates were incubated for an hour, washed and biotinylated IFNAR2 detection was performed using streptavidin-HRP and standard ELISA protocols. As shown in FIG. 22A-H, DBA-cytokine complexes AF2659, AF2666, AF2645, AF2615 and AF2616 show a dose-dependent induction of IFNAR2 binding in the presence of PD-L1 protein but were not affected by the same dose range of Her2 protein, demonstrating PD-L1 dependent INF activity in five DBA constructs derived from three different parental PD-L1/IFNA dual-binding antibodies. IFNAR2 binding to the three control antibody complexes AF2696, AF2697 and AF2698 was not significantly affected by PD-L1 concentration. Protein complexes of the present invention can be produced from multiple dual-binding antibodies using standard antibody engineering methods.

TABLE 26

DBA-cytokine protein complexes

| Protein Complex | SEQ ID NO: | Sequence |
|---|---|---|
| AF2659 | SEQ ID NO: 276 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEVPGVG VPGAGVPGVGVPGGGVPGVGVPGGGVPGAGVPGGGVPGVGVPGAGVPGVGV PGGGGQVQLVQSGAEVKKPGASVKVSCKASGYTFSNYYIHWVRQAPGQGLEWMG WMDSNSGYTGYAQKFQGRVTMTRDTSTSTVYMELSSLRSEDTAVYYCAKEVFSG WYDYWGQGTLVTVSSAKTTAPSVYPLAPVCGDTTGSSVTLGCLVKGYFPEPVTLT WNSGSLSSGVHTFPAVLQSDLYTLSSSVTVTSSTWPSQSITCNVAHPASSTKVDKKI EPRGPTIKPCPPCKCPAPNAAGGPSVFIFPPKIKDVLMISLSPIVTCVVVDVSEDDPD VQISWFVNNVEVHTAQTQTHREDYNSTLRVVSALPIQHQDWMSGKEFKCKVNN KDLGAPIERTISKPKGSVRAPQVYVLPPPEEEMTKKQVTLTCMVTDFMPEDIYVEW TNNGKTELNYKNTEPVLDSDGSYFMYSKLRVEKKNWVERNSYSCSVVHEGLHNHH TTKSFSRTPGK |
| | SEQ ID NO: 277 | DIQMTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIKRADAAPTV SIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC |
| AF2666 | SEQ ID NO: 96 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEVPGVG VPGAGVPGVGVPGGGVPGVGVPGGGVPGAGVPGGGVPGVGVPGAGVPGVGV PGGGGQVQLVQSGAEVKKPGASVKVSCKASGYTFSNYYIHWVRQAPGQGLEWMG WMDSNSGYTGYAQQFQGRVTMTRDTSTSTVYMELSSLRSEDTAVYYCAKEVFSG WYDYWGQGTLVTVSSAKTTAPSVYPLAPVCGDTTGSSVTLGCLVKGYFPEPVTLT WNSGSLSSGVHTFPAVLQSDLYTLSSSVTVTSSTWPSQSITCNVAHPASSTKVDKKI EPRGPTIKPCPPCKCPAPNAAGGPSVFIFPPKIKDVLMISLSPIVTCVVVDVSEDDPD VQISWFVNNVEVHTAQTQTHREDYNSTLRVVSALPIQHQDWMSGKEFKCKVNN KDLGAPIERTISKPKGSVRAPQVYVLPPPEEEMTKKQVTLTCMVTDFMPEDIYVEW TNNGKTELNYKNTEPVLDSDGSYFMYSKLRVEKKNWVERNSYSCSVVHEGLHNHH TTKSFSRTPGK |
| | SEQ ID NO: 277 | DIQMTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIKRADAAPTV SIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC |
| AF2645 | SEQ ID NO: 95 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEVPGVG VPGAGVPGVGVPGGGVPGVGVPGGGVPGAGVPGGGVPGVGVPGAGVPGVGV PGGGGQVQLVQSGAEVKKPGASVKVSCKASGGTFSSYAISWVRQAPGQGLEWMG IIDPSVTYTRYAQKFQGRVTMTRDTSTSTVYMELSSLRSEDTAVYYCARSLFPTIFGV EVAFDIWGQGTLVTVSSAKTTAPSVYPLAPVCGDTTGSSVTLGCLVKGYFPEPVTLT WNSGSLSSGVHTFPAVLQSDLYTLSSSVTVTSSTWPSQSITCNVAHPASSTKVDKKI EPRGPTIKPCPPCKCPAPNAAGGPSVFIFPPKIKDVLMISLSPIVTCVVVDVSEDDPD VQISWFVNNVEVHTAQTQTHREDYNSTLRVVSALPIQHQDWMSGKEFKCKVNN KDLGAPIERTISKPKGSVRAPQVYVLPPPEEEMTKKQVTLTCMVTDFMPEDIYVEW TNNGKTELNYKNTEPVLDSDGSYFMYSKLRVEKKNWVERNSYSCSVVHEGLHNHH TTKSFSRTPGK |
| | SEQ ID NO: 112 | DIQMTQSPSSLSASVGDRVTITCRASQSISNRLAWYQQKPGKAPKLLIYKASSLESG VPSRFSGSGSGTDFTLTISSLQPEDFATYYCQQSNSTPFTFGQGTKVEIKRADAAPTV SIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC |
| AF2615 | SEQ ID NO: 279 | QVQLVQSGAEVKKPGASVKVSCKASGNTFTDYYMHWVRQAPGQGLEWMGWM NPNSGNTGYAQKFQGRVTMTRDTSTSTVYMELSSLRSEDTAVYYCARSLFPTIFGV EVAFDIWGQGTLVTVSSAKTTAPSVYPLAPVCGDTTGSSVTLGCLVKGYFPEPVTLT WNSGSLSSGVHTFPAVLQSDLYTLSSSVTVTSSTWPSQSITCNVAHPASSTKVDKKI EPRGPTIKPCPPCKCPAPNAAGGPSVFIFPPKIKDVLMISLSPIVTCVVVDVSEDDPD VQISWFVNNVEVHTAQTQTHREDYNSTLRVVSALPIQHQDWMSGKEFKCKVNN KDLGAPIERTISKPKGSVRAPQVYVLPPPEEEMTKKQVTLTCMVTDFMPEDIYVEW TNNGKTELNYKNTEPVLDSDGSYFMYSKLRVEKKNWVERNSYSCSVVHEGLHNHH TTKSFSRTPGK |
| | SEQ ID NO: 280 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSDIQMTQSPSSLSASVGDRVTITCQASQDISNYLNWYQQK PGKAPKLLIYAASSLQSGVPSRFSGSGSGTDFTLTISSLQPEDFATYYCQQSYSTPPTF GQGTRLEIKRADAAPTVSIFPPSSEQLTSGGASVVCFLNNFYPKDINVKWKIDGSER QNGVLNSWTDQDSKDSTYSMSSTLTLTKDEYERHNSYTCEATHKTSTSPIVKSFNR NEC |

TABLE 26-continued

DBA-cytokine protein complexes

| Protein Complex | SEQ ID NO: | Sequence |
|---|---|---|
| AF2616 | SEQ ID NO: 281 | QVQLVQSGAEVKKPGASVKVSCKASGGTFSSYAISWVRQAPGQGLEWMGIIDPS VTYTRYAQKFQGRVTMTRDTSTSTVYMELSSLRSEDTAVYYCARSLFPTIFGVEVAF DIWGQGTLVTVSSAKTTAPSVYPLAPVCGDTTGSSVTLGCLVKGYFPEPVTLTWNS GSLSSGVHTFPAVLQSDLYTLSSSVTVTSSTWPSQSITCNVAHPASSTKVDKKIEPRG PTIKPCPPCKCPAPNAAGGPSVFIFPPKIKDVLMISLSPIVTCVVVDVSEDDPDVQIS WFVNNVEVHTAQTQTHREDYNSTLRVVSALPIQHQDWMSGKEFKCKVNNKDLG APIERTISKPKGSVRAPQVYVLPPPEEEMTKKQVTLTCMVTDFMPEDIYVEWTNN GKTELNYKNTEPVLDSDGSYFMYSKLRVEKKNWVERNSYSCSVVHEGLHNHHTTK SFSRTPGK |
| | SEQ ID NO: 282 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGGGGGSGGGGSDIQMTQSPSSLSASVGDRVTITCQASQSISNRLAWYQQK PGKAPKLLIYKASSLESGVPSRFSGSGSGTDFTLTISSLQPEDFATYYCQQTYSTPITFG QGTKVEIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKSFNRN EC |
| AF2696 | SEQ ID NO: 283 | QVQLVQSGAEVKKPGASVKVSCKASGYTFSGYYMHWVRQAPGQGLEWMGWM DPNSGYTGYAHQFQGRVTMTRDTSTSTVYMELSSLRSEDTAVYYCAKEVFSGWYD YWGQGTLVTVSSAKTTAPSVYPLAPVCGDTTGSSVTLGCLVKGYFPEPVTLTWNSG SLSSGVHTFPAVLQSDLYTLSSSVTVTSSTWPSQSITCNVAHPASSTKVDKKIEPRGP TIKPCPPCKCPAPNAAGGPSVFIFPPKIKDVLMISLSPIVTCVVVDVSEDDPDVQISW FVNNVEVHTAQTQTHREDYNSTLRVVSALPIQHQDWMSGKEFKCKVNNKDLGAP IERTISKPKGSVRAPQVYVLPPPEEEMTKKQVTLTCMVTDFMPEDIYVEWTNNGKT ELNYKNTEPVLDSDGSYFMYSKLRVEKKNWVERNSYSCSVVHEGLHNHHTTKSFSR TPGK |
| | SEQ ID NO: 284 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSDIQMTQSPSSLSASVGDRVTITCRASQTISSYLNWYQQKP GKAPKLLIYAASTLESGVPSRFSGSGSGTDFTLTISSLQPEDFATYYCQQGYSTPITFG PGTKVDIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKSFNRN EC |
| AF2697 | SEQ ID NO: 214 | EVQLVESGGGLVQPGGSLRLSCAASGFNIKDTYIHWVRQAPGKGLEWVARIYPTN GYTRYADSVKGRFTISADTSKNTAYLQMNSLRAEDTAVYYCSRWGGDGFYAMDY WGQGTLVTVSSAKTTAPSVYPLAPVCGDTTGSSVTLGCLVKGYFPEPVTLTWNSGS LSSGVHTFPAVLQSDLYTLSSSVTVTSSTWPSQSITCNVAHPASSTKVDKKIEPRGPT IKPCPPCKCPAPNAAGGPSVFIFPPKIKDVLMISLSPIVTCVVVDVSEDDPDVQISWF VNNVEVHTAQTQTHREDYNSTLRVVSALPIQHQDWMSGKEFKCKVNNKDLGAPI ERTISKPKGSVRAPQVYVLPPPEEEMTKKQVTLTCMVTDFMPEDIYVEWTNNGKT ELNYKNTEPVLDSDGSYFMYSKLRVEKKNWVERNSYSCSVVHEGLHNHHTTKSFSR TPGK |
| | SEQ ID NO: 286 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSDIQMTQSPSSLSASVGDRVTITCRASQDVNTAVAWYQQ KPGKAPKLLIYSASFLYSGVPSRFSGSRSGTDFTLTISSLQPEDFATYYCQQHYTTPPT FGQGTKVEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSPIVKSFN RNEC |
| AF2698 | SEQ ID NO: 287 | EVQLVESGGGLVQPGGSLRLSCATSGYTFTEYIIHWVRQAPGKGLEWVASINPDYD ITNYNQRFKGRFTISLDKSKRTAYLQMNSLRAEDTAVYYCASWISDFFDYWGQGTL VTVSSAKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTIKPCPPC KCPAPNAAGGPSVFIFPPKIKDVLMISLSPIVTCVVVDVSEDDPDVQISWFVNNVEV HTAQTQTHREDYNSTLRVVSALPIQHQDWMSGKEFKCKVNNKDLGAPIERTISKP KGSVRAPQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSRTPGK |
| | SEQ ID NO: 288 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSDIQMTQSPSSLSASVGDRVTITCRASQSVSTSSYSYMHW |

TABLE 26-continued

DBA-cytokine protein complexes

| Protein Complex | SEQ ID NO: | Sequence |
|---|---|---|
| | | YQQKPGKAPKVLISYASNLESGVPSRFSGSGSGTDFTLTISSLQPEDFATYYCQHSW GIPRTFGQGTKVEIKRADAAPTVSIFPPSSEQLTSGGASVVCFLNNFYPKDINVKWKI DGSERQNGVLNSWTDQDSKDSTYSMSSTLTLTKDEYERHNSYTCEATHKTSTSPIV KSFNRNEC |

Example 29

Selection of IL-15 and PD-L1 Specific Dual Binding Antibodies

This example describes isolation of sensor domains of the present disclosure, specifically, selection of IL-15 and PD-L1 specific dual binding antibodies (DBAs). Anti-PD-L1 and anti-IL-15 DBAs were isolated from the IFNα Tumbler antibody phage display library described in EXAMPLE 1. The selection was similar to the protocol described in EXAMPLE 1, alternating between PD-L1 selection and IL-15 selection.

The final selection was plated as single colonies and 380 colonies were picked for Sanger sequencing. Thirty-eight unique clones were screened for PD-L1 and IL-15 binding. The scFv DNA sequence for each clone was synthesized as a gBlock (Integrated DNA Technologies, Inc.) with a T7 promoter, a translation initiation site, a Myc tag, the scFv sequence, a V5 tag and a T7 terminator. Proteins were expressed using the PUREfrex2.1 cell-free transcription/translation system as described in previous examples. The scFv samples were subjected to ELISA analysis to detect PDL1 and IL15 binding. In these experiments, wells of a 384-well plate were coated with an anti-V5 antibody (Sv5-Pk1, BioRad) at 1 ug/ml overnight at 4 degrees. After washing, wells were blocked with SuperBlock (ThermoFisher, 37515) followed by addition of saturating levels of scFvs in SuperBlock. After washing, antigens were added and plates incubated for one hour (PDL1-hFc-Avi, Acro Biosystems, PDL-H82F2); AF33 (SEQ ID NO: 298-299), biotinylated using standard methods; controls of PD1-hFc-Avi (Acro Biosystems, PD1-H82F1); AF35 (SEQ ID 63-64), biotinylated using standard methods). Biotinylated antigens were detected using streptavidin HRP using standard methods. Varying amounts of labeled test antigen were added to show binding and to estimate relative affinities of the different scFvs. FIGS. 23A-D show the ELISA binding data for four exemplary dual-binding scFvs AF635 (SEQ ID NO: 216), AF636 (SEQ ID NO: 217), AF666 (SEQ ID NO: 218) and AF614 (SEQ ID NO: 219). All four antibodies show binding to both PD-L1 and IL-15, with binding to PD-L1 detectable at a lower concentration of the antigen. Protein complex sequences are summarized in TABLE 27 below.

TABLE 27

DBA-cytokine protein complexes, and control protein complexes

| Protein Complex | SEQ ID NO: | Sequence |
|---|---|---|
| AF33 | SEQ ID NO: 298 | EVQLVESGGGLVQPGGSLRLSCAASGFNIKDTYIHWVRQAPGKGLEWVARIYPTN GYTRYADSVKGRFTISADTSKNTAYLQMNSLRAEDTAVYYCSRWGGDGFYAMDY WGQGTLVTVSSAKTTAPSVYPLAPVCGDTTGSSVTLGCLVKGYFPEPVTLTWNSGS LSSGVHTFPAVLQSDLYTLSSSVTVTSSTWPSQSITCNVAHPASSTKVDKKIEPRGPT IKPCPPCKCPAPNAAGGPSVFIFPPKIKDVLMISLSPIVTCVVVDVSEDDPDVQISWF VNNVEVHTAQTQTHREDYNSTLRVVSALPIQHQDWMSGKEFKCKVNNKDLGAPI ERTISKPKGSVRAPQVYVLPPPEEEMTKKQVTLTCMVTDFMPEDIYVEWTNNGKT ELNYKNTEPVLDSDGSYFMYSKLRVEKKNWVERNSYSCSVVHEGLHNHHTTKSFSR TPGKGGGSGGGSHHHHHH |
| | SEQ ID NO: 299 | ITCPPPMSVEHADIWVKSYSLYSRERYICNSGFKRKAGTSSLTECVLNKATNVAHWT TPSLKCIRDPALVHQRPAPPSGGSGGGSGGGSGGGGSLQNWVNVISDLKKIEDLI QSMHIDATLYTESDVHPSCKVTAMKCFLLELQVISLESGDASIHDTVENLIILANNSL SSNGNVTESGCKECEELEEKNIKEFLQSFVHIVQMFINTSGGGGSGGGGSGGGGSG GGGSDIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGTKVEIKRA DAAPTVSIFPPSSEQLTSGGASVVCFLNNFYPKDINVKWKIDGSERQNGVLNSWTD QDSKDSTYSMSSTLTLTKDEYERHNSYTCEATHKTSTSPIVKSFNRNEC |
| AF35 | SEQ ID NO: 63 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSEVQLVESGGGLVQPGGSLRLSCAASGFNIKDTYIHWVRQ APGKGLEWVARIYPTNGYTRYADSVKGRFTISADTSKNTAYLQMNSLRAEDTAVYY CSRWGGDGFYAMDYWGQGTLVTVSSAKTTAPSVYPLAPVCGDTTGSSVTLGCLV KGYFPEPVTLTWNSGSLSSGVHTFPAVLQSDLYTLSSSVTVTSSTWPSQSITCNVAH PASSTKVDKKIEPRGPTIKPCPPCKCPAPNAAGGPSVFIFPPKIKDVLMISLSPIVTCV VVDVSEDDPDVQISWFVNNVEVHTAQTQTHREDYNSTLRVVSALPIQHQDWMS GKEFKCKVNNKDLGAPIERTISKPKGSVRAPQVYVLPPPEEEMTKKQVTLTCMVTD FMPEDIYVEWTNNGKTELNYKNTEPVLDSDGSYFMYSKLRVEKKNWVERNSYSCS VVHEGLHNHHTTKSFSRTPGK |

TABLE 27-continued

DBA-cytokine protein complexes, and control protein complexes

| Protein Complex | SEQ ID NO: | Sequence |
|---|---|---|
|  | SEQ ID NO: 64 | DIQMTQSPSSLSASVGDRVTITCRASQDVNTAVAWYQQKPGKAPKLLIYSASFLYS GVPSRFSGSRSGTDFTLTISSLQPEDFATYYCQQHYTTPPTFGQGTKVEIKRADAAP TVSIFPPSSEQLTSGGASVVCFLNNFYPKDINVKWKIDGSERQNGVLNSWTDQDSK DSTYSMSSTLTLTKDEYERHNSYTCEATHKTSTSPIVKSFNRNEC |
| AF635 | SEQ ID NO: 216 | MSTSTEQKLISEEDLQVQLVQSGAEVKKPGASVKVSCKASGYTFTGYYIHWVRQAP GQGLEWMGIINPSGGSTRYAQKFQGRVTMTRDTSTSTVYMELSSLRSEDTAVYYC ARSLFPTIFGVEVAFDIWGQGTLVTVSSASGGGGSGGGGSGGGGSHASDIQMTQ SPSSLSASVGDRVTITCRASQSIRTYLNWYQQKPGKAPKLLIYSASNLQSGVPSRFSG SGSGTDFTLTISSLQPEDFATYYCQQANSFPFTFGPGTKVDIKGKPIPNPLLGLDST |
| AF636 | SEQ ID NO: 217 | MSTSTEQKLISEEDLQVQLVQSGAEVKKPGASVKVSCKASGYSFTSYYLHWVRQAP GQGLEWMGRISPRSGGTKNAQNFQGRVTMTRDTSTSTVYMELSSLRSEDTAVYY CVRSLFPTIFGVEVAFDIWGQGTLVTVSSASGGGGSGGGGSGGGGSHASDIQMT QSPSSLSASVGDRVTITCRASQSISSWLAWYQQKPGKAPKLLIYYASSLQSGVPSRFS GSGSGTDFTLTISSLQPEDFATYYCQQGYQYPYTFGQGTKLEIKGKPIPNPLLGLDST |
| AF666 | SEQ ID NO: 218 | MSTSTEQKLISEEDLQVQLVQSGAEVKKPGASVKVSCKASGYTFSTYYIHWVRQAP GQGLEWMGWMNPNSGNTGYAQTFQGRVTMTRDTSTSTVYMELSSLRSEDTAV YYCARSLFPTIFGVEVAFDIWGQGTLVTVSSASGGGGSGGGGSGGGGSHASDIQM TQSPSSLSASVGDRVTITCRASQSISSYLNWYQQKPGKAPKLLIYAASSLQSGVPSRF SGSGSGTDFTLTISSLQPEDFATYYCQQGYSTPRTFGQGTKVEIKGKPIPNPLLGLDS T |
| AF614 | SEQ ID NO: 219 | MSTSTEQKLISEEDLQVQLVQSGAEVKKPGASVKVSCKASGYTFTNYYMHWVRQA PGQGLEWMGWMNPNSGNTGYAQKFQGRVTMTRDTSTSTVYMELSSLRSEDTA VYYCARSLFPTIFGVEVAFDIWGQGTLVTVSSASGGGGSGGGGSGGGGSHASDIQ MTQSPSSLSASVGDRVTITCRASQSISSYLNWYQQKPGKAPKLLIYAASSLQSGVPS RFSGSGSGTDFTLTISSLQPEDFATYYCQQSYSTPRTFGQGTKLEIKGKPIPNPLLGLD ST |

Example 30

Regulated IL-2 Receptor Signaling by a PD-L1/IL-15 Dual Binding Antibody (DBA) Cytokine Complex This example describes regulated IL-15 activity in a reporter cell line by PD-L1/IL-15 DBA-cytokine complexes. HEK-Blue™ IL-2 reporter cells (Invivogen Catalog #hkb-i12) were grown according to the vendors instructions. The cells express IL-2 receptor and respond to IL-2 or IL-15 signaling by induction of an enzyme that can be read with a colorimetric assay. The exemplary dual-binding scFv sequences AF635 (SEQ ID NO: 216), AF636 (SEQ ID NO: 217), AF666 (SEQ ID NO: 218) and AF614 (SEQ ID NO: 219) described in EXAMPLE 29 and TABLE 28, were used to assemble scFv DBA-cytokine complexes AF4455 (SEQ ID NO: 220), AF4456 (SEQ ID NO: 221), AF4457 (SQ ID NO: 222), and AF4440 (SEQ ID NO: 223) respectively. Two monospecific anti-IL-15 scFv sequences were assembled into cytokine-scFv complexes AF4478 (SEQ ID NO: 224) and AF4479 (SEQ ID NO: 225) to serve as negative controls. Protein complex sequences are provided in TABLE 28 below. The proteins were expressed using a PUREfrex2.1 cell-free transcription/translation system. 384-well ELISA plates (Corning 3700) were coated with 25 microliters per well of 1 microgram per ml anti-V5 antibody (SV5-pk1) in 100 mM bicarbonate solution pH 9.0 overnight at 4° C. The plates were washed three times with 100 microliters PBS+Tween and once with 50 µl/well of SuperBlock. The PUREfrex reactions for each sample were diluted 1:2, 160 in Superblock, added to the anti-V5-coated plates at 20 µl/well and incubated for 1 hour at room temperature to capture a uniform quantity of the scFv protein on the plate. Each plate was then washed three times with PBS with 0.05% Tween 20 (PBST). PDL-1 protein (Acro Biosystems Product #PD1-H5358) or Fc protein (Acro Biosystems Product #FCC-H5214) was diluted in growth media (DMEM complete) to 2-fold higher than the final concentration and 12.5 microliters added per well. After a 15 minute incubation 12.5 microliters of HEK-Blue™ IL-2 reporter cells (12,500 cells) were added to each well and incubated overnight. Five microliters from each well was transferred to a new plate containing 45 microliters of QuantiBlue solution (Invivogen Product #rep-qbs). After 30 to 60 minutes the absorbance at 630 nm was determined using a Perkin-Elmer Envision.

TABLE 28

DBA-cytokine protein complexes, and control protein complexes

| Protein Complex | SEQ ID NO: | Sequence |
|---|---|---|
| AF4455 | SEQ ID NO: 220 | MSTSTITCPPPMSVEHADIWVKSYSLYSRERYICNSGFKRKAGTSSLTECVLNKATN VAHWTTPSLKCIRDPALVHQRPAPPSGGSGGGGSGGGSGGGGSLQNWVNVISDL KKIEDLIQSMHIDATLYTESDVHPSCKVTAMKCFLLELQVISLESGDASIHDTVENLIIL ANNSLSSNGNVTESGCKECEELEEKNIKEFLQSFVHIVQMFINTSGGSGSGSGGSG GSGSGGSGSQVQLVQSGAEVKKPGASVKVSCKASGYTFTGYYIHWVRQAPGQGL |

TABLE 28-continued

DBA-cytokine protein complexes, and control protein complexes

| Protein Complex | SEQ ID NO: | Sequence |
|---|---|---|
| | | EWMGIINPSGGSTRYAQKFQGRVTMTRDTSTSTVYMELSSLRSEDTAVYYCARSLF<br>PTIFGVEVAFDIWGQGTLVTVSSASGGGGSGGGGSGGGGSHASDIQMTQSPSSLS<br>ASVGDRVTITCRASQSIRTYLNWYQQKPGKAPKLLIYSASNLQSGVPSRFSGSGSGT<br>DFTLTISSLQPEDFATYYCQQANSFPFTFGPGTKVDIKAAAGSGSEQKLISEEDLGKPI<br>PNPLLGLDSTNA |
| AF4456 | SEQ ID NO: 221 | MSTSTITCPPPMSVEHADIWVKSYSLYSRERYICNSGFKRKAGTSSLTECVLNKATN<br>VAHWTTPSLKCIRDPALVHQRPAPPSGGSGGGGSGGGSGGGGSLQNWVNVISDL<br>KKIEDLIQSMHIDATLYTESDVHPSCKVTAMKCFLLELQVISLESGDASIHDTVENLIIL<br>ANNSLSSNGNVTESGCKECEELEEKNIKEFLQSFVHIVQMFINTSGGSGSGSGGSG<br>GSGSGGSGSQVQLVQSGAEVKKPGASVKVSCKASGYSFTSYYLHWVRQAPGQGL<br>EWMGRISPRSGGTKNAQNFQGRVTMTRDTSTSTVYMELSSLRSEDTAVYYCVRSL<br>FPTIFGVEVAFDIWGQGTLVTVSSASGGGGSGGGGSGGGGSHASDIQMTQSPSSL<br>SASVGDRVTITCRASQSISSWLAWYQQKPGKAPKLLIYYASSLQSGVPSRFSGSGSG<br>TDFTLTISSLQPEDFATYYCQQGYQYPYTFGQGTKLEIKAAAGSGSEQKLISEEDLGK<br>PIPNPLLGLDSTNA |
| AF4457 | SEQ ID NO: 222 | MSTSTITCPPPMSVEHADIWVKSYSLYSRERYICNSGFKRKAGTSSLTECVLNKATN<br>VAHWTTPSLKCIRDPALVHQRPAPPSGGSGGGGSGGGSGGGGSLQNWVNVISDL<br>KKIEDLIQSMHIDATLYTESDVHPSCKVTAMKCFLLELQVISLESGDASIHDTVENLIIL<br>ANNSLSSNGNVTESGCKECEELEEKNIKEFLQSFVHIVQMFINTSGGSGSGSGGSG<br>GSGSGGSGSQVQLVQSGAEVKKPGASVKVSCKASGYTFSTYYIHWVRQAPGQGLE<br>WMGWMNPNSGNTGYAQTFQGRVTMTRDTSTSTVYMELSSLRSEDTAVYYCARS<br>LFPTIFGVEVAFDIWGQGTLVTVSSASGGGGSGGGGSGGGGSHASDIQMTQSPSS<br>LSASVGDRVTITCRASQSISSYLNWYQQKPGKAPKLLIYAASSLQSGVPSRFSGSGSG<br>TDFTLTISSLQPEDFATYYCQQGYSTPRTFGQGTKVEIKAAAGSGSEQKLISEEDLGK<br>PIPNPLLGLDSTNA |
| AF4440 | SEQ ID NO: 223 | MSTSTITCPPPMSVEHADIWVKSYSLYSRERYICNSGFKRKAGTSSLTECVLNKATN<br>VAHWTTPSLKCIRDPALVHQRPAPPSGGSGGGGSGGGSGGGGSLQNWVNVISDL<br>KKIEDLIQSMHIDATLYTESDVHPSCKVTAMKCFLLELQVISLESGDASIHDTVENLIIL<br>ANNSLSSNGNVTESGCKECEELEEKNIKEFLQSFVHIVQMFINTSGGSGSGSGGSG<br>GSGSGGSGSQVQLVQSGAEVKKPGASVKVSCKASGYTFTNYYMHWVRQAPGQG<br>LEWMGWMNPNSGNTGYAQKFQGRVTMTRDTSTSTVYMELSSLRSEDTAVYYCA<br>RSLFPTIFGVEVAFDIWGQGTLVTVSSASGGGGSGGGGSGGGGSHASDIQMTQSP<br>SSLSASVGDRVTITCRASQSISSYLNWYQQKPGKAPKLLIYAASSLQSGVPSRFSGSG<br>SGTDFTLTISSLQPEDFATYYCQQSYSTPRTFGQGTKLEIKAAAGSGSEQKLISEEDLG<br>KPIPNPLLGLDSTNA |
| AF4478 | SEQ ID NO: 224 | MSTSTITCPPPMSVEHADIWVKSYSLYSRERYICNSGFKRKAGTSSLTECVLNKATN<br>VAHWTTPSLKCIRDPALVHQRPAPPSGGSGGGGSGGGSGGGGSLQNWVNVISDL<br>KKIEDLIQSMHIDATLYTESDVHPSCKVTAMKCFLLELQVISLESGDASIHDTVENLIIL<br>ANNSLSSNGNVTESGCKECEELEEKNIKEFLQSFVHIVQMFINTSGGSGSGSGGSG<br>GSGSGGSGSQVQLVQSGAEVKKPGASVKVSCKASGYTFTGYYIHWVRQAPGQGL<br>EWMGWMNPNSGNTGYAQKFQGRVTMTRDTSTSTVYMELSSLRSEDTAVYYCA<br>RSLFPTIFGVEVAFDIWGQGTLVTVSSASGGGGSGGGGSGGGGSHASDIQMTQSP<br>SSLSASVGDRVTITCRASRSISSYLNWYQQKPGKAPKLLIYAASSLQSGVPSRFSGSG<br>SGTDFTLTISSLQPEDFATYYCQQSYSTPRTFGQGTKVEIKAAAGSGSEQKLISEEDL<br>GKPIPNPLLGLDSTNA |
| AF4479 | SEQ ID NO: 225 | MSTSTITCPPPMSVEHADIWVKSYSLYSRERYICNSGFKRKAGTSSLTECVLNKATN<br>VAHWTTPSLKCIRDPALVHQRPAPPSGGSGGGGSGGGSGGGGSLQNWVNVISDL<br>KKIEDLIQSMHIDATLYTESDVHPSCKVTAMKCFLLELQVISLESGDASIHDTVENLIIL<br>ANNSLSSNGNVTESGCKECEELEEKNIKEFLQSFVHIVQMFINTSGGSGSGSGGSG<br>GSGSGGSGSQVQLVQSGAEVKKPGSSVKVSCKASGYSFTDYYVHWVRQAPGQGL<br>EWVGGINPKRGDTVFAQKFQGRVTITADESTSTAYMELSSLRSEDTAVYYCARGGL<br>GVFGVVDVWGQGTTVTVSSASGGGGSGGGGSGGGGSHASDIVMTQSPLSLPVT<br>PGEPASISCRSSQSLLHSNGYNYLDWYLQKPGQSPQLLIYAATTLQSGVPDRFSGSG<br>SGTDFTLKISRVEAEDVGVYYCMQALQTPLTFGGGTKLEIKAAAGSGSEQKLISEEDL<br>GKPIPNPLLGLDST |

The results are shown in FIGS. 24A-F. IL-15 activity increased in a dose dependent manner with the addition of PD-L1 (circles) but not with the addition of Fc protein (squares) for DBA-cytokine complexes AF4455 (SEQ ID NO: 220), AF4456 (SEQ ID NO: 221), AF4457 (SEQ ID NO: 222) and AF4440 (SEQ ID NO: 223). IL-15 activity from the monospecific IL-15 scFv cytokine complexes AF4478 (SEQ ID NO: 224) and AF4479 (SEQ ID NO: 225) did not change with the addition of PD-L1 or Fc protein.

The exemplary dual-binding antibody sequences from AF614 (SEQ ID NO: 219) and AF666 (SEQ ID NO: 218) were assembled into asymmetric IgG molecules with IL-15 appended to the N-terminus of one heavy chain through a flexible linker (as shown schematically in FIG. 9b) to create AF4591 (SEQ ID NO: 226-228) and AF4592 (SEQ ID NO: 229-231) respectively. Two controls were assembled in the same format from an anti-IL-15 antibody (AF4659, SEQ ID NO: 232-234) and a PDL1-IFN dual-binding antibody (AF4660, SEQ ID NO: 235-237). Protein complex sequences are summarized in TABLE 29. The proteins were expressed in mammalian cells and purified using standard protocols. The four antibody-cytokine complexes were assayed for IL-15 activity using HEK-Blue™ IL-2 reporter cells in an assay similar to that described above, with the exception that all of the proteins were in solution in the growth media. The purified antibody-cytokine complexes were diluted to a final concentration of 100 pM and assayed in varying concentrations of PD-L1 or a control IgG1 antibody.

TABLE 29

DBA-cytokine protein complexes, and control protein complexes

| Protein Complex | SEQ ID NO: | Sequence |
|---|---|---|
| AF4591 | SEQ ID NO: 226 | ITCPPPMSVEHADIWVKSYSLYSRERYICNSGFKRKAGTSSLTECVLNKATN VAHWTTPSLKCIRDPALVHQRPAPPSGGSGGGGSGGGSGGGGSLQNW VNVISDLKKIEDLIQSMHIDATLYTESDVHPSCKVTAMKCFLLELQVISLESG DASIHDTVENLIILANNSLSSNGNVTESGCKECEELEEKNIKEFLQSFVHIVQ MFINTSGGGGSGGGGSGGGGSGGGGSQVQLVQSGAEVKKPGASVKVS CKASGYTFTNYYMHWVRQAPGQGLEWMGWMNPNSGNTGYAQKFQ GRVTMTRDTSTSTVYMELSSLRSEDTAVYYCARSLFPTIFGVEVAFDIWGQ GTLVTVSSAKTTAPSVYPLAPVCGDTTGSSVTLGCLVKGYFPEPVTLTWNS GSLSSGVHTFPAVLQSDLYTLSSSVTVTSSTWPSQSITCNVAHPASSTKVD KKIEPRGPTIKPCPPCKCPAPNAAGGPSVFIFPPKIKDVLMISLSPIVTCVVV DVSEDDPDVQISWFVNNVEVHTAQTQTHREDYNSTLRVVSALPIQHQD WMSGKEFKCKVNNKDLGAPIERTISKPKGSVRAPQVYVLPPPEEEMTKK QVTLTCMVTDFMPEDIYVEWTNNGKTELNYKNTEPVLDSDGSYFMYSDL RVEKKNWVERNSYSCSVVHEGLHNHHTTESFSRTPGK |
| | SEQ ID NO: 227 | QVQLVQSGAEVKKPGASVKVSCKASGYTFTNYYMHWVRQAPGQGLEW MGWMNPNSGNTGYAQKFQGRVTMTRDTSTSTVYMELSSLRSEDTAVY YCARSLFPTIFGVEVAFDIWGQGTLVTVSSAKTTAPSVYPLAPVCGDTTGS SVTLGCLVKGYFPEPVTLTWNSGSLSSGVHTFPAVLQSDLYTLSSSVTVTSS TWPSQSITCNVAHPASSTKVDKKIEPRGPTIKPCPPCKCPAPNAAGGPSVF IFPPKIKDVLMISLSPIVTCVVVDVSEDDPDVQISWFVNNVEVHTAQTQTH REDYNSTLRVVSALPIQHQDWMSGKEFKCKVNNKDLGAPIERTISKPKGS VRAPQVYVLPPPEKEMTKKQVSLTCLVKDFMPEDIYVEWTNNGKTELNY KNTEPVLKSDGSYFMYSKLTVEKKNWVERNSYSCSVVHEGLHNHHTTKSF SRTPGK |
| | SEQ ID NO: 228 | DIQMTQSPSSLSASVGDRVTITCRASQSISSYLNWYQQKPGKAPKLLIYAA SSLQSGVPSRFSGSGSGTDFTLTISSLQPEDFATYYCQQSYSTPRTFGQGTK LEIKRADAAPTVSIFPPSSEQLTSGGASVVCFLNNFYPKDINVKWKIDGSER QNGVLNSWTDQDSKDSTYSMSSTLTLTKDEYERHNSYTCEATHKTSTSPI VKSFNRNEC |
| AF4592 | SEQ ID NO: 229 | ITCPPPMSVEHADIWVKSYSLYSRERYICNSGFKRKAGTSSLTECVLNKATN VAHWTTPSLKCIRDPALVHQRPAPPSGGSGGGGSGGGSGGGGSLQNW VNVISDLKKIEDLIQSMHIDATLYTESDVHPSCKVTAMKCFLLELQVISLESG DASIHDTVENLIILANNSLSSNGNVTESGCKECEELEEKNIKEFLQSFVHIVQ MFINTSGGGGSGGGGSGGGGSGGGGSQVQLVQSGAEVKKPGASVKVS CKASGYTFSTYYIHWVRQAPGQGLEWMGWMNPNSGNTGYAQTFQGR VTMTRDTSTSTVYMELSSLRSEDTAVYYCARSLFPTIFGVEVAFDIWGQGT LVTVSSAKTTAPSVYPLAPVCGDTTGSSVTLGCLVKGYFPEPVTLTWNSGS LSSGVHTFPAVLQSDLYTLSSSVTVTSSTWPSQSITCNVAHPASSTKVDKKI EPRGPTIKPCPPCKCPAPNAAGGPSVFIFPPKIKDVLMISLSPIVTCVVVDV SEDDPDVQISWFVNNVEVHTAQTQTHREDYNSTLRVVSALPIQHQDW MSGKEFKCKVNNKDLGAPIERTISKPKGSVRAPQVYVLPPPEEEMTKKQV TLTCMVTDFMPEDIYVEWTNNGKTELNYKNTEPVLDSDGSYFMYSDLRV EKKNWVERNSYSCSVVHEGLHNHHTTESFSRTPGK |
| | SEQ ID NO: 230 | QVQLVQSGAEVKKPGASVKVSCKASGYTFSTYYIHWVRQAPGQGLEWM GWMNPNSGNTGYAQTFQGRVTMTRDTSTSTVYMELSSLRSEDTAVYYC ARSLFPTIFGVEVAFDIWGQGTLVTVSSAKTTAPSVYPLAPVCGDTTGSSV TLGCLVKGYFPEPVTLTWNSGSLSSGVHTFPAVLQSDLYTLSSSVTVTSST WPSQSITCNVAHPASSTKVDKKIEPRGPTIKPCPPCKCPAPNAAGGPSVFI FPPKIKDVLMISLSPIVTCVVVDVSEDDPDVQISWFVNNVEVHTAQTQTH REDYNSTLRVVSALPIQHQDWMSGKEFKCKVNNKDLGAPIERTISKPKGS VRAPQVYVLPPPEKEMTKKQVSLTCLVKDFMPEDIYVEWTNNGKTELNY KNTEPVLKSDGSYFMYSKLTVEKKNWVERNSYSCSVVHEGLHNHHTTKSF SRTPGK |
| | SEQ ID NO: 231 | DIQMTQSPSSLSASVGDRVTITCRASQSISSYLNWYQQKPGKAPKLLIYAA SSLQSGVPSRFSGSGSGTDFTLTISSLQPEDFATYYCQQGYSTPRTFGQGT KVEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSP IVKSFNRNEC |

TABLE 29-continued

DBA-cytokine protein complexes, and control protein complexes

| Protein Complex | SEQ ID NO: | Sequence |
|---|---|---|
| AF4659 | SEQ ID NO: 232 | ITCPPPMSVEHADIWVKSYSLYSRERYICNSGFKRKAGTSSLTECVLNKATN VAHWTTPSLKCIRDPALVHQRPAPPSGGSGGGGSGGGSGGGGSLQNW VNVISDLKKIEDLIQSMHIDATLYTESDVHPSCKVTAMKCFLLELQVISLESG DASIHDTVENLIILANNSLSSNGNVTESGCKECEELEEKNIKEFLQSFVHIVQ MFINTSGGGGSGGGGSGGGGSGGGGSQVQLVQSGAEVKKPGASVKVS CKASGDTFSSYAISWVRQAPGQGLEWMGWMNPNSGNTGYAQKFQGR VTMTRDTSTSTVYMELSSLRSEDTAVYYCATGITMIGYWGQGTLVTVSSA KTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTI KPCPPCKCPAPNAAGGPSVFIFPPKIKDVLMISLSPIVTCVVVDVSEDDPD VQISWFVNNVEVHTAQTQTHREDYNSTLRVVSALPIQHQDWMSGKEFK CKVNNKDLGAPIERTISKPKGSVRAPQVYVLPPPEEEMTKKQVTLTCMVT DFMPEDIYVEWTNNGKTELNYKNTEPVLDSDGSYFMYSDLRVEKKNWV ERNSYSCSVVHEGLHNHHTTESFSRTPGK |
| | SEQ ID NO: 233 | QVQLVQSGAEVKKPGASVKVSCKASGDTFSSYAISWVRQAPGQGLEWM GWMNPNSGNTGYAQKFQGRVTMTRDTSTSTVYMELSSLRSEDTAVYYC ATGITMIGYWGQGTLVTVSSAKTTAPSVYPLAPVCGDTTGSSVTLGCLVK GYFPEPVTLTWNSGSLSSGVHTFPAVLQSDLYTLSSSVTVTSSTWPSQSITC NVAHPASSTKVDKKIEPRGPTIKPCPPCKCPAPNAAGGPSVFIFPPKIKDVL MISLSPIVTCVVVDVSEDDPDVQISWFVNNVEVHTAQTQTHREDYNSTL RVVSALPIQHQDWMSGKEFKCKVNNKDLGAPIERTISKPKGSVRAPQVY VLPPPEKEMTKKQVSLTCLVKDFMPEDIYVEWTNNGKTELNYKNTEPVLK SDGSYFMYSKLTVEKKNWVERNSYSCSVVHEGLHNHHTTKSFSRTPGK |
| | SEQ ID NO: 234 | DIQMTQSPSSLSASVGDRVTITCQASQDISSYLNWYQQKPGKAPKLLIYAA STLQSGVPSRFSGSGSGTDFTLTISSLQPEDFATYYCQQSYSTPYTFGQGTK VEIKRADAAPTVSIFPPSSEQLTSGGASVVCFLNNFYPKDINVKWKIDGSER QNGVLNSWTDQDSKDSTYSMSSTLTLTKDEYERHNSYTCEATHKTSTSPI VKSFNRNEC |
| AF4660 | SEQ ID NO: 235 | ITCPPPMSVEHADIWVKSYSLYSRERYICNSGFKRKAGTSSLTECVLNKATN VAHWTTPSLKCIRDPALVHQRPAPPSGGSGGGGSGGGSGGGGSLQNW VNVISDLKKIEDLIQSMHIDATLYTESDVHPSCKVTAMKCFLLELQVISLESG DASIHDTVENLIILANNSLSSNGNVTESGCKECEELEEKNIKEFLQSFVHIVQ MFINTSGGGGSGGGGSGGGGSGGGGSQVQLVQSGAEVKKPGASVKVS CKASGGTFSSYAISWVRQAPGQGLEWMGIIDPSMTYTRYAQKFQGRVT MTRDTSTSTVYMELSSLRSEDTAVYYCARSLFPTIFGLEVAFDIWGQGTLV TVSSAKTTAPSVYPLAPVCGDTTGSSVTLGCLVKGYFPEPVTLTWNSGSLS SGVHTFPAVLQSDLYTLSSSVTVTSSTWPSQSITCNVAHPASSTKVDKKIEP RGPTIKPCPPCKCPAPNAAGGPSVFIFPPKIKDVLMISLSPIVTCVVVDVSE DDPDVQISWFVNNVEVHTAQTQTHREDYNSTLRVVSALPIQHQDWMS GKEFKCKVNNKDLGAPIERTISKPKGSVRAPQVYVLPPPEEEMTKKQVTLT CMVTDFMPEDIYVEWTNNGKTELNYKNTEPVLDSDGSYFMYSDLRVEKK NWVERNSYSCSVVHEGLHNHHTTESFSRTPGK |
| | SEQ ID NO: 236 | QVQLVQSGAEVKKPGASVKVSCKASGGTFSSYAISWVRQAPGQGLEWM GIIDPSMTYTRYAQKFQGRVTMTRDTSTSTVYMELSSLRSEDTAVYYCAR SLFPTIFGLEVAFDIWGQGTLVTVSSAKTTAPSVYPLAPVCGDTTGSSVTLG CLVKGYFPEPVTLTWNSGSLSSGVHTFPAVLQSDLYTLSSSVTVTSSTWPS QSITCNVAHPASSTKVDKKIEPRGPTIKPCPPCKCPAPNAAGGPSVFIFPPK IKDVLMISLSPIVTCVVVDVSEDDPDVQISWFVNNVEVHTAQTQTHREDY NSTLRVVSALPIQHQDWMSGKEFKCKVNNKDLGAPIERTISKPKGSVRAP QVYVLPPPEKEMTKKQVSLTCLVKDFMPEDIYVEWTNNGKTELNYKNTE PVLKSDGSYFMYSKLTVEKKNWVERNSYSCSVVHEGLHNHHTTKSFSRTP GK |
| | SEQ ID NO: 237 | DIQMTQSPSSLSASVGDRVTITCQASQSISNRLAWYQQKPGKAPKLLIYKA SSLESGVPSRFSGSGSGTDFTLTISSLQPEDFATYYCQQTYSTPITFGQGTK VEIKRADAAPTVSIFPPSSEQLTSGGASVVCFLNNFYPKDINVKWKIDGSER QNGVLNSWTDQDSKDSTYSMSSTLTLTKDEYERHNSYTCEATHKTSTSPI VKSFNRNEC |

The results are shown in FIGS. 25A-D. IL-15 activity increased in a dose dependent manner with the addition of PD-L1 but not with the addition of Fc protein for DBA-cytokine complexes AF4591 (SEQ ID NO: 226-228) and AF4592 (SEQ ID NO: 229-231). IL-15 activity from the monospecific IL-15 scFv cytokine complexes AF4659 (SEQ ID NO: 232-234) and AF4660 (SEQ ID NO: 235-237) did not change with the addition of PD-L1 or Fc protein.

Protein complexes of the present invention based on four different PD-L1/IL-15 dual-binding antibodies produced in two different formats showed PD-L1-dependent IL-15 activity.

Example 31

Selection and Binding of IFN and CEA Specific Dual Binding Antibodies

This example describes isolation of sensor domains of the present disclosure, specifically, selection of IFNα and CEA specific dual binding antibodies (DBAs). Anti-CEA and anti-IFNα DBAs were isolated from a Tumbler antibody phage display library similar to the library described in EXAMPLE 1. The antibody phage display library was constructed to incorporate the heavy chain CDR1, heavy chain CDR2, and light chain diversity of the Superhuman 2.0 antibody library combined with various heavy chain ("HC") CDR3 sequences from anti-IFNα antibodies (TABLE 18). The selection was similar to the protocol described in EXAMPLE 1, using one round of IFNα selection (IFNα2b, GenScript, Z03002, biotinylated using standard protocols) and one round of CEA selection (CEA-hFc, Sino Biologicals, 11077-H02H).

Figure 26:
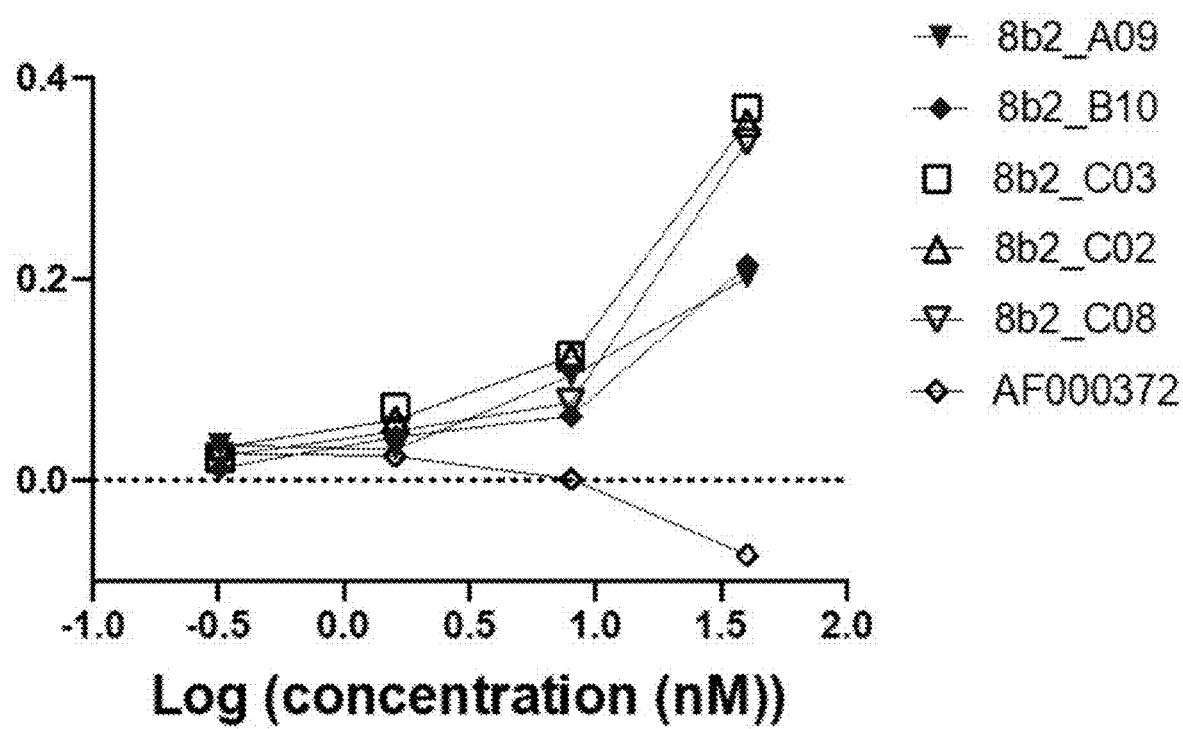
FIG. 26 shows ELISA binding data for five dual-binding scFvs binding to CEA.

Following two rounds of selection in phage, the resulting library of DBAs was subcloned into a yeast surface display vector and transformed into yeast for further screening using standard protocols. The yeast library was sorted four times for binding to CEA and IFNα. In each round of sorting, the library was labeled with either CEA-Fc-biotin or IFNα-biotin, then with Streptavidin-PE (Abcam #ab239759), and sorted based on PE fluorescence on a Sony MA900 cell sorter. The four sorts were carried out with labelling at 100 nM CEA-Fc-biotin, 1000 nM IFNα-biotin, 10 nM CEA-Fc-biotin, and 20 nM CEA-Fc-biotin. Plasmids were rescued from the yeast after the final sort using a Zymoprep Yeast Plasmid Miniprep II kit (Zymo research D2004) and transformed into DH5a *E. coli* for cloning. Ninety-six colonies were picked for Sanger sequencing, from which thirty-four unique clones were identified and screened for IFNα and CEA binding. The scFv DNA sequence for each clone, including c-myc and V5 tags, was amplified by PCR using a forward primer containing a T7 promoter and a translation initiation site, and a reverse primer containing a T7 terminator. Proteins were expressed using the PUREfrex2.1 cell-free transcription/translation system as described in previous examples. The scFv samples were subjected to ELISA analysis to detect CEA and IFNα binding. In these experiments, wells of a 384-well plate are coated with an anti-V5 antibody (Sv5-Pk1, BioRad) at 1 ug/ml overnight at 4 degrees. After washing, wells are blocked with SuperBlock (ThermoFisher, 37515) followed by addition of saturating levels of scFvs in SuperBlock. After washing, antigens are added and plates incubated for one hour. Biotinylated IFNα is detected using streptavidin HRP and CEA-Fc is detected using anti-hFc-HRP, and developed using standard methods. Varying amounts of labelled test antigen were added to show binding and to estimate relative affinities of the different scFvs. FIG. 26 shows the ELISA binding data for five exemplary dual-binding scFvs binding to CEA. Because the binding affinity for IFNα was too low to detect by ELISA, the binding to IFNα was measured by Biolayer Interferom-

TABLE 18

HC-CDR3 of IFNα binders

| SEQ ID NO | Sequence | Description |
| --- | --- | --- |
| SEQ ID NO: 238 | CASGGSYSPWYFDLW | HC-CDR3 of IFNα binder |
| SEQ ID NO: 239 | CASLAAAGPYYYYGMDVW | HC-CDR3 of IFNα binder |
| SEQ ID NO: 240 | CVSSVGAGAYYYQGLDVW | HC-CDR3 of IFNα binder |
| SEQ ID NO: 241 | CARDHDYLTSFGYW | HC-CDR3 of IFNα binder |
| SEQ ID NO: 242 | CAFSSPTYYYYYGMDVW | HC-CDR3 of IFNα binder |
| SEQ ID NO: 243 | CARVNYDFWSGQSLRFDPW | HC-CDR3 of IFNα binder |
| SEQ ID NO: 244 | CATIKGLGAYYYYGMDVW | HC-CDR3 of IFNα binder |
| SEQ ID NO: 245 | CASDHGWLDAFDIW | HC-CDR3 of IFNα binder |
| SEQ ID NO: 246 | CARDWYGDYFDYW | HC-CDR3 of IFNα binder |
| SEQ ID NO: 247 | CARGILSDYGDHAFDYW | HC-CDR3 of IFNα binder |
| SEQ ID NO: 248 | CARVDSSSSLHFDYW | HC-CDR3 of IFNα binder |
| SEQ ID NO: 249 | CARTSGYDLLFDYW | HC-CDR3 of IFNα binder |
| SEQ ID NO: 250 | CARVGGWGIYYYYGMDVW | HC-CDR3 of IFNα binder |
| SEQ ID NO: 251 | CARDPSYSTGYYDYW | HC-CDR3 of IFNα binder |
| SEQ ID NO: 252 | CARGSRADYW | HC-CDR3 of IFNα binder | etry (OctetRED96e) as described in Example 5. Results are tabulated in TABLE 19. All five show binding to both CEA and IFN, with binding to CEA detectable at a lower concentration of the antigen.

TABLE 19

Anti-IFNα Binding Results

| CloneID | IFNα binding (@5uM) | ELISA | SEQUENCES | HC-CDR3 |
|---|---|---|---|---|
| 8b2_A09 | + | − | (SEQ ID NO: 253) MSTSTEVQLLESGGGLVQPGGSLRLSCAAS GFTFSSYAMHWVRQAPGKGLEWVSAIGA GGGTYYADSVKGRFTISRDDSKNTLYLQM NSLKTEDTAVYYCVSSVGAGAYYYQGLDV WGQGTLVTVSSASGGGGSGGGGSGGGG SHASDIQMTQSPSSLSASVGDRVTITCRAS QDIFTYLNWYQQRPGKAPKLLIYDASRLQT GVPSRFSGSGSGTDFTLTISSLQPEDFATYY CQQSYSIPYTFGQGTKLEIKRAAAGSGSEQ KLISEEDLGKPIPNPLLGLDST | SEQ ID NO: 240 |
| 8b2_B10 | + | − | (SEQ ID NO: 254) MSTSTEVQLLESGAEVKKPGGSLR LSCAASGFTVSSNYMSWVRQAPG KGLEWVSAISGSGGSTYYADFVKG RFTISRDNSKNTLYLQMNSLRAED TAVYYCVSSVGAGAYYYQGLDV WGQGTLVTVSSASGGGGSGGGGS GGGGSHASDIQMTQSPSSLSASVG DRVTITCRASQGVGNFLAWYQQKP GKAPKLLIYGASTLQSGVPSRFSGS GSGTDFTLTISSLQPEDFATYYCQQ SYSTPFTFGGGTKLEIKRAAAGSGS EQKLISEEDLGKPIPNPLLGLDST | SEQ ID NO: 240 |
| 8b2_C02 | + | − | - | |
| 8b2_C03 | + | − | - | |
| 8b2_C08 | + | − | (SEQ ID NO: 256) MSTSTEVQLLESGAEVKKPGGSLR LSCAASGFTFSSYAMSWVRQAPGK GLEWVSAISGSGGSTYYADSVKGR FTISRDNSKNTLYLQMNSLRAEDT AVYYCARVDSSSSLHFDYWGQGT LVTVSSASGGGGSGGGGSGGGGSH ASDIQMTQSPSSLSASVGDRVTITC RASQRIGTYLNWYQQKPGKAPKLL IYAASNLQSGVPSRFSGSGSGTDFT LTISSLQPEDFATYYCLQTFNTPFTF GPGTKVDIKRAAAGSGSEQKLISEE DLGKPIPNPLLGLDST | SEQ ID NO: 248 |
| AF317 | (KD < 10nM) | +++ | (SEQ ID NO: 257) MSTSTEQKLISEEDLQVQLVQSGAE VKKPGASVKVSCKASGYSFTSYDI NWVRQAPGQGLEWIGMINPSSGFT SAAQTFQGRVTMTRDTSTSTVYME LSSLRSEDTAVYYCATIKGLGAYY YYGMDVWGQGTTVTVSSASGGGG SGGGGSGGGGSHASDIQMTQSPSS LSASVGDRVTITCRASQSIDRYLNW YQQKPGKAPKLLIYAASSLQSGVPS RFSGSGSGTDFTLTISSLQPEDFATY YCQQSYSPPLTFGGGTKVEIKGSGL NDIFEAQKIEWHEGKPIPNPLLGLD ST | SEQ ID NO: 244 |
| AF372 | − | − | (SEQ ID NO: 258) MSTSTEQKLISEEDLEVQLVESGGG LVQPGGSLRLSCAASGFNIKDTYIH WVRQAPGKGLEWVARIYPTNGYT RYADSVKGRFTISADTSKNTAYLQ MNSLRAEDTAVYYCSRWGGDGFY AMDYWGQGTLVTVSSASGGGGSG GGSGGGGSHASDIQMTQSPSSLS ASVGDRVTITCRASQDVNTAVAW | - |

TABLE 19-continued

Anti-IFNα Binding Results

| CloneID | IFNα binding (@5uM) | ELISA | SEQUENCES | HC-CDR3 |
|---|---|---|---|---|
| | | | YQQKPGKAPKLLIYSASFLYSGVPS RFSGSRSGTDFTLTISSLQPEDFATY YCQQHYTTPPTFGQGTKVEIKGSG LNDIFEAQKIEWHEGKPIPNPLLGL DST | |

Example 32

Figure 27A:
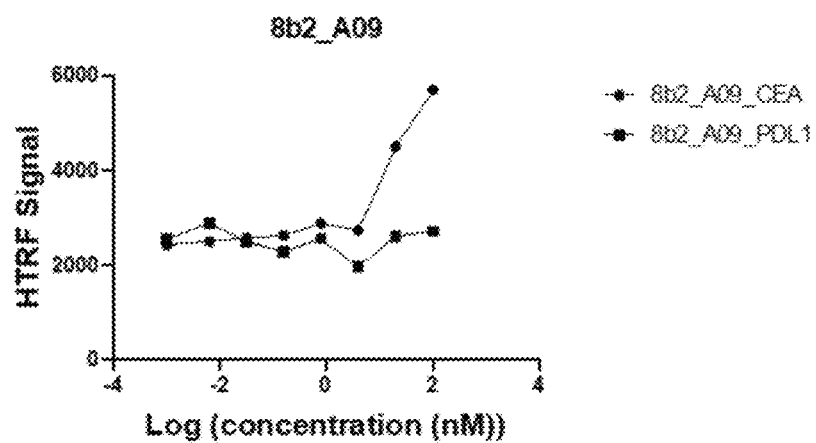
FIG. 27A, FIG. 27B, FIG. 27C, FIG. 27D, FIG. 27E, and FIG. 27F demonstrate IFNAR2 binding by three DBA-cytokine protein complexes, an IFNα monospecific binding scFv, and two non-IFNα binding scFvs.
Figure 27B:
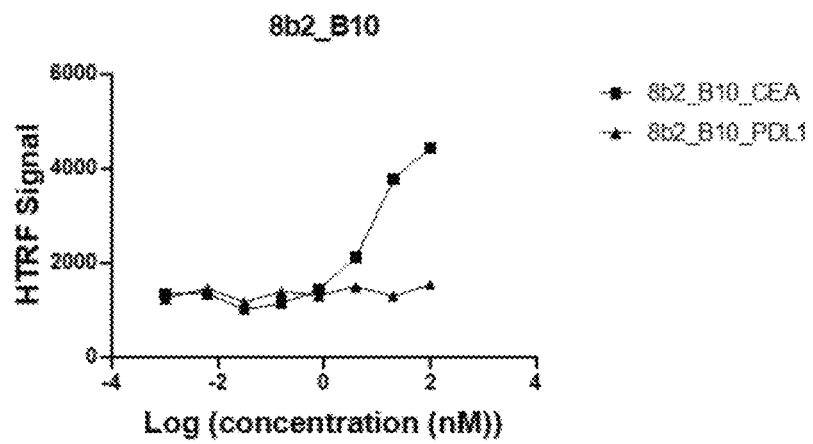
Figure 27C:
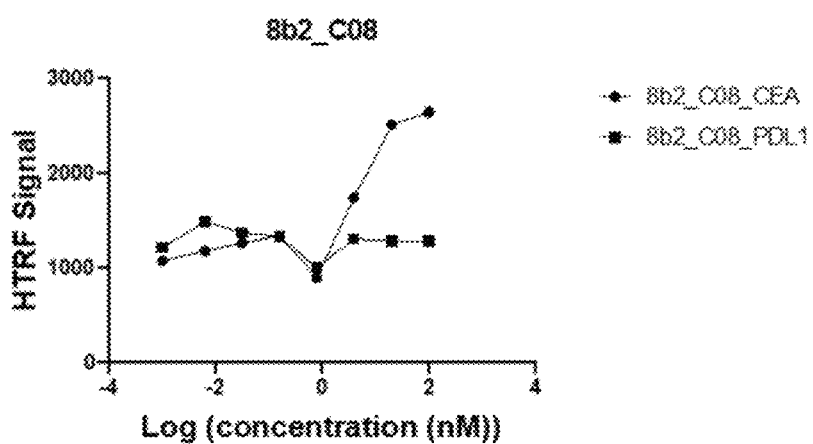
Figure 27D:
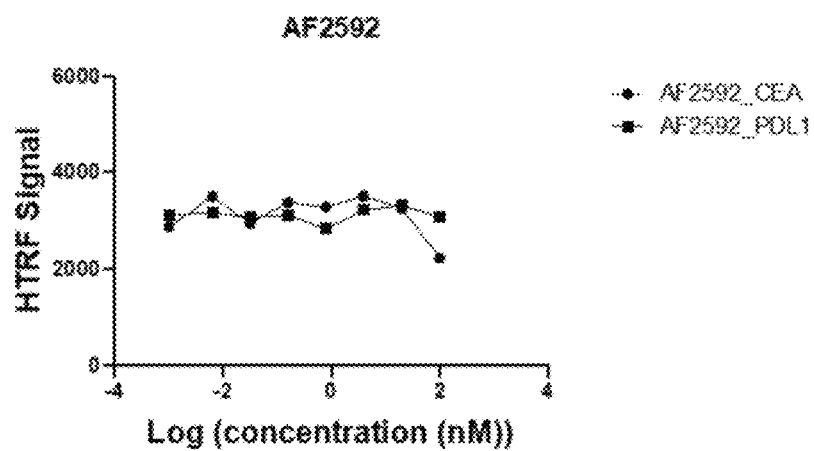
Figure 27E:
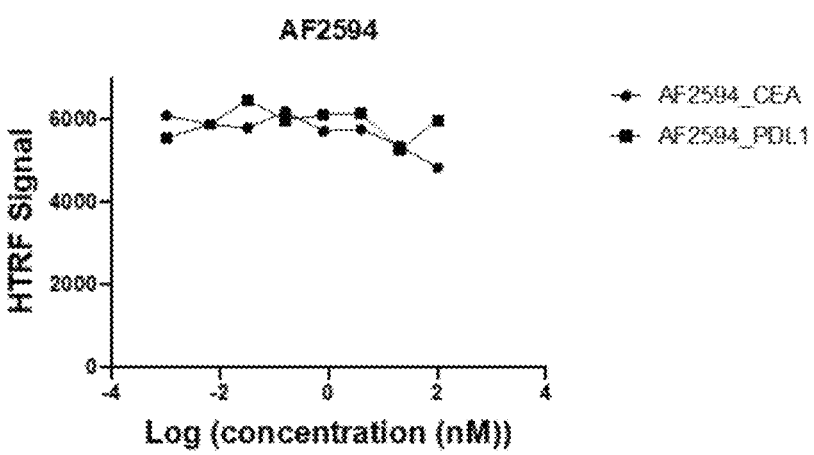
Figure 27F:
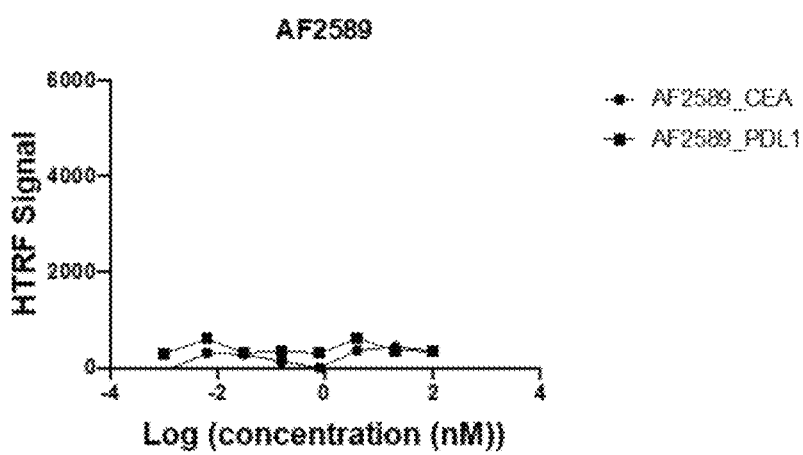

Regulated IFNAR2 (IFNα Receptor 2) Binding by a CEA-IFNα Dual Binding Antibody (DBA) Cytokine Complex This example describes regulated binding of IFN to the receptor IFNAR2 by CEA/IFN DBA-cytokine complexes in the form shown in FIG. 8. DBA-cytokine complexes of SEQ ID NO: 259, SEQ ID NO: 260 and SEQ ID NO: 261 were chosen for analysis with a negative control with a similar structure based on an IFNα monospecific binding scFv (SEQ ID NO: 300) and two non-IFNα binding scFvs (one with SEQ ID NO: 301 and one with SEQ ID NO: 302). DBA-cytokine complex and control protein complex sequences are summarized in TABLE 30. To test the ability of Carcino Embryonic Antigen (CEA) to regulate the binding of IFNAR2, V5-tagged constructs were generated consisting of a CEA-IFN-α DBA scFv linked to IFN-α. scFvs were synthesized using the PUREfrex 2.1 in vitro translation system and added to a 384 well plate at a single dilution. Titrating concentrations of either CEA-Fc (SINO Biological) or PDL1-Fc (ACROBiosystems) were added, and the plate was incubated for 30 minutes at room temperature. Eu-labeled IFNAR2 (ACROBiosystems) and Alexa Fluor 647-labeled anti-V5 antibody (Perkin Elmer) were added to all wells and incubated for 24 hours at room temperature. The HTRF signal was then read on an Envision 2105 microplate reader (Perkin Elmer). IFNAR2 was able to bind IFN-α on the DBA-scFv complex in the presence of increasing concentrations of CEA-Fc. No increase in IFNAR2 binding was seen in the presence of the PD-L1-Fc control protein, which does not bind the DBA-scFv protein complex. Results shown in FIGS. 27A-F demonstrate IFNAR2 binding increased in a dose dependent manner with the addition of CEA but not with the addition of control protein PDL1 for DBA-cytokine complexes of SEQ ID NO: 259 (FIG. 27A), SEQ ID NO: 260 (FIG. 27B) and SEQ ID NO: 261 (FIG. 27C). IFNAR2 binding from the monospecific IFN scFv cytokine complexes did not change with the addition of CEA or PD-L1.

TABLE 30

DBA-cytokine protein complexes, and control protein complexes

| Protein Complex | SEQ ID NO: | Sequence |
|---|---|---|
| DBA-cytokine complex | SEQ ID NO: 259 | MSTSTCDLPQTHSLGSRRTLMLLAQMRRISLFSCLKDRHDFGFPQE EFGNQFQKAETIPVLHEMIQQIFNLFSTKDSSAAWDETLLDKFYTEL YQQLNDLEACVIQGVGVTETPLMKEDSILAVRKYFQRITLYLKEKK YSPCAWEVVRAEIMRSFSLSTNLQESLRSKEGGSGSGSGGSGGSGS GGSGSEVQLLESGGGLVQPGGSLRLSCAASGFTFSSYAMHWVRQA PGKGLEWVSAIGAGGGTYYADSVKGRFTISRDDSKNTLYLQMNSL KTEDTAVYYCVSSVGAGAYYYQGLDVWGQGTLVTVSSASGGGGS GGGGSGGGGSHASDIQMTQSPSSLSASVGDRVTITCRASQDIFTYL NWYQQRPGKAPKLLIYDASRLQTGVPSRFSGSGSGTDFTLTISSLQP EDFATYYCQQSYSIPYTFGQGTKLEIKRAAAGSGSEQKLISEEDLGK PIPNPLLGLDST |
| DBA-cytokine complex | SEQ ID NO: 260 | MSTSTCDLPQTHSLGSRRTLMLLAQMRRISLFSCLKDRHDFGFPQE EFGNQFQKAETIPVLHEMIQQIFNLFSTKDSSAAWDETLLDKFYTEL YQQLNDLEACVIQGVGVTETPLMKEDSILAVRKYFQRITLYLKEKK YSPCAWEVVRAEIMRSFSLSTNLQESLRSKEGGSGSGSGGSGGSGS GGSGSEVQLLESGAEVKKPGGSLRLSCAASGFTVSSNYMSWVRQA PGKGLEWVSAISGSGGSTYYADFVKGRFTISRDNSKNTLYLQMNSL RAEDTAVYYCVSSVGAGAYYYQGLDVWGQGTLVTVSSASGGGGS GGGGSGGGGSHASDIQMTQSPSSLSASVGDRVTITCRASQGVGNFL AWYQQKPGKAPKLLIYGASTLQSGVPSRFSGSGSGTDFTLTISSLQP EDFATYYCQQSYSTPFTFGGGTKLEIKRAAAGSGSEQKLISEEDLGK PIPNPLLGLDST |
| DBA-cytokine complex | SEQ ID NO: 261 | MSTSTCDLPQTHSLGSRRTLMLLAQMRRISLFSCLKDRHDFGFPQE EFGNQFQKAETIPVLHEMIQQIFNLFSTKDSSAAWDETLLDKFYTEL YQQLNDLEACVIQGVGVTETPLMKEDSILAVRKYFQRITLYLKEKK YSPCAWEVVRAEIMRSFSLSTNLQESLRSKEGGSGSGSGGSGGSGS GGSGSEVQLLESGAEVKKPGGSLRLSCAASGFTFSSYAMSWVRQA PGKGLEWVSAISGSGGSTYYADSVKGRFTISRDNSKNTLYLQMNSL RAEDTAVYYCARVDSSSSLHFDYWGQGTLVTVSSASGGGGSGGGG GSGGGGSHASDIQMTQSPSSLSASVGDRVTITCRASQRIGTYLNWY |

TABLE 30-continued

DBA-cytokine protein complexes, and control protein complexes

| Protein Complex | SEQ ID NO: | Sequence |
|---|---|---|
| | | QQKPGKAPKLLIYAASNLQSGVPSRFSGSGSGTDFTLTISSLQPEDF ATYYCLQTFNTPFTFGPGTKVDIKRAAAGSGSEQKLISEEDLGKPIP NPLLGLDST |
| AF2589 | SEQ ID NO: 300 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGVTET PLMKEDSILAVRKYFQRITLYLKEKKYSPCAWEVVRAEIMRSFSLSTNLQESLRSKEG GGGSGGGGGGGSGGGGSQVQLVQSGAEVKKPGASVKVSCKASGYSFTSYDIN WVRQAPGQGLEWIGMINPSSGFTSAAQTFQGRVTMTRDTSTSTVYMELSSLRSE DTAVYYCATIKGLGAYYYYGMDVWGQGTTVTVSSASGGGGSGGGGSGGGGSHA SDIQMTQSPSSLSASVGDRVTITCRASQSIDRYLNWYQQKPGKAPKLLIYAASSLQS GVPSRFSGSGSGTDFTLTISSLQPEDFATYYCQQSYSPPLTFGGGTKVEIKGKPIPNPL LGLDST |
| AF2592 | SEQ ID NO: 301 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGVTET PLMKEDSILAVRKYFQRITLYLKEKKYSPCAWEVVRAEIMRSFSLSTNLQESLRSKEG GGGSGGGGSGGGGSGGGGSQVQLVQSGAEVKKPGASVKVSCKASGGTFSSYAIS WVRQAPGQGLEWMGWINPNSGGTNYAQKFQGRVTMTRDTSTSTVYMELSSLR SEDTAVYYCARSLFPTIFGVEVAFDIWGQGTTVTVSSASGGGGSGGGGSGGGGSH ASDIQMTQSPSSLSASVGDRVTITCRASQSIIDRLAWYQQKPGKAPKLLIYKASSLES GVPSRFSGSGSGTDFTLTISSLQPEDFATYYCQQSYSTPFTFGPGTKVDIKGKPIPNPL LGLDST |
| AF2594 | SEQ ID NO: 302 | MSTSTCDLPQTHSLGSRRTLMLLAQMRRISLFSCLKDRHDFGFPQEEFGNQFQKAE TIPVLHEMIQQIFNLFSTKDSSAAWDETLLDKFYTELYQQLNDLEACVIQGVGVTET PLMKEDSILAVRKYFQRITLYLKEKKYSPCAWEVVRAEIMRSFSLSTNLQESLRSKEG GGGSGGGGSGGGGSGGGGSEVQLVESGGGLVQPGGSLRLSCAASGFNIKDTYIH WVRQAPGKGLEWVARIYPTNGYTRYADSVKGRFTISADTSKNTAYLQMNSLRAED TAVYYCSRWGGDGFYAMDYWGQGTLVTVSSASGGGGSGGGGSGGGGSHASDI QMTQSPSSLSASVGDRVTITCRASQDVNTAVAWYQQKPGKAPKLLIYSASFLYSGV PSRFSGSRSGTDFTLTISSLQPEDFATYYCQQHYTTPPTFGQGTKVEIKGKPIPNPLL GLDST |

Example 33

Selection and Binding of LRRC15 and IFNα Specific Dual Binding Antibodies

This example describes isolation of sensor domains of the present disclosure, specifically, selection of LRRC15 and IFNα specific dual binding antibodies (DBAs). Anti-LRRC15 and anti-IFNα DBAs were isolated from the IFNα Tumbler antibody phage display library described in EXAMPLE 31. The selection was similar to the protocol described in EXAMPLE 1, using one round of IFNα selection (IFNα2b, GenScript, Z03002, biotinylated using standard protocols) and one round of LRRC15 selection (LRRC15-hFc, Sino Biologicals, 15786-H02H).

Figures 28A, 28B:
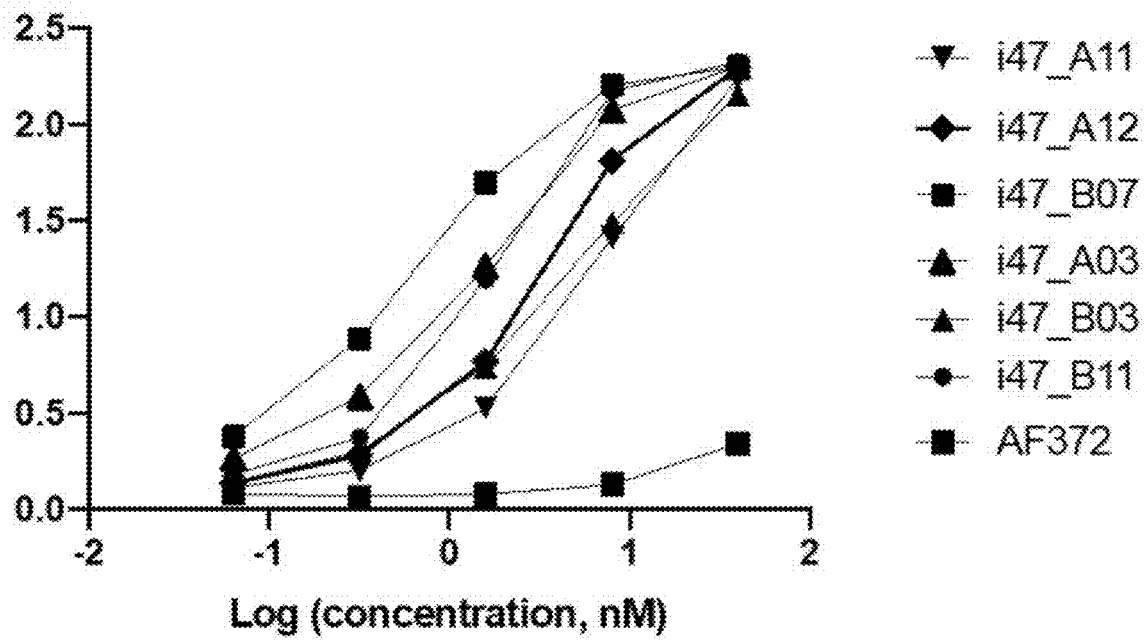
FIG. 28A provides ELISA binding data for six scFvs to LRRC15. Results from FIG. 28A are summarized in FIG. 28B.
Figure 29A:
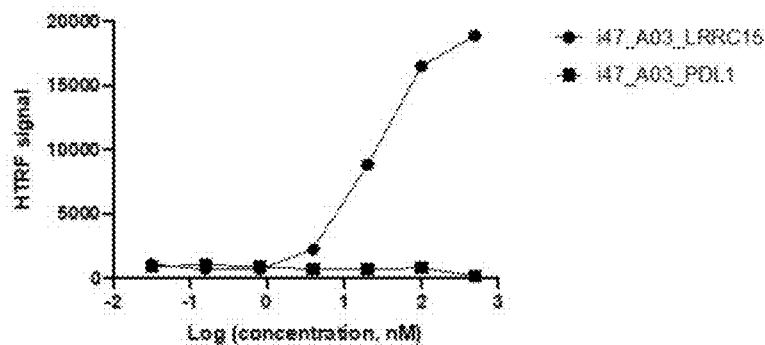
FIG. 29A, FIG. 29B, FIG. 29C, FIG. 29D, FIG. 29E, and FIG. 29F summarize IFNAR2 binding by four LRRC15-IFN-α DBA-IFNα complexes and two control complexes.
Figure 29B:
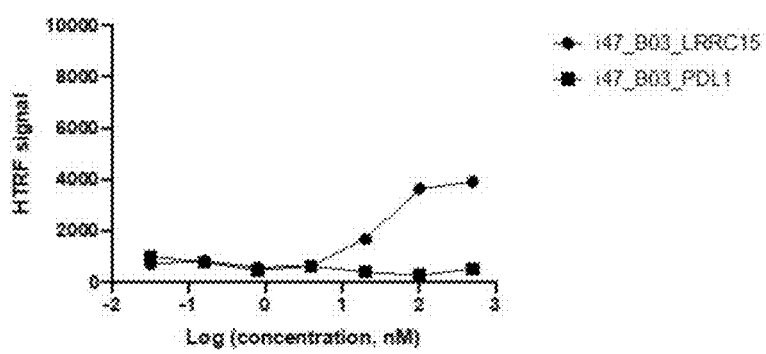
Figure 29C:
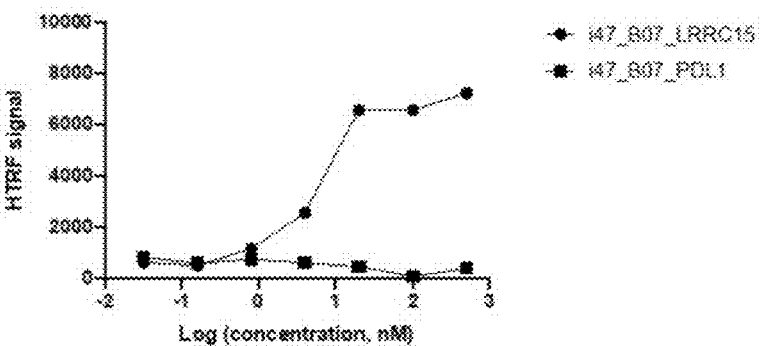
Figure 29D:
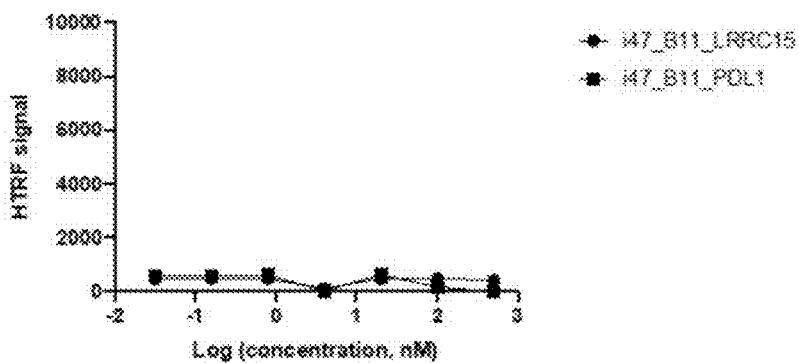
Figure 29E:
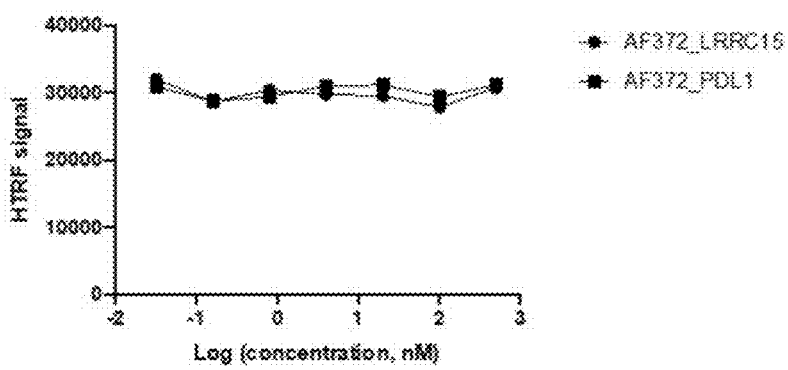
Figure 29F:
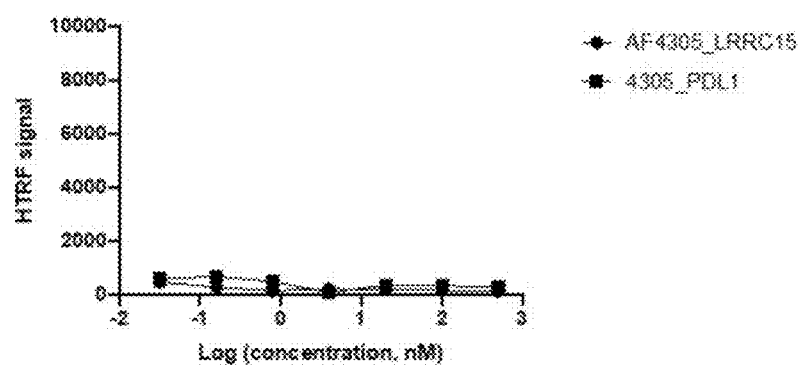

After a first round of selection in phage on 100 nM IFNα and a second round on 100 nM LRRC15, the resulting library of DBAs was subcloned into a yeast surface display vector and transformed into yeast for further screening using standard protocols. The yeast library was sorted four times for binding to LRRC15 and IFNα. In each round of sorting, the library was labeled with either LRRC15-Fc-biotin or IFNα-biotin, then with Streptavidin-PE (Abcam #ab239759) and sorted based on PE fluorescence on a Sony MA900 cell sorter. The four sorts were carried out with labelling at 100 nM LRRC15-Fc-biotin, 1000 nM IFNα-biotin, 10 nM LRRC15-Fc-biotin, and 10 nM LRRC15-Fc-biotin. Plasmids were rescued from the yeast after the final sort using a Zymoprep Yeast Plasmid Miniprep II kit (Zymo research D2004) and transformed into DH5a E. coli for cloning. Ninety-six colonies were picked for Sanger sequencing, from which twenty-four unique clones were identified and screened for IFNα and LRRC15 binding. The scFv DNA sequence for each clone, including c-myc and V5 tags, was amplified by PCR using a forward primer containing a T7 promoter and a translation initiation site, and a reverse primer containing a T7 terminator. Proteins were expressed using the PUREfrex2.1 cell-free transcription/translation system as described in previous examples. The scFv samples were subjected to ELISA analysis to detect LRRC15 and IFNα binding. FIG. 28A shows the ELISA binding data for six exemplary scFvs to LRRC15. Because the IFNα binding affinity was too low to detect by ELISA for some scFvs, the binding to IFNα was also measured by Biolayer Interferometry (OctetRED96e) as described in Example 5. Results and antibody sequences are tabulated in FIG. 28B. All six show binding to both LRRC15 and IFNα, with binding to LRRC15 detectable at a lower concentration of the antigen. Protein complex sequences are provided in TABLE 31.

TABLE 31

DBA-cytokine protein complexes, and control protein complexes

| Protein Complex | SEQ ID NO: | Sequence |
|---|---|---|
| A03 | SEQ ID NO: 262 | MSTSTQVQLVQSGAEVKKPGASVKVSCKASGYTFTGYYMHWVRQAPGQGLEW MGWMDPNNDDADYAQRFQGRVTMTRDTSTSTVYMELSSLRSEDTAVYYCASLA AAGPYYYYGMDVWGQGTLVTVSSASGGGGSGGGGSGGGGSHASDIQMTQSPS SLSASVGDRVTITCRASQSINNYLNWYQQKPGKAPKLLIYGASNLETGVPSRFSGSG SGTDFTLTISSLQPEDFATYYCQQSYGTPLTFGGGTKVEIKRAAAGSGSEQKLISEED LGKPIPNPLLGLDST |
| i47_A11 | SEQ ID NO: 314 | MSTSTQVQLVQSGAEVKKPGSSVKVSCKASGYTFTSYDINWVRQA PGQGLEWMGTINPSDGDTTYAQKFQGRVTITADESTSTAYMELSSL RSEDTAVYYCARVGGWGIYYYYGMDVWGQGTLVTVSSASGGGG SGGGGSGGGGSHASDIQMTQSPSSLSASVGDRVTITCRASQSINSW LAWYQQKPGKAPKLLIYAASSLQSGVPSRFSGSGSGTDFTLTISSLQ PEDFATYYCQQTYTVPFSFGQGTKLEIKRAAAGSGSEQKLISEEDLG KPIPNPLLGLDST |
| i47_A12 | SEQ ID NO: 315 | MSTSTQVQLVQSGAEVKKPGSSVKVSCKASGYTFINNDINWVRQA PGQGLEWMGGTIPIFGVHIYAQKFQGRVTITADESTSTAYMELSSL RSEDTAVYYCVSSVGAGAYYYYGMDVWGQGTLVTVSSASGGGG SGGGGSGGGGSHASDIQMTQSPSSLSASVGDRVTITCQASQDISNY LNWYQQKPGKAPKLLIYAASSLQSGVPSRFSGSGSGTDFTLTISSLQ PEDFATYYCQQSYSLPYTFGQGTRLEIKRAAAGSGSEQKLISEEDLG KPIPNPLLGLDST |
| B03 | SEQ ID NO: 263 | MSTSTQVQLVQSGAEVKKPGASVEVSCKASGGTFSSYAINWVRQAPGQGLEWM GWIDPKSGDTTYAQKFQGRVTMTRDTSTSTVYMELSSLRSEDTAVYYCASGGSYSP WYFDLWGQGTLVTVSSASGGGGSGGGGSGGGGSHASDIQMTQSPSSLSASVGD RVTITCRASQSISSWLAWYQQKSGKAPKLLIYAASSLQSGVPSRFSGSGSGTDFTLTI SSLQPEDFATYYCQQAYSFPFTFGPGTKVDIKRAAAGSGSEQKLISEEDLGKPIPNPL LGLDST |
| B07 | SEQ ID NO: 264 | MSTSTQVQLVQSGAEVKKPGASVKVSCKASGYTFTGYYMHWVRQAPGQGLEW MGWMDPNNDDADYAQRFQGRVTMTRDTSTSTVYMELSSLRSEDTAVYYCASLA AAGPYYYYGMDVWGQGTLVTVSSASGGGGSGGGGSGGGGSHASDIQMTQSPS SLSASVGDRVTITCQASQDISNYLNWYQQKPGKAPKLLIYGASILEAGVPSRFSGSG SGTDFTLTISSLQPEDFATYYCQQSYSAPITFGQGTRLEIKRAAAGSGSEQKLISEEDL GKPIPNPLLGLDST |
| B11 | SEQ ID NO: 265 | MSTSTQVQLVQSGAEVKKPGSSVKVSCKASGYTFTSYDINWVRQAPGQGLEWLG GTVPLFGISHYAQKFQGRVTITADESTSTAYMELSSLRSEDTAVYYCVSSVGAGAYY YQGLDVWGQGTLVTVSSASGGGGSGGGGSGGGGSHASDIQMTQSPSSLSASVG DRVTITCRASQSISSYLNWYQQKPGKAPKLLIYAASSLQSGVPSRFSGSGSGTDFTLT ISSLLPEDFATYYCQQSYLPPYSFGQGTKLEIKRAAAGSGSEQKLISEEDLGKPIPNPLL GLDST |
| AF372 | SEQ ID NO: 258 | MSTSTEQKLISEEDLEVQLVESGGGLVQPGGSLRLSCAASGFNIKDTYIHWVRQAP GKGLEWVARIYPTNGYTRYADSVKGRFTISADTSKNTAYLQMNSLRAEDTAVYYCS RWGGDGFYAMDYWGQGTLVTVSSASGGGGSGGGGSGGGGSHASDIQMTQSP SSLSASVGDRVTITCRASQDVNTAVAWYQQKPGKAPKLLIYSASFLYSGVPSRFSGS RSGTDFTLTISSLQPEDFATYYCQQHYTTPPTFGQGTKVEIKGSGLNDIFEAQKIEW HEGKPIPNPLLGLDST |

Example 34

Regulated IFNAR2 (IFNα Receptor 2) Binding by a LRRC15-IFNα Dual Binding Antibody (DBA) Cytokine Complex This example describes LRRC15 dependent binding of IFN to the receptor IFNAR2 by LRRC15/IFN DBA-cytokine complexes. The cytokine complexes of this example are composed of a LRRC15-IFN-α DBA IgG with IFN-α linked to the N-terminus of one heavy chain (a schematic of the structure is shown in FIG. 9B). DBA-cytokine complexes AF4581 (SEQ ID NO: 266-268), AF4586 (SEQ ID NO: 269-271), AF4587 (SEQ ID NO: 266-267, 272) and AF4588 (SEQ ID NO: 273-275) were chosen for analysis. Two cytokine complexes with the same structure were included as controls: AF4305 (SEQ ID NO: 294-296), which is based on a neutralizing anti-IFNα antibody, and AF4306 (SEQ ID NO: 64, 192, 297), which is based on an anti-Her2 antibody. Protein complex sequences are provided in TABLE 32. The six IgG-cytokines were expressed in mammalian cells using standard protocols and added to a 384 well plate at a single dilution. Titrating concentrations of either LRRC15-Fc (SINO Biological), PDL1-Fc (ACROBiosystems) or CEA-Fc (SINO Biological) were added, and the plate was incubated for 30 minutes at room temperature. Eu-labeled IFNAR2 (ACROBiosystems) and Alexa Fluor 647-labeled anti-V5 antibody (Perkin Elmer) were added to all wells and incubated for 24 hours at room temperature. The HTRF signal was then read on an Envision 2105 microplate reader (Perkin Elmer). Results shown in FIGS. 29A-F demonstrate IFNAR2 binding increased in a dose dependent manner with the addition of LRRC15 but not with the addition of control protein PDL1 for DBA-cytokine complexes of AF4581, AF4586 and AF4587, demonstrating LRRC15-dependent regulation of IFNAR-binding activity. IFNAR2 binding from AF4588 and the monospecific IFN scFv cytokine complexes AF4305 and AF4306 did not change with the addition of LRRC15 or PD-L1.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

TABLE 32

DBA-cytokine protein complexes, and control protein complexes

| Protein Complex | SEQ ID NO: | Sequence |
|---|---|---|
| AF4581 | SEQ ID NO: 266 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSQVQLVQSGAEVKKPGASVKVSCKASGYTFTGYYMHWV RQAPGQGLEWMGWMDPNNDDADYAQRFQGRVTMTRDTSTSTVYMELSSLRS EDTAVYYCASLAAAGPYYYYGMDVWGQGTLVTVSSAKTTAPSVYPLAPVCGDTTG SSVTLGCLVKGYFPEPVTLTWNSGSLSSGVHTFPAVLQSDLYTLSSSVTVTSSTWPS QSITCNVAHPASSTKVDKKIEPRGPTIKPCPPCKCPAPNAAGGPSVFIFPPKIKDVLM ISLSPIVTCVVVDVSEDDPDVQISWFVNNVEVHTAQTQTHREDYNSTLRVVSALPI QHQDWMSGKEFKCKVNNKDLGAPIERTISKPKGSVRAPQVYVLPPPEEEMTKKQ VTLTCMVTDFMPEDIYVEWTNNGKTELNYKNTEPVLDSDGSYFMYSDLRVEKKN WVERNSYSCSVVHEGLHNHHTTESFSRTPGK |
| | SEQ ID NO: 267 | QVQLVQSGAEVKKPGASVKVSCKASGYTFTGYYMHWVRQAPGQGLEWMGWM DPNNDDADYAQRFQGRVTMTRDTSTSTVYMELSSLRSEDTAVYYCASLAAAGPYY YYGMDVWGQGTLVTVSSAKTTAPSVYPLAPVCGDTTGSSVTLGCLVKGYFPEPVTL TWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVVVDSEDDPD VQISWFVNNVEVHTAQTQTHREDYNSTLRVVSALPIQHQDWMSGKEFKCKVNN KDLGAPIERTISKPKGSVRAPQVYVLPPPEKEMTKKQVSLTCLVKDFMPEDIYVEWT NNGKTELNYKNTEPVLKSDGSYFMYSKLTVEKKNWVERNSYSCSVVHEGLHNHHT TKSFSRTPGK |
| | SEQ ID NO: 268 | DIQMTQSPSSLSASVGDRVTITCRASQSINNYLNWYQQKPGKAPKLLIYGASNLET GVPSRFSGSGSGTDFTLTISSLQPEDFATYYCQQSYGTPLTFGGGTKVEIKRADAAPT VSIFPPSSEQLTSGGASVVCFLNNFYPKDINVKWKIDGSERQNGVLNSWTDQDSK DSTYSMSSTLTLTKDEYERHNSYTCEATHKTSTSPIVKSFNRNEC |
| AF4586 | SEQ ID NO: 269 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSQVQLVQSGAEVKKPGASVEVSCKASGGTFSSYAINWVR QAPGQGLEWMGWIDPKSGDTTYAQKFQGRVTMTRDTSTSTVYMELSSLRSEDT AVYYCASGGSYSPWYFDLWGQGTLVTVSSAKTTAPSVYPLAPVCGDTTGSSVTLG CLVKGYFPEPVTLTWNSGSLSSGVHTFPAVLQSDLYTLSSSVTVTSSTWPSQSITCN VAHPASSTKVDKKIEPRGPTIKPCPPCKCPAPNAAGGPSVFIFPPKIKDVLMISLSPIV TCVVVDVSEDDPDVQISWFVNNVEVHTAQTQTHREDYNSTLRVVSALPIQHQDW MSGKEFKCKVNNKDLGAPIERTISKPKGSVRAPQVYVLPPPEEEMTKKQVTLTCMV TDFMPEDIYVEWTNNGKTELNYKNTEPVLDSDGSYFMYSDLRVEKKNWVERNSYS CSVVHEGLHNHHTTESFSRTPGK |
| | SEQ ID NO: 270 | QVQLVQSGAEVKKPGASVEVSCKASGGTFSSYAINWVRQAPGQGLEWMGWIDP KSGDTTYAQKFQGRVTMTRDTSTSTVYMELSSLRSEDTAVYYCASGGSYSPWYFDL WGQGTLVTVSSAKTTAPSVYPLAPVCGDTTGSSVTLGCLVKGYFPEPVTLTWNSGS LSSGVHTFPAVLQSDLYTLSSSVTVTSSTWPSQSITCNVAHPASSTKVDKKIEPRGPT IKPCPPCKCPAPNAAGGPSVFIFPPKIKDVLMISLSPIVTCVVVDSEDDPDVQISWF VNNVEVHTAQTQTHREDYNSTLRVVSALPIQHQDWMSGKEFKCKVNNKDLGAPI ERTISKPKGSVRAPQVYVLPPPEKEMTKKQVSLTCLVKDFMPEDIYVEWTNNGKTE LNYKNTEPVLKSDGSYFMYSKLTVEKKNWVERNSYSCSVVHEGLHNHHTTKSFSRT PGK |
| | SEQ ID NO: 271 | DIQMTQSPSSLSASVGDRVTITCRASQSISSWLAWYQQKSGKAPKLLIYAASSLQSG VPSRFSGSGSGTDFTLTISSLQPEDFATYYCQQAYSFPFTFGPGTKVDIKRADAAPTV SIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC |
| AF4587 | SEQ ID NO: 266 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSQVQLVQSGAEVKKPGASVKVSCKASGYTFTGYYMHWV RQAPGQGLEWMGWMDPNNDDADYAQRFQGRVTMTRDTSTSTVYMELSSLRS EDTAVYYCASLAAAGPYYYYGMDVWGQGTLVTVSSAKTTAPSVYPLAPVCGDTTG SSVTLGCLVKGYFPEPVTLTWNSGSLSSGVHTFPAVLQSDLYTLSSSVTVTSSTWPS QSITCNVAHPASSTKVDKKIEPRGPTIKPCPPCKCPAPNAAGGPSVFIFPPKIKDVLM |

TABLE 32-continued

DBA-cytokine protein complexes, and control protein complexes

| Protein Complex | SEQ ID NO: | Sequence |
|---|---|---|
| | | ISLSPIVTCVVVDVSEDDPDVQISWFVNNVEVHTAQTQTHREDYNSTLRVVSALPI QHQDWMSGKEFKCKVNNKDLGAPIERTISKPKGSVRAPQVYVLPPPEEEMTKKQ VTLTCMVTDFMPEDIYVEWTNNGKTELNYKNTEPVLDSDGSYFMYSDLRVEKKN WVERNSYSCSVVHEGLHNHHTTESFSRTPGK |
| | SEQ ID NO: 267 | QVQLVQSGAEVKKPGASVKVSCKASGYTFTGYYMHWVRQAPGQGLEWMGWM DPNNDDADYAQRFQGRVTMTRDTSTSTVYMELSSLRSEDTAVYYCASLAAAGPYY YYGMDVWGQGTLVTVSSAKTTAPSVYPLAPVCGDTTGSSVTLGCLVKGYFPEPVTL TWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVVVDSEDDPD VQISWFVNNVEVHTAQTQTHREDYNSTLRVVSALPIQHQDWMSGKEFKCKVNN KDLGAPIERTISKPKGSVRAPQVYVLPPPEKEMTKKQVSLTCLVKDFMPEDIYVEWT NNGKTELNYKNTEPVLKSDGSYFMYSKLTVEKKNWVERNSYSCSVVHEGLHNHHT TKSFSRTPGK |
| | SEQ ID NO: 272 | DIQMTQSPSSLSASVGDRVTITCQASQDISNYLNWYQQKPGKAPKLLIYGASILEAG VPSRFSGSGSGTDFTLTISSLQPEDFATYYCQQSYSAPITFGQGTRLEIKRADAAPTV SIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC |
| AF4588 | SEQ ID NO: 273 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSQVQLVQSGAEVKKPGSSVKVSCKASGYTFTSYDINWVRQ APGQGLEWLGGTVPLFGISHYAQKFQGRVTITADESTSTAYMELSSLRSEDTAVYY CVSSVGAGAYYYQGLDVWGQGTLVTVSSAKTTAPSVYPLAPVCGDTTGSSVTLGC LVKGYFPEPVTLTWNSGSLSSGVHTFPAVLQSDLYTLSSSVTVTSSTWPSQSITCNV AHPASSTKVDKKIEPRGPTIKPCPPCKCPAPNAAGGPSVFIFPPKIKDVLMISLSPIVT CVVVDSEDDPDVQISWFVNNVEVHTAQTQTHREDYNSTLRVVSALPIQHQDW MSGKEFKCKVNNKDLGAPIERTISKPKGSVRAPQVYVLPPPEEEMTKKQVTLTCMV TDFMPEDIYVEWTNNGKTELNYKNTEPVLDSDGSYFMYSDLRVEKKNWVERNSYS CSVVHEGLHNHHTTESFSRTPGK |
| | SEQ ID NO: 274 | QVQLVQSGAEVKKPGSSVKVSCKASGYTFTSYDINWVRQAPGQGLEWLGGTVPL FGISHYAQKFQGRVTITADESTSTAYMELSSLRSEDTAVYYCVSSVGAGAYYYQGLD VWGQGTLVTVSSAKTTAPSVYPLAPVCGDTTGSSVTLGCLVKGYFPEPVTLTWNS GSLSSGVHTFPAVLQSDLYTLSSSVTVTSSTWPSQSITCNVAHPASSTKVDKKIEPRG PTIKPCPPCKCPAPNAAGGPSVFIFPPKIKDVLMISLSPIVTCVVVDSEDDPDVQIS WFVNNVEVHTAQTQTHREDYNSTLRVVSALPIQHQDWMSGKEFKCKVNNKDLG APIERTISKPKGSVRAPQVYVLPPPEKEMTKKQVSLTCLVKDFMPEDIYVEWTNNG KTELNYKNTEPVLKSDGSYFMYSKLTVEKKNWVERNSYSCSVVHEGLHNHHTTKSF SRTPGK |
| | SEQ ID NO: 275 | DIQMTQSPSSLSASVGDRVTITCRASQSISSYLNWYQQKPGKAPKLLIYAASSLQSG VPSRFSGSGSGTDFTLTISSLLPEDFATYYCQQSYLPPYSFGQGTKLEIKRADAAPTVS IFPPSSEQLTSGGASVVCFLNNFYPKDINVKWKIDGSERQNGVLNSWTDQDSKDST YSMSSTLTLTKDEYERHNSYTCEATHKTSTSPIVKSFNRNEC |
| AF4305 | SEQ ID NO: 294 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSQVQLVQSGAEVKKPGSSVKVSCKASGYTFTAYDINWVR QAPGQGLEWVGIINPGSGSPMYAQKFQGRVTITADESTSTAYMELSSLRSEDTAV YYCVSSVGAGAYYYQGLDVWGQGTLVTVSSAKTTAPSVYPLAPVCGDTTGSSVTL GCLVKGYFPEPVTLTWNSGSLSSGVHTFPAVLQSDLYTLSSSVTVTSSTWPSQSITC NVAHPASSTKVDKKIEPRGPTIKPCPPCKCPAPNAAGGPSVFIFPPKIKDVLMISLSPI VTCVVVDSEDDPDVQISWFVNNVEVHTAQTQTHREDYNSTLRVVSALPIQHQD WMSGKEFKCKVNNKDLGAPIERTISKPKGSVRAPQVYVLPPPEEEMTKKQVTLTC MVTDFMPEDIYVEWTNNGKTELNYKNTEPVLDSDGSYFMYSDLRVEKKNWVERN SYSCSVVHEGLHNHHTTESFSRTPGK |
| | SEQ ID NO: 295 | QVQLVQSGAEVKKPGSSVKVSCKASGYTFTAYDINWVRQAPGQGLEWVGIINPGS GSPMYAQKFQGRVTITADESTSTAYMELSSLRSEDTAVYYCVSSVGAGAYYYQGLD VWGQGTLVTVSSAKTTAPSVYPLAPVCGDTTGSSVTLGCLVKGYFPEPVTLTWNS GSLSSGVHTFPAVLQSDLYTLSSSVTVTSSTWPSQSITCNVAHPASSTKVDKKIEPRG PTIKPCPPCKCPAPNAAGGPSVFIFPPKIKDVLMISLSPIVTCVVVDSEDDPDVQIS WFVNNVEVHTAQTQTHREDYNSTLRVVSALPIQHQDWMSGKEFKCKVNNKDLG APIERTISKPKGSVRAPQVYVLPPPEKEMTKKQVSLTCLVKDFMPEDIYVEWTNNG KTELNYKNTEPVLKSDGSYFMYSKLTVEKKNWVERNSYSCSVVHEGLHNHHTTKSF SRTPGGGSGGGSHHHHHH |
| | SEQ ID NO: 296 | DIQMTQSPSSLSASVGDRVTITCQASQDIANYLNWYQQKPGKAPKLLIYSASNLQS GVPSRFSGSGSGTDFTLTISSLQPEDFATYYCQQSYSTQWTFGQGTKVEIKRADAA PTVSIFPPSSEQLTSGGASVVCFLNNFYPKDINVKWKIDGSERQNGVLNSWTDQDS KDSTYSMSSTLTLTKDEYERHNSYTCEATHKTSTSPIVKSFNRNEC |

TABLE 32-continued

DBA-cytokine protein complexes, and control protein complexes

| Protein Complex | SEQ ID NO: | Sequence |
|---|---|---|
| AF4306 | SEQ ID NO: 64 | DIQMTQSPSSLSASVGDRVTITCRASQDVNTAVAWYQQKPGKAPKLLIYSASFLYS GVPSRFSGSRSGTDFTLTISSLQPEDFATYYCQQHYTTPPTFGQGTKVEIKRADAAP TVSIFPPSSEQLTSGGASVVCFLNNFYPKDINVKWKIDGSERQNGVLNSWTDQDSK DSTYSMSSTLTLTKDEYERHNSYTCEATHKTSTSPIVKSFNRNEC |
|  | SEQ ID NO: 192 | EVQLVESGGGLVQPGGSLRLSCAASGFNIKDTYIHWVRQAPGKGLEWVARIYPTNGYTRY ADSVKGRFTISADTSKNTAYLQMNSLRAEDTAVYYCSRWGGDGFYAMDYWGQGTLVTVS SAKTTAPSVYPLAPVCGDTTGSSVTLGCLVKGYFPEPVTLTWNSGSLSSGVHTFPAVLQSDL YTLSSSVTVTSSTWPSQSITCNVAHPASSTKVDKKIEPRGPTIKPCPPCKCPAPNAAGGPSVF IFPPKIKDVLMISLSPIVTCVVVDVSEDDPDVQISWFVNNVEVHTAQTQTHREDYNSTLRVV SALPIQHQDWMSGKEFKCKVNNKDLGAPIERTISKPKGSVRAPQVYVLPPPEKEMTKKQV SLTCLVKDFMPEDIYVEWTNNGKTELNYKNTEPVLKSDGSYFMYSKLTVEKKNWVERNSYS CSVVHEGLHNHHTTKSFSRTPGGGSGGGSHHHHHH |
|  | SEQ ID NO: 297 | CDLPQTHSLGSRRTLMLLAQMRRISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKEGGGGS GGGGSGGGGSGGGGSEVQLVESGGGLVQPGGSLRLSCAASGFNIKDTYIHWVRQ APGKGLEWVARIYPTNGYTRYADSVKGRFTISADTSKNTAYLQMNSLRAEDTAVYY CSRWGGDGFYAMDYWGQGTLVTVSSAKTTAPSVYPLAPVCGDTTGSSVTLGCLV KGYFPEPVTLTWNSGSLSSGVHTFPAVLQSDLYTLSSSVTVTSSTWPSQSITCNVAH PASSTKVDKKIEPRGPTIKPCPPCKCPAPNAAGGPSVFIFPPKIKDVLMISLSPIVTCV VVDVSEDDPDVQISWFVNNVEVHTAQTQTHREDYNSTLRVVSALPIQHQDWMS GKEFKCKVNNKDLGAPIERTISKPKGSVRAPQVYVLPPPEEEMTKKQVTLTCMVTD FMPEDIYVEWTNNGKTELNYKNTEPVLDSDGSYFMYSDLRVEKKNWVERNSYSCS VVHEGLHNHHTTESFSRTPGK |

What is claimed is:

1. A method of selectively activating cytokine receptor signaling in a presence of a marker, the method comprising:

(a) obtaining a self-regulating complex that adopts an inactive state in an absence of the marker and an active state in the presence of the marker, the self-regulating complex comprising a cytokine and a sensor domain, wherein the cytokine is linked to the sensor domain by a flexible linker, wherein the sensor domain is a dual-binding antibody comprising a heavy chain variable domain and a light chain variable domain; wherein the sensor domain comprises a binding affinity for the cytokine and a binding affinity for the marker, wherein the cytokine and the marker compete for binding to the sensor domain and the sensor domain binds the cytokine and the marker, but not both simultaneously;

(b) binding the sensor domain to the cytokine, thereby blocking the cytokine from binding to its cytokine receptor and rendering the cytokine inactive;

(c) contacting the self-regulating complex to the marker, wherein upon the contacting:

(i) the sensor domain binds to the marker;

(ii) the sensor domain is blocked from binding the cytokine; and (iii) the cytokine is capable of binding to its cytokine receptor; and (d) contacting the self-regulating complex to the cytokine receptor, wherein the cytokine binds to the cytokine receptor, thereby selectively activating the cytokine receptor signaling in the presence of the marker;

wherein:

(I) the heavy chain variable domain and the light chain variable domain are present in a Fab of an immunoglobulin G (IgG) isotype antibody, wherein a C-terminus of the cytokine is joined to an N-terminus of the heavy chain variable domain or the light chain variable domain by the flexible linker;

(II) the heavy chain variable domain and the light chain variable domain are present in a single chain variable fragment (scFv), wherein the C-terminus of the cytokine is joined to the N-terminus of the heavy chain variable domain or the light chain variable domain by the flexible linker; or (III) the heavy chain variable domain and the light chain variable domain are present in a scFv, wherein an N-terminus of the scFv is joined to a C-terminus of a first heavy chain of an IgG isotype antibody, and an N-terminus of the cytokine is joined to a C-terminus of a second heavy chain of the IgG isotype antibody;

wherein:

the marker is human Leucine Rich Repeat Containing 15 (LRRC15) and the cytokine is human interferon (IFN)-α;

the marker is human Carcino Embryonic Antigen (CEA) and the cytokine is human IFN-α;

the marker is human PD-L1 and the cytokine is human IFN-α;

the marker is human PD-1 and the cytokine is human interleukin (IL)-2; or the marker is human PD-L1 and the cytokine is human IL-15.

2. The method of claim 1, wherein the activating the cytokine receptor signaling is reversible and upon unbinding of the sensor domain from the marker, the sensor domain re-binds to the cytokine, thereby rendering the cytokine therapeutically inactive.

3. The method of claim 1, wherein the cytokine receptor signaling is activated by the marker in a dose-dependent manner.

4. The method of claim 1, wherein the heavy chain variable domain and the light chain variable domain are present in the Fab of the IgG isotype antibody.

5. The method of claim 1, wherein the heavy chain variable domain and the light chain variable domain are present in the scFv.

6. The method of claim 1, wherein the self-regulating complex comprises two heavy chains and two light chains.

7. The method of claim 1, wherein the self-regulating complex comprises an Fc domain.

8. The method of claim 1, further comprising administering the self-regulating complex to a subject that has cancer.

9. The method of claim 8, wherein the self-regulating complex is administered systemically to the subject.

10. The method of claim 8, wherein on-target toxicity is reduced as compared to administration of a control compound comprising the cytokine, wherein the cytokine of the control compound is therapeutically active in the absence of the marker.

11. The method of claim 1, wherein the marker is the human LRRC15 and the cytokine is the human IFN-α.

12. The method of claim 1, wherein the marker is the human CEA and the cytokine is the human IFN-α.

13. The method of claim 1, wherein the flexible linker comprises at least five amino acids.

14. The method of claim 1, wherein the flexible linker has a length and flexibility to allow the cytokine to bind its cytokine receptor when the cytokine is not bound to the sensor domain.

15. The method of claim 14, wherein the flexible linker has a length and flexibility to favor binding of the cytokine to the sensor domain in the absence of the marker.

16. The method of claim 1, wherein the IgG isotype antibody is a human IgG isotype antibody.

17. The method of claim 1, wherein the marker is the human PD-L1 and the cytokine is the human IFN-α.

18. The method of claim 1, wherein the marker is human PD-1 and the cytokine is the human IL-2.

19. The method of claim 1, wherein the marker is the human PD-L1 and the cytokine is the human IL-15.

* * * * *

SEQUENCE LISTING

```
Sequence total quantity: 328
SEQ ID NO: 1              moltype = AA   length = 14
FEATURE                   Location/Qualifiers
REGION                    1..14
                          note = Description of Artificial Sequence: Synthetic peptide
REGION                    1..14
                          note = PDL1_DB01_F08 HCDR3
source                    1..14
                          mol_type = protein
                          organism = synthetic construct
SEQUENCE: 1
CARDRIAVAG FDYW                                                           14

SEQ ID NO: 2              moltype = AA   length = 13
FEATURE                   Location/Qualifiers
REGION                    1..13
                          note = Description of Artificial Sequence: Synthetic peptide
REGION                    1..13
                          note = PDL1_DB02_A08 HCDR3
source                    1..13
                          mol_type = protein
                          organism = synthetic construct
SEQUENCE: 2
CAKEVFSGWY DYW                                                            13

SEQ ID NO: 3              moltype = AA   length = 17
FEATURE                   Location/Qualifiers
REGION                    1..17
                          note = Description of Artificial Sequence: Synthetic peptide
REGION                    1..17
                          note = PDL1_DB02_D10 HCDR3
source                    1..17
                          mol_type = protein
                          organism = synthetic construct
SEQUENCE: 3
CTTDLLSLEL DDAFDIW                                                        17

SEQ ID NO: 4              moltype = AA   length = 19
FEATURE                   Location/Qualifiers
REGION                    1..19
```

```
                        note = Description of Artificial Sequence: Synthetic peptide
REGION                  1..19
                        note = PDL1_DB03_G11 HCDR3
source                  1..19
                        mol_type = protein
                        organism = synthetic construct
SEQUENCE: 4
CARSLFPTIF GVEVAFDIW                                                    19

SEQ ID NO: 5            moltype = AA  length = 14
FEATURE                 Location/Qualifiers
REGION                  1..14
                        note = Description of Artificial Sequence: Synthetic peptide
REGION                  1..14
                        note = PDL1_DB03_H02 HCDR3
source                  1..14
                        mol_type = protein
                        organism = synthetic construct
SEQUENCE: 5
CARDSYYYDS FDYW                                                         14

SEQ ID NO: 6            moltype = AA  length = 16
FEATURE                 Location/Qualifiers
REGION                  1..16
                        note = Description of Artificial Sequence: Synthetic peptide
REGION                  1..16
                        note = PDL1_DB04_A07 HCDR3
source                  1..16
                        mol_type = protein
                        organism = synthetic construct
SEQUENCE: 6
CARHGEWGSG WPFDYW                                                       16

SEQ ID NO: 7            moltype = AA  length = 21
FEATURE                 Location/Qualifiers
REGION                  1..21
                        note = Description of Artificial Sequence: Synthetic peptide
REGION                  1..21
                        note = PDL1_DB04_B08 HCDR3
source                  1..21
                        mol_type = protein
                        organism = synthetic construct
SEQUENCE: 7
CARDLLPAIF SGEVNDAFDI W                                                 21

SEQ ID NO: 8            moltype = AA  length = 14
FEATURE                 Location/Qualifiers
REGION                  1..14
                        note = Description of Artificial Sequence: Synthetic peptide
REGION                  1..14
                        note = PDL1_DB04_B09 HCDR3
source                  1..14
                        mol_type = protein
                        organism = synthetic construct
SEQUENCE: 8
CARETIAVAG FDPW                                                         14

SEQ ID NO: 9            moltype = AA  length = 20
FEATURE                 Location/Qualifiers
REGION                  1..20
                        note = Description of Artificial Sequence: Synthetic peptide
REGION                  1..20
                        note = PDL1_DB04_F02 HCDR3
source                  1..20
                        mol_type = protein
                        organism = synthetic construct
SEQUENCE: 9
CARDVLPTIF GVVSDAFDIW                                                   20

SEQ ID NO: 10           moltype = AA  length = 13
FEATURE                 Location/Qualifiers
REGION                  1..13
                        note = Description of Artificial Sequence: Synthetic peptide
REGION                  1..13
                        note = PDL1_DB04_F03 HCDR3
source                  1..13
                        mol_type = protein
                        organism = synthetic construct
SEQUENCE: 10
```

```
CARGDYGDYF DYW                                                              13

SEQ ID NO: 11           moltype = AA  length = 8
FEATURE                 Location/Qualifiers
REGION                  1..8
                        note = Description of Artificial Sequence: Synthetic peptide
REGION                  1..8
                        note = PD1_R04_C10
source                  1..8
                        mol_type = protein
                        organism = synthetic construct
SEQUENCE: 11
CAAGLFIW                                                                     8

SEQ ID NO: 12           moltype = AA  length = 8
FEATURE                 Location/Qualifiers
REGION                  1..8
                        note = Description of Artificial Sequence: Synthetic peptide
REGION                  1..8
                        note = PD1-R15-B02
source                  1..8
                        mol_type = protein
                        organism = synthetic construct
SEQUENCE: 12
CAGGWLDW                                                                     8

SEQ ID NO: 13           moltype = AA  length = 13
FEATURE                 Location/Qualifiers
REGION                  1..13
                        note = Description of Artificial Sequence: Synthetic peptide
REGION                  1..13
                        note = PD1-R07-D03
source                  1..13
                        mol_type = protein
                        organism = synthetic construct
SEQUENCE: 13
CARDHLGGSY QPW                                                              13

SEQ ID NO: 14           moltype = AA  length = 28
FEATURE                 Location/Qualifiers
REGION                  1..28
                        note = Description of Artificial Sequence: Synthetic peptide
REGION                  1..28
                        note = PD1-R07-C09
source                  1..28
                        mol_type = protein
                        organism = synthetic construct
SEQUENCE: 14
CARDLVGVSP GINYVPRYYY YYYGMDVW                                              28

SEQ ID NO: 15           moltype = AA  length = 19
FEATURE                 Location/Qualifiers
REGION                  1..19
                        note = Description of Artificial Sequence: Synthetic peptide
REGION                  1..19
                        note = PD1-R07-D05
source                  1..19
                        mol_type = protein
                        organism = synthetic construct
SEQUENCE: 15
CARDTGLGYY YGSGDFDYW                                                        19

SEQ ID NO: 16           moltype = AA  length = 15
FEATURE                 Location/Qualifiers
REGION                  1..15
                        note = Description of Artificial Sequence: Synthetic peptide
REGION                  1..15
                        note = PD1-R07-D06
source                  1..15
                        mol_type = protein
                        organism = synthetic construct
SEQUENCE: 16
CARSGYSYGY YFDYW                                                            15

SEQ ID NO: 17           moltype = AA  length = 13
FEATURE                 Location/Qualifiers
REGION                  1..13
                        note = Description of Artificial Sequence: Synthetic peptide
REGION                  1..13
```

```
                                note = PD1-R07-E05
source                          1..13
                                mol_type = protein
                                organism = synthetic construct
SEQUENCE: 17
CARTGGYPAI DSW                                                          13

SEQ ID NO: 18                   moltype = AA  length = 8
FEATURE                         Location/Qualifiers
REGION                          1..8
                                note = Description of Artificial Sequence: Synthetic peptide
REGION                          1..8
                                note = PD1-R07-A05
source                          1..8
                                mol_type = protein
                                organism = synthetic construct
SEQUENCE: 18
CASGWDVW                                                                 8

SEQ ID NO: 19                   moltype = AA  length = 12
FEATURE                         Location/Qualifiers
REGION                          1..12
                                note = Description of Artificial Sequence: Synthetic peptide
REGION                          1..12
                                note = PD1-R07-G12
source                          1..12
                                mol_type = protein
                                organism = synthetic construct
SEQUENCE: 19
CASSPLQWVD VW                                                           12

SEQ ID NO: 20                   moltype = AA  length = 8
FEATURE                         Location/Qualifiers
REGION                          1..8
                                note = Description of Artificial Sequence: Synthetic peptide
REGION                          1..8
                                note = PD1-R07-A10
source                          1..8
                                mol_type = protein
                                organism = synthetic construct
SEQUENCE: 20
CTSGMDVW                                                                 8

SEQ ID NO: 21                   moltype = AA  length = 245
FEATURE                         Location/Qualifiers
REGION                          1..245
                                note = Description of Artificial Sequence: Synthetic
                                 polypeptide
REGION                          1..245
                                note = PDL1-IFN-R01-A05
source                          1..245
                                mol_type = protein
                                organism = synthetic construct
SEQUENCE: 21
QVQLVQSGAE VKKPGASVKV SCKASGYTFS NYYIHWVRQA PGQGLEWMGW MDSNSGGTGY         60
AQKFQGRVTM TRDTSTSTVY MELSSLRSED TAVYYCAKEV FSGWYDYWGQ GTLVTVSSAS        120
GGGGSGGGGS GGGGSHASDI QMTQSPSSLS ASVGDRVTIT CRASQSISSY LNWYQQKPGK        180
APKLLIYAAS SLQSGVPSRF SGSGSGTDFT LTISSLQPED FATYYCQQSY STPYTFGQGT        240
KVEIK                                                                   245

SEQ ID NO: 22                   moltype = AA  length = 251
FEATURE                         Location/Qualifiers
REGION                          1..251
                                note = Description of Artificial Sequence: Synthetic
                                 polypeptide
REGION                          1..251
                                note = PDL1-IFN-R01-A06
source                          1..251
                                mol_type = protein
                                organism = synthetic construct
SEQUENCE: 22
QVQLVQSGAE VKKPGASVKV SCKASGGTFS SYAISWVRQA PGQGLEWVGW MDPKSGNTGY         60
AQKFQGRVTM TRDTSTSTVY MELSSLRSED TAVYYCARSL FPTIFGVEVA FDIWGQGTLV        120
TVSSASGGGG SGGGGSGGGG SHASDIQMTQ SPSSLSASVG DRVTITCQAS QDINNYLNWY        180
QQKPGKAPKL LIYKASSLEP GVPSRFSGSG SGTDFTLTIS SLQPEDFATY YCQKSNDVPF        240
TFGQGTKVEI K                                                            251

SEQ ID NO: 23                   moltype = AA  length = 251
FEATURE                         Location/Qualifiers
```

```
REGION                  1..251
                        note = Description of Artificial Sequence: Synthetic
                           polypeptide
REGION                  1..251
                        note = PDL1-IFN-R01-A11
source                  1..251
                        mol_type = protein
                        organism = synthetic construct
SEQUENCE: 23
QVQLVQSGAE VKKPGASVKV SCKASGGTFS SYYMHWVRQA PGQGLEWMGW MNPNSGNTGY    60
AQKFQGRVTM TRDTSTSTVY MELSSLRSED TAVYYCARSL FPTIFGVEVA FDIWGQGTLV   120
TVSSASGGGG SGGGGSGGGG SHASDIQMTQ SPSSLSASVG DRVTITCQAS QDITNYLNWY   180
QQKPGKAPKL LIYAASSLES GVPSRFSGSG SGTDFTLTIS SLQPEDFATY YCQQSYSIPI   240
TFGQGTRLEI K                                                       251

SEQ ID NO: 24           moltype = AA  length = 251
FEATURE                 Location/Qualifiers
REGION                  1..251
                        note = Description of Artificial Sequence: Synthetic
                           polypeptide
REGION                  1..251
                        note = PDL1-IFN-R01-B09
source                  1..251
                        mol_type = protein
                        organism = synthetic construct
SEQUENCE: 24
QVQLVQSGAE VKKPGASVKV SCKASGGTFT GYYMHWVRQA PGQGLEWMGW VNPNSGNTGY    60
AQKFQGRVTM TRDTSTSTVY MELSSLRSED TAVYYCARSL FPTIFGVEVA FDIWGQGTLV   120
TVSSASGGGG SGGGGSGGGG SHASDIQMTQ SPSSLSASVG DRVTITCQAS QDISNYLNWY   180
QQKPGKAPKL LIYAASSLQS GVPSRFSGSG SGTDFTLTIS SLQPEDFATY YCQQSYSPPP   240
TFGQGTKLEI K                                                       251

SEQ ID NO: 25           moltype = AA  length = 251
FEATURE                 Location/Qualifiers
REGION                  1..251
                        note = Description of Artificial Sequence: Synthetic
                           polypeptide
REGION                  1..251
                        note = PDL1-IFN-R01-B12
source                  1..251
                        mol_type = protein
                        organism = synthetic construct
SEQUENCE: 25
QVQLVQSGAE VKKPGASVKV SCKASGNTFT DYYMHWVRQA PGQGLEWMGW MNPNSGNTGY    60
AQKFQGRVTM TRDTSTSTVY MELSSLRSED TAVYYCARSL FPTIFGVEVA FDIWGQGTLV   120
TVSSASGGGG SGGGGSGGGG SHASDIQMTQ SPSSLSASVG DRVTITCQAS QDISNYLNWY   180
QQKPGKAPKL LIYAASSLQS GVPSRFSGSG SGTDFTLTIS SLQPEDFATY YCQQSYSTPP   240
TFGQGTRLEI K                                                       251

SEQ ID NO: 26           moltype = AA  length = 251
FEATURE                 Location/Qualifiers
REGION                  1..251
                        note = Description of Artificial Sequence: Synthetic
                           polypeptide
REGION                  1..251
                        note = PDL1-IFN-R01-C08
source                  1..251
                        mol_type = protein
                        organism = synthetic construct
SEQUENCE: 26
QVQLVQSGAE VKKPGASVKV SCKASGGTFS SYAISWVRQA PGQGLEWMGI IDPSVTYTRY    60
AQKFQGRVTM TRDTSTSTVY MELSSLRSED TAVYYCARSL FPTIFGVEVA FDIWGQGTLV   120
TVSSASGGGG SGGGGSGGGG SHASDIQMTQ SPSSLSASVG DRVTITCQAS QDISNYLNWY   180
QQKPGKAPKL LIYGASTLQS GVPSRFSGSG SGTDFTLTIS SLQPEDFATY YCQQTYSTPI   240
TFGQGTKVEI K                                                       251

SEQ ID NO: 27           moltype = AA  length = 251
FEATURE                 Location/Qualifiers
REGION                  1..251
                        note = Description of Artificial Sequence: Synthetic
                           polypeptide
REGION                  1..251
                        note = PDL1-IFN-R01-C11
source                  1..251
                        mol_type = protein
                        organism = synthetic construct
SEQUENCE: 27
QVQLVQSGAE VKKPGASVKV SCKASGGTFS SYAISWVRQA PGQGLEWMGW MDANNGNTGY    60
AQKFQGRVTM TRDTSTSTVY MELSSLRSED TAVYYCARSL FPTIFGVEVA FDIWGQGTLV   120
```

```
TVSSASGGGG  SGGGGSGGGG  SHASDIQMTQ  SPSSLSASVG  DRVTITCRAS  QSVSSYLNWY   180
QQKPGKAPKL  LIYKASSLES  GVPSRFSGSG  SGTDFTLTIS  SLQPEDFATY  YCQQSSSTPL   240
SFGGGTKVEI  K                                                           251

SEQ ID NO: 28           moltype = AA  length = 247
FEATURE                 Location/Qualifiers
REGION                  1..247
                        note = Description of Artificial Sequence: Synthetic
                         polypeptide
REGION                  1..247
                        note = anti-Her2 control (trastuzumab)
source                  1..247
                        mol_type = protein
                        organism = synthetic construct
SEQUENCE: 28
EVQLVESGGG  LVQPGGSLRL  SCAASGFNIK  DTYIHWVRQA  PGKGLEWVAR  IYPTNGYTRY    60
ADSVKGRFTI  SADTSKNTAY  LQMNSLRAED  TAVYYCSRWG  GDGFYAMDYW  GQGTLVTVSS   120
ASGGGGSGGG  GSGGGGSHAS  DIQMTQSPSS  LSASVGDRVT  ITCRASQDVN  TAVAWYQQKP   180
GKAPKLLIYS  ASFLYSGVPS  RFSGSRSGTD  FTLTISSLQP  EDFATYYCQQ  HYTTPPTFGQ   240
GTKVEIK                                                                 247

SEQ ID NO: 29           moltype = AA  length = 246
FEATURE                 Location/Qualifiers
REGION                  1..246
                        note = Description of Artificial Sequence: Synthetic
                         polypeptide
REGION                  1..246
                        note = Anti-PD-L1 control (atezolizumab)
source                  1..246
                        mol_type = protein
                        organism = synthetic construct
SEQUENCE: 29
EVQLVESGGG  LVQPGGSLRL  SCAASGFTFS  DSWIHWVRQA  PGKGLEWVAW  ISPYGGSTYY    60
ADSVKGRFTI  SADTSKNTAY  LQMNSLRAED  TAVYYCARRH  WPGGFDYWGQ  GTLVTVSSAA   120
SGGGGSGGGG  SGGGGSHASD  IQMTQSPSSL  SASVGDRVTI  TCRASQDVST  AVAWYQQKPG   180
KAPKLLIYSA  SFLYSGVPSR  FSGSGSGTDF  TLTISSLQPE  DFATYYCQQY  LYHPATFGQG   240
TKVEIK                                                                  246

SEQ ID NO: 30           moltype = AA  length = 248
FEATURE                 Location/Qualifiers
REGION                  1..248
                        note = Description of Artificial Sequence: Synthetic
                         polypeptide
REGION                  1..248
                        note = Anti-IFN control (rontalizumab)
source                  1..248
                        mol_type = protein
                        organism = synthetic construct
SEQUENCE: 30
EVQLVESGGG  LVQPGGSLRL  SCATSGYTFT  EYIIHWVRQA  PGKGLEWVAS  INPDYDITNY    60
NQRFKGRFTI  SLDKSKRTAY  LQMNSLRAED  TAVYYCASWI  SDFFDYWGQG  TLVTVSSASG   120
GGGSGGGGSG  GGGSHASDIQ  MTQSPSSLSA  SVGDRVTITC  RASQSVSTSS  YSYMHWYQQK   180
PGKAPKVLIS  YASNLESGVP  SRFSGSGSGT  DFTLTISSLQ  PEDFATYYCQ  HSWGIPRTFG   240
QGTKVEIK                                                                248

SEQ ID NO: 31           moltype = AA  length = 251
FEATURE                 Location/Qualifiers
REGION                  1..251
                        note = Description of Artificial Sequence: Synthetic
                         polypeptide
REGION                  1..251
                        note = PD1-IL2-R02-C02
source                  1..251
                        mol_type = protein
                        organism = synthetic construct
SEQUENCE: 31
QVQLVQSGAE  VKKPGVSVKV  SCKASGYTFP  RSYIHWVRQA  PGQGLEWMGW  INPHSGDTYY    60
AQNFQGRVTM  TRDTSTSTVY  MELSSLRSED  TAVYYCARDT  GLGYYYGSGD  FDYWGQGTLV   120
TVSSASGGGG  SGGGGSGGGG  SHASDIQMTQ  SPSSLSASVG  DRVTITCRAS  QSISRYLNWY   180
QQKPGKAPKL  LIYTASSLQS  GVPSRFSGSG  SGTDFTLTIS  SLQPEDFATY  YCQQANRFPL   240
TFGPGTKVDI  K                                                           251

SEQ ID NO: 32           moltype = AA  length = 251
FEATURE                 Location/Qualifiers
REGION                  1..251
                        note = Description of Artificial Sequence: Synthetic
                         polypeptide
REGION                  1..251
                        note = PD1-IL2-R02-C03
```

|      |      |      |
| ---- | ---- | ---- |
| source | 1..251<br>mol_type = protein<br>organism = synthetic construct | |
| SEQUENCE: 32 | | |
| QVQLVQSGAE VKKPGASVKV SCKASGYTFP RYHIHWVRQA PGQGLEWMGM INPSGGTTTY | | 60 |
| AQKFQGRVTM TRDTSTSTVY MELSSLRSED TAVYYCARDT GLGYYYGSGD FDYWGQGTLV | | 120 |
| TVSSASGGGG SGGGGSGGGG SHASDIQMTQ SPSSLSASVG DRVTITCRAS QSISSWLAWY | | 180 |
| QQKPGKAPKL LIYAASSLQS GVPSRFSGSG SGTDFTLTIS SLQPEDFATY YCQQSHSFPL | | 240 |
| TFGGGTKVEI K | | 251 |
| | | |
| SEQ ID NO: 33 | moltype = AA   length = 245 | |
| FEATURE | Location/Qualifiers | |
| REGION | 1..245<br>note = Description of Artificial Sequence: Synthetic<br>polypeptide | |
| REGION | 1..245<br>note = PD1-IL2-R06-E04 | |
| source | 1..245<br>mol_type = protein<br>organism = synthetic construct | |
| SEQUENCE: 33 | | |
| QVQLVQSGAE VKKPGASVKV SCKASGYTFT RYYIHWVRQA PGQGLEWMGW INAYNGDTNY | | 60 |
| AQKLQGRVTM TRDTSTSTVY MELSSLRSED TAVYYCARDS YYYDSFDYWG QGTLVTVSSA | | 120 |
| SGGGGSGGGG SGGGGSHASD IQMTQSPSSL SASVGDRVTI TCRASQTITD WLAWYQQKPG | | 180 |
| KAPKLLIYGA SNLQGGVPSR FSGSGSGTDF TLTISSLQPE DFATYYCQQY YSSWTFGQGT | | 240 |
| KVEIK | | 245 |
| | | |
| SEQ ID NO: 34 | moltype = AA   length = 246 | |
| FEATURE | Location/Qualifiers | |
| REGION | 1..246<br>note = Description of Artificial Sequence: Synthetic<br>polypeptide | |
| REGION | 1..246<br>note = PD1-IL2-R07-A09 | |
| source | 1..246<br>mol_type = protein<br>organism = synthetic construct | |
| SEQUENCE: 34 | | |
| QVQLVQSGAE VKKPGASVKV SCKASGYTFT SYYMHWVRQA PGQGLEWMGI INPSDGSTTY | | 60 |
| AQSFQGRVTM TRDTSTSTVY MELSSLRSED TAVYYCASGW DVWGQGTLVT VSSASGGGGS | | 120 |
| GGGGSGGGGS HASDIVMTQS PDSLAVSLGE RATINCKSSQ SVFSSANNKN YLAWYQQKPG | | 180 |
| QPPKLLIYWA STRESGVPDR FSGSGSGTDF TLTISSLQAE DVAVYYCQQY FGTPVTFGGG | | 240 |
| TKVEIK | | 246 |
| | | |
| SEQ ID NO: 35 | moltype = AA   length = 245 | |
| FEATURE | Location/Qualifiers | |
| REGION | 1..245<br>note = Description of Artificial Sequence: Synthetic<br>polypeptide | |
| REGION | 1..245<br>note = H_N36G | |
| source | 1..245<br>mol_type = protein<br>organism = synthetic construct | |
| SEQUENCE: 35 | | |
| QVQLVQSGAE VKKPGASVKV SCKASGYTFS GYYIHWVRQA PGQGLEWMGW MDSNSGGTGY | | 60 |
| AQKFQGRVTM TRDTSTSTVY MELSSLRSED TAVYYCAKEV FSGWYDYWGQ GTLVTVSSAS | | 120 |
| GGGGSGGGGS GGGGSHASDI QMTQSPSSLS ASVGDRVTIT CRASQSISSY LNWYQQKPGK | | 180 |
| APKLLIYAAS SLQSGVPSRF SGSGSGTDFT LTISSLQPED FATYYCQQSY STPYTFGQGT | | 240 |
| KVEIK | | 245 |
| | | |
| SEQ ID NO: 36 | moltype = AA   length = 245 | |
| FEATURE | Location/Qualifiers | |
| REGION | 1..245<br>note = Description of Artificial Sequence: Synthetic<br>polypeptide | |
| REGION | 1..245<br>note = H_I39V_S58P_Q69H_K70Q | |
| source | 1..245<br>mol_type = protein<br>organism = synthetic construct | |
| SEQUENCE: 36 | | |
| QVQLVQSGAE VKKPGASVKV SCKASGYTFS NYYVHWVRQA PGQGLEWMGW MDPNSGGTGY | | 60 |
| AHQFQGRVTM TRDTSTSTVY MELSSLRSED TAVYYCAKEV FSGWYDYWGQ GTLVTVSSAS | | 120 |
| GGGGSGGGGS GGGGSHASDI QMTQSPSSLS ASVGDRVTIT CRASQSISSY LNWYQQKPGK | | 180 |
| APKLLIYAAS SLQSGVPSRF SGSGSGTDFT LTISSLQPED FATYYCQQSY STPYTFGQGT | | 240 |
| KVEIK | | 245 |
| | | |
| SEQ ID NO: 37 | moltype = AA   length = 245 | |

```
FEATURE                    Location/Qualifiers
REGION                     1..245
                           note = Description of Artificial Sequence: Synthetic
                            polypeptide
REGION                     1..245
                           note = H_G64Y_Q69H
source                     1..245
                           mol_type = protein
                           organism = synthetic construct
SEQUENCE: 37
QVQLVQSGAE VKKPGASVKV SCKASGYTFS NYYIHWVRQA PGQGLEWMGW MDSNSGYTGY      60
AHKFQGRVTM TRDTSTSTVY MELSSLRSED TAVYYCAKEV FSGWYDYWGQ GTLVTVSSAS     120
GGGGSGGGGS GGGGSHASDI QMTQSPSSLS ASVGDRVTIT CRASQSISSY LNWYQQKPGK     180
APKLLIYAAS SLQSGVPSRF SGSGSGTDFT LTISSLQPED FATYYCQQSY STPYTFGQGT     240
KVEIK                                                                 245

SEQ ID NO: 38              moltype = AA   length = 245
FEATURE                    Location/Qualifiers
REGION                     1..245
                           note = Description of Artificial Sequence: Synthetic
                            polypeptide
REGION                     1..245
                           note = L_Q68E
source                     1..245
                           mol_type = protein
                           organism = synthetic construct
SEQUENCE: 38
QVQLVQSGAE VKKPGASVKV SCKASGYTFS NYYIHWVRQA PGQGLEWMGW MDSNSGGTGY      60
AQKFQGRVTM TRDTSTSTVY MELSSLRSED TAVYYCAKEV FSGWYDYWGQ GTLVTVSSAS     120
GGGGSGGGGS GGGGSHASDI QMTQSPSSLS ASVGDRVTIT CRASQSISSY LNWYQQKPGK     180
APKLLIYAAS SLESGVPSRF SGSGSGTDFT LTISSLQPED FATYYCQQSY STPYTFGQGT     240
KVEIK                                                                 245

SEQ ID NO: 39              moltype = AA   length = 245
FEATURE                    Location/Qualifiers
REGION                     1..245
                           note = Description of Artificial Sequence: Synthetic
                            polypeptide
REGION                     1..245
                           note = L_Q68E_E125D
source                     1..245
                           mol_type = protein
                           organism = synthetic construct
SEQUENCE: 39
QVQLVQSGAE VKKPGASVKV SCKASGYTFS NYYIHWVRQA PGQGLEWMGW MDSNSGGTGY      60
AQKFQGRVTM TRDTSTSTVY MELSSLRSED TAVYYCAKEV FSGWYDYWGQ GTLVTVSSAS     120
GGGGSGGGGS GGGGSHASDI QMTQSPSSLS ASVGDRVTIT CRASQSISSY LNWYQQKPGK     180
APKLLIYAAS SLESGVPSRF SGSGSGTDFT LTISSLQPED FATYYCQQSY STPYTFGQGT     240
KVDIK                                                                 245

SEQ ID NO: 40              moltype = DNA   length = 924
FEATURE                    Location/Qualifiers
misc_feature               1..924
                           note = Description of Artificial Sequence: Synthetic
                            polynucleotide
misc_feature               1..924
                           note = scFv_PDL1-IFN_R01_C08_gBlock
source                     1..924
                           mol_type = other DNA
                           organism = synthetic construct
SEQUENCE: 40
gcgaattaat acgactcact atagggctta agtataagga gaataatata tgtctacttc      60
aacagaacaa aagttaatta gtgaagaaga tttacaggtc cagttggttc agtcaggcgc     120
agaagtcaaa aagccgggag cgagtgtcaa agtatcttgt aaagcgagcg gtgtgacttc     180
tagtagttat gcgatttcct gggttcgcca agcccgggga cagggtctgg aatggatggg     240
tattattgac ccttccgtga cttacacccg ctacgctcag aaattccagg acgtgttac     300
catgacccgc gataccagca ccagtaccgt ttacatggaa ctttcctccc tgagatcgga     360
agacacggcc gtgtattatt gcgctcgctc actctttccg accatcttcg gcgttgaagt     420
cgccttcgac atctgggcc agggcacgct ggttacggta gttccgcaa gtggcggtcg     480
tggtagtggt ggaggtggat caggaggagg tggttctcac gcatcagaca ttcaaatgac     540
acagagtcca tcatccccttt ctgcctccgt gggtgaccgg gtgacgataa cctgccaagc     600
tagccaagac attagcaact atctgaactg gtaccagcaa aagcctggga agctccgaa     660
actattgatt tacggtgcgt cgactctcca gagtgggta cctagtcgtt tttccggttc     720
agggtcgggt acagattta cccttactat ttcctctctg cagccagaag actttgctac     780
ttattactgc caacagactt attcgactcc gattacgttt ggccaggaa ccaaagtcga     840
aatcaaaggc aagccgatcc cgaaccctc gctgggatta gacagcacgt aactagcata     900
accctctct aaacggaggg gttt                                             924

SEQ ID NO: 41              moltype = AA   length = 449
```

```
FEATURE                 Location/Qualifiers
REGION                  1..449
                        note = Description of Artificial Sequence: Synthetic
                         polypeptide
REGION                  1..449
                        note = AF2719 (H_I39V_S58P_Q69H_K70Q)
source                  1..449
                        mol_type = protein
                        organism = synthetic construct
SEQUENCE: 41
MSTSTCDLPQ THSLGSRRTL MLLAQMRRIS LFSCLKDRHD FGFPQEEFGN QFQKAETIPV    60
LHEMIQQIFN LFSTKDSSAA WDETLLDKFY TELYQQLNDL EACVIQGVGV TETPLMKEDS   120
ILAVRKYFQR ITLYLKEKKY SPCAWEVVRA EIMRSFSLST NLQESLRSKE GGGGSGGGGS   180
GGGGSGGGGS QVQLVQSGAE VKKPGASVKV SCKASGYTFS NYYVHWVRQA PGQGLEWMGW   240
MDPNSGGTGY AHQFQGRVTM TRDTSTSTVY MELSSLRSED TAVYYCAKEV FSGWYDYWGQ   300
GTLVTVSSAS GGGGSGGGGS GGGGSHASDI QMTQSPSSLS ASVGDRVTIT CRASQSISSY   360
LNWYQQKPGK APKLLIYAAS SLQSGVPSRF SGSGSGTDFT LTISSLQPED FATYYCQQSY   420
STPYTFGQGT KVEIKGKPIP NPLLGLDST                                    449

SEQ ID NO: 42           moltype = AA  length = 481
FEATURE                 Location/Qualifiers
REGION                  1..481
                        note = Description of Artificial Sequence: Synthetic
                         polypeptide
REGION                  1..481
                        note = PDL1-IFN_uIFN_2D10scFv_KiH_PDL1-IFN_1A05_H_N36G_Pep1
source                  1..481
                        mol_type = protein
                        organism = synthetic construct
SEQUENCE: 42
QVQLVQSGAE VKKPGASVKV SCKASGYTFT KNYMHWVRQA PGQGLEWLGW VSPDSGYTGY    60
AQKFQGRVTM TRDTSTSTVY MELSSLRSED TAVYYCTTDL LSLELDDAFD IWGQGTMVTV   120
SSASGGGGGS GGGGSGGGGSH ASDIQMTQSP SSLSASVGDR VTITCRASQS ISSWLAWYQQ   180
KPGKAPKLLI YAASTLQSGV PSRFSGSGSG TDFTLTISSL QPEDFATYYC QQSYSTPLTF   240
GGGTKLEIKP RGPTIKPCPP CKCPAPNAAG GPSVFIFPPK IKDVLMISLS PIVTCVVVDV   300
SEDDPDVQIS WFVNNVEVHT AQTQTHREDY NSTLRVVSAL PIQHQDWMSG KEFKCKVNNK   360
DLGAPIERTI SKPKGSVRAP QVYVLPPCEE EMTKKQVTLS CAVTDFMPED IYVEWTNNGK   420
TELNYKNTEP VLDSDGSYFM VSKLRVEKKN WVERNSYSCS VVHEGLHNHH TTKSFSRTPG   480
K                                                                  481

SEQ ID NO: 43           moltype = AA  length = 633
FEATURE                 Location/Qualifiers
REGION                  1..633
                        note = Description of Artificial Sequence: Synthetic
                         polypeptide
REGION                  1..633
                        note = PDL1-IFN_uIFN_2D10scFv_KiH_PDL1-IFN_1A05_H_N36G_Pep2
source                  1..633
                        mol_type = protein
                        organism = synthetic construct
SEQUENCE: 43
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GYTFSGYYIH WVRQAPGQGL EWMGWMDSNS   240
GGTGYAQKFQ GRVTMTRDTS TSTVYMELSS LRSEDTAVYY CAKEVFSGWY DYWGQGTLVT   300
VSSAKTTAPS VYPLAPVCGD TTGSSVTLGC LVKGYFPEPV TLTWNSGSLS SGVHTFPAVL   360
QSDLYTLSSS VTVTSSTWPS QSITCNVAHP ASSTKVDKKI EPRGPTIKPC PPCKCPAPNA   420
AGGPSVFIFP PKIKDVLMIS LSPIVTCVVV DVSEDDPDVQ ISWFVNNVEV HTAQTQTHRE   480
DYNSTLRVVS ALPIQHQDWM SGKEFKCKVN NKDLGAPIER TISKPKGSVR APQVCVLPPP   540
EEEMTKKQVT LWCMVTDFMP EDIYVEWTNN GKTELNYKNT EPVLDSDGSY FMYSKLRVEK   600
KNWVERNSYS CSVVHEGLHN HHTTKSFSRT PGK                                633

SEQ ID NO: 44           moltype = AA  length = 214
FEATURE                 Location/Qualifiers
REGION                  1..214
                        note = Description of Artificial Sequence: Synthetic
                         polypeptide
REGION                  1..214
                        note = PDL1-IFN_uIFN_2D10scFv_KiH_PDL1-IFN_1A05_H_N36G_Pep3
source                  1..214
                        mol_type = protein
                        organism = synthetic construct
SEQUENCE: 44
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPYTFGQ GTKVEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214
```

```
SEQ ID NO: 45           moltype = AA  length = 454
FEATURE                 Location/Qualifiers
REGION                  1..454
                        note = Description of Artificial Sequence: Synthetic
                        polypeptide
REGION                  1..454
                        note =
                        uIFN_IgG_KH_PDL1-IFN_R01_C08_28S_N40A_G56K_T66S_Q68E_Pep1
source                  1..454
                        mol_type = protein
                        organism = synthetic construct
SEQUENCE: 45
QVQLVQSGAE VKKPGASVKV SCKASGGTFS SYAISWVRQA PGQGLEWMGI IDPSVTYTRY   60
AQKFQGRVTM TRDTSTSTVY MELSSLRSED TAVYYCARSL FPTIFGVEVA FDIWGQGTLV  120
TVSSAKTTAP SVYPLAPVCG DTTGSSVTLG CLVKGYFPEP VTLTWNSGSL SSGVHTFPAV  180
LQSDLYTLSS SVTVTSSTWP SQSITCNVAH PASSTKVDKK IEPRGPTIKP CPPCKCPAPN  240
AAGGPSVFIF PPKIKDVLMI SLSPIVTCVV VDVSEDDPDV QISWFVNNVE VHTAQTQTHR  300
EDYNSTLRVV SALPIQHQDW MSGKEFKCKV NNKDLGAPIE RTISKPKGSV RAPQVYVLPP  360
CEEEMTKKQV TLSCAVTDFM PEDIYVEWTN NGKTELNYKN TEPVLDSDGS YFMVSKLRVE  420
KKNWVERNSY SCSVVHEGLH NHHTTKSFSR TPGK                              454

SEQ ID NO: 46           moltype = AA  length = 639
FEATURE                 Location/Qualifiers
REGION                  1..639
                        note = Description of Artificial Sequence: Synthetic
                        polypeptide
REGION                  1..639
                        note =
                        uIFN_IgG_KH_PDL1-IFN_R01_C08_28S_N40A_G56K_T66S_Q68E_Pep2
source                  1..639
                        mol_type = protein
                        organism = synthetic construct
SEQUENCE: 46
CDLPQTHSLG SRRTLMLLAQ MRRISLFSCL KDRHDFGFPQ EEFGNQFQKA ETIPVLHEMI   60
QQIFNLFSTK DSSAAWDETL LDKFCTELYQ QLNDLEACVM QEERVGETPL MNADSILAVK  120
KYFRRITLYL TEKKYSPCAW EVVRAEIVRS LSLSTNLQER LRRKEGGGGS GGGGSGGGGS  180
GGGGSQVQLV QSGAEVKKPG ASVKVSCKAS GGTFSSYAIS WVRQAPGQGL EWMGIIDPSV  240
TYTRYAQKFQ GRVTMTRDTS TSTVYMELSS LRSEDTAVYY CARSLFPTIF GVEVAFDIWG  300
QGTLVTVSSA KTTAPSVYPL APVCGDTTGS SVTLGCLVKG YFPEPVTLTW NSGSLSSGVH  360
TFPAVLQSDL YTLSSSVTVT SSTWPSQSIT CNVAHPASST KVDKKIEPRG PTIKPCPPCK  420
CPAPNAAGGP SVFIFPPKIK DVLMISLSPI VTCVVVDVSE DDPDVQISWF VNNVEVHTAQ  480
TQTHREDYNS TLRVVSALPI QHQDWMSGKE FKCKVNNKDL GAPIERTISK PKGSVRAPQV  540
CVLPPPEEEM TKKQVTLWCM VTDFMPEDIY VEWTNNGKTE LNYKNTEPVL DSDGSYFMYS  600
KLRVEKKNWV ERNSYSCSVV HEGLHNHHTT KSFSRTPGK                         639

SEQ ID NO: 47           moltype = AA  length = 214
FEATURE                 Location/Qualifiers
REGION                  1..214
                        note = Description of Artificial Sequence: Synthetic
                        polypeptide
REGION                  1..214
                        note =
                        uIFN_IgG_KH_PDL1-IFN_R01_C08_28S_N40A_G56K_T66S_Q68E_Pep3
source                  1..214
                        mol_type = protein
                        organism = synthetic construct
SEQUENCE: 47
DIQMTQSPSS LSASVGDRVT ITCQASQSIS NYLAWYQQKP GKAPKLLIYK ASSLESGVPS   60
RFSGSGSGTD FTLTISSLQP EDFATYYCQQ TYSTPITFGQ GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 48           moltype = AA  length = 766
FEATURE                 Location/Qualifiers
REGION                  1..766
                        note = Description of Artificial Sequence: Synthetic
                        polypeptide
REGION                  1..766
                        note = ExemplarySeq_C_Pep1
source                  1..766
                        mol_type = protein
                        organism = synthetic construct
SEQUENCE: 48
CDLPQTHSLG SRRTLMLLAQ MRRISLFSCL KDRHDFGFPQ EEFGNQFQKA ETIPVLHEMI   60
QQIFNLFSTK DSSAAWDETL LDKFCTELYQ QLNDLEACVM QEERVGETPL MNADSILAVK  120
KYFRRITLYL TEKKYSPCAW EVVRAEIVRS LSLSTNLQER LRRKEGGGGS GGGGSGGGGS  180
GGGGSQVQLV QSGAEVKKPG ASVKVSCKAS GGTFSSYAIS WVRQAPGQGL EWMGIIDPSV  240
TYTRYAQKFQ GRVTMTRDTS TSTVYMELSS LRSEDTAVYY CARSLFPTIF GVEVAFDIWG  300
QGTLVTVSSA SGGGGSGGGG SGGGGSHASD IQMTQSPSSL SASVGDRVTI TCQASQDISN  360
```

```
YLNWYQQKPG KAPKLLIYGA STLQSGVPSR FSGSGSGTDF TLTISSLQPE DFATYYCQQT  420
YSTPITFGQG TKVEIKAKTT APSVYPLAPV CGDTTGSSVT LGCLVKGYFP EPVTLTWNSG  480
SLSSGVHTFP AVLQSDLYTL SSSVTVTSST WPSQSITCNV AHPASSTKVD KKIEPRGPTI  540
KPCPPCKCPA PNAAGGPSVF IFPPKIKDVL MISLSPIVTC VVVDVSEDDP DVQISWFVNN  600
VEVHTAQTQT HREDYNSTLR VVSALPIQHQ DWMSGKEFKC KVNNKDLGAP IERTISKPKG  660
SVRAPQVYVL PPCEEEMTKK QVTLSCAVTD FMPEDIYVEW TNNGKTELNY KNTEPVLDSD  720
GSYFMVSKLR VEKKNWVERN SYSCSVVHEG LHNHHTTKSF SRTPGK                 766

SEQ ID NO: 49          moltype = AA  length = 448
FEATURE                Location/Qualifiers
REGION                 1..448
                       note = Description of Artificial Sequence: Synthetic
                        polypeptide
REGION                 1..448
                       note = ExemplarySeq_C_Pep2
source                 1..448
                       mol_type = protein
                       organism = synthetic construct
SEQUENCE: 49
QVQLVQSGAE VKKPGASVKV SCKASGYTFS GYYIHWVRQA PGQGLEWMGW MDSNSGGTGY   60
AQKFQGRVTM TRDTSTSTVY MELSSLRSED TAVYYCAKEV FSGWYDYWGQ GTLVTVSSAK  120
TTAPSVYPLA PVCGDTTGSS VTLGCLVKGY FPEPVTLTWN SGSLSSGVHT FPAVLQSDLY  180
TLSSSVTVTS STWPSQSITC NVAHPASSTK VDKKIEPRGP TIKPCPPCKC PAPNAAGGPS  240
VFIFPPKIKD VLMISLSPIV TCVVVDVSED DPDVQISWFV NNVEVHTAQT QTHREDYNST  300
LRVVSALPIQ HQDWMSGKEF KCKVNNKDLG APIERTISKP KGSVRAPQVC VLPPPEEEMT  360
KKQVTLWCMV TDFMPEDIYV EWTNNGKTEL NYKNTEPVLD SDGSYFMYSK LRVEKKNWVE  420
RNSYSCSVVH EGLHNHHTTK SFSRTPGK                                     448

SEQ ID NO: 50          moltype = AA  length = 214
FEATURE                Location/Qualifiers
REGION                 1..214
                       note = Description of Artificial Sequence: Synthetic
                        polypeptide
REGION                 1..214
                       note = ExemplarySeq_C_Pep3
source                 1..214
                       mol_type = protein
                       organism = synthetic construct
SEQUENCE: 50
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPYTFGQ GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 51          moltype = AA  length = 443
FEATURE                Location/Qualifiers
REGION                 1..443
                       note = Description of Artificial Sequence: Synthetic
                        polypeptide
REGION                 1..443
                       note = PD1-IL2_6C12_N36T_Sym_L_Long_Pep1
source                 1..443
                       mol_type = protein
                       organism = synthetic construct
SEQUENCE: 51
QVQLVQSGAE VKKPGASVKV SCKASGYTFS TYYIHWVRQA PGQGLEWMGI INPSGGGTVY   60
AQKFQGRVTM TRDTSTSTVY MELSSLRSED TAVYYCAAGL FIWGQGTLVT VSSAKTTAPS  120
VYPLAPVCGD TTGSSVTLGC LVKGYFPEPV TLTWNSGSLS SGVHTFPAVL QSDLYTLSSS  180
VTVTSSTWPS QSITCNVAHP ASSTKVDKKI EPRGPTIKPC PPCKCPAPNA AGGPSVFIFP  240
PKIKDVLMIS LSPIVTCVVV DVSEDDPDVQ ISWFVNNVEV HTAQTQTHRE DYNSTLRVVS  300
ALPIQHQDWM SGKEFKCKVN NKDLGAPIER TISKPKGSVR APQVYVLPPP EEEMTKKQVT  360
LTCMVTDFMP EDIYVEWTNN GKTELNYKNT EPVLDSDGSY FMYSKLRVEK KNWVERNSYS  420
CSVVHEGLHN HHTTKSFSRT PGK                                          443

SEQ ID NO: 52          moltype = AA  length = 407
FEATURE                Location/Qualifiers
REGION                 1..407
                       note = Description of Artificial Sequence: Synthetic
                        polypeptide
REGION                 1..407
                       note = PD1-IL2_6C12_N36T_Sym_L_Long_Pep2
source                 1..407
                       mol_type = protein
                       organism = synthetic construct
SEQUENCE: 52
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTVPGVGVP GAGVPGVGVP GGGVPGVGVP GGGVPGAGVP GGGVPGVGVP  180
GAGVPGVGVP GGGDIQMTQS PSSLSASVGD RVTITCRASQ YISSGLAWYQ QKPGKAPKLL  240
```

```
IYKASSLDNG VPSRFSGSGS GTDFTLTISS LQPEDFATYY CQQYERLPLT FGGGTKVEIK    300
RADAAPTVSI FPPSSEQLTS GGASVVCFLN NFYPKDINVK WKIDGSERQN GVLNSWTDQD    360
SKDSTYSMSS TLTLTKDEYE RHNSYTCEAT HKTSTSPIVK SFNRNEC                  407

SEQ ID NO: 53           moltype = AA  length = 596
FEATURE                 Location/Qualifiers
REGION                  1..596
                        note = Description of Artificial Sequence: Synthetic
                         polypeptide
REGION                  1..596
                        note = PD1-IL2_6C12_N36T_D68E_Sym_H_Short_Pep1
source                  1..596
                        mol_type = protein
                        organism = synthetic construct
SEQUENCE: 53
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTGGGGSGG GGSGGGGSGG GGSQVQLVQS GAEVKKPGAS VKVSCKASGY    180
TFSTYYIHWV RQAPGQGLEW MGIINPSGGG TVYAQKFQGR VTMTRDTSTS TVYMELSSLR    240
SEDTAVYYCA AGLFIWGQGT LVTVSSAKTT APSVYPLAPV CGDTTGSSVT LGCLVKGYFP    300
EPVTLTWNSG SLSSGVHTFP AVLQSDLYTL SSSVTVTSST WPSQSITCNV AHPASSTKVD    360
KKIEPRGPTI KPCPPCKCPA PNAAGGPSVF IFPPKIKDVL MISLSPIVTC VVVDVSEDDP    420
DVQISWFVNN VEVHTAQTQT HREDYNSTLR VVSALPIQHQ DWMSGKEFKC KVNNKDLGAP    480
IERTISKPKG SVRAPQVYVL PPPEEEMTKK QVTLTCMVTD FMPEDIYVEW TNNGKTELNY    540
KNTEPVLDSD GSYFMYSKLR VEKKNWVERN SYSCSVVHEG LHNHHTTKSF SRTPGK        596

SEQ ID NO: 54           moltype = AA  length = 214
FEATURE                 Location/Qualifiers
REGION                  1..214
                        note = Description of Artificial Sequence: Synthetic
                         polypeptide
REGION                  1..214
                        note = PD1-IL2_6C12_N36T_D68E_Sym_H_Short_Pep2
source                  1..214
                        mol_type = protein
                        organism = synthetic construct
SEQUENCE: 54
DIQMTQSPSS LSASVGDRVT ITCRASQYIS SGLAWYQQKP GKAPKLLIYK ASSLENGVPS     60
RFSGSGSGTD FTLTISSLQP EDFATYYCQQ YERLPLTFGG GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 55           moltype = AA  length = 455
FEATURE                 Location/Qualifiers
REGION                  1..455
                        note = Description of Artificial Sequence: Synthetic
                         polypeptide
REGION                  1..455
                        note = AF002718
source                  1..455
                        mol_type = protein
                        organism = synthetic construct
SEQUENCE: 55
MSTSTCDLPQ THSLGSRRTL MLLAQMRRIS LFSCLKDRHD FGFPQEEFGN QFQKAETIPV     60
LHEMIQQIFN LFSTKDSSAA WDETLLDKFY TELYQQLNDL EACVIQGVGV TETPLMKEDS    120
ILAVRKYFQR ITLYLKEKKY SPCAWEVVRA EIMRSFSLST NLQESLRSKE GGGGSGGGGS    180
GGGGSGGGGS QVQLVQSGAE VKKPGASVKV SCKASGNTFT DYYMHWVRQA PGQGLEWMGW    240
MNPNSGNTGY AQKFQGRVTM TRDTSTSTVY MELSSLRSED TAVYYCARSL FPTIFGVEVA    300
FDIWGQGTLV TVSSASGGGG SGGGGSGGGG SHASDIQMTQ SPSSLSASVG DRVTITCQAS    360
QDISNYLNWY QQKPGKAPKL LIYAASSLES GVPSRFSGSG SGTDFTLTIS SLQPEDFATY    420
YCQQSYSTPP TFGQGTRLEI KGKPIPNPLL GLDST                               455

SEQ ID NO: 56           moltype = AA  length = 451
FEATURE                 Location/Qualifiers
REGION                  1..451
                        note = Description of Artificial Sequence: Synthetic
                         polypeptide
REGION                  1..451
                        note = anti-Her2-IFNa
source                  1..451
                        mol_type = protein
                        organism = synthetic construct
SEQUENCE: 56
MSTSTCDLPQ THSLGSRRTL MLLAQMRRIS LFSCLKDRHD FGFPQEEFGN QFQKAETIPV     60
LHEMIQQIFN LFSTKDSSAA WDETLLDKFY TELYQQLNDL EACVIQGVGV TETPLMKEDS    120
ILAVRKYFQR ITLYLKEKKY SPCAWEVVRA EIMRSFSLST NLQESLRSKE GGGGSGGGGS    180
GGGGSGGGGS EVQLVESGGG LVQPGGSLRL SCAASGFNIK DTYIHWVRQA PGKGLEWVAR    240
IYPTNGYTRY ADSVKGRFTI SADTSKNTAY LQMNSLRAED TAVYYCSRWG GDGFYAMDYW    300
GQGTLVTVSS ASGGGGSGGG GSGGGGSHAS DIQMTQSPSS LSASVGDRVT ITCRASQDVN    360
```

```
TAVAWYQQKP GKAPKLLIYS ASFLYSGVPS RFSGSRSGTD FTLTISSLQP EDFATYYCQQ    420
HYTTPPTFGQ GTKVEIKGKP IPNPLLGLDS T                                   451

SEQ ID NO: 57             moltype = AA  length = 639
FEATURE                   Location/Qualifiers
REGION                    1..639
                          note = Description of Artificial Sequence: Synthetic
                           polypeptide
REGION                    1..639
                          note = C08 IFNa heavy chain
source                    1..639
                          mol_type = protein
                          organism = synthetic construct
SEQUENCE: 57
CDLPQTHSLG SRRTLMLLAQ MRRISLFSCL KDRHDFGFPQ EEFGNQFQKA ETIPVLHEMI     60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKEGGGGS GGGGSGGGGS    180
GGGGSQVQLV QSGAEVKKPG ASVKVSCKAS GGTFSSYAIS WVRQAPGQGL EWMGIIDPSV    240
TYTRYAQKFQ GRVTMTRDTS TSTVYMELSS LRSEDTAVYY CARSLFPTIF GVEVAFDIWG    300
QGTLVTVSSA KTTAPSVYPL APVCGDTTGS SVTLGCLVKG YFPEPVTLTW NSGSLSSGVH    360
TFPAVLQSDL YTLSSSVTVT SSTWPSQSIT CNVAHPASST KVDKKIEPRG PTIKPCPPCK    420
CPAPNAAGGP SVFIFPPKIK DVLMISLSPI VTCVVVDVSE DDPDVQISWF VNNVEVHTAQ    480
TQTHREDYNS TLRVVSALPI QHQDWMSGKE FKCKVNNKDL GAPIERTISK PKGSVRAPQV    540
YVLPPPEEEM TKKQVTLTCM VTDFMPEDIY VEWTNNGKTE LNYKNTEPVL DSDGSYFMYS    600
KLRVEKKNWV ERNSYSCSVV HEGLHNHHTT KSFSRTPGK                           639

SEQ ID NO: 58             moltype = AA  length = 214
FEATURE                   Location/Qualifiers
REGION                    1..214
                          note = Description of Artificial Sequence: Synthetic
                           polypeptide
REGION                    1..214
                          note = C08 IFNa light chain
source                    1..214
                          mol_type = protein
                          organism = synthetic construct
SEQUENCE: 58
DIQMTQSPSS LSASVGDRVT ITCQASQDIS NYLNWYQQKP GKAPKLLIYG ASTLQSGVPS     60
RFSGSGSGTD FTLTISSLQP EDFATYYCQQ TYSTPITFGQ GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 59             moltype = AA  length = 639
FEATURE                   Location/Qualifiers
REGION                    1..639
                          note = Description of Artificial Sequence: Synthetic
                           polypeptide
REGION                    1..639
                          note = B09 IFNa heavy chain
source                    1..639
                          mol_type = protein
                          organism = synthetic construct
SEQUENCE: 59
CDLPQTHSLG SRRTLMLLAQ MRRISLFSCL KDRHDFGFPQ EEFGNQFQKA ETIPVLHEMI     60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKEGGGGS GGGGSGGGGS    180
GGGGSQVQLV QSGAEVKKPG ASVKVSCKAS GGTFTGYYMH WVRQAPGQGL EWMGWVNPNS    240
GNTGYAQKFQ GRVTMTRDTS TSTVYMELSS LRSEDTAVYY CARSLFPTIF GVEVAFDIWG    300
QGTLVTVSSA KTTAPSVYPL APVCGDTTGS SVTLGCLVKG YFPEPVTLTW NSGSLSSGVH    360
TFPAVLQSDL YTLSSSVTVT SSTWPSQSIT CNVAHPASST KVDKKIEPRG PTIKPCPPCK    420
CPAPNAAGGP SVFIFPPKIK DVLMISLSPI VTCVVVDVSE DDPDVQISWF VNNVEVHTAQ    480
TQTHREDYNS TLRVVSALPI QHQDWMSGKE FKCKVNNKDL GAPIERTISK PKGSVRAPQV    540
YVLPPPEEEM TKKQVTLTCM VTDFMPEDIY VEWTNNGKTE LNYKNTEPVL DSDGSYFMYS    600
KLRVEKKNWV ERNSYSCSVV HEGLHNHHTT KSFSRTPGK                           639

SEQ ID NO: 60             moltype = AA  length = 214
FEATURE                   Location/Qualifiers
REGION                    1..214
                          note = Description of Artificial Sequence: Synthetic
                           polypeptide
REGION                    1..214
                          note = B09 IFNa light chain
source                    1..214
                          mol_type = protein
                          organism = synthetic construct
SEQUENCE: 60
DIQMTQSPSS LSASVGDRVT ITCQASQDIS NYLNWYQQKP GKAPKLLIYA ASSLQSGVPS     60
RFSGSGSGTD FTLTISSLQP EDFATYYCQQ SYSPPPTFGQ GTKLEIKRAD AAPTVSIFPP    120
SSEQLTSGGA SVVCFLNNFY PKDINVKWKI DGSERQNGVL NSWTDQDSKD STYSMSSTLT    180
```

```
LTKDEYERHN SYTCEATHKT STSPIVKSFN RNEC                                   214

SEQ ID NO: 61             moltype = AA  length = 639
FEATURE                   Location/Qualifiers
REGION                    1..639
                          note = Description of Artificial Sequence: Synthetic
                          polypeptide
REGION                    1..639
                          note = anti-PD-L1-IFNa heavy chain
source                    1..639
                          mol_type = protein
                          organism = synthetic construct
SEQUENCE: 61
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSQVQLV QSGAEVKKPG ASVKVSCKAS GGTFSSYAIS WVRQAPGQGL EWMGWINPNS   240
GGTNYAQKFQ GRVTMTRDTS TSTVYMELSS LRSEDTAVYY CARSLFPTIF GVEVAFDIWG   300
QGTTVTVSSA KTTAPSVYPL APVCGDTTGS SVTLGCLVKG YFPEPVTLTW NSGSLSSGVH   360
TFPAVLQSDL YTLSSSVTVT SSTWPSQSIT CNVAHPASST KVDKKIEPRG PTIKPCPPCK   420
CPAPNAAGGP SVFIFPPKIK DVLMISLSPI VTCVVVDVSE DDPDVQISWF VNNVEVHTAQ   480
TQTHREDYNS TLRVVSALPI QHQDWMSGKE FKCKVNNKDL GAPIERTISK PKGSVRAPQV   540
YVLPPPEEEM TKKQVTLTCM VTDFMPEDIY VEWTNNGKTE LNYKNTEPVL DSDGSYFMYS   600
KLRVEKKNWV ERNSYSCSVV HEGLHNHHTT KSFSRTPGK                          639

SEQ ID NO: 62             moltype = AA  length = 214
FEATURE                   Location/Qualifiers
REGION                    1..214
                          note = Description of Artificial Sequence: Synthetic
                          polypeptide
REGION                    1..214
                          note = anti-PD-L1-IFNa light chain
source                    1..214
                          mol_type = protein
                          organism = synthetic construct
SEQUENCE: 62
DIQMTQSPSS LSASVGDRVT ITCRASQSII DRLAWYQQKP GKAPKLLIYK ASSLESGVPS    60
RFSGSGSGTD FTLTISSLQP EDFATYYCQQ SYSTPFTFGP GTKVDIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 63             moltype = AA  length = 635
FEATURE                   Location/Qualifiers
REGION                    1..635
                          note = Description of Artificial Sequence: Synthetic
                          polypeptide
REGION                    1..635
                          note = anti-HER2-IFNa heavy chain
source                    1..635
                          mol_type = protein
                          organism = synthetic construct
SEQUENCE: 63
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSEVQLV ESGGGLVQPG GSLRLSCAAS GFNIKDTYIH WVRQAPGKGL EWVARIYPTN   240
GYTRYADSVK GRFTISADTS KNTAYLQMNS LRAEDTAVYY CSRWGGDGFY AMDYWGQGTL   300
VTVSSAKTTA PSVYPLAPVC GDTTGSSVTL GCLVKGYFPE PVTLTWNSGS LSSGVHTFPA   360
VLQSDLYTLS SSVTVTSSTW PSQSITCNVA HPASSTKVDK KIEPRGPTIK PCPPCKCPAP   420
NAAGGPSVFI FPPKIKDVLM ISLSPIVTCV VVDSEDDPD VQISWFVNNV EVHTAQTQTH   480
REDYNSTLRV VSALPIQHQD WMSGKEFKCK VNNKDLGAPI ERTISKPKGS VRAPQVYVLP   540
PPEEEMTKKQ VTLTCMVTDF MPEDIYVEWT NNGKTELNYK NTEPVLDSDG SYFMYSKLRV   600
EKKNWVERNS YSCSVVHEGL HNHHTTKSFS RTPGK                              635

SEQ ID NO: 64             moltype = AA  length = 214
FEATURE                   Location/Qualifiers
REGION                    1..214
                          note = Description of Artificial Sequence: Synthetic
                          polypeptide
REGION                    1..214
                          note = anti-HER2-IFNa light chain
source                    1..214
                          mol_type = protein
                          organism = synthetic construct
SEQUENCE: 64
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214
```

```
SEQ ID NO: 65           moltype = AA  length = 450
FEATURE                 Location/Qualifiers
REGION                  1..450
                        note = Description of Artificial Sequence: Synthetic
                         polypeptide
REGION                  1..450
                        note = Anti-HER2 heavy chain
source                  1..450
                        mol_type = protein
                        organism = synthetic construct
SEQUENCE: 65
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
AKTTAPSVYP LAPVCGDTTG SSVTLGCLVK GYFPEPVTLT WNSGSLSSGV HTFPAVLQSD   180
LYTLSSSVTV TSSTWPSQSI TCNVAHPASS TKVDKKIEPR GPTIKPCPPC KCPAPNAAGG   240
PSVFIFPPKI KDVLMISLSP IVTCVVVDVS EDDPDVQISW FVNNVEVHTA QTQTHREDYN   300
STLRVVSALP IQHQDWMSGK EFKCKVNNKD LGAPIERTIS KPKGSVRAPQ VYVLPPPEEE   360
MTKKQVTLTC MVTDFMPEDI YVEWTNNGKT ELNYKNTEPV LDSDGSYFMY SKLRVEKKNW   420
VERNSYSCSV VHEGLHNHHT TKSFSRTPGK                                   450

SEQ ID NO: 66           moltype = AA  length = 407
FEATURE                 Location/Qualifiers
REGION                  1..407
                        note = Description of Artificial Sequence: Synthetic
                         polypeptide
REGION                  1..407
                        note = Anti-HER2 light chain
source                  1..407
                        mol_type = protein
                        organism = synthetic construct
SEQUENCE: 66
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTVPGVGVP GAGVPGVGVP GGGVPGVGVP GGGVPGAGVP GGGVPGVGVP   180
GAGVPGVGVP GGGDIQMTQS PSSLSASVGD RVTITCRASQ DVNTAVAWYQ QKPGKAPKLL   240
IYSASFLYSG VPSRFSGSRS GTDFTLTISS LQPEDFATYY CQQHYTTPPT FGQGTKVEIK   300
RADAAPTVSI FPPSSEQLTS GGASVVCFLN NFYPKDINVK WKIDGSERQN GVLNSWTDQD   360
SKDSTYSMSS TLTLTKDEYE RHNSYTCEAT HKTSTSPIVK SFNRNEC                407

SEQ ID NO: 67           moltype = AA  length = 454
FEATURE                 Location/Qualifiers
REGION                  1..454
                        note = Description of Artificial Sequence: Synthetic
                         polypeptide
REGION                  1..454
                        note = 2_A08 heavy chain
source                  1..454
                        mol_type = protein
                        organism = synthetic construct
SEQUENCE: 67
QVQLVQSGAE VKKPGASVKV SCKVSGYTFT SYDINWVRQA PGQGLEWMGW INPNSGDTGY    60
AQKFQGRVTM TRDTSTSTVY MELSSLRSED TAVYYCARDT GLGYYYGSGD FDYWGQGTLV   120
TVSSAKTTAP SVYPLAPVCG DTTGSSVTLG CLVKGYFPEP VTLTWNSGSL SSGVHTFPAV   180
LQSDLYTLSS SVTVTSSTWP SQSITCNVAH PASSTKVDKK IEPRGPTIKP CPPCKCPAPN   240
AAGGPSVFIF PPKIKDVLMI SLSPIVTCVV VDVSEDDPDV QISWFVNNVE VHTAQTQTHR   300
EDYNSTLRVV SALPIQHQDW MSGKEFKCKV NNKDLGAPIE RTISKPKGSV RAPQVYVLPP   360
PEEEMTKKQV TLTCMVTDFM PEDIYVEWTN NGKTELNYKN TEPVLDSDGS YFMYSKLRVE   420
KKNWVERNSY SCSVVHEGLH NHHTTKSFSR TPGK                              454

SEQ ID NO: 68           moltype = AA  length = 407
FEATURE                 Location/Qualifiers
REGION                  1..407
                        note = Description of Artificial Sequence: Synthetic
                         polypeptide
REGION                  1..407
                        note = 2_A08 light chain
source                  1..407
                        mol_type = protein
                        organism = synthetic construct
SEQUENCE: 68
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTVPGVGVP GAGVPGVGVP GGGVPGVGVP GGGVPGAGVP GGGVPGVGVP   180
GAGVPGVGVP GGGDIQMTQS PSSLSASVGD RVTITCQASQ DIHNYLNWYQ QKPGKAPKLL   240
IYDVSNLETG VPSRFSGSGS GTDFTLTISS LQPEDFATYY CQQAISFPLT FGGGTKVEIK   300
RADAAPTVSI FPPSSEQLTS GGASVVCFLN NFYPKDINVK WKIDGSERQN GVLNSWTDQD   360
SKDSTYSMSS TLTLTKDEYE RHNSYTCEAT HKTSTSPIVK SFNRNEC                407
```

| SEQ ID NO: 69 | moltype = AA length = 443 |
|---|---|
| FEATURE | Location/Qualifiers |
| REGION | 1..443 |
| | note = Description of Artificial Sequence: Synthetic polypeptide |
| REGION | 1..443 |
| | note = 2_A11 heavy chain |
| source | 1..443 |
| | mol_type = protein |
| | organism = synthetic construct |

SEQUENCE: 69
```
QVQLVQSGAE VKKPGASVKV SCKASGHTFT RYYMHWVRQA PGQGLEWMGI INPSGGYATY    60
AQKFQGRVTM TRDTSTSTVY MELSSLRSED TAVYYCASGW DVWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EEEMTKKQVT   360
LTCMVTDFMP EDIYVEWTNN GKTELNYKNT EPVLDSDGSY FMYSKLRVEK KNWVERNSYS   420
CSVVHEGLHN HHTTKSFSRT PGK                                          443
```

| SEQ ID NO: 70 | moltype = AA length = 407 |
|---|---|
| FEATURE | Location/Qualifiers |
| REGION | 1..407 |
| | note = Description of Artificial Sequence: Synthetic polypeptide |
| REGION | 1..407 |
| | note = 2_A11 light chain |
| source | 1..407 |
| | mol_type = protein |
| | organism = synthetic construct |

SEQUENCE: 70
```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTVPGVGVP GAGVPGVGVP GGGVPGVGVP GGGVPGAGVP GGGVPGVGVP   180
GAGVPGVGVP GGGDIQMTQS PSSLSASVGD RVTITCRASQ SINSWLAWYQ QKPGKAPKLL   240
IYATSTLESG VPSRFSGSGS GTDFTLTISS LQPEDFATYY CQQSYSFPPT FGQGTKVEIK   300
RADAAPTVSI FPPSSEQLTS GGASVVCFLN NFYPKDINVK WKIDGSERQN GVLNSWTDQD   360
SKDSTYSMSS TLTLTKDEYE RHNSYTCEAT HKTSTSPIVK SFNRNEC                407
```

| SEQ ID NO: 71 | moltype = AA length = 443 |
|---|---|
| FEATURE | Location/Qualifiers |
| REGION | 1..443 |
| | note = Description of Artificial Sequence: Synthetic polypeptide |
| REGION | 1..443 |
| | note = 2_B05 heavy chain |
| source | 1..443 |
| | mol_type = protein |
| | organism = synthetic construct |

SEQUENCE: 71
```
QVQLVQSGAE VKKPGASVKV SCKASGYTFT NYYIHWVRQA PGQGLEWMGI INPRAGYTSY    60
ALKFQGRVTM TRDTSTSTVY MELSSLRSED TAVYYCAGGW LDWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EEEMTKKQVT   360
LTCMVTDFMP EDIYVEWTNN GKTELNYKNT EPVLDSDGSY FMYSKLRVEK KNWVERNSYS   420
CSVVHEGLHN HHTTKSFSRT PGK                                          443
```

| SEQ ID NO: 72 | moltype = AA length = 407 |
|---|---|
| FEATURE | Location/Qualifiers |
| REGION | 1..407 |
| | note = Description of Artificial Sequence: Synthetic polypeptide |
| REGION | 1..407 |
| | note = 2_B05 light chain |
| source | 1..407 |
| | mol_type = protein |
| | organism = synthetic construct |

SEQUENCE: 72
```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTVPGVGVP GAGVPGVGVP GGGVPGVGVP GGGVPGAGVP GGGVPGVGVP   180
GAGVPGVGVP GGGDIQMTQS PSSLSASVGD RVTITCRASQ SISSWLAWYQ QKPGKAPKLL   240
IYAASSLQSG VPSRFSGSGS GTDFTLTISS LQPEDFATYY CQQSFTMPIT FGQGTRLEIK   300
RADAAPTVSI FPPSSEQLTS GGASVVCFLN NFYPKDINVK WKIDGSERQN GVLNSWTDQD   360
SKDSTYSMSS TLTLTKDEYE RHNSYTCEAT HKTSTSPIVK SFNRNEC                407
```

| SEQ ID NO: 73 | moltype = AA length = 443 |
|---|---|

```
FEATURE                 Location/Qualifiers
REGION                  1..443
                        note = Description of Artificial Sequence: Synthetic
                         polypeptide
REGION                  1..443
                        note = 2_B07 heavy chain
source                  1..443
                        mol_type = protein
                        organism = synthetic construct
SEQUENCE: 73
QVQLVQSGAE VKKPGASVKV SCKASGDTFT RHYVHWVRQA PGQGLEWMGI INPSGGYASY    60
AQKFQGRVTM TRDTSTSTVY MELSSLRSED TAVYYCAAGL FIWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EEEMTKKQVT   360
LTCMVTDFMP EDIYVEWTNN GKTELNYKNT EPVLDSDGSY FMYSKLRVEK KNWVERNSYS   420
CSVVHEGLHN HHTTKSFSRT PGK                                          443

SEQ ID NO: 74           moltype = AA  length = 407
FEATURE                 Location/Qualifiers
REGION                  1..407
                        note = Description of Artificial Sequence: Synthetic
                         polypeptide
REGION                  1..407
                        note = 2_B07 light chain
source                  1..407
                        mol_type = protein
                        organism = synthetic construct
SEQUENCE: 74
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTVPGVGVP GAGVPGVGVP GGGVPGVGVP GGGVPGAGVP GGGVPGVGVP   180
GAGVPGVGVP GGGDIQMTQS PSSLSASVGD RVTITCRASQ SIGRWLAWYQ QKPGKAPKLL   240
IYSASNLETG VPSRFSGSGS GTDFTLTISS LQPEDFATYY CQQANSFPVT FGPGTKVDIK   300
RADAAPTVSI FPPSSEQLTS GGASVVCFLN NFYPKDINVK WKIDGSERQN GVLNSWTDQD   360
SKDSTYSMSS TLTLTKDEYE RHNSYTCEAT HKTSTSPIVK SFNRNEC                407

SEQ ID NO: 75           moltype = AA  length = 443
FEATURE                 Location/Qualifiers
REGION                  1..443
                        note = Description of Artificial Sequence: Synthetic
                         polypeptide
REGION                  1..443
                        note = 7_A04 heavy chain
source                  1..443
                        mol_type = protein
                        organism = synthetic construct
SEQUENCE: 75
QVQLVQSGAE VKKPGASVKV SCKASGYTFT DYYMHWVRQA PGQGLEWMGI INPRAGYTSY    60
ALKFQGRVTM TRDTSTSTVY MELSSLRSED TAVYYCTSGM DVWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EEEMTKKQVT   360
LTCMVTDFMP EDIYVEWTNN GKTELNYKNT EPVLDSDGSY FMYSKLRVEK KNWVERNSYS   420
CSVVHEGLHN HHTTKSFSRT PGK                                          443

SEQ ID NO: 76           moltype = AA  length = 407
FEATURE                 Location/Qualifiers
REGION                  1..407
                        note = Description of Artificial Sequence: Synthetic
                         polypeptide
REGION                  1..407
                        note = 7_A04 light chain
source                  1..407
                        mol_type = protein
                        organism = synthetic construct
SEQUENCE: 76
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTVPGVGVP GAGVPGVGVP GGGVPGVGVP GGGVPGAGVP GGGVPGVGVP   180
GAGVPGVGVP GGGDIQMTQS PSSLSASVGD RVTITCRASQ SISTWLAWYQ QKPGKAPKLL   240
IYAASSLQSG VPSRFSGSGS GTDFTLTISS LQPEDFATYY CQQSYSFPVT FGPGTKVEIK   300
RADAAPTVSI FPPSSEQLTS GGASVVCFLN NFYPKDINVK WKIDGSERQN GVLNSWTDQD   360
SKDSTYSMSS TLTLTKDEYE RHNSYTCEAT HKTSTSPIVK SFNRNEC                407

SEQ ID NO: 77           moltype = AA  length = 443
FEATURE                 Location/Qualifiers
```

| | | |
|---|---|---|
| REGION | 1..443 | |
| | note = Description of Artificial Sequence: Synthetic polypeptide | |
| REGION | 1..443 | |
| | note = PD1-IL2_L_7A05scFv_PD1-R07-A05_Pep1 | |
| source | 1..443 | |
| | mol_type = protein | |
| | organism = synthetic construct | |

SEQUENCE: 77
```
QVQLVQSGAE VKKPGASVKV SCKASGYTFT TYYVHWVRQA PGQGLEWMGI INPSGGSTSY   60
AQNFQGRVTM TRDTSTSTVY MELSSLRSED TAVYYCASGW DVWGQGTTVT VSSAKTTAPS  120
VYPLAPVCGD TTGSSVTLGC LVKGYFPEPV TLTWNSGSLS SGVHTFPAVL QSDLYTLSSS  180
VTVTSSTWPS QSITCNVAHP ASSTKVDKKI EPRGPTIKPC PPCKCPAPNA AGGPSVFIFP  240
PKIKDVLMIS LSPIVTCVVV DVSEDDPDVQ ISWFVNNVEV HTAQTQTHRE DYNSTLRVVS  300
ALPIQHQDWM SGKEFKCKVN NKDLGAPIER TISKPKGSVR APQVYVLPPP EEEMTKKQVT  360
LTCMVTDFMP EDIYVEWTNN GKTELNYKNT EPVLDSDGSY FMYSDLRVEK KNWVERNSYS  420
CSVVHEGLHN HHTTESFSRT PGK                                         443
```

| | | |
|---|---|---|
| SEQ ID NO: 78 | moltype = AA   length = 485 | |
| FEATURE | Location/Qualifiers | |
| REGION | 1..485 | |
| | note = Description of Artificial Sequence: Synthetic polypeptide | |
| REGION | 1..485 | |
| | note = PD1-IL2_L_7A05scFv_PD1-R07-A05_Pep2 | |
| source | 1..485 | |
| | mol_type = protein | |
| | organism = synthetic construct | |

SEQUENCE: 78
```
QVQLVQSGAE VKKPGASVKV SCKASGYTFT TYYVHWVRQA PGQGLEWMGI INPSGGSTSY   60
AQNFQGRVTM TRDTSTSTVY MELSSLRSED TAVYYCASGW DVWGQGTTVT VSSASGGGGS  120
GGGGSGGGGS HASEIVMTQS PATLSVSPGE RATLSCRASQ SVNTYLAWYQ QKPGQAPRLL  180
IYGASTRATG IPARFSGSGS GTEFTLTISS LQSEDFAVYY CQQYGSSPVT FGQGTRLEIK  240
PRGPTIKPCP PCKCPAPNAA GGPSVFIFPP KIKDVLMISL SPIVTCVVVD VSEDDPDVQI  300
SWFVNNVEVH TAQTQTHRED YNSTLRVVSA LPIQHQDWMS GKEFKCKVNN KDLGAPIERT  360
ISKPKGSVRA PQVYVLPPPE KEMTKKQVSL TCLVKDFMPE DIYVEWTNNG KTELNYKNTE  420
PVLKSDGSYF MYSKLTVEKK NWVERNSYSC SVVHEGLHNH HTTKSFSRTP GGGGSGGGSH  480
HHHHH                                                             485
```

| | | |
|---|---|---|
| SEQ ID NO: 79 | moltype = AA   length = 367 | |
| FEATURE | Location/Qualifiers | |
| REGION | 1..367 | |
| | note = Description of Artificial Sequence: Synthetic polypeptide | |
| REGION | 1..367 | |
| | note = PD1-IL2_L_7A05scFv_PD1-R07-A05_Pep3 | |
| source | 1..367 | |
| | mol_type = protein | |
| | organism = synthetic construct | |

SEQUENCE: 79
```
APTSSSTKKT QLQLEHLLLD LQMILNGINN YKNPKLTDML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSEIVMTQS PATLSVSPGE RATLSCRASQ  180
SVNTYLAWYQ QKPGQAPRLL IYGASTRATG IPARFSGSGS GTEFTLTISS LQSEDFAVYY  240
CQQYGSSPVT FGQGTRLEIK RADAAPTVSI FPPSSEQLTS GGASVVCFLN NFYPKDINVK  300
WKIDGSERQN GVLNSWTDQD SKDSTYSMSS TLTLTKDEYE RHNSYTCEAT HKTSTSPIVK  360
SFNRNEC                                                           367
```

| | | |
|---|---|---|
| SEQ ID NO: 80 | moltype = AA   length = 596 | |
| FEATURE | Location/Qualifiers | |
| REGION | 1..596 | |
| | note = Description of Artificial Sequence: Synthetic polypeptide | |
| REGION | 1..596 | |
| | note = AF003229_Pep1 | |
| source | 1..596 | |
| | mol_type = protein | |
| | organism = synthetic construct | |

SEQUENCE: 80
```
APTSSSTKKT QLQLEHLLLD LQMILNGINN YKNPKLTDML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSQVQLVQS GAEVKKPGAS VKVSCKASGD  180
TFSTYVHWV RQAPGQGLEW MGIINPSGGG TVYAQKFQGR VTMTRDTSTS TVYMELSSLR  240
SEDTAVYYCA AGLFIWGQGT LVTVSSAKTT APSVYPLAPV CGDTTGSSVT LGCLVKGYFP  300
EPVTLTWNSG SLSSGVHTFP AVLQSDLYTL SSSVTVTSST WPSQSITCNV AHPASSTKVD  360
KKIEPRGPTI KPCPPCKCPA PNAAGGPSVF IFPPKIKDVL MISLSPIVTC VVVDVSEDDP  420
DVQISWFVNN VEVHTAQTQT HREDYNSTLR VVSALPIQHQ DWMSGKEFKC KVNNKDLGAP  480
IERTISKPKG SVRAPQVYVL PPPEEEMTKK QVTLTCMVTD FMPEDIYVEW TNNGKTELNY  540
KNTEPVLDSD GSYFMYSDLR VEKKNWVERN SYSCSVVHEG LHNHHTTESF SRTPGK      596
```

```
SEQ ID NO: 81              moltype = AA   length = 596
FEATURE                    Location/Qualifiers
REGION                     1..596
                           note = Description of Artificial Sequence: Synthetic
                            polypeptide
REGION                     1..596
                           note = AF003230_Pep1
source                     1..596
                           mol_type = protein
                           organism = synthetic construct
SEQUENCE: 81
APTSSSTKKT QLQLEHLLLD LQMILNGINN YKNPKLTDML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSGG GGSQVQLVQS GAEVKKPGAS VKVSCKASGY   180
TFSNYYIHWV RQAPGQGLEW MGIINPSGGG TVYAQKFQGR VTMTRDTSTS TVYMELSSLR   240
SEDTAVYYCA AGLFIWGQGT LVTVSSAKTT APSVYPLAPV CGDTTGSSVT LGCLVKGYFP   300
EPVTLTWNSG SLSSGVHTFP AVLQSDLYTL SSSVTVTSST WPSQSITCNV AHPASSTKVD   360
KKIEPRGPTI KPCPPCKCPA PNAAGGPSVF IFPPKIKDVL MISLSPIVTC VVVDVSEDDP   420
DVQISWFVNN VEVHTAQTQT HREDYNSTLR VVSALPIQHQ DWMSGKEFKC KVNNKDLGAP   480
IERTISKPKG SVRAPQVYVL PPPEEEMTKK QVTLTCMVTD FMPEDIYVEW TNNGKTELNY   540
KNTEPVLDSD GSYFMYSDLR VEKKNWVERN SYSCSVVHEG LHNHHTTESF SRTPGK       596

SEQ ID NO: 82              moltype = AA   length = 596
FEATURE                    Location/Qualifiers
REGION                     1..596
                           note = Description of Artificial Sequence: Synthetic
                            polypeptide
REGION                     1..596
                           note = AF003232_Pep1
source                     1..596
                           mol_type = protein
                           organism = synthetic construct
SEQUENCE: 82
APTSSSTKKT QLQLEHLLLD LQMILNGINN YKNPKLTDML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSGG GGSQVQLVQS GAEVKKPGAS VKVSCKASGD   180
TFTRHYVHWV RQAPGQGLEW MGIINPSGGY ASYAQKFQGR VTMTRDTSTS TVYMELSSLR   240
SEDTAVYYCA AGLFIWGQGT LVTVSSAKTT APSVYPLAPV CGDTTGSSVT LGCLVKGYFP   300
EPVTLTWNSG SLSSGVHTFP AVLQSDLYTL SSSVTVTSST WPSQSITCNV AHPASSTKVD   360
KKIEPRGPTI KPCPPCKCPA PNAAGGPSVF IFPPKIKDVL MISLSPIVTC VVVDVSEDDP   420
DVQISWFVNN VEVHTAQTQT HREDYNSTLR VVSALPIQHQ DWMSGKEFKC KVNNKDLGAP   480
IERTISKPKG SVRAPQVYVL PPPEEEMTKK QVTLTCMVTD FMPEDIYVEW TNNGKTELNY   540
KNTEPVLDSD GSYFMYSDLR VEKKNWVERN SYSCSVVHEG LHNHHTTESF SRTPGK       596

SEQ ID NO: 83              moltype = AA   length = 596
FEATURE                    Location/Qualifiers
REGION                     1..596
                           note = Description of Artificial Sequence: Synthetic
                            polypeptide
REGION                     1..596
                           note = AF003250_Pep1
source                     1..596
                           mol_type = protein
                           organism = synthetic construct
SEQUENCE: 83
APTSSSTKKT QLQLEHLLLD LQMILNGINN YKNPKLTDML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSGG GGSQVQLVQS GAEVKKPGAS VKVSCKASGD   180
TFSTYYVHWV RQAPGQGLEW MGIINPSGGG TVYAQKFQGR VTMTRDTSTS TVYMELSSLR   240
SEDTAVYYCA AGLFIWGQGT LVTVSSAKTT APSVYPLAPV CGDTTGSSVT LGCLVKGYFP   300
EPVTLTWNSG SLSSGVHTFP AVLQSDLYTL SSSVTVTSST WPSQSITCNV AHPASSTKVD   360
KKIEPRGPTI KPCPPCKCPA PNAAGGPSVF IFPPKIKDVL MISLSPIVTC VVVDVSEDDP   420
DVQISWFVNN VEVHTAQTQT HREDYNSTLR VVSALPIQHQ DWMSGKEFKC KVNNKDLGAP   480
IERTISKPKG SVRAPQVYVL PPPEEEMTKK QVTLTCMVTD FMPEDIYVEW TNNGKTELNY   540
KNTEPVLDSD GSYFMYSDLR VEKKNWVERN SYSCSVVHEG LHNHHTTESF SRTPGK       596

SEQ ID NO: 84              moltype = AA   length = 596
FEATURE                    Location/Qualifiers
REGION                     1..596
                           note = Description of Artificial Sequence: Synthetic
                            polypeptide
REGION                     1..596
                           note = AF003251_Pep1
source                     1..596
                           mol_type = protein
                           organism = synthetic construct
SEQUENCE: 84
APTSSSTKKT QLQLEHLLLD LQMILNGINN YKNPKLTDML TFKFYMPKKA TELKHLQCLE    60
```

```
EELKPLEEVL NLAQSKNFHL RPRDLISNIN VIVLELKGSE TTFMCEYADE TATIVEFLNR    120
WITFCQSIIS TLTGGGGSGG GGSGGGGSGG GGSQVQLVQS GAEVKKPGAS VKVSCKASGY    180
TFSNYYIHWV RQAPGQGLEW MGIINPSGGG TVYAQKFQGR VTMTRDTSTS TVYMELSSLR    240
SEDTAVYYCA AGLFIWGQGT LVTVSSAKTT APSVYPLAPV CGDTTGSSVT LGCLVKGYFP    300
EPVTLTWNSG SLSSGVHTFP AVLQSDLYTL SSSVTVTSST WPSQSITCNV AHPASSTKVD    360
KKIEPRGPTI KPCPPCKCPA PNAAGGPSVF IFPPKIKDVL MISLSPIVTC VVVDVSEDDP    420
DVQISWFVNN VEVHTAQTQT HREDYNSTLR VVSALPIQHQ DWMSGKEFKC KVNNKDLGAP    480
IERTISKPKG SVRAPQVYVL PPPEEEMTKK QVTLTCMVTD FMPEDIYVEW TNNGKTELNY    540
KNTEPVLDSD GSYFMYSDLR VEKKNWVERN SYSCSVVHEG LHNHHTTESF SRTPGK       596

SEQ ID NO: 85              moltype = AA  length = 596
FEATURE                    Location/Qualifiers
REGION                     1..596
                           note = Description of Artificial Sequence: Synthetic
                            polypeptide
REGION                     1..596
                           note = AF003253_Pep1
source                     1..596
                           mol_type = protein
                           organism = synthetic construct
SEQUENCE: 85
APTSSSTKKT QLQLEHLLLD LQMILNGINN YKNPKLTDML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSGG GGSQVQLVQS GAEVKKPGAS VKVSCKASGD   180
TFTRHYVHWV RQAPGQGLEW MGIINPSGGY ASYAQKFQGR VTMTRDTSTS TVYMELSSLR   240
SEDTAVYYCA AGLFIWGQGT LVTVSSAKTT APSVYPLAPV CGDTTGSSVT LGCLVKGYFP   300
EPVTLTWNSG SLSSGVHTFP AVLQSDLYTL SSSVTVTSST WPSQSITCNV AHPASSTKVD   360
KKIEPRGPTI KPCPPCKCPA PNAAGGPSVF IFPPKIKDVL MISLSPIVTC VVVDVSEDDP   420
DVQISWFVNN VEVHTAQTQT HREDYNSTLR VVSALPIQHQ DWMSGKEFKC KVNNKDLGAP   480
IERTISKPKG SVRAPQVYVL PPPEEEMTKK QVTLTCMVTD FMPEDIYVEW TNNGKTELNY   540
KNTEPVLDSD GSYFMYSDLR VEKKNWVERN SYSCSVVHEG LHNHHTTESF SRTPGK      596

SEQ ID NO: 86              moltype = AA  length = 639
FEATURE                    Location/Qualifiers
REGION                     1..639
                           note = Description of Artificial Sequence: Synthetic
                            polypeptide
REGION                     1..639
                           note = AF003103_Pep1
source                     1..639
                           mol_type = protein
                           organism = synthetic construct
SEQUENCE: 86
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GGTFSSYAIS WVRQAPGQGL EWMGIIDPSV   240
TYTRYAQKFQ GRVTMTRDTS TSTVYMELSS LRSEDTAVYY CARSLFPTIF GVEVAFDIWG   300
QGTLVTVSSA KTTAPSVYPL APVCGDTTGS SVTLGCLVKG YFPEPVTLTW NSGSLSSGVH   360
TFPAVLQSDL YTLSSSVTVT SSTWPSQSIT CNVAHPASST KVDKKIEPRG PTIKPCPPCK   420
CPAPNAAGGP SVFIFPPKIK DVLMISLSPI VTCVVVDVSE DDPDVQISWF VNNVEVHTAQ   480
TQTHREDYNS TLRVVSALPI QHQDWMSGKE FKCKVNNKDL GAPIERTISK PKGSVRAPQV   540
CVLPPPEEEM TKKQVTLWCM VTDFMPEDIY VEWTNNGKTE LNYKNTEPVL DSDGSYFMYS   600
KLRVEKKNWV ERNSYSCSVV HEGLHNHHTT KSFSRTPGK                          639

SEQ ID NO: 87              moltype = AA  length = 633
FEATURE                    Location/Qualifiers
REGION                     1..633
                           note = Description of Artificial Sequence: Synthetic
                            polypeptide
REGION                     1..633
                           note = AF003104_Pep1
source                     1..633
                           mol_type = protein
                           organism = synthetic construct
SEQUENCE: 87
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GYTFSNYYIH WVRQAPGQGL EWMGWMDSNS   240
GGTGYAQKFQ GRVTMTRDTS TSTVYMELSS LRSEDTAVYY CAKEVFSGWY DYWGQGTLVT   300
VSSAKTTAPS VYPLAPVCGD TTGSSVTLGC LVKGYFPEPV TLTWNSGSLS SGVHTFPAVL   360
QSDLYTLSSS VTVTSSTWPS QSITCNVAHP ASSTKVDKKI EPRGPTIKPC PPCKCPAPNA   420
AGGPSVFIFP PKIKDVLMIS LSPIVTCVVV DVSEDDPDVQ ISWFVNNVEV HTAQTQTHRE   480
DYNSTLRVVS ALPIQHQDWM SGKEFKCKVN NKDLGAPIER TISKPKGSVR APQVCVLPPP   540
EEEMTKKQVT LWCMVTDFMP EDIYVEWTNN GKTELNYKNT EPVLDSDGSY FMYSKLRVEK   600
KNWVERNSYS CSVVHEGLHN HHTTKSFSRT PGK                                633

SEQ ID NO: 88              moltype = AA  length = 633
```

| FEATURE | Location/Qualifiers |
|---|---|
| REGION | 1..633 |
| | note = Description of Artificial Sequence: Synthetic polypeptide |
| REGION | 1..633 |
| | note = AF003105_Pep1 |
| source | 1..633 |
| | mol_type = protein |
| | organism = synthetic construct |

SEQUENCE: 88

```
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GYTFSGYYIH WVRQAPGQGL EWMGWMDSNS   240
GGTGYAQKFQ GRVTMTRDTS TSTVYMELSS LRSEDTAVYY CAKEVFSGWY DYWGQGTLVT   300
VSSAKTTAPS VYPLAPVCGD TTGSSVTLGC LVKGYFPEPV TLTWNSGSLS SGVHTFPAVL   360
QSDLYTLSSS VTVTSSTWPS QSITCNVAHP ASSTKVDKKI EPRGPTIKPC PPCKCPAPNA   420
AGGPSVFIFP PKIKDVLMIS LSPIVTCVVV DVSEDDPDVQ ISWFVNNVEV HTAQTQTHRE   480
DYNSTLRVVS ALPIQHQDWM SGKEFKCKVN NKDLGAPIER TISKPKGSVR APQVCVLPPP   540
EEEMTKKQVT LWCMVTDFMP EDIYVEWTNN GKTELNYKNT EPVLDSDGSY FMYSKLRVEK   600
KNWVERNSYS CSVVHEGLHN HHTTKSFSRT PGK                                633
```

| SEQ ID NO: 89 | moltype = AA   length = 633 |
|---|---|
| FEATURE | Location/Qualifiers |
| REGION | 1..633 |
| | note = Description of Artificial Sequence: Synthetic polypeptide |
| REGION | 1..633 |
| | note = AF003106_Pep1 |
| source | 1..633 |
| | mol_type = protein |
| | organism = synthetic construct |

SEQUENCE: 89

```
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GYTFSNYYIH WVRQAPGQGL EWMGWMDSNS   240
GYTGYAQQFQ GRVTMTRDTS TSTVYMELSS LRSEDTAVYY CAKEVFSGWY DYWGQGTLVT   300
VSSAKTTAPS VYPLAPVCGD TTGSSVTLGC LVKGYFPEPV TLTWNSGSLS SGVHTFPAVL   360
QSDLYTLSSS VTVTSSTWPS QSITCNVAHP ASSTKVDKKI EPRGPTIKPC PPCKCPAPNA   420
AGGPSVFIFP PKIKDVLMIS LSPIVTCVVV DVSEDDPDVQ ISWFVNNVEV HTAQTQTHRE   480
DYNSTLRVVS ALPIQHQDWM SGKEFKCKVN NKDLGAPIER TISKPKGSVR APQVCVLPPP   540
EEEMTKKQVT LWCMVTDFMP EDIYVEWTNN GKTELNYKNT EPVLDSDGSY FMYSKLRVEK   600
KNWVERNSYS CSVVHEGLHN HHTTKSFSRT PGK                                633
```

| SEQ ID NO: 90 | moltype = AA   length = 639 |
|---|---|
| FEATURE | Location/Qualifiers |
| REGION | 1..639 |
| | note = Description of Artificial Sequence: Synthetic polypeptide |
| REGION | 1..639 |
| | note = AF003217_Pep1 |
| source | 1..639 |
| | mol_type = protein |
| | organism = synthetic construct |

SEQUENCE: 90

```
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GGTFSSYAIS WVRQAPGQGL EWMGIIDPSV   240
TYTRYAQKFQ GRVTMTRDTS TSTVYMELSS LRSEDTAVYY CARSLFPTIF GVEVAFDIWG   300
QGTLVTVSSA KTTAPSVYPL APVCGDTTGS SVTLGCLVKG YFPEPVTLTW NSGSLSSGVH   360
TFPAVLQSDL YTLSSSVTVT SSTWPSQSIT CNVAHPASST KVDKKIEPRG PTIKPCPPCK   420
CPAPNAAGGP SVFIFPPKIK DVLMISLSPI VTCVVVDVSE DDPDVQISWF VNNVEVHTAQ   480
TQTHREDYNS TLRVVSALPI QHQDWMSGKE FKCKVNNKDL GAPIERTISK PKGSVRAPQV   540
CVLPPPEEEM TKKQVTLWCM VTDFMPEDIY VEWTNNGKTE LNYKNTEPVL DSDGSYFMYS   600
KLRVEKKNWV ERNSYSCSVV HEGLHNHHTT KSFSRTPGK                          639
```

| SEQ ID NO: 91 | moltype = AA   length = 633 |
|---|---|
| FEATURE | Location/Qualifiers |
| REGION | 1..633 |
| | note = Description of Artificial Sequence: Synthetic polypeptide |
| REGION | 1..633 |
| | note = AF003218_Pep1 |
| source | 1..633 |
| | mol_type = protein |
| | organism = synthetic construct |

SEQUENCE: 91

```
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GYTFSGYYIH WVRQAPGQGL EWMGWMDSNS   240
GGTGYAQKFQ GRVTMTRDTS TSTVYMELSS LRSEDTAVYY CAKEVFSGWY DYWGQGTLVT   300
VSSAKTTAPS VYPLAPVCGD TTGSSVTLGC LVKGYFPEPV TLTWNSGSLS SGVHTFPAVL   360
QSDLYTLSSS VTVTSSTWPS QSITCNVAHP ASSTKVDKKI EPRGPTIKPC PPCKCPAPNA   420
AGGPSVFIFP PKIKDVLMIS LSPIVTCVVV DVSEDDPDVQ ISWFVNNVEV HTAQTQTHRE   480
DYNSTLRVVS ALPIQHQDWM SGKEFKCKVN NKDLGAPIER TISKPKGSVR APQVCVLPPP   540
EEEMTKKQVT LWCMVTDFMP EDIYVEWTNN GKTELNYKNT EPVLDSDGSY FMYSKLRVEK   600
KNWVERNSYS CSVVHEGLHN HHTTKSFSRT PGK                                633

SEQ ID NO: 92           moltype = AA  length = 633
FEATURE                 Location/Qualifiers
REGION                  1..633
                        note = Description of Artificial Sequence: Synthetic
                         polypeptide
REGION                  1..633
                        note = AF003219_Pep1
source                  1..633
                        mol_type = protein
                        organism = synthetic construct
SEQUENCE: 92
CDLPQTHSLG SRRTLMLLAQ MRRISLFSCL KDRHDFGFPQ EEFGNQFQKA ETIPVLHEMI    60
QQIFNLFSTK DSSAAWDETL LDKFCTELYQ QLNDLEACVM QEERVGETPL MNADSILAVK   120
KYFRRITLYL TEKKYSPCAW EVVRAEIVRS LSLSTNLQER LRRKEGGGGS GGGGSGGGGS   180
GGGGSQVQLV QSGAEVKKPG ASVKVSCKAS GYTFSNYYIH WVRQAPGQGL EWMGWMDSNS   240
GGTGYAQKFQ GRVTMTRDTS TSTVYMELSS LRSEDTAVYY CAKEVFSGWY DYWGQGTLVT   300
VSSAKTTAPS VYPLAPVCGD TTGSSVTLGC LVKGYFPEPV TLTWNSGSLS SGVHTFPAVL   360
QSDLYTLSSS VTVTSSTWPS QSITCNVAHP ASSTKVDKKI EPRGPTIKPC PPCKCPAPNA   420
AGGPSVFIFP PKIKDVLMIS LSPIVTCVVV DVSEDDPDVQ ISWFVNNVEV HTAQTQTHRE   480
DYNSTLRVVS ALPIQHQDWM SGKEFKCKVN NKDLGAPIER TISKPKGSVR APQVCVLPPP   540
EEEMTKKQVT LWCMVTDFMP EDIYVEWTNN GKTELNYKNT EPVLDSDGSY FMYSKLRVEK   600
KNWVERNSYS CSVVHEGLHN HHTTKSFSRT PGK                                633

SEQ ID NO: 93           moltype = AA  length = 454
FEATURE                 Location/Qualifiers
REGION                  1..454
                        note = Description of Artificial Sequence: Synthetic
                         polypeptide
REGION                  1..454
                        note = AF002618_Pep1
source                  1..454
                        mol_type = protein
                        organism = synthetic construct
SEQUENCE: 93
QVQLVQSGAE VKKPGASVKV SCKASGGTFS SYAISWVRQA PGQGLEWMGI IDPSVTYTRY    60
AQKFQGRVTM TRDTSTSTVY MELSSLRSED TAVYYCARSL FPTIFGVEVA FDIWGQGTLV   120
TVSSAKTTAP SVYPLAPVCG DTTGSSVTLG CLVKGYFPEP VTLTWNSGSL SSGVHTFPAV   180
LQSDLYTLSS SVTVTSSTWP SQSITCNVAH PASSTKVDKK IEPRGPTIKP CPPCKCPAPN   240
AAGGPSVFIF PPKIKDVLMI SLSPIVTCVV VDVSEDDPDV QISWFVNNVE VHTAQTQTHR   300
EDYNSTLRVV SALPIQHQDW MSGKEFKCKV NNKDLGAPIE RTISKPKGSV RAPQVYVLPP   360
PEEEMTKKQV TLTCMVTDFM PEDIYVEWTN NGKTELNYKN TEPVLDSDGS YFMYSKLRVE   420
KKNWVERNSY SCSVVHEGLH NHHTTKSFSR TPGK                               454

SEQ ID NO: 94           moltype = AA  length = 448
FEATURE                 Location/Qualifiers
REGION                  1..448
                        note = Description of Artificial Sequence: Synthetic
                         polypeptide
REGION                  1..448
                        note = AF002639_Pep1
source                  1..448
                        mol_type = protein
                        organism = synthetic construct
SEQUENCE: 94
QVQLVQSGAE VKKPGASVKV SCKASGYTFS NYYIHWVRQA PGQGLEWMGW MDSNSGYTGY    60
AQQFQGRVTM TRDTSTSTVY MELSSLRSED TAVYYCAKEV FSGWYDYWGQ GTLVTVSSAK   120
TTAPSVYPLA PVCGDTTGSS VTLGCLVKGY FPEPVTLTWN SGSLSSGVHT FPAVLQSDLY   180
TLSSSVTVTS STWPSQSITC NVAHPASSTK VDKKIEPRGP TIKPCPPCKC PAPNAAGGPS   240
VFIFPPKIKD VLMISLSPIV TCVVVDVSED DPDVQISWFV NNVEVHTAQT QTHREDYNST   300
LRVVSALPIQ HQDWMSGKEF KCKVNNKDLG APIERTISKP KGSVRAPQVY VLPPPEEEMT   360
KKQVTLTCMV TDFMPEDIYV EWTNNGKTEL NYKNTEPVLD SDGSYFMYSK LRVEKKNWVE   420
RNSYSCSVVH EGLHNHHTTK SFSRTPGK                                      448

SEQ ID NO: 95           moltype = AA  length = 679
FEATURE                 Location/Qualifiers
REGION                  1..679
                        note = Description of Artificial Sequence: Synthetic
```

```
                              polypeptide
REGION                        1..679
                              note = AF002645_Pep1
source                        1..679
                              mol_type = protein
                              organism = synthetic construct
SEQUENCE: 95
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEVPGVG VPGAGVPGVG   180
VPGGGVPGVG VPGGGVPGAG VPGGGVPGVG VPGAGVPGVG VPGGGQVQLV QSGAEVKKPG   240
ASVKVSCKAS GGTFSSYAIS WVRQAPGQGL EWMGIIDPSV TYTRYAQKFQ GRVTMTRDTS   300
TSTVYMELSS LRSEDTAVYY CARSLFPTIF GVEVAFDIWG QGTLVTVSSA KTTAPSVYPL   360
APVCGDTTGS SVTLGCLVKG YFPEPVTLTW NSGSLSSGVH TFPAVLQSDL YTLSSSVTVT   420
SSTWPSQSIT CNVAHPASST KVDKKIEPRG PTIKPCPPCK CPAPNAAGGP SVFIFPPKIK   480
DVLMISLSPI VTCVVVDVSE DDPDVQISWF VNNVEVHTAQ TQTHREDYNS TLRVVSALPI   540
QHQDWMSGKE FKCKVNNKDL GAPIERTISK PKGSVRAPQY YVLPPPEEEM TKKQVTLTCM   600
VTDFMPEDIY VEWTNNGKTE LNYKNTEPVL DSDGSYFMYS KLRVEKKNWV ERNSYSCSVV   660
HEGLHNHHTT KSFSRTPGK                                                679

SEQ ID NO: 96             moltype = AA  length = 673
FEATURE                   Location/Qualifiers
REGION                    1..673
                          note = Description of Artificial Sequence: Synthetic
                           polypeptide
REGION                    1..673
                          note = AF002666_Pep1
source                    1..673
                          mol_type = protein
                          organism = synthetic construct
SEQUENCE: 96
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEVPGVG VPGAGVPGVG   180
VPGGGVPGVG VPGGGVPGAG VPGGGVPGVG VPGAGVPGVG VPGGGQVQLV QSGAEVKKPG   240
ASVKVSCKAS GYTFSNYYIH WVRQAPGQGL EWMGWMDSNS GYTGYAQQFQ GRVTMTRDTS   300
TSTVYMELSS LRSEDTAVYY CAKEVFSGWY DYWGQGTLVT VSSAKTTAPS VYPLAPVCGD   360
TTGSSVTLGC LVKGYFPEPV TLTWNSGSLS SGVHTFPAVL QSDLYTLSSS VTVTSSTWPS   420
QSITCNVAHP ASSTKVDKKI EPRGPTIKPC PPCKCPAPNA AGGPSVFIFP PKIKDVLMIS   480
LSPIVTCVVV DVSEDDPDVQ ISWFVNNVEV HTAQTQTHRE DYNSTLRVVS ALPIQHQDWM   540
SGKEFKCKVN NKDLGAPIER TISKPKGSVR APQYYVLPPP EEEMTKKQVT LTCMVTDFMP   600
EDIYVEWTNN GKTELNYKNT EPVLDSDGSY FMYSKLRVEK KNWVERNSYS CSVVHEGLHN   660
HHTTKSFSRT PGK                                                     673

SEQ ID NO: 97             moltype = AA  length = 456
FEATURE                   Location/Qualifiers
REGION                    1..456
                          note = Description of Artificial Sequence: Synthetic
                           polypeptide
REGION                    1..456
                          note = AF003229_Pep2
source                    1..456
                          mol_type = protein
                          organism = synthetic construct
SEQUENCE: 97
QVQLVQSGAE VKKPGASVKV SCKASGDTFS TYYVHWVRQA PGQGLEWMGI INPSGGGTVY    60
AQKFQGRVTM TRDTSTSTVY MELSSLRSED TAVYYCAAGL FIWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQYYVLPPP EKEMTKKQVS   360
LTCLVKDFMP EDIYVEWTNN GKTELNYKNT EPVLKSDGSY FMYSKLTVEK KNWVERNSYS   420
CSVVHEGLHN HHTTKSFSRT PGGGGSGGGS HHHHHH                             456

SEQ ID NO: 98             moltype = AA  length = 456
FEATURE                   Location/Qualifiers
REGION                    1..456
                          note = Description of Artificial Sequence: Synthetic
                           polypeptide
REGION                    1..456
                          note = AF003230_Pep2
source                    1..456
                          mol_type = protein
                          organism = synthetic construct
SEQUENCE: 98
QVQLVQSGAE VKKPGASVKV SCKASGYTFS NYYIHWVRQA PGQGLEWMGI INPSGGGTVY    60
AQKFQGRVTM TRDTSTSTVY MELSSLRSED TAVYYCAAGL FIWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
```

```
PKIKDVLMIS LSPIVTCVVV DVSEDDPDVQ ISWFVNNVEV HTAQTQTHRE DYNSTLRVVS    300
ALPIQHQDWM SGKEFKCKVN NKDLGAPIER TISKPKGSVR APQVYVLPPP EKEMTKKQVS    360
LTCLVKDFMP EDIYVEWTNN GKTELNYKNT EPVLKSDGSY FMYSKLTVEK KNWVERNSYS    420
CSVVHEGLHN HHTTKSFSRT PGGGGSGGGS HHHHHH                              456

SEQ ID NO: 99           moltype = AA   length = 456
FEATURE                 Location/Qualifiers
REGION                  1..456
                        note = Description of Artificial Sequence: Synthetic
                         polypeptide
REGION                  1..456
                        note = AF003232_Pep2
source                  1..456
                        mol_type = protein
                        organism = synthetic construct
SEQUENCE: 99
QVQLVQSGAE VKKPGASVKV SCKASGDTFT RHYVHWVRQA PGQGLEWMGI INPSGGYASY     60
AQKFQGRVTM TRDTSTSTVY MELSSLRSED TAVYYCAAGL FIWGQGTLVT VSSAKTTAPS    120
VYPLAPVCGD TTGSSVTLGC LVKGYFPEPV TLTWNSGSLS SGVHTFPAVL QSDLYTLSSS    180
VTVTSSTWPS QSITCNVAHP ASSTKVDKKI EPRGPTIKPC PPCKCPAPNA AGGPSVFIFP    240
PKIKDVLMIS LSPIVTCVVV DVSEDDPDVQ ISWFVNNVEV HTAQTQTHRE DYNSTLRVVS    300
ALPIQHQDWM SGKEFKCKVN NKDLGAPIER TISKPKGSVR APQVYVLPPP EKEMTKKQVS    360
LTCLVKDFMP EDIYVEWTNN GKTELNYKNT EPVLKSDGSY FMYSKLTVEK KNWVERNSYS    420
CSVVHEGLHN HHTTKSFSRT PGGGGSGGGS HHHHHH                              456

SEQ ID NO: 100          moltype = AA   length = 485
FEATURE                 Location/Qualifiers
REGION                  1..485
                        note = Description of Artificial Sequence: Synthetic
                         polypeptide
REGION                  1..485
                        note = AF003250_Pep2
source                  1..485
                        mol_type = protein
                        organism = synthetic construct
SEQUENCE: 100
QVQLVQSGAE VKKPGASVKV SCKASGYTFT TYYVHWVRQA PGQGLEWMGI INPSGGSTSY     60
AQNFQGRVTM TRDTSTSTVY MELSSLRSED TAVYYCASGW DVWGQGTTVT VSSASGGGGS    120
GGGGSGGGGS HASEIVMTQS PATLSVSPGE RATLSCRASQ SVNTYLAWYQ QKPGQAPRLL    180
IYGASTRATG IPARFSGSGS GTEFTLTISS LQSEDFAVYY CQQYGSSPVT FGQGTRLEIK    240
PRGPTIKPCP PCKCPAPNAA GGPSVFIFPP KIKDVLMISL SPIVTCVVVD VSEDDPDVQI    300
SWFVNNVEVH TAQTQTHRED YNSTLRVVSA LPIQHQDWMS GKEFKCKVNN KDLGAPIERT    360
ISKPKGSVRA PQVYVLPPPE KEMTKKQVSL TCLVKDFMPE DIYVEWTNNG KTELNYKNTE    420
PVLKSDGSYF MYSKLTVEKK NWVERNSYSC SVVHEGLHNH HTTKSFSRTP GGGGSGGGSH    480
HHHHH                                                                485

SEQ ID NO: 101          moltype = AA   length = 485
FEATURE                 Location/Qualifiers
REGION                  1..485
                        note = Description of Artificial Sequence: Synthetic
                         polypeptide
REGION                  1..485
                        note = AF003251_Pep2
source                  1..485
                        mol_type = protein
                        organism = synthetic construct
SEQUENCE: 101
QVQLVQSGAE VKKPGASVKV SCKASGYTFT TYYVHWVRQA PGQGLEWMGI INPSGGSTSY     60
AQNFQGRVTM TRDTSTSTVY MELSSLRSED TAVYYCASGW DVWGQGTTVT VSSASGGGGS    120
GGGGSGGGGS HASEIVMTQS PATLSVSPGE RATLSCRASQ SVNTYLAWYQ QKPGQAPRLL    180
IYGASTRATG IPARFSGSGS GTEFTLTISS LQSEDFAVYY CQQYGSSPVT FGQGTRLEIK    240
PRGPTIKPCP PCKCPAPNAA GGPSVFIFPP KIKDVLMISL SPIVTCVVVD VSEDDPDVQI    300
SWFVNNVEVH TAQTQTHRED YNSTLRVVSA LPIQHQDWMS GKEFKCKVNN KDLGAPIERT    360
ISKPKGSVRA PQVYVLPPPE KEMTKKQVSL TCLVKDFMPE DIYVEWTNNG KTELNYKNTE    420
PVLKSDGSYF MYSKLTVEKK NWVERNSYSC SVVHEGLHNH HTTKSFSRTP GGGGSGGGSH    480
HHHHH                                                                485

SEQ ID NO: 102          moltype = AA   length = 485
FEATURE                 Location/Qualifiers
REGION                  1..485
                        note = Description of Artificial Sequence: Synthetic
                         polypeptide
REGION                  1..485
                        note = AF003253_Pep2
source                  1..485
                        mol_type = protein
                        organism = synthetic construct
SEQUENCE: 102
QVQLVQSGAE VKKPGASVKV SCKASGYTFT TYYVHWVRQA PGQGLEWMGI INPSGGSTSY     60
```

```
AQNFQGRVTM TRDTSTSTVY MELSSLRSED TAVYYCASGW DVWGQGTTVT VSSASGGGGS    120
GGGGSGGGGS HASEIVMTQS PATLSVSPGE RATLSCRASQ SVNTYLAWYQ QKPGQAPRLL    180
IYGASTRATG IPARFSGSGS GTEFTLTISS LQSEDFAVYY CQQYGSSPVT FGQGTRLEIK    240
PRGPTIKPCP PCKCPAPNAA GGPSVFIFPP KIKDVLMISL SPIVTCVVVD VSEDDPDVQI    300
SWFVNNVEVH TAQTQTHRED YNSTLRVVSA LPIQHQDWMS GKEFKCKVNN KDLGAPIERT    360
ISKPKGSVRA PQVYVLPPPE KEMTKKQVSL TCLVKDFMPE DIYVEWTNNG KTELNYKNTE    420
PVLKSDGSYF MYSKLTVEKK NWVERNSYSC SVVHEGLHNH HTTKSFSRTP GGGGSGGGSH    480
HHHHH                                                                485

SEQ ID NO: 103          moltype = AA   length = 460
FEATURE                 Location/Qualifiers
REGION                  1..460
                        note = Description of Artificial Sequence: Synthetic
                         polypeptide
REGION                  1..460
                        note = AF003103_Pep2
source                  1..460
                        mol_type = protein
                        organism = synthetic construct
SEQUENCE: 103
QVQLVQSGAE VKKPGASVKV SCKASGGTFS SYAISWVRQA PGQGLEWMGI IDPSVTYTRY     60
AQKFQGRVTM TRDTSTSTVY MELSSLRSED TAVYYCARSL FPTIFGVEVA FDIWGQGTLV    120
TVSSAKTTAP SVYPLAPVCG DTTGSSVTLG CLVKGYFPEP VTLTWNSGSL SSGVHTFPAV    180
LQSDLYTLSS SVTVTSSTWP SQSITCNVAH PASSTKVDKK IEPRGPTIKP CPPCKCPAPN    240
AAGGPSVFIF PPKIKDVLMI SLSPIVTCVV VDVSEDDPDV QISWFVNNVE VHTAQTQTHR    300
EDYNSTLRVV SALPIQHQDW MSGKEFKCKV NNKDLGAPIE RTISKPKGSV RAPQVYVLPP    360
CEEEMTKKQV TLSCAVTDFM PEDIYVEWTN NGKTELNYKN TEPVLDSDGS YFMVSKLRVE    420
KKNWVERNSY SCSVVHEGLH NHHTTKSFSR TPGKHHHHHH                           460

SEQ ID NO: 104          moltype = AA   length = 454
FEATURE                 Location/Qualifiers
REGION                  1..454
                        note = Description of Artificial Sequence: Synthetic
                         polypeptide
REGION                  1..454
                        note = AF003104_Pep2
source                  1..454
                        mol_type = protein
                        organism = synthetic construct
SEQUENCE: 104
QVQLVQSGAE VKKPGASVKV SCKASGYTFS NYYIHWVRQA PGQGLEWMGW MDSNSGGTGY     60
AQKFQGRVTM TRDTSTSTVY MELSSLRSED TAVYYCAKEV FSGWYDYWGQ GTLVTVSSAK    120
TTAPSVYPLA PVCGDTTGSS VTLGCLVKGY FPEPVTLTWN SGSLSSGVHT FPAVLQSDLY    180
TLSSSVTVTS STWPSQSITC NVAHPASSTK VDKKIEPRGP TIKPCPPCKC PAPNAAGGPS    240
VFIFPPKIKD VLMISLSPIV TCVVVDVSED DPDVQISWFV NNVEVHTAQT QTHREDYNST    300
LRVVSALPIQ HQDWMSGKEF KCKVNNKDLG APIERTISKP KGSVRAPQVY VLPPCEEEMT    360
KKQVTLSCAV TDFMPEDIYV EWTNNGKTEL NYKNTEPVLD SDGSYFMVSK LRVEKKNWVE    420
RNSYSCSVVH EGLHNHHTTK SFSRTPGKHH HHHH                                454

SEQ ID NO: 105          moltype = AA   length = 454
FEATURE                 Location/Qualifiers
REGION                  1..454
                        note = Description of Artificial Sequence: Synthetic
                         polypeptide
REGION                  1..454
                        note = AF003105_Pep2
source                  1..454
                        mol_type = protein
                        organism = synthetic construct
SEQUENCE: 105
QVQLVQSGAE VKKPGASVKV SCKASGYTFS GYYIHWVRQA PGQGLEWMGW MDSNSGGTGY     60
AQKFQGRVTM TRDTSTSTVY MELSSLRSED TAVYYCAKEV FSGWYDYWGQ GTLVTVSSAK    120
TTAPSVYPLA PVCGDTTGSS VTLGCLVKGY FPEPVTLTWN SGSLSSGVHT FPAVLQSDLY    180
TLSSSVTVTS STWPSQSITC NVAHPASSTK VDKKIEPRGP TIKPCPPCKC PAPNAAGGPS    240
VFIFPPKIKD VLMISLSPIV TCVVVDVSED DPDVQISWFV NNVEVHTAQT QTHREDYNST    300
LRVVSALPIQ HQDWMSGKEF KCKVNNKDLG APIERTISKP KGSVRAPQVY VLPPCEEEMT    360
KKQVTLSCAV TDFMPEDIYV EWTNNGKTEL NYKNTEPVLD SDGSYFMVSK LRVEKKNWVE    420
RNSYSCSVVH EGLHNHHTTK SFSRTPGKHH HHHH                                454

SEQ ID NO: 106          moltype = AA   length = 454
FEATURE                 Location/Qualifiers
REGION                  1..454
                        note = Description of Artificial Sequence: Synthetic
                         polypeptide
REGION                  1..454
                        note = AF003106_Pep2
source                  1..454
                        mol_type = protein
                        organism = synthetic construct
```

```
SEQUENCE: 106
QVQLVQSGAE VKKPGASVKV SCKASGYTFS NYYIHWVRQA PGQGLEWMGW MDSNSGYTGY      60
AQQFQGRVTM TRDTSTSTVY MELSSLRSED TAVYYCAKEV FSGWYDYWGQ GTLVTVSSAK     120
TTAPSVYPLA PVCGDTTGSS VTLGCLVKGY FPEPVTLTWN SGSLSSGVHT FPAVLQSDLY     180
TLSSSVTVTS STWPSQSITC NVAHPASSTK VDKKIEPRGP TIKPCPPCKC PAPNAAGGPS     240
VFIFPPKIKD VLMISLSPIV TCVVVDVSED DPDVQISWFV NNVEVHTAQT QTHREDYNST     300
LRVVSALPIQ HQDWMSGKEF KCKVNNKDLG APIERTISKP KGSVRAPQVY VLPPCEEEMT     360
KKQVTLSCAV TDFMPEDIYV EWTNNGKTEL NYKNTEPVLD SDGSYFMVSK LRVEKKNWVE     420
RNSYSCSVVH EGLHNHHTTK SFSRTPGKHH HHH                                  454

SEQ ID NO: 107           moltype = AA   length = 481
FEATURE                  Location/Qualifiers
REGION                   1..481
                         note = Description of Artificial Sequence: Synthetic
                         polypeptide
REGION                   1..481
                         note = AF003217_Pep2
source                   1..481
                         mol_type = protein
                         organism = synthetic construct
SEQUENCE: 107
QVQLVQSGAE VKKPGASVKV SCKASGYTFT KNYMHWVRQA PGQGLEWLGW VSPDSGYTGY      60
AQKFQGRVTM TRDTSTSTVY MELSSLRSED TAVYYCTTDL LSLELDDAFD IWGQGTMVTV     120
SSASGGGGSG GGGSGGGGSH ASDIQMTQSP SSLSASVGDR VTITCRASQS ISSWLAWYQQ     180
KPGKAPKLLI YAASTLQSGV PSRFSGSGSG TDFTLTISSL QPEDFATYYC QQSYSTPLTF     240
GGGTKLEIKP RGPTIKPCPP CKCPAPNAAG GPSVFIFPPK IKDVLMISLS PIVTCVVVDV     300
SEDDPDVQIS WFVNNVEVHT AQTQTHREDY NSTLRVVSAL PIQHQDWMSG KEFKCKVNNK     360
DLGAPIERTI SKPKGSVRAP QVYVLPPCEE EMTKKQVTLS CAVTDFMPED IYVEWTNNGK     420
TELNYKNTEP VLDSDGSYFM VSKLRVEKKN WVERNSYSCS VVHEGLHNHH TTKSFSRTPG     480
K                                                                      481

SEQ ID NO: 108           moltype = AA   length = 481
FEATURE                  Location/Qualifiers
REGION                   1..481
                         note = Description of Artificial Sequence: Synthetic
                         polypeptide
REGION                   1..481
                         note = AF003218_Pep2
source                   1..481
                         mol_type = protein
                         organism = synthetic construct
SEQUENCE: 108
QVQLVQSGAE VKKPGASVKV SCKASGYTFT KNYMHWVRQA PGQGLEWLGW VSPDSGYTGY      60
AQKFQGRVTM TRDTSTSTVY MELSSLRSED TAVYYCTTDL LSLELDDAFD IWGQGTMVTV     120
SSASGGGGSG GGGSGGGGSH ASDIQMTQSP SSLSASVGDR VTITCRASQS ISSWLAWYQQ     180
KPGKAPKLLI YAASTLQSGV PSRFSGSGSG TDFTLTISSL QPEDFATYYC QQSYSTPLTF     240
GGGTKLEIKP RGPTIKPCPP CKCPAPNAAG GPSVFIFPPK IKDVLMISLS PIVTCVVVDV     300
SEDDPDVQIS WFVNNVEVHT AQTQTHREDY NSTLRVVSAL PIQHQDWMSG KEFKCKVNNK     360
DLGAPIERTI SKPKGSVRAP QVYVLPPCEE EMTKKQVTLS CAVTDFMPED IYVEWTNNGK     420
TELNYKNTEP VLDSDGSYFM VSKLRVEKKN WVERNSYSCS VVHEGLHNHH TTKSFSRTPG     480
K                                                                      481

SEQ ID NO: 109           moltype = AA   length = 481
FEATURE                  Location/Qualifiers
REGION                   1..481
                         note = Description of Artificial Sequence: Synthetic
                         polypeptide
REGION                   1..481
                         note = AF003219_Pep2
source                   1..481
                         mol_type = protein
                         organism = synthetic construct
SEQUENCE: 109
QVQLVQSGAE VKKPGASVKV SCKASGYTFT KNYMHWVRQA PGQGLEWLGW VSPDSGYTGY      60
AQKFQGRVTM TRDTSTSTVY MELSSLRSED TAVYYCTTDL LSLELDDAFD IWGQGTMVTV     120
SSASGGGGSG GGGSGGGGSH ASDIQMTQSP SSLSASVGDR VTITCRASQS ISSWLAWYQQ     180
KPGKAPKLLI YAASTLQSGV PSRFSGSGSG TDFTLTISSL QPEDFATYYC QQSYSTPLTF     240
GGGTKLEIKP RGPTIKPCPP CKCPAPNAAG GPSVFIFPPK IKDVLMISLS PIVTCVVVDV     300
SEDDPDVQIS WFVNNVEVHT AQTQTHREDY NSTLRVVSAL PIQHQDWMSG KEFKCKVNNK     360
DLGAPIERTI SKPKGSVRAP QVYVLPPCEE EMTKKQVTLS CAVTDFMPED IYVEWTNNGK     420
TELNYKNTEP VLDSDGSYFM VSKLRVEKKN WVERNSYSCS VVHEGLHNHH TTKSFSRTPG     480
K                                                                      481

SEQ ID NO: 110           moltype = AA   length = 399
FEATURE                  Location/Qualifiers
REGION                   1..399
                         note = Description of Artificial Sequence: Synthetic
                         polypeptide
REGION                   1..399
```

```
                        note = AF002618_Pep2
source                  1..399
                        mol_type = protein
                        organism = synthetic construct
SEQUENCE: 110
CDLPQTHSLG SRRTLMLLAQ MRRISLFSCL KDRHDFGFPQ EEFGNQFQKA ETIPVLHEMI   60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKEGGGGS GGGGSGGGGS  180
GGGGSDIQMT QSPSSLSASV GDRVTITCRA SQSISNRLAW YQQKPGKAPK LLIYKASSLE  240
SGVPSRFSGS GSGTDFTLTI SSLQPEDFAT YYCQQSNSTP FTFGQGTKVE IKRADAAPTV  300
SIFPPSSEQL TSGGASVVCF LNNFYPKDIN VKWKIDGSER QNGVLNSWTD QDSKDSTYSM  360
SSTLTLTKDE YERHNSYTCE ATHKTSTSPI VKSFNRNEC                        399

SEQ ID NO: 111          moltype = AA  length = 399
FEATURE                 Location/Qualifiers
REGION                  1..399
                        note = Description of Artificial Sequence: Synthetic
                         polypeptide
REGION                  1..399
                        note = AF002639_Pep2
source                  1..399
                        mol_type = protein
                        organism = synthetic construct
SEQUENCE: 111
CDLPQTHSLG SRRTLMLLAQ MRRISLFSCL KDRHDFGFPQ EEFGNQFQKA ETIPVLHEMI   60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKEGGGGS GGGGSGGGGS  180
GGGGSDIQMT QSPSSLSASV GDRVTITCRA SQSISSYLNW YQQKPGKAPK LLIYAASSLQ  240
SGVPSRFSGS GSGTDFTLTI SSLQPEDFAT YYCQQSYSTP YTFGQGTKVE IKRADAAPTV  300
SIFPPSSEQL TSGGASVVCF LNNFYPKDIN VKWKIDGSER QNGVLNSWTD QDSKDSTYSM  360
SSTLTLTKDE YERHNSYTCE ATHKTSTSPI VKSFNRNEC                        399

SEQ ID NO: 112          moltype = AA  length = 214
FEATURE                 Location/Qualifiers
REGION                  1..214
                        note = Description of Artificial Sequence: Synthetic
                         polypeptide
REGION                  1..214
                        note = AF002645_Pep2
source                  1..214
                        mol_type = protein
                        organism = synthetic construct
SEQUENCE: 112
DIQMTQSPSS LSASVGDRVT ITCRASQSIS NRLAWYQQKP GKAPKLLIYK ASSLESGVPS   60
RFSGSGSGTD FTLTISSLQP EDFATYYCQQ SNSTPFTFGQ GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                             214

SEQ ID NO: 113          moltype =   length =
SEQUENCE: 113
000

SEQ ID NO: 114          moltype = AA  length = 214
FEATURE                 Location/Qualifiers
REGION                  1..214
                        note = Description of Artificial Sequence: Synthetic
                         polypeptide
REGION                  1..214
                        note = AF003229_Pep3
source                  1..214
                        mol_type = protein
                        organism = synthetic construct
SEQUENCE: 114
DIQMTQSPSS LSASVGDRVT ITCRASQYIS SGLAWYQQKP GKAPKLLIYK ASSLDNGVPS   60
RFSGSGSGTD FTLTISSLQP EDFATYYCQQ YERLPLTFGG GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                             214

SEQ ID NO: 115          moltype = AA  length = 214
FEATURE                 Location/Qualifiers
REGION                  1..214
                        note = Description of Artificial Sequence: Synthetic
                         polypeptide
REGION                  1..214
                        note = AF003230_Pep3
source                  1..214
                        mol_type = protein
                        organism = synthetic construct
SEQUENCE: 115
```

```
DIQMTQSPSS LSASVGDRVT ITCRASQSIG TGLAWYQQKP GKAPKLLIYK ASSLDNGVPS    60
RFSGSGSGTD FTLTISSLQP EDFATYYCQQ YNRAPLTFGG GTKVEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 116         moltype = AA   length = 214
FEATURE                Location/Qualifiers
REGION                 1..214
                       note = Description of Artificial Sequence: Synthetic
                        polypeptide
REGION                 1..214
                       note = AF003232_Pep3
source                 1..214
                       mol_type = protein
                       organism = synthetic construct
SEQUENCE: 116
DIQMTQSPSS LSASVGDRVT ITCRASQSIG RWLAWYQQKP GKAPKLLIYS ASNLETGVPS    60
RFSGSGSGTD FTLTISSLQP EDFATYYCQQ YESFPVTFGP GTKVDIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 117         moltype =   length =
SEQUENCE: 117
000

SEQ ID NO: 118         moltype =   length =
SEQUENCE: 118
000

SEQ ID NO: 119         moltype =   length =
SEQUENCE: 119
000

SEQ ID NO: 120         moltype =   length =
SEQUENCE: 120
000

SEQ ID NO: 121         moltype =   length =
SEQUENCE: 121
000

SEQ ID NO: 122         moltype =   length =
SEQUENCE: 122
000

SEQ ID NO: 123         moltype =   length =
SEQUENCE: 123
000

SEQ ID NO: 124         moltype =   length =
SEQUENCE: 124
000

SEQ ID NO: 125         moltype =   length =
SEQUENCE: 125
000

SEQ ID NO: 126         moltype = AA   length = 214
FEATURE                Location/Qualifiers
REGION                 1..214
                       note = Description of Artificial Sequence: Synthetic
                        polypeptide
REGION                 1..214
                       note = AF003219_Pep3
source                 1..214
                       mol_type = protein
                       organism = synthetic construct
SEQUENCE: 126
DIQMTQSPSS LSASVGDRVT ITCRASQSIS SYLNWYQQKP GKAPKLLIYA ASSLESGVPS    60
RFSGSGSGTD FTLTISSLQP EDFATYYCQQ SYSTPYTFGQ GTKVDIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 127         moltype = AA   length = 113
FEATURE                Location/Qualifiers
REGION                 1..113
                       note = Description of Artificial Sequence: Synthetic
                        polypeptide
REGION                 1..113
```

```
                           note = AB001718_HV
source                     1..113
                           mol_type = protein
                           organism = synthetic construct
SEQUENCE: 127
QVQLVQSGAE VKKPGASVKV SCKASGDTFS TYYVHWVRQA PGQGLEWMGI INPSGGGTVY    60
AQKFQGRVTM TRDTSTSTVY MELSSLRSED TAVYYCAAGL FIWGQGTLVT VSS          113

SEQ ID NO: 128             moltype = AA   length = 113
FEATURE                    Location/Qualifiers
REGION                     1..113
                           note = Description of Artificial Sequence: Synthetic
                            polypeptide
REGION                     1..113
                           note = AB001744_HV
source                     1..113
                           mol_type = protein
                           organism = synthetic construct
SEQUENCE: 128
QVQLVQSGAE VKKPGASVKV SCKASGYTFS NYYIHWVRQA PGQGLEWMGI INPSGGGTVY    60
AQKFQGRVTM TRDTSTSTVY MELSSLRSED TAVYYCAAGL FIWGQGTLVT VSS          113

SEQ ID NO: 129             moltype = AA   length = 113
FEATURE                    Location/Qualifiers
REGION                     1..113
                           note = Description of Artificial Sequence: Synthetic
                            polypeptide
REGION                     1..113
                           note = AB002022_HV
source                     1..113
                           mol_type = protein
                           organism = synthetic construct
SEQUENCE: 129
QVQLVQSGAE VKKPGASVKV SCKASGDTFT RHYVHWVRQA PGQGLEWMGI INPSGGYASY    60
AQKFQGRVTM TRDTSTSTVY MELSSLRSED TAVYYCAAGL FIWGQGTLVT VSS          113

SEQ ID NO: 130             moltype = AA   length = 124
FEATURE                    Location/Qualifiers
REGION                     1..124
                           note = Description of Artificial Sequence: Synthetic
                            polypeptide
REGION                     1..124
                           note = AB001609_HV
source                     1..124
                           mol_type = protein
                           organism = synthetic construct
SEQUENCE: 130
QVQLVQSGAE VKKPGASVKV SCKASGGTFS SYAISWVRQA PGQGLEWMGI IDPSVTYTRY    60
AQKFQGRVTM TRDTSTSTVY MELSSLRSED TAVYYCARSL FPTIFGVEVA FDIWGQGTLV   120
TVSS                                                               124

SEQ ID NO: 131             moltype = AA   length = 118
FEATURE                    Location/Qualifiers
REGION                     1..118
                           note = Description of Artificial Sequence: Synthetic
                            polypeptide
REGION                     1..118
                           note = AB001843_HV
source                     1..118
                           mol_type = protein
                           organism = synthetic construct
SEQUENCE: 131
QVQLVQSGAE VKKPGASVKV SCKASGYTFS GYYIHWVRQA PGQGLEWMGW MDSNSGGTGY    60
AQKFQGRVTM TRDTSTSTVY MELSSLRSED TAVYYCAKEV FSGWYDYWGQ GTLVTVSS    118

SEQ ID NO: 132             moltype = AA   length = 118
FEATURE                    Location/Qualifiers
REGION                     1..118
                           note = Description of Artificial Sequence: Synthetic
                            polypeptide
REGION                     1..118
                           note = AB001866_HV
source                     1..118
                           mol_type = protein
                           organism = synthetic construct
SEQUENCE: 132
QVQLVQSGAE VKKPGASVKV SCKASGYTFS NYYHWVRQA PGQGLEWMGW MDPNSGGTGY     60
AHQFQGRVTM TRDTSTSTVY MELSSLRSED TAVYYCAKEV FSGWYDYWGQ GTLVTVSS    118
```

```
SEQ ID NO: 133          moltype = AA  length = 118
FEATURE                 Location/Qualifiers
REGION                  1..118
                        note = Description of Artificial Sequence: Synthetic
                        polypeptide
REGION                  1..118
                        note = AB001875_HV
source                  1..118
                        mol_type = protein
                        organism = synthetic construct
SEQUENCE: 133
QVQLVQSGAE VKKPGASVKV SCKASGYTFS NYYIHWVRQA PGQGLEWMGW MDSNSGYTGY    60
AQQFQGRVTM TRDTSTSTVY MELSSLRSED TAVYYCAKEV FSGWYDYWGQ GTLVTVSS    118

SEQ ID NO: 134          moltype = AA  length = 118
FEATURE                 Location/Qualifiers
REGION                  1..118
                        note = Description of Artificial Sequence: Synthetic
                        polypeptide
REGION                  1..118
                        note = AB001909_HV
source                  1..118
                        mol_type = protein
                        organism = synthetic construct
SEQUENCE: 134
QVQLVQSGAE VKKPGASVKV SCKASGYTFS NYYIHWVRQA PGQGLEWMGW MDSNSGGTGY    60
AQKFQGRVTM TRDTSTSTVY MELSSLRSED TAVYYCAKEV FSGWYDYWGQ GTLVTVSS    118

SEQ ID NO: 135          moltype = AA  length = 107
FEATURE                 Location/Qualifiers
REGION                  1..107
                        note = Description of Artificial Sequence: Synthetic
                        polypeptide
REGION                  1..107
                        note = AB001718_LV
source                  1..107
                        mol_type = protein
                        organism = synthetic construct
SEQUENCE: 135
DIQMTQSPSS LSASVGDRVT ITCRASQYIS SGLAWYQQKP GKAPKLLIYK ASSLDNGVPS    60
RFSGSGSGTD FTLTISSLQP EDFATYYCQQ YERLPLTFGG GTKVEIK              107

SEQ ID NO: 136          moltype = AA  length = 107
FEATURE                 Location/Qualifiers
REGION                  1..107
                        note = Description of Artificial Sequence: Synthetic
                        polypeptide
REGION                  1..107
                        note = AB001744_LV
source                  1..107
                        mol_type = protein
                        organism = synthetic construct
SEQUENCE: 136
DIQMTQSPSS LSASVGDRVT ITCRASQSIG TGLAWYQQKP GKAPKLLIYK ASSLDNGVPS    60
RFSGSGSGTD FTLTISSLQP EDFATYYCQQ YNRAPLTFGG GTKVEIK              107

SEQ ID NO: 137          moltype = AA  length = 107
FEATURE                 Location/Qualifiers
REGION                  1..107
                        note = Description of Artificial Sequence: Synthetic
                        polypeptide
REGION                  1..107
                        note = AB002022_LV
source                  1..107
                        mol_type = protein
                        organism = synthetic construct
SEQUENCE: 137
DIQMTQSPSS LSASVGDRVT ITCRASQSIG RWLAWYQQKP GKAPKLLIYS ASNLETGVPS    60
RFSGSGSGTD FTLTISSLQP EDFATYYCQQ YESFPVTFGP GTKVDIK              107

SEQ ID NO: 138          moltype = AA  length = 107
FEATURE                 Location/Qualifiers
REGION                  1..107
                        note = Description of Artificial Sequence: Synthetic
                        polypeptide
REGION                  1..107
                        note = AB001609_LV
source                  1..107
                        mol_type = protein
```

```
                        organism = synthetic construct
SEQUENCE: 138
DIQMTQSPSS LSASVGDRVT ITCRASQSIS NRLAWYQQKP GKAPKLLIYK ASSLESGVPS    60
RFSGSGSGTD FTLTISSLQP EDFATYYCQQ SNSTPFTFGQ GTKVEIK                 107

SEQ ID NO: 139          moltype = AA  length = 107
FEATURE                 Location/Qualifiers
REGION                  1..107
                        note = Description of Artificial Sequence: Synthetic
                         polypeptide
REGION                  1..107
                        note = AB001638_LV
source                  1..107
                        mol_type = protein
                        organism = synthetic construct
SEQUENCE: 139
DIQMTQSPSS LSASVGDRVT ITCQASQSIS NYLAWYQQKP GKAPKLLIYK ASSLESGVPS    60
RFSGSGSGTD FTLTISSLQP EDFATYYCQQ TYSTPITFGQ GTKVEIK                 107

SEQ ID NO: 140          moltype = AA  length = 107
FEATURE                 Location/Qualifiers
REGION                  1..107
                        note = Description of Artificial Sequence: Synthetic
                         polypeptide
REGION                  1..107
                        note = AB001843_LV
source                  1..107
                        mol_type = protein
                        organism = synthetic construct
SEQUENCE: 140
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPYTFGQ GTKVEIK                 107

SEQ ID NO: 141          moltype = AA  length = 107
FEATURE                 Location/Qualifiers
REGION                  1..107
                        note = Description of Artificial Sequence: Synthetic
                         polypeptide
REGION                  1..107
                        note = AB001909_LV
source                  1..107
                        mol_type = protein
                        organism = synthetic construct
SEQUENCE: 141
DIQMTQSPSS LSASVGDRVT ITCRASQSIS SYLNWYQQKP GKAPKLLIYA ASSLESGVPS    60
RFSGSGSGTD FTLTISSLQP EDFATYYCQQ SYSTPYTFGQ GTKVDIK                 107

SEQ ID NO: 142          moltype = AA  length = 10
FEATURE                 Location/Qualifiers
REGION                  1..10
                        note = Description of Artificial Sequence: Synthetic peptide
REGION                  1..10
                        note = AB001718_HV_cdr1
source                  1..10
                        mol_type = protein
                        organism = synthetic construct
SEQUENCE: 142
GDTFSTYYVH                                                          10

SEQ ID NO: 143          moltype = AA  length = 10
FEATURE                 Location/Qualifiers
REGION                  1..10
                        note = Description of Artificial Sequence: Synthetic peptide
REGION                  1..10
                        note = AB001744_HV_cdr1
source                  1..10
                        mol_type = protein
                        organism = synthetic construct
SEQUENCE: 143
GYTFSNYYIH                                                          10

SEQ ID NO: 144          moltype = AA  length = 10
FEATURE                 Location/Qualifiers
REGION                  1..10
                        note = Description of Artificial Sequence: Synthetic peptide
REGION                  1..10
                        note = AB002022_HV_cdr1
source                  1..10
                        mol_type = protein
```

```
                       -continued

SEQUENCE: 144
GDTFTRHYVH                                                           10

SEQ ID NO: 145         moltype = AA  length = 10
FEATURE                Location/Qualifiers
REGION                 1..10
                       note = Description of Artificial Sequence: Synthetic peptide
REGION                 1..10
                       note = AB001609_HV_cdr1
source                 1..10
                       mol_type = protein
                       organism = synthetic construct
SEQUENCE: 145
GGTFSSYAIS                                                           10

SEQ ID NO: 146         moltype = AA  length = 10
FEATURE                Location/Qualifiers
REGION                 1..10
                       note = Description of Artificial Sequence: Synthetic peptide
REGION                 1..10
                       note = AB001843_HV_cdr1
source                 1..10
                       mol_type = protein
                       organism = synthetic construct
SEQUENCE: 146
GYTFSGYYIH                                                           10

SEQ ID NO: 147         moltype = AA  length = 10
FEATURE                Location/Qualifiers
REGION                 1..10
                       note = Description of Artificial Sequence: Synthetic peptide
REGION                 1..10
                       note = AB001866_HV_cdr1
source                 1..10
                       mol_type = protein
                       organism = synthetic construct
SEQUENCE: 147
GYTFSNYYVH                                                           10

SEQ ID NO: 148         moltype = AA  length = 17
FEATURE                Location/Qualifiers
REGION                 1..17
                       note = Description of Artificial Sequence: Synthetic peptide
REGION                 1..17
                       note = AB001718_HV_cdr2
source                 1..17
                       mol_type = protein
                       organism = synthetic construct
SEQUENCE: 148
IINPSGGGTV YAQKFQG                                                   17

SEQ ID NO: 149         moltype = AA  length = 17
FEATURE                Location/Qualifiers
REGION                 1..17
                       note = Description of Artificial Sequence: Synthetic peptide
REGION                 1..17
                       note = AB002022_HV_cdr2
source                 1..17
                       mol_type = protein
                       organism = synthetic construct
SEQUENCE: 149
IINPSGGYAS YAQKFQG                                                   17

SEQ ID NO: 150         moltype = AA  length = 17
FEATURE                Location/Qualifiers
REGION                 1..17
                       note = Description of Artificial Sequence: Synthetic peptide
REGION                 1..17
                       note = AB001609_HV_cdr2
source                 1..17
                       mol_type = protein
                       organism = synthetic construct
SEQUENCE: 150
IIDPSVTYTR YAQKFQG                                                   17

SEQ ID NO: 151         moltype = AA  length = 17
FEATURE                Location/Qualifiers
REGION                 1..17
```

```
                    note = Description of Artificial Sequence: Synthetic peptide
REGION              1..17
                    note = AB001843_HV_cdr2
source              1..17
                    mol_type = protein
                    organism = synthetic construct
SEQUENCE: 151
WMDSNSGGTG YAQKFQG                                                        17

SEQ ID NO: 152      moltype = AA  length = 17
FEATURE             Location/Qualifiers
REGION              1..17
                    note = Description of Artificial Sequence: Synthetic peptide
REGION              1..17
                    note = AB001866_HV_cdr2
source              1..17
                    mol_type = protein
                    organism = synthetic construct
SEQUENCE: 152
WMDPNSGGTG YAHQFQG                                                        17

SEQ ID NO: 153      moltype = AA  length = 17
FEATURE             Location/Qualifiers
REGION              1..17
                    note = Description of Artificial Sequence: Synthetic peptide
REGION              1..17
                    note = AB001875_HV_cdr2
source              1..17
                    mol_type = protein
                    organism = synthetic construct
SEQUENCE: 153
WMDSNSGYTG YAQQFQG                                                        17

SEQ ID NO: 154      moltype = AA  length = 6
FEATURE             Location/Qualifiers
REGION              1..6
                    note = Description of Artificial Sequence: Synthetic peptide
REGION              1..6
                    note = AB001718_HV_cdr3
source              1..6
                    mol_type = protein
                    organism = synthetic construct
SEQUENCE: 154
AAGLFI                                                                     6

SEQ ID NO: 155      moltype = AA  length = 17
FEATURE             Location/Qualifiers
REGION              1..17
                    note = Description of Artificial Sequence: Synthetic peptide
REGION              1..17
                    note = AB001609_HV_cdr3
source              1..17
                    mol_type = protein
                    organism = synthetic construct
SEQUENCE: 155
ARSLFPTIFG VEVAFDI                                                        17

SEQ ID NO: 156      moltype = AA  length = 11
FEATURE             Location/Qualifiers
REGION              1..11
                    note = Description of Artificial Sequence: Synthetic peptide
REGION              1..11
                    note = AB001843_HV_cdr3
source              1..11
                    mol_type = protein
                    organism = synthetic construct
SEQUENCE: 156
AKEVFSGWYD Y                                                              11

SEQ ID NO: 157      moltype = AA  length = 11
FEATURE             Location/Qualifiers
REGION              1..11
                    note = Description of Artificial Sequence: Synthetic peptide
REGION              1..11
                    note = AB001718_LV_cdr1
source              1..11
                    mol_type = protein
                    organism = synthetic construct
SEQUENCE: 157
```

```
                                                  -continued

RASQYISSGL A                                                            11

SEQ ID NO: 158          moltype = AA  length = 11
FEATURE                 Location/Qualifiers
REGION                  1..11
                        note = Description of Artificial Sequence: Synthetic peptide
REGION                  1..11
                        note = AB001744_LV_cdr1
source                  1..11
                        mol_type = protein
                        organism = synthetic construct SEQUENCE: 158
RASQSIGTGL A                                                            11

SEQ ID NO: 159          moltype = AA  length = 11
FEATURE                 Location/Qualifiers
REGION                  1..11
                        note = Description of Artificial Sequence: Synthetic peptide
REGION                  1..11
                        note = AB002022_LV_cdr1
source                  1..11
                        mol_type = protein
                        organism = synthetic construct SEQUENCE: 159
RASQSIGRWL A                                                            11

SEQ ID NO: 160          moltype = AA  length = 11
FEATURE                 Location/Qualifiers
REGION                  1..11
                        note = Description of Artificial Sequence: Synthetic peptide
REGION                  1..11
                        note = AB001609_LV_cdr1
source                  1..11
                        mol_type = protein
                        organism = synthetic construct SEQUENCE: 160
RASQSISNRL A                                                            11

SEQ ID NO: 161          moltype = AA  length = 11
FEATURE                 Location/Qualifiers
REGION                  1..11
                        note = Description of Artificial Sequence: Synthetic peptide
REGION                  1..11
                        note = AB001638_LV_cdr1
source                  1..11
                        mol_type = protein
                        organism = synthetic construct SEQUENCE: 161
QASQSISNYL A                                                            11

SEQ ID NO: 162          moltype = AA  length = 11
FEATURE                 Location/Qualifiers
REGION                  1..11
                        note = Description of Artificial Sequence: Synthetic peptide
REGION                  1..11
                        note = AB001843_LV_cdr1
source                  1..11
                        mol_type = protein
                        organism = synthetic construct SEQUENCE: 162
RASQSISSYL N                                                            11

SEQ ID NO: 163          moltype = AA  length = 7
FEATURE                 Location/Qualifiers
REGION                  1..7
                        note = Description of Artificial Sequence: Synthetic peptide
REGION                  1..7
                        note = AB001718_LV_cdr2
source                  1..7
                        mol_type = protein
                        organism = synthetic construct SEQUENCE: 163
KASSLDN                                                                 7

SEQ ID NO: 164          moltype = AA  length = 7
FEATURE                 Location/Qualifiers
REGION                  1..7
                        note = Description of Artificial Sequence: Synthetic peptide
REGION                  1..7
```

```
                        note = AB002022_LV_cdr2
source                  1..7
                        mol_type = protein
                        organism = synthetic construct
SEQUENCE: 164
SASNLET                                                                     7

SEQ ID NO: 165          moltype = AA  length = 7
FEATURE                 Location/Qualifiers
REGION                  1..7
                        note = Description of Artificial Sequence: Synthetic peptide
REGION                  1..7
                        note = AB001609_LV_cdr2
source                  1..7
                        mol_type = protein
                        organism = synthetic construct
SEQUENCE: 165
KASSLES                                                                     7

SEQ ID NO: 166          moltype = AA  length = 7
FEATURE                 Location/Qualifiers
REGION                  1..7
                        note = Description of Artificial Sequence: Synthetic peptide
REGION                  1..7
                        note = AB001843_LV_cdr2
source                  1..7
                        mol_type = protein
                        organism = synthetic construct
SEQUENCE: 166
AASSLQS                                                                     7

SEQ ID NO: 167          moltype = AA  length = 7
FEATURE                 Location/Qualifiers
REGION                  1..7
                        note = Description of Artificial Sequence: Synthetic peptide
REGION                  1..7
                        note = AB001909_LV_cdr2
source                  1..7
                        mol_type = protein
                        organism = synthetic construct
SEQUENCE: 167
AASSLES                                                                     7

SEQ ID NO: 168          moltype = AA  length = 8
FEATURE                 Location/Qualifiers
REGION                  1..8
                        note = Description of Artificial Sequence: Synthetic peptide
REGION                  1..8
                        note = AB001718_LV_cdr3
source                  1..8
                        mol_type = protein
                        organism = synthetic construct
SEQUENCE: 168
QQYERLPL                                                                    8

SEQ ID NO: 169          moltype = AA  length = 8
FEATURE                 Location/Qualifiers
REGION                  1..8
                        note = Description of Artificial Sequence: Synthetic peptide
REGION                  1..8
                        note = AB001744_LV_cdr3
source                  1..8
                        mol_type = protein
                        organism = synthetic construct
SEQUENCE: 169
QQYNRAPL                                                                    8

SEQ ID NO: 170          moltype = AA  length = 8
FEATURE                 Location/Qualifiers
REGION                  1..8
                        note = Description of Artificial Sequence: Synthetic peptide
REGION                  1..8
                        note = AB002022_LV_cdr3
source                  1..8
                        mol_type = protein
                        organism = synthetic construct
SEQUENCE: 170
QQYESFPV                                                                    8
```

```
SEQ ID NO: 171          moltype = AA   length = 8
FEATURE                 Location/Qualifiers
REGION                  1..8
                        note = Description of Artificial Sequence: Synthetic peptide
REGION                  1..8
                        note = AB001609_LV_cdr3
source                  1..8
                        mol_type = protein
                        organism = synthetic construct
SEQUENCE: 171
QQSNSTPF                                                                  8

SEQ ID NO: 172          moltype = AA   length = 8
FEATURE                 Location/Qualifiers
REGION                  1..8
                        note = Description of Artificial Sequence: Synthetic peptide
REGION                  1..8
                        note = AB001638_LV_cdr3
source                  1..8
                        mol_type = protein
                        organism = synthetic construct
SEQUENCE: 172
QQTYSTPI                                                                  8

SEQ ID NO: 173          moltype = AA   length = 8
FEATURE                 Location/Qualifiers
REGION                  1..8
                        note = Description of Artificial Sequence: Synthetic peptide
REGION                  1..8
                        note = AB001843_LV_cdr3
source                  1..8
                        mol_type = protein
                        organism = synthetic construct
SEQUENCE: 173
QQSYSTPY                                                                  8

SEQ ID NO: 174          moltype = AA   length = 596
FEATURE                 Location/Qualifiers
REGION                  1..596
                        note = Description of Artificial Sequence: Synthetic
                        polypeptide
REGION                  1..596
                        note = AF4379_pep1
source                  1..596
                        mol_type = protein
                        organism = synthetic construct
SEQUENCE: 174
APTSSSTKKT QLQLEHLLLD LQMILNGINN YKNPKLTDML TFEFYMPKKA TELKHLQCLE    60
RELKPLEEVL NLAQSKNFHL RPRDLISNIN VIVLELKGSE TTFMCEYADE TATIVEFLNR   120
WITFCQSIIS TLTGGGGSGG GGSGGGGSGG GGSQVQLVQS GAEVKKPGAS VKVSCKASGD   180
TFTRYYVHWV RQAPGQGLEW MGIINPSGGY ASYAQKFQGR VTMTRDTSTS TVYMELSSLR   240
SEDTAVYYCA AGLFIWGQGT LVTVSSAKTT APSVYPLAPV CGDTTGSSVT LGCLVKGYFP   300
EPVTLTWNSG SLSSGVHTFP AVLQSDLYTL SSSVTVTSST WPSQSITCNV AHPASSTKVD   360
KKIEPRGPTI KPCPPCKCPA PNAAGGPSVF IFPPKIKDVL MISLSPIVTC VVVDVSEDDP   420
DVQISWFVNN VEVHTAQTQT HREDYNSTLR VVSALPIQHQ DWMSGKEFKC KVNNKDLGAP   480
IERTISKPKG SVRAPQVYVL PPPEEEMTKK QVTLTCMVTD FMPEDIYVEW TNNGKTELNY   540
KNTEPVLDSD GSYFMYSKLR VEKKNWVERN SYSCSVVHEG LHNHHTTKSF SRTPGK       596

SEQ ID NO: 175          moltype = AA   length = 214
FEATURE                 Location/Qualifiers
REGION                  1..214
                        note = Description of Artificial Sequence: Synthetic
                        polypeptide
REGION                  1..214
                        note = AF4379_pep2
source                  1..214
                        mol_type = protein
                        organism = synthetic construct
SEQUENCE: 175
DIQMTQSPSS LSASVGDRVT ITCRASQSIG RYLAWYQQKP GKAPKLLIYS ASNLETGVPS    60
RFSGSGSGTD FTLTISSLQP EDFATYYCQQ YNSFPVTFGP GTKVDIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 176          moltype = AA   length = 603
FEATURE                 Location/Qualifiers
REGION                  1..603
                        note = Description of Artificial Sequence: Synthetic
                        polypeptide
```

```
REGION                  1..603
                        note = AF4377_pep1
source                  1..603
                        mol_type = protein
                        organism = synthetic construct
SEQUENCE: 176
APTSSSTKKT QLQLEHLLLD LQMILNGINN YKNPKLTDML TFEFYMPKKA TELKHLQCLE    60
RELKPLEEVL NLAQSKNFHL RPRDLISNIN VIVLELKGSE TTFMCEYADE TATIVEFLNR   120
WITFCQSIIS TLTGGGGSGG GGSGGGGSGG GGSEVQLVES GGGLVQPGGS LRLSCAASGF   180
NIKDTYIHWV RQAPGKGLEW VARIYPTNGY TRYADSVKGR FTISADTSKN TAYLQMNSLR   240
AEDTAVYYCS RWGGDGFYAM DYWGQGTLVT VSSAKTTAPS VYPLAPVCGD TTGSSVTLGC   300
LVKGYFPEPV TLTWNSGSLS SGVHTFPAVL QSDLYTLSSS VTVTSSTWPS QSITCNVAHP   360
ASSTKVDKKI EPRGPTIKPC PPCKCPAPNA AGGPSVFIFP PKIKDVLMIS LSPIVTCVVV   420
DVSEDDPDVQ ISWFVNNVEV HTAQTQTHRE DYNSTLRVVS ALPIQHQDWM SGKEFKCKVN   480
NKDLGAPIER TISKPKGSVR APQVYVLPPP EEEMTKKQVT LTCMVTDFMP EDIYVEWTNN   540
GKTELNYKNT EPVLDSDGSY FMYSKLRVEK KNWVERNSYS CSVVHEGLHN HHTTKSFSRT   600
PGK                                                                 603

SEQ ID NO: 177          moltype = AA   length = 600
FEATURE                 Location/Qualifiers
REGION                  1..600
                        note = Description of Artificial Sequence: Synthetic
                         polypeptide
REGION                  1..600
                        note = AF4378_pep1
source                  1..600
                        mol_type = protein
                        organism = synthetic construct
SEQUENCE: 177
APTSSSTKKT QLQLEHLLLD LQMILNGINN YKNPKLTDML TFEFYMPKKA TELKHLQCLE    60
RELKPLEEVL NLAQSKNFHL RPRDLISNIN VIVLELKGSE TTFMCEYADE TATIVEFLNR   120
WITFCQSIIS TLTGGGGSGG GGSGGGGSGG GGSEVQLVES GGGLVKPGGS LRLSCAASGF   180
TFSSYTLAWV RQAPGKGLEW VAAIDSSSYT YSPDTVRGRF TISRDNAKNS LYLQMNSLRA   240
EDTAVYYCAR DSNWDALDYW GQGTLVTVSS AKTTAPSVYP LAPVCGDTTG SSVTLGCLVK   300
GYFPEPVTLT WNSGSLSSGV HTFPAVLQSD LYTLSSSVTV TSSTWPSQSI TCNVAHPASS   360
TKVDKKIEPR GPTIKPCPPC KCPAPNAAGG PSVFIFPPKI KDVLMISLSP IVTCVVVDVS   420
EDDPDVQISW FVNNVEVHTA QTQTHREDYN STLRVVSALP IQHQDWMSGK EFKCKVNNKD   480
LGAPIERTIS KPKGSVRAPQ VYVLPPPEEE MTKKQVTLTC MVTDFMPEDI YVEWTNNGKT   540
ELNYKNTEPV LDSDGSYFMY SKLRVEKKNW VERNSYSCSV VHEGLHNHHT TKSFSRTPGK   600

SEQ ID NO: 178          moltype = AA   length = 214
FEATURE                 Location/Qualifiers
REGION                  1..214
                        note = Description of Artificial Sequence: Synthetic
                         polypeptide
REGION                  1..214
                        note = AF4378_pep2
source                  1..214
                        mol_type = protein
                        organism = synthetic construct
SEQUENCE: 178
DIQMTQSPSS LSASVGDRVS ITCKASQNVG TNVGWYQQKP GKAPKALIYS ASFRYSGVPS    60
RFSGSGSGTD FTLTISSLQP EDFATYFCQQ YYTYPYTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 179          moltype = AA   length = 596
FEATURE                 Location/Qualifiers
REGION                  1..596
                        note = Description of Artificial Sequence: Synthetic
                         polypeptide
REGION                  1..596
                        note = AF4376_pep1
source                  1..596
                        mol_type = protein
                        organism = synthetic construct
SEQUENCE: 179
APTSSSTKKT QLQLEHLLLD LQMILNGINN YKNPKLTDML TFEFYMPKKA TELKHLQCLE    60
RELKPLEEVL NLAQSKNFHL RPRDLISNIN VIVLELKGSE TTFMCEYADE TATIVEFLNR   120
WITFCQSIIS TLTGGGGSGG GGSGGGGSGG GGSQVQLVES GGGVVQPGRS LRLDCKASGI   180
TFSNSGMHWV RQAPGKGLEW VAVIWYDGSK RYYADSVKGR FTISRDNSKN TLFLQMNSLR   240
AEDTAVYYCA TNDDYWGQGT LVTVSSAKTT APSVYPLAPV CGDTTGSSVT LGCLVKGYFP   300
EPVTLTWNSG SLSSGVHTFP AVLQSDLYTL SSSVTVTSST WPSQSITCNV AHPASSTKVD   360
KKIEPRGPTI KPCPPCKCPA PNAAGGPSVF IFPPKIKDVL MISLSPIVTC VVVDVSEDDP   420
DVQISWFVNN VEVHTAQTQT HREDYNSTLR VVSALPIQHQ DWMSGKEFKC KVNNKDLGAP   480
IERTISKPKG SVRAPQVYVL PPPEEEMTKK QVTLTCMVTD FMPEDIYVEW TNNGKTELNY   540
KNTEPVLDSD GSYFMYSKLR VEKKNWVERN SYSCSVVHEG LHNHHTTKSF SRTPGK       596

SEQ ID NO: 180          moltype = AA   length = 214
```

```
FEATURE                     Location/Qualifiers
REGION                      1..214
                            note = Description of Artificial Sequence: Synthetic
                             polypeptide
REGION                      1..214
                            note = AF4376_pep2
source                      1..214
                            mol_type = protein
                            organism = synthetic construct
SEQUENCE: 180
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ SSNWPRTFGQ GTKVEIKRAD AAPTVSIFPP     120
SSEQLTSGGA SVVCFLNNFY PKDINVKWKI DGSERQNGVL NSWTDQDSKD STYSMSSTLT     180
LTKDEYERHN SYTCEATHKT STSPIVKSFN RNEC                                 214

SEQ ID NO: 181              moltype = AA  length = 596
FEATURE                     Location/Qualifiers
REGION                      1..596
                            note = Description of Artificial Sequence: Synthetic
                             polypeptide
REGION                      1..596
                            note = AF4386_pep1
source                      1..596
                            mol_type = protein
                            organism = synthetic construct
SEQUENCE: 181
APTSSSTKKT QLQLEHLLLD LQMILNGINN YKNPKLTDML TFEFYMPKKA TELKHLQCLE      60
RELKPLEEVL NLAQSKNFHL RPRDLISNIN VIVLELKGSE TTFMCEYADE TATIVEFLNR     120
WITFCQSIIS TLTGGGGSGG GGSGGGGSGG GGSQVQLVQS GAEVKKPGAS VKVSCKASGD     180
TFTRYYVHWV RQAPGQGLEW MGIINPSGGY ASYAQKFQGR VTMTRDTSTS TVYMELSSLR     240
SEDTAVYYCA AGLFIWGQGT LVTVSSAKTT APSVYPLAPV CGDTTGSSVT LGCLVKGYFP     300
EPVTLTWNSG SLSSGVHTFP AVLQSDLYTL SSSVTVTSST WPSQSITCNV AHPASSTKVD     360
KKIEPRGPTI KPCPPCKCPA PNAAGGPSVF IFPPKIKDVL MISLSPIVTC VVVDSEDDP      420
DVQISWFVNN VEVHTAQTQT HREDYNSTLR VVSALPIQHQ DWMSGKEFKC KVNNKDLGAP     480
IERTISKPKG SVRAPQVYVL PPPEEEMTKK QVTLTCMVTD FMPEDIYVEW TNNGKTELNY     540
KNTEPVLDSD GSYFMYSDLR VEKKNWVERN SYSCSVVHEG LHNHHTTESF SRTPGK        596

SEQ ID NO: 182              moltype = AA  length = 456
FEATURE                     Location/Qualifiers
REGION                      1..456
                            note = Description of Artificial Sequence: Synthetic
                             polypeptide
REGION                      1..456
                            note = AF4386_pep2
source                      1..456
                            mol_type = protein
                            organism = synthetic construct
SEQUENCE: 182
QVQLVQSGAE VKKPGASVKV SCKASGDTFT RYYVHWVRQA PGQGLEWMGI INPSGGYASY      60
AQKFQGRVTM TRDTSTSTVY MELSSLRSED TAVYYCAAGL FIWGQGTLVT VSSAKTTAPS     120
VYPLAPVCGD TTGSSVTLGC LVKGYFPEPV TLTWNSGSLS SGVHTFPAVL QSDLYTLSSS     180
VTVTSSTWPS QSITCNVAHP ASSTKVDKKI EPRGPTIKPC PPCKCPAPNA AGGPSVFIFP     240
PKIKDVLMIS LSPIVTCVVV DSEDDPDVQ ISWFVNNVEV HTAQTQTHRE DYNSTLRVVS     300
ALPIQHQDWM SGKEFKCKVN NKDLGAPIER TISKPKGSVR APQVYVLPPP EKEMTKKQVS     360
LTCLVKDFMP EDIYVEWTNN GKTELNYKNT EPVLKSDGSY FMYSKLTVEK KNWVERNSYS     420
CSVVHEGLHN HHTTKSFSRT PGGGGSGGGS HHHHHH                              456

SEQ ID NO: 183              moltype = AA  length = 596
FEATURE                     Location/Qualifiers
REGION                      1..596
                            note = Description of Artificial Sequence: Synthetic
                             polypeptide
REGION                      1..596
                            note = AF4387_pep1
source                      1..596
                            mol_type = protein
                            organism = synthetic construct
SEQUENCE: 183
APTSSSTKKT QLQLEHLLLD LQMILNGINN YKNPKLTDML TFEFYMPKKA TELKHLQCLE      60
RELKPLEEVL NLAQSKNFHL RPRDLISNIN VIVLELKGSE TTFMCEYADE TATIVEFLNR     120
WITFCQSIIS TLTGGGGSGG GGSGGGGSGG GGSQVQLVQS GAEVKKPGAS VKVSCKASGY     180
TFTDYYMHWV RQAPGQGLEW MGIINPRAGY TSYALKFQGR VTMTRDTSTS TVYMELSSLR     240
SEDTAVYYCT SGWDVWGQGT LVTVSSAKTT APSVYPLAPV CGDTTGSSVT LGCLVKGYFP     300
EPVTLTWNSG SLSSGVHTFP AVLQSDLYTL SSSVTVTSST WPSQSITCNV AHPASSTKVD     360
KKIEPRGPTI KPCPPCKCPA PNAAGGPSVF IFPPKIKDVL MISLSPIVTC VVVDSEDDP      420
DVQISWFVNN VEVHTAQTQT HREDYNSTLR VVSALPIQHQ DWMSGKEFKC KVNNKDLGAP     480
IERTISKPKG SVRAPQVYVL PPPEEEMTKK QVTLTCMVTD FMPEDIYVEW TNNGKTELNY     540
KNTEPVLDSD GSYFMYSDLR VEKKNWVERN SYSCSVVHEG LHNHHTTESF SRTPGK        596
```

```
SEQ ID NO: 184            moltype = AA  length = 456
FEATURE                   Location/Qualifiers
REGION                    1..456
                          note = Description of Artificial Sequence: Synthetic
                          polypeptide
REGION                    1..456
                          note = AF4387_pep2
source                    1..456
                          mol_type = protein
                          organism = synthetic construct
SEQUENCE: 184
QVQLVQSGAE VKKPGASVKV SCKASGYTFT DYYMHWVRQA PGQGLEWMGI INPRAGYTSY  60
ALKFQGRVTM TRDTSTSTVY MELSSLRSED TAVYYCTSGW DVWGQGTLVT VSSAKTTAPS 120
VYPLAPVCGD TTGSSVTLGC LVKGYFPEPV TLTWNSGSLS SGVHTFPAVL QSDLYTLSSS 180
VTVTSSTWPS QSITCNVAHP ASSTKVDKKI EPRGPTIKPC PPCKCPAPNA AGGPSVIFP  240
PKIKDVLMIS LSPIVTCVVV DVSEDDPDVQ ISWFVNNVEV HTAQTQTHRE DYNSTLRVVS 300
ALPIQHQDWM SGKEFKCKVN NKDLGAPIER TISKPKGSVR APQVYVLPPP EKEMTKKQVS 360
LTCLVKDFMP EDIYVEWTNN GKTELNYKNT EPVLKSDGSY FMYSKLTVEK KNWVERNSYS 420
CSVVHEGLHN HHTTKSFSRT PGGGGSGGGS HHHHHH                          456

SEQ ID NO: 185            moltype = AA  length = 214
FEATURE                   Location/Qualifiers
REGION                    1..214
                          note = Description of Artificial Sequence: Synthetic
                          polypeptide
REGION                    1..214
                          note = AF4387_pep3
source                    1..214
                          mol_type = protein
                          organism = synthetic construct
SEQUENCE: 185
DIQMTQSPSS LSASVGDRVT ITCRASQSIS TWLAWYQQKP GKAPKLLIYA ASSLDSGVPS  60
RFSGSGSGTD FTLTISSLQP EDFATYYCQQ SYSFPVTFGQ GTKVEIKRAD AAPTVSIFPP 120
SSEQLTSGGA SVVCFLNNFY PKDINVKWKI DGSERQNGVL NSWTDQDSKD STYSMSSTLT 180
LTKDEYERHN SYTCEATHKT STSPIVKSFN RNEC                             214

SEQ ID NO: 186            moltype = AA  length = 596
FEATURE                   Location/Qualifiers
REGION                    1..596
                          note = Description of Artificial Sequence: Synthetic
                          polypeptide
REGION                    1..596
                          note = AF4389_pep1
source                    1..596
                          mol_type = protein
                          organism = synthetic construct
SEQUENCE: 186
APTSSSTKKT QLQLEHLLLD LQMILNGINN YKNPKLTDML TFEFYMPKKA TELKHLQCLE  60
RELKPLEEVL NLAQSKNFHL RPRDLISNIN VIVLELKGSE TTFMCEYADE TATIVEFLNR 120
WITFCQSIIS TLTGGGGSGG GGSGGGGSGG GGSQVQLVQS GAEVKKPGAS VKVSCKASGH 180
TFTRYYMHWV RQAPGQGLEW MGIINPSGGY ATYAQKFQGR VTMTRDTSTS TVYMELSSLR 240
SEDTAVYYCA SGLFIWGQGT LVTVSSAKTT APSVYPLAPV CGDTTGSSVT LGCLVKGYFP 300
EPVTLTWNSG SLSSGVHTFP AVLQSDLYTL SSSVTVTSST WPSQSITCNV AHPASSTKVD 360
KKIEPRGPTI KPCPPCKCPA PNAAGGPSVF IFPPKIKDVL MISLSPIVTC VVVDSEDDP  420
DVQISWFVNN VEVHTAQTQT HREDYNSTLR VVSALPIQHQ DWMSGKEFKC KVNNKDLGAP 480
IERTISKPKG SVRAPQVYVL PPPEEEMTKK QVTLTCMVTD FMPEDIYVEW TNNGKTELNY 540
KNTEPVLDSD GSYFMYSDLR VEKKNWVERN SYSCSVVHEG LHNHHTTESF SRTPGK    596

SEQ ID NO: 187            moltype = AA  length = 456
FEATURE                   Location/Qualifiers
REGION                    1..456
                          note = Description of Artificial Sequence: Synthetic
                          polypeptide
REGION                    1..456
                          note = AF4389_pep2
source                    1..456
                          mol_type = protein
                          organism = synthetic construct
SEQUENCE: 187
QVQLVQSGAE VKKPGASVKV SCKASGHTFT RYYMHWVRQA PGQGLEWMGI INPSGGYATY  60
AQKFQGRVTM TRDTSTSTVY MELSSLRSED TAVYYCASGL FIWGQGTLVT VSSAKTTAPS 120
VYPLAPVCGD TTGSSVTLGC LVKGYFPEPV TLTWNSGSLS SGVHTFPAVL QSDLYTLSSS 180
VTVTSSTWPS QSITCNVAHP ASSTKVDKKI EPRGPTIKPC PPCKCPAPNA AGGPSVIFP  240
PKIKDVLMIS LSPIVTCVVV DVSEDDPDVQ ISWFVNNVEV HTAQTQTHRE DYNSTLRVVS 300
ALPIQHQDWM SGKEFKCKVN NKDLGAPIER TISKPKGSVR APQVYVLPPP EKEMTKKQVS 360
LTCLVKDFMP EDIYVEWTNN GKTELNYKNT EPVLKSDGSY FMYSKLTVEK KNWVERNSYS 420
CSVVHEGLHN HHTTKSFSRT PGGGGSGGGS HHHHHH                          456

SEQ ID NO: 188            moltype = AA  length = 214
```

```
FEATURE                 Location/Qualifiers
REGION                  1..214
                        note = Description of Artificial Sequence: Synthetic
                         polypeptide
REGION                  1..214
                        note = AF4389_pep3
source                  1..214
                        mol_type = protein
                        organism = synthetic construct
SEQUENCE: 188
DIQMTQSPSS LSASVGDRVT ITCRASQSIN SWLAWYQQKP GKAPKLLIYA TSTLESGVPS   60
RFSGSGSGTD FTLTISSLQP EDFATYYCQQ YYRFPVTFGQ GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 189          moltype = AA  length = 596
FEATURE                 Location/Qualifiers
REGION                  1..596
                        note = Description of Artificial Sequence: Synthetic
                         polypeptide
REGION                  1..596
                        note = AF4380_pep1
source                  1..596
                        mol_type = protein
                        organism = synthetic construct
SEQUENCE: 189
APTSSSTKKT QLQLEHLLLD LQMILNGINN YKNPKLTDML TFEFYMPKKA TELKHLQCLE   60
RELKPLEEVL NLAQSKNFHL RPRDLISNIN VIVLELKGSE TTFMCEYADE TATIVEFLNR  120
WITFCQSIIS TLTGGGGSGG GGSGGGGSGG GGSQVQLVES GGGVVQPGRS LRLDCKASGI  180
TFSNSGMHWV RQAPGKGLEW VAVIWYDGSK RYYADSVKGR FTISRDNSKN TLFLQMNSLR  240
AEDTAVYYCA TNDDYWGQGT LVTVSSAKTT APSVYPLAPV CGDTTGSSVT LGCLVKGYFP  300
EPVTLTWNSG SLSSGVHTFP AVLQSDLYTL SSSVTVTSST WPSQSITCNV AHPASSTKVD  360
KKIEPRGPTI KPCPPCKCPA PNAAGGPSVF IFPPKIKDVL MISLSPIVTC VVVDSEDDP  420
DVQISWFVNN VEVHTAQTQT HREDYNSTLR VVSALPIQHQ DWMSGKEFKC KVNNKDLGAP  480
IERTISKPKG SVRAPQVYVL PPPEEEMTKK QVTLTCMVTD FMPEDIYVEW TNNGKTELNY  540
KNTEPVLDSD GSYFMYSDLR VEKKNWVERN SYSCSVVHEG LHNHHTTESF SRTPGK      596

SEQ ID NO: 190          moltype = AA  length = 456
FEATURE                 Location/Qualifiers
REGION                  1..456
                        note = Description of Artificial Sequence: Synthetic
                         polypeptide
REGION                  1..456
                        note = AF4380_pep2
source                  1..456
                        mol_type = protein
                        organism = synthetic construct
SEQUENCE: 190
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSAKTTAPS  120
VYPLAPVCGD TTGSSVTLGC LVKGYFPEPV TLTWNSGSLS SGVHTFPAVL QSDLYTLSSS  180
VTVTSSTWPS QSITCNVAHP ASSTKVDKKI EPRGPTIKPC PPCKCPAPNA AGGPSVFIFP  240
PKIKDVLMIS LSPIVTCVVV DVSEDDPDVQ ISWFVNNVEV HTAQTQTHRE DYNSTLRVVS  300
ALPIQHQDWM SGKEFKCKVN NKDLGAPIER TISKPKGSVR APQVYVLPPP EKEMTKKQVS  360
LTCLVKDFMP EDIYVEWTNN GKTELNYKNT EPVLKSDGSY FMYSKLTVEK KNWVERNSYS  420
CSVVHEGLHN HHTTKSFSRT PGGGGSGGGS HHHHHH                            456

SEQ ID NO: 191          moltype = AA  length = 603
FEATURE                 Location/Qualifiers
REGION                  1..603
                        note = Description of Artificial Sequence: Synthetic
                         polypeptide
REGION                  1..603
                        note = AF4383_pep1
source                  1..603
                        mol_type = protein
                        organism = synthetic construct
SEQUENCE: 191
APTSSSTKKT QLQLEHLLLD LQMILNGINN YKNPKLTDML TFEFYMPKKA TELKHLQCLE   60
RELKPLEEVL NLAQSKNFHL RPRDLISNIN VIVLELKGSE TTFMCEYADE TATIVEFLNR  120
WITFCQSIIS TLTGGGGSGG GGSGGGGSGG GGSEVQLVES GGGLVQPGGS LRLSCAASGF  180
NIKDTYIHWV RQAPGKGLEW VARIYPTNGY TRYADSVKGR FTISADTSKN TAYLQMNSLR  240
AEDTAVYYCS RWGGDGFYAM DYWGQGTLVT VSSAKTTAPS VYPLAPVCGD TTGSSVTLGC  300
LVKGYFPEPV TLTWNSGSLS SGVHTFPAVL QSDLYTLSSS VTVTSSTWPS QSITCNVAHP  360
ASSTKVDKKI EPRGPTIKPC PPCKCPAPNA AGGPSVFIFP PKIKDVLMIS LSPIVTCVVV  420
DVSEDDPDVQ ISWFVNNVEV HTAQTQTHRE DYNSTLRVVS ALPIQHQDWM SGKEFKCKVN  480
NKDLGAPIER TISKPKGSVR APQVYVLPPP EEEMTKKQVT LTCMVTDFMP EDIYVEWTNN  540
GKTELNYKNT EPVLDSDGSY FMYSDLRVEK KNWVERNSYS CSVVHEGLHN HHTTESFSRT  600
PGK                                                                603
```

```
SEQ ID NO: 192          moltype = AA  length = 463
FEATURE                 Location/Qualifiers
REGION                  1..463
                        note = Description of Artificial Sequence: Synthetic
                         polypeptide
REGION                  1..463
                        note = AF4383_pep2
source                  1..463
                        mol_type = protein
                        organism = synthetic construct
SEQUENCE: 192
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
AKTTAPSVYP LAPVCGDTTG SSVTLGCLVK GYFPEPVTLT WNSGSLSSGV HTFPAVLQSD   180
LYTLSSSVTV TSSTWPSQSI TCNVAHPASS TKVDKKIEPR GPTIKPCPPC KCPAPNAAGG   240
PSVFIFPPKI KDVLMISLSP IVTCVVVDVS EDDPDVQISW FVNNVEVHTA QTQTHREDYN   300
STLRVVSALP IQHQDWMSGK EFKCKVNNKD LGAPIERTIS KPKGSVRAPQ VYVLPPPEKE   360
MTKKQVSLTC LVKDFMPEDI YVEWTNNGKT ELNYKNTEPV LKSDGSYFMY SKLTVEKKNW   420
VERNSYSCSV VHEGLHNHHT TKSFSRTPGG GGSGGGSHHH HHH                     463

SEQ ID NO: 193          moltype = AA  length = 600
FEATURE                 Location/Qualifiers
REGION                  1..600
                        note = Description of Artificial Sequence: Synthetic
                         polypeptide
REGION                  1..600
                        note = AF4384_pep1
source                  1..600
                        mol_type = protein
                        organism = synthetic construct
SEQUENCE: 193
APTSSSTKKT QLQLEHLLLD LQMILNGINN YKNPKLTDML TFEFYMPKKA TELKHLQCLE    60
RELKPLEEVL NLAQSKNFHL RPRDLISNIN VIVLELKGSE TTFMCEYADE TATIVEFLNR   120
WITFCQSIIS TLTGGGGSGG GGSGGGGSGG GGSEVQLVES GGGLVKPGGS LRLSCAASGF   180
TFSSYTLAWV RQAPGKGLEW VAAIDSSSYT YSPDTVRGRF TISRDNAKNS LYLQMNSLRA   240
EDTAVYYCAR DSNWDALDYW GQGTLVTVSS AKTTAPSVYP LAPVCGDTTG SSVTLGCLVK   300
GYFPEPVTLT WNSGSLSSGV HTFPAVLQSD LYTLSSSVTV TSSTWPSQSI TCNVAHPASS   360
TKVDKKIEPR GPTIKPCPPC KCPAPNAAGG PSVFIFPPKI KDVLMISLSP IVTCVVVDVS   420
EDDPDVQISW FVNNVEVHTA QTQTHREDYN STLRVVSALP IQHQDWMSGK EFKCKVNNKD   480
LGAPIERTIS KPKGSVRAPQ VYVLPPPEEE MTKKQVTLTC MVTDFMPEDI YVEWTNNGKT   540
ELNYKNTEPV LDSDGSYFMY SDLRVEKKNW VERNSYSCSV VHEGLHNHHT TESFSRTPGK   600

SEQ ID NO: 194          moltype = AA  length = 460
FEATURE                 Location/Qualifiers
REGION                  1..460
                        note = Description of Artificial Sequence: Synthetic
                         polypeptide
REGION                  1..460
                        note = AF4384_pep2
source                  1..460
                        mol_type = protein
                        organism = synthetic construct
SEQUENCE: 194
EVQLVESGGG LVKPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TLVTVSSAKT   120
TAPSVYPLAP VCGDTTGSSV TLGCLVKGYF PEPVTLTWNS GSLSSGVHTF PAVLQSDLYT   180
LSSSVTVTSS TWPSQSITCN VAHPASSTKV DKKIEPRGPT IKPCPPCKCP APNAAGGPSV   240
FIFPPKIKDV LMISLSPIVT CVVVDVSEDD PDVQISWFVN NVEVHTAQTQ THREDYNSTL   300
RVVSALPIQH QDWMSGKEFK CKVNNKDLGA PIERTISKPK GSVRAPQVYV LPPPEKEMTK   360
KQVSLTCLVK DFMPEDIYVE WTNNGKTELN YKNTEPVLKS DGSYFMYSKL TVEKKNWVER   420
NSYSCSVVHE GLHNHHTTKS FSRTPGGGGS GGGSHHHHHH                         460

SEQ ID NO: 195          moltype = AA  length = 716
FEATURE                 Location/Qualifiers
REGION                  1..716
                        note = Description of Artificial Sequence: Synthetic
                         polypeptide
REGION                  1..716
                        note = AF4403_pep1
source                  1..716
                        mol_type = protein
                        organism = synthetic construct
SEQUENCE: 195
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
```

```
ALPIQHQDWM SGKEFKCKVN NKDLGAPIER TISKPKGSVR APQVYVLPPP EKEMTKKQVS   360
LTCLVKDFMP EDIYVEWTNN GKTELNYKNT EPVLKSDGSY FMYSKLTVEK KNWVERNSYS   420
CSVVHEGLHN HHTTKSFSRT PGGGGSGGG GSGGGGSGGG GSQVQLVQSG AEVKKPGASV   480
KVSCKASGDT FTRYYVHWVR QAPGQGLEWM GIINPSGGYA SYAQKFQGRV TMTRDTSTST   540
VYMELSSLRS EDTAVYYCAA GLFIWGQGTL VTVSSASGG GSGGGGSGGG GSHASDIQMT   600
QSPSSLSASV GDRVTITCRA SQSIGRYLAW YQQKPGKAPK LLIYSASNLE TGVPSRFSGS   660
GSGTDFTLTI SSLQPEDFAT YYCQQYNSFP VTFGPGTKVD IKGGGSGGGS HHHHHH       716

SEQ ID NO: 196         moltype = AA  length = 716
FEATURE                Location/Qualifiers
REGION                 1..716
                       note = Description of Artificial Sequence: Synthetic
                        polypeptide
REGION                 1..716
                       note = AF4404_pep1
source                 1..716
                       mol_type = protein
                       organism = synthetic construct
SEQUENCE: 196
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSAKTTAPS  120
VYPLAPVCGD TTGSSVTLGC LVKGYFPEPV TLTWNSGSLS SGVHTFPAVL QSDLYTLSSS  180
VTVTSSWPS QSITCNVAHP ASSTKVDKKI EPRGPTIKPC PPCKCPAPNA AGGPSVFIFP  240
PKIKDVLMIS LSPIVTCVVV DVSEDDPDVQ ISWFVNNVEV HTAQTQTHRE DYNSTLRVVS  300
ALPIQHQDWM SGKEFKCKVN NKDLGAPIER TISKPKGSVR APQVYVLPPP EKEMTKKQVS  360
LTCLVKDFMP EDIYVEWTNN GKTELNYKNT EPVLKSDGSY FMYSKLTVEK KNWVERNSYS  420
CSVVHEGLHN HHTTKSFSRT PGGGGSGGG GSGGGGSGGG GSQVQLVQSG AEVKKPGASV  480
KVSCKASGYT FTDYYMHWVR QAPGQGLEWM GIINPRAGYT SYALKFQGRV TMTRDTSTST  540
VYMELSSLRS EDTAVYYCTS GWDVWGQGTL VTVSSASGGG GSGGGGSGGG GSHASDIQMT  600
QSPSSLSASV GDRVTITCRA SQSISTWLAW YQQKPGKAPK LLIYAASSLD SGVPSRFSGS  660
GSGTDFTLTI SSLQPEDFAT YYCQQSYSFP VTFGQGTKVE IKGGGSGGGS HHHHHH      716

SEQ ID NO: 197         moltype = AA  length = 723
FEATURE                Location/Qualifiers
REGION                 1..723
                       note = Description of Artificial Sequence: Synthetic
                        polypeptide
REGION                 1..723
                       note = AF4395_pep1
source                 1..723
                       mol_type = protein
                       organism = synthetic construct
SEQUENCE: 197
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
AKTTAPSVYP LAPVCGDTTG SSVTLGCLVK GYFPEPVTLT WNSGSLSSGV HTFPAVLQSD  180
LYTLSSSVTV TSSWPSQSI TCNVAHPASS TKVDKKIEPR GPTIKPCPPC KCPAPNAAGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LGAPIERTIS KPKGSVRAPQ VYVLPPPEKE  360
MTKKQVSLTC LVKDFMPEDI YVEWTNNGKT ELNYKNTEPV LKSDGSYFMY SKLTVEKKNW  420
VERNSYCSV VHEGLHNHHT TKSFSRTPGG GGSGGGGSG GGGSGGGGSQ VQLVQSGAEV  480
KKPGASVKVS CKASGDTFTR YYVHWVRQAP GQGLEWMGII NPSGGYASYA QKFQGRVTMT  540
RDTSTSTVYM ELSSLRSEDT AVYYCAAGLF IWGQGTLVTV SSASGGGGS GGGSGGGGSH  600
ASDIQMTQSP SSLSASVGDR VTITCRASQS IGRYLAWYQQ KPGKAPKLLI YSASNLETGV  660
PSRFSGSGSG TDFTLTISSL QPEDFATYYC QQYNSFPVTF GPGTKVDIKG GGSGGGSHHH  720
HHH                                                                723

SEQ ID NO: 198         moltype = AA  length = 723
FEATURE                Location/Qualifiers
REGION                 1..723
                       note = Description of Artificial Sequence: Synthetic
                        polypeptide
REGION                 1..723
                       note = AF4396_pep1
source                 1..723
                       mol_type = protein
                       organism = synthetic construct
SEQUENCE: 198
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
AKTTAPSVYP LAPVCGDTTG SSVTLGCLVK GYFPEPVTLT WNSGSLSSGV HTFPAVLQSD  180
LYTLSSSVTV TSSWPSQSI TCNVAHPASS TKVDKKIEPR GPTIKPCPPC KCPAPNAAGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LGAPIERTIS KPKGSVRAPQ VYVLPPPEKE  360
MTKKQVSLTC LVKDFMPEDI YVEWTNNGKT ELNYKNTEPV LKSDGSYFMY SKLTVEKKNW  420
VERNSYCSV VHEGLHNHHT TKSFSRTPGG GGSGGGGSG GGGSGGGGSQ VQLVQSGAEV  480
KKPGASVKVS CKASGYTFTD YYMHWVRQAP GQGLEWMGII NPRAGYTSYA LKFQGRVTMT  540
RDTSTSTVYM ELSSLRSEDT AVYYCTSGWD VWGQGTLVTV SSASGGGGS GGGSGGGGSH  600
ASDIQMTQSP SSLSASVGDR VTITCRASQS ISTWLAWYQQ KPGKAPKLLI YAASSLDSGV  660
```

```
PSRFSGSGSG TDFTLTISSL QPEDFATYYC QQSYSFPVTF GQGTKVEIKG GGSGGGSHHH   720
HHH                                                                723

SEQ ID NO: 199          moltype = AA  length = 590
FEATURE                 Location/Qualifiers
REGION                  1..590
                        note = Description of Artificial Sequence: Synthetic
                        polypeptide
REGION                  1..590
                        note = AF4400_pep1
source                  1..590
                        mol_type = protein
                        organism = synthetic construct
SEQUENCE: 199
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EEEMTKKQVT   360
LTCMVTDFMP EDIYVEWTNN GKTELNYKNT EPVLDSDGSY FMYSDLRVEK KNWVERNSYS   420
CSVVHEGLHN HHTTESFSRT PGGGGGSGGG GSGGGGSAPT SSSTKKTQLQ LEHLLLDLQM   480
ILNGINNYKN PKLTDMLTFE FYMPKKATEL KHLQCLEREL KPLEEVLNLA QSKNFHLRPR   540
DLISNINVIV LELKGSETTF MCEYADETAT IVEFLNRWIT FCQSIISTLT             590

SEQ ID NO: 200          moltype = AA  length = 723
FEATURE                 Location/Qualifiers
REGION                  1..723
                        note = Description of Artificial Sequence: Synthetic
                        polypeptide
REGION                  1..723
                        note = AF4400_pep2
source                  1..723
                        mol_type = protein
                        organism = synthetic construct
SEQUENCE: 200
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EKEMTKKQVS   360
LTCLVKDFMP EDIYVEWTNN GKTELNYKNT EPVLKSDGSY FMYSKLTVEK KNWVERNSYS   420
CSVVHEGLHN HHTTKSFSRT PGGGGSGGG GSGGGGSGGG GSEVQLVESG GGLVQPGGSL   480
RLSCAASGFN IKDTYIHWVR QAPGKGLEWV ARIYPTNGYT RYADSVKGRF TISADTSKNT   540
AYLQMNSLRA EDTAVYYCSR WGGDGFYAMD YWGQGTLVTV SSASGGGGSG GGGSGGGGSH   600
ASDIQMTQSP SSLSASVGDR VTITCRASQD VNTAVAWYQQ KPGKAPKLLI YSASFLYSGV   660
PSRFSGSRSG TDFTLTISSL QPEDFATYYC QQHYTTPPTF GQGTKVEIKG GGSGGGSHHH   720
HHH                                                                723

SEQ ID NO: 201          moltype = AA  length = 720
FEATURE                 Location/Qualifiers
REGION                  1..720
                        note = Description of Artificial Sequence: Synthetic
                        polypeptide
REGION                  1..720
                        note = AF4401_pep1
source                  1..720
                        mol_type = protein
                        organism = synthetic construct
SEQUENCE: 201
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSAKTTAPS   120
VYPLAPVCGD TTGSSVTLGC LVKGYFPEPV TLTWNSGSLS SGVHTFPAVL QSDLYTLSSS   180
VTVTSSTWPS QSITCNVAHP ASSTKVDKKI EPRGPTIKPC PPCKCPAPNA AGGPSVFIFP   240
PKIKDVLMIS LSPIVTCVVV DVSEDDPDVQ ISWFVNNVEV HTAQTQTHRE DYNSTLRVVS   300
ALPIQHQDWM SGKEFKCKVN NKDLGAPIER TISKPKGSVR APQVYVLPPP EKEMTKKQVS   360
LTCLVKDFMP EDIYVEWTNN GKTELNYKNT EPVLKSDGSY FMYSKLTVEK KNWVERNSYS   420
CSVVHEGLHN HHTTKSFSRT PGGGGSGGG GSGGGGSGGG GSEVQLVESG GGLVKPGGSL   480
RLSCAASGFT FSSYTLAWVR QAPGKGLEWV AAIDSSSYTY SPDTVRGRFT ISRDNAKNSL   540
YLQMNSLRAE DTAVYYCARD SNWDALDYWG QGTLVTVSSA SGGGGSGGGG SGGGGSHASD   600
IQMTQSPSSL SASVGDRVSI TCKASQNVGT NVGWYQQKPG KAPKALIYSA SFRYSGVPSR   660
FSGSGSGTDF TLTISSLQPE DFATYFCQQY YTYPYTFGGG TKLEIKGGGS GGGSHHHHHH   720

SEQ ID NO: 202          moltype = AA  length = 597
FEATURE                 Location/Qualifiers
REGION                  1..597
                        note = Description of Artificial Sequence: Synthetic
                        polypeptide
```

```
REGION                  1..597
                        note = AF4392_pep1
source                  1..597
                        mol_type = protein
                        organism = synthetic construct
SEQUENCE: 202
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
AKTTAPSVYP LAPVCGDTTG SSVTLGCLVK GYFPEPVTLT WNSGSLSSGV HTFPAVLQSD   180
LYTLSSSVTV TSSTWPSQSI TCNVAHPASS TKVDKKIEPR GPTIKPCPPC KCPAPNAAGG   240
PSVFIFPPKI KDVLMISLSP IVTCVVVDVS EDDPDVQISW FVNNVEVHTA QTQTHREDYN   300
STLRVVSALP IQHQDWMSGK EFKCKVNNKD LGAPIERTIS KPKGSVRAPQ VYVLPPPEEE   360
MTKKQVTLTC MVTDFMPEDI YVEWTNNGKT ELNYKNTEPV LDSDGSYFMY SDLRVEKKNW   420
VERNSYSCSV VHEGLHNHHT TESFSRTPGG GGGSGGGGSG GGGSAPTSSS TKKTQLQLEH   480
LLLDLQMILN GINNYKNPKL TDMLTFEFYM PKKATELKHL QCLERELKPL EEVLNLAQSK   540
NFPHLRPRDLI SNINVIVLEL KGSETTFMCE YADETATIVE FLNRWITFCQ SIISTLT     597

SEQ ID NO: 203          moltype = AA  length = 730
FEATURE                 Location/Qualifiers
REGION                  1..730
                        note = Description of Artificial Sequence: Synthetic
                        polypeptide
REGION                  1..730
                        note = AF4392_pep2
source                  1..730
                        mol_type = protein
                        organism = synthetic construct
SEQUENCE: 203
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
AKTTAPSVYP LAPVCGDTTG SSVTLGCLVK GYFPEPVTLT WNSGSLSSGV HTFPAVLQSD   180
LYTLSSSVTV TSSTWPSQSI TCNVAHPASS TKVDKKIEPR GPTIKPCPPC KCPAPNAAGG   240
PSVFIFPPKI KDVLMISLSP IVTCVVVDVS EDDPDVQISW FVNNVEVHTA QTQTHREDYN   300
STLRVVSALP IQHQDWMSGK EFKCKVNNKD LGAPIERTIS KPKGSVRAPQ VYVLPPPEKE   360
MTKKQVSLTC LVKDFMPEDI YVEWTNNGKT ELNYKNTEPV LKSDGSYFMY SKLTVEKKNW   420
VERNSYSCSV VHEGLHNHHT TKSFSRTPGG GGGSGGGGSG GGGSGGGGSE VQLVESGGGL   480
VQPGGSLRLS CAASGFNIKD TYIHWVRQAP GKGLEWVARI YPTNGYTRYA DSVKGRFTIS   540
ADTSKNTAYL QMNSLRAEDT AVYYCSRWGG DGFYAMDYWG QGTLVTVSSA SGGGGSGGGG   600
SGGGGSHASD IQMTQSPSSL SASVGDRVTI TCRASQDVNT AVAWYQQKPG KAPKLLIYSA   660
SFLYSGVPSR FSGSRSGTDF TLTISSLQPE DFATYYCQQH YTTPPTFGQG TKVEIKGGGS   720
GGGSHHHHHH                                                         730

SEQ ID NO: 204          moltype = AA  length = 727
FEATURE                 Location/Qualifiers
REGION                  1..727
                        note = Description of Artificial Sequence: Synthetic
                        polypeptide
REGION                  1..727
                        note = AF4393_pep1
source                  1..727
                        mol_type = protein
                        organism = synthetic construct
SEQUENCE: 204
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
AKTTAPSVYP LAPVCGDTTG SSVTLGCLVK GYFPEPVTLT WNSGSLSSGV HTFPAVLQSD   180
LYTLSSSVTV TSSTWPSQSI TCNVAHPASS TKVDKKIEPR GPTIKPCPPC KCPAPNAAGG   240
PSVFIFPPKI KDVLMISLSP IVTCVVVDVS EDDPDVQISW FVNNVEVHTA QTQTHREDYN   300
STLRVVSALP IQHQDWMSGK EFKCKVNNKD LGAPIERTIS KPKGSVRAPQ VYVLPPPEKE   360
MTKKQVSLTC LVKDFMPEDI YVEWTNNGKT ELNYKNTEPV LKSDGSYFMY SKLTVEKKNW   420
VERNSYSCSV VHEGLHNHHT TKSFSRTPGG GGGSGGGGSG GGGSGGGGSE VQLVESGGGL   480
VKPGGSLRLS CAASGFTFSS YTLAWVRQAP GKGLEWVAAI DSSSYTYSPD TVRGRFTISR   540
DNAKNSLYLQ MNSLRAEDTA VYYCARDSNW DALDYWGQGT LVTVSSASGG GSGGGGSGGG   600
GGSHASDIQM TQSPSSLSAS VGDRVSITCK ASQNVGTNVG WYQQKPGKAP KALIYSASFR   660
YSGVPSRFSG SGSGTDFTLT ISSLQPEDFA TYFCQQYYTY PYTFGGGTKL EIKGGGSGGG   720
SHHHHHH                                                            727

SEQ ID NO: 205          moltype = AA  length = 596
FEATURE                 Location/Qualifiers
REGION                  1..596
                        note = Description of Artificial Sequence: Synthetic
                        polypeptide
REGION                  1..596
                        note = AF003247_pep1
source                  1..596
                        mol_type = protein
                        organism = synthetic construct
SEQUENCE: 205
APASSSTKKT QLQLEHLLLD LQMILNGINN YKNPKLTRML TAKFAMPKKA TELKHLQCLE    60
```

```
EELKPLEEVL NGAQSKNFHL RPRDLISNIN VIVLELKGSE TTFMCEYADE TATIVEFLNR    120
WITFAQSIIS TLTGGGGSGG GGSGGGGSGG GGSQVQLVQS GAEVKKPGAS VKVSCKASGD    180
TFTRHYVHWV RQAPGQGLEW MGIINPSGGY ASYAQKFQGR VTMTRDTSTS TVYMELSSLR    240
SEDTAVYYCA AGLFIWGQGT LVTVSSAKTT APSVYPLAPV CGDTTGSSVT LGCLVKGYFP    300
EPVTLTWNSG SLSSGVHTFP AVLQSDLYTL SSSVTVTSST WPSQSITCNV AHPASSTKVD    360
KKIEPRGPTI KPCPPCKCPA PNAAGGPSVF IFPPKIKDVL MISLSPIVTC VVVDVSEDDP    420
DVQISWFVNN VEVHTAQTQT HREDYNSTLR VVSALPIQHQ DWMSGKEFKC KVNNKDLGAP    480
IERTISKPKG SVRAPQVYVL PPPEEEMTKK QVTLTCMVTD FMPEDIYVEW TNNGKTELNY    540
KNTEPVLDSD GSYFMYSKLR VEKKNWVERN SYSCSVVHEG LHNHHTTKSF SRTPGK        596

SEQ ID NO: 206          moltype = AA  length = 214
FEATURE                 Location/Qualifiers
REGION                  1..214
                        note = Description of Artificial Sequence: Synthetic
                         polypeptide
REGION                  1..214
                        note = AF003247_pep2
source                  1..214
                        mol_type = protein
                        organism = synthetic construct
SEQUENCE: 206
DIQMTQSPSS LSASVGDRVT ITCRASQSIG RWLAWYQQKP GKAPKLLIYS ASNLETGVPS     60
RFSGSGSGTD FTLTISSLQP EDFATYYCQQ YESFPVTFGP GTKVDIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 207          moltype = AA  length = 603
FEATURE                 Location/Qualifiers
REGION                  1..603
                        note = Description of Artificial Sequence: Synthetic
                         polypeptide
REGION                  1..603
                        note = AF003243_pep1
source                  1..603
                        mol_type = protein
                        organism = synthetic construct
SEQUENCE: 207
APASSSTKKT QLQLEHLLLD LQMILNGINN YKNPKLTRML TAKFAMPKKA TELKHLQCLE     60
EELKPLEEVL NGAQSKNFHL RPRDLISNIN VIVLELKGSE TTFMCEYADE TATIVEFLNR    120
WITFAQSIIS TLTGGGGSGG GGSGGGGSGG GGSEVQLVES GGGLVQPGGS LRLSCAASGF    180
NIKDTYIHWV RQAPGKGLEW VARIYPTNGY TRYADSVKGR FTISADTSKN TAYLQMNSLR    240
AEDTAVYYCS RWGGDGFYAM DYWGQGTLVT VSSAKTTAPS VYPLAPVCGD TTGSSVTLGC    300
LVKGYFPEPV TLTWNSGSLS SGVHTFPAVL QSDLYTLSSS VTVTSSTWPS QSITCNVAHP    360
ASSTKVDKKI EPRGPTIKPC PPCKCPAPNA AGGPSVFIFP PKIKDVLMIS LSPIVTCVVV    420
DVSEDDPDVQ ISWFVNNVEV HTAQTQTHRE DYNSTLRVVS ALPIQHQDWM SGKEFKCKVN    480
NKDLGAPIER TISKPKGSVR APQVYVLPPP EEEMTKKQVT LTCMVTDFMP EDIYVEWTNN    540
GKTELNYKNT EPVLDSDGSY FMYSKLRVEK KNWVERNSYS CSVVHEGLHN HHTTKSFSRT    600
PGK                                                                  603

SEQ ID NO: 208          moltype = AA  length = 600
FEATURE                 Location/Qualifiers
REGION                  1..600
                        note = Description of Artificial Sequence: Synthetic
                         polypeptide
REGION                  1..600
                        note = AF003246_pep1
source                  1..600
                        mol_type = protein
                        organism = synthetic construct
SEQUENCE: 208
APASSSTKKT QLQLEHLLLD LQMILNGINN YKNPKLTRML TAKFAMPKKA TELKHLQCLE     60
EELKPLEEVL NGAQSKNFHL RPRDLISNIN VIVLELKGSE TTFMCEYADE TATIVEFLNR    120
WITFAQSIIS TLTGGGGSGG GGSGGGGSGG GGSEVQLVKP GGS LRLSCAASGF            180
TFSSYTLAWV RQAPGKGLEW VAAIDSSSYT YSPDTVRGRF TISRDNAKNS LYLQMNSLRA    240
EDTAVYYCAR DSNWDALDYW GQGTLVTVSS AKTTAPSVYP LAPVCGDTTG SSVTLGCLVK    300
GYFPEPVTLT WNSGSLSSGV HTFPAVLQSD LYTLSSSVTV TSSTWPSQSI TCNVAHPASS    360
TKVDKKIEPR GPTIKPCPPC KCPAPNAAGG PSVFIFPPKI KDVLMISLSP IVTCVVVDVS    420
EDDPDVQISW FVNNVEVHTA QTQTHREDYN STLRVVSALP IQHQDWMSGK EFKCKVNNKD    480
LGAPIERTIS KPKGSVRAPQ VYVLPPPEEE MTKKQVTLTC MVTDFMPEDI YVEWTNNGKT    540
ELNYKNTEPV LDSDGSYFMY SKLRVEKKNW VERNSYSCSV VHEGLHNHHT TKSFSRTPGK    600

SEQ ID NO: 209          moltype = AA  length = 214
FEATURE                 Location/Qualifiers
REGION                  1..214
                        note = Description of Artificial Sequence: Synthetic
                         polypeptide
REGION                  1..214
                        note = AF003246_pep2
source                  1..214
```

```
                        mol_type = protein
                        organism = synthetic construct
SEQUENCE: 209
DIQMTQSPSS LSASVGDRVS ITCKASQNVG TNVGWYQQKP GKAPKALIYS ASFRYSGVPS     60
RFSGSGSGTD FTLTISSLQP EDFATYFCQQ YYTYPYTFGG GTKLEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 210          moltype = AA  length = 596
FEATURE                 Location/Qualifiers
REGION                  1..596
                        note = Description of Artificial Sequence: Synthetic
                         polypeptide
REGION                  1..596
                        note = AF003747_pep1
source                  1..596
                        mol_type = protein
                        organism = synthetic construct
SEQUENCE: 210
APASSSTKKT QLQLEHLLLD LQMILNGINN YKNPKLTRML TAKFAMPKKA TELKHLQCLE     60
EELKPLEEVL NGAQSKNFHL RPRDLISNIN VIVLELKGSE TTFMCEYADE TATIVEFLNR    120
WITFAQSIIS TLTGGGSGG GGSGGGGSGG GGSQVQLVQS GAEVKKPGAS VKVSCKASGD     180
TFTRYYVHWV RQAPGQGLEW MGIINPSGGY ASYAQKFQGR VTMTRDTSTS TVYMELSSLR    240
SEDTAVYYCA AGLFIWGQGT LVTVSSAKTT APSVYPLAPV CGDTTGSSVT LGCLVKGYFP    300
EPVTLTWNSG SLSSGVHTFP AVLQSDLYTL SSSVTVTSST WPSQSITCNV AHPASSTKVD    360
KKIEPRGPTI KPCPPCKCPA PNAAGGPSVF IFPPKIDKVL MISLSPIVTC VVVDVSEDDP    420
DVQISWFVNN VEVHTAQTQT HREDYNSTLR VVSALPIQHQ DWMSGKEFKC KVNNKDLGAP    480
IERTISKPKG SVRAPQVYVL PPPEEEMTKK QVTLTCMVTD FMPEDIYVEW TNNGKTELNY    540
KNTEPVLDSD GSYFMYSDLR VEKKNWVERN SYSCSVVHEG LHNHHTTESF SRTPGK        596

SEQ ID NO: 211          moltype = AA  length = 443
FEATURE                 Location/Qualifiers
REGION                  1..443
                        note = Description of Artificial Sequence: Synthetic
                         polypeptide
REGION                  1..443
                        note = AF003747_pep2
source                  1..443
                        mol_type = protein
                        organism = synthetic construct
SEQUENCE: 211
QVQLVQSGAE VKKPGASVKV SCKASGDTFT RYYVHWVRQA PGQGLEWMGI INPSGGYASY     60
AQKFQGRVTM TRDTSTSTVY MELSSLRSED TAVYYCAAGL FIWGQGTLVT VSSAKTTAPS    120
VYPLAPVCGD TTGSSVTLGC LVKGYFPEPV TLTWNSGSLS SGVHTFPAVL QSDLYTLSSS    180
VTVTSSTWPS QSITCNVAHP ASSTKVDKKI EPRGPTIKPC PPCKCPAPNA AGGPSVFIFP    240
PKIKDVLMIS LSPIVTCVVV DVSEDDPDVQ ISWFVNNVEV HTAQTQTHRE DYNSTLRVVS    300
ALPIQHQDWM SGKEFKCKVN NKDLGAPIER TISKPKGSVR APQVYVLPPP EKEMTKKQVS    360
LTCLVKDFMP EDIYVEWTNN GKTELNYKNT EPVLKSDGSY FMYSKLTVEK KNWVERNSYS    420
CSVVHEGLHN HHTTKSFSRT PGK                                            443

SEQ ID NO: 212          moltype = AA  length = 214
FEATURE                 Location/Qualifiers
REGION                  1..214
                        note = Description of Artificial Sequence: Synthetic
                         polypeptide
REGION                  1..214
                        note = AF003747_pep3
source                  1..214
                        mol_type = protein
                        organism = synthetic construct
SEQUENCE: 212
DIQMTQSPSS LSASVGDRVT ITCRASQSIG RYLAWYQQKP GKAPKLLIYS ASNLETGVPS     60
RFSGSGSGTD FTLTISSLQP EDFATYYCQQ YNSFPVTFGP GTKVDIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 213          moltype = AA  length = 443
FEATURE                 Location/Qualifiers
REGION                  1..443
                        note = Description of Artificial Sequence: Synthetic
                         polypeptide
REGION                  1..443
                        note = AF004205_pep1
source                  1..443
                        mol_type = protein
                        organism = synthetic construct
SEQUENCE: 213
QVQLVQSGAE VKKPGASVKV SCKASGDTFT RYYVHWVRQA PGQGLEWMGI INPSGGYASY     60
AQKFQGRVTM TRDTSTSTVY MELSSLRSED TAVYYCAAGL FIWGQGTLVT VSSAKTTAPS    120
```

```
VYPLAPVCGD TTGSSVTLGC LVKGYFPEPV TLTWNSGSLS SGVHTFPAVL QSDLYTLSSS    180
VTVTSSTWPS QSITCNVAHP ASSTKVDKKI EPRGPTIKPC PPCKCPAPNA AGGPSVFIFP    240
PKIKDVLMIS LSPIVTCVVV DVSEDDPDVQ ISWFVNNVEV HTAQTQTHRE DYNSTLRVVS    300
ALPIQHQDWM SGKEFKCKVN NKDLGAPIER TISKPKGSVR APQVYVLPPP EEEMTKKQVT    360
LTCMVTDFMP EDIYVEWTNN GKTELNYKNT EPVLDSDGSY FMYSKLRVEK KNWVERNSYS    420
CSVVHEGLHN HHTTKSFSRT PGK                                           443

SEQ ID NO: 214          moltype = AA  length = 450
FEATURE                 Location/Qualifiers
REGION                  1..450
                        note = Description of Artificial Sequence: Synthetic
                         polypeptide
REGION                  1..450
                        note = AF002725_pep1
source                  1..450
                        mol_type = protein
                        organism = synthetic construct
SEQUENCE: 214
EVQLVESGGG LVQPGGSLRL SCAASGFNIK DTYIHWVRQA PGKGLEWVAR IYPTNGYTRY     60
ADSVKGRFTI SADTSKNTAY LQMNSLRAED TAVYYCSRWG GDGFYAMDYW GQGTLVTVSS    120
AKTTAPSVYP LAPVCGDTTG SSVTLGCLVK GYFPEPVTLT WNSGSLSSGV HTFPAVLQSD    180
LYTLSSSVTV TSSTWPSQSI TCNVAHPASS TKVDKKIEPR GPTIKPCPPC KCPAPNAAGG    240
PSVFIFPPKI KDVLMISLSP IVTCVVVDVS EDDPDVQISW FVNNVEVHTA QTQTHREDYN    300
STLRVVSALP IQHQDWMSGK EFKCKVNNKD LGAPIERTIS KPKGSVRAPQ VYVLPPPEEE    360
MTKKQVTLTC MVTDFMPEDI YVEWTNNGKT ELNYKNTEPV LDSDGSYFMY SKLRVEKKNW    420
VERNSYSCSV VHEGLHNHHT TKSFSRTPGK                                    450

SEQ ID NO: 215          moltype = AA  length = 214
FEATURE                 Location/Qualifiers
REGION                  1..214
                        note = Description of Artificial Sequence: Synthetic
                         polypeptide
REGION                  1..214
                        note = AF002725_pep2
source                  1..214
                        mol_type = protein
                        organism = synthetic construct
SEQUENCE: 215
DIQMTQSPSS LSASVGDRVT ITCRASQDVN TAVAWYQQKP GKAPKLLIYS ASFLYSGVPS     60
RFSGSRSGTD FTLTISSLQP EDFATYYCQQ HYTTPPTFGQ GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                               214

SEQ ID NO: 216          moltype = AA  length = 280
FEATURE                 Location/Qualifiers
REGION                  1..280
                        note = Description of Artificial Sequence: Synthetic
                         polypeptide
REGION                  1..280
                        note = AF000635
source                  1..280
                        mol_type = protein
                        organism = synthetic construct
SEQUENCE: 216
MSTSTEQKLI SEEDLQVQLV QSGAEVKKPG ASVKVSCKAS GYTFTGYYIH WVRQAPGQGL     60
EWMGIINPSG GSTRYAQKFQ GRVTMTRDTS TSTVYMELSS LRSEDTAVYY CARSLFPTIF    120
GVEVAFDIWG QGTLVTVSSA SGGGGSGGGG SGGGGSHASD IQMTQSPSSL SASVGDRVTI    180
TCRASQSIRT YLNWYQQKPG KAPKLLIYSA SNLQSGVPSR FSGSGSGTDF TLTISSLQPE    240
DFATYYCQQA NSFPPFTFGPG TKVDIKGKPI PNPLLGLDST                        280

SEQ ID NO: 217          moltype = AA  length = 280
FEATURE                 Location/Qualifiers
REGION                  1..280
                        note = Description of Artificial Sequence: Synthetic
                         polypeptide
REGION                  1..280
                        note = AF000636
source                  1..280
                        mol_type = protein
                        organism = synthetic construct
SEQUENCE: 217
MSTSTEQKLI SEEDLQVQLV QSGAEVKKPG ASVKVSCKAS GYSFTSYYLH WVRQAPGQGL     60
EWMGRISPRS GGTKNAQNFQ GRVTMTRDTS TSTVYMELSS LRSEDTAVYY CVRSLFPTIF    120
GVEVAFDIWG QGTLVTVSSA SGGGGSGGGG SGGGGSHASD IQMTQSPSSL SASVGDRVTI    180
TCRASQSISS WLAWYQQKPG KAPKLLIYYA SSLQSGVPSR FSGSGSGTDF TLTISSLQPE    240
DFATYYCQQG YQYPYTFGQG TKLEIKGKPI PNPLLGLDST                         280

SEQ ID NO: 218          moltype = AA  length = 280
FEATURE                 Location/Qualifiers
```

```
REGION                  1..280
                        note = Description of Artificial Sequence: Synthetic
                        polypeptide
REGION                  1..280
                        note = AF000666
source                  1..280
                        mol_type = protein
                        organism = synthetic construct
SEQUENCE: 218
MSTSTEQKLI SEEDLQVQLV QSGAEVKKPG ASVKVSCKAS GYTFSTYYIH WVRQAPGQGL    60
EWMGWMNPNS GNTGYAQTFQ GRVTMTRDTS TSTVYMELSS LRSEDTAVYY CARSLFPTIF   120
GVEVAFDIWG QGTLVTVSSA SGGGGSGGGG SGGGGSHASD IQMTQSPSSL SASVGDRVTI   180
TCRASQSISS YLNWYQQKPG KAPKLLIYAA SSLQSGVPSR FSGSGSGTDF TLTISSLQPE   240
DFATYYCQQG YSTPRTFGQG TKVEIKGKPI PNPLLGLDST                        280

SEQ ID NO: 219          moltype = AA  length = 280
FEATURE                 Location/Qualifiers
REGION                  1..280
                        note = Description of Artificial Sequence: Synthetic
                        polypeptide
REGION                  1..280
                        note = AF000614
source                  1..280
                        mol_type = protein
                        organism = synthetic construct
SEQUENCE: 219
MSTSTEQKLI SEEDLQVQLV QSGAEVKKPG ASVKVSCKAS GYTFTNYYMH WVRQAPGQGL    60
EWMGWMNPNS GNTGYAQKFQ GRVTMTRDTS TSTVYMELSS LRSEDTAVYY CARSLFPTIF   120
GVEVAFDIWG QGTLVTVSSA SGGGGSGGGG SGGGGSHASD IQMTQSPSSL SASVGDRVTI   180
TCRASQSISS YLNWYQQKPG KAPKLLIYAA SSLQSGVPSR FSGSGSGTDF TLTISSLQPE   240
DFATYYCQQS YSTPRTFGQG TKLEIKGKPI PNPLLGLDST                        280

SEQ ID NO: 220          moltype = AA  length = 520
FEATURE                 Location/Qualifiers
REGION                  1..520
                        note = Description of Artificial Sequence: Synthetic
                        polypeptide
REGION                  1..520
                        note = AF004455
source                  1..520
                        mol_type = protein
                        organism = synthetic construct
SEQUENCE: 220
MSTSTITCPP PMSVEHADIW VKSYSLYSRE RYICNSGFKR KAGTSSLTEC VLNKATNVAH    60
WTTPSLKCIR DPALVHQRPA PPSGGSGGGG SGGGSGGGGS LQNWVNVISD LKKIEDLIQS   120
MHIDATLYTE SDVHPSCKVT AMKCFLLELQ VISLESGDAS IHDTVENLII LANNSLSSNG   180
NVTESGCKEC EELEEKNIKE FLQSFVHIVQ MFINTSGGSG SGGGSGGSG SGGGSGSQVQL   240
VQSGAEVKKP GASVKVSCKA SGYTFTGYYI HWVRQAPGQG LEWMGIINPS GGSTRYAQKF   300
QGRVTMTRDT STSTVYMELS SLRSEDTAVY YCARSLFPTI FGVEVAFDIW GQGTLVTVSS   360
ASGGGGSGGG GSGGGGSHAS DIQMTQSPSS LSASVGDRVT ITCRASQSIR TYLNWYQQKP   420
GKAPKLLIYS ASNLQSGVPS RFSGSGSGTD FTLTISSLQP EDFATYYCQQ ANSFPFTFGP   480
GTKVDIKAAA GSGSEQKLIS EEDLGKPIPN PLLGLDSTNA                        520

SEQ ID NO: 221          moltype = AA  length = 520
FEATURE                 Location/Qualifiers
REGION                  1..520
                        note = Description of Artificial Sequence: Synthetic
                        polypeptide
REGION                  1..520
                        note = AF004456
source                  1..520
                        mol_type = protein
                        organism = synthetic construct
SEQUENCE: 221
MSTSTITCPP PMSVEHADIW VKSYSLYSRE RYICNSGFKR KAGTSSLTEC VLNKATNVAH    60
WTTPSLKCIR DPALVHQRPA PPSGGSGGGG SGGGSGGGGS LQNWVNVISD LKKIEDLIQS   120
MHIDATLYTE SDVHPSCKVT AMKCFLLELQ VISLESGDAS IHDTVENLII LANNSLSSNG   180
NVTESGCKEC EELEEKNIKE FLQSFVHIVQ MFINTSGGSG SGGGSGGSG SGGGSGSQVQL   240
VQSGAEVKKP GASVKVSCKA SGYSFTSYYL HWVRQAPGQG LEWMGRISPR SGGTKNAQNF   300
QGRVTMTRDT STSTVYMELS SLRSEDTAVY YCVRSLFPTI FGVEVAFDIW GQGTLVTVSS   360
ASGGGGSGGG GSGGGGSHAS DIQMTQSPSS LSASVGDRVT ITCRASQSIS SWLAWYQQKP   420
GKAPKLLIYY ASSLQSGVPS RFSGSGSGTD FTLTISSLQP EDFATYYCQQ GYQYPYTFGQ   480
GTKLEIKAAA GSGSEQKLIS EEDLGKPIPN PLLGLDSTNA                        520

SEQ ID NO: 222          moltype = AA  length = 520
FEATURE                 Location/Qualifiers
REGION                  1..520
                        note = Description of Artificial Sequence: Synthetic
                        polypeptide
```

```
REGION                          1..520
                                note = AF004457
source                          1..520
                                mol_type = protein
                                organism = synthetic construct
SEQUENCE: 222
MSTSTITCPP PMSVEHADIW VKSYSLYSRE RYICNSGFKR KAGTSSLTEC VLNKATNVAH    60
WTTPSLKCIR DPALVHQRPA PPSGGSGGGG SGGGSGGGGS LQNWVNVISD LKKIEDLIQS   120
MHIDATLYTE SDVHPSCKVT AMKCFLLELQ VISLESGDAS IHDTVENLII LANNSLSSNG   180
NVTESGCKEC EELEEKNIKE FLQSFVHIVQ MFINTSGGSG SGSGGSGGSG SGGSGSQVQL   240
VQSGAEVKKP GASVKVSCKA SGYTFSTYYI HWVRQAPGQG LEWMGWMNPN SGNTGYAQTF   300
QGRVTMTRDT STSTVYMELS SLRSEDTAVY YCARSLFPTI FGVEVAFDIW GQGTLVTVSS   360
ASGGGGSGGG GSGGGGSHAS DIQMTQSPSS LSASVGDRVT ITCRASQSIS SYLNWYQQKP   420
GKAPKLLIYA ASSLQSGVPS RFSGSGSGTD FTLTISSLQP EDFATYYCQQ GYSTPRTFGQ   480
GTKVEIKAAA GSGSEQKLIS EEDLGKPIPN PLLGLDSTNA                        520

SEQ ID NO: 223                  moltype = AA  length = 520
FEATURE                         Location/Qualifiers
REGION                          1..520
                                note = Description of Artificial Sequence: Synthetic
                                polypeptide
REGION                          1..520
                                note = AF004440
source                          1..520
                                mol_type = protein
                                organism = synthetic construct
SEQUENCE: 223
MSTSTITCPP PMSVEHADIW VKSYSLYSRE RYICNSGFKR KAGTSSLTEC VLNKATNVAH    60
WTTPSLKCIR DPALVHQRPA PPSGGSGGGG SGGGSGGGGS LQNWVNVISD LKKIEDLIQS   120
MHIDATLYTE SDVHPSCKVT AMKCFLLELQ VISLESGDAS IHDTVENLII LANNSLSSNG   180
NVTESGCKEC EELEEKNIKE FLQSFVHIVQ MFINTSGGSG SGSGGSGGSG SGGSGSQVQL   240
VQSGAEVKKP GASVKVSCKA SGYTFTNYYM HWVRQAPGQG LEWMGWMNPN SGNTGYAQKF   300
QGRVTMTRDT STSTVYMELS SLRSEDTAVY YCARSLFPTI FGVEVAFDIW GQGTLVTVSS   360
ASGGGGSGGG GSGGGGSHAS DIQMTQSPSS LSASVGDRVT ITCRASQSIS SYLNWYQQKP   420
GKAPKLLIYA ASSLQSGVPS RFSGSGSGTD FTLTISSLQP EDFATYYCQQ SYSTPRTFGQ   480
GTKLEIKAAA GSGSEQKLIS EEDLGKPIPN PLLGLDSTNA                        520

SEQ ID NO: 224                  moltype = AA  length = 520
FEATURE                         Location/Qualifiers
REGION                          1..520
                                note = Description of Artificial Sequence: Synthetic
                                polypeptide
REGION                          1..520
                                note = AF004447
source                          1..520
                                mol_type = protein
                                organism = synthetic construct
SEQUENCE: 224
MSTSTITCPP PMSVEHADIW VKSYSLYSRE RYICNSGFKR KAGTSSLTEC VLNKATNVAH    60
WTTPSLKCIR DPALVHQRPA PPSGGSGGGG SGGGSGGGGS LQNWVNVISD LKKIEDLIQS   120
MHIDATLYTE SDVHPSCKVT AMKCFLLELQ VISLESGDAS IHDTVENLII LANNSLSSNG   180
NVTESGCKEC EELEEKNIKE FLQSFVHIVQ MFINTSGGSG SGSGGSGGSG SGGSGSQVQL   240
VQSGAEVKKP GASVKVSCKA SGYTFTGYYI HWVRQAPGQG LEWMGWMNPN SGNTGYAQKF   300
QGRVTMTRDT STSTVYMELS SLRSEDTAVY YCARSLFPTI FGVEVAFDIW GQGTLVTVSS   360
ASGGGGSGGG GSGGGGSHAS DIQMTQSPSS LSASVGDRVT ITCRASRSIS SYLNWYQQKP   420
GKAPKLLIYA ASSLQSGVPS RFSGSGSGTD FTLTISSLQP EDFATYYCQQ SYSTPRTFGQ   480
GTKVEIKAAA GSGSEQKLIS EEDLGKPIPN PLLGLDSTNA                        520

SEQ ID NO: 225                  moltype = AA  length = 519
FEATURE                         Location/Qualifiers
REGION                          1..519
                                note = Description of Artificial Sequence: Synthetic
                                polypeptide
REGION                          1..519
                                note = AF004479
source                          1..519
                                mol_type = protein
                                organism = synthetic construct
SEQUENCE: 225
MSTSTITCPP PMSVEHADIW VKSYSLYSRE RYICNSGFKR KAGTSSLTEC VLNKATNVAH    60
WTTPSLKCIR DPALVHQRPA PPSGGSGGGG SGGGSGGGGS LQNWVNVISD LKKIEDLIQS   120
MHIDATLYTE SDVHPSCKVT AMKCFLLELQ VISLESGDAS IHDTVENLII LANNSLSSNG   180
NVTESGCKEC EELEEKNIKE FLQSFVHIVQ MFINTSGGSG SGGGSGGSG SGGSGSQVQL   240
VQSGAEVKKP GSSVKVSCKA SGYSFTDYYV HWVRQAPGQG LEWVGGINPK RGDTVFAQKF   300
QGRVTITADE STSTAYMELS SLRSEDTAVY YCARGGLGVF GVVDVWGQGT TVTVSSASGG   360
GGSGGGGSGG GGSHASDIVM TQSPLSLPVT PGEPASISCR SSQSLLHSNG YNYLDWYLQK   420
PGQSPQLLIY AATTLQSGVP DRFSGSGSGT DFTLKISRVE AEDVGVYYCM QALQTPLTFG   480
GGTKLEIKAA AGSGSEQKLI SEEDLGKPIP NPLLGLDST                         519
```

```
SEQ ID NO: 226          moltype = AA  length = 685
FEATURE                 Location/Qualifiers
REGION                  1..685
                        note = Description of Artificial Sequence: Synthetic
                         polypeptide
REGION                  1..685
                        note = AF004591_Pep1
source                  1..685
                        mol_type = protein
                        organism = synthetic construct
SEQUENCE: 226
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ENLIILANNS LSSNGNVTES  180
GCKECEELEE KNIKEFLQSF VHIVQMFINT SGGGGSGGGG SGGGGSGGGG SQVQLVQSGA  240
EVKKPGASVK VSCKASGYTF TNYYMHWVRQ APGQGLEWMG WMNPNSGNTG YAQKFQGRVT  300
MTRDTSTSTV YMELSSLRSE DTAVYYCARS LFPTIFGVEV AFDIWGQGTL VTVSSAKTTA  360
PSVYPLAPVC GDTTGSSVTL GCLVKGYFPE PVTLTWNSGS LSSGVHTFPA VLQSDLYTLS  420
SSVTVTSSTW PSQSITCNVA HPASSTKVDK KIEPRGPTIK PCPPCKCPAP NAAGGPSVFI  480
FPPKIKDVLM ISLSPIVTCV VVDVSEDDPD VQISWFVNNV EVHTAQTQTH REDYNSTLRV  540
VSALPIQHQD WMSGKEFKCK VNNKDLGAPI ERTISKPKGS VRAPQVYVLP PPEEEMTKKQ  600
VTLTCMVTDF MPEDIYVEWT NNGKTELNYK NTEPVLDSDG SYFMYSDLRV EKKNWVERNS  660
YSCSVVHEGL HNHHTTESFS RTPGK                                       685

SEQ ID NO: 227          moltype = AA  length = 454
FEATURE                 Location/Qualifiers
REGION                  1..454
                        note = Description of Artificial Sequence: Synthetic
                         polypeptide
REGION                  1..454
                        note = AF004591_Pep2
source                  1..454
                        mol_type = protein
                        organism = synthetic construct
SEQUENCE: 227
QVQLVQSGAE VKKPGASVKV SCKASGYTFT NYYMHWVRQA PGQGLEWMGW MNPNSGNTGY   60
AQKFQGRVTM TRDTSTSTVY MELSSLRSED TAVYYCARSL FPTIFGVEVA FDIWGQGTLV  120
TVSSAKTTAP SVYPLAPVCG DTTGSSVTLG CLVKGYFPEP VTLTWNSGSL SSGVHTFPAV  180
LQSDLYTLSS SVTVTSSTWP SQSITCNVAH PASSTKVDKK IEPRGPTIKP CPPCKCPAPN  240
AAGGPSVFIF PPKIKDVLMI SLSPIVTCVV VDVSEDDPDV QISWFVNNVE VHTAQTQTHR  300
EDYNSTLRVV SALPIQHQDW MSGKEFKCKV NNKDLGAPIE RTISKPKGSV RAPQVYVLPP  360
PEKEMTKKQV SLTCLVKDFM PEDIYVEWTN NGKTELNYKN TEPVLKSDGS YFMYSKLTVE  420
KKNWVERNSY SCSVVHEGLH NHHTTKSFSR TPGK                              454

SEQ ID NO: 228          moltype = AA  length = 214
FEATURE                 Location/Qualifiers
REGION                  1..214
                        note = Description of Artificial Sequence: Synthetic
                         polypeptide
REGION                  1..214
                        note = AF004591_Pep3
source                  1..214
                        mol_type = protein
                        organism = synthetic construct
SEQUENCE: 228
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPRTFGQ GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 229          moltype = AA  length = 685
FEATURE                 Location/Qualifiers
REGION                  1..685
                        note = Description of Artificial Sequence: Synthetic
                         polypeptide
REGION                  1..685
                        note = AF004592_Pep1
source                  1..685
                        mol_type = protein
                        organism = synthetic construct
SEQUENCE: 229
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ENLIILANNS LSSNGNVTES  180
GCKECEELEE KNIKEFLQSF VHIVQMFINT SGGGGSGGGG SGGGGSGGGG SQVQLVQSGA  240
EVKKPGASVK VSCKASGYTF STYYIHWVRQ APGQGLEWMG WMNPNSGNTG YAQTFQGRVT  300
MTRDTSTSTV YMELSSLRSE DTAVYYCARS LFPTIFGVEV AFDIWGQGTL VTVSSAKTTA  360
PSVYPLAPVC GDTTGSSVTL GCLVKGYFPE PVTLTWNSGS LSSGVHTFPA VLQSDLYTLS  420
SSVTVTSSTW PSQSITCNVA HPASSTKVDK KIEPRGPTIK PCPPCKCPAP NAAGGPSVFI  480
```

```
FPPKIKDVLM ISLSPIVTCV VVDVSEDDPD VQISWFVNNV EVHTAQTQTH REDYNSTLRV   540
VSALPIQHQD WMSGKEFKCK VNNKDLGAPI ERTISKPKGS VRAPQVYVLP PPEEEMTKKQ   600
VTLTCMVTDF MPEDIYVEWT NNGKTELNYK NTEPVLDSDG SYFMYSDLRV EKKNWVERNS   660
YSCSVVHEGL HNHHTTESFS RTPGK                                        685

SEQ ID NO: 230         moltype = AA   length = 454
FEATURE                Location/Qualifiers
REGION                 1..454
                       note = Description of Artificial Sequence: Synthetic
                        polypeptide
REGION                 1..454
                       note = AF004592_Pep2
source                 1..454
                       mol_type = protein
                       organism = synthetic construct
SEQUENCE: 230
QVQLVQSGAE VKKPGASVKV SCKASGYTFS TYYIHWVRQA PGQGLEWMGW MNPNSGNTGY    60
AQTFQGRVTM TRDTSTSTVY MELSSLRSED TAVYYCARSL FPTIFGVEVA FDIWGQGTLV   120
TVSSAKTTAP SVYPLAPVCG DTTGSSVTLG CLVKGYFPEP VTLTWNSGSL SSGVHTFPAV   180
LQSDLYTLSS SVTVTSSTWP SQSITCNVAH PASSTKVDKK IEPRGPTIKP CPPCKCPAPN   240
AAGGPSVFIF PPKIKDVLMI SLSPIVTCVV VDVSEDDPDV QISWFVNNVE VHTAQTQTHR   300
EDYNSTLRVV SALPIQHQDW MSGKEFKCKV NNKDLGAPIE RTISKPKGSV RAPQVYVLPP   360
PEKEMTKKQV SLTCLVKDFM PEDIYVEWTN NGKTELNYKN TEPVLKSDGS YFMYSKLTVE   420
KKNWVERNSY SCSVVHEGLH NHHTTKSFSR TPGK                              454

SEQ ID NO: 231         moltype = AA   length = 214
FEATURE                Location/Qualifiers
REGION                 1..214
                       note = Description of Artificial Sequence: Synthetic
                        polypeptide
REGION                 1..214
                       note = AF004592_Pep3
source                 1..214
                       mol_type = protein
                       organism = synthetic construct
SEQUENCE: 231
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ GYSTPRTFGQ GTKVEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                              214

SEQ ID NO: 232         moltype = AA   length = 677
FEATURE                Location/Qualifiers
REGION                 1..677
                       note = Description of Artificial Sequence: Synthetic
                        polypeptide
REGION                 1..677
                       note = AF004659_Pep1
source                 1..677
                       mol_type = protein
                       organism = synthetic construct
SEQUENCE: 232
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGSGGGG SGGGGSGGGG SQVQLVQSGA   240
EVKKPGASVK VSCKASGDTF SSYAISWVRQ APGQGLEWMG WMNPNSGNTG YAQKFQGRVT   300
MTRDTSTSTV YMELSSLRSE DTAVYYCATG ITMIGYWGQG TLVTVSSAKT TAPSVYPLAP   360
VCGDTTGSSV TLGCLVKGYF PEPVTLTWNS GSLSSGVHTF PAVLQSDLYT LSSSVTVTSS   420
TWPSQSITCN VAHPASSTKV DKKIEPRGPT IKPCPPCKCP APNAAGGPSV FIFPPKIKDV   480
LMISLSPIVT CVVVDVSEDD PDVQISWFVN NVEVHTAQTQ THREDYNSTL RVVSALPIQH   540
QDWMSGKEFK CKVNNKDLGA PIERTISKPK GSVRAPQVYV LPPPEEEMTK KQVTLTCMVT   600
DFMPEDIYVE WTNNGKTELN YKNTEPVLDS DGSYFMYSDL RVEKKNWVER NSYSCSVVHE   660
GLHNHHTTES FSRTPGK                                                 677

SEQ ID NO: 233         moltype = AA   length = 446
FEATURE                Location/Qualifiers
REGION                 1..446
                       note = Description of Artificial Sequence: Synthetic
                        polypeptide
REGION                 1..446
                       note = AF004659_Pep2
source                 1..446
                       mol_type = protein
                       organism = synthetic construct
SEQUENCE: 233
QVQLVQSGAE VKKPGASVKV SCKASGDTFS SYAISWVRQA PGQGLEWMGW MNPNSGNTGY    60
AQKFQGRVTM TRDTSTSTVY MELSSLRSED TAVYYCATGI TMIGYWGQGT LVTVSSAKTT   120
APSVYPLAPV CGDTTGSSVT LGCLVKGYFP EPVTLTWNSG SLSSGVHTFP AVLQSDLYTL   180
```

```
SSSVTVTSST WPSQSITCNV AHPASSTKVD KKIEPRGPTI KPCPPCKCPA PNAAGGPSVF    240
IFPPKIKDVL MISLSPIVTC VVVDVSEDDP DVQISWFVNN VEVHTAQTQT HREDYNSTLR    300
VVSALPIQHQ DWMSGKEFKC KVNNKDLGAP IERTISKPKG SVRAPQVYVL PPPEKEMTKK    360
QVSLTCLVKD FMPEDIYVEW TNNGKTELNY KNTEPVLKSD GSYFMYSKLT VEKKNWVERN    420
SYSCSVVHEG LHNHHTTKSF SRTPGK                                        446

SEQ ID NO: 234              moltype = AA   length = 214
FEATURE                     Location/Qualifiers
REGION                      1..214
                            note = Description of Artificial Sequence: Synthetic
                             polypeptide
REGION                      1..214
                            note = AF004659_Pep3
source                      1..214
                            mol_type = protein
                            organism = synthetic construct
SEQUENCE: 234
DIQMTQSPSS LSASVGDRVT ITCQASQDIS SYLNWYQQKP GKAPKLLIYA ASTLQSGVPS    60
RFSGSGSGTD FTLTISSLQP EDFATYYCQQ SYSTPYTFGQ GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                               214

SEQ ID NO: 235              moltype = AA   length = 685
FEATURE                     Location/Qualifiers
REGION                      1..685
                            note = Description of Artificial Sequence: Synthetic
                             polypeptide
REGION                      1..685
                            note = AF004660_Pep1
source                      1..685
                            mol_type = protein
                            organism = synthetic construct
SEQUENCE: 235
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA    120
TLYTESDVHP SCKVTAMKCF LLELQVISLE SGDASIHDTV ENLIILANNS LSSNGNVTES    180
GCKEECEELEE KNIKEFLQSF VHIVQMFINT SGGGGSGGGG SGGGGSGGGG SQVQLVQSGA    240
EVKKPGASVK VSCKASGGTF SSYAISWVRQ APGQGLEWMG IIDPSMTYTR YAQKFQGRVT    300
MTRDTSTSTV YMELSSLRSE DTAVYYCARS LFPTIFGLEV AFDIWGQGTL VTVSSAKTTA    360
PSVYPLAPVC GDTTGSSVTL GCLVKGYFPE PVTLTWNSGS LSSGVHTFPA VLQSDLYTLS    420
SSVTVTSSTW PSQSITCNVA HPASSTKVDK KIEPRGPTIK PCPPCKCPAP NAAGGPSVFI    480
FPPKIKDVLM ISLSPIVTCV VVDVSEDDPD VQISWFVNNV EVHTAQTQTH REDYNSTLRV    540
VSALPIQHQD WMSGKEFKCK VNNKDLGAPI ERTISKPKGS VRAPQVYVLP PPEEEMTKKQ    600
VTLTCMVTDF MPEDIYVEWT NNGKTELNYK NTEPVLDSDG SYFMYSDLRV EKKNWVERNS    660
YSCSVVHEGL HNHHTTESFS RTPGK                                         685

SEQ ID NO: 236              moltype = AA   length = 454
FEATURE                     Location/Qualifiers
REGION                      1..454
                            note = Description of Artificial Sequence: Synthetic
                             polypeptide
REGION                      1..454
                            note = AF004660_Pep2
source                      1..454
                            mol_type = protein
                            organism = synthetic construct
SEQUENCE: 236
QVQLVQSGAE VKKPGASVKV SCKASGGTFS SYAISWVRQA PGQGLEWMGI IDPSMTYTRY    60
AQKFQGRVTM TRDTSTSTVY MELSSLRSED TAVYYCARSL FPTIFGLEVA FDIWGQGTLV    120
TVSSAKTTAP SVYPLAPVCG DTTGSSVTLG CLVKGYFPEP VTLTWNSGSL SSGVHTFPAV    180
LQSDLYTLSS SVTVTSSTWP SQSITCNVAH PASSTKVDKK IEPRGPTIKP CPPCKCPAPN    240
AAGGPSVFIF PPKIKDVLMI SLSPIVTCVV VDVSEDDPDV QISWFVNNVE VHTAQTQTHR    300
EDYNSTLRVV SALPIQHQDW MSGKEFKCKV NNKDLGAPIE RTISKPKGSV RAPQVYVLPP    360
PEKEMTKKQV SLTCLVKDFM PEDIYVEWTN NGKTELNYKN TEPVLKSDGS YFMYSKLTVE    420
KKNWVERNSY SCSVVHEGLH NHHTTKSFSR TPGK                               454

SEQ ID NO: 237              moltype = AA   length = 214
FEATURE                     Location/Qualifiers
REGION                      1..214
                            note = Description of Artificial Sequence: Synthetic
                             polypeptide
REGION                      1..214
                            note = AF004660_Pep3
source                      1..214
                            mol_type = protein
                            organism = synthetic construct
SEQUENCE: 237
DIQMTQSPSS LSASVGDRVT ITCQASQSIS NRLAWYQQKP GKAPKLLIYK ASSLESGVPS    60
RFSGSGSGTD FTLTISSLQP EDFATYYCQQ TYSTPITFGQ GTKVEIKRAD AAPTVSIFPP    120
```

```
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 238          moltype = AA  length = 15
FEATURE                 Location/Qualifiers
REGION                  1..15
                        note = Description of Artificial Sequence: Synthetic peptide
REGION                  1..15
                        note = HC-CDR3 of IFNa binder
source                  1..15
                        mol_type = protein
                        organism = synthetic construct
SEQUENCE: 238
CASGGSYSPW YFDLW                                                     15

SEQ ID NO: 239          moltype = AA  length = 18
FEATURE                 Location/Qualifiers
REGION                  1..18
                        note = Description of Artificial Sequence: Synthetic peptide
REGION                  1..18
                        note = HC-CDR3 of IFNa binder
source                  1..18
                        mol_type = protein
                        organism = synthetic construct
SEQUENCE: 239
CASLAAAGPY YYYGMDVW                                                  18

SEQ ID NO: 240          moltype = AA  length = 18
FEATURE                 Location/Qualifiers
REGION                  1..18
                        note = Description of Artificial Sequence: Synthetic peptide
REGION                  1..18
                        note = HC-CDR3 of IFNa binder
source                  1..18
                        mol_type = protein
                        organism = synthetic construct
SEQUENCE: 240
CVSSVGAGAY YYQGLDVW                                                  18

SEQ ID NO: 241          moltype = AA  length = 14
FEATURE                 Location/Qualifiers
REGION                  1..14
                        note = Description of Artificial Sequence: Synthetic peptide
REGION                  1..14
                        note = HC-CDR3 of IFNa binder
source                  1..14
                        mol_type = protein
                        organism = synthetic construct
SEQUENCE: 241
CARDHDYLTS FGYW                                                      14

SEQ ID NO: 242          moltype = AA  length = 17
FEATURE                 Location/Qualifiers
REGION                  1..17
                        note = Description of Artificial Sequence: Synthetic peptide
REGION                  1..17
                        note = HC-CDR3 of IFNa binder
source                  1..17
                        mol_type = protein
                        organism = synthetic construct
SEQUENCE: 242
CAFSSPTYYY YYGMDVW                                                   17

SEQ ID NO: 243          moltype = AA  length = 19
FEATURE                 Location/Qualifiers
REGION                  1..19
                        note = Description of Artificial Sequence: Synthetic peptide
REGION                  1..19
                        note = HC-CDR3 of IFNa binder
source                  1..19
                        mol_type = protein
                        organism = synthetic construct
SEQUENCE: 243
CARVNYDFWS GQSLRFDPW                                                 19

SEQ ID NO: 244          moltype = AA  length = 18
FEATURE                 Location/Qualifiers
REGION                  1..18
                        note = Description of Artificial Sequence: Synthetic peptide
```

```
REGION                  1..18
                        note = HC-CDR3 of IFNa binder
source                  1..18
                        mol_type = protein
                        organism = synthetic construct
SEQUENCE: 244
CATIKGLGAY YYYGMDVW                                                         18

SEQ ID NO: 245          moltype = AA  length = 14
FEATURE                 Location/Qualifiers
REGION                  1..14
                        note = Description of Artificial Sequence: Synthetic peptide
REGION                  1..14
                        note = HC-CDR3 of IFNa binder
source                  1..14
                        mol_type = protein
                        organism = synthetic construct
SEQUENCE: 245
CASDHGWLDA FDIW                                                             14

SEQ ID NO: 246          moltype = AA  length = 13
FEATURE                 Location/Qualifiers
REGION                  1..13
                        note = Description of Artificial Sequence: Synthetic peptide
REGION                  1..13
                        note = HC-CDR3 of IFNa binder
source                  1..13
                        mol_type = protein
                        organism = synthetic construct
SEQUENCE: 246
CARDWYGDYF DYW                                                              13

SEQ ID NO: 247          moltype = AA  length = 17
FEATURE                 Location/Qualifiers
REGION                  1..17
                        note = Description of Artificial Sequence: Synthetic peptide
REGION                  1..17
                        note = HC-CDR3 of IFNa binder
source                  1..17
                        mol_type = protein
                        organism = synthetic construct
SEQUENCE: 247
CARGILSDYG DHAFDYW                                                          17

SEQ ID NO: 248          moltype = AA  length = 15
FEATURE                 Location/Qualifiers
REGION                  1..15
                        note = Description of Artificial Sequence: Synthetic peptide
REGION                  1..15
                        note = HC-CDR3 of IFNa binder
source                  1..15
                        mol_type = protein
                        organism = synthetic construct
SEQUENCE: 248
CARVDSSSSL HFDYW                                                            15

SEQ ID NO: 249          moltype = AA  length = 14
FEATURE                 Location/Qualifiers
REGION                  1..14
                        note = Description of Artificial Sequence: Synthetic peptide
REGION                  1..14
                        note = HC-CDR3 of IFNa binder
source                  1..14
                        mol_type = protein
                        organism = synthetic construct
SEQUENCE: 249
CARTSGYDLL FDYW                                                             14

SEQ ID NO: 250          moltype = AA  length = 18
FEATURE                 Location/Qualifiers
REGION                  1..18
                        note = Description of Artificial Sequence: Synthetic peptide
REGION                  1..18
                        note = HC-CDR3 of IFNa binder
source                  1..18
                        mol_type = protein
                        organism = synthetic construct
SEQUENCE: 250
CARVGGWGIY YYYGMDVW                                                         18
```

```
SEQ ID NO: 251          moltype = AA  length = 15
FEATURE                 Location/Qualifiers
REGION                  1..15
                        note = Description of Artificial Sequence: Synthetic peptide
REGION                  1..15
                        note = HC-CDR3 of IFNa binder
source                  1..15
                        mol_type = protein
                        organism = synthetic construct
SEQUENCE: 251
CARDPSYSTG YYDYW                                                          15

SEQ ID NO: 252          moltype = AA  length = 10
FEATURE                 Location/Qualifiers
REGION                  1..10
                        note = Description of Artificial Sequence: Synthetic peptide
REGION                  1..10
                        note = HC-CDR3 of IFNa binder
source                  1..10
                        mol_type = protein
                        organism = synthetic construct
SEQUENCE: 252
CARGSRADYW                                                                10

SEQ ID NO: 253          moltype = AA  length = 286
FEATURE                 Location/Qualifiers
REGION                  1..286
                        note = Description of Artificial Sequence: Synthetic
                        polypeptide
REGION                  1..286
                        note = 8b2_A09
source                  1..286
                        mol_type = protein
                        organism = synthetic construct
SEQUENCE: 253
MSTSTEVQLL ESGGGLVQPG GSLRLSCAAS GFTFSSYAMH WVRQAPGKGL EWVSAIGAGG   60
GTYYADSVKG RFTISRDDSK NTLYLQMNSL KTEDTAVYYC VSSVGAGAYY YQGLDVWGQG  120
TLVTVSSASG GGGSGGGGSG GGGSHASDIQ MTQSPSSLSA SVGDRVTITC RASQDIFTYL  180
NWYQQRPGKA PKLLIYDASR LQTGVPSRFS GSGSGTDFTL TISSLQPEDF ATYYCQQSYS  240
IPYTFGQGTK LEIKRAAAGS GSEQKLISEE DLGKPIPNPL LGLDST              286

SEQ ID NO: 254          moltype = AA  length = 287
FEATURE                 Location/Qualifiers
REGION                  1..287
                        note = Description of Artificial Sequence: Synthetic
                        polypeptide
REGION                  1..287
                        note = 8b2_B10
source                  1..287
                        mol_type = protein
                        organism = synthetic construct
SEQUENCE: 254
MSTSTEVQLL ESGAEVKKPG GSLRLSCAAS GFTVSSNYMS WVRQAPGKGL EWVSAISGSG   60
GSTYYADFVK GRFTISRDNS KNTLYLQMNS LRAEDTAVYY CVSSVGAGAY YYQGLDVWGQ  120
GTLVTVSSAS GGGGSGGGGS GGGSHASDI QMTQSPSSLS ASVGDRVTIT CRASQGVGNF  180
LAWYQQKPGK APKLLIYGAS TLQSGVPSRF SGSGSGTDFT LTISSLQPED FATYYCQQSY  240
STPFTFGGGT KLEIKRAAAG SGSEQKLISE EDLGKPIPNP LLGLDST           287

SEQ ID NO: 255          moltype =    length =
SEQUENCE: 255
000

SEQ ID NO: 256          moltype = AA  length = 284
FEATURE                 Location/Qualifiers
REGION                  1..284
                        note = Description of Artificial Sequence: Synthetic
                        polypeptide
REGION                  1..284
                        note = 8b2_C08
source                  1..284
                        mol_type = protein
                        organism = synthetic construct
SEQUENCE: 256
MSTSTEVQLL ESGAEVKKPG GSLRLSCAAS GFTFSSYAMS WVRQAPGKGL EWVSAISGSG   60
GSTYYADSVK GRFTISRDNS KNTLYLQMNS LRAEDTAVYY CARVDSSSSL HFDYWGQGTL  120
VTVSSASGGG GSGGGGSGGG GSHASDIQMT QSPSSLSASV GDRVTITCRA SQRIGTYLNW  180
YQQKPGKAPK LLIYAASNLQ SGVPSRFSGS GSGTDFTLTI SSLQPEDFAT YYCLQTFNTP  240
FTFGPGTKVD IKRAAAGSGS EQKLISEEDL GKPIPNPLLG LDST               284
```

```
SEQ ID NO: 257          moltype = AA   length = 296
FEATURE                 Location/Qualifiers
REGION                  1..296
                        note = Description of Artificial Sequence: Synthetic
                         polypeptide
REGION                  1..296
                        note = AF000317
source                  1..296
                        mol_type = protein
                        organism = synthetic construct
SEQUENCE: 257
MSTSTEQKLI SEEDLQVQLV QSGAEVKKPG ASVKVSCKAS GYSFTSYDIN WVRQAPGQGL   60
EWIGMINPSS GFTSAAQTFQ GRVTMTRDTS TSTVYMELSS LRSEDTAVYY CATIKGLGAY  120
YYYGMDVWGQ GTTVTVSSAS GGGGSGGGGS GGGGSHASDI QMTQSPSSLS ASVGDRVTIT  180
CRASQSIDRY LNWYQQKPGK APKLLIYAAS SLQSGVPSRF SGSGSGTDFT LTISSLQPED  240
FATYYCQQSY SPPLTFGGGT KVEIKGSGLN DIFEAQKIEW HEGKPIPNPL LGLDST      296

SEQ ID NO: 258          moltype = AA   length = 293
FEATURE                 Location/Qualifiers
REGION                  1..293
                        note = Description of Artificial Sequence: Synthetic
                         polypeptide
REGION                  1..293
                        note = AF000372
source                  1..293
                        mol_type = protein
                        organism = synthetic construct
SEQUENCE: 258
MSTSTEQKLI SEEDLEVQLV ESGGGLVQPG GSLRLSCAAS GFNIKDTYIH WVRQAPGKGL   60
EWVARIYPTN GYTRYADSVK GRFTISADTS KNTAYLQMNS LRAEDTAVYY CSRWGGDGFY  120
AMDYWGQGTL VTVSSASGGG GSGGGGSGGG GSHASDIQMT QSPSSLSASV GDRVTITCRA  180
SQDVNTAVAW YQQKPGKAPK LLIYSASFLY SGVPSRFSGS RSGTDFTLTI SSLQPEDFAT  240
YYCQQHYTTP PTFGQGTKVE IKGSGLNDIF EAQKIEWHEG KPIPNPLLGL DST         293

SEQ ID NO: 259          moltype = AA   length = 471
FEATURE                 Location/Qualifiers
REGION                  1..471
                        note = Description of Artificial Sequence: Synthetic
                         polypeptide
REGION                  1..471
                        note = IFN-8b2_A09
source                  1..471
                        mol_type = protein
                        organism = synthetic construct
SEQUENCE: 259
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGSGSGSGGS  180
GGSGSGSGS EVQLLESGGG LVQPGGSLRL SCAASGFTFS SYAMHWVRQA PGKGLEWVSA  240
IGAGGGTYYA DSVKGRFTIS RDDSKNTLYL QMNSLKTEDT AVYYCVSSVG AGAYYYQGLD  300
VWGQGTLVTV SSASGGGGSG GGGSGGGGSH ASDIQMTQSP SSLSASVGDR VTITCRASQD  360
IFTYLNWYQQ RPGKAPKLLI YDASRLQTGV PSRFSGSGSG TDFTLTISSL QPEDFATYYC  420
QQSYSIPYTF GQGTKLEIKR AAAGSGSEQK LISEEDLGKP IPNPLLGLDS T           471

SEQ ID NO: 260          moltype = AA   length = 472
FEATURE                 Location/Qualifiers
REGION                  1..472
                        note = Description of Artificial Sequence: Synthetic
                         polypeptide
REGION                  1..472
                        note = IFN-8b2_B10
source                  1..472
                        mol_type = protein
                        organism = synthetic construct
SEQUENCE: 260
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGSGSGSGGS  180
GGSGSGGSGS EVQLLESGAE VKKPGGSLRL SCAASGFTVS SNYMSWVRQA PGKGLEWVSA  240
ISGSGGSTYY ADFVKGRFTI SRDNSKNTLY LQMNSLRAED TAVYYCVSSV GAGAYYYQGL  300
DVWGQGTLVT VSSASGGGGS GGGGSGGGGS HASDIQMTQS PSSLSASVGD RVTITCRASQ  360
GVGNFLAWYQ QKPGKAPKLL IYGASTLQSG VPSRFSGSGS GTDFTLTISS LQPEDFATYY  420
CQQSYSTPFT FGGGTKLEIK RAAAGSGSEQ KLISEEDLGK PIPNPLLGLD ST          472

SEQ ID NO: 261          moltype = AA   length = 469
FEATURE                 Location/Qualifiers
REGION                  1..469
                        note = Description of Artificial Sequence: Synthetic
```

```
                              polypeptide
REGION                        1..469
                              note = IFN-8b2_C08
source                        1..469
                              mol_type = protein
                              organism = synthetic construct
SEQUENCE: 261
MSTSTCDLPQ THSLGSRRTL MLLAQMRRIS LFSCLKDRHD FGFPQEEFGN QFQKAETIPV    60
LHEMIQQIFN LFSTKDSSAA WDETLLDKFY TELYQQLNDL EACVIQGVGV TETPLMKEDS   120
ILAVRKYFQR ITLYLKEKKY SPCAWEVVRA EIMRSFSLST NLQESLRSKE GGSGSGSGGS   180
GGSGSGGSGS EVQLLESGAE VKKPGGSLRL SCAASGFTFS SYAMSWVRQA PGKGLEWVSA   240
ISGSGGSTYY ADSVKGRFTI SRDNSKNTLY LQMNSLRAED TAVYYCARVD SSSSLHFDYW   300
GQGTLVTVSS ASGGGGSGGG GSGGGGSHAS DIQMTQSPSS LSASVGDRVT ITCRASQRIG   360
TYLNWYQQKP GKAPKLLIYA ASNLQSGVPS RFSGSGSGTD FTLTISSLQP EDFATYYCLQ   420
TFNTPFTFGP GTKVDIKRAA AGSGSEQKLI SEEDLGKPIP NPLLGLDST              469

SEQ ID NO: 262                moltype = AA   length = 287
FEATURE                       Location/Qualifiers
REGION                        1..287
                              note = Description of Artificial Sequence: Synthetic
                              polypeptide
REGION                        1..287
                              note = i47_A03
source                        1..287
                              mol_type = protein
                              organism = synthetic construct
SEQUENCE: 262
MSTSTQVQLV QSGAEVKKPG ASVKVSCKAS GYTFTGYYMH WVRQAPGQGL EWMGWMDPNN    60
DDADYAQRFQ GRVTMTRDTS TSTVYMELSS LRSEDTAVYY CASLAAAGPY YYYGMDVWGQ   120
GTLVTVSSAS GGGGSGGGGS GGGGSHASDI QMTQSPSSLS ASVGDRVTIT CRASQSINNY   180
LNWYQQKPGK APKLLIYGAS NLETGVPSRF SGSGSGTDFT LTISSLQPED FATYYCQQSY   240
GTPLTFGGGT KVEIKRAAAG SGSEQKLISE EDLGKPIPNP LLGLDST                287

SEQ ID NO: 263                moltype = AA   length = 284
FEATURE                       Location/Qualifiers
REGION                        1..284
                              note = Description of Artificial Sequence: Synthetic
                              polypeptide
REGION                        1..284
                              note = i47_B03
source                        1..284
                              mol_type = protein
                              organism = synthetic construct
SEQUENCE: 263
MSTSTQVQLV QSGAEVKKPG ASVEVSCKAS GGTFSSYAIN WVRQAPGQGL EWMGWIDPKS    60
GDTTYAQKFQ GRVTMTRDTS TSTVYMELSS LRSEDTAVYY CASGGSYSPW YFDLWGQGTL   120
VTVSSASGGG GSGGGGSGGG GSHASDIQMT QSPSSLSASV GDRVTITCRA SQSISSWLAW   180
YQQKSGKAPK LLIYAASSLQ SGVPSRFSGS GSGTDFTLTI SSLQPEDFAT YYCQQAYSFP   240
FTFGPGTKVD IKRAAAGSGS EQKLISEEDL GKPIPNPLLG LDST                   284

SEQ ID NO: 264                moltype = AA   length = 287
FEATURE                       Location/Qualifiers
REGION                        1..287
                              note = Description of Artificial Sequence: Synthetic
                              polypeptide
REGION                        1..287
                              note = i47_B07
source                        1..287
                              mol_type = protein
                              organism = synthetic construct
SEQUENCE: 264
MSTSTQVQLV QSGAEVKKPG ASVKVSCKAS GYTFTGYYMH WVRQAPGQGL EWMGWMDPNN    60
DDADYAQRFQ GRVTMTRDTS TSTVYMELSS LRSEDTAVYY CASLAAAGPY YYYGMDVWGQ   120
GTLVTVSSAS GGGGSGGGGS GGGGSHASDI QMTQSPSSLS ASVGDRVTIT CQASQDISNY   180
LNWYQQKPGK APKLLIYGAS ILEAGVPSRF SGSGSGTDFT LTISSLQPED FATYYCQQSY   240
SAPITFGQGT RLEIKRAAAG SGSEQKLISE EDLGKPIPNP LLGLDST                287

SEQ ID NO: 265                moltype = AA   length = 287
FEATURE                       Location/Qualifiers
REGION                        1..287
                              note = Description of Artificial Sequence: Synthetic
                              polypeptide
REGION                        1..287
                              note = i47_B11
source                        1..287
                              mol_type = protein
                              organism = synthetic construct
SEQUENCE: 265
MSTSTQVQLV QSGAEVKKPG SSVKVSCKAS GYTFTSYDIN WVRQAPGQGL EWLGGTVPLF    60
```

```
GISHYAQKFQ GRVTITADES TSTAYMELSS LRSEDTAVYY CVSSVGAGAY YYQGLDVWGQ    120
GTLVTVSSAS GGGGSGGGGS GGGGSHASDI QMTQSPSSLS ASVGDRVTIT CRASQSISSY    180
LNWYQQKPGK APKLLIYAAS SLQSGVPSRF SGSGSGTDFT LTISSLLPED FATYYCQQSY    240
LPPYSFGQGT KLEIKRAAAG SGSEQKLISE EDLGKPIPNP LLGLDST                 287

SEQ ID NO: 266         moltype = AA   length = 638
FEATURE                Location/Qualifiers
REGION                 1..638
                       note = Description of Artificial Sequence: Synthetic
                        polypeptide
REGION                 1..638
                       note = AF004581_pep1
source                 1..638
                       mol_type = protein
                       organism = synthetic construct
SEQUENCE: 266
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKEGGGGS GGGGSGGGGS    180
GGGGSQVQLV QSGAEVKKPG ASVKVSCKAS GYTFTGYYMH WVRQAPGQGL EWMGWMDPNN    240
DDADYAQRFQ GRVTMTRDTS TSTVYMELSS LRSEDTAVYY CASLAAAGPY YYYGMDVWGQ    300
GTLVTVSSAK TTAPSVYPLA PVCGDTTGSS VTLGCLVKGY FPEPVTLTWN SGSLSSGVHT    360
FPAVLQSDLY TLSSSVTVTS STWPSQSITC NVAHPASSTK VDKKIEPRGP TIKPCPPCKC    420
PAPNAAGGPS VFIFPPKIKD VLMISLSPIV TCVVVDVSED DPDVQISWFV NNVEVHTAQT    480
QTHREDYNST LRVVSALPIQ HQDWMSGKEF KCKVNNKDLG APIERTISKP KGSVRAPQVY    540
VLPPPEEEMT KKQVTLTCMV TDFMPEDIYV EWTNNGKTEL NYKNTEPVLD SDGSYFMYSD    600
LRVEKKNWVE RNSYSCSVVH EGLHNHHTTE SFSRTPGK                           638

SEQ ID NO: 267         moltype = AA   length = 453
FEATURE                Location/Qualifiers
REGION                 1..453
                       note = Description of Artificial Sequence: Synthetic
                        polypeptide
REGION                 1..453
                       note = AF004581_pep2
source                 1..453
                       mol_type = protein
                       organism = synthetic construct
SEQUENCE: 267
QVQLVQSGAE VKKPGASVKV SCKASGYTFT GYYMHWVRQA PGQGLEWMGW MDPNNDDADY    60
AQRFQGRVTM TRDTSTSTVY MELSSLRSED TAVYYCASLA AAGPYYYYGM DVWGQGTLVT    120
VSSAKTTAPS VYPLAPVCGD TTGSSVTLGC LVKGYFPEPV TLTWNSGSLS SGVHTFPAVL    180
QSDLYTLSSS VTVTSSTWPS QSITCNVAHP ASSTKVDKKI EPRGPTIKPC PPCKPAPNA    240
AGGPSVFIFP PKIKDVLMIS LSPIVTCVVV DVSEDDPDVQ ISWFVNNVEV HTAQTQTHRE    300
DYNSTLRVVS ALPIQHQDWM SGKEFKCKVN NKDLGAPIER TISKPKGSVR APQVYVLPPP    360
EKEMTKKQVS LTCLVKDFMP EDIYVEWTNN GKTELNYKNT EPVLKSDGSY FMYSKLTVEK    420
KNWVERNSYS CSVVHEGLHN HHTTKSFSRT PGK                                453

SEQ ID NO: 268         moltype = AA   length = 214
FEATURE                Location/Qualifiers
REGION                 1..214
                       note = Description of Artificial Sequence: Synthetic
                        polypeptide
REGION                 1..214
                       note = AF004581_pep3
source                 1..214
                       mol_type = protein
                       organism = synthetic construct
SEQUENCE: 268
DIQMTQSPSS LSASVGDRVT ITCRASQSIN NYLNWYQQKP GKAPKLLIYG ASNLETGVPS    60
RFSGSGSGTD FTLTISSLQP EDFATYYCQQ SYGTPLTFGG GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                               214

SEQ ID NO: 269         moltype = AA   length = 635
FEATURE                Location/Qualifiers
REGION                 1..635
                       note = Description of Artificial Sequence: Synthetic
                        polypeptide
REGION                 1..635
                       note = AF004586_pep1
source                 1..635
                       mol_type = protein
                       organism = synthetic construct
SEQUENCE: 269
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKEGGGGS GGGGSGGGGS    180
GGGGSQVQLV QSGAEVKKPG ASVEVSCKAS GGTFSSYAIN WVRQAPGQGL EWMGWIDPKS    240
```

```
GDTTYAQKFQ  GRVTMTRDTS  TSTVYMELSS  LRSEDTAVYY  CASGGSYSPW  YFDLWGQGTL   300
VTVSSAKTTA  PSVYPLAPVC  GDTTGSSVTL  GCLVKGYFPE  PVTLTWNSGS  LSSGVHTFPA   360
VLQSDLYTLS  SSVTVTSSTW  PSQSITCNVA  HPASSTKVDK  KIEPRGPTIK  PCPPCKCPAP   420
NAAGGPSVFI  FPPKIKDVLM  ISLSPIVTCV  VVDVSEDDPD  VQISWFVNNV  EVHTAQTQTH   480
REDYNSTLRV  VSALPIQHQD  WMSGKEFKCK  VNNKDLGAPI  ERTISKPKGS  VRAPQVYVLP   540
PPEEEMTKKQ  VTLTCMVTDF  MPEDIYVEWT  NNGKTELNYK  NTEPVLDSDG  SYFMYSDLRV   600
EKKNWVERNS  YSCSVVHEGL  HNHHTTESFS  RTPGK                                635

SEQ ID NO: 270           moltype = AA   length = 450
FEATURE                  Location/Qualifiers
REGION                   1..450
                         note = Description of Artificial Sequence: Synthetic
                          polypeptide
REGION                   1..450
                         note = AF004586_pep2
source                   1..450
                         mol_type = protein
                         organism = synthetic construct
SEQUENCE: 270
QVQLVQSGAE  VKKPGASVEV  SCKASGGTFS  SYAINWVRQA  PGQGLEWMGW  IDPKSGDTTY    60
AQKFQGRVTM  TRDTSTSTVY  MELSSLRSED  TAVYYCASGG  SYSPWYFDLW  GQGTLVTVSS   120
AKTTAPSVYP  LAPVCGDTTG  SSVTLGCLVK  GYFPEPVTLT  WNSGSLSSGV  HTFPAVLQSD   180
LYTLSSSVTV  TSSTWPSQSI  TCNVAHPASS  TKVDKKIEPR  GPTIKPCPPC  KCPAPNAAGG   240
PSVFIFPPKI  KDVLMISLSP  IVTCVVVDVS  EDDPDVQISW  FVNNVEVHTA  QTQTHREDYN   300
STLRVVSALP  IQHQDWMSGK  EFKCKVNNKD  LGAPIERTIS  KPKGSVRAPQ  VYVLPPPEKE   360
MTKKQVSLTC  LVKDFMPEDI  YVEWTNNGKT  ELNYKNTEPV  LKSDGSYFMY  SKLTVEKKNW   420
VERNSYSCSV  VHEGLHNHHT  TKSFSRTPGK                                      450

SEQ ID NO: 271           moltype = AA   length = 214
FEATURE                  Location/Qualifiers
REGION                   1..214
                         note = Description of Artificial Sequence: Synthetic
                          polypeptide
REGION                   1..214
                         note = AF004586_pep3
source                   1..214
                         mol_type = protein
                         organism = synthetic construct
SEQUENCE: 271
DIQMTQSPSS  LSASVGDRVT  ITCRASQSIS  SWLAWYQQKS  GKAPKLLIYA  ASSLQSGVPS    60
RFSGSGSGTD  FTLTISSLQP  EDFATYYCQQ  AYSFPFTFGP  GTKVDIKRAD  AAPTVSIFPP   120
SSEQLTSGGA  SVVCFLNNFY  PKDINVKWKI  DGSERQNGVL  NSWTDQDSKD  STYSMSSTLT   180
LTKDEYERHN  SYTCEATHKT  STSPIVKSFN  RNEC                                 214

SEQ ID NO: 272           moltype = AA   length = 214
FEATURE                  Location/Qualifiers
REGION                   1..214
                         note = Description of Artificial Sequence: Synthetic
                          polypeptide
REGION                   1..214
                         note = AF004587_pep1
source                   1..214
                         mol_type = protein
                         organism = synthetic construct
SEQUENCE: 272
DIQMTQSPSS  LSASVGDRVT  ITCQASQDIS  NYLNWYQQKP  GKAPKLLIYG  ASILEAGVPS    60
RFSGSGSGTD  FTLTISSLQP  EDFATYYCQQ  SYSAPITFGQ  GTRLEIKRAD  AAPTVSIFPP   120
SSEQLTSGGA  SVVCFLNNFY  PKDINVKWKI  DGSERQNGVL  NSWTDQDSKD  STYSMSSTLT   180
LTKDEYERHN  SYTCEATHKT  STSPIVKSFN  RNEC                                 214

SEQ ID NO: 273           moltype = AA   length = 638
FEATURE                  Location/Qualifiers
REGION                   1..638
                         note = Description of Artificial Sequence: Synthetic
                          polypeptide
REGION                   1..638
                         note = AF004588_pep1
source                   1..638
                         mol_type = protein
                         organism = synthetic construct
SEQUENCE: 273
CDLPQTHSLG  SRRTLMLLAQ  MRRISLFSCL  KDRHDFGFPQ  EEFGNQFQKA  ETIPVLHEMI    60
QQIFNLFSTK  DSSAAWDETL  LDKFYTELYQ  QLNDLEACVI  QGVGVTETPL  MKEDSILAVR   120
KYFQRITLYL  KEKKYSPCAW  EVVRAEIMRS  FSLSTNLQES  LRSKEGGGGS  GGGGSGGGGS   180
GGGGSQVQLV  QSGAEVKKPG  SSVKVSCKAS  GYTFTSYDIN  WVRQAPGQGL  EWLGGTVPLF   240
GISHYAQKFQ  GRVTITADES  TSTAYMELSS  LRSEDTAVYY  CVSSVGAGAY  YYQGLDVWGQ   300
GTLVTVSSAK  TTAPSVYPLA  PVCGDTTGSS  VTLGCLVKGY  FPEPVTLTWN  SGSLSSGVHT   360
FPAVLQSDLY  TLSSSVTVTS  STWPSQSITC  NVAHPASSTK  VDKKIEPRGP  TIKPCPPCKC   420
PAPNAAGGPS  VFIFPPKIKD  VLMISLSPIV  TCVVVDVSED  DPDVQISWFV  NNVEVHTAQT   480
```

```
QTHREDYNST LRVVSALPIQ HQDWMSGKEF KCKVNNKDLG APIERTISKP KGSVRAPQVY   540
VLPPPEEEMT KKQVTLTCMV TDFMPEDIYV EWTNNGKTEL NYKNTEPVLD SDGSYFMYSD   600
LRVEKKNWVE RNSYSCSVVH EGLHNHHTTE SFSRTPGK                           638

SEQ ID NO: 274           moltype = AA   length = 453
FEATURE                  Location/Qualifiers
REGION                   1..453
                         note = Description of Artificial Sequence: Synthetic
                          polypeptide
REGION                   1..453
                         note = AF004588_pep2
source                   1..453
                         mol_type = protein
                         organism = synthetic construct
SEQUENCE: 274
QVQLVQSGAE VKKPGSSVKV SCKASGYTFT SYDINWVRQA PGQGLEWLGG TVPLFGISHY    60
AQKFQGRVTI TADESTSTAY MELSSLRSED TAVYYCVSSV GAGAYYYQGL DVWGQGTLVT   120
VSSAKTTAPS VYPLAPVCGD TTGSSVTLGC LVKGYFPEPV TLTWNSGSLS SGVHTFPAVL   180
QSDLYTLSSS VTVTSSTWPS QSITCNVAHP ASSTKVDKKI EPRGPTIKPC PPCKCPAPNA   240
AGGPSVFIFP PKIKDVLMIS LSPIVTCVVV DVSEDDPDVQ ISWFVNNVEV HTAQTQTHRE   300
DYNSTLRVVS ALPIQHQDWM SGKEFKCKVN NKDLGAPIER TISKPKGSVR APQVYVLPPP   360
EKEMTKKQVS LTCLVKDFMP EDIYVEWTNN GKTELNYKNT EPVLKSDGSY FMYSKLTVEK   420
KNWVERNSYS CSVVHEGLHN HHTTKSFSRT PGK                                453

SEQ ID NO: 275           moltype = AA   length = 214
FEATURE                  Location/Qualifiers
REGION                   1..214
                         note = Description of Artificial Sequence: Synthetic
                          polypeptide
REGION                   1..214
                         note = AF004588_pep3
source                   1..214
                         mol_type = protein
                         organism = synthetic construct
SEQUENCE: 275
DIQMTQSPSS LSASVGDRVT ITCRASQSIS SYLNWYQQKP GKAPKLLIYA ASSLQSGVPS    60
RFSGSGSGTD FTLTISSLLP EDFATYYCQQ SYLPPYSFGQ GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 276           moltype = AA   length = 673
FEATURE                  Location/Qualifiers
REGION                   1..673
                         note = Description of Artificial Sequence: Synthetic
                          polypeptide
REGION                   1..673
                         note = AF002659_Pep1
source                   1..673
                         mol_type = protein
                         organism = synthetic construct
SEQUENCE: 276
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEVPGVG VPGAGVPGVG   180
VPGGGVPGAG VPGGGVPGVG VPGAGVPGVG VPGGGVPGVG VPGGGVPGVG   VPGGGVPGVG
VPGGGVPGAG VPGGGVPGVG VPGAGVPGVG VPGGGVPGVG VPGGGVPGVG   240
VPGGGVPGAG VPGGGVPGVG VPGAGVPGVG VPGGGVPGVG VPGGGVPGVG
VPGGGVPGAG VPGGGVPGVG VPGAGVPGVG VPGGGVPGVG VPGGGVPGVG
VPGGGVPGAG VPGGGVPGVG VPGAGVPGVG VPGGGVPGVG VPGGGVPGVG
ASVKVSCKAS GYTFSNYYIH WVRQAPGQGL EWMGWMDSNS GYTGYAQKFQ GRVTMTRDTS   300
TSTVYMELSS LRSEDTAVYY CAKEVFSGWY DYWGQGTLVT VSSAKTTAPS VYPLAPVCGD   360
TTGSSVTLGC LVKGYFPEPV TLTWNSGSLS SGVHTFPAVL QSDLYTLSSS VTVTSSTWPS   420
QSITCNVAHP ASSTKVDKKI EPRGPTIKPC PPCKCPAPNA AGGPSVFIFP PKIKDVLMIS   480
LSPIVTCVVV DVSEDDPDVQ ISWFVNNVEV HTAQTQTHRE DYNSTLRVVS ALPIQHQDWM   540
SGKEFKCKVN NKDLGAPIER TISKPKGSVR APQVYVLPPP EEEMTKKQVT LTCMVTDFMP   600
EDIYVEWTNN GKTELNYKNT EPVLSDGSY FMYSKLRVEK KNWVERNSYS CSVVHEGLHN   660
HHTTKSFSRT PGK                                                      673

SEQ ID NO: 277           moltype = AA   length = 214
FEATURE                  Location/Qualifiers
REGION                   1..214
                         note = Description of Artificial Sequence: Synthetic
                          polypeptide
REGION                   1..214
                         note = AF002659_Pep2
source                   1..214
                         mol_type = protein
                         organism = synthetic construct
SEQUENCE: 277
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPYTFGQ GTKVEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214
```

```
SEQ ID NO: 278          moltype =    length =
SEQUENCE: 278
000

SEQ ID NO: 279          moltype = AA   length = 454
FEATURE                 Location/Qualifiers
REGION                  1..454
                        note = Description of Artificial Sequence: Synthetic
                         polypeptide
REGION                  1..454
                        note = AF002615_pep1
source                  1..454
                        mol_type = protein
                        organism = synthetic construct
SEQUENCE: 279
QVQLVQSGAE VKKPGASVKV SCKASGNTFT DYYMHWVRQA PGQGLEWMGW MNPNSGNTGY    60
AQKFQGRVTM TRDTSTSTVY MELSSLRSED TAVYYCARSL FPTIFGVEVA FDIWGQGTLV   120
TVSSAKTTAP SVYPLAPVCG DTTGSSVTLG CLVKGYFPEP VTLTWNSGSL SSGVHTFPAV   180
LQSDLYTLSS SVTVTSSTWP SQSITCNVAH PASSTKVDKK IEPRGPTIKP CPPCKCPAPN   240
AAGGPSVFIF PPKIKDVLMI SLSPIVTCVV VDVSEDDPDV QISWFVNNVE VHTAQTQTHR   300
EDYNSTLRVV SALPIQHQDW MSGKEFKCKV NNKDLGAPIE RTISKPKGSV RAPQVYVLPP   360
PEEEMTKKQV TLTCMVTDFM PEDIYVEWTN NGKTELNYKN TEPVLDSDGS YFMYSKLRVE   420
KKNWVERNSY SCSVVHEGLH NHHTTKSFSR TPGK                               454

SEQ ID NO: 280          moltype = AA   length = 399
FEATURE                 Location/Qualifiers
REGION                  1..399
                        note = Description of Artificial Sequence: Synthetic
                         polypeptide
REGION                  1..399
                        note = AF002615_Pep2
source                  1..399
                        mol_type = protein
                        organism = synthetic construct
SEQUENCE: 280
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSDIQMT QSPSSLSASV GDRVTITCQA SQDISNYLNW YQQKPGKAPK LLIYAASSLQ   240
SGVPSRFSGS GSGTDFTLTI SSLQPEDFAT YYCQQSYSTP PTFGQGTRLE IKRADAAPTV   300
SIFPPSSEQL TSGGASVVCF LNNFYPKDIN VKWKIDGSER QNGVLNSWTD QDSKDSTYSM   360
SSTLTLTKDE YERHNSYTCE ATHKTSTSPI VKSFNRNEC                          399

SEQ ID NO: 281          moltype = AA   length = 454
FEATURE                 Location/Qualifiers
REGION                  1..454
                        note = Description of Artificial Sequence: Synthetic
                         polypeptide
REGION                  1..454
                        note = AF002616_Pep1
source                  1..454
                        mol_type = protein
                        organism = synthetic construct
SEQUENCE: 281
QVQLVQSGAE VKKPGASVKV SCKASGGTFS SYAISWVRQA PGQGLEWMGI IDPSVTYTRY    60
AQKFQGRVTM TRDTSTSTVY MELSSLRSED TAVYYCARSL FPTIFGVEVA FDIWGQGTLV   120
TVSSAKTTAP SVYPLAPVCG DTTGSSVTLG CLVKGYFPEP VTLTWNSGSL SSGVHTFPAV   180
LQSDLYTLSS SVTVTSSTWP SQSITCNVAH PASSTKVDKK IEPRGPTIKP CPPCKCPAPN   240
AAGGPSVFIF PPKIKDVLMI SLSPIVTCVV VDVSEDDPDV QISWFVNNVE VHTAQTQTHR   300
EDYNSTLRVV SALPIQHQDW MSGKEFKCKV NNKDLGAPIE RTISKPKGSV RAPQVYVLPP   360
PEEEMTKKQV TLTCMVTDFM PEDIYVEWTN NGKTELNYKN TEPVLDSDGS YFMYSKLRVE   420
KKNWVERNSY SCSVVHEGLH NHHTTKSFSR TPGK                               454

SEQ ID NO: 282          moltype = AA   length = 399
FEATURE                 Location/Qualifiers
REGION                  1..399
                        note = Description of Artificial Sequence: Synthetic
                         polypeptide
REGION                  1..399
                        note = AF002616_Pep2
source                  1..399
                        mol_type = protein
                        organism = synthetic construct
SEQUENCE: 282
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSDIQMT QSPSSLSASV GDRVTITCQA SQSISNRLAW YQQKPGKAPK LLIYKASSLE   240
```

```
SGVPSRFSGS GSGTDFTLTI SSLQPEDFAT YYCQQTYSTP ITFGQGTKVE IKRADAAPTV   300
SIFPPSSEQL TSGGASVVCF LNNFYPKDIN VKWKIDGSER QNGVLNSWTD QDSKDSTYSM   360
SSTLTLTKDE YERHNSYTCE ATHKTSTSPI VKSFNRNEC                         399

SEQ ID NO: 283          moltype = AA  length = 448
FEATURE                 Location/Qualifiers
REGION                  1..448
                        note = Description of Artificial Sequence: Synthetic
                         polypeptide
REGION                  1..448
                        note = AF002696_Pep1
source                  1..448
                        mol_type = protein
                        organism = synthetic construct
SEQUENCE: 283
QVQLVQSGAE VKKPGASVKV SCKASGYTFS GYYMHWVRQA PGQGLEWMGW MDPNSGYTGY    60
AHQFQGRVTM TRDTSTSTVY MELSSLRSED TAVYYCAKEV FSGWYDYWGQ GTLVTVSSAK   120
TTAPSVYPLA PVCGDTTGSS VTLGCLVKGY FPEPVTLTWN SGSLSSGVHT FPAVLQSDLY   180
TLSSSVTVTS STWPSQSITC NVAHPASSTK VDKKIEPRGP TIKPCPPCKC PAPNAAGGPS   240
VFIFPPKIKD VLMISLSPIV TCVVVDVSED DPDVQISWFV NNVEVHTAQT QTHREDYNST   300
LRVVSALPIQ HQDWMSGKEF KCKVNNKDLG APIERTISKP KGSVRAPQVY VLPPPEEEMT   360
KKQVTLTCMV TDFMPEDIYV EWTNNGKTEL NYKNTEPVLD SDGSYFMYSK LRVEKKNWVE   420
RNSYSCSVVH EGLHNHHTTK SFSRTPGK                                     448

SEQ ID NO: 284          moltype = AA  length = 399
FEATURE                 Location/Qualifiers
REGION                  1..399
                        note = Description of Artificial Sequence: Synthetic
                         polypeptide
REGION                  1..399
                        note = AF002696_Pep2
source                  1..399
                        mol_type = protein
                        organism = synthetic construct
SEQUENCE: 284
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSDIQMT QSPSSLSASV GDRVTITCRA SQTISSYLNW YQQKPGKAPK LLIYAASTLE   240
SGVPSRFSGS GSGTDFTLTI SSLQPEDFAT YYCQQGYSTP ITFGPGTKVD IKRADAAPTV   300
SIFPPSSEQL TSGGASVVCF LNNFYPKDIN VKWKIDGSER QNGVLNSWTD QDSKDSTYSM   360
SSTLTLTKDE YERHNSYTCE ATHKTSTSPI VKSFNRNEC                         399

SEQ ID NO: 285          moltype =     length =
SEQUENCE: 285
000

SEQ ID NO: 286          moltype = AA  length = 399
FEATURE                 Location/Qualifiers
REGION                  1..399
                        note = Description of Artificial Sequence: Synthetic
                         polypeptide
REGION                  1..399
                        note = AF002697_Pep2
source                  1..399
                        mol_type = protein
                        organism = synthetic construct
SEQUENCE: 286
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSDIQMT QSPSSLSASV GDRVTITCRA SQDVNTAVAW YQQKPGKAPK LLIYSASFLY   240
SGVPSRFSGS RSGTDFTLTI SSLQPEDFAT YYCQQHYTTP PTFGQGTKVE IKRADAAPTV   300
SIFPPSSEQL TSGGASVVCF LNNFYPKDIN VKWKIDGSER QNGVLNSWTD QDSKDSTYSM   360
SSTLTLTKDE YERHNSYTCE ATHKTSTSPI VKSFNRNEC                         399

SEQ ID NO: 287          moltype = AA  length = 447
FEATURE                 Location/Qualifiers
REGION                  1..447
                        note = Description of Artificial Sequence: Synthetic
                         polypeptide
REGION                  1..447
                        note = AF002698_Pep1
source                  1..447
                        mol_type = protein
                        organism = synthetic construct
SEQUENCE: 287
EVQLVESGGG LVQPGGSLRL SCATSGYTFT EYIIHWVRQA PGKGLEWVAS INPDYDITNY    60
NQRFKGRFTI SLDKSKRTAY LQMNSLRAED TAVYYCASWI SDFFDYWGQG TLVTVSSAKT   120
```

```
TAPSVYPLAP VCGDTTGSSV TLGCLVKGYF PEPVTLTWNS GSLSSGVHTF PAVLQSDLYT  180
LSSSVTVTSS TWPSQSITCN VAHPASSTKV DKKIEPRGPT IKPCPPCKCP APNAAGGPSV  240
FIFPPKIKDV LMISLSPIVT CVVVDVSEDD PDVQISWFVN NVEVHTAQTQ THREDYNSTL  300
RVVSALPIQH QDWMSGKEFK CKVNNKDLGA PIERTISKPK GSVRAPQVYV LPPPEEEMTK  360
KQVTLTCMVT DFMPEDIYVE WTNNGKTELN YKNTEPVLDS DGSYFMYSKL RVEKKNWVER  420
NSYSCSVVHE GLHNHHTTKS FSRTPGK                                     447

SEQ ID NO: 288          moltype = AA  length = 403
FEATURE                 Location/Qualifiers
REGION                  1..403
                        note = Description of Artificial Sequence: Synthetic
                         polypeptide
REGION                  1..403
                        note = AF002698_Pep2
source                  1..403
                        mol_type = protein
                        organism = synthetic construct
SEQUENCE: 288
CDLPQTHSLG SRRTLMLLAQ MRRISLFSCL KDRHDFGFPQ EEFGNQFQKA ETIPVLHEMI   60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKEGGGGS GGGGSGGGGS  180
GGGGSDIQMT QSPSSLSASV GDRVTITCRA SQSVSTSSYS YMHWYQQKPG KAPKVLISYA  240
SNLESGVPSR FSGSGSGTDF TLTISSLQPE DFATYYCQHS WGIPRTFGQG TKVEIKRADA  300
APTVSIFPPS SEQLTSGGAS VVCFLNNFYP KDINVKWKID GSERQNGVLN SWTDQDSKDS  360
TYSMSSTLTL TKDEYERHNS YTCEATHKTS TSPIVKSFNR NEC                   403

SEQ ID NO: 289          moltype = AA  length = 449
FEATURE                 Location/Qualifiers
REGION                  1..449
                        note = Description of Artificial Sequence: Synthetic
                         polypeptide
REGION                  1..449
                        note = AF003101
source                  1..449
                        mol_type = protein
                        organism = synthetic construct
SEQUENCE: 289
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGGGSGGGGS  180
GGGGSGGGGS QVQLVQSGAE VKKPGASVKV SCKASGYTFS NYYIHWVRQA PGQGLEWMGW  240
MDGNSGGTGY AQKFQGRVTM TRDTSTSTVY MELSSLRSED TAVYYCAKEV FSGWYDYWGQ  300
GTLVTVSSAS GGGGSGGGGS GGGGSHASDI QMTQSPSSLS ASVGDRVTIT CRASQSISSY  360
LNWYQQKPGK APKLLIYAAS SLQSGVPSRF SGSGSGTDFT LTISSLQPED FATYYCQQSY  420
STPYTFGQGT KVEIKGKPIP NPLLGLDST                                   449

SEQ ID NO: 290          moltype = AA  length = 449
FEATURE                 Location/Qualifiers
REGION                  1..449
                        note = Description of Artificial Sequence: Synthetic
                         polypeptide
REGION                  1..449
                        note = AF003093
source                  1..449
                        mol_type = protein
                        organism = synthetic construct
SEQUENCE: 290
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGGGSGGGGS  180
GGGGSGGGGS QVQLVQSGAE VKKPGASVKV SCKASGYTFS NYYIHWVRQA PGQGLEWMGW  240
MDSNSGYTGY AQKFQGRVTM TRDTSTSTVY MELSSLRSED TAVYYCAKEV FSGWYDYWGQ  300
GTLVTVSSAS GGGGSGGGGS GGGGSHASDI QMTQSPSSLS ASVGDRVTIT CRASQSISSY  360
LNWYQQKPGK APKLLIYAAS SLQSGVPSRF SGSGSGTDFT LTISSLQPED FATYYCQQSY  420
STPYTFGQGT KVEIKGKPIP NPLLGLDST                                   449

SEQ ID NO: 291          moltype = AA  length = 449
FEATURE                 Location/Qualifiers
REGION                  1..449
                        note = Description of Artificial Sequence: Synthetic
                         polypeptide
REGION                  1..449
                        note = AF003094
source                  1..449
                        mol_type = protein
                        organism = synthetic construct
SEQUENCE: 291
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
```

```
ILAVRKYFQR ITLYLKEKKY SPCAWEVVRA EIMRSFSLST NLQESLRSKE GGGGSGGGGS   180
GGGGSGGGGS QVQLVQSGAE VKKPGASVKV SCKASGYTFS NYYIHWVRQA PGQGLEWMGW   240
MDPNSGYTGY AHQFQGRVTM TRDTSTSTVY MELSSLRSED TAVYYCAKEV FSGWYDYWGQ   300
GTLVTVSSAS GGGGSGGGGS GGGGSHASDI QMTQSPSSLS ASVGDRVTIT CRASQSISSY   360
LNWYQQKPGK APKLLIYAAS SLQSGVPSRF SGSGSGTDFT LTISSLQPED FATYYCQQSY   420
STPYTFGQGT KVEIKGKPIP NPLLGLDST                                    449

SEQ ID NO: 292           moltype = AA   length = 449
FEATURE                  Location/Qualifiers
REGION                   1..449
                         note = Description of Artificial Sequence: Synthetic
                         polypeptide
REGION                   1..449
                         note = AF003092
source                   1..449
                         mol_type = protein
                         organism = synthetic construct
SEQUENCE: 292
MSTSTCDLPQ THSLGSRRTL MLLAQMRRIS LFSCLKDRHD FGFPQEEFGN QFQKAETIPV    60
LHEMIQQIFN LFSTKDSSAA WDETLLDKFY TELYQQLNDL EACVIQGVGV TETPLMKEDS   120
ILAVRKYFQR ITLYLKEKKY SPCAWEVVRA EIMRSFSLST NLQESLRSKE GGGGSGGGGS   180
GGGGSGGGGS QVQLVQSGAE VKKPGASVKV SCKASGYTFS NYYIHWVRQA PGQGLEWMGW   240
MDPNSGGTGY AQKFQGRVTM TRDTSTSTVY MELSSLRSED TAVYYCAKEV FSGWYDYWGQ   300
GTLVTVSSAS GGGGSGGGGS GGGGSHASDI QMTQSPSSLS ASVGDRVTIT CRASQSISSY   360
LNWYQQKPGK APKLLIYAAS SLQSGVPSRF SGSGSGTDFT LTISSLQPED FATYYCQQSY   420
STPYTFGQGT KVEIKGKPIP NPLLGLDST                                    449

SEQ ID NO: 293           moltype = AA   length = 449
FEATURE                  Location/Qualifiers
REGION                   1..449
                         note = Description of Artificial Sequence: Synthetic
                         polypeptide
REGION                   1..449
                         note = AF003099
source                   1..449
                         mol_type = protein
                         organism = synthetic construct
SEQUENCE: 293
MSTSTCDLPQ THSLGSRRTL MLLAQMRRIS LFSCLKDRHD FGFPQEEFGN QFQKAETIPV    60
LHEMIQQIFN LFSTKDSSAA WDETLLDKFY TELYQQLNDL EACVIQGVGV TETPLMKEDS   120
ILAVRKYFQR ITLYLKEKKY SPCAWEVVRA EIMRSFSLST NLQESLRSKE GGGGSGGGGS   180
GGGGSGGGGS QVQLVQSGAE VKKPGASVKV SCKASGYTFS GYYIHWVRQA PGQGLEWMGW   240
MDSNSGGTGY AQKFQGRVTM TRDTSTSTVY MELSSLRSED TAVYYCAKEV FSGWYDYWGQ   300
GTLVTVSSAS GGGGSGGGGS GGGGSHASDI QMTQSPSSLS ASVGDRVTIT CRASQSISSY   360
LNWYQQKPGK APKLLIYAAS SLQSGVPSRF SGSGSGTDFT LTISSLQPED FATYYCQQSY   420
STPYTFGQGT KVEIKGKPIP NPLLGLDST                                    449

SEQ ID NO: 294           moltype = AA   length = 638
FEATURE                  Location/Qualifiers
REGION                   1..638
                         note = Description of Artificial Sequence: Synthetic
                         polypeptide
REGION                   1..638
                         note = AF004305_pep1
source                   1..638
                         mol_type = protein
                         organism = synthetic construct
SEQUENCE: 294
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKEGGGGS GGGGSGGGGS   180
GGGGSQVQLV QSGAEVKKPG SSVKVSCKAS GYTFTAYDIN WVRQAPGQGL EWVGIINPGS   240
GSPMYAQKFQ GRVTITADES TSTAYMELSS LRSEDTAVYY CVSSVGAGAY YYQGLDVWGQ   300
GTLVTVSSAK TTAPSVYPLA PVCGDTTGSS VTLGCLVKGY FPEPVTLTWN SGSLSSGVHT   360
FPAVLQSDLY TLSSSVTVTS STWPSQSITC NVAHPASSTK VDKKIEPRGP TIKPCPPCKC   420
PAPNAAGGPS VFIFPPKIKD VLMISLSPIV TCVVVDVSED DPDVQISWFV NNVEVHTAQT   480
QTHREDYNST LRVVSALPIQ HQDWMSGKEF KCKVNNKDLG APIERTISKP KGSVRAPQVY   540
VLPPPEEEMT KKQVTLTCMV TDFMPEDIYV EWTNNGKTEL NYKNTEPVLD SDGSYFMYSD   600
LRVEKKNWVE RNSYSCSVVH EGLHNHHTTE SFSRTPGK                          638

SEQ ID NO: 295           moltype = AA   length = 466
FEATURE                  Location/Qualifiers
REGION                   1..466
                         note = Description of Artificial Sequence: Synthetic
                         polypeptide
REGION                   1..466
                         note = AF004305_pep2
source                   1..466
                         mol_type = protein
```

```
                        organism = synthetic construct
SEQUENCE: 295
QVQLVQSGAE VKKPGSSVKV SCKASGYTFT AYDINWVRQA PGQGLEWVGI INPGSGSPMY     60
AQKFQGRVTI TADESTSTAY MELSSLRSED TAVYYCVSSV GAGAYYYQGL DVWGQGTLVT    120
VSSAKTTAPS VYPLAPVCGD TTGSSVTLGC LVKGYFPEPV TLTWNSGSLS SGVHTFPAVL    180
QSDLYTLSSS VTVTSSTWPS QSITCNVAHP ASSTKVDKKI EPRGPTIKPC PPCKCPAPNA    240
AGGPSVFIFP PKIKDVLMIS LSPIVTCVVV DVSEDDPDVQ ISWFVNNVEV HTAQTQTHRE    300
DYNSTLRVVS ALPIQHQDWM SGKEFKCKVN NKDLGAPIER TISKPKGSVR APQVYVLPPP    360
EKEMTKKQVS LTCLVKDFMP EDIYVEWTNN GKTELNYKNT EPVLKSDGSY FMYSKLTVEK    420
KNWVERNSYS CSVVHEGLHN HHTTKSFSRT PGGGSGGGS  HHHHHH                   466

SEQ ID NO: 296          moltype = AA  length = 214
FEATURE                 Location/Qualifiers
REGION                  1..214
                        note = Description of Artificial Sequence: Synthetic
                         polypeptide
REGION                  1..214
                        note = AF004305_pep3
source                  1..214
                        mol_type = protein
                        organism = synthetic construct
SEQUENCE: 296
DIQMTQSPSS LSASVGDRVT ITCQASQDIA NYLNWYQQKP GKAPKLLIYS ASNLQSGVPS     60
RFSGSGSGTD FTLTISSLQP EDFATYYCQQ SYSTQWTFGQ GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 297          moltype = AA  length = 635
FEATURE                 Location/Qualifiers
REGION                  1..635
                        note = Description of Artificial Sequence: Synthetic
                         polypeptide
REGION                  1..635
                        note = AF004306_pep1
source                  1..635
                        mol_type = protein
                        organism = synthetic construct
SEQUENCE: 297
CDLPQTHSLG SRRTLMLLAQ MRRISLFSCL KDRHDFGFPQ EEFGNQFQKA ETIPVLHEMI     60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKEGGGGS GGGGSGGGGS    180
GGGGSEVQLV ESGGGLVQPG GSLRLSCAAS GFNIKDTYIH WVRQAPGKGL EWVARIYPTN    240
GYTRYADSVK GRFTISADTS KNTAYLQMNS LRAEDTAVYY CSRWGGDGFY AMDYWGQGTL    300
VTVSSAKTTA PSVYPLAPVC GDTTGSSVTL GCLVKGYFPE PVTLTWNSGS LSSGVHTFPA    360
VLQSDLYTLS SSVTVTSSTW PSQSITCNVA HPASSTKVDK KIEPRGPTIK PCPPCKCPAP    420
NAAGGPSVFI FPPKIKDVLM ISLSPIVTCV VVDVSEDDPD VQISWFVNNV EVHTAQTQTH    480
REDYNSTLRV VSALPIQHQD WMSGKEFKCK VNNKDLGAPI ERTISKPKGS VRAPQVYVLP    540
PPEEEMTKKQ VTLTCMVTDF MPEDIYVEWT NNGKTELNYK NTEPVLDSDG SYFMYSDLRV    600
EKKNWVERNS YSCSVVHEGL HNHHTTESFS RTPGK                               635

SEQ ID NO: 298          moltype = AA  length = 464
FEATURE                 Location/Qualifiers
REGION                  1..464
                        note = Description of Artificial Sequence: Synthetic
                         polypeptide
REGION                  1..464
                        note = AF33_pep1
source                  1..464
                        mol_type = protein
                        organism = synthetic construct
SEQUENCE: 298
EVQLVESGGG LVQPGGSLRL SCAASGFNIK DTYIHWVRQA PGKGLEWVAR IYPTNGYTRY     60
ADSVKGRFTI SADTSKNTAY LQMNSLRAED TAVYYCSRWG GDGFYAMDYW GQGTLVTVSS    120
AKTTAPSVYP LAPVCGDTTG SSVTLGCLVK GYFPEPVTLT WNSGSLSSGV HTFPAVLQSD    180
LYTLSSSVTV TSSTWPSQSI TCNVAHPASS TKVDKKIEPR GPTIKPCPPC KCPAPNAAGG    240
PSVFIFPPKI KDVLMISLSP IVTCVVVDVS EDDPDVQISW FVNNVEVHTA QTQTHREDYN    300
STLRVVSALP IQHQDWMSGK EFKCKVNNKD LGAPIERTIS KPKGSVRAPQ VYVLPPPEEE    360
MTKKQVTLTC MVTDFMPEDI YVEWTNNGKT ELNYKNTEPV LDSDGSYFMY SKLRVEKKNW    420
VERNSYSCSV VHEGLHNHHT TKSFSRTPGK GGGSGGGSH  HHHH                     464

SEQ ID NO: 299          moltype = AA  length = 445
FEATURE                 Location/Qualifiers
REGION                  1..445
                        note = Description of Artificial Sequence: Synthetic
                         polypeptide
REGION                  1..445
                        note = AF33_pep2
source                  1..445
                        mol_type = protein
```

```
                        organism = synthetic construct
SEQUENCE: 299
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ENLIILANNS LSSNGNVTES  180
GCKECEELEE KNIKEFLQSF VHIVQMFINT SGGGGSGGGG SGGGGSGGGG SDIQMTQSPS  240
SLSASVGDRV TITCRASQDV NTAVAWYQQK PGKAPKLLIY SASFLYSGVP SRFSGSRSGT  300
DFTLTISSLQ PEDFATYYCQ QHYTTPPTFG QGTKVEIKRA DAAPTVSIFP PSSEQLTSGG  360
ASVVCFLNNF YPKDINVKWK IDGSERQNGV LNSWTDQDSK DSTYSMSSTL TLTKDEYERH  420
NSYTCEATHK TSTSPIVKSF NRNEC                                       445

SEQ ID NO: 300          moltype = AA  length = 454
FEATURE                 Location/Qualifiers
REGION                  1..454
                        note = Description of Artificial Sequence: Synthetic
                         polypeptide
REGION                  1..454
                        note = AF002589
source                  1..454
                        mol_type = protein
                        organism = synthetic construct
SEQUENCE: 300
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGGGSGGGGS  180
GGGGSGGGGS QVQLVQSGAE VKKPGASVKV SCKASGYSFT SYDINWVRQA PGQGLEWIGM  240
INPSSGFTSA AQTFQGRVTM TRDTSTSTVY MELSSLRSED TAVYYCATIK GLGAYYYGM   300
DVWGQGTTVT VSSASGGGGS GGGGSGGGGS HASDIQMTQS PSSLSASVGD RVTITCRASQ  360
SIDRYLNWYQ QKPGKAPKLL IYAASSLQSG VPSRFSGSGS GTDFTLTISS LQPEDFATYY  420
CQQSYSPPLT FGGGTKVEIK GKPIPNPLLG LDST                             454

SEQ ID NO: 301          moltype = AA  length = 455
FEATURE                 Location/Qualifiers
REGION                  1..455
                        note = Description of Artificial Sequence: Synthetic
                         polypeptide
REGION                  1..455
                        note = AF002592
source                  1..455
                        mol_type = protein
                        organism = synthetic construct
SEQUENCE: 301
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGGGSGGGGS  180
GGGGSGGGGS QVQLVQSGAE VKKPGASVKV SCKASGGTFS SYAISWVRQA PGQGLEWMGW  240
INPNSGGTNY AQKFQGRVTM TRDTSTSTVY MELSSLRSED TAVYYCARSL FPTIFGVEVA  300
FDIWGQGTTV TVSSASGGGG SGGGGSGGGG SHASDIQMTQ SPSSLSASVG DRVTITCRAS  360
QSIIDRLAWY QQKPGKAPKL LIYKASSLES GVPSRFSGSG SGTDFTLTIS SLQPEDFATY  420
YCQQSYSTPF TFGPGTKVDI KGKPIPNPLL GLDST                            455

SEQ ID NO: 302          moltype = AA  length = 451
FEATURE                 Location/Qualifiers
REGION                  1..451
                        note = Description of Artificial Sequence: Synthetic
                         polypeptide
REGION                  1..451
                        note = AF002594
source                  1..451
                        mol_type = protein
                        organism = synthetic construct
SEQUENCE: 302
MSTSTCDLPQ THSLGSRRTL MLLAQMRRIS LFSCLKDRHD FGFPQEEFGN QFQKAETIPV   60
LHEMIQQIFN LFSTKDSSAA WDETLLDKFY TELYQQLNDL EACVIQGVGV TETPLMKEDS  120
ILAVRKYFQR ITLYLKEKKY SPCAWEVVRA EIMRSFSLST NLQESLRSKE GGGGSGGGGS  180
GGGGSGGGGS EVQLVESGGG LVQPGGSLRL SCAASGFNIK DTYIHWVRQA PGKGLEWVAR  240
IYPTNGYTRY ADSVKGRFTI SADTSKNTAY LQMNSLRAED TAVYYCSRWG GDGFYAMDYW  300
GQGTLVTVSS ASGGGGSGGG GSGGGGSHAS DIQMTQSPSS LSASVGDRVT ITCRASQDVN  360
TAVAWYQQKP GKAPKLLIYS ASFLYSGVPS RFSGSRSGTD FTLTISSLQP EDFATYYCQQ  420
HYTTPPTFGQ GTKVEIKGKP IPNPLLGLDS T                                451

SEQ ID NO: 303          moltype = AA  length = 702
FEATURE                 Location/Qualifiers
REGION                  1..702
                        note = Description of Artificial Sequence: Synthetic
                         polypeptide
REGION                  1..702
                        note = AF4505_pep2
source                  1..702
```

```
                        mol_type = protein
                        organism = synthetic construct
SEQUENCE: 303
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSAKTTAPS  120
VYPLAPVCGD TTGSSVTLGC LVKGYFPEPV TLTWNSGSLS SGVHTFPAVL QSDLYTLSSS  180
VTVTSSTWPS QSITCNVAHP ASSTKVDKKI EPRGPTIKPC PPCKCPAPNA AGGPSVFIFP  240
PKIKDVLMIS LSPIVTCVVV DVSEDDPDVQ ISWFVNNVEV HTAQTQTHRE DYNSTLRVVS  300
ALPIQHQDWM SGKEFKCKVN NKDLGAPIER TISKPKGSVR APQVYVLPPP EKEMTKKQVS  360
LTCLVKDFMP EDIYVEWTNN GKTELNYKNT EPVLKSDGSY FMYSKLTVEK KNWVERNSYS  420
CSVVHEGLHN HHTTKSFSRT PGGGGSGGG GSGGGGSGGG GSQVQLVQSG AEVKKPGASV  480
KVSCKASGDT FTRYYVHWVR QAPGQGLEWM GIINPSGGYA SYAQKFQGRV TMTRDTSTST  540
VYMELSSLRS EDTAVYYCAA GLFIWGQGTL VTVSSASGGG GSGGGGSGGG GSHASDIQMT  600
QSPSSLSASV GDRVTITCRA SQSIGRWLAW YQQKPGKAPK LLIYSASNLE TGVPSRFSGS  660
GSGTDFTLTI SSLQPEDFAT YYCQQYNRFP VTFGPGTKVD IK                    702

SEQ ID NO: 304        moltype = AA  length = 702
FEATURE               Location/Qualifiers
REGION                1..702
                      note = Description of Artificial Sequence: Synthetic
                       polypeptide
REGION                1..702
                      note = AF4504_pep2
source                1..702
                      mol_type = protein
                      organism = synthetic construct
SEQUENCE: 304
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSAKTTAPS  120
VYPLAPVCGD TTGSSVTLGC LVKGYFPEPV TLTWNSGSLS SGVHTFPAVL QSDLYTLSSS  180
VTVTSSTWPS QSITCNVAHP ASSTKVDKKI EPRGPTIKPC PPCKCPAPNA AGGPSVFIFP  240
PKIKDVLMIS LSPIVTCVVV DVSEDDPDVQ ISWFVNNVEV HTAQTQTHRE DYNSTLRVVS  300
ALPIQHQDWM SGKEFKCKVN NKDLGAPIER TISKPKGSVR APQVYVLPPP EKEMTKKQVS  360
LTCLVKDFMP EDIYVEWTNN GKTELNYKNT EPVLKSDGSY FMYSKLTVEK KNWVERNSYS  420
CSVVHEGLHN HHTTKSFSRT PGGGGSGGG GSGGGGSGGG GSQVQLVQSG AEVKKPGASV  480
KVSCKASGYT FTRYYMHWVR QAPGQGLEWM GIINPRAGYT SYALKFQGRV TMTRDTSTST  540
VYMELSSLRS EDTAVYYCTS GWDVWGQGTL VTVSSASGGG GSGGGGSGGG GSHASDIQMT  600
QSPSSLSASV GDRVTITCRA SQSISTWLAW YQQKPGKAPK LLIYAASSLD SGVPSRFSGS  660
GSGTDFTLTI SSLQPEDFAT YYCQQSYSFP VTFGQGTKVE IK                    702

SEQ ID NO: 305        moltype = AA  length = 15
FEATURE               Location/Qualifiers
REGION                1..15
                      note = Description of Artificial Sequence: Synthetic peptide
REGION                1..15
                      note = Parental monospecific antibody PDL1_02_A08
source                1..15
                      mol_type = protein
                      organism = synthetic construct
SEQUENCE: 305
CKASGYTFSG YYMHW                                                   15

SEQ ID NO: 306        moltype = AA  length = 15
FEATURE               Location/Qualifiers
REGION                1..15
                      note = Description of Artificial Sequence: Synthetic peptide
REGION                1..15
                      note = Dual-binding antibody (DBA) PDL1-IFN R01 A05
source                1..15
                      mol_type = protein
                      organism = synthetic construct
SEQUENCE: 306
CKASGYTFSN YYIHW                                                   15

SEQ ID NO: 307        moltype = AA  length = 15
FEATURE               Location/Qualifiers
REGION                1..15
                      note = Description of Artificial Sequence: Synthetic peptide
REGION                1..15
                      note = DBA variant H_N36G
source                1..15
                      mol_type = protein
                      organism = synthetic construct
SEQUENCE: 307
CKASGYTFSG YYIHW                                                   15

SEQ ID NO: 308        moltype = AA  length = 15
FEATURE               Location/Qualifiers
REGION                1..15
```

```
                        note = Description of Artificial Sequence: Synthetic peptide
REGION                  1..15
                        note = DBA variant H_I39V_S58P_Q69H_K70Q
source                  1..15
                        mol_type = protein
                        organism = synthetic construct
SEQUENCE: 308
CKASGYTFSN YYVHW                                                           15

SEQ ID NO: 309          moltype = AA  length = 15
FEATURE                 Location/Qualifiers
REGION                  1..15
                        note = Description of Artificial Sequence: Synthetic peptide
REGION                  1..15
                        note = DBA variant H_G64Y_Q69H
source                  1..15
                        mol_type = protein
                        organism = synthetic construct
SEQUENCE: 309
CKASGYTFSN YYIHW                                                           15

SEQ ID NO: 310          moltype = AA  length = 14
FEATURE                 Location/Qualifiers
REGION                  1..14
                        note = Description of Artificial Sequence: Synthetic peptide
REGION                  1..14
                        note = Parental monospecific antibody PDL1_02_A08
source                  1..14
                        mol_type = protein
                        organism = synthetic construct
SEQUENCE: 310
CRASQTISSY LNWY                                                            14

SEQ ID NO: 311          moltype = AA  length = 14
FEATURE                 Location/Qualifiers
REGION                  1..14
                        note = Description of Artificial Sequence: Synthetic peptide
REGION                  1..14
                        note = Dual-binding antibody (DBA) PDL1-IFN_R01_A05
source                  1..14
                        mol_type = protein
                        organism = synthetic construct
SEQUENCE: 311
CRASQSISSY LNWY                                                            14

SEQ ID NO: 312          moltype = AA  length = 14
FEATURE                 Location/Qualifiers
REGION                  1..14
                        note = Description of Artificial Sequence: Synthetic peptide
REGION                  1..14
                        note = L_Q68E
source                  1..14
                        mol_type = protein
                        organism = synthetic construct
SEQUENCE: 312
CRASQSISSY LNWY                                                            14

SEQ ID NO: 313          moltype = AA  length = 14
FEATURE                 Location/Qualifiers
REGION                  1..14
                        note = Description of Artificial Sequence: Synthetic peptide
REGION                  1..14
                        note = L_Q68E_E125D
source                  1..14
                        mol_type = protein
                        organism = synthetic construct
SEQUENCE: 313
CRASQSISSY LNWY                                                            14

SEQ ID NO: 314          moltype = AA  length = 287
FEATURE                 Location/Qualifiers
REGION                  1..287
                        note = Description of Artificial Sequence: Synthetic
                         polypeptide
REGION                  1..287
                        note = i47_A11
source                  1..287
                        mol_type = protein
                        organism = synthetic construct
```

```
SEQUENCE: 314
MSTSTQVQLV QSGAEVKKPG SSVKVSCKAS GYTFTSYDIN WVRQAPGQGL EWMGTINPSD    60
GDTTYAQKFQ GRVTITADES TSTAYMELSS LRSEDTAVYY CARVGGWGIY YYYGMDVWGQ   120
GTLVTVSSAS GGGGSGGGGS GGGGSHASDI QMTQSPSSLS ASVGDRVTIT CRASQSINSW   180
LAWYQQKPGK APKLLIYAAS SLQSGVPSRF SGSGSGTDFT LTISSLQPED FATYYCQQTY   240
TVPFSFGQGT KLEIKRAAAG SGSEQKLISE EDLGKPIPNP LLGLDST                287

SEQ ID NO: 315          moltype = AA  length = 287
FEATURE                 Location/Qualifiers
REGION                  1..287
                        note = Description of Artificial Sequence: Synthetic
                        polypeptide
REGION                  1..287
                        note = i47_A12
source                  1..287
                        mol_type = protein
                        organism = synthetic construct
SEQUENCE: 315
MSTSTQVQLV QSGAEVKKPG SSVKVSCKAS GYTFINNDIN WVRQAPGQGL EWMGGTIPIF    60
GVHIYAQKFQ GRVTITADES TSTAYMELSS LRSEDTAVYY CVSSVGAGAY YYYGMDVWGQ   120
GTLVTVSSAS GGGGSGGGGS GGGGSHASDI QMTQSPSSLS ASVGDRVTIT CQASQDISNY   180
LNWYQQKPGK APKLLIYAAS SLQSGVPSRF SGSGSGTDFT LTISSLQPED FATYYCQQSY   240
SLPYTFGQGT RLEIKRAAAG SGSEQKLISE EDLGKPIPNP LLGLDST                287

SEQ ID NO: 316          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 316
WMGWMDPNSG YTGYAHQFQG RV                                            22

SEQ ID NO: 317          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 317
WMGWMDSNSG GTGYAQKFQG RV                                            22

SEQ ID NO: 318          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 318
WMGWMDPNSG GTGYAHQFQG RV                                            22

SEQ ID NO: 319          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 319
WMGWMDSNSG YTGYAHKFQG RV                                            22

SEQ ID NO: 320          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 320
IYAASTLESG VPSR                                                     14

SEQ ID NO: 321          moltype = AA  length = 14
FEATURE                 Location/Qualifiers
REGION                  1..14
                        note = Description of Artificial Sequence: Synthetic peptide
source                  1..14
```

-continued

```
                        mol_type = protein
                        organism = synthetic construct
SEQUENCE: 321
IYAASSLQSG VPSR                                                         14

SEQ ID NO: 322          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 322
IYAASSLESG VPSR                                                         14

SEQ ID NO: 323          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 323
CAKEVFSGWY DYWGQ                                                        15

SEQ ID NO: 324          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 324
YYCQQGYSTP ITFGPGTKVD IK                                                22

SEQ ID NO: 325          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 325
YYCQQSYSTP YTFGQGTKVE IK                                                22

SEQ ID NO: 326          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 326
YYCQQSYSTP YTFGQGTKVD IK                                                22

SEQ ID NO: 327          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 327
GGGGSGGGGS GGGGSGGGGS                                                   20

SEQ ID NO: 328          moltype = AA  length = 280
FEATURE                 Location/Qualifiers
REGION                  1..280
                        note = Description of Artificial Sequence: Synthetic
                         polypeptide
source                  1..280
                        mol_type = protein
                        organism = synthetic construct
```

-continued

```
SEQUENCE: 328
MSTSTEQKLI SEEDLQVQLV QSGAEVKKPG ASVKVSCKAS GGTFSSYAIS WVRQAPGQGL  60
EWMGIIDPSV TYTRYAQKFQ GRVTMTRDTS TSTVYMELSS LRSEDTAVYY CARSLFPTIF  120
GVEVAFDIWG QGTLVTVSSA SGGGGSGGGG SGGGGSHASD IQMTQSPSSL SASVGDRVTI  180
TCQASQDISN YLNWYQQKPG KAPKLLIYGA STLQSGVPSR FSGSGSGTDF TLTISSLQPE  240
DFATYYCQQT YSTPITFGQG TKVEIKGKPI PNPLLGLDST                       280
```